United States Patent
Igawa et al.

(10) Patent No.: US 10,253,100 B2
(45) Date of Patent: *Apr. 9, 2019

(54) THERAPEUTIC ANTIGEN-BINDING MOLECULE WITH A FCRN-BINDING DOMAIN THAT PROMOTES ANTIGEN CLEARANCE

(71) Applicant: Chugai Seiyaku Kabushiki Kaisha, Tokyo (JP)

(72) Inventors: Tomoyuki Igawa, Shizuoka (JP); Atsuhiko Maeda, Shizuoka (JP); Futa Mimoto, Shizuoka (JP); Taichi Kuramochi, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 1022 days.

This patent is subject to a terminal disclaimer.

(21) Appl. No.: 14/347,187

(22) PCT Filed: Sep. 28, 2012

(86) PCT No.: PCT/JP2012/006218
§ 371 (c)(1),
(2) Date: Jul. 25, 2014

(87) PCT Pub. No.: WO2013/046704
PCT Pub. Date: Apr. 4, 2013

(65) Prior Publication Data
US 2014/0363428 A1    Dec. 11, 2014

(30) Foreign Application Priority Data

Sep. 30, 2011  (JP) ................................. 2011-218736
Mar. 30, 2012  (WO) ................. PCT/JP2012/058603

(Continued)

(51) Int. Cl.
*A61K 39/395*    (2006.01)
*C07K 16/28*      (2006.01)
*A61K 39/00*      (2006.01)

(52) U.S. Cl.
CPC ...... *C07K 16/2866* (2013.01); *C07K 16/2812* (2013.01); *A61K 2039/505* (2013.01);
(Continued)

(58) Field of Classification Search
None
See application file for complete search history.

(56) References Cited

U.S. PATENT DOCUMENTS 4,801,687 A    1/1989  Ngo
5,322,678 A    6/1994  Morgan et al.
(Continued)

FOREIGN PATENT DOCUMENTS

CA    2 647 846    10/2007
CA    2 700 986    4/2009
(Continued)

OTHER PUBLICATIONS

Janeway et al., Immunobiology, 3$^{rd}$ edition 1997, Garland Publishing, Inc., pp. 3:1-3:11.*

(Continued)

*Primary Examiner* — Michael Szperka
(74) *Attorney, Agent, or Firm* — Fish & Richardson P.C.

(57) ABSTRACT

The present invention provides: a modified FcRn-binding domain having an enhanced affinity for the Fc Receptor neonatal (FcRn) at neutral pH; an antigen-binding molecule comprising said FcRn-binding domain, which has low immunogenicity, high stability and form only a few aggregates; a modified antigen-binding molecule having an increased FcRn-binding activity at neutral or acidic pH without an increased binding activity at neutral pH for a (Continued)

pre-existing anti-drug antibody; use of the antigen-binding molecules for improving antigen-binding molecule-mediated antigen uptake into cells; use of the antigen-binding molecules for reducing the plasma concentration of a specific antigen; use of the modified FcRn-binding domain for increasing the total number of antigens to which a single antigen-binding molecule can bind before its degradation; use of the modified FcRn-binding domain for improving pharmacokinetics of an antigen-binding molecule; methods for decreasing the binding activity for a pre-existing anti-drug antibody; and methods for producing said antigen-binding molecules.

36 Claims, 82 Drawing Sheets

Specification includes a Sequence Listing.

(30) Foreign Application Priority Data

| May 30, 2012 | (JP) | ................ | 2012-123773 |
|---|---|---|---|
| May 30, 2012 | (JP) | ................ | 2012-123781 |
| May 30, 2012 | (JP) | ................ | 2012-123782 |
| Jun. 20, 2012 | (JP) | ................ | 2012-139211 |
| Aug. 9, 2012 | (JP) | ................ | 2012-177311 |

(52) U.S. Cl.
CPC ...... C07K 2317/34 (2013.01); C07K 2317/52 (2013.01); C07K 2317/524 (2013.01); C07K 2317/526 (2013.01); C07K 2317/94 (2013.01)

(56) References Cited

U.S. PATENT DOCUMENTS

| 5,639,641 | A | 6/1997 | Pedersen et al. |
|---|---|---|---|
| 5,795,965 | A | 8/1998 | Tsuchiya et al. |
| 5,935,935 | A | 8/1999 | Connelly et al. |
| 5,990,286 | A | 11/1999 | Khawli et al. |
| 6,074,642 | A | 6/2000 | Wang et al. |
| 6,329,511 | B1 | 12/2001 | Vasquez et al. |
| 6,485,943 | B2 | 11/2002 | Stevens et al. |
| 6,602,684 | B1 | 8/2003 | Umana et al. |
| 6,677,436 | B1 | 1/2004 | Sato et al. |
| 6,737,056 | B1 | 5/2004 | Presta |
| 6,884,879 | B1 | 4/2005 | Baca et al. |
| 6,913,747 | B1 | 7/2005 | Co et al. |
| 7,052,873 | B2 | 5/2006 | Tsuchiya |
| 7,662,925 | B2 | 2/2010 | Lazar et al. |
| 7,960,512 | B2 | 6/2011 | Stavenhagen et al. |
| 8,101,720 | B2 | 1/2012 | Lazar et al. |
| 8,188,231 | B2 | 5/2012 | Lazar et al. |
| 8,329,867 | B2 | 12/2012 | Lazar et al. |
| 8,367,805 | B2 | 2/2013 | Chamberlain et al. |
| 8,388,955 | B2 | 3/2013 | Lazar et al. |
| 8,562,991 | B2 | 10/2013 | Igawa et al. |
| 8,568,726 | B2 * | 10/2013 | Beaumont .......... A61K 31/7088 424/159.1 |
| 8,735,545 | B2 | 5/2014 | Lazar et al. |
| 8,802,820 | B2 | 8/2014 | Chamberlain et al. |
| 9,029,515 | B2 | 5/2015 | Pons et al. |
| 9,079,949 | B1 | 7/2015 | Andrien et al. |
| 9,096,651 | B2 | 8/2015 | Igawa et al. |
| 9,200,079 | B2 | 12/2015 | Chamberlain et al. |
| 9,765,135 | B2 * | 9/2017 | Ruike ................ A61K 31/519 |
| 9,828,429 | B2 | 11/2017 | Igawa et al. |
| 9,868,948 | B2 | 1/2018 | Igawa et al. |
| 9,890,377 | B2 | 2/2018 | Igawa et al. |
| 9,969,800 | B2 * | 5/2018 | Igawa ................ C07K 16/4291 |
| 10,024,867 | B2 * | 7/2018 | Igawa ................ G01N 33/6854 |
| 2002/0098193 | A1 | 7/2002 | Ward |
| 2002/0137897 | A1 | 9/2002 | Stevens et al. |
| 2002/0142374 | A1 | 10/2002 | Gallo et al. |
| 2002/0164339 | A1 | 11/2002 | Do et al. |
| 2003/0059937 | A1 | 3/2003 | Ruben et al. |
| 2003/0103970 | A1 | 6/2003 | Tsuchiya |
| 2003/0224397 | A1 | 12/2003 | Lowman et al. |
| 2004/0081651 | A1 | 4/2004 | Karpusas et al. |
| 2004/0110226 | A1 | 6/2004 | Lazar et al. |
| 2004/0133357 | A1 | 7/2004 | Zhong et al. |
| 2004/0236080 | A1 | 11/2004 | Aburatani et al. |
| 2005/0095243 | A1 | 5/2005 | Chan et al. |
| 2005/0244403 | A1 | 11/2005 | Lazar et al. |
| 2005/0260213 | A1 | 11/2005 | Koenig et al. |
| 2005/0260711 | A1 | 11/2005 | Datta et al. |
| 2005/0261229 | A1 | 11/2005 | Gillies et al. |
| 2006/0014156 | A1 | 1/2006 | Rabbani et al. |
| 2006/0019342 | A1 | 1/2006 | Dall'Acqua et al. |
| 2006/0063228 | A1 | 3/2006 | Kasaian et al. |
| 2006/0067930 | A1 | 3/2006 | Adams et al. |
| 2006/0134709 | A1 | 6/2006 | Stavenhagen et al. |
| 2006/0141456 | A1 | 6/2006 | Edwards et al. |
| 2006/0153860 | A1 | 7/2006 | Cho et al. |
| 2007/0009523 | A1 * | 1/2007 | Presta ................ C07K 16/00 424/144.1 |
| 2007/0036785 | A1 | 2/2007 | Kishimoto et al. |
| 2007/0037734 | A1 | 2/2007 | Rossi et al. |
| 2007/0041978 | A1 | 2/2007 | Hattori et al. |
| 2007/0059312 | A1 | 3/2007 | Baca et al. |
| 2007/0148164 | A1 * | 6/2007 | Farrington ............ C07K 16/00 424/133.1 |
| 2007/0160598 | A1 | 7/2007 | Dennis et al. |
| 2007/0231329 | A1 | 10/2007 | Lazar et al. |
| 2007/0237767 | A1 | 10/2007 | Lazar et al. |
| 2007/0248602 | A1 | 10/2007 | Lazar et al. |
| 2007/0253951 | A1 | 11/2007 | Ng et al. |
| 2007/0269371 | A1 | 11/2007 | Krummen et al. |
| 2008/0044417 | A1 | 2/2008 | Johnson et al. |
| 2008/0089892 | A1 * | 4/2008 | Allan ................ C07K 16/00 424/143.1 |
| 2008/0138349 | A1 | 6/2008 | Stavenhagen et al. |
| 2008/0166756 | A1 | 7/2008 | Tsuchiya et al. |
| 2008/0199471 | A1 | 8/2008 | Bernett et al. |
| 2008/0292637 | A1 | 11/2008 | Fishman |
| 2009/0041770 | A1 | 2/2009 | Chamberlain et al. |
| 2009/0053240 | A1 | 2/2009 | Lazar et al. |
| 2009/0076251 | A1 | 3/2009 | Koenig et al. |
| 2009/0136485 | A1 | 5/2009 | Chu et al. |
| 2009/0142340 | A1 | 6/2009 | Lazar |
| 2009/0215991 | A1 | 8/2009 | Lazar et al. |
| 2009/0263392 | A1 | 10/2009 | Igawa et al. |
| 2009/0324589 | A1 | 12/2009 | Igawa et al. |
| 2010/0003254 | A1 | 1/2010 | Hattori et al. |
| 2010/0098730 | A1 | 4/2010 | Lowman et al. |
| 2010/0184959 | A1 | 7/2010 | Guler-Gane et al. |
| 2010/0216187 | A1 | 8/2010 | Lasters et al. |
| 2010/0239577 | A1 | 9/2010 | Igawa et al. |
| 2010/0292443 | A1 | 11/2010 | Sabbadini et al. |
| 2010/0298542 | A1 | 11/2010 | Igawa et al. |
| 2011/0044986 | A1 | 2/2011 | Biere-Citron et al. |
| 2011/0076275 | A1 | 3/2011 | Igawa et al. |
| 2011/0098450 | A1 | 4/2011 | Igawa et al. |
| 2011/0111406 | A1 * | 5/2011 | Igawa ................ C07K 16/248 435/6.14 |
| 2011/0150888 | A1 | 6/2011 | Foltz et al. |
| 2011/0223658 | A1 | 9/2011 | Beliard et al. |
| 2011/0229489 | A1 | 9/2011 | Pons et al. |
| 2011/0245473 | A1 | 10/2011 | Igawa et al. |
| 2012/0321620 | A1 | 12/2012 | Chu et al. |
| 2013/0011866 | A1 | 1/2013 | Igawa et al. |
| 2013/0131319 | A1 | 5/2013 | Igawa et al. |
| 2013/0303396 | A1 | 11/2013 | Igawa et al. |
| 2013/0336963 | A1 | 12/2013 | Igawa et al. |
| 2014/0086916 | A1 | 3/2014 | Zha |
| 2014/0093496 | A1 | 4/2014 | Mimoto et al. |
| 2014/0105889 | A1 | 4/2014 | Igawa et al. |
| 2014/0112926 | A1 | 4/2014 | Liu |
| 2014/0234340 | A1 | 8/2014 | Igawa et al. |
| 2014/0255398 | A1 | 9/2014 | Igawa et al. |
| 2014/0335089 | A1 | 11/2014 | Igawa et al. |
| 2015/0050269 | A1 | 2/2015 | Igawa et al. |

(56) References Cited

U.S. PATENT DOCUMENTS

| | | |
|---|---|---|
| 2015/0056182 A1 | 2/2015 | Igawa et al. |
| 2015/0166654 A1 | 6/2015 | Igawa et al. |
| 2015/0203577 A1 | 7/2015 | Igawa et al. |
| 2015/0210763 A1 | 7/2015 | Kuramochi et al. |
| 2015/0247849 A1 | 9/2015 | Tamburini |
| 2015/0284465 A1 | 10/2015 | Igawa et al. |
| 2015/0299296 A1 | 10/2015 | Katada et al. |
| 2015/0299313 A1 | 10/2015 | Igawa et al. |
| 2015/0315278 A1 | 11/2015 | Igawa et al. |
| 2015/0353630 A1 | 12/2015 | Igawa et al. |
| 2016/0039912 A1 | 2/2016 | Mimoto et al. |
| 2016/0046693 A1 | 2/2016 | Igawa et al. |
| 2016/0068592 A1 | 3/2016 | Chung et al. |
| 2016/0244526 A1 | 8/2016 | Igawa et al. |
| 2017/0022270 A1 | 1/2017 | Igawa et al. |
| 2017/0226206 A1 | 8/2017 | Igawa et al. |
| 2018/0142027 A1 | 5/2018 | Igawa et al. |
| 2018/0258161 A1 | 9/2018 | Igawa et al. |

FOREIGN PATENT DOCUMENTS

| | | | | |
|---|---|---|---|---|
| CA | 2 794 860 | 10/2011 | | |
| CA | 2 827 923 | 8/2012 | | |
| CA | 2 831 770 | 10/2012 | | |
| CN | 1763097 | 4/2006 | | |
| CN | 101001873 | 7/2007 | | |
| CN | 101014619 | 8/2007 | | |
| CN | 101098890 | 1/2008 | | |
| CN | 102056946 | 5/2011 | | |
| CN | 103492565 | 1/2014 | | |
| CN | 102633880 | 2/2015 | | |
| EP | 0 182 495 | 5/1986 | | |
| EP | 0 329 185 | 4/1994 | | |
| EP | 0 783 893 | 7/1997 | | |
| EP | 1 069 185 | 1/2001 | | |
| EP | 1 773 391 | 4/2007 | | |
| EP | 1 601 697 | 5/2007 | | |
| EP | 1 787 998 | 5/2007 | | |
| EP | 1 870 459 | 12/2007 | | |
| EP | 2 006 381 | 12/2008 | | |
| EP | 2 009 101 | 12/2008 | | |
| EP | 2 189 526 | 5/2010 | | |
| EP | 2 196 541 | 6/2010 | | |
| EP | 2 202 245 | 6/2010 | | |
| EP | 2 275 443 | 1/2011 | | |
| EP | 2 314 618 | 4/2011 | | |
| EP | 2 366 713 | 9/2011 | | |
| EP | 2 368 911 | 9/2011 | | |
| EP | 2 647 706 | 10/2013 | | |
| EP | 2 679 681 | 1/2014 | | |
| EP | 2 698 431 | 2/2014 | | |
| EP | 2 762 166 | 8/2014 | | |
| EP | 2 889 377 | 7/2015 | | |
| JP | S61-117457 | 6/1986 | | |
| JP | S63-52890 | 3/1988 | | |
| JP | H01-144991 | 6/1989 | | |
| JP | H02-028200 | 1/1990 | | |
| JP | H02-501112 | 4/1990 | | |
| JP | H02-163085 | 6/1990 | | |
| JP | H03-500664 | 2/1991 | | |
| JP | 07-67688 | 3/1995 | | |
| JP | 2003-512019 | 4/2003 | | |
| JP | 2004-511426 | 4/2004 | | |
| JP | 2005-101105 | 3/2005 | | |
| JP | 2005-535341 | 11/2005 | | |
| JP | 2005-378266 | 12/2005 | | |
| JP | WO 2006/020114 | 2/2006 | | |
| JP | 2007-532139 | 11/2007 | | |
| JP | 2008-505174 | 2/2008 | | |
| JP | 2008-510466 | 4/2008 | | |
| JP | 2008-511292 | 4/2008 | | |
| JP | 2008-519860 | 6/2008 | | |
| JP | WO 2009125825 A1 * | 10/2009 | ........... | C07K 16/244 |
| JP | 2010-505436 | 2/2010 | | |
| JP | 2010-079667 | 3/2010 | | |
| JP | 2010-514460 | 5/2010 | | |
| JP | 2010-250830 | 11/2010 | | |
| JP | 2011-184418 | 9/2011 | | |
| JP | WO 2011122011 A2 * | 10/2011 | ........ | C07K 16/4241 |
| JP | 2012-505833 | 3/2012 | | |
| JP | 5144499 | 2/2013 | | |
| JP | 2013-518131 | 5/2013 | | |
| JP | 2013-165716 | 8/2013 | | |
| JP | 5334319 | 11/2013 | | |
| JP | 2015-130883 | 7/2015 | | |
| KR | 2011/0004435 | 1/2011 | | |
| RU | 2225721 | 3/2004 | | |
| RU | 2266298 | 12/2005 | | |
| RU | 2005/112742 | 1/2006 | | |
| RU | 2337107 | 10/2008 | | |
| RU | 2007/121679 | 12/2008 | | |
| RU | 2367667 | 9/2009 | | |
| RU | 2390527 | 5/2010 | | |
| RU | 2430111 | 9/2011 | | |
| RU | 2010/116152 | 11/2011 | | |
| SG | 183867 | 10/2012 | | |
| SG | 192945 | 9/2013 | | |
| TW | 2010/00127 | 1/2010 | | |
| TW | 2012/02419 | 1/2012 | | |
| WO | WO 88/04692 | 6/1988 | | |
| WO | WO 89/01343 | 2/1989 | | |
| WO | WO 92/19759 | 11/1992 | | |
| WO | WO 95/02187 | 1/1995 | | |
| WO | WO 95/14710 | 6/1995 | | |
| WO | WO 96/11020 | 4/1996 | | |
| WO | WO 96/12503 | 5/1996 | | |
| WO | WO 97/34631 | 9/1997 | | |
| WO | WO 98/03546 | 1/1998 | | |
| WO | WO 99/18212 | 4/1999 | | |
| WO | WO 99/51743 | 10/1999 | | |
| WO | WO 99/58572 | 11/1999 | | |
| WO | WO 2000/014220 | 3/2000 | | |
| WO | WO 00/42072 | 7/2000 | | |
| WO | WO 01/30854 | 5/2001 | | |
| WO | WO 01/82899 | 11/2001 | | |
| WO | WO 02/060919 | 8/2002 | | |
| WO | WO 2003/000883 | 1/2003 | | |
| WO | WO 03/020949 | 3/2003 | | |
| WO | WO 03/057881 | 7/2003 | | |
| WO | WO 2003/070760 | 8/2003 | | |
| WO | WO 03/105757 | 12/2003 | | |
| WO | WO 2003/107009 | 12/2003 | | |
| WO | WO 2004/016740 | 2/2004 | | |
| WO | WO 2004/029207 | 4/2004 | | |
| WO | WO 2004/035752 | 4/2004 | | |
| WO | WO 2004/039826 | 5/2004 | | |
| WO | WO 2004/068931 | 8/2004 | | |
| WO | WO 2004/092219 | 10/2004 | | |
| WO | WO 2004/096273 | 11/2004 | | |
| WO | WO 2004/099249 | 11/2004 | | |
| WO | WO 2005/035756 | 4/2005 | | |
| WO | WO 2005/037867 | 4/2005 | | |
| WO | WO 2005/047327 | 5/2005 | | |
| WO | WO 2005/059106 | 6/2005 | | |
| WO | WO 2005/067620 | 7/2005 | | |
| WO | WO 2005/070963 | 8/2005 | | |
| WO | WO 2005/077981 | 8/2005 | | |
| WO | WO 2005/112564 | 12/2005 | | |
| WO | WO 2005/115452 | 12/2005 | | |
| WO | WO 2005/123126 | 12/2005 | | |
| WO | WO 2005/123780 | 12/2005 | | |
| WO | WO 2006/004663 | 1/2006 | | |
| WO | WO 2006/016644 | 2/2006 | | |
| WO | WO 2006/019447 | 2/2006 | | |
| WO | WO 2006/023403 | 3/2006 | | |
| WO | WO 2006/030200 | 3/2006 | | |
| WO | WO 2006/030220 | 3/2006 | | |
| WO | WO 2006/031370 | 3/2006 | | |
| WO | WO 2006/050166 | 5/2006 | | |
| WO | WO 2006/050491 | 5/2006 | | |
| WO | WO 2006/053301 | 5/2006 | | |
| WO | WO 2006/066598 | 6/2006 | | |
| WO | WO 2006/067913 | 6/2006 | | |
| WO | WO 2009/095235 | 8/2006 | | |

(56) References Cited

FOREIGN PATENT DOCUMENTS

| | | |
|---|---|---|
| WO | WO 2006/105338 | 10/2006 |
| WO | WO 2006/106905 | 10/2006 |
| WO | WO 2006/109592 | 10/2006 |
| WO | WO 2006/116260 | 11/2006 |
| WO | WO 2006/121852 | 11/2006 |
| WO | WO 2006/130834 | 12/2006 |
| WO | WO 2007/021841 | 2/2007 |
| WO | WO 2007/024249 | 3/2007 |
| WO | WO 2007/024535 | 3/2007 |
| WO | WO 2007/041635 | 4/2007 |
| WO | WO 2007/060411 | 5/2007 |
| WO | WO 2007/076524 | 7/2007 |
| WO | WO 2007/114319 | 10/2007 |
| WO | WO 2007/114325 | 10/2007 |
| WO | WO 2007/142325 | 12/2007 |
| WO | WO 2008/002933 | 1/2008 |
| WO | WO 2008/022152 | 2/2008 |
| WO | WO 2008/043822 | 4/2008 |
| WO | WO 2008/060785 | 5/2008 |
| WO | WO 2008/091954 | 7/2008 |
| WO | WO 2008/092117 | 7/2008 |
| WO | WO 2008/143954 | 11/2008 |
| WO | WO 2009/006338 | 1/2009 |
| WO | WO 2009/008529 | 1/2009 |
| WO | WO 2009/041062 | 4/2009 |
| WO | WO 2009/041643 | 4/2009 |
| WO | WO 2009/053358 | 4/2009 |
| WO | WO 2009/058492 | 5/2009 |
| WO | WO 2009/062083 | 5/2009 |
| WO | WO 2009/086320 | 7/2009 |
| WO | WO 2009/125825 | 10/2009 |
| WO | WO 2009/139822 | 11/2009 |
| WO | WO 2009/155513 | 12/2009 |
| WO | WO 2010/045193 | 4/2010 |
| WO | WO 2010/058860 | 5/2010 |
| WO | WO 2010/081173 | 7/2010 |
| WO | WO 2010/085682 | 7/2010 |
| WO | WO 2010/106180 | 9/2010 |
| WO | WO 2010/107109 | 9/2010 |
| WO | WO 2011/043643 | 4/2011 |
| WO | WO 2011/044368 | 4/2011 |
| WO | WO 2011/094593 | 8/2011 |
| WO | WO 2011/111007 | 9/2011 |
| WO | WO 2011/122011 | 10/2011 |
| WO | WO 2012/033953 | 3/2012 |
| WO | WO 2012/073992 | 6/2012 |
| WO | WO 2012/115241 | 8/2012 |
| WO | WO 2012/132067 | 10/2012 |
| WO | WO 2012/133782 | 10/2012 |
| WO | WO 2013/004842 | 1/2013 |
| WO | WO 2013/047729 | 4/2013 |
| WO | WO 2013/047748 | 4/2013 |
| WO | WO 2013/047752 | 4/2013 |
| WO | WO 2013/081143 | 6/2013 |
| WO | WO 2013/125667 | 8/2013 |
| WO | WO 2013/180200 | 12/2013 |
| WO | WO 2013/180201 | 12/2013 |
| WO | WO 2014/028354 | 2/2014 |
| WO | WO 2014/030728 | 2/2014 |
| WO | WO 2014/144080 | 9/2014 |
| WO | WO 2014/144575 | 9/2014 |
| WO | WO 2014/163101 | 10/2014 |
| WO | WO 2016/000813 | 1/2016 |

OTHER PUBLICATIONS

Rudikoff et al., Proc Natl Acad Sci U S A. Mar. 1982;79(6):1979-83.*
International Search Report for App. Ser. No. PCT/JP2012/081185, dated Feb. 26, 2013, 9 pages.
International Preliminary Report on Patentability for App. Ser. No. PCT/JP2012/081185, dated Jun. 3, 2014, 9 pages.
Alley et al., "Antibody-drug conjugates: targeted drug delivery for cancer," *Curr Opin Chem Biol.*, Aug. 2010; 14(4):529-37. doi: 10.1016/j.cbpa.2010.06.170. Epub Jul. 17, 2010.
Baeuerle et al., "BiTE: Teaching antibodies to engage T-cells for cancer therapy," *Curr Opin Mol Ther.*, 11(1):22-30 (2009).
Davda et al., "Properties of a general PK/PD model of antibody-ligand interactions for therapeutic antibodies that bind to soluble endogenous targets," *MAbs*, Sep.-Oct.; 2(5):576-88. doi: 10.4161/mabs.2.5.12833. Epub Sep. 1, 2010.
De Bono et al., "ING-1, a monoclonal antibody targeting Ep-CAM in patients with advanced adenocarcinomas," *Clin Cancer Res.*, 10(22):7555-65 (2004).
Deng et al., "Pharmacokinetics of humanized monoclonal anti-tumor necrosis factor-{alpha} antibody and its neonatal Fc receptor variants in mice and cynomolgus monkeys," *Drug Metab Dispos.*, Apr. 2010;38(4):600-5. doi: 10.1124/dmd.109.031310. Epub Jan. 13, 2010.
Desjarlais et al., "Optimizing engagement of the immune system by anti-tumor antibodies: an engineer's perspective," *Drug Discov Today*, Nov. 2007; 12(21-22):898-910. Epub Oct. 22, 2007.
Haringman et al., "A randomized controlled trial with an anti-CCL2 (anti-monocyte chemotactic protein 1) monoclonal antibody in patients with rheumatoid arthritis," *Arthritis Rheum.*, 54(8):2387-92 (2006).
Juszczak et al., "Ipilimumab: a novel immunomodulating therapy causing autoimmune hypophysitis: a case report and review," *Eur J Endocrinol.*, Jul. 2012; 167(1):1-5. doi: 10.1530/EJE-12-0167. Epub Apr. 10, 2012.
Lewis et al., "Differential responses of human tumor cell lines to anti-p185HER2 monoclonal antibodies," *Cancer Immunol Immunother.*, 37(4):255-63 (1993).
Lutterbuese et al., "T cell-engaging BiTE antibodies specific for EGFR potently eliminate KRAS- and BRAF-mutated colorectal cancer cells," *Proc Natl Acad Sci U S A.*, Jul. 13, 2010; 107(28):12605-10. doi: 10.1073/pnas.1000976107. Epub Jun. 28, 2010.
Martin et al., "Preclinical safety and immune-modulatng effects of therapeutic monoclonal antibodies to interleukin-6 and tumor necrosis factor-α in cynomolgus macaques," *J Immunotoxicol.*, Jul. 1, 2004;1(3):131-9. doi:10.1080/15476910490894904.
Nam et al., "Current evidence for the management of rheumatoid arthritis with biological disease-modifying antirheumatic drugs: a systematic literature review informing the EULAR recommendations for the management of RA," *Ann Rheum Dis.*, Jun. 2010; 69(6):976-86. doi: 10.1136/ard.2009.126573. Epub May 6, 2010.
Nishimoto et al., "Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease," *Blood*, Nov. 15, 2008;112(10):3959-64. doi: 10.1182/blood-2008-05-155846. Epub Sep. 10, 2008.
Petkova et al., "Enhanced half-life of genetically engineered human IgG1 antibodies in a humanized FcRn mouse model: potential application in humorally mediated autoimmune disease," *Int Immunol.*, 18(12):1759-69 (2006).
Reverberi et al., "Factors affecting the antigen-antibody reaction," *Blood Transfus.*, Nov. 2007;5(4):227-40. doi: 10.2450/2007.0047-07.
Riechelmann et al., "Phase I trial with the CD44v6-targeting immunoconjugate bivatuzumab mertansine in head and neck squamous cell carcinoma," *Oral Oncol.*, Sep. 2008; 44(9):823-9. doi: 10.1016/j.oraloncology.2007.10.009. Epub Jan. 18, 2008.
Roopenian et al., "FcRn: the neonatal Fc receptor comes of age," *Nat Rev Immunol.*, 7(9):715-25 (2007).
Satoh et al., "Non-fucosylated therapeutic antibodies as next-generation therapeutic antibodies," *Expert Opin Biol Ther.*, 6(11):1161-73 (2006).
Takeuchi et al., "The Japanese experience with biologic therapies for rheumatoid arthritis," *Nat Rev Rheumatol.*, Nov. 2010; 6(11):644-52. doi: 10.1038/nrrheum.2010.154. Epub Sep. 28, 2010.
Trinh et al., "Ipilimumab in the treatment of melanoma," *Expert Opin Biol Ther.*, Jun. 2012; 12(6):773-82. doi: 10.1517/14712598.2012.675325. Epub Apr. 14, 2012.

(56) References Cited

OTHER PUBLICATIONS

Vaccaro et al., "Engineering the Fc region of immunoglobulin G to modulate in vivo antibody levels," *Nat Biotechnol.*, 23(10):1283-8 (2005).

Weiner et al., "Monoclonal antibodies: versatile platforms for cancer immunotherapy," *Nat Rev Immunol.*, May 2010; 10(5):317-27. doi: 10.1038/nri2744.

Xiao et al., "Pharmacokinetics of anti-hepcidin monoclonal antibody Ab 12B9m and hepcidin in cynomolgus monkeys," *AAPS J.*, Dec. 2010;12(4):646-57. doi: 10.1208/s12248-010-9222-0. Epub Aug. 25, 2010.

Zheng et al., "Translational pharmacokinetics and pharmacodynamics of an FcRn-variant anti-CD4 monoclonal antibody from preclinical model to phase I study," *Clin Pharmacol Ther.*, Feb. 2011; 89(2):283-90. doi: 10.1038/clpt.2010.311. Epub Dec. 29, 2010.

Algonomics—TripoleR applications [Online], Retrieved from the Internet on Feb. 29, 2012: http://www.algonomics.com/proteinengineering/tripole_applications.php, 2 pages, available online on Feb. 21, 2009.

Almagro et al., "Humanization of antibodies," *Front. Biosci.* Jan. 1, 2008; 13:1619-33.

Araujo et al., "Increased rheumatoid factor interference observed during immunogenicity assessment of an Fc-engineered therapeutic antibody," *J. Pharm. Biomed. Anlys.* Jul. 15, 2011;55(5):1041-9. doi: 10.1016/j.jpba.2011.03.008. Epub Mar. 11, 2011.

Armour et al., "Recombinant human IgG molecules lacking Fcγ receptor I binding and monocyte triggering activities," *Eur. J. Immunol.* Aug. 5, 1999; 29(8):2613-24.

Bayry et al., "Immuno affinity purification of foot and mouth disease virus type specific antibodies using recombinant protein absorbed to polystyrene wells," *J. Virol. Methods.* Aug. 1999; 81(1-2):21-30.

Chau et al., "HuM291(Nuvion), a humanized Fc receptor-nonbinding antibody against CD3, anergizes peripheral blood T cells as partial agonist of the T cell receptor," *Transplantation* Apr. 15, 2001; 71(7):941-50.

Chen et al., "Generation and Analysis of Random Point Mutations in an Antibody CDR2 Sequence: Many Mutated Antibodies Lose Their Ability to Bind Antigen," *J. Exp. Med.* Sep. 1, 1992; 176(3):855-66.

Chen et al., "Defective Secretion of an Immunoglobulin Caused by Mutations in the Heavy Chain Complementarity Determining Region 2," *Exp. Med.* Aug. 1, 1994; 180(2):577-86.

Chu et al., "Accumulation of Succinimide in a Recombinant Monoclonal Antibody in Mildly Acidic Buffers Under Elevated Temperatures," *Pharm. Res.* Jun. 2007; 24(6):1145-56. Epub Mar. 24, 2007.

Cole et al., "Human IgC2 Variants of Chimeric Anti-CD3 Are Nonmitogenic to T Cells," *J. Immunol.* Oct. 1, 1997; 159(7):3613-21.

Comper et al., "Charge selectivity in kidney ultrafiltration," *Kidney Int.* May 1995; 47(5):1242-51.

Cordoba et al., "Non-enzymatic hinge region fragmentation of antibodies in solution," *J. Chromatogr. B—Analyt. Technol. Biomed. Life Sci.* Apr. 25, 2005; 818(2):115-21.

Cuatrecasas et al., "Affinity Chromatography", *Methods Enzymol.* 1971; 12:345-78.

Damschroder et al., "Framework shuffling of antibodies to reduce immunogenicity and manipulate functional and biophysical properties," *Mol. Immunol.* Apr. 2007; 44(11):3049-60. Epub Jan. 22, 2007.

De Groot et al., "De-immunization of Therapeutic Proteins by T-cell Epitope Modification," *Dev. Biol. (Basel).* Feb. 2005; 122:171-94.

Deen et al., "Structural determinants of glomerular permeability," *Am. J. Physiol. Renal Physiol.* Oct. 1, 2001; 281(4): F579-96.

Del Rio et al., "An engineered penicillin acylase with altered surface charge is more stable in alkaline pH," *Ann. N.Y. Acad. Sci.* Oct. 12, 1996; 799:61-4.

Durkee et al., "Immunoaffinity Chromatographic Purification of Russell's Viper Venom Factor X Activator Using Elution in High Concentrations of Magnesium Chloride," *Protein Expr. Purif.* Oct. 1993; 4(5):405-11.

Fujii, "Antibody affinity maturation by random mutagenesis," *Antibody Engineering, Methods Mol. Biol. Series*, 2004; 248:345-59.

Gerstner et al., "Sequence Plasticity in the Antigen-binding Site of a Therapeutic Anti-HER2 Antibody," *J. Mol. Biol.* Aug. 30, 2002; 321(5):851-62.

Gessner et al., "The IgG Fc receptor family," *Ann. Hematol.* Jun. 1998; 76(6):231-48.

Ghetie et al., "Multiple roles for the major histocompatibility complex class I-related receptor FcRn," *Ann. Rev. Immunol.* Apr. 2000; 18:739-66.

Guyre et al., "Increased potency of Fc-receptor-targeted antigens," *Cancer Immunol. Immunother.* Nov. 1997; 45(3-4):146-8.

Hironiwa et al., "Calcium-dependent antigen binding as a novel modality for antibody recycling by endosomal antigen dissociation," *MAbs.* Jan. 2016; 8(1):65-73. doi: 10.1080/19420862.2015.1110660. Epub Oct. 23, 2015.

Igawa et al., "Engineering the variable region of therapeutic IgG antibodies," *MAbs.* May-Jun. 2011; 3(3):243-52. Epub May 1, 2011.

Katayose et al., "MUC1-specific targeting immunotherapy with bispecific antibodies: inhibition of xenografted human bile duct carcinoma growth," *Cancer Res.* Sep. 15, 1996; 56(18):4205-12.

Khawli et al., "Improved tumor localization and radioimaging with chemically modified monoclonal antibodies," *Cancer Biother. Radiopharm.* Jun. 1996; 11(3):203-15.

Kim et al., "Lowering of pI by acylation improves the renal uptake of 99mTc-labeled anti-Tac dsFv: effect of different acylating reagents," *Nucl. Med. Biol.* Nov. 2002; 29(8):795-801.

Kim et al., "Chemical modification to reduce renal uptake of disulfide-bonded variable region fragment of anti-Tac monoclonal antibody labeled with 99mTc," *Bioconjug. Chem.* May 1999; 10(3):447-53. Online Publication Mar. 20, 1999.

Kobayashi et al., "A monoclonal antibody specific for a distinct region of hen egg-white lysozyme," *Mol. Immunol.* Apr. 1982; 19(4):619-30.

Kobayashi et al., "The pharmacokinetic characteristics of glycolated humanized anti-Tac Fabs are determined by their isoelectric points," *Cancer Res.* Jan. 15, 1999; 59(2):422-30.

Komissarov et al., "Site-specific Mutagenesis of a Recombinant Anti-single-stranded DNA Fab Role of Heavy Chain Complementarity—Determining Region 3 Residues in Antigen Interaction," *J. Biol. Chem.* Oct. 24, 1997; 272(43):26864-70.

Leong et al., "Adapting pharmacokinetic properties of a humanized anti-interleukin-8 antibody for therapeutic applications using site-specific pegylation," *Cytokine.* Nov. 7, 2001; 16(3):106-19.

Liu et al., "Heterogeneity of Monoclonal Antibodies," *J. Pharm. Sci.* Jul. 2008; 97(7):2426-47. Available Online Sep. 7, 2007.

Maeda et al., "pH-dependent receptor/ligand dissociation as a determining factor for intracellular sorting of ligands for epidermal growth factor receptors in rat hepatocytes," *J. Control Release.* Jul. 18, 2002; 82(1):71-82.

Maier et al., "Assessment of fully automated antibody homology modeling protocols in molecular operating environment," *Proteins.* Aug. 2014; 82(8):1599-610. doi: 10.1002/prot.24576. Epub Apr. 23, 2014.

Martin et al., "Crystal structure at 2.8 A of an FcRn/heterodimeric Fc complex: mechanism of pH-dependent binding," *Mol. Cell.* Apr. 2001; 7(4):867-77.

Matsunaga et al., "A pH-dependent conformational transition of Abeta peptide and physicochemical properties of the conformers in the glial cell," *Biochem. J.* Feb. 1, 2002; 361(3):547-56.

Maurer et al., "Antigenicity of polypeptides (poly alpha amino acids): calcium-dependent and independent antibodies," *J. Immunol.* Sep. 1, 1970; 105(3):567-73.

Maxfield et al., "Endocytic recycling," *Nat. Rev. Mol. Cell Biol.* Feb. 2004; 5(2):121-32.

Mohan et al, CALBIOCHEM, "Buffers—A guide for the preparation and use of buffers in biological systems," by Chandra Mohan, Ph.D., CALBIOCHEM Buffers Booklet, 2003, Copyright 2003 EMD Biosciences, Inc., 37 pages.

Nesterova et al., AACR Abstract No. 656 (2007), Los Angeles, CA. Apr. 4-18, 2007, 3 pages.

(56) References Cited

OTHER PUBLICATIONS

Ono et al., "The humanized anti-HMI.24 antibody effectively kills multiple myeloma cells by human effector cell-mediated cytotoxicity," Mol. Immunol. Apr. 1999; 36(6):387-95.

Ozhegov et al., Tolkovyi Slovar Russkogo iazyka: 2004, p. 292 (with an English translation of the relevant passage defining "control").

Pardridge et al., "Enhanced Endocytosis in Cultured Human Breast Carcinoma Cells and In Vivo Biodistribution in Rats of a Humanized Monoclonal Antibody after Cationization of the Protein," J. Pharmacol. Exp. Ther. Jul. 1, 1998; 286(1):548-54.

Pavlinkova et al., "Charge-Modified Single Chain Antibody Constructs of Monoclonal Antibody CC49: Generation, Characterization, Pharmacokinetics, and Biodistribution Analysis," Nucl. Med. Biol. Jan. 1999; 26(1):27-34.

Pons et al., "Energetic analysis of an antigen/antibody interface: Alanine scanning mutagenesis and double mutant cycles on the HyHEL-10/lysozyme interaction," Protein Sci. May 1999; 8(5):958-68.

Presta, "Engineering of therapeutic antibodies to minimize immunogenicity and optimize function," Adv. Drug Deliv. Rev. Aug. 7, 2006; 58(5-6):640-56. Epub May 23, 2006.

Reddy et al., "Elimination of Fc Receptor-Dependent Effector Functions of a Modified IgG4 Monoclonal Antibody to Human CD4," J. Immunol. Feb. 15, 2000; 164(4):1925-33.

Reichert et al., "Development trends for monoclonal antibody cancer therapeutics," Nat. Rev. Drug Discovery May 2007; 6(5):349-56.

Schaeffer et al., "The rat glomerular filtration barrier does not show negative charge selectivity," Microcirculation. Oct. 2002; 9(5):329-42.

Schmitz et al., "Phage display: a molecular tool for the generation of antibodies—a review," Placenta Mar. 2000; vol. 21 Suppl A:S106-12.

Singer et al., Genes & Genomes, 1991; pp. 67-69.

Tan et al., "Engineering the isoelectric point of a renal cell carcinoma targeting antibody greatly enhances scFv solubility," Immunotechnology. Oct. 1998; 4(2):107-14.

Teeling et al., "The Biological Activity of Human CD20 Monoclonal Antibodies Is Linked to Unique Epitopes on CD20," J. Immunol. Jul. 1, 2006; 177(1):362-71.

Ten Kate, et al., "Effect of isoelectric point on biodistribution and inflammation: imaging with indium-111-labelled IgG," Eur. J. Nucl. Med. Jun. 1990; 17(6-8):305-9 (abstract) [Database BIOSIS Accession No. 1991910742 20].

Tsuchiya, Credit Suisse Seminar, "Therapeutic Antibody," at Fuji-Gotemba Laboratories, p. 21, Sep. 22, 2006. English translation.

Vaisitti et al., "Cationization of monoclonal anti bodies: Another step towards the "Magic Bullet"?" J. Biol. Regul. Homeost. Agents Jul.-Dec. 2005; 19(3-4):105-12.

Vajdos et al., "Comprehensive Functional Maps of the Antigen-binding Site of an Anti-ErbB2 Antibody Obtained with Shotgun Scanning Mutagenesis," J. Mol. Biol. Jul. 5, 2002; 320(2):415-28.

Van Walle et al., "Immunogenicity screening in protein drug development," Expert Opin. Biol. Ther. Mar. 2007; 7(3):405-18. Published online Feb. 19, 2007.

Wang et al., "Monoclonal Antibodies with Identical Fc Sequences Can Bind to FcRn Differentially with Pharmacokinetic Consequences," Drug Metabolism and Disposition, Sep. 2011; 39(9):1469-77. doi: 10.1124/dmd.111.039453. Epub May 24, 2011.

Wiens et al., "Somatic Mutation in VH Complementarity-Determining Region 2 and Framework Region 2," J. Immunol. Aug 1, 1997; 159(3):1293-302.

Wiens et al., "Mutation of a Single Conserved Residue in VH Complementarity-Determining Region 2 Results in a Severe Ig Secretion Defect," J. Immunol. Aug. 15, 2001;167(4):2179-86.

Wikipedia, "Chaotropic agent" [online], retrieved on Nov. 2, 2015. Retrieved from the Internet at: https://en.wikipedia.org/wiki/Chaotropic_agent. 3 pages.

Wu et al., "Humanization of a murine monoclonal antibody by simultaneous optimization of framework and CDR residues," J. Mol. Biol., Nov. 19, 1999; 294(1):151-62.

Yang et al., "Tailoring structure-function and pharmacokinetic properties of single-chain Fv proteins by site-specific PEGylation," Protein Eng. Oct. 1, 2003; 16(10):761-70.

Zwick et al., "The Long Third Complementarity-Determining Region of the Heavy Chain Is Important in the Activity of the Broadly Neutralizing Anti-Human Immunodeficiency Virus Type 1 Antibody 2F5," J. Virol. Mar. 2004; 78(6):3155-61.

Fish & Richardson P.C., Reply to Office Action dated Nov. 23, 2016 in U.S. Appl. No. 13/595,139, filed Mar. 22, 2016, 29 pages.

Fish & Richardson P.C., Reply to Non-Final Office Action dated Apr. 16, 2015 in U.S. Appl. No. 14/347,034, filed Sep. 16, 2015, 28 pages.

Clark, "An alignment of IgG sequences from Human, Mouse and Rat," Part II Immunoglobulin lectures (v4), pp. 5(i)-(ii) [retrieved on Jul. 25, 2014]. Retrieved from the Internet: http://www.path.cam.ac.uk/~mrc7/lecturenotes/handout1a.pdf.

Haakenstad et a., "The disappearance kinetics and glomerular deposition of small-latticed soluble immune complexes," *Immunology*, 47(3):407-14 (1982).

Hebert LA, "The clearance of immune complexes from the circulation of man and other primates," *Am J Kidney Dis.*, 17(3):352-61 (1991).

Montero-Julian et al., "Pharmacokinetic study of anti-interleukin-6 (IL-6) therapy with monoclonal antibodies: enhancement of IL-6 clearance by cocktails of anti-IL-6 antibodies," *Blood*, 85(4):917-24 (1995).

Rudge et al.,, "VEGF Trap complex formation measures production rates of VEGF, providing a biomarker for predicting efficacious angiogenic blockade," *Proc Natl Acad Sci USA.*, 104(47):18363-70 (2007).

USPTO Non-Final Office Action in U.S. Appl. No. 13/889,484, dated Apr. 6, 2015, 12 pages.

International Search Report for App. Ser. No. PCT/JP2013/072507, dated Oct. 29, 2013, 4 pages.

International Preliminary Report on Patentability for App. Ser. No. PCT/JP2013/072507, dated Feb. 24, 2015, 6 pages.

Drake et al., "Chapter 5: Biophysical Considerations for Development of Antibody-Based Therapeutics," *Biophysical Considerations for Development of Antibody-Based Therapeutics*, Springer Springer Science+Business Media New York, 95-7 (2012).

Lin et al., "Preclinical pharmacokinetics, interspecies scaling, and tissue distribution of a humanized monoclonal antibody against vascular endothelial growth factor," *J Pharmacol Exp Ther.*, 288(1):371-8 (1999).

Cartron et al., "Therapeutic activity of humanized anti-CD20 monoclonal antibody and polymorphism in IgG Fc receptor FcgammaRIIIa gene," *Blood*, 99(3):754-8 (2002).

Clynes et al., "Fc receptors are required in passive and active immunity to melanoma," *Proc Natl Acad Sci USA*, 95(2):652-6 (1998).

Clynes et al., "Inhibitory Fc receptors modulate in vivo cytotoxicity against tumor targets," *Nat Med.*, 6(4):443-6 (2000).

Desai et al., "Fc gamma receptor IIB on dendritic cells enforces peripheral tolerance by inhibiting effector T cell responses," *J Immunol.*, 178(10):6217-26 (2007).

Horton et al., "Potent in vitro and in vivo activity of an Fc-engineered anti-CD19 monoclonal antibody against lymphoma and leukemia," *Cancer Res.*, Oct. 1, 2008;68(19):8049-57. doi: 10.1158/0008-5472.CAN-08-2268.

Lazar et al., "Engineered antibody Fc variants with enhanced effector function," *Proc Natl Acad Sci USA*, Mar. 14, 2006;103(11):4005-10. Epub Mar. 6, 2006.

Li et al., "Apoptotic and antitumor activity of death receptor antibodies require inhibitory Fcγ receptor engagement," *Proc Natl Acad Sci USA.*, Jul. 3, 2012;109(27):10966-71. doi: 10.1073/pnas.1208698109. Epub Jun. 20, 2012.

Nimmerjahn et al., "Divergent immunoglobulin g subclass activity through selective Fc receptor binding," *Science*, 310(5753):1510-2 (2005).

(56) References Cited

OTHER PUBLICATIONS

Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J Biol Chem.*, Jan. 31, 2003;278(5):3466-73. Epub Nov. 8, 2002.
Zalevsky et al., "Enhanced antibody half-life improves in vivo activity," *Nat Biotechnol.*, Feb. 2010;28(2):157-9. doi: 10.1038/nbt. 1601. Epub Jan. 17, 2010.
International Search Report for App. Ser. No. PCT/JP2013/054461, dated May 7, 2013, 7 pages.
International Preliminary Report on Patentability for App. Ser. No. PCT/JP2013/054461, dated Aug. 26, 2014, 6 pages.
International Search Report for App. Ser. No. PCT/JP2012/075092, dated Dec. 25, 2012, 4 pages.
International Preliminary Report on Patentability for App. Ser. No. PCT/JP2012/075092, dated Apr. 1, 2014, 10 pages.
Janeway et al., Immunobiology, The Immune System in Health and Disease, 3$^{rd}$ Edition, 1997 Garland Publishing Inc., pp. 3:1-3:11.
Patton et al., "An acid dissociation bridging ELISA for detection of antibodies directed against therapeutic proteins in the presence of antigen," *J Immunol Methods*, Sep. 2005;304(1-2):189-95.
Rudikoff et al., "Single amino acid substitution altering antigen-binding specificity," *Proc Natl Acad Sci U S A.*, Mar. 1982;79(6):1979-83.
Schuster et al., "Signaling of human ciliary neurotrophic factor (CNTF) revisited. The interleukin-6 receptor can serve as an alpha-receptor for CTNF," *J Biol Chem.*, Mar. 14, 2003;278(11):9528-35.
Seda et al., "B-cell receptor signalling and its crosstalk with other pathways in normal and malignant cells," *Eur J Haematol.*, Aug. 1, 2014. doi: 10.1111/ejh.12427.
Horn et al., "Analysis of the binding of pro-urokinase and urokinase-plasminogen activator inhibitor-1 complex to the low density lipoprotein receptor-related protein using a Fab fragment selected from a phage-displayed Fab library," *J Biol Chem.*, May 19, 1995;270(20):11770-5.
Fish & Richardson P.C., Amendment and Reply to Office Action dated Apr. 6, 2015 in U.S. Appl. No. 13/889,484, filed Jul. 6, 2015, 14 pages.
Malbec et al., "Antibodies against growth factor receptors can inhibit the proliferation of transformed cells via a cis-interaction with inhibitory FcR," *Immunol Lett.*, Mar. 30, 2012;143(1):28-33.
Wenink et al., "The inhibitory Fc gamma IIb receptor dampens TLR4-mediated immune responses and is selectively up-regulated on dendritic cells from rheumatoid arthritis patients with quiescent disease," *J Immunol.*, Oct. 1, 2009;183(7):4509-20. doi: 10.4049/jimmunol.0900153. Epub Sep. 4, 2009.
Zhang et al., "Immune complex/Ig negatively regulate TLR4-triggered inflammatory response in macrophages through Fc gamma RIIb-dependent PGE2 production," *J Immunol.*, Jan. 1, 2009;182(1):554-62.
U.S. Appl. No. 14/347,034, Igawa et al.
International Preliminary Report on Patentability for App. Ser. No. PCT/JP2012/075083, dated Apr. 1, 2014, 8 pages.
Clarkson et al., "Blockade of clearance of immune complexes by an anti-Fc gamma receptor monoclonal antibody," *J Exp Med.*, Aug. 1, 1986;164(2):474-89.
Prickett et al., "A calcium-dependent antibody for identification and purification of recombinant proteins," *Biotechniques*, Jun. 1989;7(6):580-9.
Schulke et al., "The homodimer of prostate-specific membrane antigen is a functional target for cancer therapy," *Proc Natl Acad Sci U S A.*, Oct. 28, 2003;100(22):12590-5.
Yarmush et al., "Immunoadsorption: strategies for antigen elution and production of reusable adsorbents," *Biotechnol Prog.*, May-Jun. 1992;8(3):168-78.
Ejima et al., "Effective elution of antibodies by arginine and arginine derivatives in affinity column chromatography," *Anal Biochem.*, Oct. 15, 2005;345(2):250-7.
Rojas et al., "Formation, distribution, and elimination of infliximab and anti-infliximab immune complexes in cynomolgus monkeys," *J Pharmacol Exp Ther.*, May 2005;313(2):578-85. Epub Jan. 12, 2005.
Singer et al., "Genes & Genomes," Moscow, "Mir," 1998;1:63-64.
USPTO Interview Summary in U.S. Appl. No. 14/347,034, dated Aug. 17, 2015, 3 pages.
Fish & Richardson P.C., Amendment in Reply to Office Action dated Nov. 14, 2012 in U.S. Appl. No. 13/595,139, filed May 14, 2013, 19 pages.
USPTO Final Office Action in U.S. Appl. No. 13/595,139, dated Aug. 1, 2013, 8 pages.
USPTO Notice of Allowance in U.S. Appl. No. 13/595,139, dated Oct. 11, 2013, 15 pages.
USPTO Non-Final Office Action in U.S. Appl. No. 13/595,139, dated Mar. 13, 2015, 12 pages.
Fish & Richardson P.C., Amendment and Reply to Office Action dated Mar. 13, 2015 in U.S. Appl. No. 13/595,139, filed Jun. 11, 2015, 19 pages.
USPTO Non-Final Office Action in U.S. Appl. No. 13/595,139, dated Aug. 3, 2015, 13 pages.
USPTO Final Office Action in U.S. Appl. No. 13/889,484, dated Aug. 4, 2015, 12 pages.
U.S. Appl. No. 15/210,353, filed Jul. 14, 2016, Igawa et al.
U.S. Appl. No. 15/210,360, filed Jul. 14, 2016, Igawa et al.
Dufner et al., "Harnessing phage and ribosome display for antibody optimization," Trends Biotechnol., Nov. 2006;24(11):523-9. Epub Sep. 26, 2006.
Matsumiya et al., "Structural comparison of fucosylated and nonfucosylated Fc fragments of human immunoglobulin G1," J Mol Biol., May 4, 2007;368(3):767-79. Epub Feb. 22, 2007.
Strohl, Optimization of Fc-mediated effector functions of monoclonal antibodies, Curr Opin Biotechnol., Dec. 2009;20(6):685-91. doi: 10.1016/j.copbio.2009.10.011. Epub Nov. 4, 2009.
Beringhelli et al., "pH and ionic strength dependence of protein (un)folding and ligand binding to bovine beta-lactoglobulins A and B," *Biochemistry*, Dec. 24, 2002;41(51):15415-22.
Epstein, "Non-randomness of amino-acid changes in the evolution of homologous proteins," *Nature*, Jul. 22, 1967;215(5099):355-9.
Fillipovich, Biochemical basis of human life, VLADOS, 2005:49-50 (with English translation).
Idusogie et al., "Engineered antibodies with increased activity to recruit complement," *J Immunol.*, Feb. 15, 2001;166(4):2571-5.
Luttrell et al., "Reaction coupling of chelation and antigen binding in the calcium ion-dependent antibody binding of cyclic AMP," *J Biol Chem.*, Nov. 15, 1991;266(32):21626-30.
Moore et al., "Engineered Fc variant antibodies with enhanced ability to recruit complement and mediate effector functions," *MAbs.*, Mar.-Apr. 2010;2(2):181-9.
Schroter et al., "A generic approach to engineer antibody pH-switches using combinatorial histidine scanning libraries and yeast display," *MAbs.*, 2015;7(1):138-51. doi: 10.4161/19420862.2014. 985993.
Zalevsky et al., "The impact of Fc engineering on an anti-CD19 antibody: increased Fcgamma receptor affinity enhances B-cell clearing in nonhuman primates," *Blood*, 113(16):3735-43 (2009). Epub Dec. 24, 2008.
Fish & Richardson P.C., Reply to Office Action dated Feb. 12, 2016 in U.S. Appl. No. 13/595,139, filed Jul. 11, 2016, 4 pages.
Tarditi et al., "Selective high-performance liquid chromatographic purification of bispecific monoclonal antibodies," J. Chromatogr., 599(1-2):13-20 (1992).
U.S. Appl. No. 13/889,484, filed May 8, 2013, Igawa et al.
U.S. Appl. No. 13/889,512, filed May 8, 2013, Igawa et al.
U.S. Appl. No. 13/990,158, filed May 29, 2013, Igawa et al.
U.S. Appl. No. 14/007,947, filed Sep. 26, 2013, Igawa et al.
Adams et al., "Humanization of a recombinant monoclonal antibody to produce a therapeutic HER dimerization inhibitor, pertuzumab," *Cancer Immunol. Immunother.*, 55:717-727 (2006).
Amersham Biosciences, "Affinity Chromatography: Principles and Methods," Edition AD, pp. 16-18, 137 (2002).
Amigorena et al., "Fc gamma RII expression in resting and activated B lymphocytes," *Eur J Immunol.*, (8):1379-85 (1989).

(56) References Cited

OTHER PUBLICATIONS

Amigorena et al., "Cytoplasmic domain heterogeneity and functions of IgG Fc receptors in B lymphocytes," *Science*, 256(5065):1808-12 (1992).
Armour et al., "Differential binding to human FcgammaRIIa and FcgammaRIIb receptors by human IgG wildtype and mutant antibodies," *Mol Immunol.*, 40(9):585-93 (2003).
Bartelds et al., "Clinical response to adalimumab: relationship to anti-adalimumab antibodies and serum adalimumab concentrations in rheumatoid arthritis," *Ann Rheum. Dis.*, 66:921-926 (2007).
Beck et al., "Strategies and challenges for the next generation of therapeutic antibodies," *Nat Rev Immunol.*, 10(5):345-52 (2010).
Bender et al., "Immunogenicity, efficacy and adverse events of adalimumab in RA patients," *Rheumatol. Int.*, 27:269-274 (2007).
Binz et al., "Engineering novel binding proteins from nonimmunoglobulin domains," *Nat. Biotechnol.*, 23:1257-68 (2005).
Blank et al., Decreased transcription of the human FCGR2B gene mediated by the -343 G/C promoter polymorphism and association with systemic lupus erythematosus. *Hum Genet.*, 117(2-3):220-7 (2005).
Boruchov et al., "Activating and inhibitory IgG Fc receptors on human DCs mediate opposing functions," *J Clin Invest.*, 115(10):2914-23 (2005).
Boumpas et al., "A short course of BG9588 (anti-CD40 ligand antibody) improves serologic activity and decreases hematuria in patients with proliferative lupus glomerulonephritis," *Arthritis Rheum.*, 48(3):719-27 (2003).
Brown et al., "Tolerance of single, but not multiple, amino acid replacements in antibody $V_H$ CDR2: a means of minimizing B cell wastage from somatic hypermutation?," *J. Immunol.*, 156(9):3285-91 (1996).
Bruhns et al., Specificity and affinity of human Fcgamma receptors and their polymorphic variants for human IgG subclasses, *Blood*, 113(16):3716-25 (2009).
Cemerski et al., "Suppression of mast cell degranulation through a dual-targeting tandem IgE-IgG Fc domain biologic engineered to bind with high affinity to FcγRIIb," *Immunol Lett.*, 143(1):34-43 (2012).
Chaparro-Riggers et al., "Increasing serum half-life and extending cholesterol lowering in vivo by engineering antibody with pH-sensitive binding to PCSK9," *J Biol Chem.*, 287(14):11090-7 (2012).
Chen et al., "Association of a transmembrane polymorphism of Fcgamma receptor IIb (FCGR2B) with systemic lupus erythematosus in Taiwanese patients," *Arthritis Rheum.*, 54(12):3908-17 (2006).
Chirino et al., "Minimizing the immunogenicity of protein therapeutics," *Drug Discov. Today.*, 9:82-90 (2004).
Chu et al., "Reduction of total IgE by targeted coengagement of IgE B-cell receptor and FcγRIIb with Fc-engineered antibody," *J Allergy Clin Immunol.*, 129(4):1102-15 (2012).
Chu et al., "Inhibition of B cell receptor-mediated activation of primary human B cells by coengagement of CD19 and FcgammaRIIb with Fc-engineered antibodies," *Mol Immunol.*, 45(15):3926-33 (2008).
Chuntharapai et al., "Isotype-dependent inhibition of tumor growth in vivo by monoclonal antibodies to death receptor 4," *J Immunol.*, 166(8):4891-8 (2001).
Clark, "IgG effector mechanisms," *Chem Immunol.*, 65:88-110 (1997).
Couto et al., "Anti-BA46 Monoclonal Antibody Mc3: Humanization Using a Novel Positional Consensus and in Vivo and in Vitro Characterization," *Cancer Res.*, 55:1717-22 (1995).
Dall'Acqua et al., "Increasing the affinity of a human IgG1 for the neonatal Fc receptor: biological consequences," *J. Immunol.*, 169(9):5171-80 (2002).
Dall'Acqua et al., "Properties of human IgG1s engineered for enhanced binding to the neonatal Fc receptor (FcRn)," *J Biol Chem.*, 281(33):23514-24 (2006).
Dall'Acqua et al., "Antibody humanization by framework shuffling," *Methods*, 36(1):43-60 (2005).
Datta-Mannan et al., "Monoclonal antibody clearance. Impact of modulating the interaction of IgG with the neonatal Fc receptor," *J Biol Chem.*, Jan. 19, 2007;282(3):1709-17. Epub Nov. 29, 2006.
Devanaboyina et al., "The effect of pH dependence of antibody-antigen interactions on subcellular trafficking dynamics," *MAbs*, 5(6):851-9 (2013).
Dhodapkar et al., "Selective blockade of inhibitory Fcgamma receptor enables human dendritic cell maturation with IL-12p70 production and immunity to antibody-coated tumor cells," *Proc Natl Acad Sci USA*, 102(8):2910-5 (2005).
Duffau et al., "Platelet CD154 potentiates interferon-alpha secretion by plasmacytoid dendritic cells in systemic lupus erythematosus," *Sci Transl Med.*, 2(47):47ra63 (2010).
Ewert et al., "Stability improvement of antibodies for extracellular and intracellular applications: CDR grafting to stable frameworks and structure-based framework engineering," *Methods*, 34:184-199 (2004).
Feinberg et al., "Mechanism of pH-dependent N-acetylgalactosamine binding by a functional mimic of the hepatocyte asialoglycoprotein receptor," *J Biol Chem.*, 275(45):35176-84 (2000).
Finkelman et al., "Anti-cytokine antibodies as carrier proteins. Prolongation of in vivo effects of exogenous cytokines by injection of cytokine-anti-cytokine antibody complexes," *J Immunol.*, 151(3):1235-44 (1993).
Floto et al., "Loss of function of a lupus-associated FcgammaRIIb polymorphism through exclusion from lipid rafts," *Nat Med.*, 11(10):1056-8 (2005).
Fournier et al., "Activation of human peripheral IgM+ B cells is transiently inhibited by BCR-independent aggregation of Fc gammaRIIB," *J Immunol.*, 181(8):5350-9 (2008).
Ghetie et al., "FcRn: the MHC class I-related receptor that is more than an IgG transporter," *Immunol. Today*, 18:592-598 (1997).
Ghetie et al., "Increasing the serum persistence of an IgG fragment by random mutagenesis," *Nat. Biotechnol.*, 15(7):637-40 (1997).
Gobburu et al., "Pharmacokinetics/dynamics of 5c8, a monoclonal antibody to CD154 (CD40 ligand) suppression of an immune response in monkeys," *J. Pharmacol. Exp. Ther.*, 286:925-930 (1998).
Graves et al., "Molecular modeling and preclinical evaluation of the humanized NR-LU-13 antibody," *Clin. Cancer Res.*, 5:899-908 (1999).
Greenwood et al., "Structural motifs involved in human IgG antibody effector functions," *Eur J Immunol.*, 23(5):1098-104 (1993).
Hamilton, "Molecular engineering: applications to the clinical laboratory," *Clin. Chem.*, 39(9):1988-97 (1993).
Hanson et al., "Catalytic antibodies and their applications," Curr. Opin. Biotechnol., 16:631-636 (2005).
He et al., "Humanization and pharmacokinetics of a monoclonal antibody with specificity for both E- and P-selectin," *J. Immunol.*, 160:1029-35 (1998).
Heyman, "Feedback regulation by IgG antibodies," *Immunol Lett.*, 88(2):157-61 (2003).
Hinton et al., "An engineered human IgG1 antibody with longer serum half-life," *J. Immunol.*, 176(1):346-56 (2006).
Hinton et al., "Engineered human IgG antibodies with longer serum half-lives in primates," *J. Biol. Chem.*, 279(8):6213-6 (2004).
Hwang et al., "Use of human germline genes in a CDR homology-based approach to antibody humanization," *Methods*, 36:35-42 (2005).
Igawa et al., "Antibody recycling by engineered pH-dependent antigen binding improves the duration of antigen neutralization," *Nat Biotechnol.*, 28(11):1203-7 (2010).
Igawa et al., "Engineered monoclonal antibody with novel antigen-sweeping activity in vivo," *PLoS One*, 8(5):e63236 (2013).
Igawa et al., "Antibody optimization technologies for developing next generation antibody therapeutics," *Bio Industry*, 28(7):15-21 (2011) (with English translation).
Ishii et al., "FcRn, a critical regulator of antibody pharmacokinetics," *Folia Pharmacol. Jpn.*, 136(5):280-284 (2010) (with English translation).

(56) References Cited

OTHER PUBLICATIONS

Ito et al., "The His-probe method: effects of histidine residues introduced into the complementarity-determining regions of antibodies on antigen-antibody interactions at different pH values," *FEBS Lett.*, 309:85-88 (1992).

Jefferis et al., "Interaction sites on human IgG-Fc for FcgammaR: current Models," *Immunol Lett.*, 82(1-2):57-65 (2002).

Johnson et al., "Cation exchange-HPLC and mass spectrometry reveal C-terminal amidation of an IgG1 heavy chain," *Anal. Biochem.*, 360:75-83 (2007).

Jones et al., "Identification and removal of a promiscuous CD4+ T cell epitope from the C1 domain of factor VIII," *Thromb. Haemost.*, 3:991-1000 (2005).

Kashmiri et al., "Generation, characterization, and in vivo studies of humanized anticarcinoma antibody CC49," *Hybridoma*, 14:461-473 (1995).

Kim et al., "Antibody Engineering for the Development of Therapeutic Antibodies," Mol. Cells, 20:17-29 (2005).

Kohrt et al., "Stimulation of natural killer cells with a CD137-specific antibody enhances trastuzumab efficacy in xenotransplant models of breast cancer," *J Clin Invest.*, 122(3):1066-75 (2012).

Lee et al., "High-affinity human antibodies from phage-displayed synthetic Fab libraries with a single framework scaffold," *J Mol Biol.*, 340(5):1073-93 (2004).

Li et al., "Inhibitory Fcγ receptor engagement drives adjuvant and anti-tumor activities of agonistic CD40 antibodies," *Science*, 333(6045):1030-4 (2011).

Li et al., "CD72 down-modulates BCR-induced signal transduction and diminishes survival in primary mature B lymphocytes," *J Immunol.*, 176(9):5321-8 (2006).

Liang et al., "Immunity against a therapeutic xenoprotein/Fc construct delivered by gene transfer is reduced through binding to the inhibitory receptor FcγRIIb," *J Gene Med.*, 13(9):470-7 (2011).

Lobo et al., "Antibody pharmacokinetics and pharmacodynamics," *J. Pharm. Sci.*, 93:2645-68 (2004).

MacCallum et al., "Antibody-antigen interactions: contact analysis and binding site topography," *J. Mol. Biol.*, 262:732-45 (1996).

Mackay et al., "Selective dysregulation of the FcgammaIIB receptor on memory B cells in SLE," *J Exp Med.*, 203(9):2157-64 (2006).

Maini et al., "Double-blind randomized controlled clinical trial of the interleukin-6 receptor antagonist, tocilizumab, in European patients with rheumatoid arthritis who had an incomplete response to methotrexate," Arthritis Rheum., 54:2817-29 (2006).

Manger et al., "Fcgamma receptor IIa polymorphism in Caucasian patients with systemic lupus erythematosus: association with clinical symptoms," *Arthritis Rheum.*, 41(7):1181-9 (1998).

Meyer et al., "Bevacizumab immune complexes activate platelets and induce thrombosis in FCGR2A transgenic mice," *J Thromb Haemost.*, 7(1):171-81 (2009). Epub Oct. 30, 2008.

Mi et al., "Targeting the neonatal fc receptor for antigen delivery using engineered fc fragments," *J Immunol.*, 181(11):7550-61 (2008).

Morgan et al., "The N-terminal end of the CH2 domain of chimeric human IgG1 anti-HLA-DR is necessary for C1q, Fc gamma RI and Fc gamma RIII binding," *Immunology.*, 86(2):319-24 (1995).

Murtaugh et al., "A combinatorial histidine scanning library approach to engineer highly pH-dependent protein switches," *Protein Sci.*, 20(9):1619-31 doi:10.1002/pro 696 (2011).

Muta et al., "A 13-amino-acid motif in the cytoplasmic domain of Fc gamma RIIB modulates B-cell receptor signaling," *Nature*,368(6466):70-3 (1994).

Nakamura et al., "Fcgamma receptor IIB-deficient mice develop Goodpasture's syndrome upon immunization with type IV collagen: a novel murine model for autoimmune glomerular basement membrane disease," *J Exp Med.*, 191(5):899-906 (2000).

Nicholas et al., "Regulation of the immune response. I. Reduction in ability of specific antibody to inhibit long-lasting IgG immunological priming after removal of the Fc fragment," *J Exp Med.*, 129(6):1183-201 (1969).

Niebecker et al., "Safety of therapeutic monoclonal antibodies," *Curr Drug Saf.*, 5(4):275-86 (2010).

Nimmerjahn et al., "Fcgamma receptors as regulators of immune responses," *Nat Rev Immunol.*, 8(1):34-47 (2008).

Nishimoto et al., "Humanized anti-interleukin-6 receptor antibody treatment of multicentric Castleman disease," *Blood*, 106:2627-32 (2005).

Nishimoto et al., "Interleukin 6: from bench to bedside," *Nat. Clin. Pract. Rheumatol.*, 2:619-626 (2006).

Olferiev et al., "The role of activating protein 1 in the transcriptional regulation of the human FCGR2B promoter mediated by the -343 G -> C polymorphism associated with systemic lupus erythematosus," *J Biol Chem.*, 282(3):1738-46 (2007).

Onda et al., "Lowering the Isoelectric Point of the Fv Portion of Recombinant Immunotoxins Leads to Decreased Nonspecific Animal Toxicity without Affecting Antitumor Activity," *Cancer Res.*, 61:5070-77 (2001).

Pakula et al., "Genetic Analysis of Protein Stability and Function," *Annu. Rev. Genet.*, 23:289-310 (1989).

Pavlou et al., "The therapeutic antibodies market to 2008," *Eur. J. Pharm. Biopharm.*, 59:389-396 (2005).

Poduslo et al., "Polyamine modification increases the permeability of proteins at the blood-nerve and blood-brain barriers," *J. Neurochem.*, 66:1599-1609 (1996).

Qiao et al., "Dependence of antibody-mediated presentation of antigen on FcRn," *Proc Natl Acad Sci USA*, 105(27):9337-42 (2008).

Radaev et al., "The role of Fc glycosylation and the binding of peptide inhibitors," *J Biol Chem.*, 276(19):16478-83 (2001).

Rajpal et al., A general method for greatly improving the affinity of antibodies by using combinatorial libraries, *Proc. Natl. Acad. Sci. USA*, 102:8466-71 (2005).

Rathanaswami et al., "Demonstration of an in vivo generated sub-picomolar affinity fully human monoclonal antibody to interleukin-8," *Biochem. Biophys. Res. Commun.*, 334:1004-13 (2005).

Ravetch et al., "Immune inhibitory receptors," *Science*, 290(5489):84-9 (2000).

Reichert et al., "Monoclonal antibody successes in the clinic," *Nat. Biotechnol.*, 23:1073-78 (2005).

Rich et al., "Grading the commercial optical biosensor literature—Class of 2008: 'The Mighty Binders'," *J. Mol. Recognit.*, 23(1):1-64 (2010). doi: 10.1002/jmr.1004.

Richards et al., "Optimization of antibody binding to FcgammaRIIa enhances macrophage phagocytosis of tumor cells," *Mol Cancer Ther.*, 7(8):2517-27 (2008).

Robles-Carrillo et al., "Anti-CD40L immune complexes potently activate platelets in vitro and cause thrombosis in FCGR2A transgenic mice," *J Immunol.*, 185(3):1577-83 (2010).

Roitt et al., Immunology, M., Mir, (2000), pp. 110-111 (in Russian, with what is believed to be a published English equivalent of those pages taken from Roitt et al., "Antibody Structure and Function," Immunology, Fifth Ed., (1998), pp. 80-81).

Rothe et al., "Ribosome display for improved biotherapeutic molecules," *Expert Opin. Biol. Ther.*, 6:177-187 (2006).

Salfeld et al., "Isotype selection in antibody engineering," *Nat. Biotechnol.*, 25:1369-72 (2007).

Salmon et al., "Fc gamma RIIA alleles are heritable risk factors for lupus nephritis in African Americans," *J Clin Invest.*, 97(5):1348-54 (1996).

Sarkar et al., Rational cytokine design for increased lifetime and enhanced potency using pH-activated "histidine switching," *Nat Biotechnol.*, 20(9):908-13 (2002).

Sato et al., "Reshaping a human antibody to inhibit the interleukin 6-dependent tumor cell growth," *Cancer Res.*, 53:851-856 (1993).

Scappaticci et al., "Arterial thromboembolic events in patients with metastatic carcinoma treated with chemotherapy and bevacizumab," *J Natl Cancer Inst.*, 99(16):1232-9 (2007).

Shields et al., "High resolution mapping of the binding site on human IgG1 for Fc gamma RI, Fc gamma RII, Fc gamma RIII, and FcRn and design of IgG1 variants with improved binding to the Fc gamma R," *J. Biol. Chem.*, 276:6591-6604 (2001) (Epub Nov. 28, 2000).

Shire et al., "Challenges in the development of high protein concentration formulations," *J. Pharm. Sci.*, 93:1390-1402 (2004).

(56) References Cited

OTHER PUBLICATIONS

Sigma-Aldrich, "Product Information: Monoclonal Anti-Flag ® M1, Clone M1 produced in mouse, purified immunoglobulin," Sigma-Aldrich.com, Catalog No. F3040. Retrieved from the Internet on Nov. 5, 2013 at: http://www.sigmaaldrich.com/content/dam/sigma-aldrich/does/Sigma/Datasheet/f3040dat.pdf.
Smith et al., "FcgammaRIIB in autoimmunity and infection: evolutionary and therapeutic implications," *Nat Rev Immunol.*, 10(5):328-43 (2010).
Stewart et al., "Site-directed mutagenesis of a catalytic antibody: an arginine and a histidine residue play key roles," *Biochemistry*, 33(8):1994-2003 (1994).
Strand et al., "Biologic therapies in rheumatology: lessons learned, future directions," *Nat. Rev. Drug Discov.*, 6:75-92 (2007).
Su et al., Expression profile of FcgammaRIIb on leukocytes and its dysregulation in systemic lupus erythematosus, *J Immunol.*, 178(5):3272-80 (2007).
Suzuki et al., "Importance of neonatal FcR in regulating the serum half-life of therapeutic proteins containing the Fc domain of human IgG1: a comparative study of the affinity of monoclonal antibodies and Fc-fusion proteins to human neonatal FcR," *J. Immunol.*, 184(4):1968-76 (2010).
Tabrizi et al., "Elimination mechanisms of therapeutic monoclonal antibodies," *Drug Discov Today*, 11(1-2):81-8 (2006).
Tsurushita et al., "Design of humanized antibodies: From anti-Tac to Zenapax," *Methods*, 36:69-83 (2005).
Vaughn et al., "Structural basis of pH-dependent antibody binding by the neonatal Fc receptor," *Structure*, 6(1):63-73 (1998).
Veri et al., "Therapeutic control of B cell activation via recruitment of Fcgamma receptor IIb (CD32B) inhibitory function with a novel bispecific antibody scaffold," *Arthritis Rheum.*, 62(7):1933-43 (2010).
Veri et al., "Monoclonal antibodies capable of discriminating the human inhibitory Fcgamma-receptor IIB (CD32B) from the activating Fcgamma-receptor IIA (CD32A): biochemical, biological and functional characterization," *Immunology*, 121(3):392-404 (2007).
Warmerdam et al., Molecular basis for a polymorphism of human Fc gamma receptor II (CD32), *J Exp Med.*, 172(1):19-25 (1990).
Wernersson et al., "IgG-mediated enhancement of antibody responses is low in Fc receptor gamma chain-deficient mice and increased in Fc gamma RII-deficient mice," *J Immunol.*, 163(2):618-22 (1999).
Wilson et al., "An Fcγ receptor-dependent mechanism drives antibody-mediated target-receptor signaling in cancer cells," *Cancer Cell*, 19(1):101-13 (2011).
Wojciak et al., "The crystal structure of sphingosine-1-phosphate in complex with a Fab fragment reveals metal bridging of an antibody and its antigen," *Proc Natl Acad Sci U S A.*, 106(42):17717-22 (2009).
Wu et al., "Development of motavizumab, an ultra-potent antibody for the prevention of respiratory syncytial virus infection in the upper and lower respiratory tract," *J. Mol. Biol.*, 368:652-665 (2007).
Xiang et al., "Study of B72.3 combining sites by molecular modeling and site-directed mutagenesis," *Protein Eng.*, 13(5):339-44 (2000).
Xu et al., "Fc gamma Rs modulate cytotoxicity of anti-Fas antibodies: implications for agonistic antibody-based therapeutics," *J Immunol.*, 171(2):562-8 (2003).
Yamamoto et al., "Molecular studies of pH-dependent ligand interactions with the low-density lipoprotein receptor," *Biochemistry*, 47(44):11647-52 (2008).
Yamasaki et al., "Pharmacokinetic analysis of in vivo disposition of succinylated proteins targeted to liver nonparenchymal cells via scavenger receptors: importance of molecular size and negative charge density for in vivo recognition by receptors," *J. Pharmacol. Exp. Ther.*, 301:467-477 (2002).
Yang et al., "CDR walking mutagenesis for the affinity maturation of a potent human anti-HIV-1 antibody into the picomolar range," *J. Mol. Biol.*, 254(3):392-403 (1995).

Yeung et al., "Engineering human IgG1 affinity to human neonatal Fc receptor: impact of affinity improvement on pharmacokinetics in primates," *J. Immunol.*, 182(12):7663-71 (2009).
Yuasa et al., "Deletion of fcgamma receptor IIB renders H-2(b) mice susceptible to collagen-induced arthritis," *J Exp Med.*, 189(1):187-94 (1999).
Zalevsky et al., "Enhanced antibody half-life improves in vivo activity," *Nat. Biotechnol.*, 28(2):157-9 (2010).
Zhang et al., "Effective therapy for a murine model of human anaplastic large-cell lymphoma with the anti-CD30 monoclonal antibody, HeFi-1,does not require activating Fc receptors," *Blood*, 108(2):705-10 (2006).
Zhou et al., "Interfacial metal and antibody recognition," *Proc Natl Acad Sci U S A.*, 102(41):14575-80 (2005).
Zhu et al., "MHC class I-related neonatal Fc receptor for IgG is functionally expressed in monocytes, intestinal macrophages, and dendritic cells," *J. Immunol.*, 166(5):3266-76 (2001).
Zuckier et al., "Chimeric human-mouse IgG antibodies with shuffled constant region exons demonstrate that multiple domains contribute to in vivo half-life," *Cancer Res.*, 58:3905-08 (1998).
International Search Report for App. Ser. No. PCT/JP2011/001888, dated Nov. 2, 2011, 7 pages.
International Preliminary Report on Patentability for App. Ser. No. PCT/JP2012/058603, dated Oct. 8, 2013, 11 pages.
International Search Report for App. Ser. No. PCT/JP2012/058603, dated May 29, 2012, 2 pages.
International Search Report for App. Ser. No. PCT/JP2011/077619, dated Feb. 28, 2012, 4 pages.
International Preliminary Report on Patentability for App. Ser. No. PCT/JP2011/077619, dated Jun. 4, 2013, 8 pages.
International Search Report for App. Ser. No. PCT/JP2012/006218, dated Mar. 26, 2013, 11 pages.
International Search Report for App. Ser. No. PCT/JP2012/075083, dated Oct. 23, 2012, 2 pages.
Amersham Biosciences, "Antibody Purification Handbook," Edition 18-1037-46 [online], [retrieved on Nov. 5, 2015]. Retrieved from the Internet: http://www.promix.ru/manuf/ge/chrom/lit/Antibody_Purification.pdf.
Batra et al., "Pharmacokinetics and biodistribution of genetically engineered antibodies," *Curr Opin Biotechnol.*, Dec. 2002;13(6):603-8.
Burmeister et al., "Crystal structure of the complex of rat neonatal Fc receptor with Fc," *Nature*, Nov. 24, 1994;372(6504):379-83.
GE Healthcare. Application note 28-9277-92 AA. "High-throughput screening of elution pH for monoclonal antibodies on MabSelect SuRe using PreDictor plates" [online], [retrieved on Nov. 5, 2015]. Retrieved from the Internet: https://www.gelifesciences.com/gehcls_images/GELS/Related%20Content/Files/1314787424814/litdoc28927792AA_20110831131840.pdf.
Mimoto et al., "Engineered antibody Fc variant with selectively enhanced FcγRIIb binding over both FcγRIIa(R131) and FcγRIIa(H131)," *Protein Eng Des Sel.*, Oct. 2013;26(10):589-98. doi: 10.1093/protein/gzt022. Epub Jun. 5, 2013.
Palladino et al., "Anti-TNF-alpha therapies: the next generation," *Nat Rev Drug Discov.*, Sep. 2003;2(9):736-46.
Radaev et al., "The structure of a human type III Fcgamma receptor in complex with Fc," *J Biol Chem.*, May 11, 2001;276(19):16469-77. Epub Jan. 31, 2001.
Sondermann et al., "The 3.2-A crystal structure of the human IgG1 Fc fragment-Fc gammaRIII complex," *Nature*, Jul. 20, 2000;406(6793):267-73.
USPTO Final Office Action in U.S. Appl. No. 14/347,034, dated Oct. 16, 2015, 5 pages.
Fish & Richardson P.C., Reply to Final Office Action dated Oct. 16, 2015 in U.S. Appl. No. 14/347,034, filed Jan. 13, 2016, 28 pages.
Fish & Richardson P.C., Reply to Office Action dated Aug. 3, 2015 in U.S. Appl. No. 13/595,139, filed Dec. 2, 2015, 28 pages.
Fish & Richardson P.C., Reply to Final Office Action dated Aug. 4, 2015 in U.S. Appl. No. 13/889,484, filed Dec. 2, 2015, 104 pages.
International Search Report for App. Ser. No. PCT/JP2014/059706, dated Jul. 15, 2014, 4 pages.
International Preliminary Report on Patentability for App. Ser. No. PCT/JP2014/059706, dated Oct. 6, 2015, 10 pages.

(56) References Cited

OTHER PUBLICATIONS

Balint et al., "Antibody engineering by parsimonious mutagenesis," *Gene.*, Dec. 27, 1993;137(1):109-18.
Bruhns, "Properties of mouse and human IgG receptors and their contribution to disease models," *Blood*, Jun. 14, 2012;119(24):5640-9. doi: 10.1182/blood-2012-01-380121. Epub Apr. 25, 2012.
Hjelm et al., "Antibody-mediated regulation of the immune response," *Scand J Immunol.*, Sep. 2006;64(3):177-84.
Idusogie et al., "Mapping of the C1q binding site on rituxan, a chimeric antibody with a human IgG1 Fc," *J Immunol.*, Apr. 15, 2000;164(8):4178-84.
Kamei et al., "Quantitative methods for developing Fc mutants with extended half-lives," *Biotechnol Bioeng.*, Dec. 20, 2005;92(6):748-60.
USPTO Notice of Allowance in U.S. Appl. No. 14/347,034, dated Feb. 17, 2016, 6 pages.
USPTO Final Office Action in U.S. Appl. No. 13/595,139, dated Feb. 12, 2016, 12 pages.
Biasini et al., "Immunopurification of pathological prion protein aggregates," *PLoS One*, Nov. 12, 2009;4(11):e7816. doi: 10.1371/journal.pone.0007816.
Brown et al., "A study of the interactions between an IgG-binding domain based on the B domain of staphylococcal protein A and rabbit IgG," *Mol Biotechnol.*, Aug. 1998;10(1):9-16.
Chen et al., "Selection and analysis of an optimized anti-VEGF antibody: crystal structure of an affinity-matured Fab in complex with antigen," *J Mol Biol.*, Nov. 5, 1999;293(4):865-81.
Coloma et al., "Position effects of variable region carbohydrate on the affinity and in vivo behavior of an anti-(1-->6) dextran antibody," *J Immunol.*, Feb. 15, 1999;162(4):2162-70.
Declaration of Nimish Gera, Ph.D., CV and Exhibits, dated Sep. 1, 2016, 24 pages.
Hird et al., "Tumour localisation with a radioactively labelled reshaped human monoclonal antibody," *Br J Cancer*, Nov. 1991;64(5):911-4.
Hong et al., "Enhanced cellular uptake and transport of polyclonal immunoglobulin G and fab after their cationization," *J Drug Target.*, 2000;8(2):67-77.
Junghans et al., "The protection receptor for IgG catabolism is the beta2-microglobulin-containing neonatal intestinal transport receptor," *Proc Natl Acad Sci U S A.*, May 28, 1996;93(11):5512-6.
Laitinen et al., "Brave new (strept)avidins in biotechnology," *Trends Biotechnol.*, Jun. 2007;25(6):269-77. Epub Apr. 12, 2007.
Li et al., "Construction and characterization of a humanized anti-human CD3 monoclonal antibody 12F6 with effective immunoregulation functions," *Immunology*, Dec. 2005;116(4):487-98.
Linder et al., "Design of a pH-dependent cellulose-binding domain," *FEBS Lett.*, Mar. 19, 1999;447(1):13-6.
Marshall et al., "Rational design and engineering of therapeutic proteins," *Drug Discov Today.*, Mar. 1, 2003;8(5):212-21.
Pardridge et al., "Enhanced cellular uptake and in vivo biodistribution of a monoclonal antibody following cationization," *J Pharm Sci.*, Aug. 1995;84(8):943-8.
Reimann et al., "A humanized form of a CD4-specific monoclonal antibody exhibits decreased antigenicity and prolonged plasma half-life in rhesus monkeys while retaining its unique biological and antiviral properties," *AIDS Res Hum Retroviruses*, Jul. 20, 1997;13(11):933-43.
Schroeder et al., "Similarity and divergence in the development and expression of the mouse and human antibody repertoires," *Dev Comp Immunol.*, 2006;30(1-2):119-35.
Sharifi et al., "Improving monoclonal antibody pharmacokinetics via chemical modification," *Q J Nucl Med.*, Dec. 1998;42(4):242-9.
Verhoeyen et al., "Construction of a reshaped HMFG1 antibody and comparison of its fine specificity with that of the parent mouse antibody," *Immunology*, Mar. 1993;78(3):364-70.
Verhoeyen et al., "Monoclonal Antibodies in Clinical Oncology," 1991, Edited by AA Epenetos, Chapter 5, pp. 37-43, Chapman and Hall.

USPTO Non-Final Office Action in U.S. Appl. No. 13/595,139, dated Nov. 23, 2016, 11 pages.
USPTO Advisory Action in U.S. Appl. No. 13/889,484, dated Jan. 7, 2016, 3 pages.
USPTO Non-Final Office Action in U.S. Appl. No. 13/889,484, dated Nov. 25, 2016, 12 pages.
USPTO Restriction Requirement in U.S. Appl. No. 14/361,013, dated Mar. 16, 2016, 15 pages.
Fish & Richardson P.C., Response to Restriction Requirement dated Mar. 16, 2016 in U.S. Appl. No. 14/361,013, filed Aug. 1, 2016, 21 pages.
USPTO Non-Final Office Action in U.S. Appl. No. 14/361,013, dated Oct. 28, 2016, 33 pages.
Nordlund et al., "Introduction of histidine residues into avidin subunit interfaces allows pH-dependent regulation of quaternary structure and biotin binding," *FEBS Lett.*, Dec. 18, 2003;555(3):449-54.
Stearns et al., "The interaction of a Ca2+-dependent monoclonal antibody with the protein C activation peptide region. Evidence for obligatory Ca2+ binding to both antigen and antibody," *J Biol Chem.*, Jan. 15, 1988;263(2):826-32.
Ward et al., "A calcium-binding monoclonal antibody that recognizes a non-calcium-binding epitope in the short consensus repeat units (SCRs) of complement C1r," *Mol Immunol.*, Jan. 1992;29(1):83-93.
USPTO Restriction Requirement in U.S. Appl. No. 14/347,034, dated Dec. 18, 2014, 9 pages.
Fish & Richardson P.C., Reply to Restriction Requirement dated Dec. 18, 2014 in U.S. Appl. No. 14/347,034, filed Mar. 18, 2015, 2 pages.
USPTO Non-Final Office Action in U.S. Appl. No. 14/347,034, dated Apr. 16, 2015, 9 pages.
Igawa et al., "Reduced elimination of IgG antibodies by engineering the variable region," *Protein Eng Des Sel.*, 23(5):385-92 (2010).
Sims et al., "HMGB1 and RAGE in inflammation and cancer," *Annu Rev Immunol.*, 28:367-88 (2010).
Wang et al., "HMG-1 as a late mediator of endotoxin lethality in mice," *Science*, 285(5425):248-51 (1999).
Fiedler et al., "An engineered IN-1 Fab fragment with improved affinity for the Nogo-A axonal growth inhibitor permits immunochemical detection and shows enhanced neutralizing activity," Protein Eng. Nov. 1, 2002: 15(11):931-41.
Foote et al., "Antibody framework residues affecting the conformation of the hypervariable loops," J. Mol. Biol., Mar. 20, 1992; 224(2):487-99.
Gera et al., "Design of pH Sensitive Binding Proteins from the Hyperthermophilic Sso7d Scaffold," PLoS One, 2012;7(11):e48928. doi: 10.1371/journal.pone.0048928. Epub Nov. 7, 2012.
Goode et al., "The glomerular basement membrane charge-selectivity barrier: an oversimplified concept?" Nephrology Dialysis Transplantation. Sep. 1, 1996; 11(9):1714-6.
Hoogenboom, "Selecting and screening recombinant antibody libraries," Nat. Biotechnol., Sep. 1, 2005; 23(9):1105-16.
Janeway et al., Immunobioiogy, 5th edition. Jun. 1, 2001. Excerpt from Chapter 3.
Janeway et al., Immunobioiogy, 5th edition. Jun. 1, 2001. Excerpt from Chapter 4.
Knappik et al., "Fully Synthetic Human Combinatorial Antibody Libraries (HuCAL) Based on Modular Consensus Frameworks and CDRs Randomized with Trinucleotides," J. Mol. Biol., Feb. 11, 2000; 296(1):57-86.
Muller et al., "VEGF and the Fab fragment of a humanized neutralizing antibody: crystal structure of the complex at 2.4 Å resolution and mutational analysis of the interface," Structure, Sep. 6, 1998; (9):1153-67.
Murata et al., "Anti-Digoxin Fab Variants Generated by Phage Display," Mol. Biotechnol. Jun. 1, 2013:54 (2) :269-77. doi: 10.1007/s12033-012-9564-1.
Ober et al., "Visualizing the Site and Dynamics of IgG Salvage by the MHC Class I-Related Receptor, FcRn," J. Immunol. Feb. 15, 2004; 172(4):2021-9.

(56) References Cited

OTHER PUBLICATIONS

Osbourn et al., "Generation of a panel of related human scFv antibodies with high affinities for human CEA," Immunotechnology Sep. 1, 1996: 2(3):181-96.

Pancook et al., "In Vitro Affinity Maturation of Human IgM Antibodies Reactive with Tumor-Associated Antigens," Hybrid Hybridomics. Oct. 1, 2001: 20(5-6):383-96.

Papista et al., "Dysfunctions of the IgA system: a common link between intestinal and renal diseases," Cell. Mol. Immunol. Mar. 2011: 8(2):126-34. doi:10.1038/cmi.2010.69. Epub Jan. 31, 2011.

Pejchal et al., "A Conformational Switch in Human Immunodeficiency Virus gp41 Revealed by the Structures of Overlapping Epitopes Recognized by Neutralizing Antibodies," J. Virol. Sep. 2009; 83(17):8451-62. doi:10.1128/ JVI. 00685-09. Epub Jun. 10, 2009.

Ramos et al., "Evaluation of CA-125 and soluble CD-23 in patients with pelvic endometriosis: a case-control study," Rev. Assoc. Med. Bras. (1992). Jan.-Feb. 2012; 58(1):26-32.

Raposo et al., "Epitope-specific antibody response is controlled by immunoglobulin Vh polymorphisms," J. Exp. Med. Mar. 10, 2014: 211(3):405-11.doi:10.1084/jem.20130968. Epub Feb. 17, 2014.

Schier et al., "Isolation of Picomolar Affinity Anti-c-erbB-2 Single-chain Fv by Molecular Evolution of the Complementarity Determining Regions in the Center of the Antibody Binding Site," J. Mol. Biol. Nov. 8, 1996: 263(4):551-67.

Vidarsson et al., "IgG subclasses and allotypes: from structure to effector functions," Front. Immunol. Oct. 20, 2014; 5:520. doi: 10.3389/fimmu.2014.00520.

Wolf et al., "BiTEs: bispecific antibody constructs with unique anti-tumor activity," Drug Discov. Today. Sep. 15, 2005; 10(18):1237-44.

Wu et al., "Stepwise in vitro affinity maturation of Vitaxin, an $\alpha v \beta 33$-specific humanized mAb," Proc. Natl. Acad. Sci. USA. May 26, 1998; 95(11):6037-42.

Xolair (omalizumab) Prescribing Information, https://www.gene.com/download/pdf/xolair_prescribing.pdf, Jul. 6, 2016, 27 pages.

Yu et al., "Interaction between Bevacizumab and Murine VEGF-A: A Reassessment," Invest Ophthalmol. Vis. Sci. Feb. 1, 2008; 49(2):522-7. doi: 10.1167/iovs.07-1175.

USPTO Non-Final Office Action in U.S. Appl. No. 14/347,034, dated May 25, 2017, 16 pages.

USPTO Final Office Action in U.S. Appl. No. 13/595,139, dated May 30, 2017, 23 pages.

USPTO Restriction Requirement in U.S. Appl. No. 14/347,321, dated Dec. 17, 2015, 10 pages.

USPTO Non-Final Office Action in U.S. Appl. No. 14/347,321, dated May 2, 2016, 34 pages.

USPTO Final Office Action in U.S. Appl. No. 14/347,321 dated Jan. 9, 2017, 60 pages.

USPTO Reply to Non-Final Office Action in U.S. Appl. No. 13/889,484, dated May 25, 2017, 16 pages.

USPTO Final Office Action in U.S. Appl. No. 13/889,484, dated Aug. 16, 2017, 14 pages.

USPTO Restriction Requirement in U.S. Appl. No. 14/347,448, dated Dec. 21, 2015, 8 pages.

USPTO Office Action in U.S. Appl. No. 14/347,448, dated May 26, 2016, 54 pages.

USPTO Final Office Action in U.S. Appl. No. 14/347,448, dated Feb. 21, 2017, 45 pages.

USPTO Interview Summary in U.S. Appl. No. 14/347,448, dated Aug. 16, 2017, 4 pages.

Fish & Richardson P.C., USPTO Response Non-Final Office Action in U.S. Appl. No. 14/361,013, dated Apr. 26, 2017, 117 pages.

USPTO Final Office Action in U.S. Appl. No. 14/361,013, dated Jul. 24, 2017, 43 pages.

Non-Final Office Action for U.S. Appl. No. 15/230,904, dated May 25, 2017, 9 pages.

Restriction Requirement in U.S. Appl. No. 14/402,574, dated Feb. 11, 2016, 10 pages.

USPTO Office Action in U.S. Appl. No. 14/402,574, dated May 6, 2016, 26 pages.

USPTO Final Office Action in U.S. Appl. No. 14/402,574, dated Oct. 31, 2016, 16 pages.

USPTO Advisory Action in U.S. Appl. No. 14/402,574, dated Feb. 16, 2017, 3 pages.

USPTO Restriction Requirement in U.S. Appl. No. 14/404,051, dated Apr. 4, 2016, 13 pages.

USPTO Non-Final Office Action in U.S. Appl. No. 14/404,051, dated Dec. 6, 2016, 22 pages.

USPTO Restriction Requirement in U.S. Appl. No. 15/015,287, dated Mar. 13, 2017, 18 pages.

U.S. Appl. No. 13/990,158, Igawa et al., filed Mar. 28, 2014.
U.S. Appl. No. 14/377,556, Igawa et al., filed Aug. 8, 2014.
U.S. Appl. No. 14/423,269, Igawa et al., filed Feb. 23, 2015.
U.S. Appl. No. 14/781,069, Igawa et al., filed Sep. 29, 2015.

Yarilin, Fundamentals of Immunology. M: Medicina, 1999, pp. 169-172, 354-8 (with English translation).

U.S. Appl. No. 14/741,786, Igawa et al., filed Jun. 17, 2015.
U.S. Appl. No. 12/936,587, Igawa et al., filed Jan. 3, 2011.
U.S. Appl. No. 13/889,484, Igawa et al., filed May 8, 2013.
U.S. Appl. No. 13/889,512, Igawa et al., filed May 8, 2013.
U.S. Appl. No. 14/361,031, Igawa et al., filed May 28, 2014.
U.S. Appl. No. 15/495,026, filed Apr. 24, 2017, Igawa et al.
U.S. Appl. No. 15/725,692, filed Oct. 5, 2017, Igawa et al.
U.S. Appl. No. 15/952,945, filed Apr. 13, 2018, Igawa et al.
U.S. Appl. No. 15/952,951, filed Apr. 13, 2018, Igawa et al.
U.S. Appl. No. 15/977,757, filed May 11, 2018, Igawa et al.
U.S. Appl. No. 15/988,348, filed May 24, 2018, Igawa et al.
U.S. Appl. No. 16/028,140, filed Jul. 5, 2018, Igawa et al.
U.S. Appl. No. 61/313,102, filed Mar. 11, 2010, Pons.

Akbarzadeh-Sharbaf et al., "In silico design, construction and cloning of Trastuzumab humanized monoclonal antibody: A possible biosimilar for Herceptin," Adv Biomed Res, Jan.-Mar. 2012, 1(1):1-6. doi: 10. 4103/ 2277-9175. 98122. Epub Jul. 6, 2012.

Alignment of constant region sequences from WO 2009/125825 (document submitted in EP opposition and posted by EPO on Feb. 2, 2018); 1 page.

Alignment of the amino acid sequences of the Fc regions of antibodies exemplified in EP 2275443 (document submitted in EP opposition and posted by EPO on Feb. 2, 2018); 1 page.

Alignment of variable heavy and light chain amino acid sequences from WO 2009/125825 (document submitted in EP opposition and posted by EPO on Feb. 2, 2018); 2 pages.

Atherton et al., "Acid-base balance: maintenance of plasma pH," Anaesthesia & Intensive Care Medicine, 2009, 10(11):557-61 (abstract).

Chen et al., "Enhancement and destruction of antibody function by somatic mutation: unequal occurrence is controlled by V gene combinatorial associations," EMBO J, Jun. 15, 1995, 14(12):2784-94.

Claims as granted for Publication No. EP 2275443, dated Jan. 19, 2011 (document submitted in EP opposition); 6 pages.

Datta-Mannan et al., "Humanized IgG1 Variants with Differential Binding Properties to the Neonatal Fc Receptor: Relationship to Pharmacokinetics in Mice and Primates," Drug Metab Dispos, Jan. 2007, 35(1):86-94. Epub Oct. 18, 2006.

Davydov, "Omalizuman (Xolair) for Treatment of Asthma," Am Fam Physician, Jan. 2005, 15:71(2):341-2.

Declaration of Nimish Gera, Ph.D., CV and Exhibits, Sep. 1, 2016 (submitted in the matter of EP 2275443, Opposition thereto by Alexion Pharmaceuticals, Inc.); 24 pages.

De Felice et al., "Formation of amyloid aggregates from human lysozyme and its disease-associated variants using hydrostatic pressure," FASEB J, Jul. 2004, 18(10):1099-101. (doi:10.1096/fj.03-1072fje; PMID 15155566).

EMA product information: Annexes to file of the tocilizumab preparation RoActemra (WC500054890), published Jan. 8, 2010, 109 pages.

EPO Register Extract EP 1915397 (document submitted in EP opposition and posted by EPO on Feb. 2, 2018); 4 pages.

Experimental data characterizing the binding of rituximab to its antigen CD20 and to human FcRn (document submitted in EP opposition and posted by EPO on Feb. 5, 2018); 6 pages.

(56) References Cited

OTHER PUBLICATIONS

Experimental information regarding off-rate of Xolair Fab for binding to human IgE at pH7.4 and pH5.5 (document submitted in EP opposition and posted by EPO on Feb. 2, 2018); 3 pages.
Expert Declaration by Dr. Madhusudan Natarajan, submitted in EP opposition regarding EP 2552955 and posted by EPO on Feb. 5, 2018; 4 pages.
Fillipovic, Biochemical basis of human life activity. VLADOS, 2005:38-43 (with English translation).
Glick et al., Molecular Biotechnology: Principles and Applications of Recombinant DNA, 3rd Edition, Chemical Industry Press, Mar. 2005, p. 168 (with English Translation).
Goebl et al., "Neonatal Fc Receptor Mediates Internalization of Fc Transfected Human Endothelial Cells," Molecular Biology of the Cell, Dec. 2008, 19(12):5490-5505.
Gurbaxani et al., "Analysis of a family of antibodies with different half-lives in mice fails to find a correlation between affinity for FcRn and serum half-life," Mol Immunol, Mar. 2006, 43(9):1462-73. Epub Sep. 1, 2005.
Hamers-Casterman et al., "Naturally occurring antibodies devoid of light chains," Nature, Jun. 3, 1993, 363(6428):446-8.
Hotzel et al., "A strategy for risk mitigation of antibodies with fast clearance," mAbs, Nov.-Dec. 2012, 4(6):753-60. doi: 10.4161/mabs.22189.
Hu et al., "Combinatorial libraries against libraries for selecting neoepitope activation-specific antibodies," Proc. Natl. Acad. Sci. USA, Apr. 2010, 107(14):6252-57.
Irani et al., Mol Immunol, Oct. 2015, 67(2 Pt A):171-82. doi: 10.1016/j.molimm.2015.03.255. Epub Apr. 18, 2015.
King, Applications and Engineering of Monoclonal Antibodies, 1998:68-71.
Kuroda et al., "Computer-aided antibody design," Protein Eng Des Sel, Oct. 2012, 25(10):507-21. Epub Jun. 2, 2012.
Kussie et al., "A single engineered amino acid substitution changes antibody fine specificity," J Immunol, Jan. 1, 1994, 152(1):146-52.
Maxwell et al., "Crystal structure of the human leukocyte Fc receptor, FcγRIIa," Nat Struct Biol., May 1999, 6(5):437-42.
Merchant et al., "An efficient route to human bispecific IgG," Nat Biotechnol, Jul. 1998, 16:677-681.
Molina et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Res, Jun. 15, 2001, 61(12):4744-9.
O'Donovan et al., "EGFR and HER-2 Antagonists in Breast Cancer," Anticancer Res, May-Jun. 2007, 27(3A):1285-94.
Official Action dated Oct. 13, 2016, issued for EP Application No. 11714860.1 and submitted as evidence during EP opposition; 3 pages.
Presta, "Molecular engineering and design of therapeutic antibodies," Curr Opin Immunol, Aug. 2008, 20(4):460-70. doi : 10.1016/j.coi.2008.06.012.
Presta at el., "Humanization of an Anti-Vascular Endothelial Growth Factor Monoclonal Antibody for the Therapy of Solid Tumors and Other Disorders," Cancer Res, Oct. 15, 1997, 57(20):4593-9.
Product labelling information for Rituxan (Rituximab), dated Nov. 1997, 2 pages.
Raghavan et al., "Analysis of the pH Dependence of the Neonatal Fc Receptor/Immunoglobulin G Interaction Using Antibody and Receptor Variants," Biochemistry, Nov. 14, 1995, 34(45):14649-5.
Ryman et al., "Pharmacokinetics of Monoclonal Antibodies," CPT Pharmacometrics Syst Pharmacol, Sep. 2017, 6(9):576-588. doi: 10.1002/psp4.12224. Epub Jul. 29, 2017.
Sondermann et al., "Molecular Basis for Immune Complex Recognition: A Comparison of Fc-Receptor Structures," J Mol Biol. Jun. 8, 2001;309(3):737-49.
Sondermann et al., "Crystal structure of the soluble form of the human Fcγ-receptor IIb: a new member of the immunoglobulin superfamily at 1.7 A resolution," EMBO J Journal, Mar. 1, 1999, 18(5):1095-103.
Stepanov, Chapter 4, Primary Structure of Protein, 4.1 Primary structure as a level of protein organization, Molecular biology. Structure and functions of proteins. M.: Nauka, 2005:61-62.
Summary of information about antibodies in Examples of patent (document submitted in EP opposition and posted by EPO on Apr. 13, 2018); 3 pages.
Supplementary data provided by opponent for EP Application No. 11714860.1 (document submitted in EP opposition and posted by EPO on Feb. 20, 2018); 3 pages.
Tanabe et al., "Characterization of the Monoclonal Antibodies Against Human Protein C Specific for Calcium Ion-induced Conformers," Japanese Journal of Thrombosis and Hemostasis, 1992, 3(1):29-35.
Tanzi et al., "Twenty years of the Alzheimer's disease amyloid hypothesis: a genetic perspective," Cell, Feb. 2005, 120(4):545-55. (doi:10.1016/j.cell.2005.02.008; PMID 15734686).
Vaccaro et al., "Divergent activities of an engineered antibody in murine and human systems have implications for therapeutic antibodies," Proc Natl Acad Sci USA, Dec. 5, 2006, 103(49):18709-14. Epub Nov. 20, 2006.
Waelbroeck et al., "The pH Dependence of Insulin Binding," J Biol Chem, Jul. 25, 1982, 257(14):8284-91.
Ward et al., "Evidence to support the cellular mechanism involved in serum IgG homeostasis in humans," Int Immunol, Feb. 2003, 15(2):187-95.
Welch et al., "Adalimumab (Humira) for the Treatment of Rheumatoid Arthritis" Am Fam Physician, Dec. 15, 2008, 78(12):1406-1408.
Written Submissions by Opponent 1 (Alexion Pharmaceuticals, Inc.) in Opposition of EP 2006381 dated Apr. 13, 2018, 19 pages.
Written Submissions by Opponent 2 (Novo Nordisk A/S) in Opposition of EP 2006381 dated Apr. 13, 2018, 14 pages.
Written Submissions by Opponent 3 (name Unknown) in Opposition of EP 2006381 dated Apr. 13, 2018, 16 pages.
Wu et al., "Ultra-potent Antibodies Against Respiratory Syncytial Virus: Effects of Binding Kinetics and Binding Valence on Viral Neutralization," J Mol Biol, 2005, 350:126-144.
Yang et al., "Dataset of the binding kinetic rate constants of anti-PCSK9 antibodies obtained using the Biacore T100, Protean XPR36, Octet RED384, and IBIS MX96 biosensor platforms," Data Brief, Jul. 27, 2016, 8:1173-83. doi: 10.1016/J.dib.2016.07.044. eCollection Sep. 2016.
Yang et al., "Maximizing in vivo target clearance by design of pH-dependent target binding antibodies with altered affinity to FcRn," mAbs, Oct. 2017, 9(7):1105-1117. doi: 10.1080/19420862.2017.1359455. Epub Aug. 8, 2017.
Yeung et al., "A Therapeutic Anti-VEGF Antibody with Increased Potency Independent of Pharmacokinetic Half-life," Cancer Res, Apr. 15, 2010, 70(8):3269-77. doi: 10.1158/0008-5472.CAN-09-4580. Epub Mar. 30, 2010.
USPTO Non-Final Office Action in U.S. Appl. No. 14/347,034, dated Jan. 8, 2018, 15 pages.
USPTO Notice of Allowance in U.S. Appl. No. 13/595,139, dated Oct. 3, 2017, 7 pages.
USPTO Notice of Allowance in U.S. Appl. No. 13/595,139, dated Nov. 28, 2017, 17 pages.
Fish & Richardson P.C., Reply to Restriction Requirement dated Dec. 17, 2015 in U.S. Appl. No. 14/347,321, filed Feb. 16, 2016, 3 pages.
USPTO Non-Final Office Action in U.S. Appl. No. 14/347,321, dated Nov. 13, 2017, 64 pages.
USPTO Notice of Allowance in U.S. Appl. No. 13/889,484, dated Nov. 16, 2017, 18 pages.
USPTO Restriction Requirement in U.S. Appl. No. 14/347,448, dated Nov. 24, 2017, 13 pages.
USPTO Non-Final Office Action in U.S. Appl. No. 14/347,448, dated Mar. 9, 2018, 32 pages.
USPTO Non-Final Office Action for U.S. Appl. No. 15/230,904, dated Jan. 8, 2018, 16 pages.
USPTO Non-Final Office Action in U.S. Appl. No. 14/402,574, dated Jan. 16, 2018, 24 pages.
USPTO Applicant-Initiated Interview Summary in U.S. Appl. No. 14/402,574, dated May 4, 2018, 27 pages.

(56) References Cited

OTHER PUBLICATIONS

USPTO Final Office Action in U.S. Appl. No. 14/402,574, dated Jul. 16, 2018, 10 pages.
USPTO Final Office Action in U.S. Appl. No. 14/404,051, dated Oct. 18, 2017, 15 pages.
USPTO Advisory Action Before the Filing of an Appeal Brief and Notice of Non-Compliant Amendment (37 CFR 1.121) in U.S. Appl. No. 14/404,051, dated Jun. 28, 2018, 4 pages.
U.S. Appl. No. 15/495,026, Igawa et al., filed Apr. 24, 2017.
U.S. Appl. No. 15/952,945, Igawa et al., filed Apr. 13, 2018.
U.S. Appl. No. 15/952,951, Igawa et al., filed Apr. 13, 2018.
U.S. Appl. No. 15/977,757, Igawa et al., filed May 11, 2018.
U.S. Appl. No. 15/988,348, Igawa et al., filed May 24, 2018.
U.S. Appl. No. 12/295,039, Igawa et al., filed Jan. 20, 2009.
U.S. Appl. No. 15/725,692, Igawa et al., filed Oct. 5, 2017.
U.S. Appl. No. 12/936,587, Igawa et al., filed Jan. 3, 2011 (abandoned).
U.S. Appl. No. 13/595,139, Igawa et al., filed Aug. 27, 2012.
U.S. Appl. No. 13/637,415, Igawa et al., filed Feb. 4, 2013.
U.S. Appl. No. 15/050,145, Igawa et al. filed Feb. 22, 2016.
U.S. Appl. No. 13/990,158, Igawa et al., filed May 29, 2013.
U.S. Appl. No. 14/007,947, Igawa et al., filed Sep. 26, 2013.
U.S. Appl. No. 14/347,034, Igawa et al., filed Mar. 25, 2014.
U.S. Appl. No. 15/230,904, Igawa et al., filed Aug. 8, 2016.
U.S. Appl. No. 16/028,140, Igawa et al., filed Jul. 5, 2018.
U.S. Appl. No. 14/347,321, Igawa et al., filed Mar. 26, 2014.
U.S. Appl. No. 14/361,013, Igawa et al., filed May 28, 2014.
U.S. Appl. No. 16/108,897, Igawa et al., filed Aug. 22, 2018.
U.S. Appl. No. 14/377,556, Kuramochi et al., filed Aug. 8, 2014.
U.S. Appl. No. 14/379,825, Igawa et al., filed Aug. 20, 2014.
U.S. Appl. No. 14/404,051, Igawa et al., filed Nov. 26, 2014.
U.S. Appl. No. 14/423,269, Katada et al., filed Feb. 23, 2015.
U.S. Appl. No. 14/781,069, Mimoto et al., filed Sep. 29, 2015.
U.S. Appl. No. 15/210,360, Igawa et al., filed Jul. 14, 2016.
U.S. Appl. No. 15/210,353, Igawa et al., filed Jul. 14, 2016.
U.S. Appl. No. 16/108,897, filed Aug. 22, 2018, Igawa et al.
Antibodies from www.bioinf.org.uk: Dr. Andrew C.R. Martin's Group, downloaded Jul. 11, 2018, nine pages.
Colman et al., "Effects of amino acid sequence changes on antibody-antigen interactions," Res Immunol, Jan. 1994, 145(1):33-6.
GE Healthcare, Biacore, Sensor Surface Handbook BR-1005-71, Edition AB, Feb. 2005, pp. 1-100.
Jaeger, Clinical Immunology and Allergology, M.: Medicina, 1990, 2:484-5 (with English translation).
King, Applications and Engineering of Monoclonal Antibodies, Taylor & Francis, ISBN 0-203-21169-3, 2005, pp. 1-236.
Lederman et al., "A Single Amino Acid Substitution in a Common African Allele of the CD4 Molecule Ablates Binding of the Monoclonal Antibody, OKT4," Mol Immunol, Nov. 1991, 28(11):1171-81.
Li et al., "β-Endorphin omission analogs: Dissociation of immunoreactivity from other biological activities," Proc Natl Acad Sci USA, Jun. 1980, 77(6):3211-4.
Mellman, "The importance of being acid: the role of acidification in intracellular membrane traffic," J Exp Biol, Nov. 1992, 172:39-45.
Popov et al., "The Stoichiometry and Affinity of the Interaction of Murine Fc Fragments with the MHC Class I-Related Receptor, FcRn," Mol Immunol, Apr. 1996, 33(6):521-30.
Roitt et al., Immunology, Moscow: Mir, 2000, pp. 373-374 (with English translation).
Yarilin, Fundamentals of Immunology, M: Medicina, 1999, pp. 172-174 (with English translation).
Yarilin, Fundamentals of Immunology, M: Medicina, 1999, pp. 175, 182 (with English translation).
USPTO Non-Final Office Action in U.S. Appl. No. 13/595,139, dated Sep. 26, 2018, 32 pages.
USPTO Final Office Action in U.S. Appl. No. 14/347,448, dated Nov. 13, 2018, 29 pages.
USPTO Advisory Action Before the Filing of an Appeal Brief in U.S. Appl. No. 14/404,051, filed Aug. 30, 2018, 3 pages.
USPTO Restriction Requirement in U.S. Appl. No. 14/974,350, dated Aug. 4, 2016, 8 pages.
USPTO Non-Final Office Action in U.S. Appl. No. 14/974,350, dated Feb. 1, 2017, 61 pages.
USPTO Restriction Requirement in U.S. Appl. No. 14/974,488, dated Jan. 24, 2017, 17 pages.
USPTO Non-Final Office Action in U.S. Appl. No. 14/974,488, dated Aug. 16, 2017, 88 pages.

\* cited by examiner

[Fig. 1A]

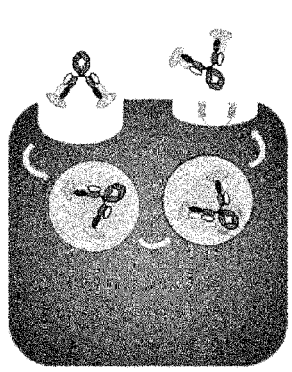
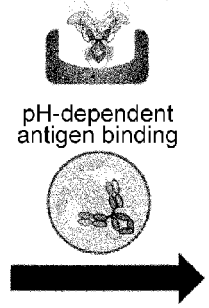
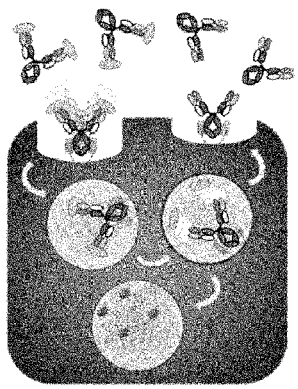

Conventional antibody → pH-dependent antigen binding antibody with enhanced FcRn binding at neutral pH Enhance binding to FcRn at neutral pH pH-dependent antigen binding

FREE ANTIBODIES BINDING TO OTHER ANTIGENS

[Fig. 1B]

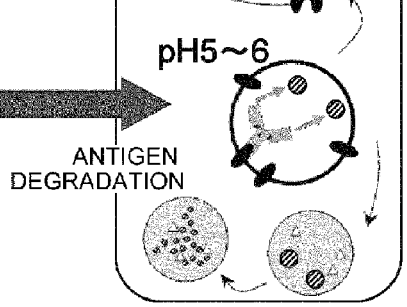

BLOOD VESSEL
NON-SPECIFIC ENDOCYTOSIS
pH7.4
ENDOTHELIAL CELL
ACIDIC ENDOSOME
pH5~6
RETURN TO PLASMA
H⁺
H⁺
LYSOSOME

ANTIGEN DEGRADATION pH5~6

:ANTIBODY :ANTIGEN :FcRn

DISSOCIATION FROM ANTIGEN IN ACIDIC ENDOSOME

[Fig. 2]
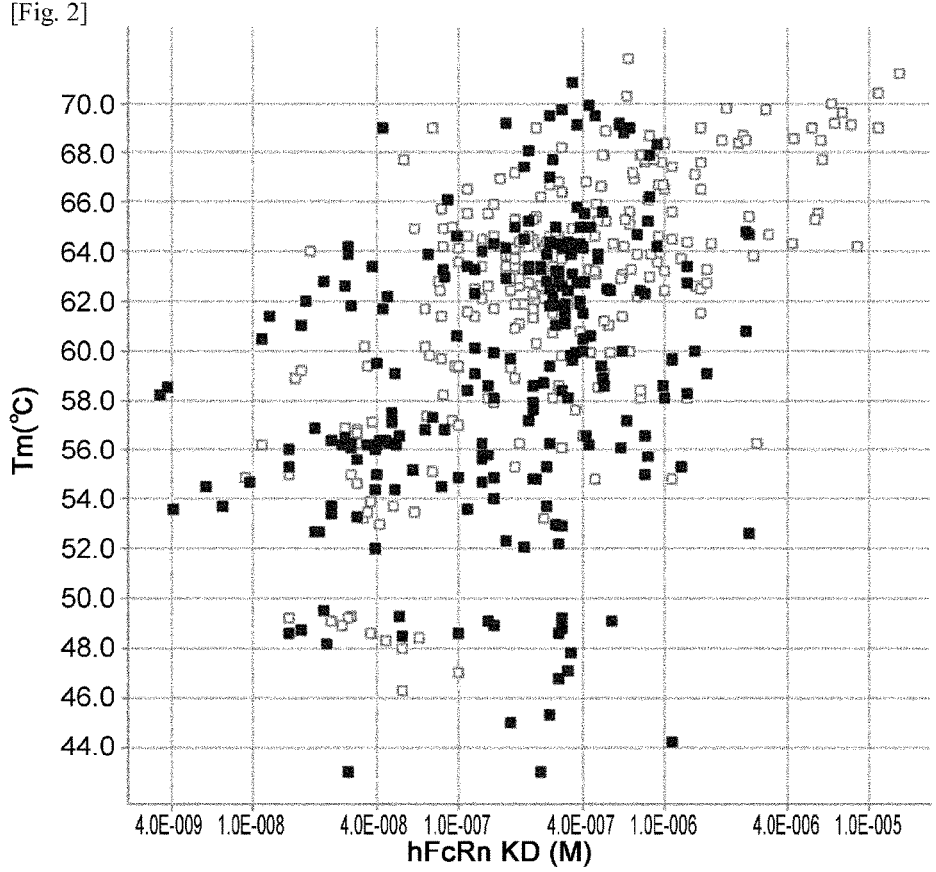

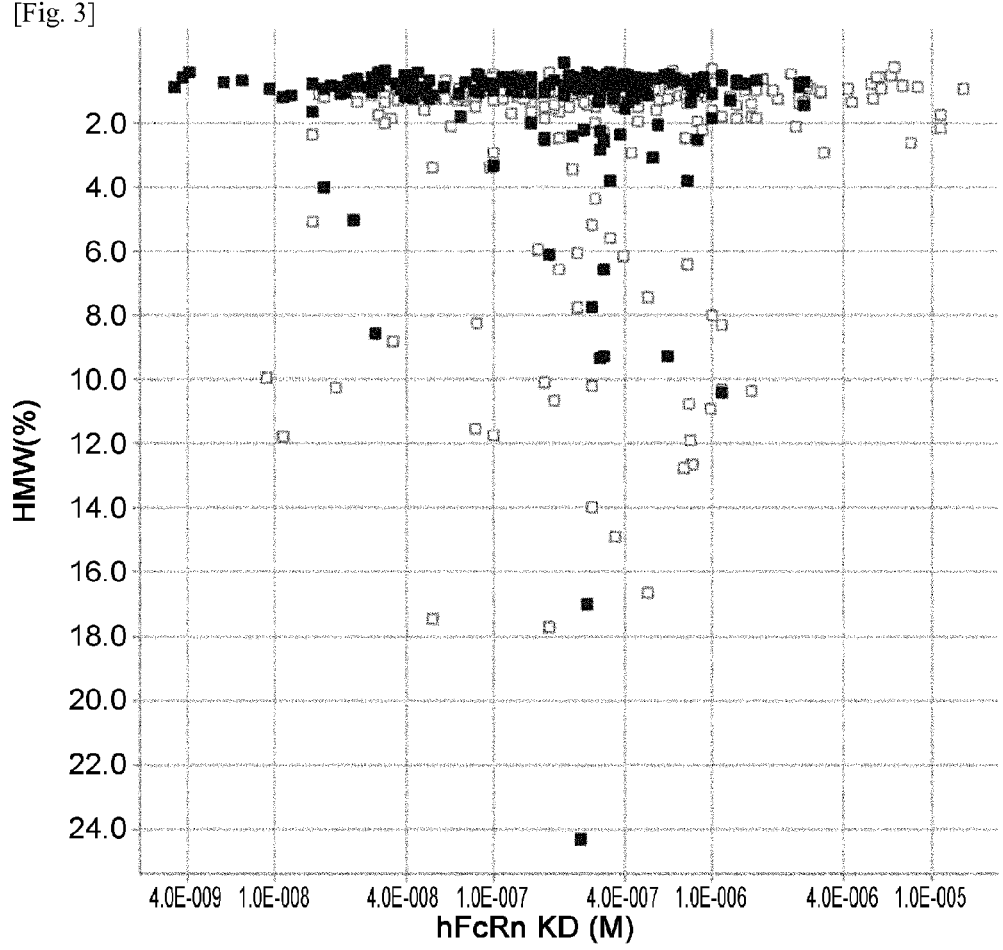
[Fig. 3]

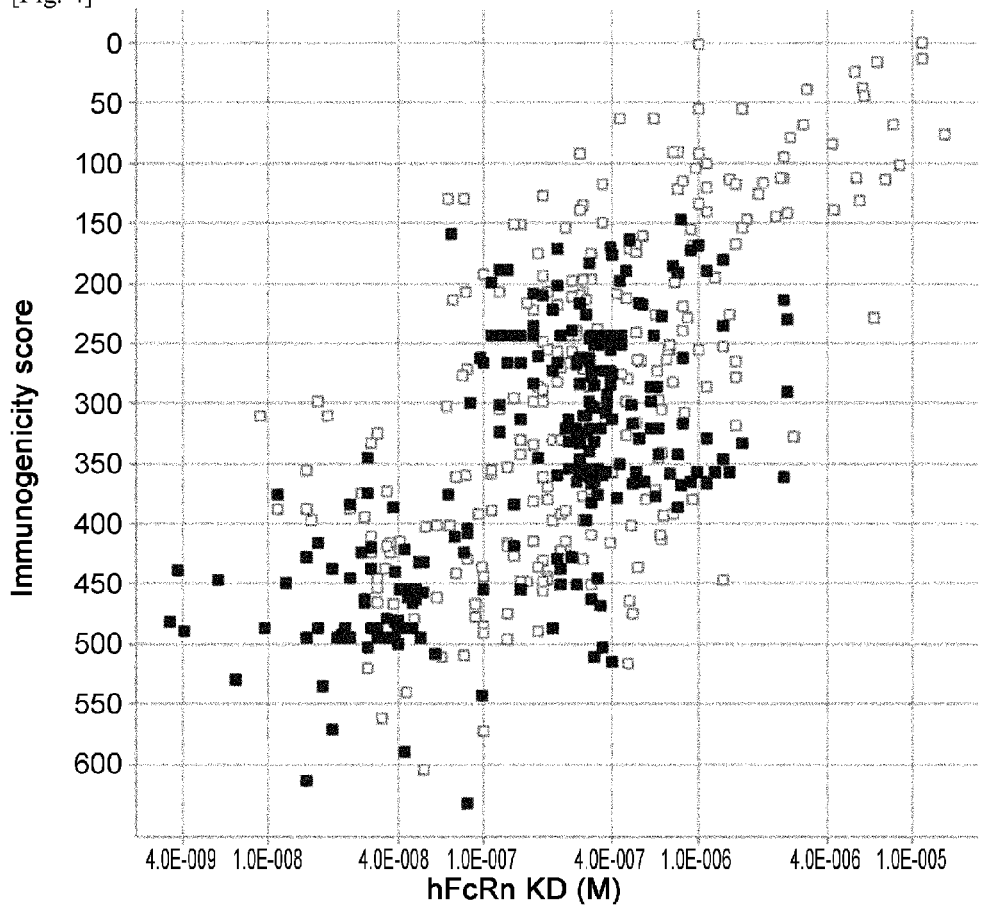
[Fig. 4]

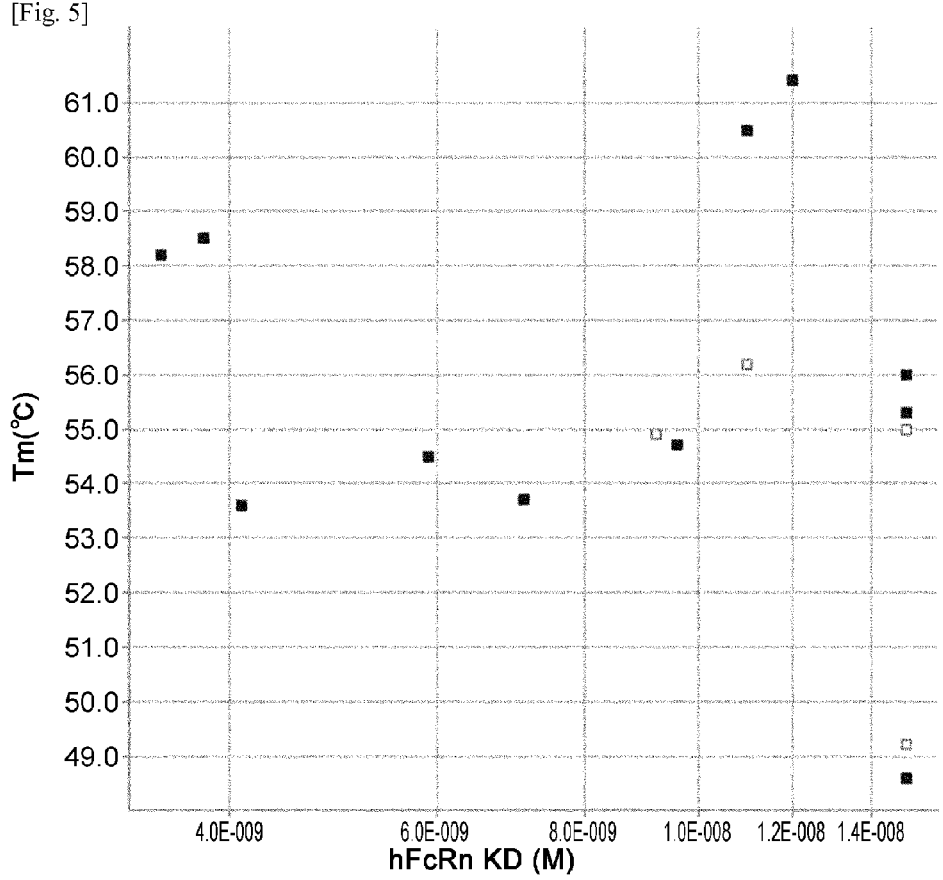
[Fig. 5]

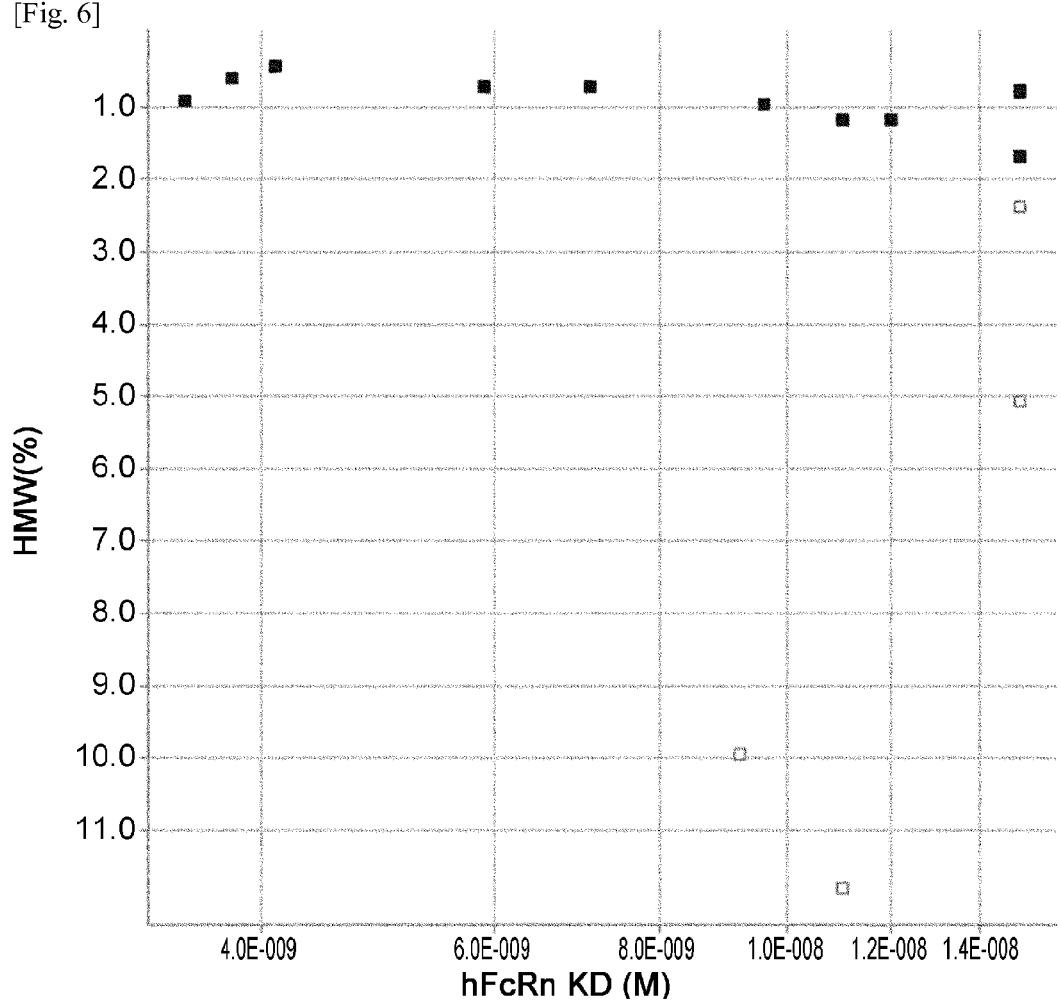
[Fig. 6]

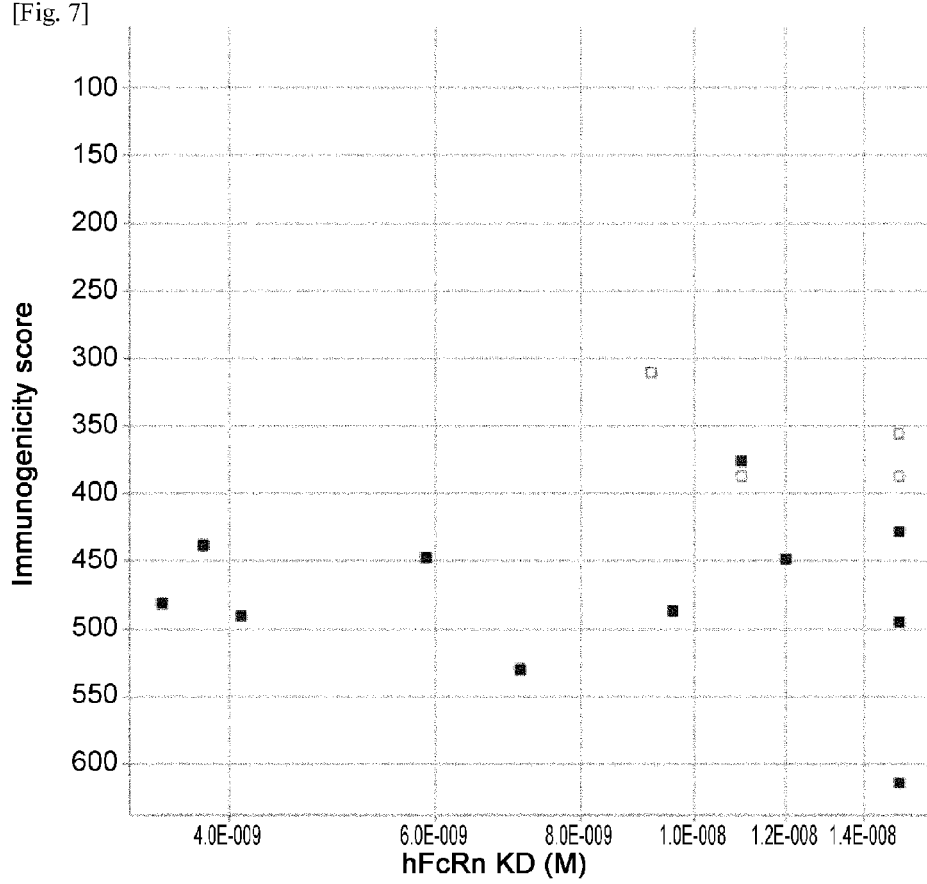

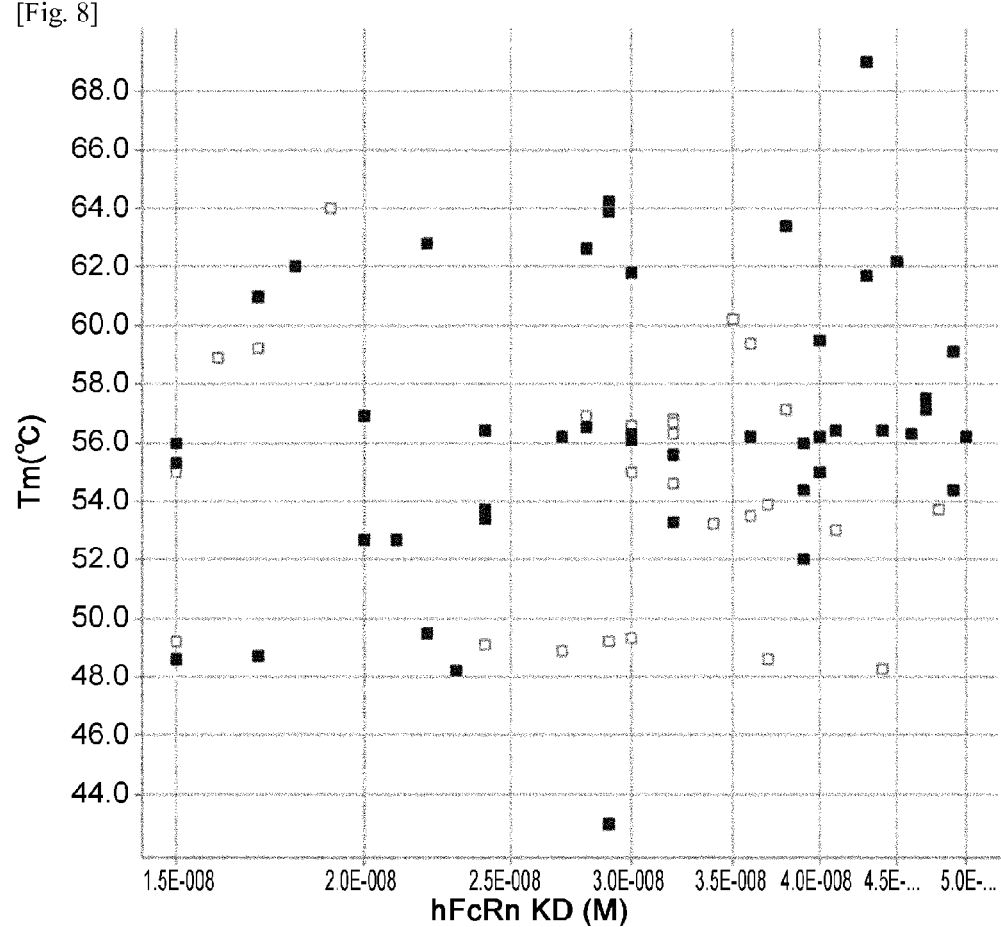
[Fig. 8]

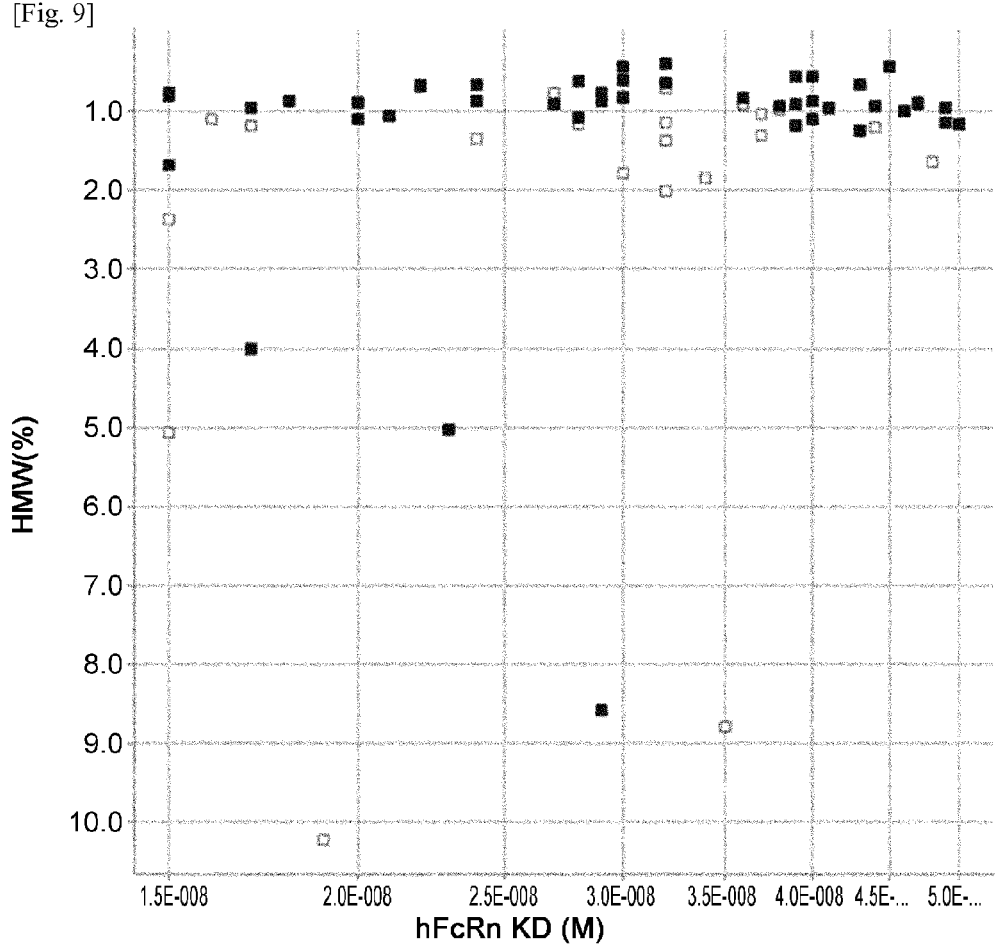
[Fig. 9]

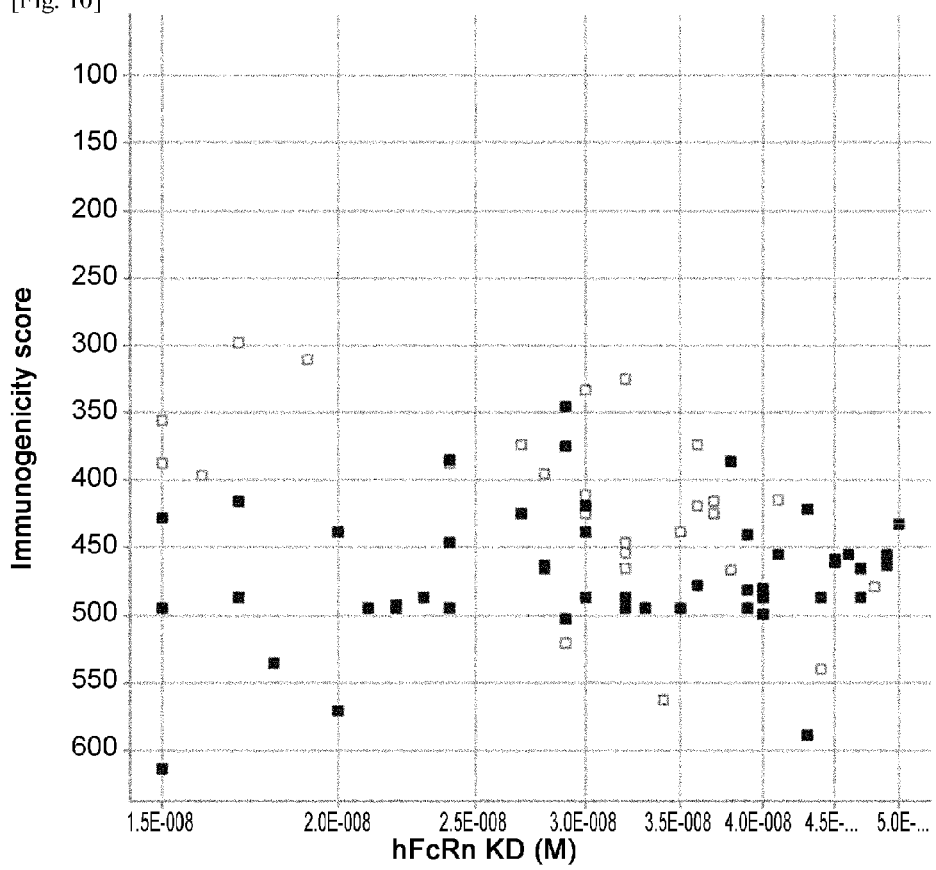
[Fig. 10]

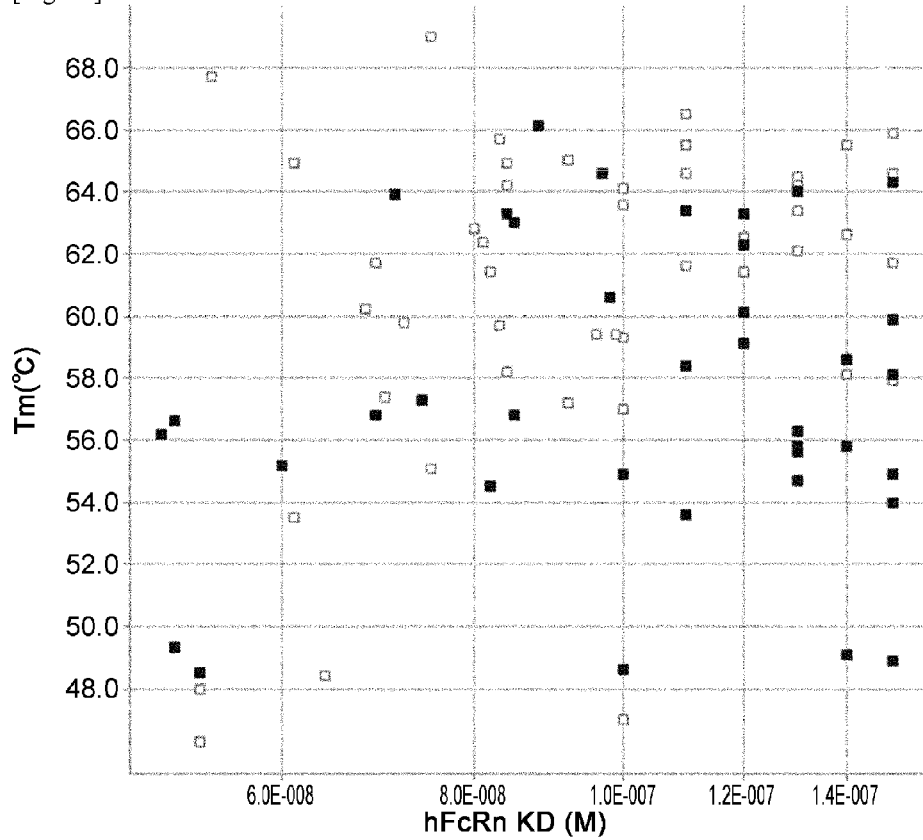
[Fig. 11]

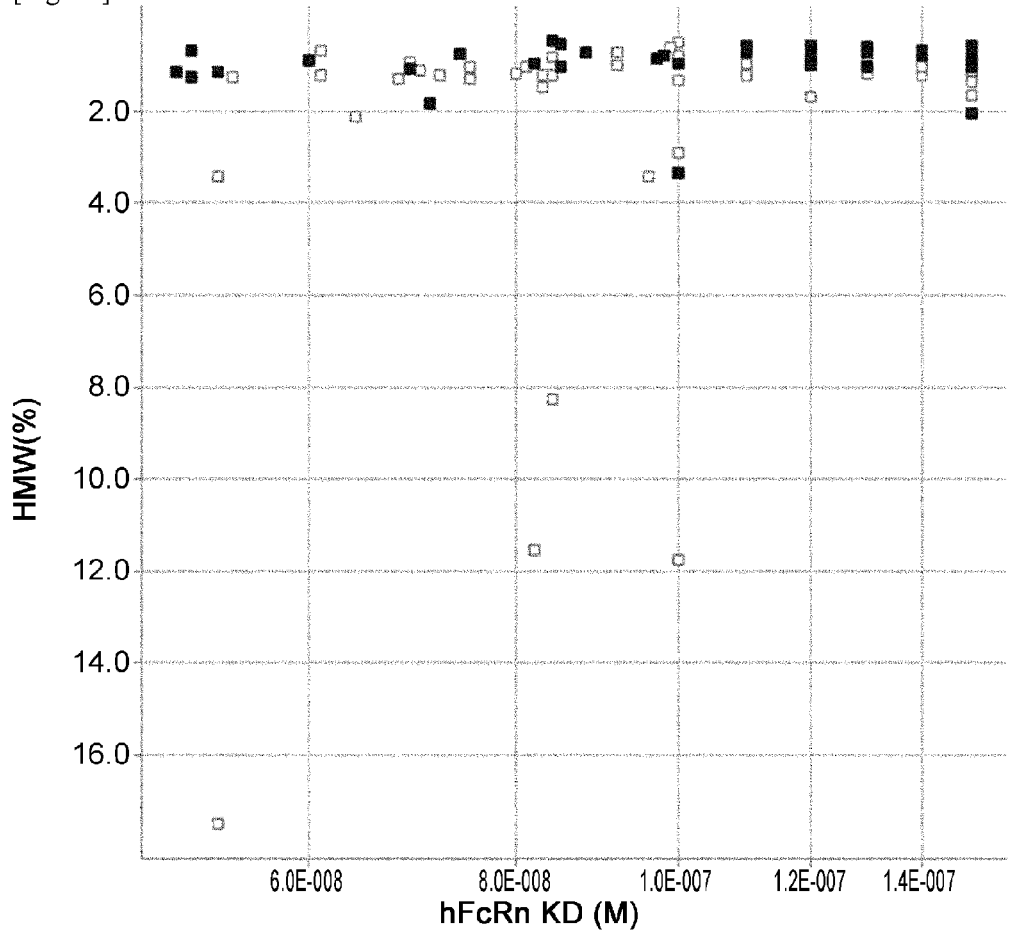
[Fig. 12]

[Fig. 13]
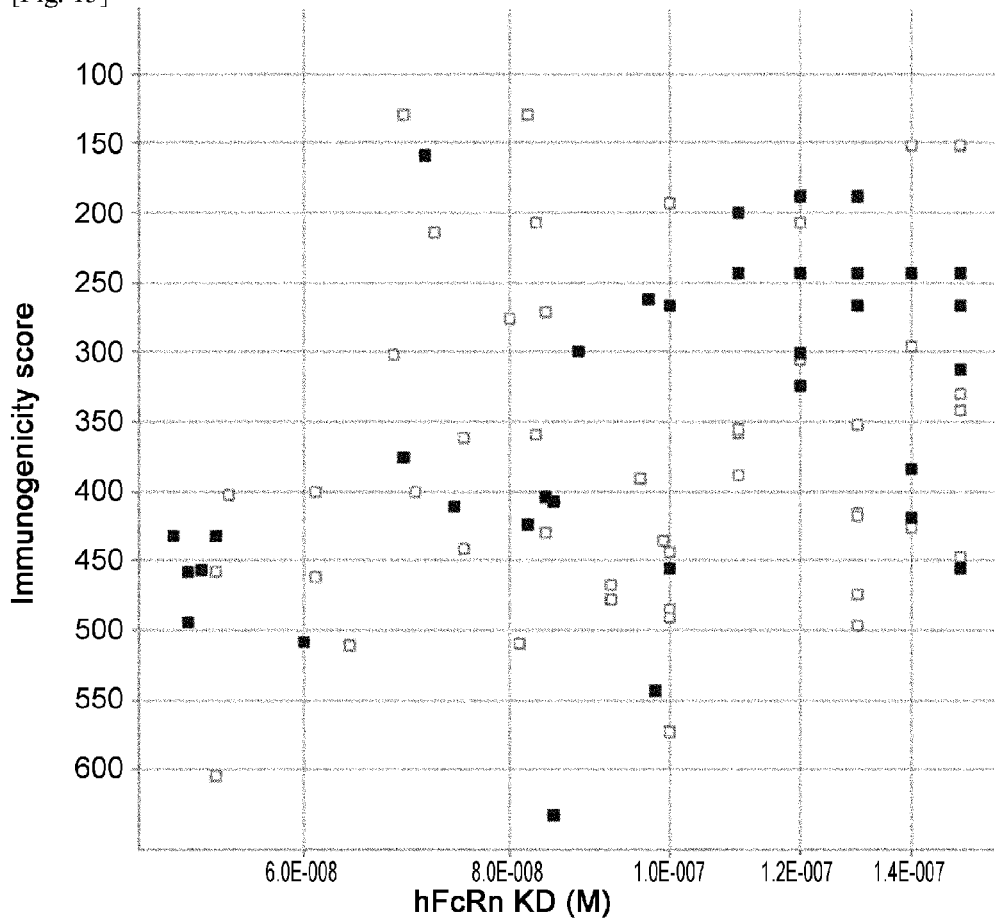

[Fig. 14]
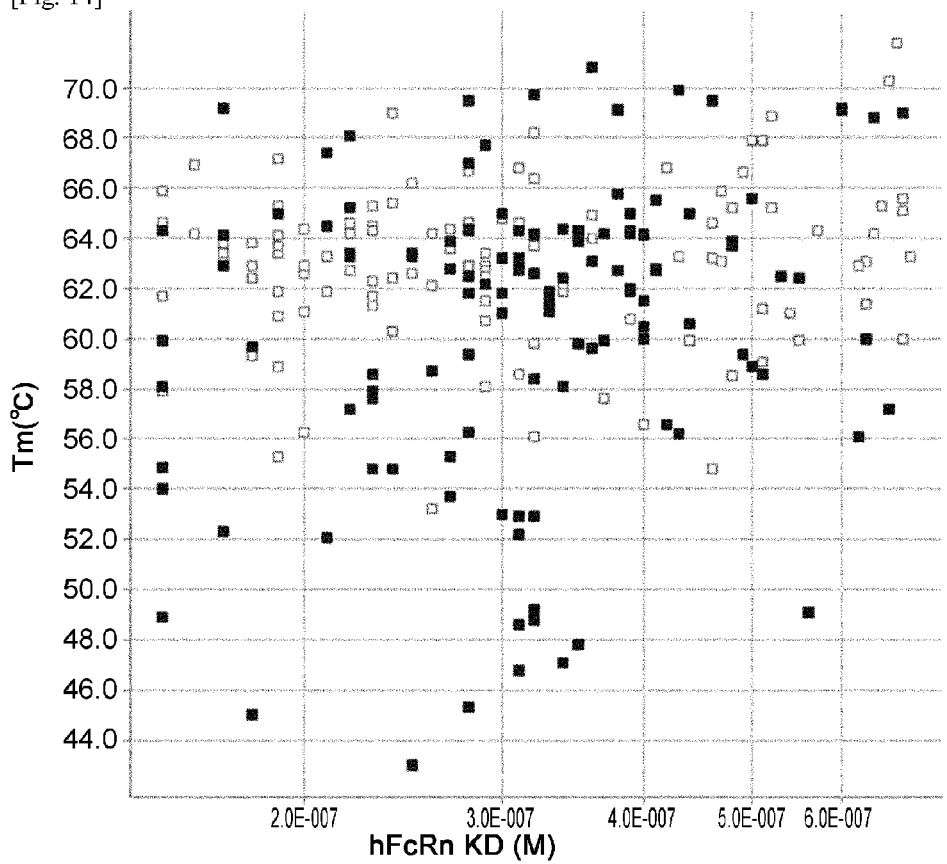

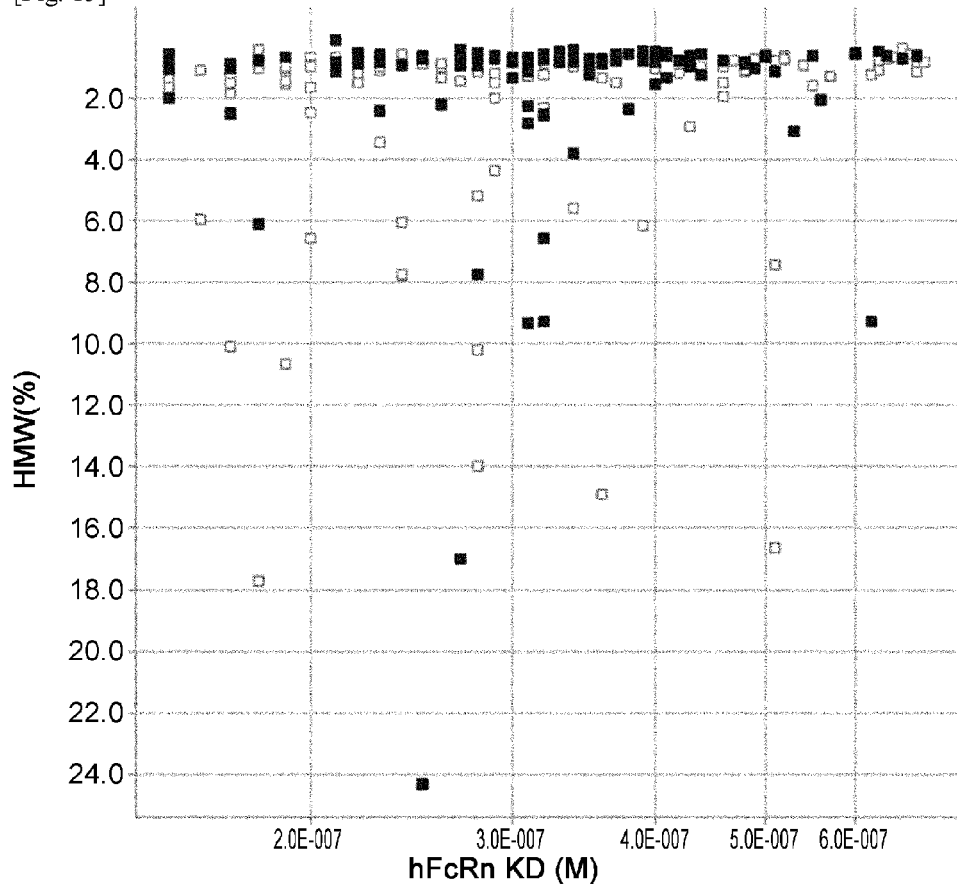
[Fig. 15]

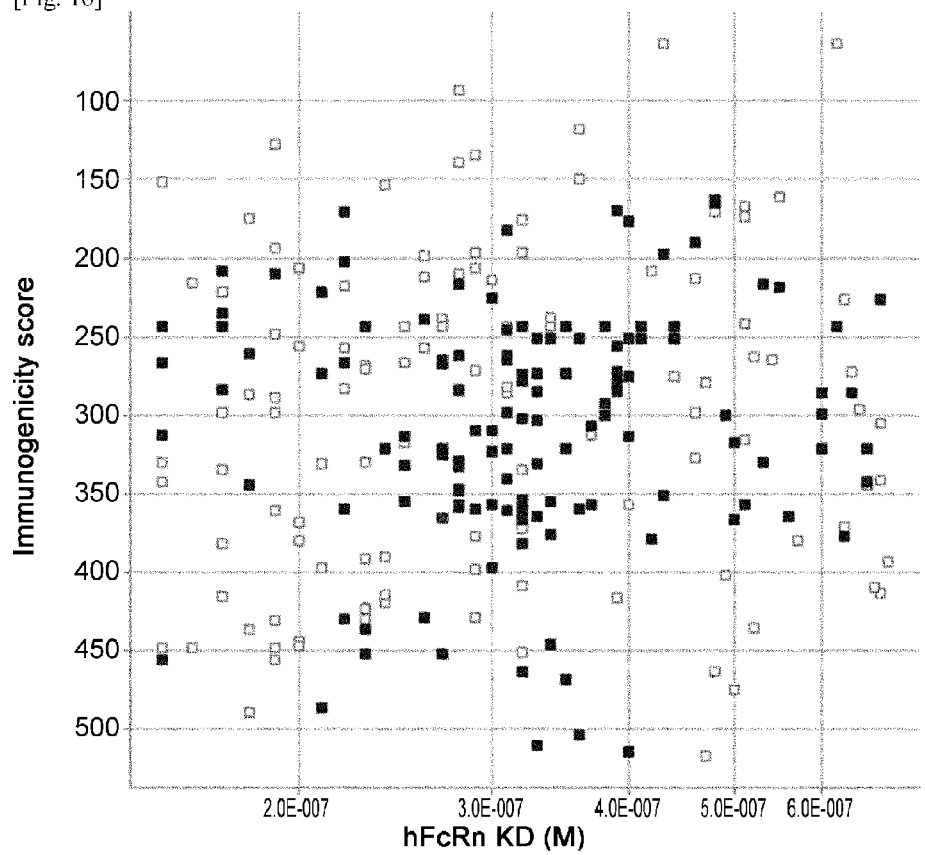
[Fig. 16]

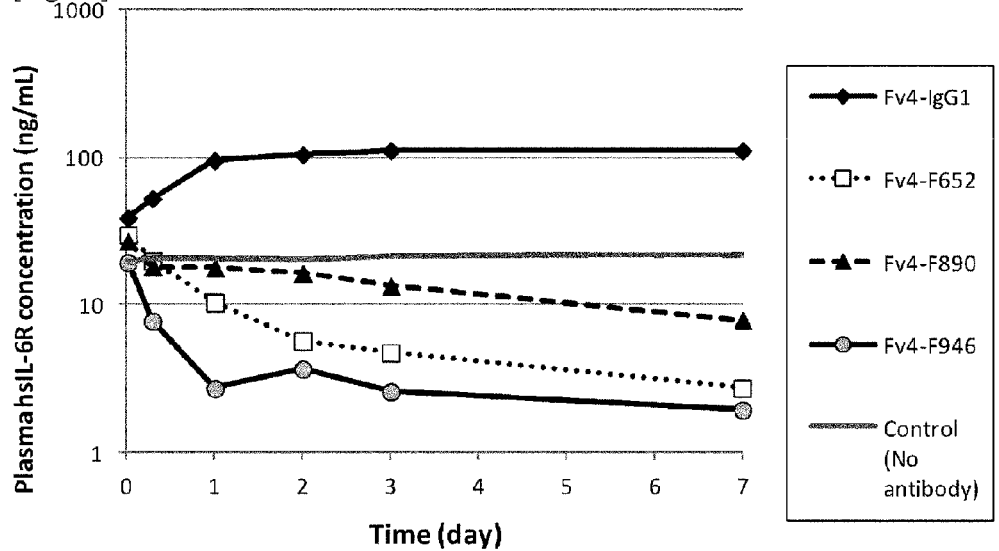
[Fig. 17]
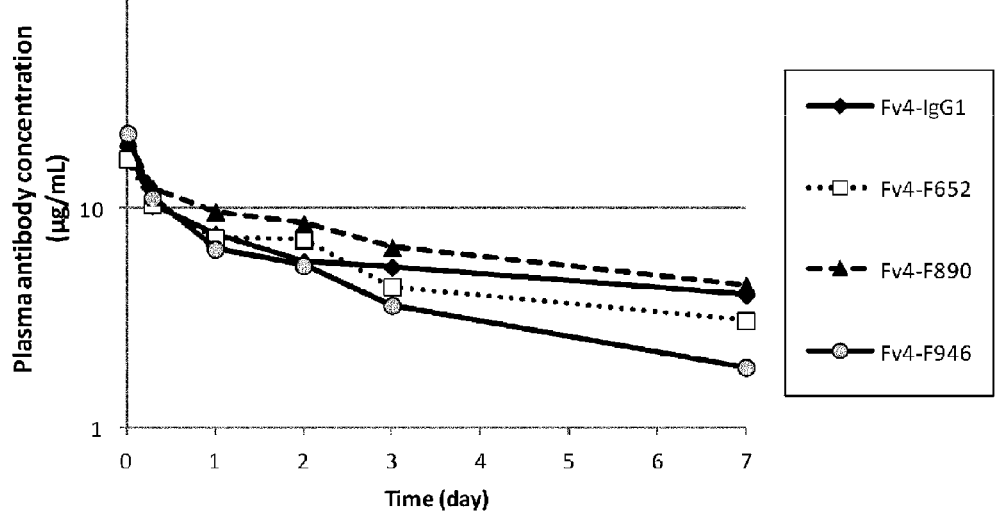
[Fig. 18]

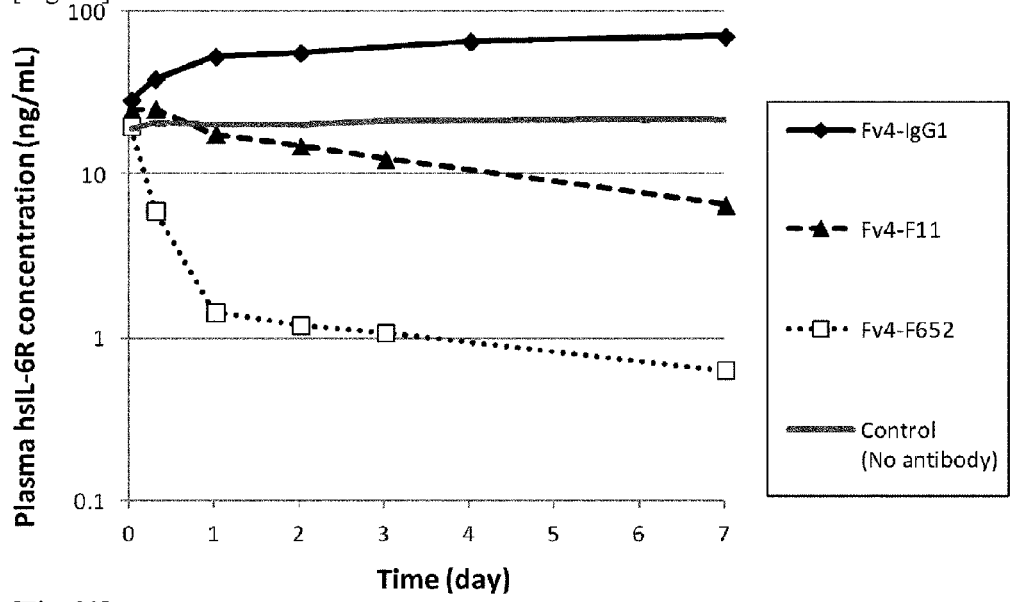
[Fig. 19]
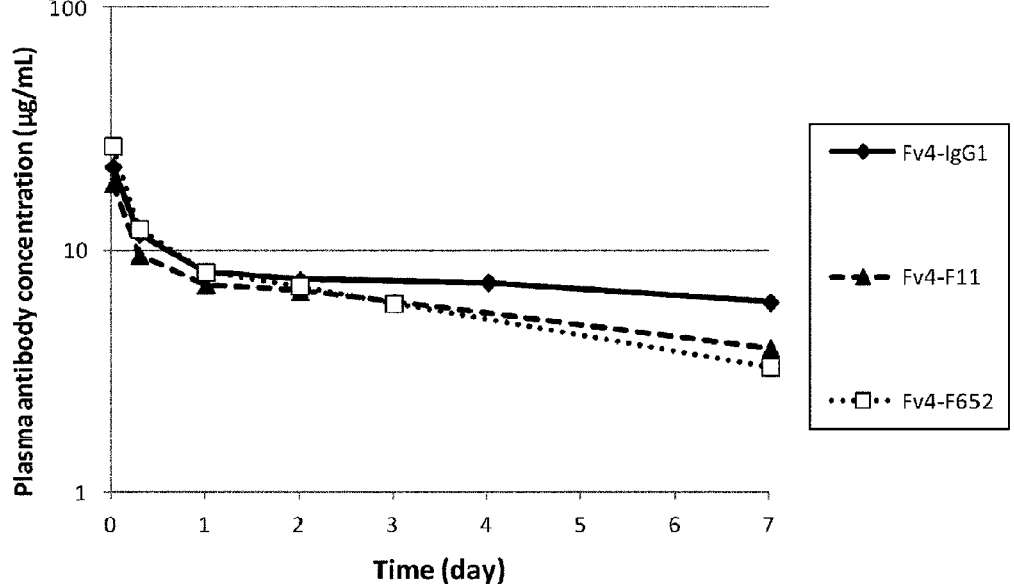
[Fig. 20]

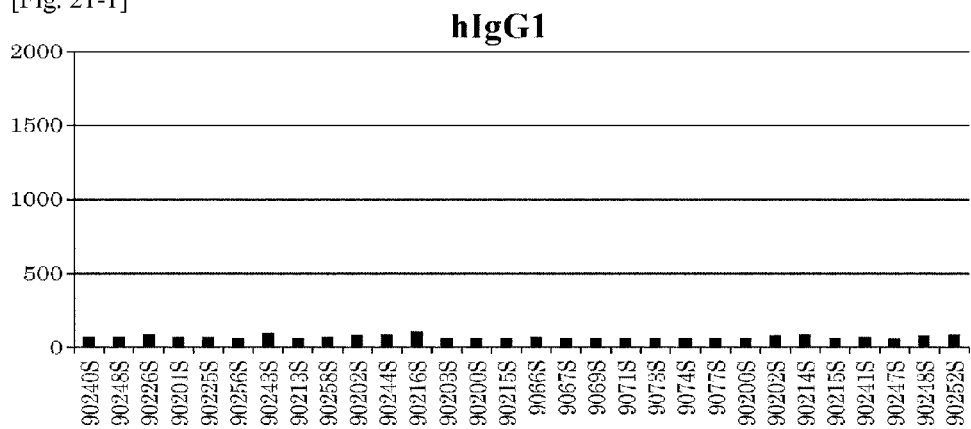

[Fig. 22-1]
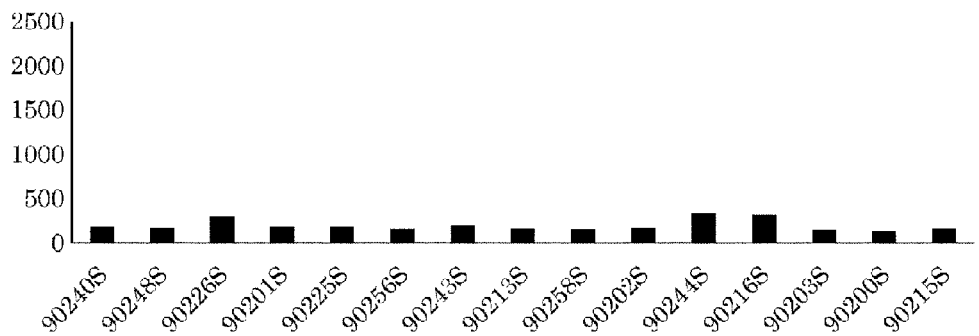
[Fig. 22-2]
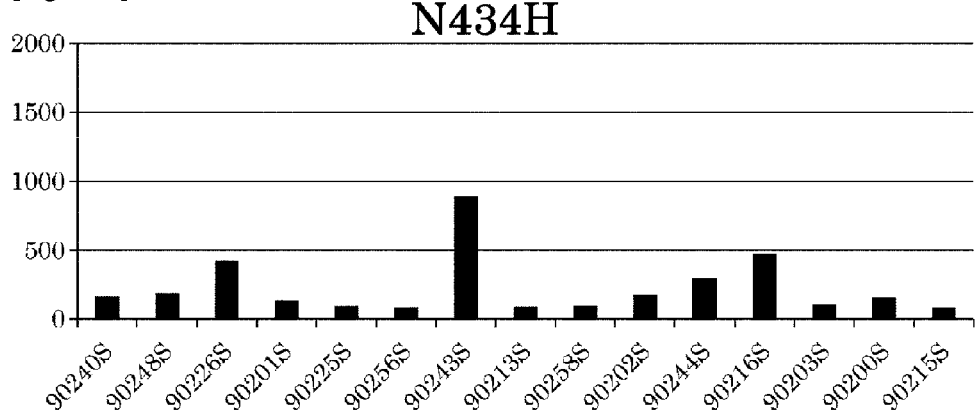
[Fig. 22-3]
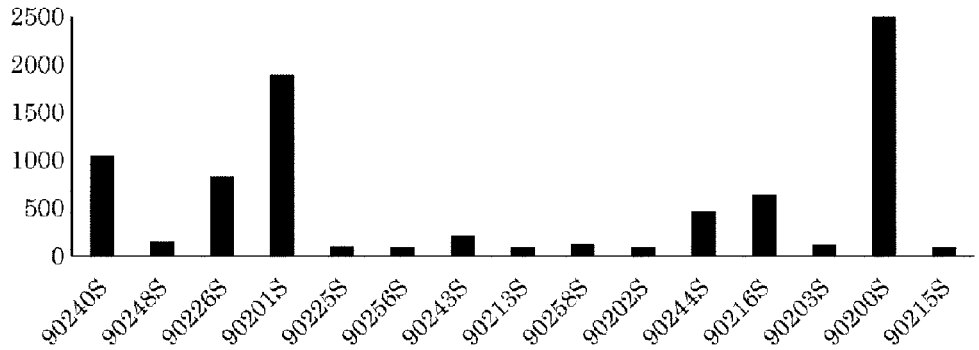

[Fig. 22-4]
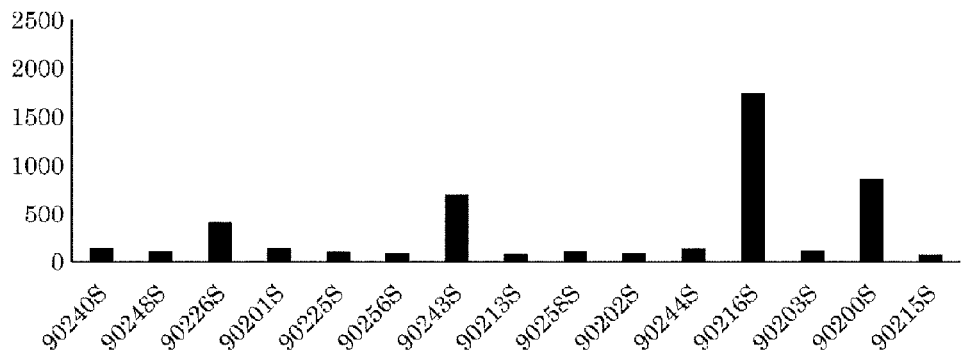
[Fig. 22-5]
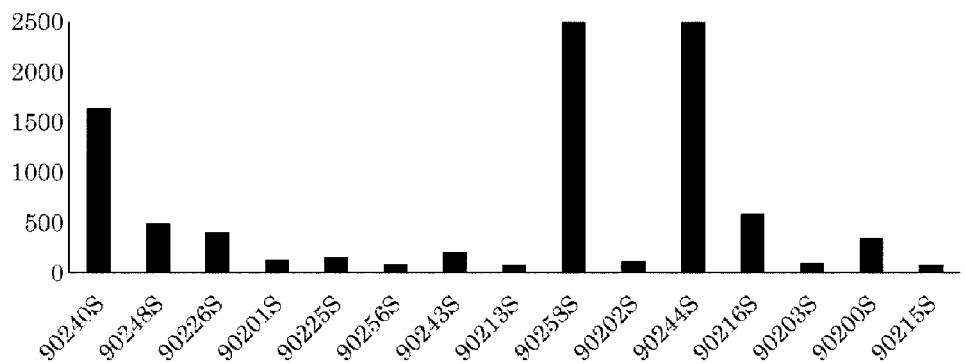
[Fig. 22-6]
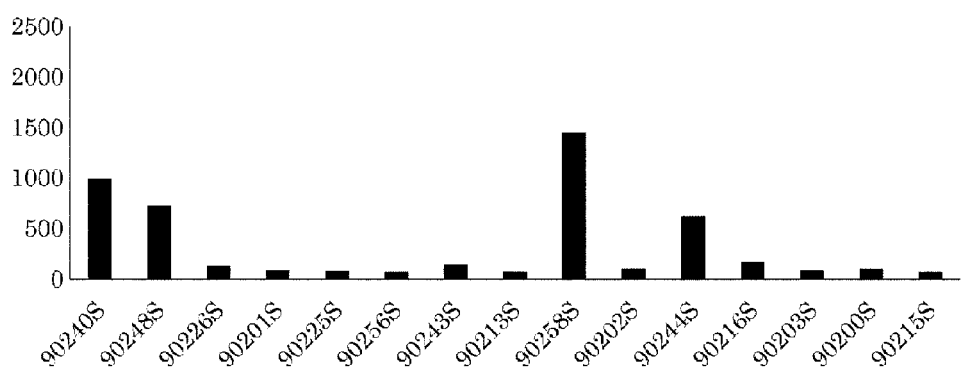

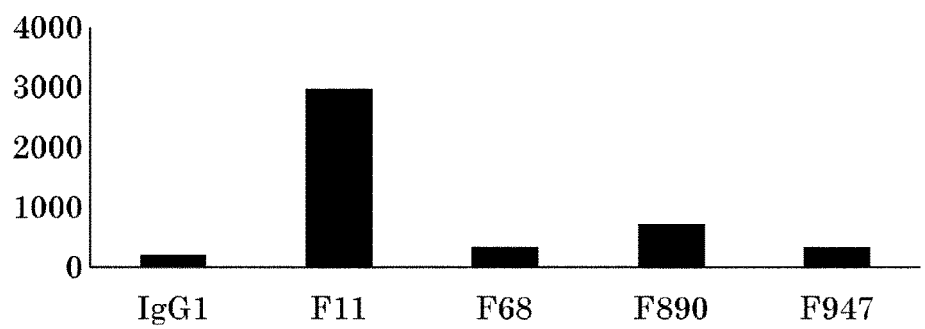
[Fig. 23-1] MEAN ECL response
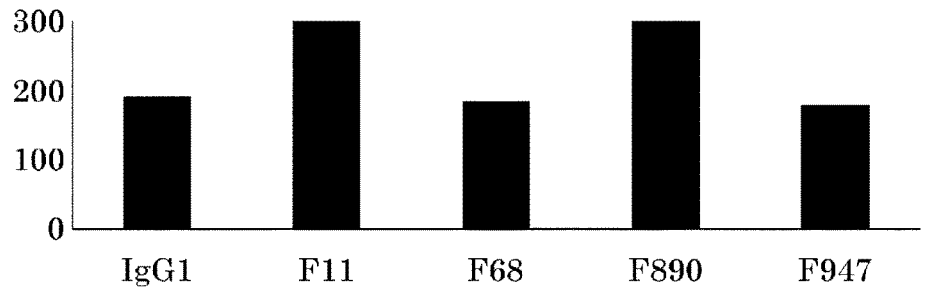
[Fig. 23-2] GEOMEAN ECL response
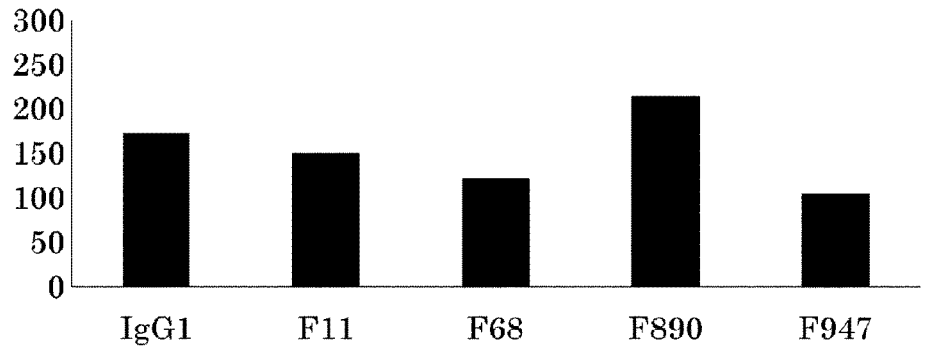
[Fig. 23-3] MEDIAN ECL response

[Fig. 24-1]
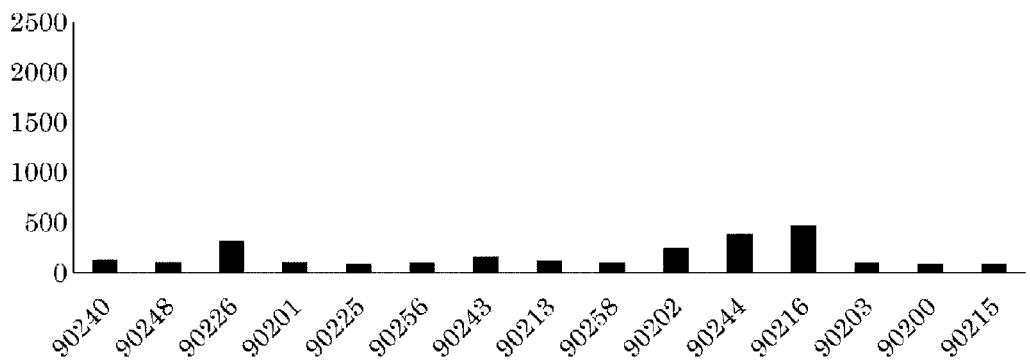
[Fig. 24-2]
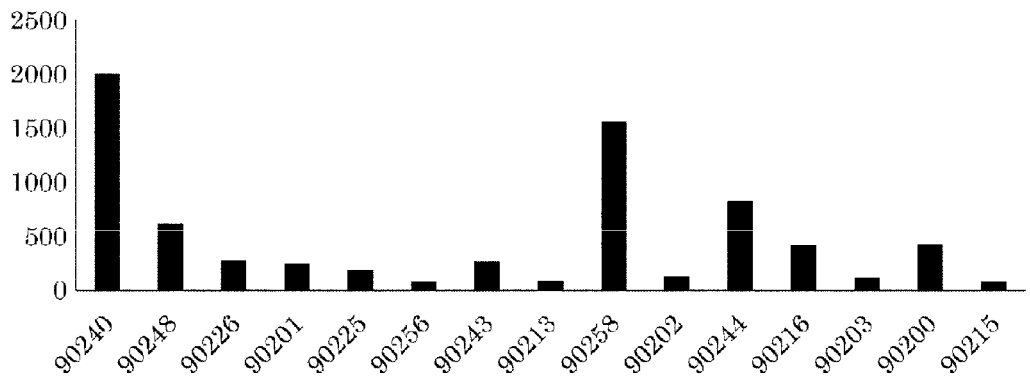
[Fig. 24-3]
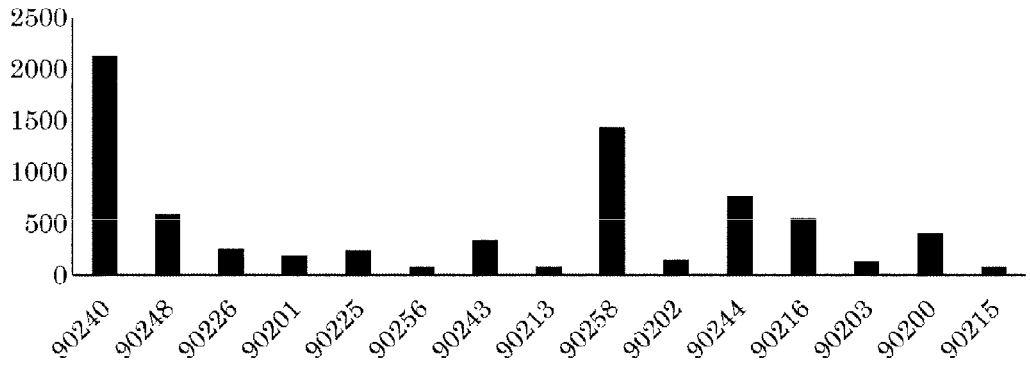

[Fig. 24-4]
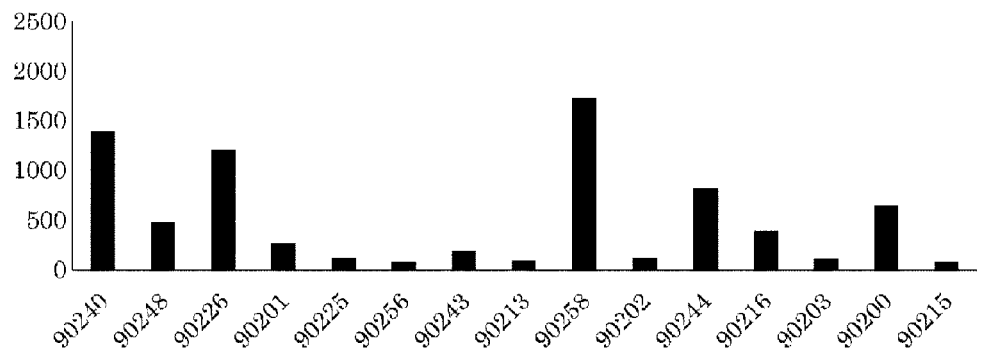
[Fig. 24-5]
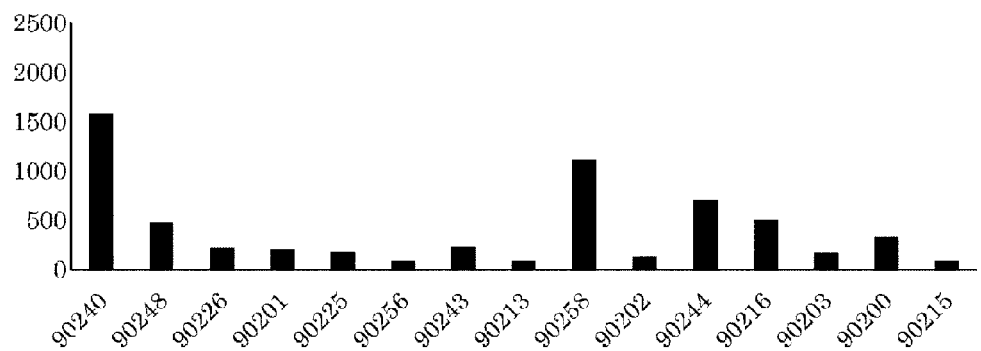
[Fig. 24-6]
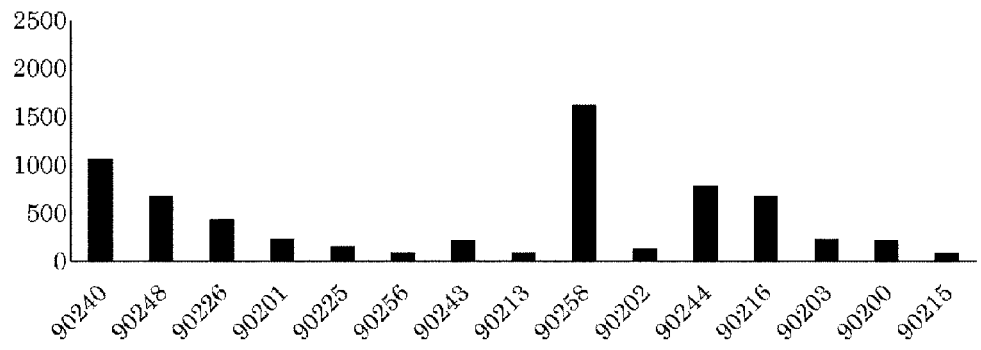

[Fig. 24-7]
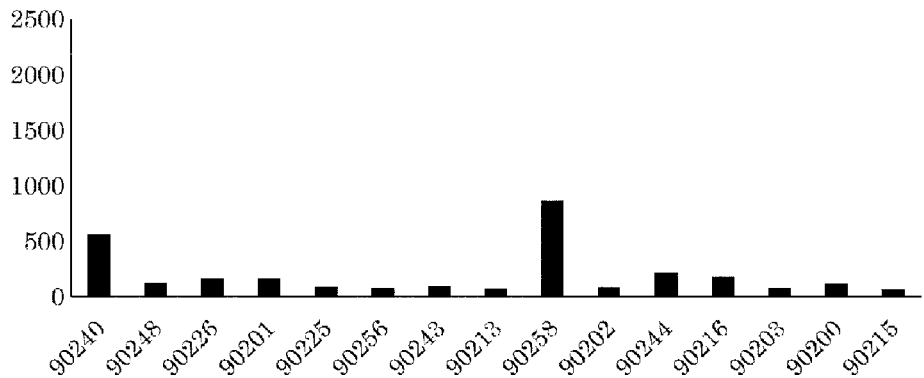
[Fig. 24-8]
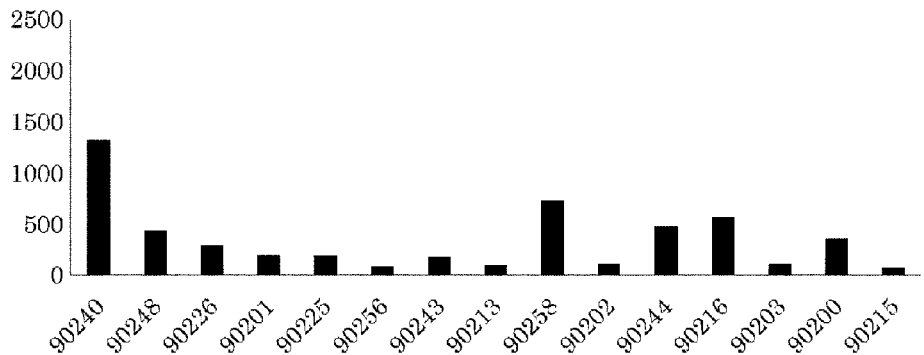
[Fig. 24-9]
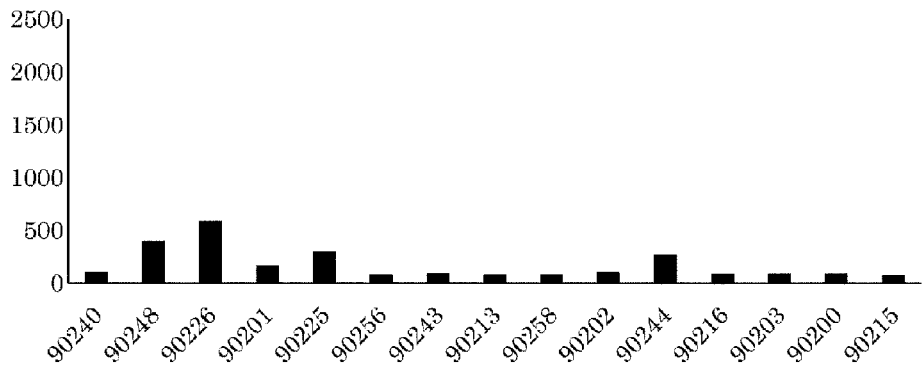

[Fig. 24-10]
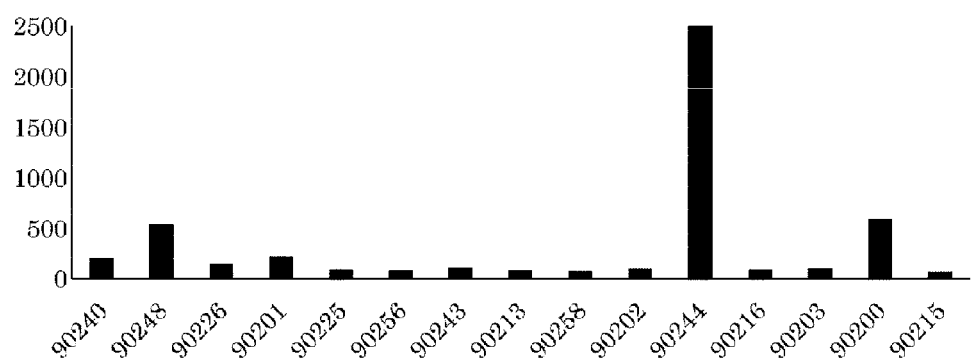
[Fig. 24-11]
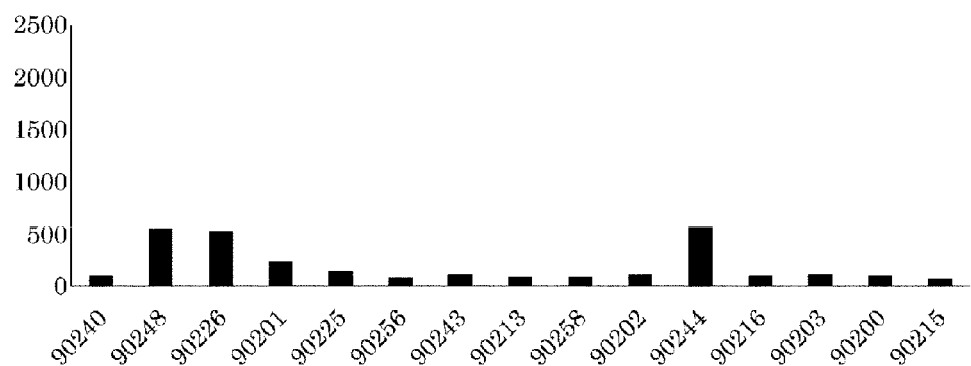
[Fig. 24-12]
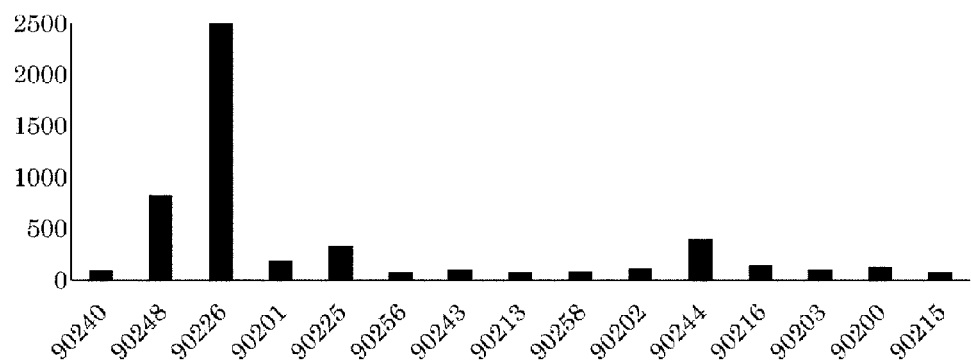

[Fig. 24-13]
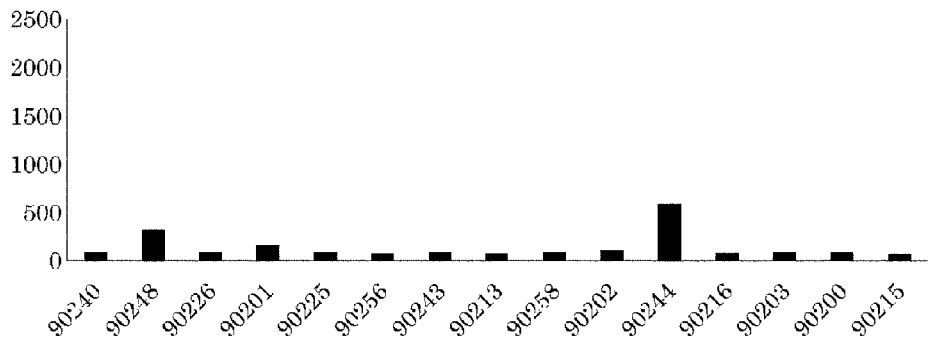
[Fig. 24-14]
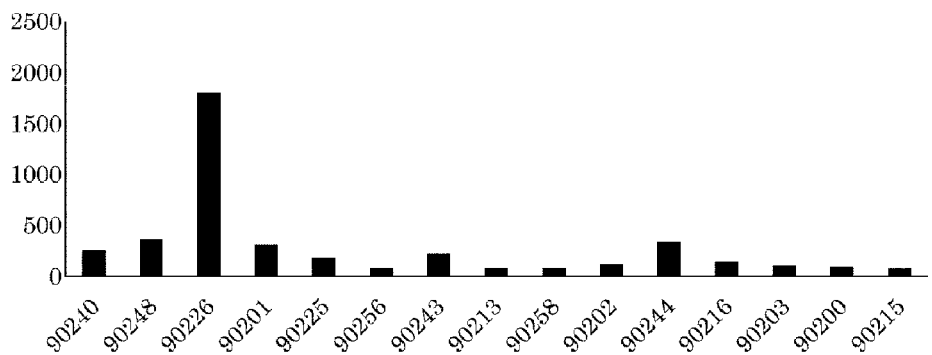
[Fig. 24-15]
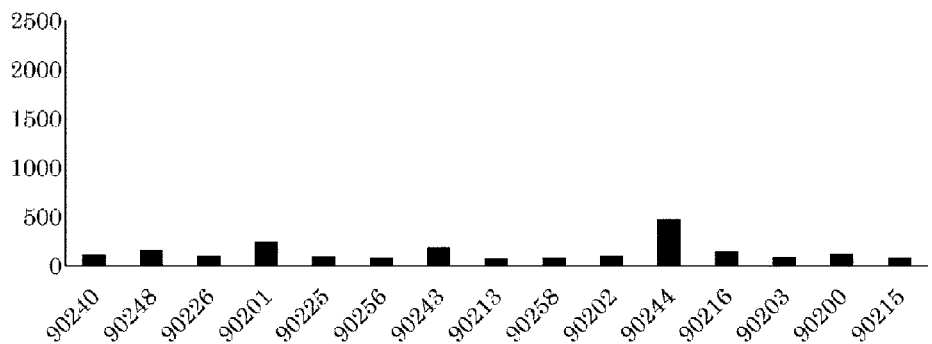

[Fig. 24-16]
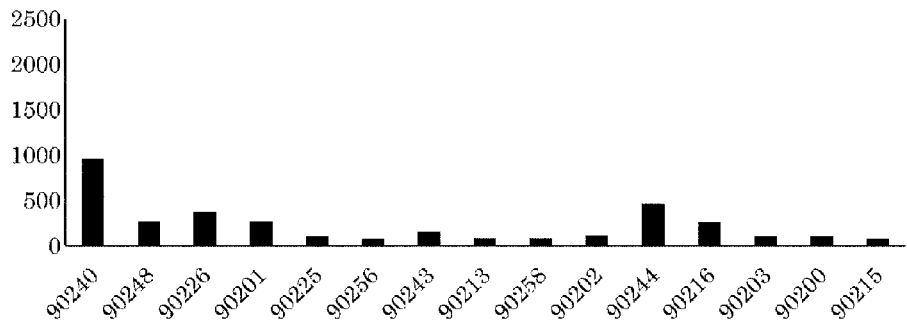
[Fig. 24-17]
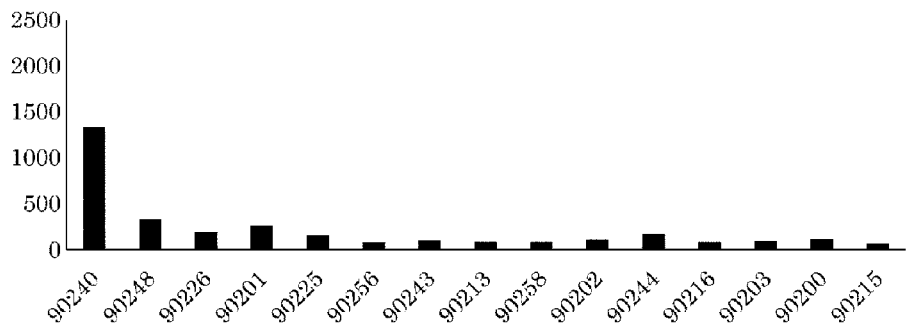
[Fig. 24-18]
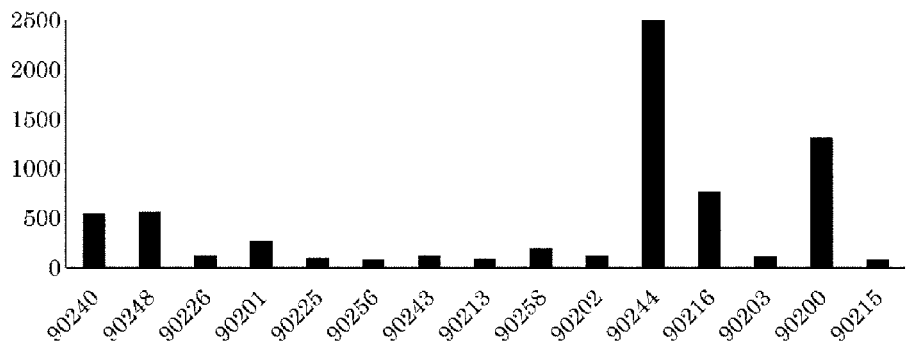

[Fig. 25-1]
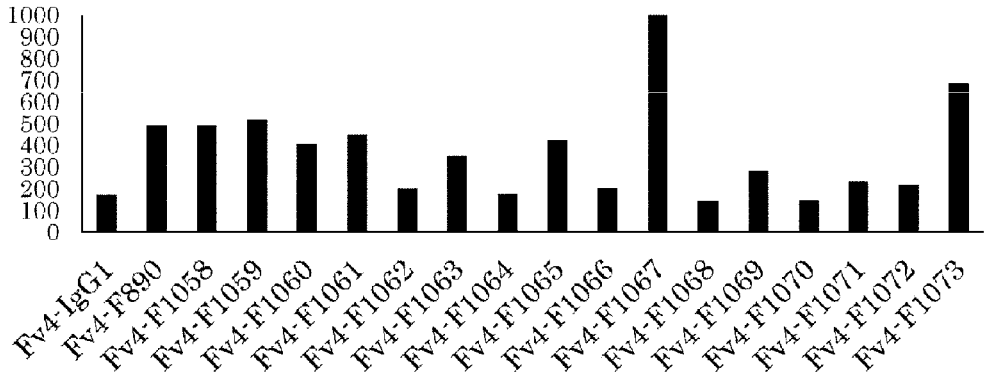
[Fig. 25-2]
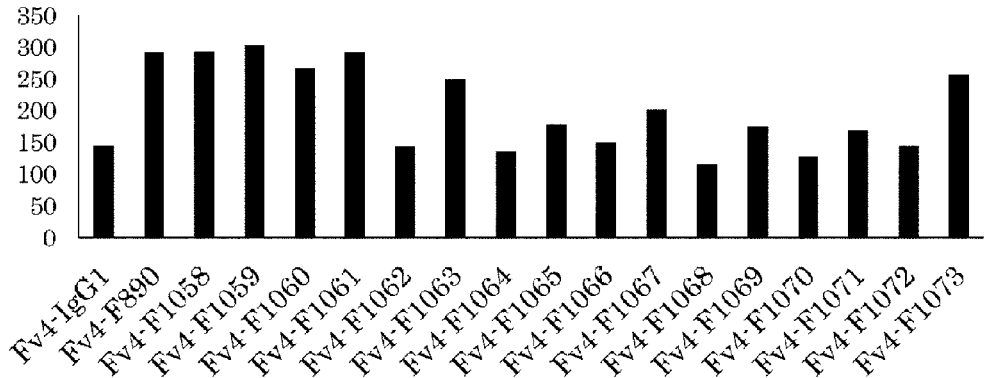
[Fig. 25-3]
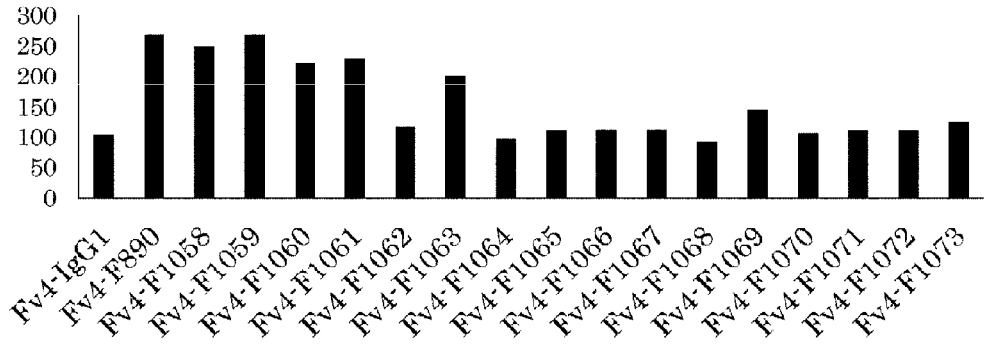

[Fig. 26-1]
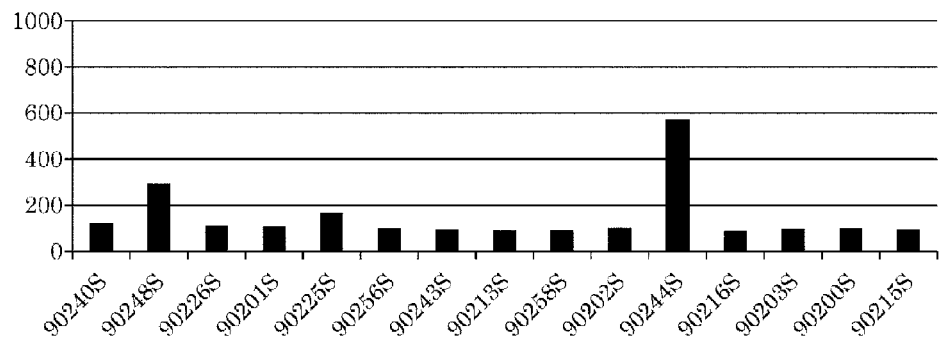
[Fig. 26-2]
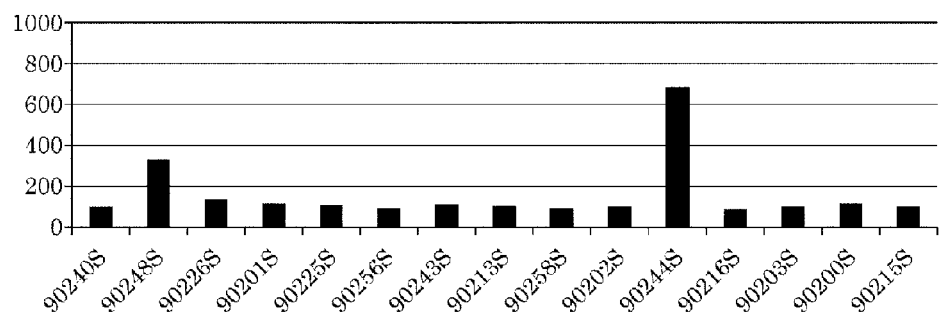
[Fig. 26-3]
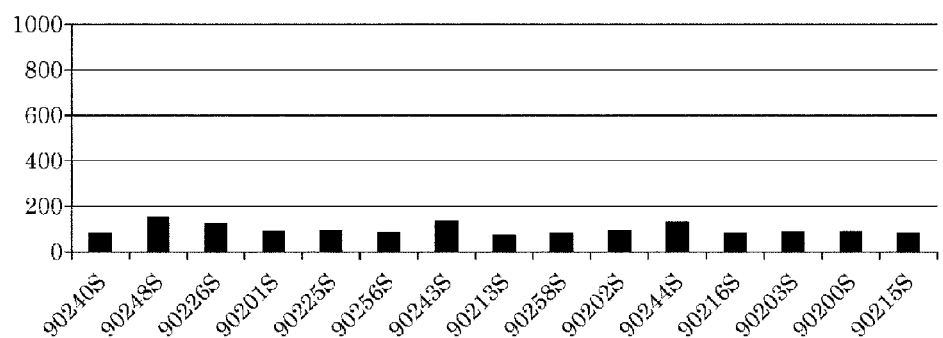

[Fig. 27-1]
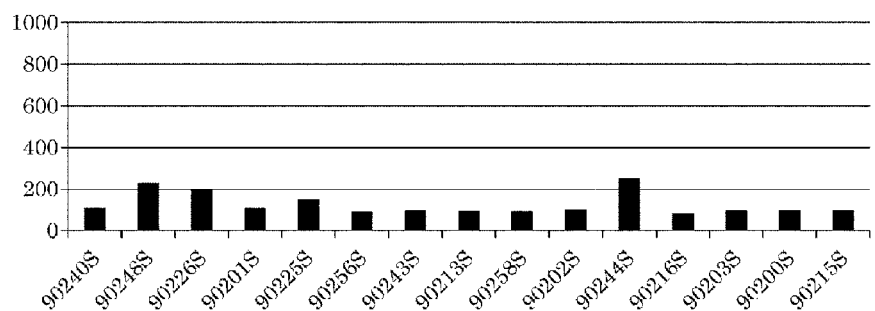
[Fig. 27-2]
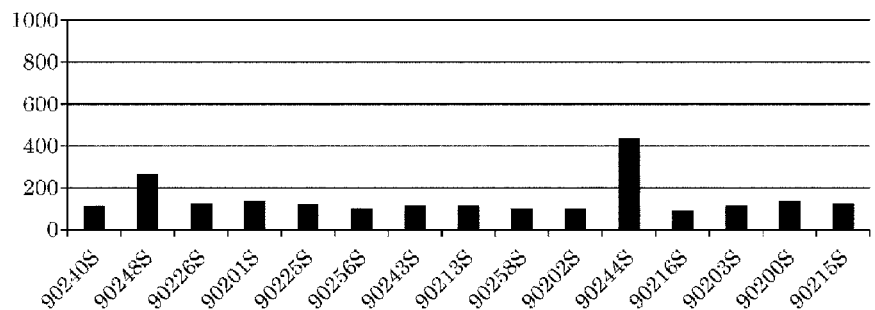
[Fig. 27-3]
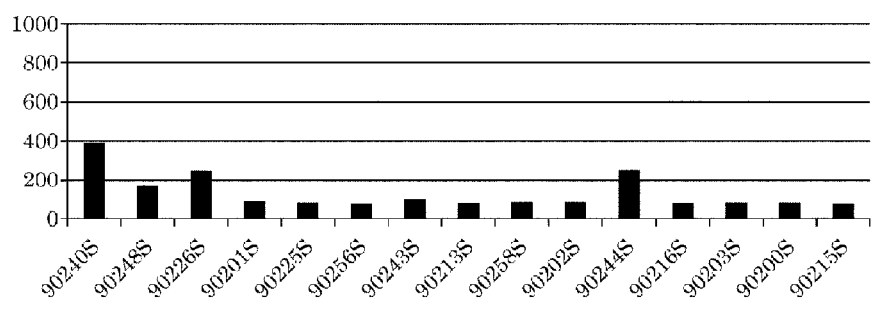

[Fig. 27-4]
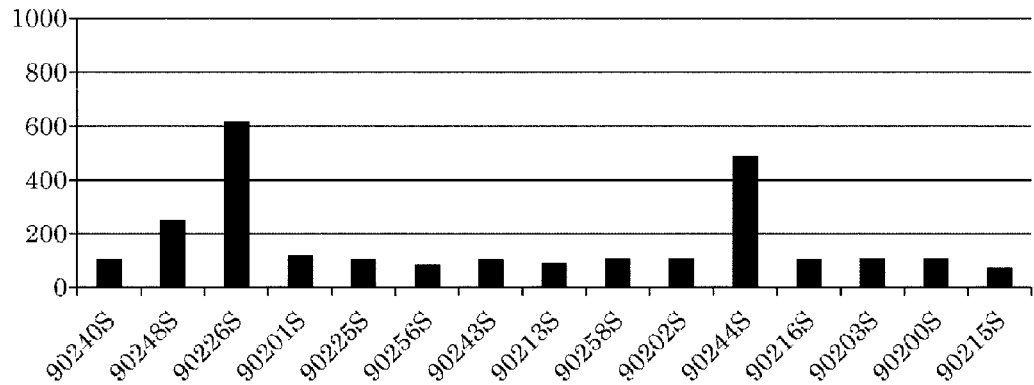
[Fig. 27-5]
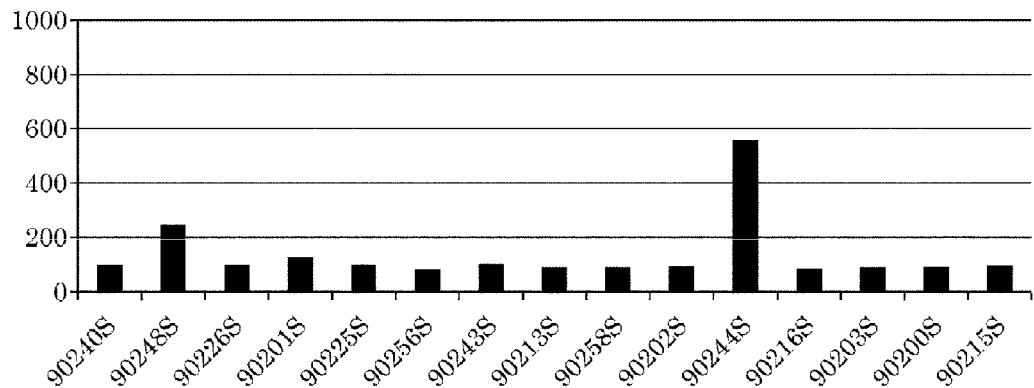
[Fig. 27-6]
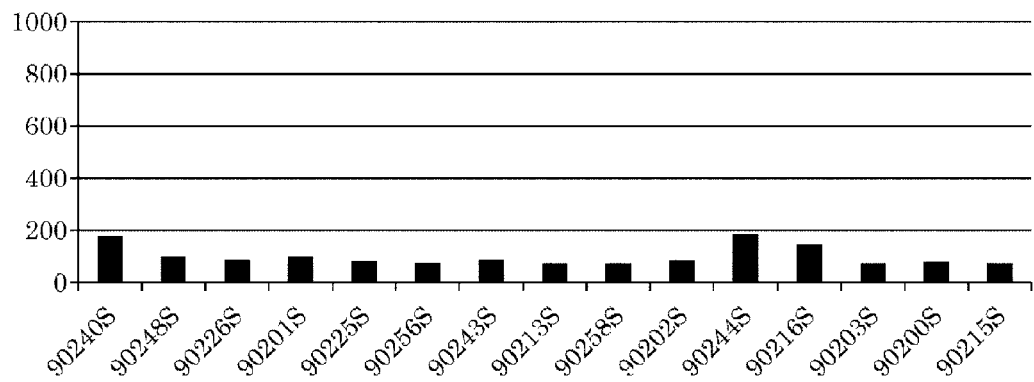

[Fig. 27-7]
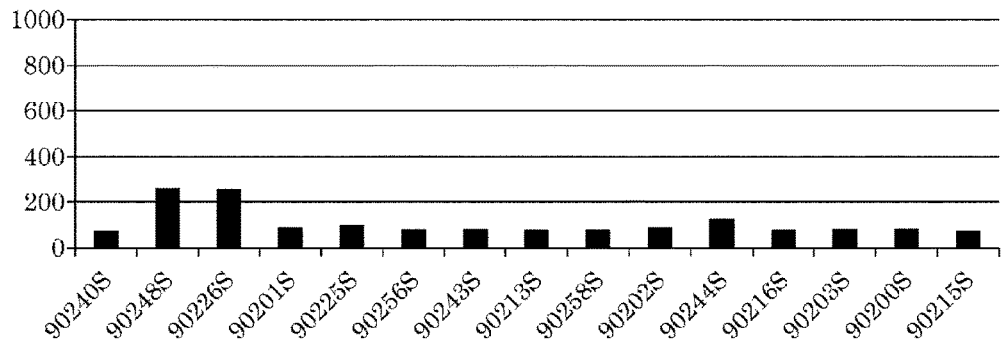
[Fig. 27-8]
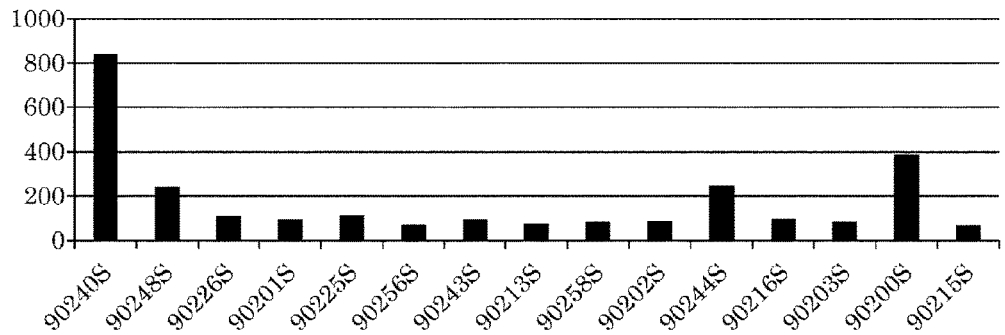
[Fig. 28-1]
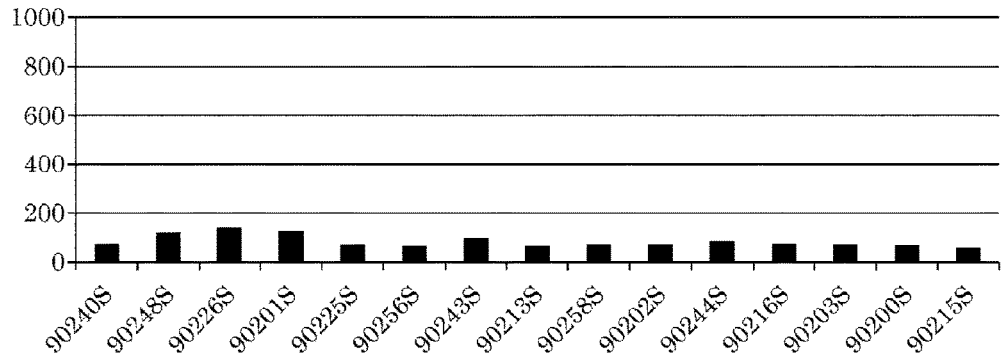

[Fig. 28-2]
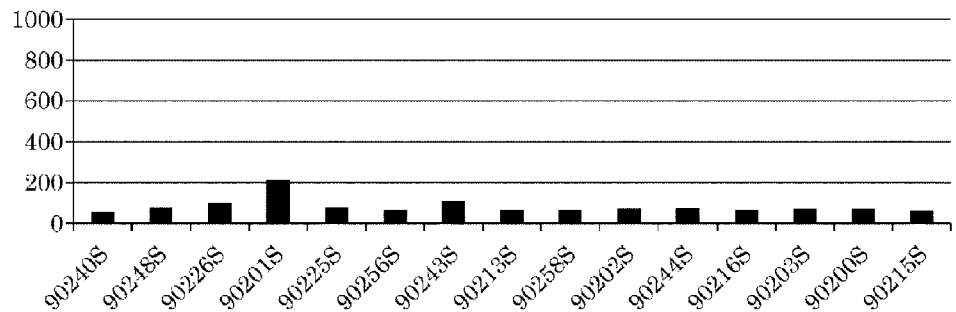
[Fig. 28-3]
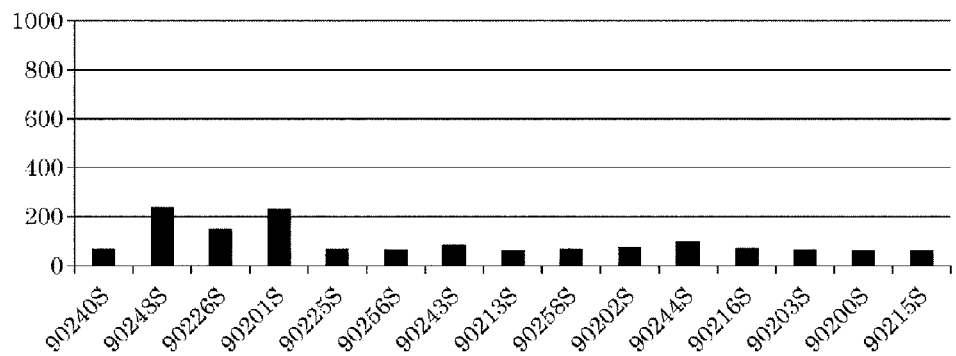
[Fig. 29-1]
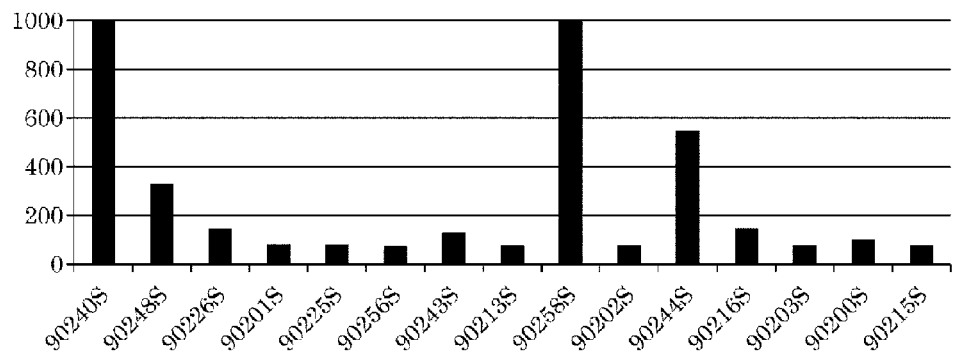

[Fig. 29-2]
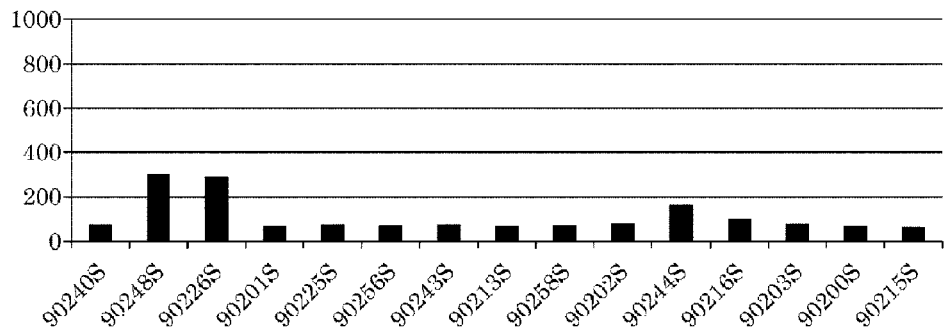
[Fig. 29-3]
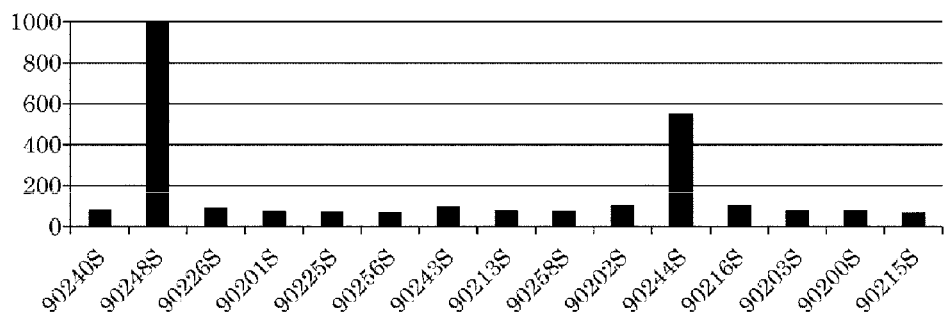
[Fig. 29-4]
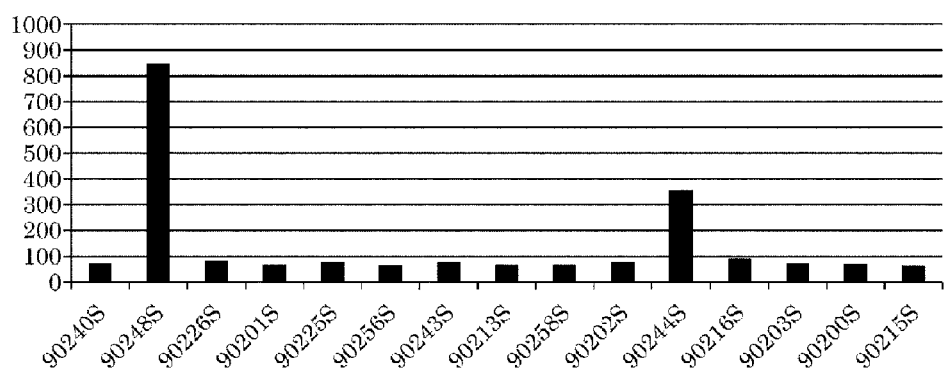

[Fig. 29-5]
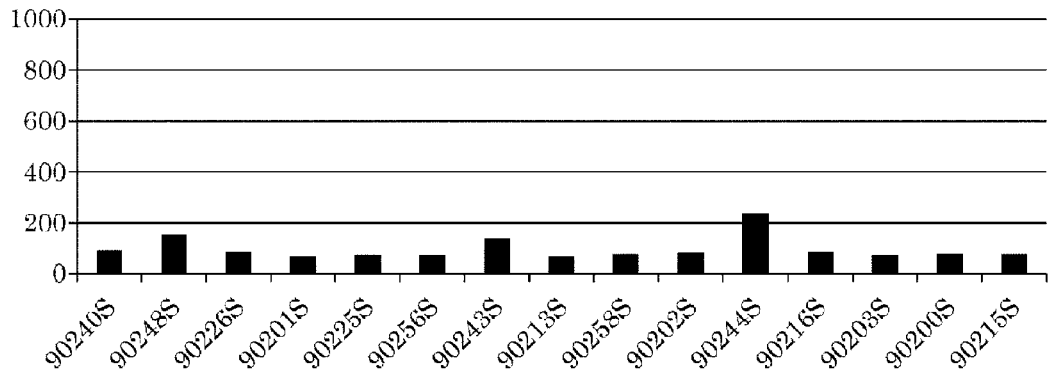
[Fig. 29-6]
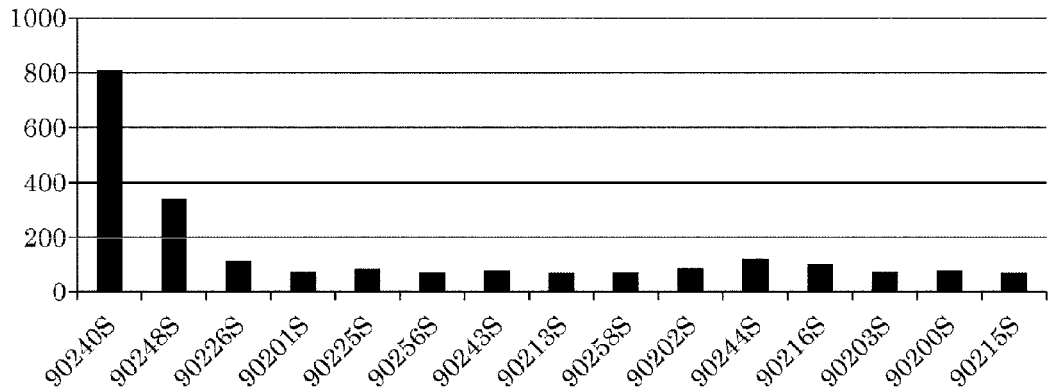
[Fig. 29-7]
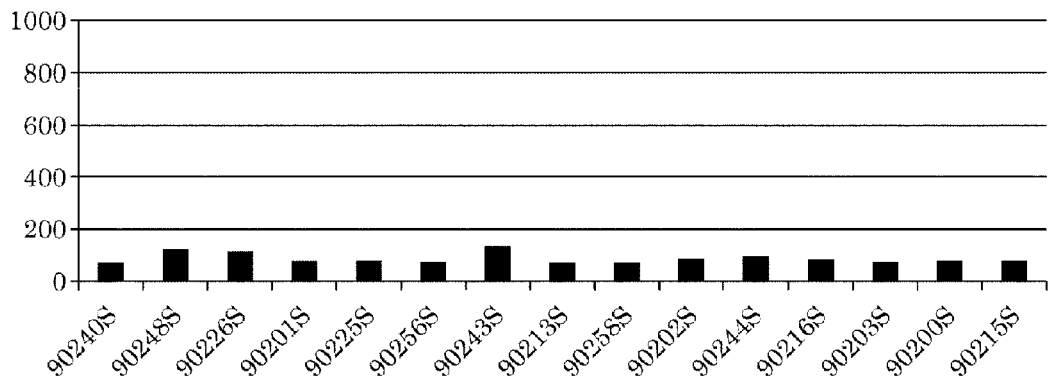

[Fig. 30-1]
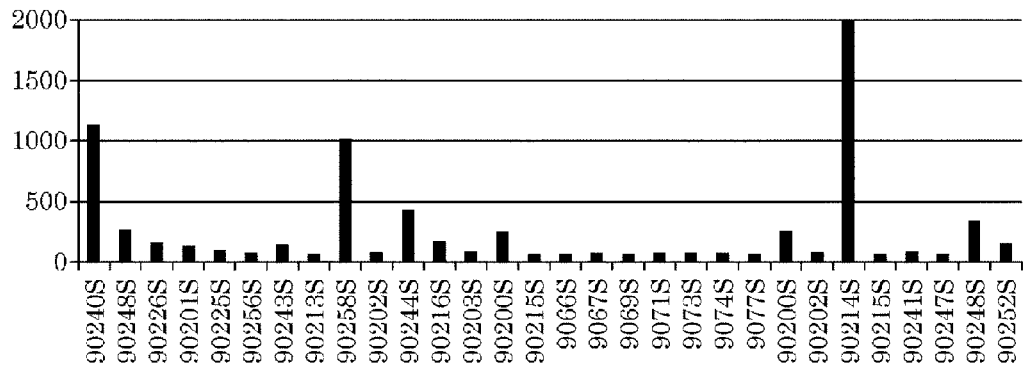
[Fig. 30-2]
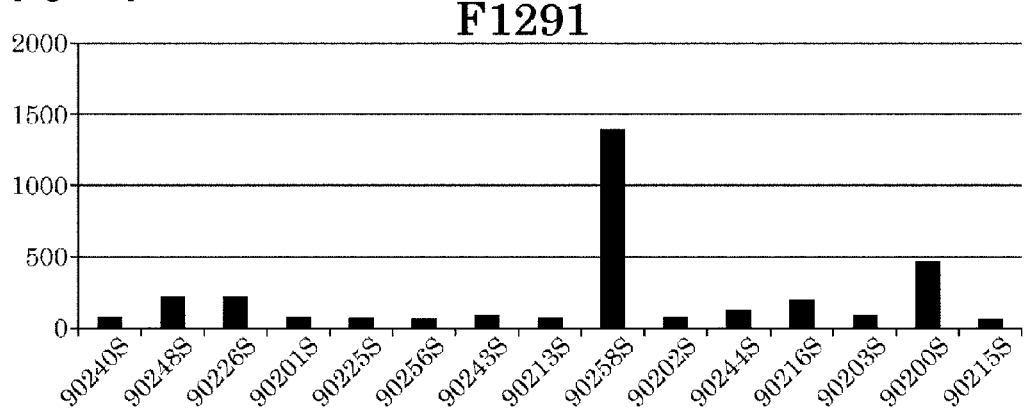
[Fig. 30-3]
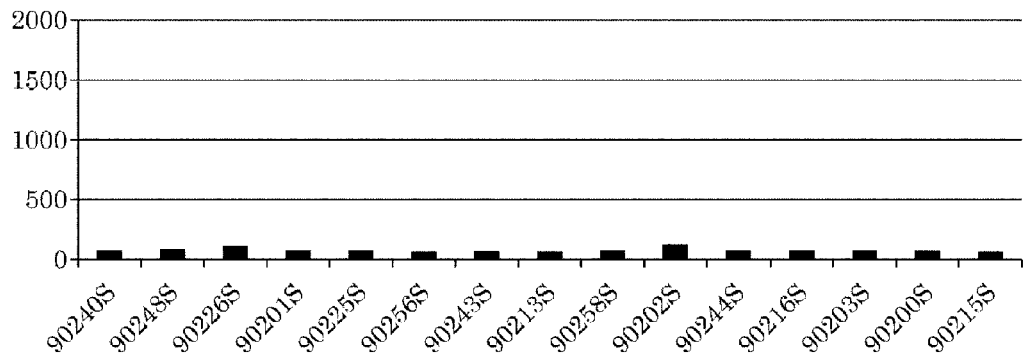

[Fig. 30-4]
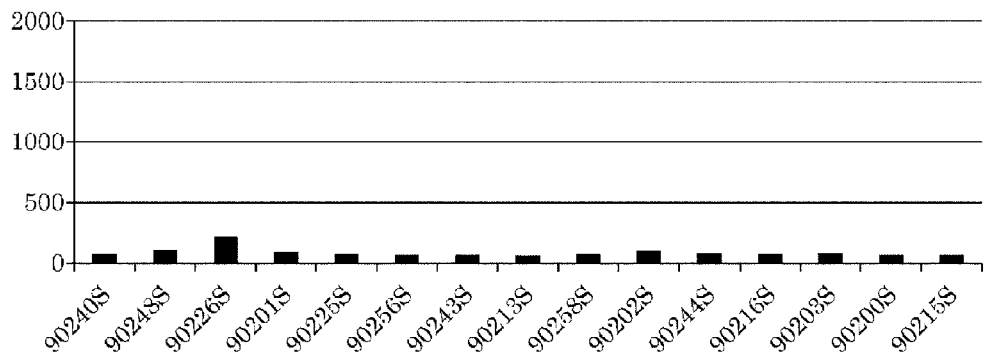
[Fig. 30-5]
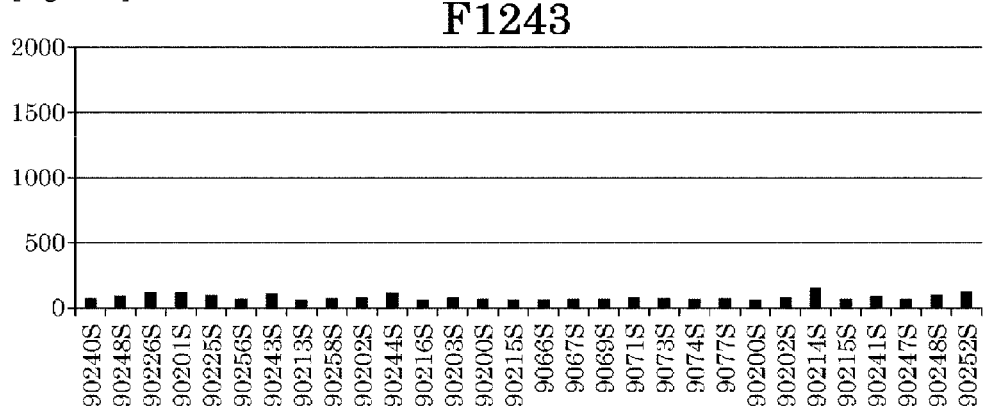
[Fig. 30-6]
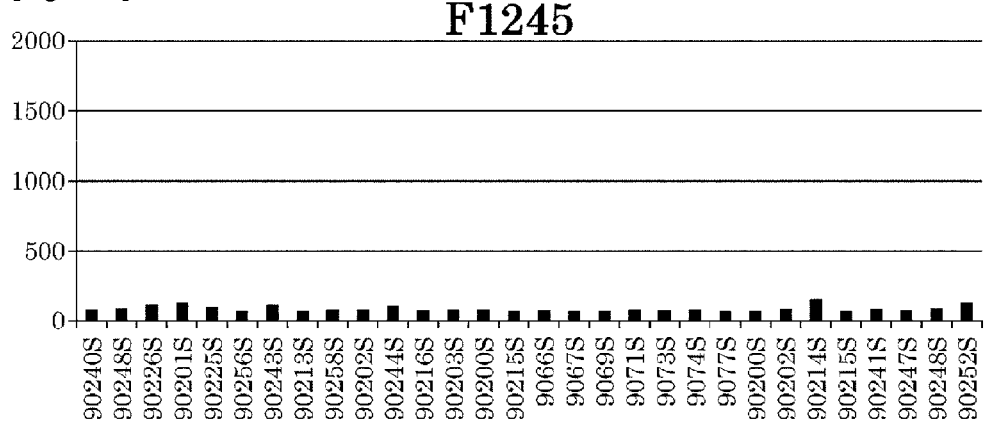

[Fig. 30-7]
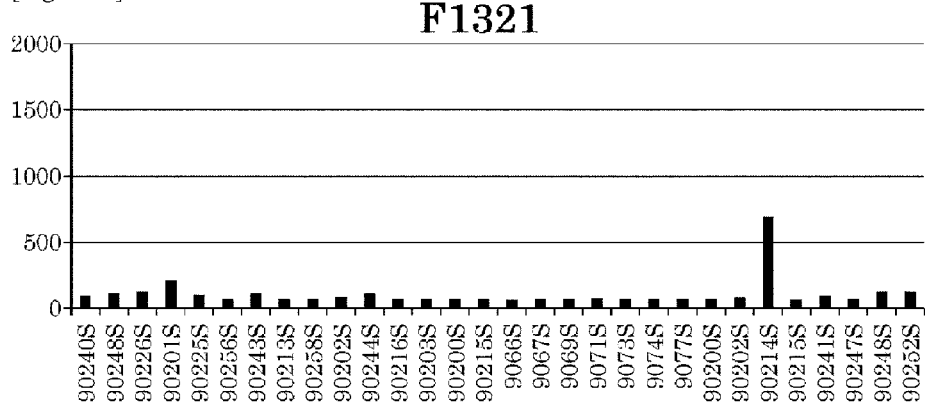
[Fig. 30-8]
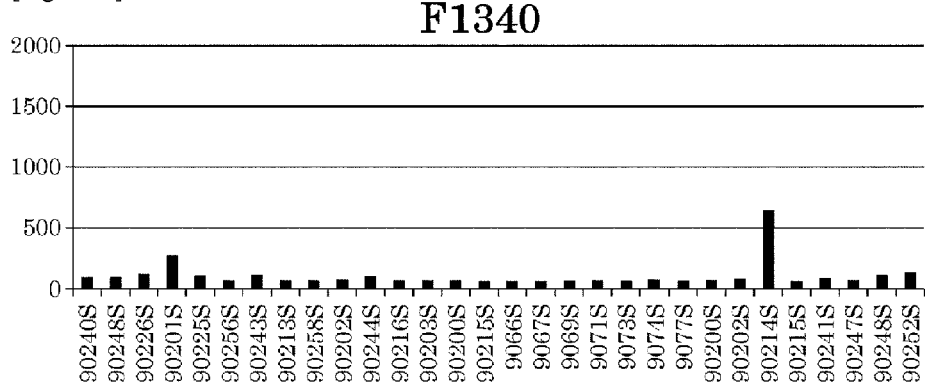
[Fig. 30-9]
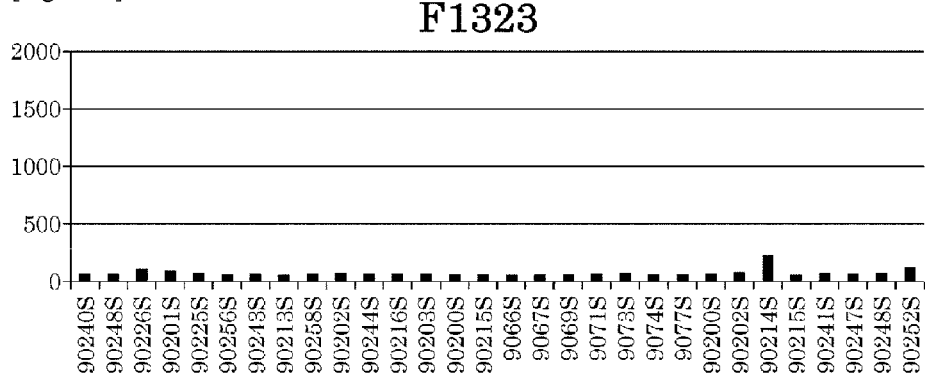

[Fig. 31-1]
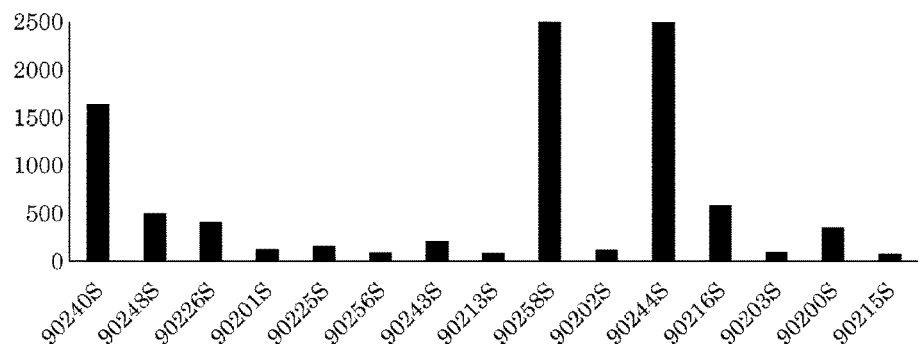
[Fig. 31-2]
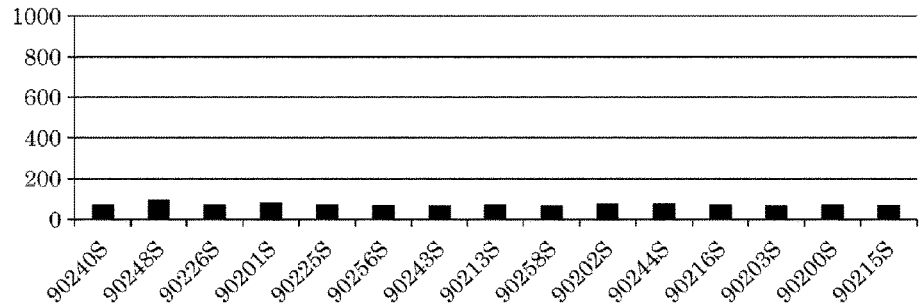
[Fig. 32-1]
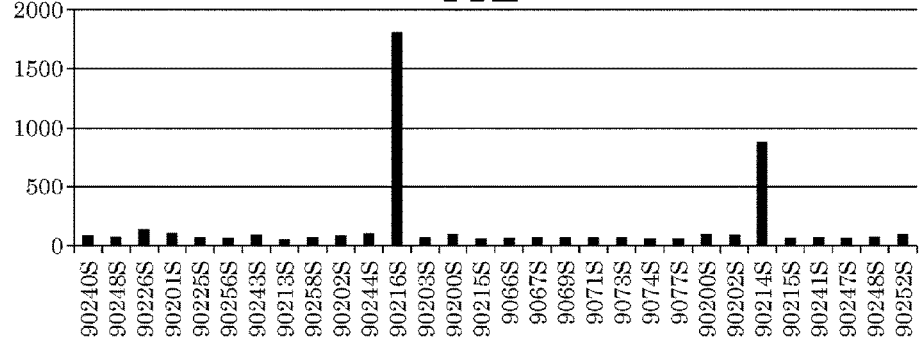

[Fig. 32-2]
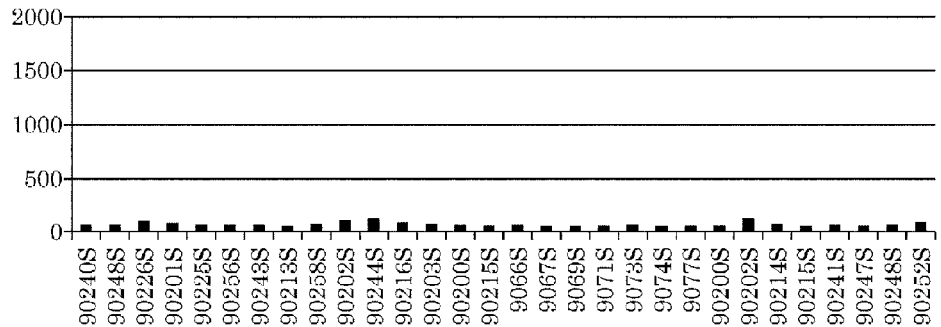
[Fig. 32-3]
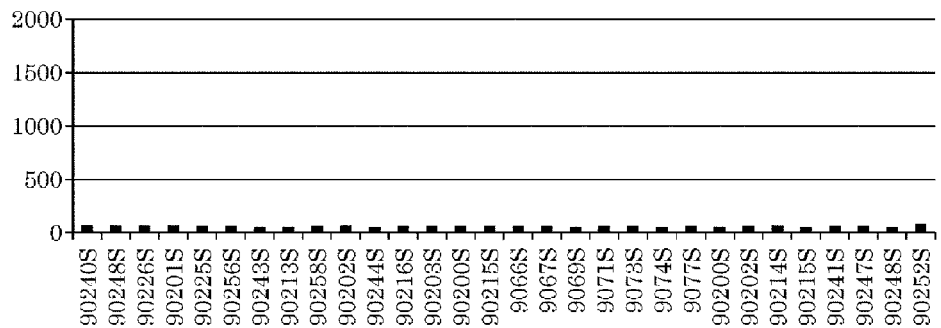
[Fig. 32-4]
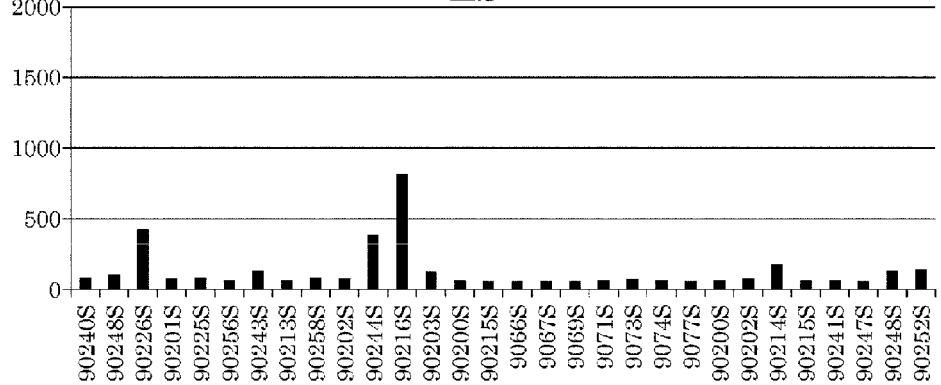

[Fig. 32-5]
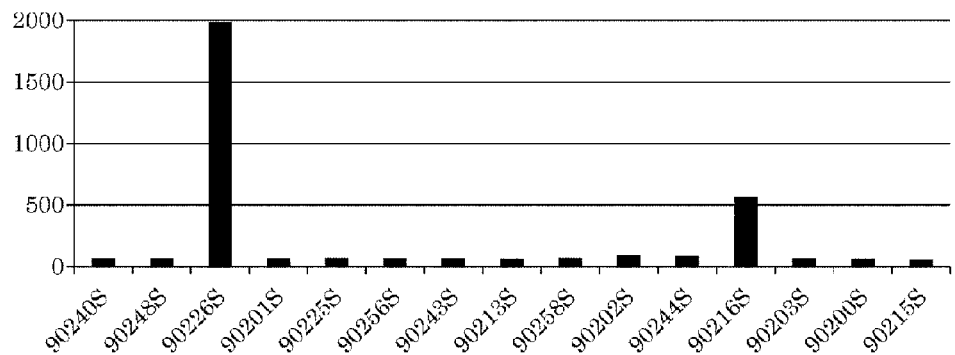
[Fig. 32-6]
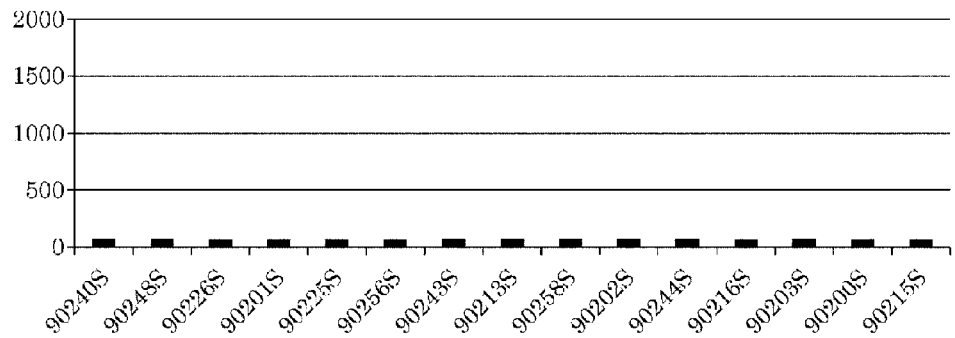
[Fig. 32-7]
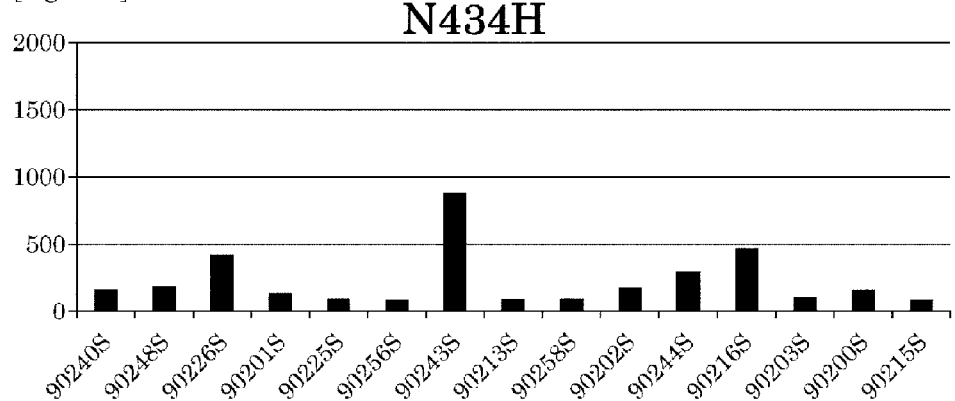

[Fig. 32-8]
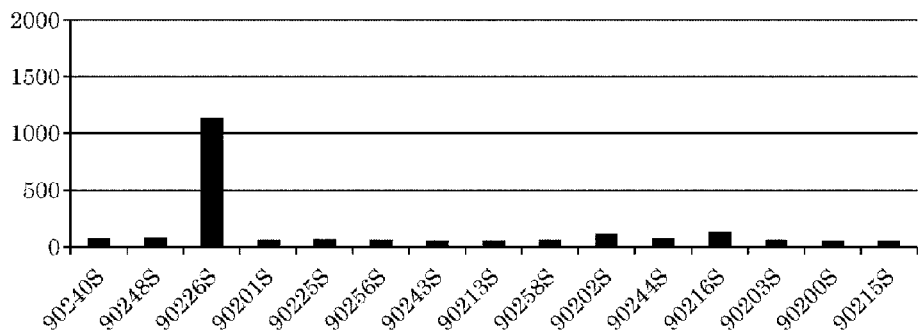
[Fig. 32-9]
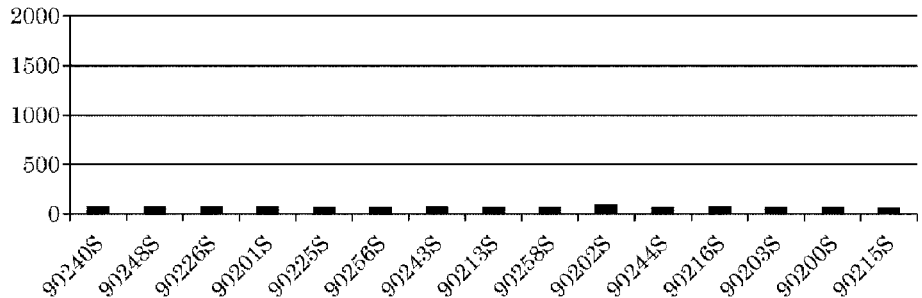
[Fig. 33-1]
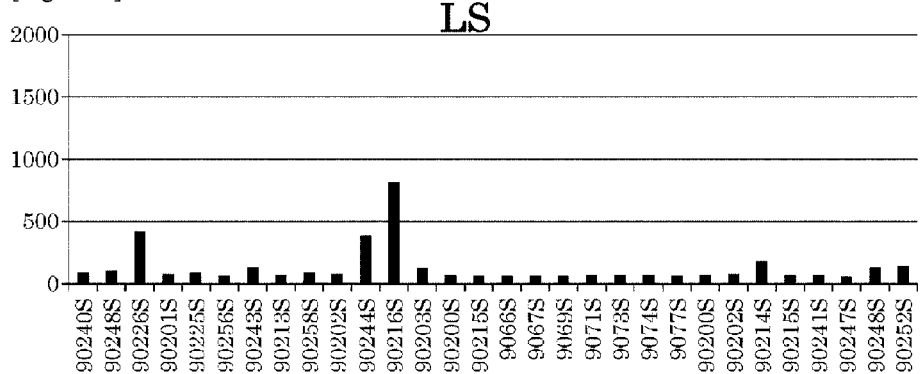

[Fig. 33-2]
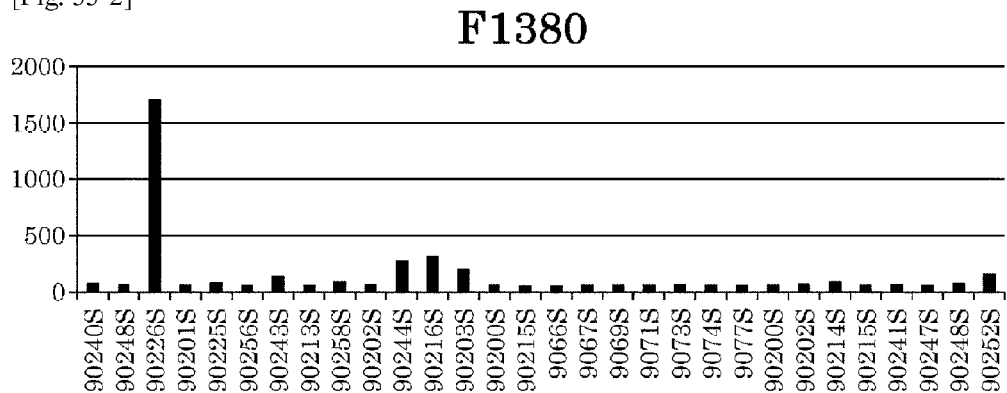
[Fig. 33-3]
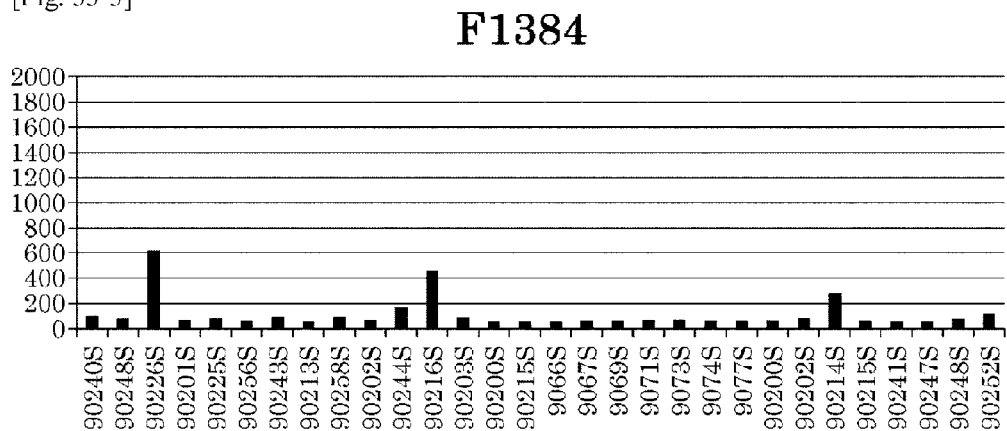
[Fig. 33-4]
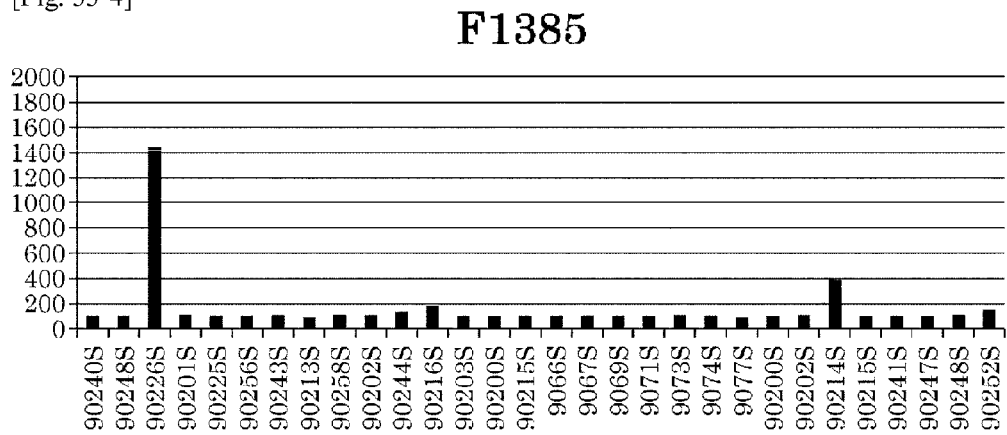

[Fig. 33-5]
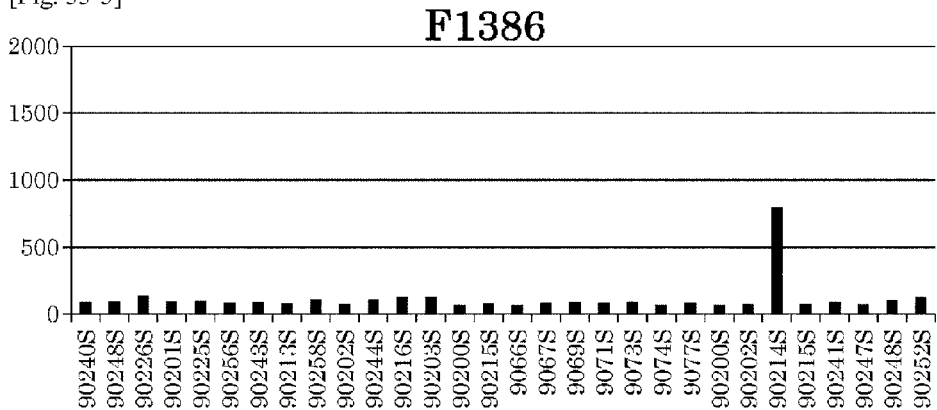
[Fig. 33-6]
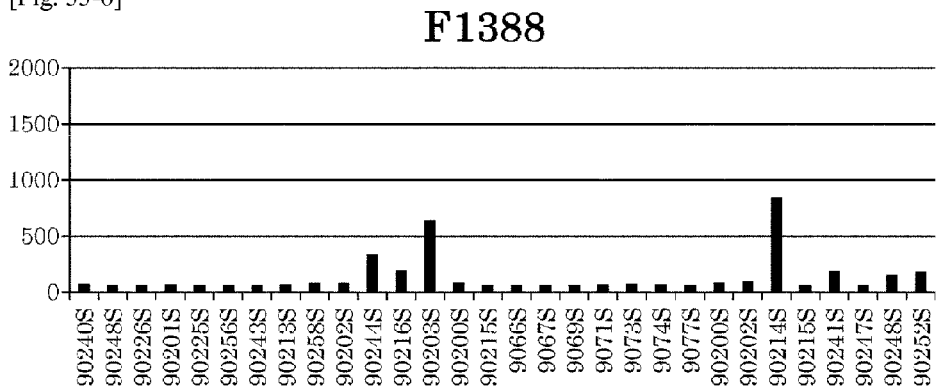
[Fig. 33-7]
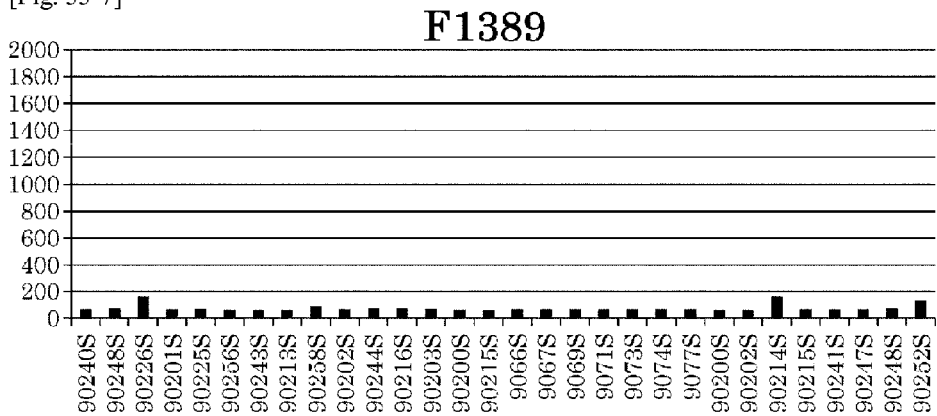

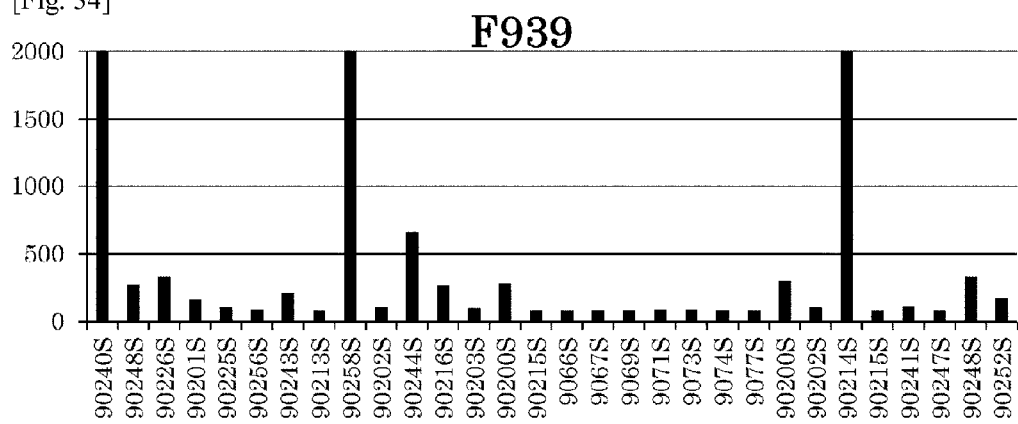
[Fig. 34]
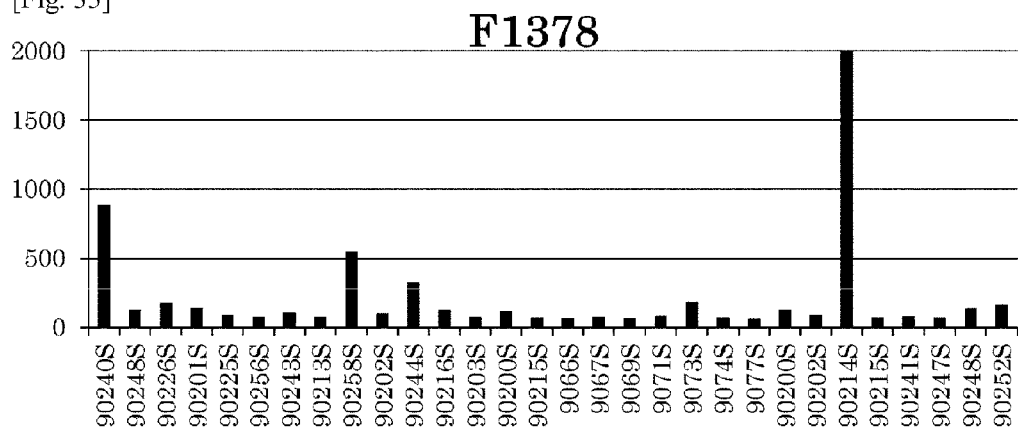
[Fig. 35]
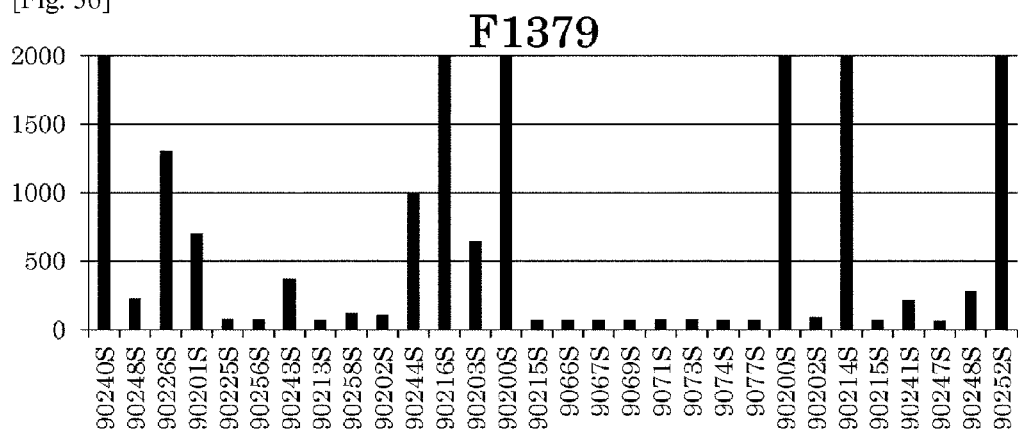
[Fig. 36]

[Fig. 37]
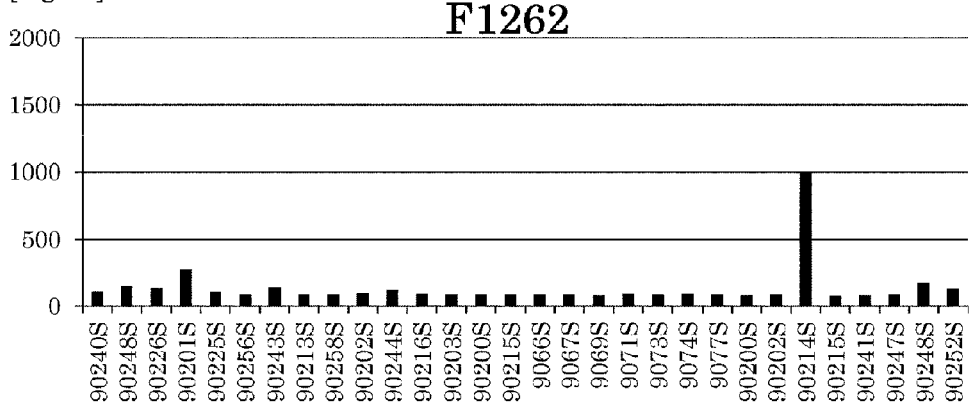
[Fig. 38]
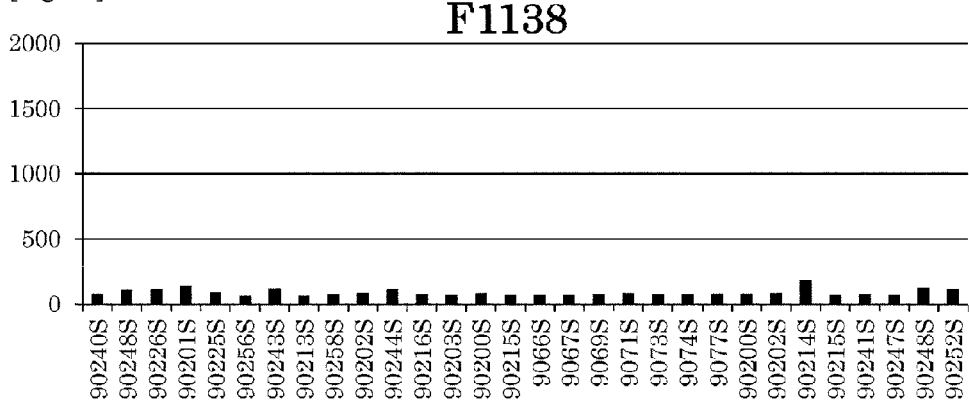
[Fig. 39]
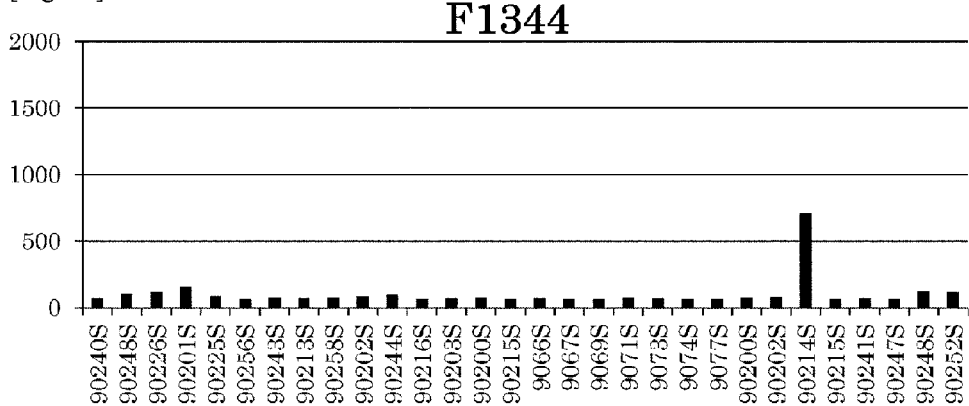

[Fig. 40]
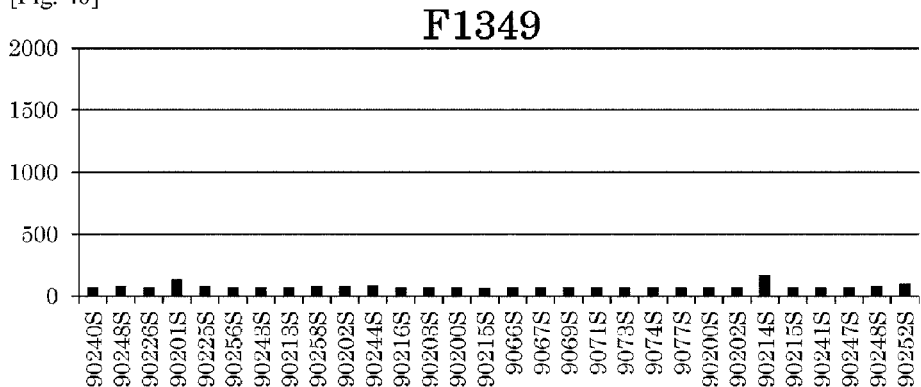
[Fig. 41]
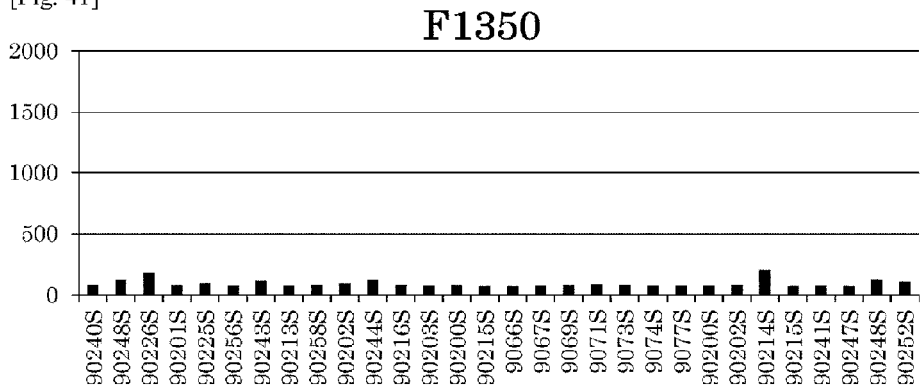
[Fig. 42]
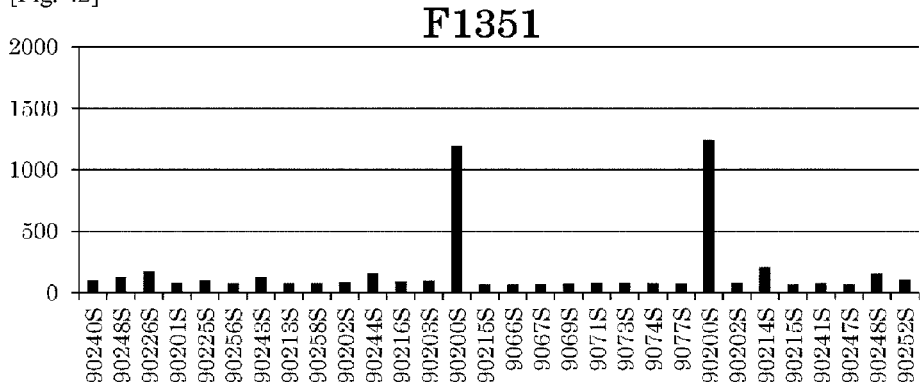

[Fig. 43]
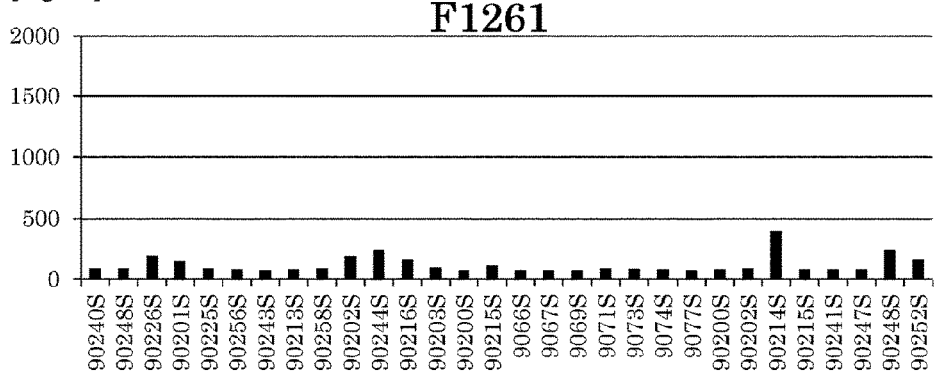
[Fig. 44]
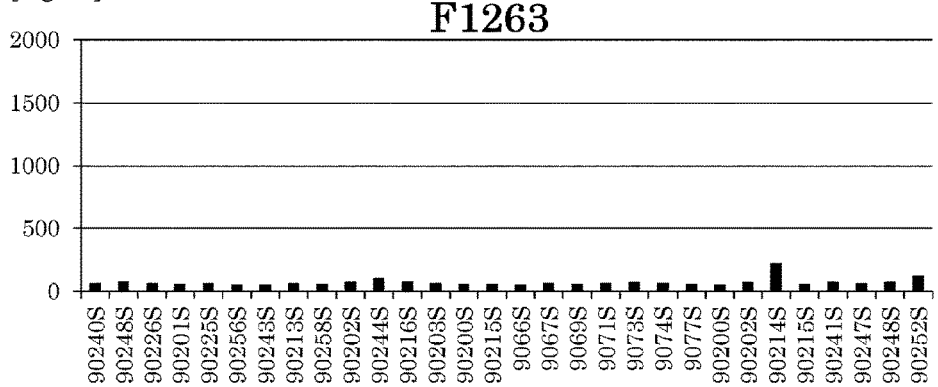
[Fig. 45]
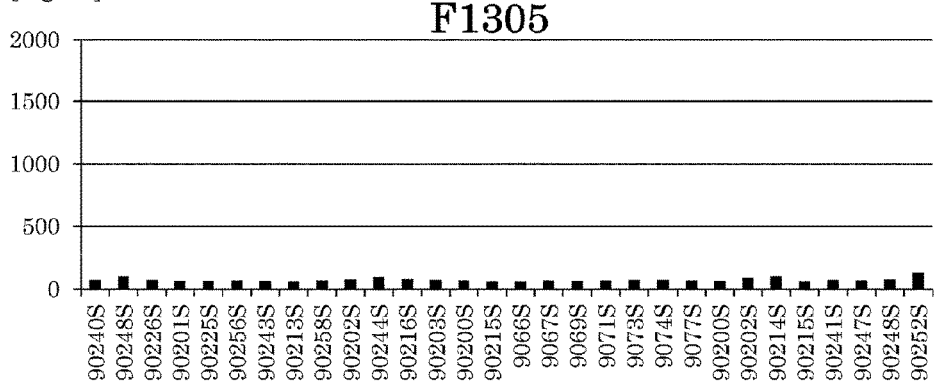

[Fig. 46]
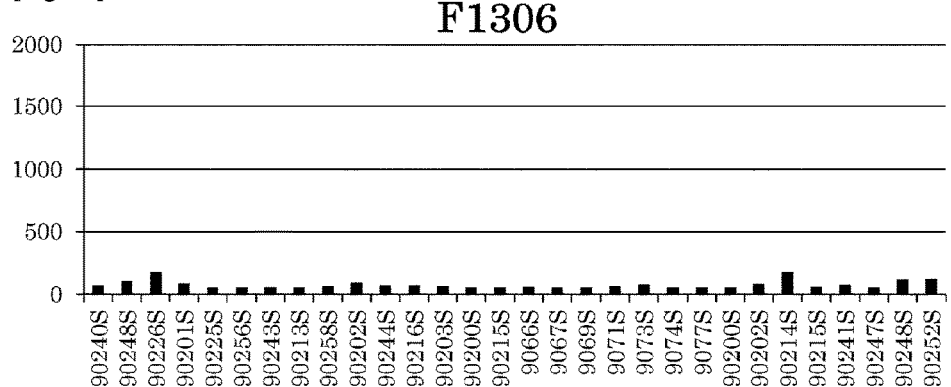
[Fig. 47]
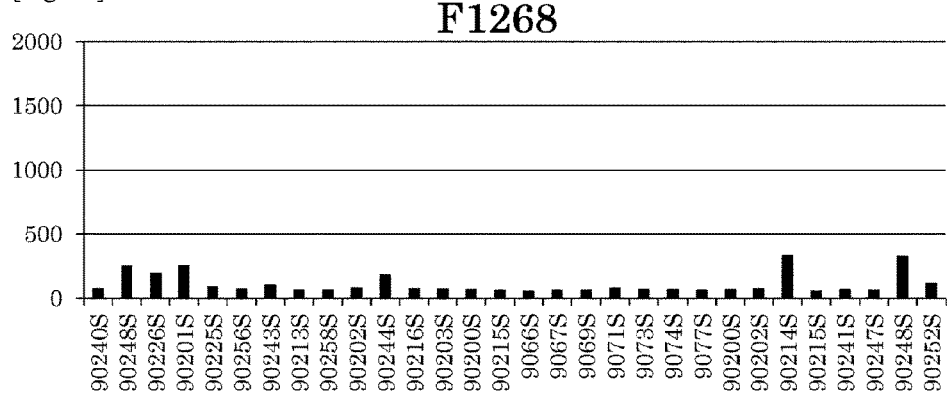
[Fig. 48]
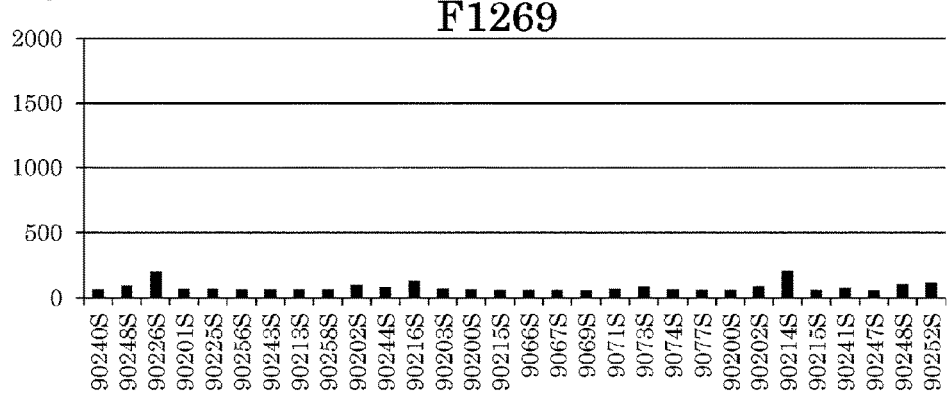

[Fig. 49]
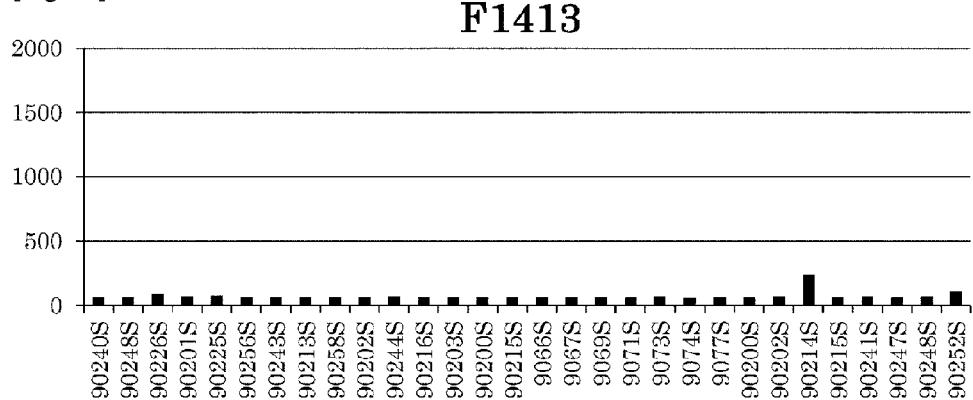
[Fig. 50]
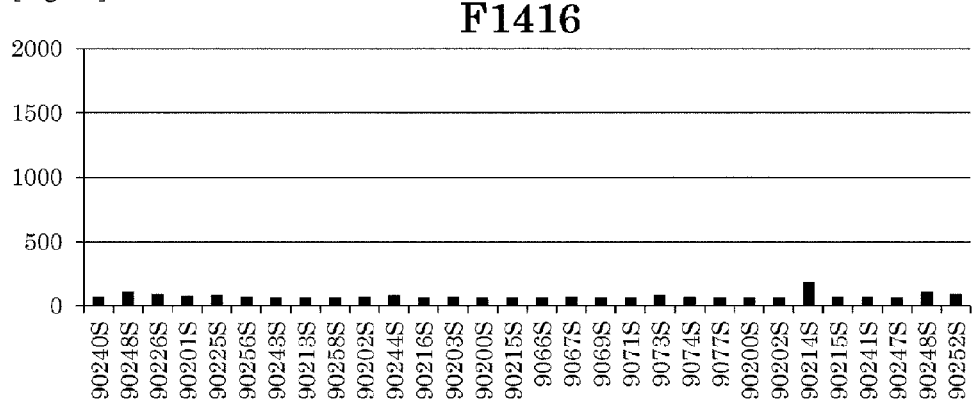
[Fig. 51]
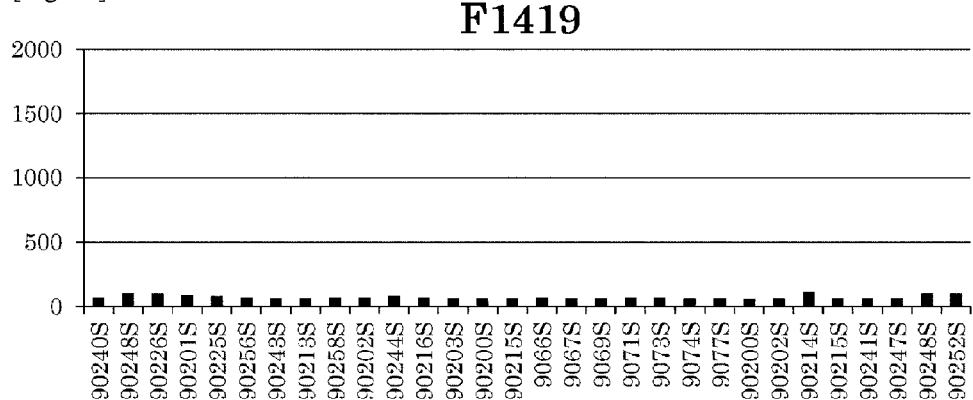

[Fig. 52]
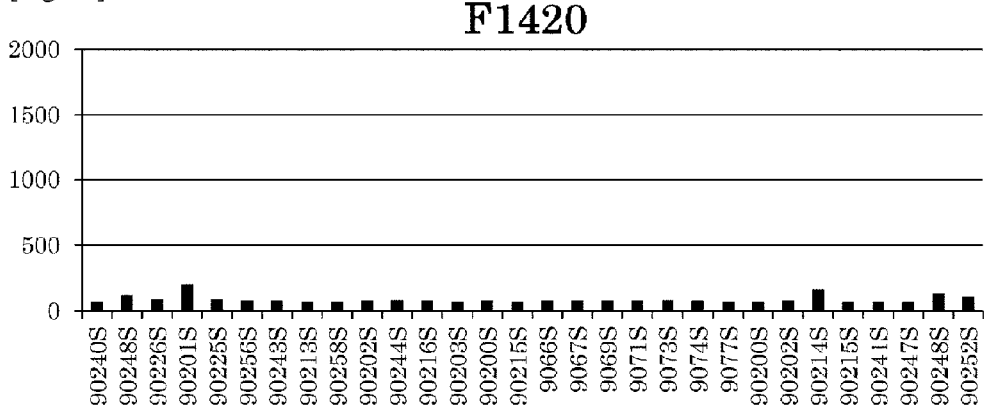
[Fig. 53]
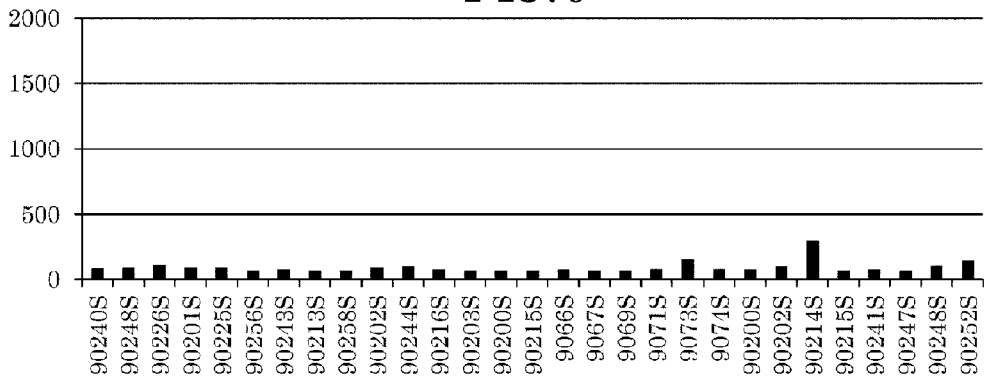
[Fig. 54]
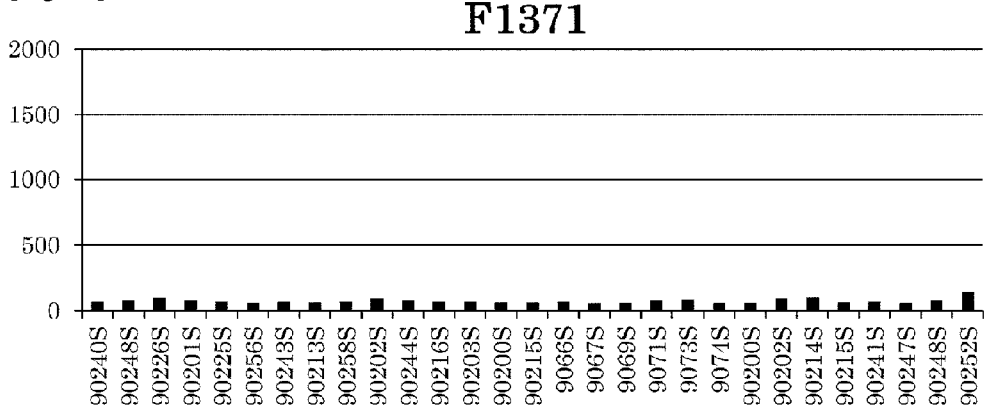

[Fig. 55]
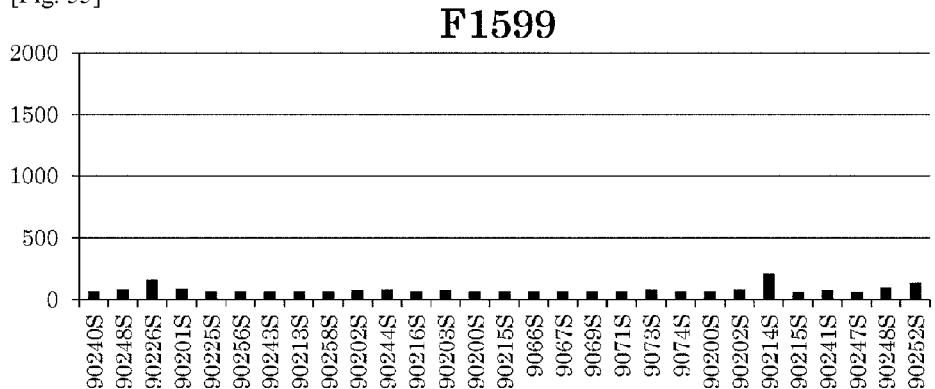
[Fig. 56]
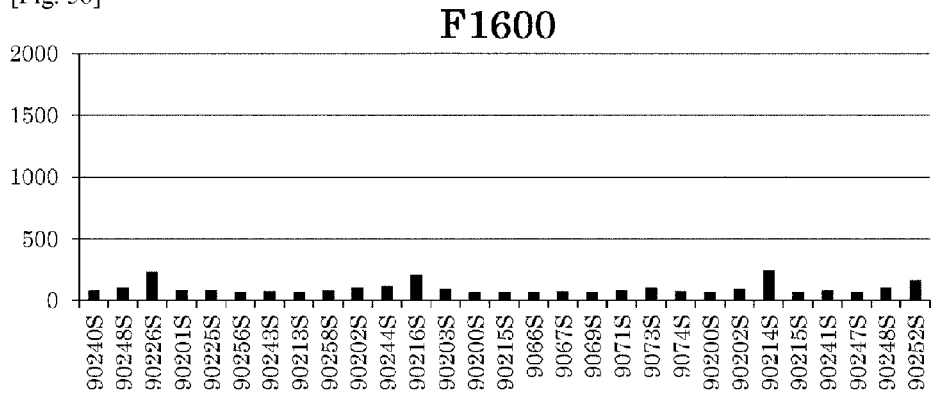
[Fig. 57]
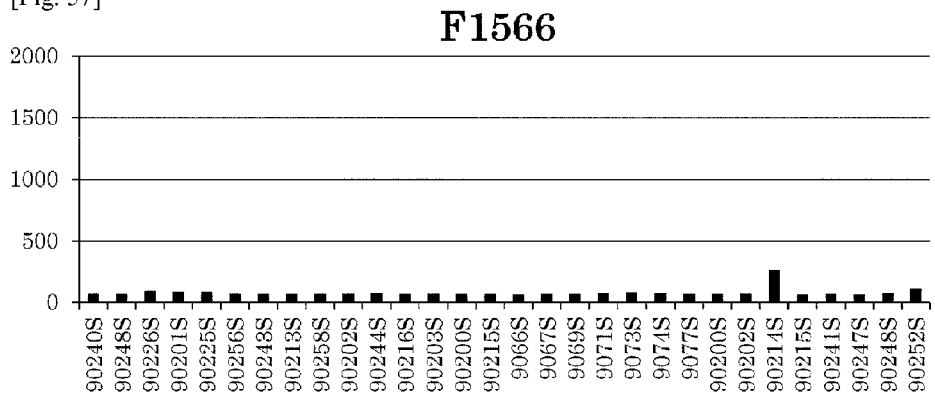

[Fig. 58]
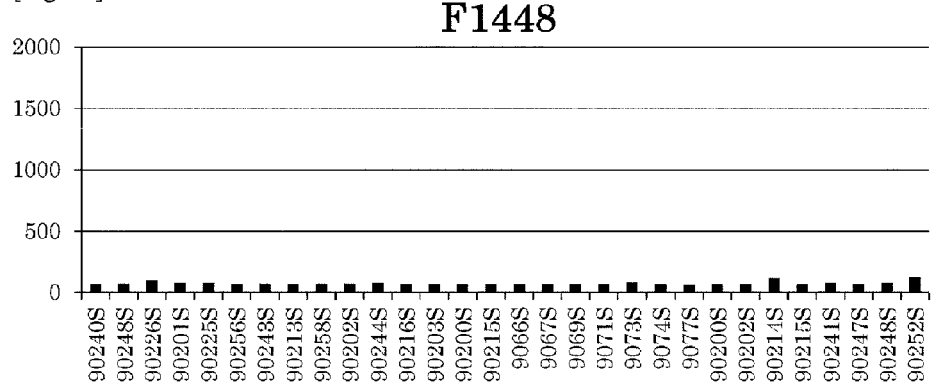
[Fig. 59]
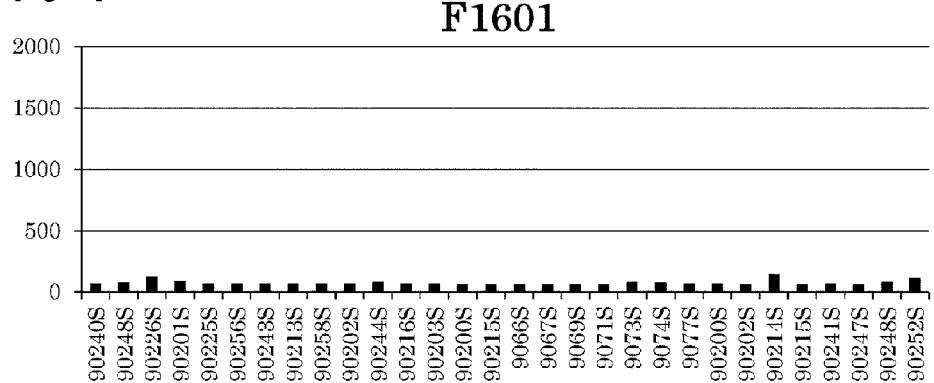
[Fig. 60]
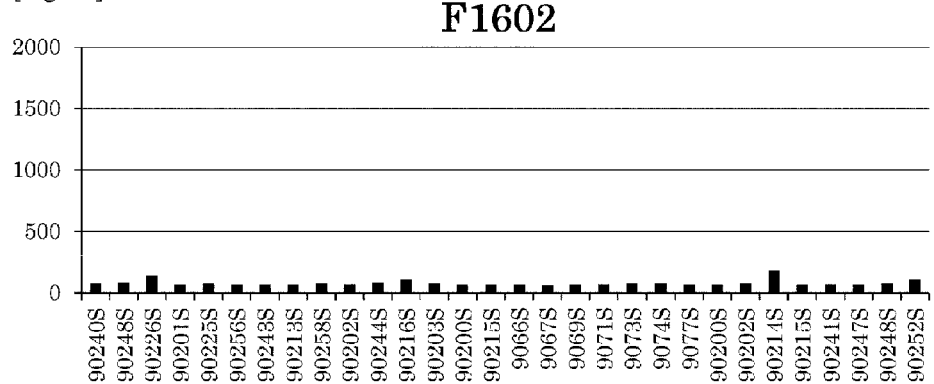

[Fig. 61]
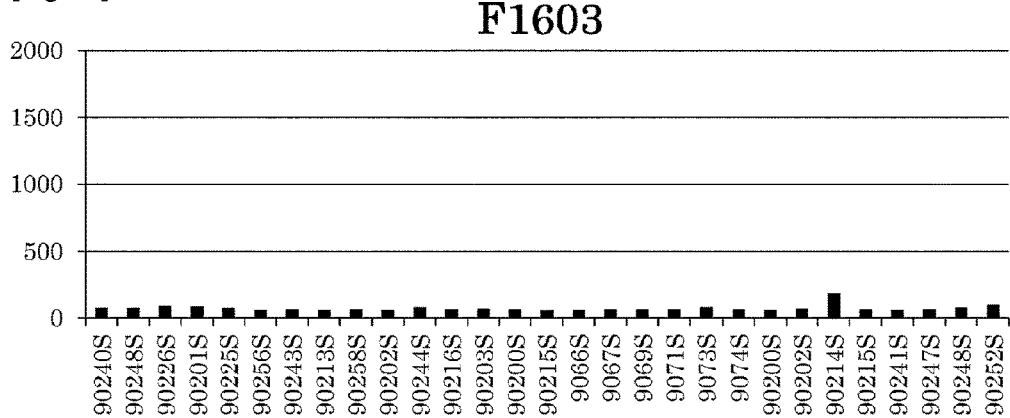
[Fig. 62]
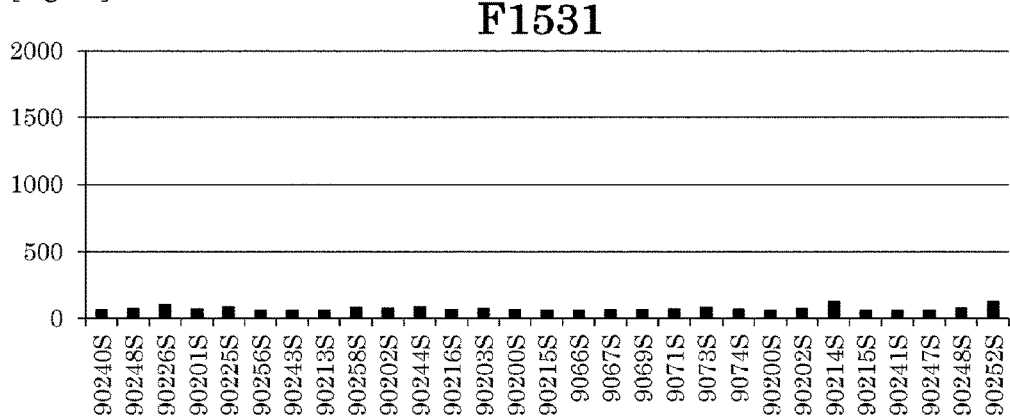
[Fig. 63]
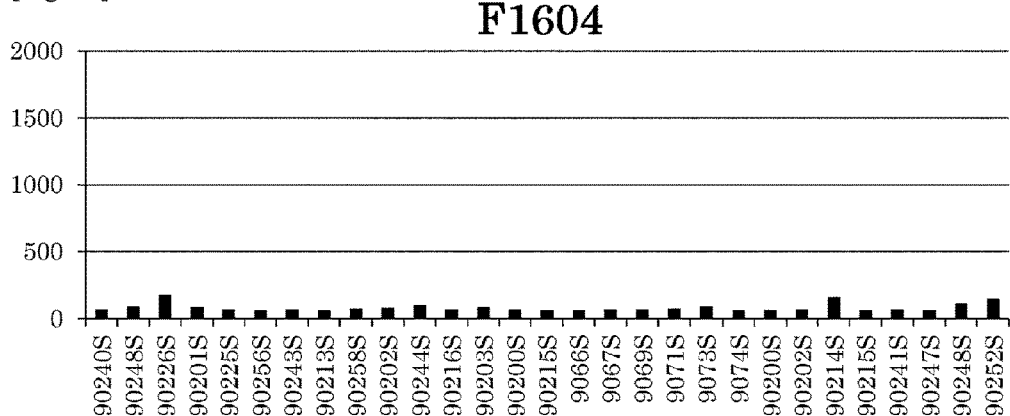

[Fig. 64]
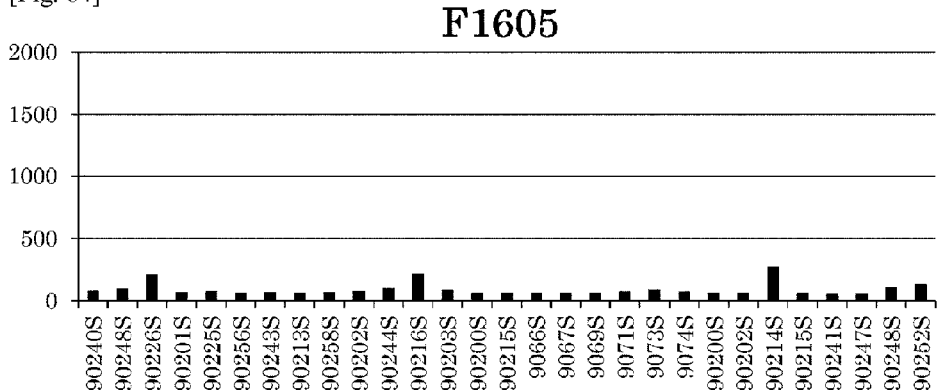
[Fig. 65]
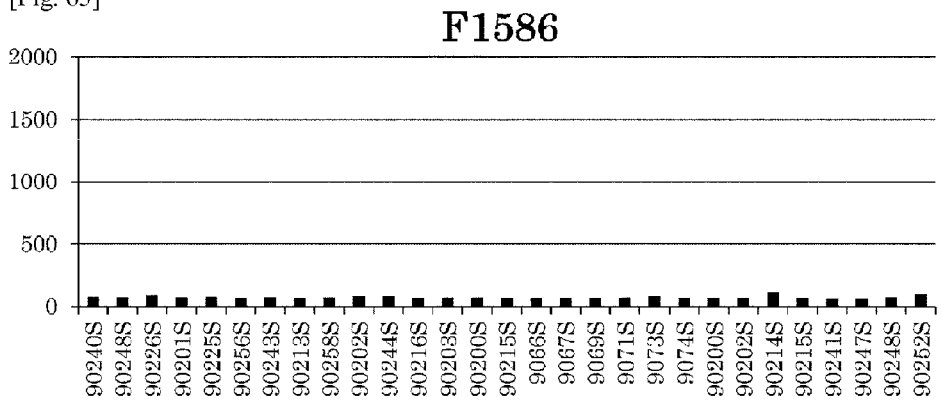
[Fig. 66]
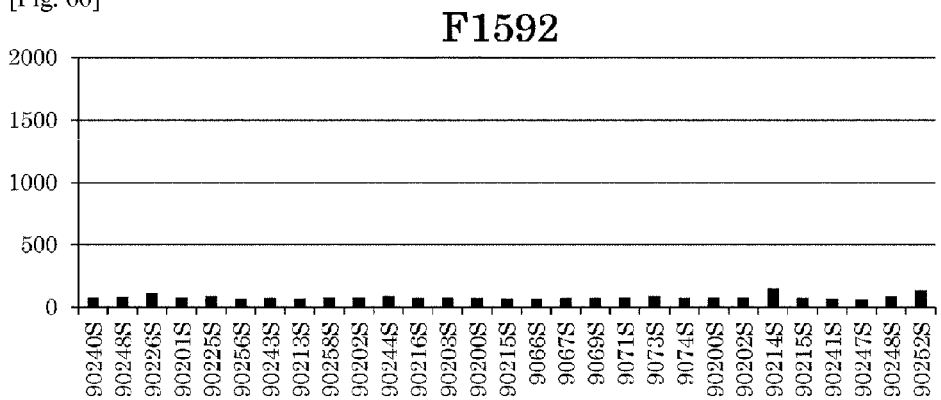

[Fig. 67]
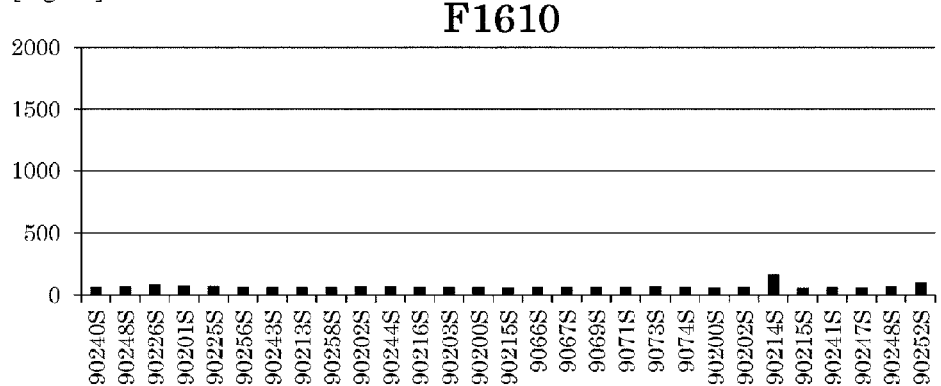
[Fig. 68]
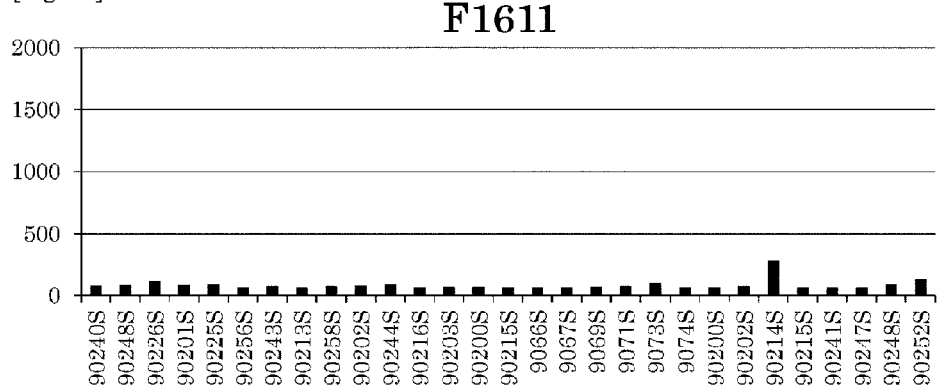
[Fig. 69]
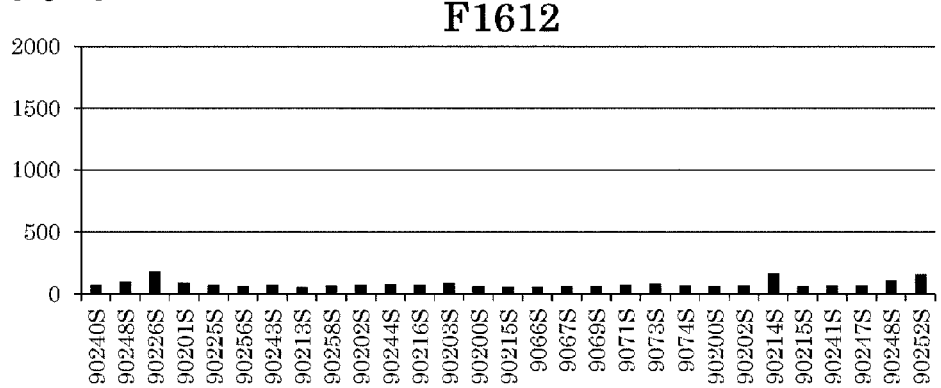

[Fig. 70]
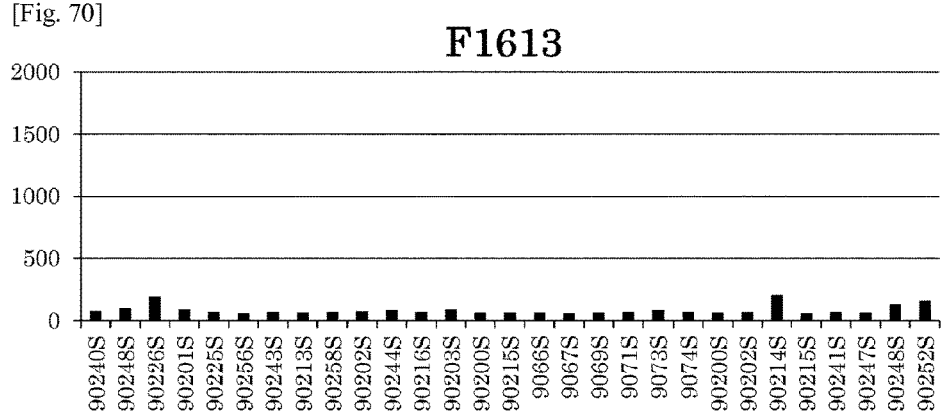
[Fig. 71]
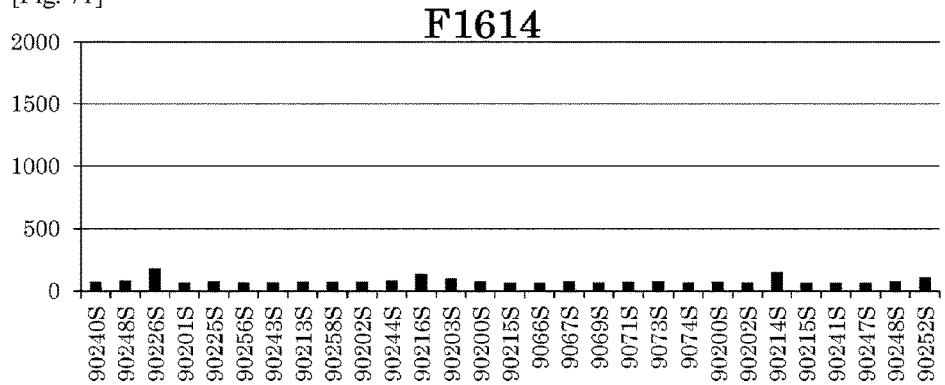
[Fig. 72]
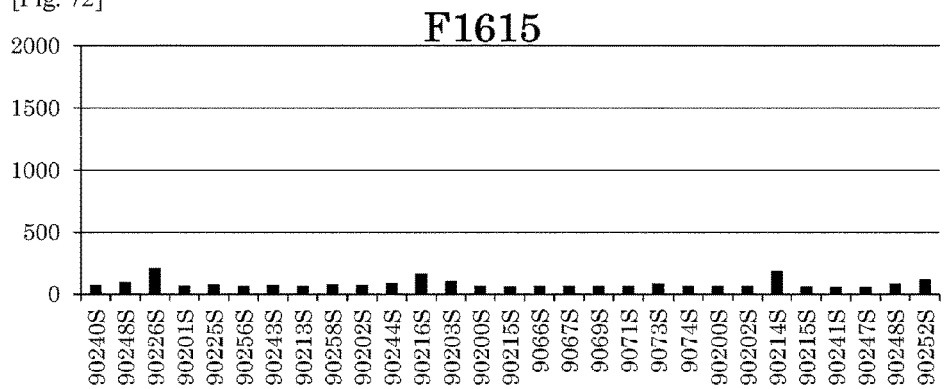

[Fig. 73]
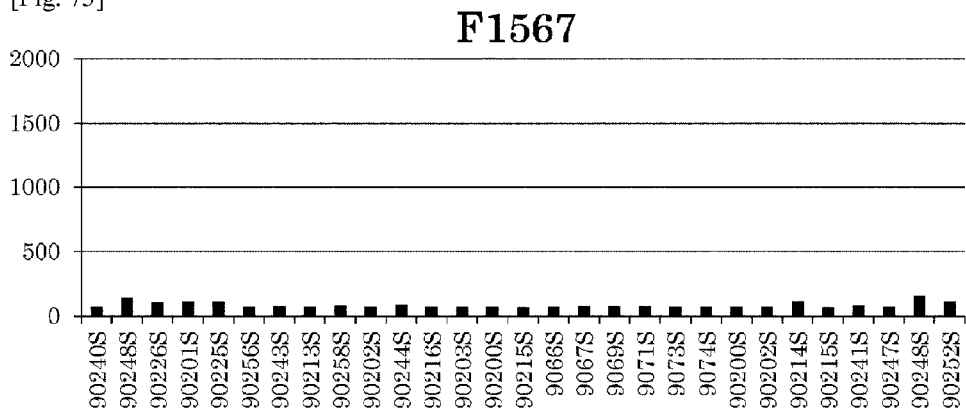
[Fig. 74]
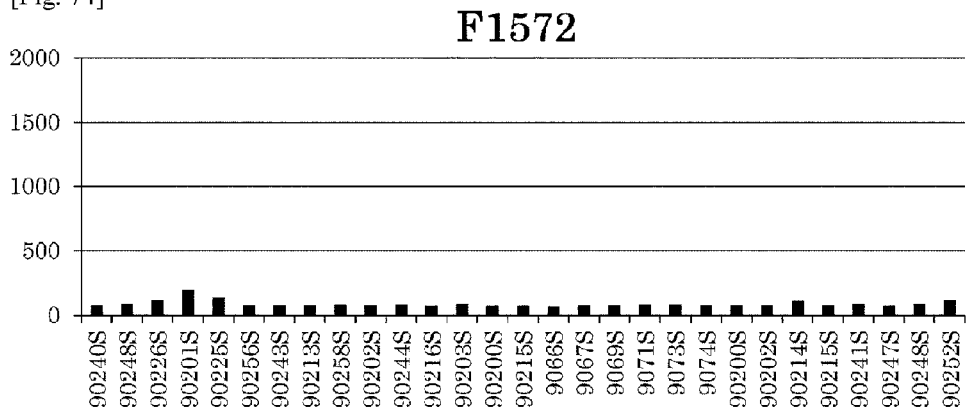
[Fig. 75]
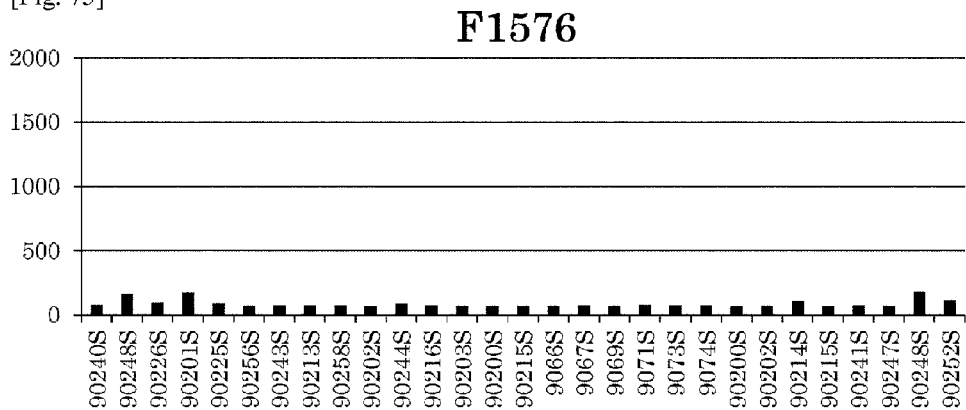

[Fig. 76]
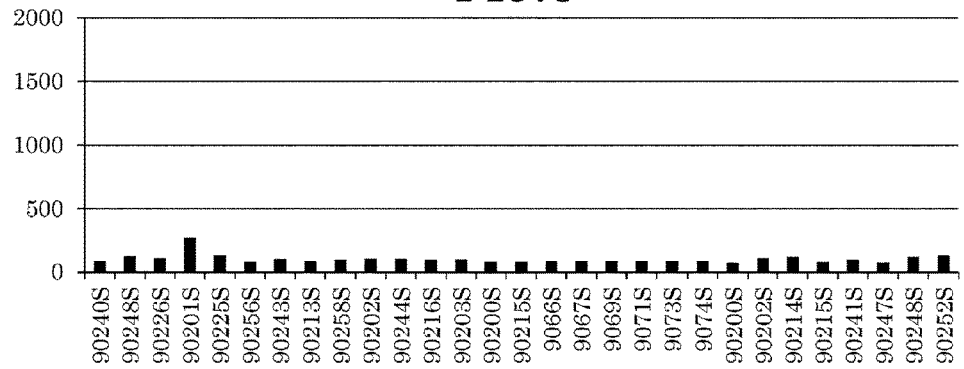
[Fig. 77]
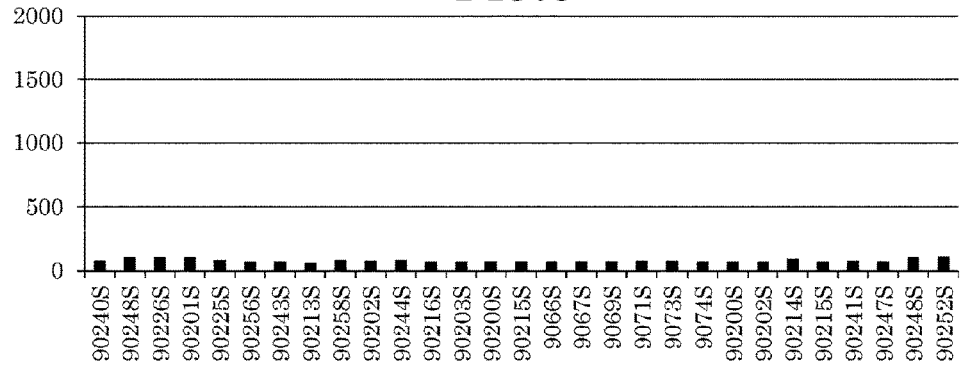
[Fig. 78]
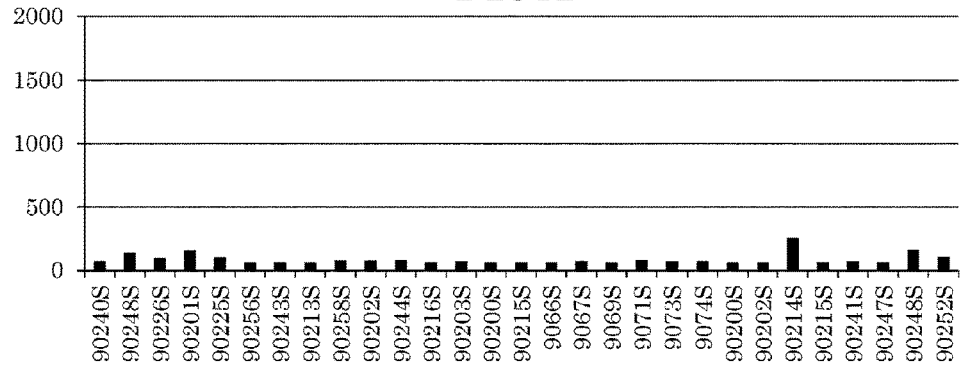

[Fig. 79]
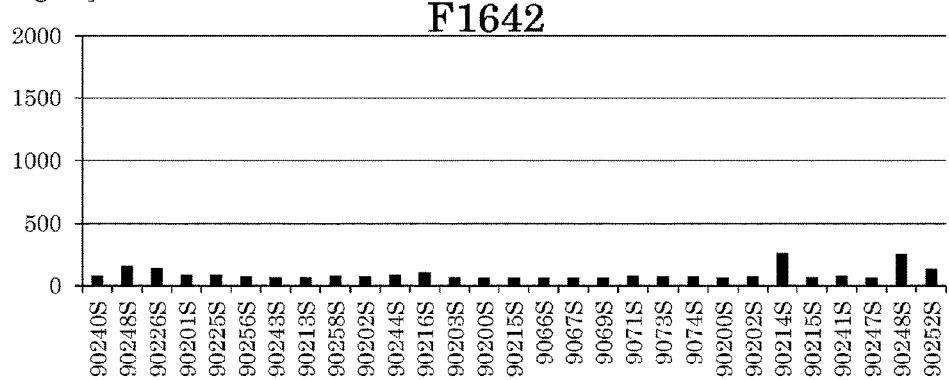
[Fig. 80]
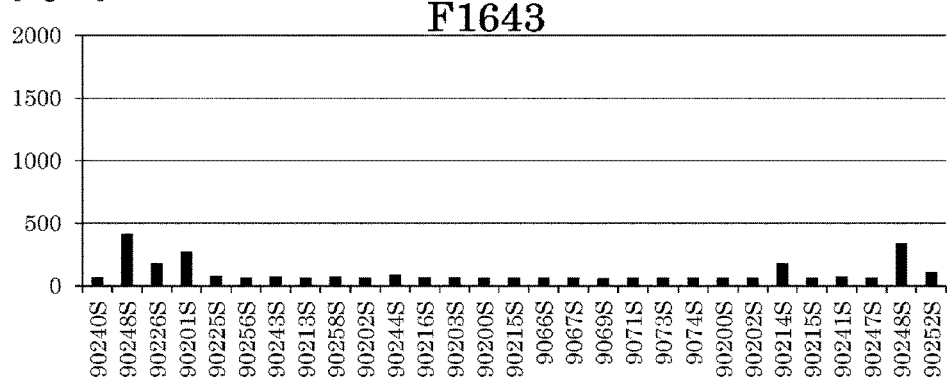
[Fig. 81]
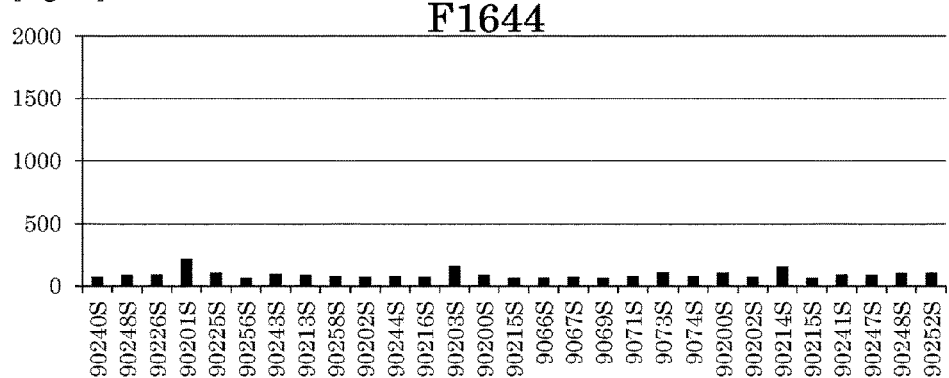

Fig. 82]
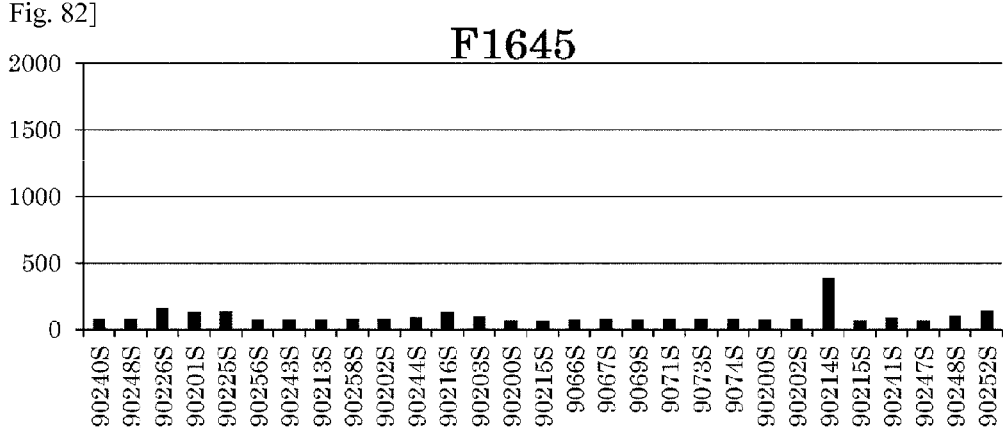
[Fig. 83]
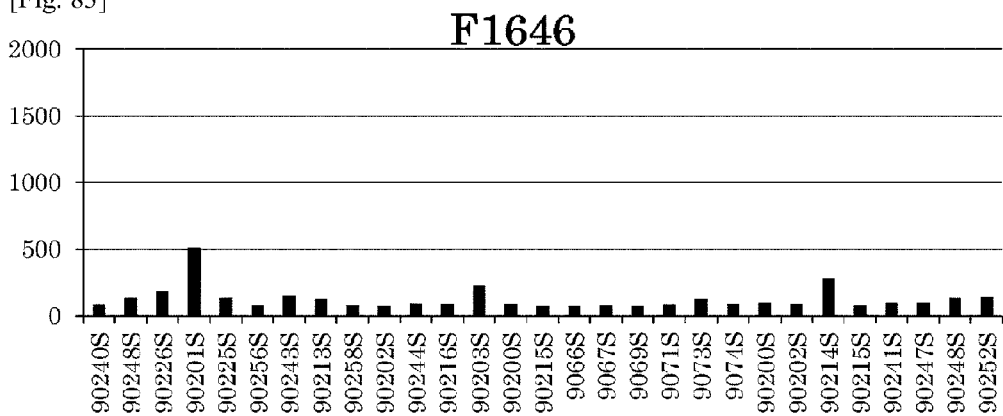
[Fig. 84]
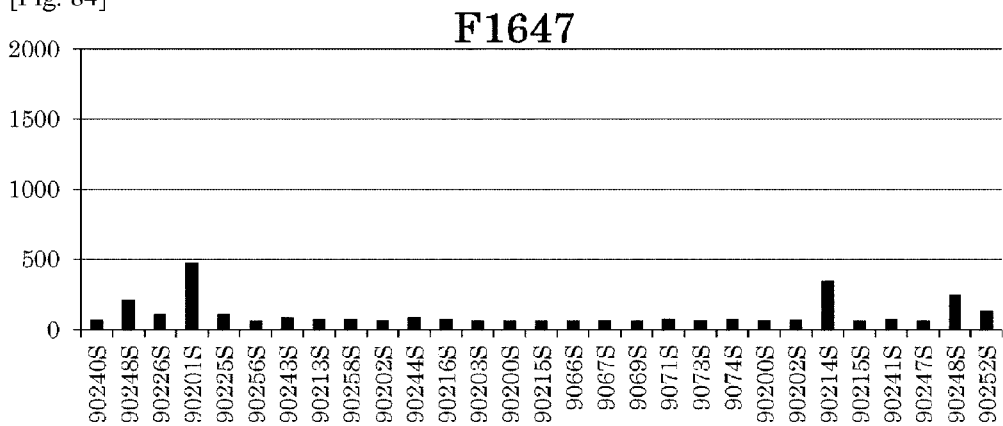

[Fig. 85]
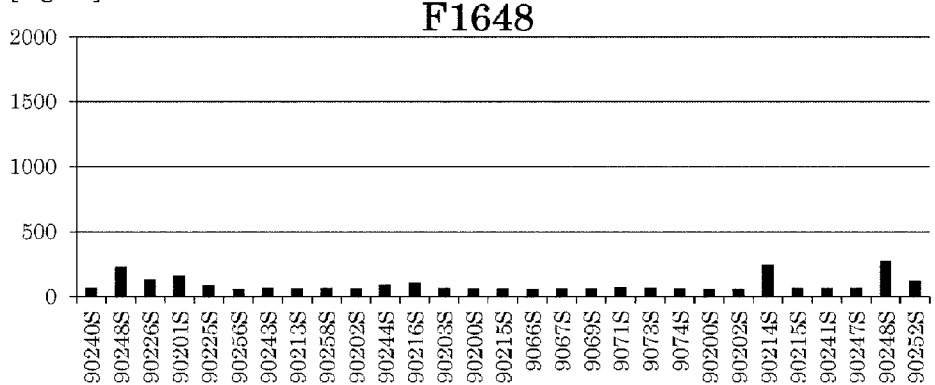
[Fig. 86]
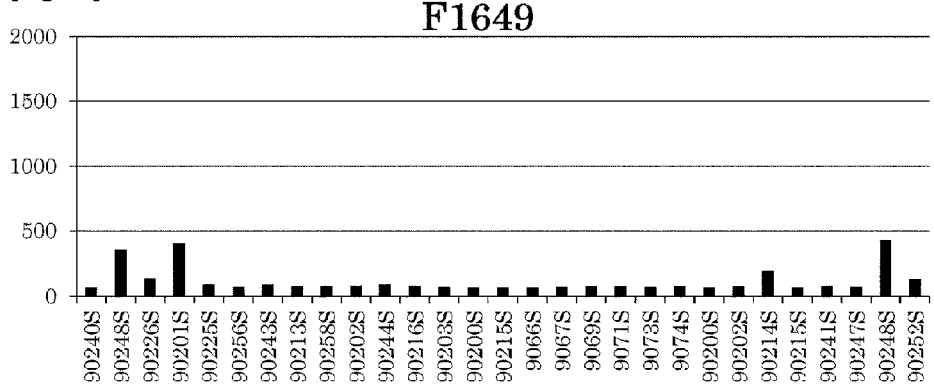
[Fig. 87]
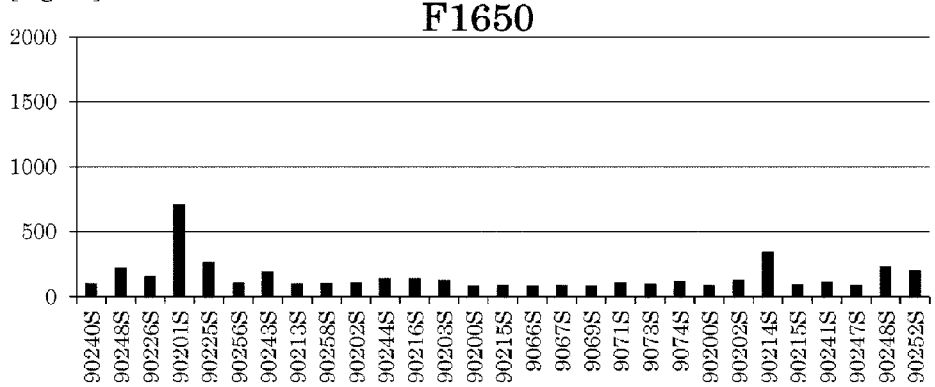

[Fig. 88]
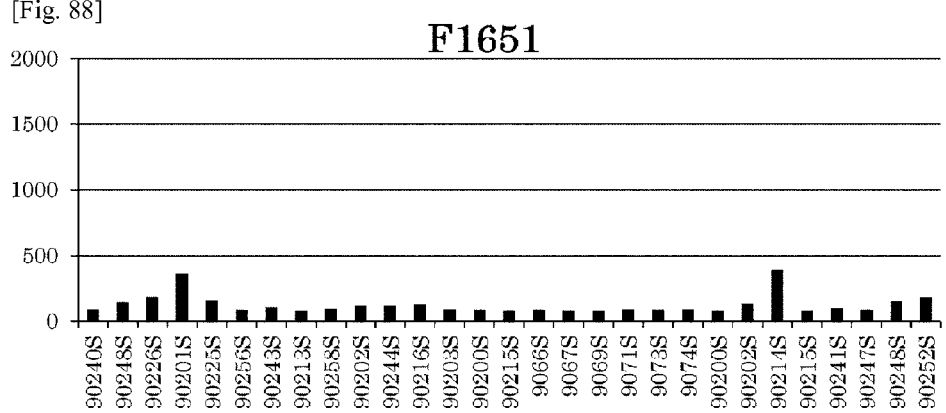
[Fig. 89]
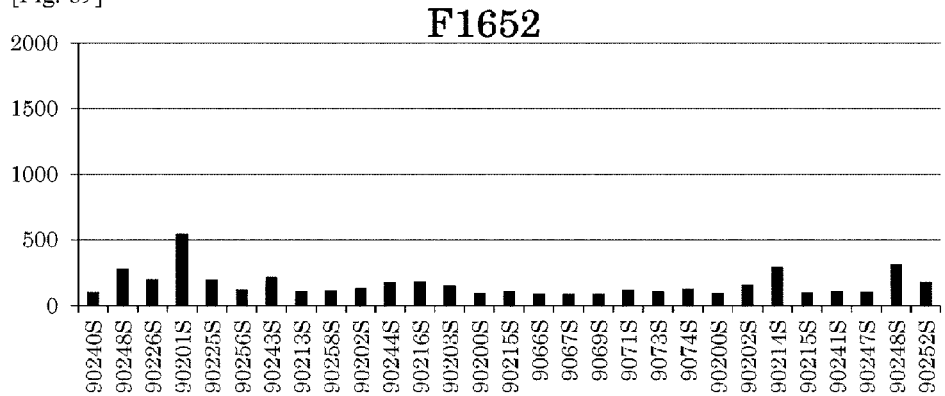
[Fig. 90]
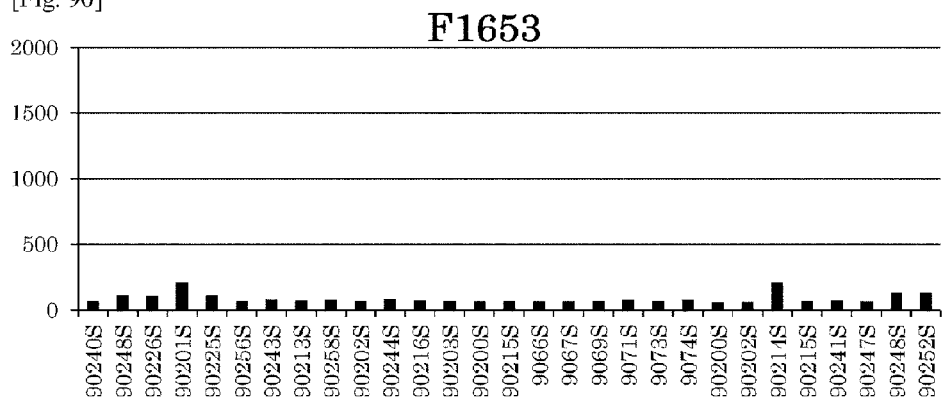

[Fig. 91]
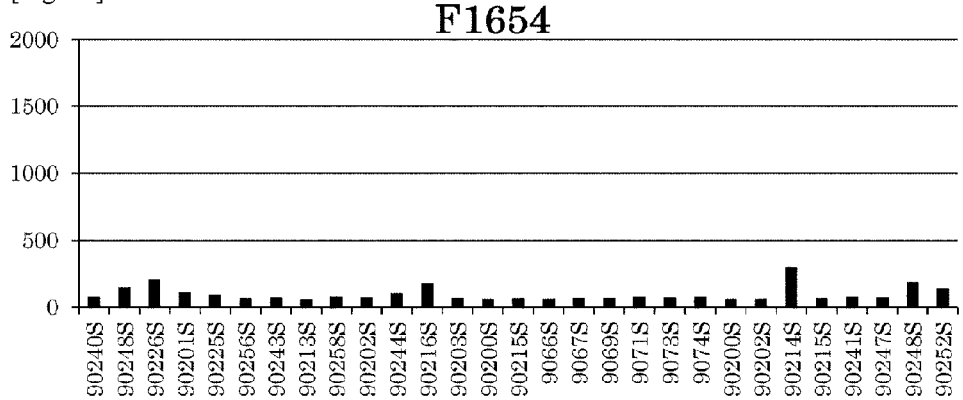
[Fig. 92]
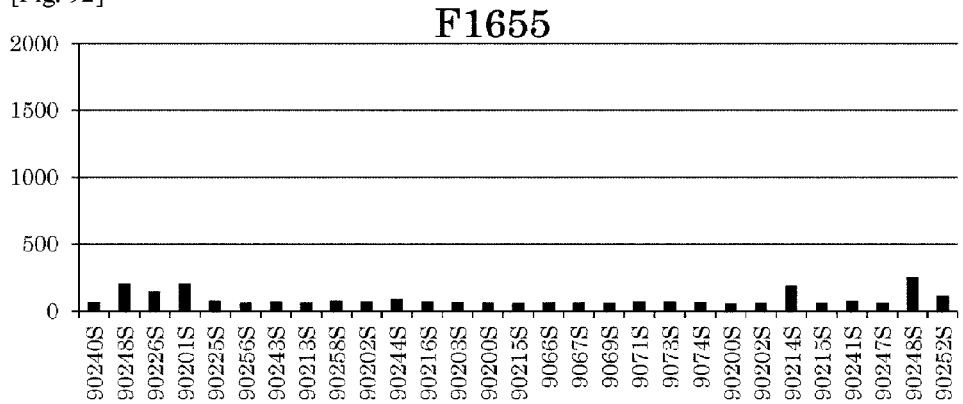
[Fig. 93]
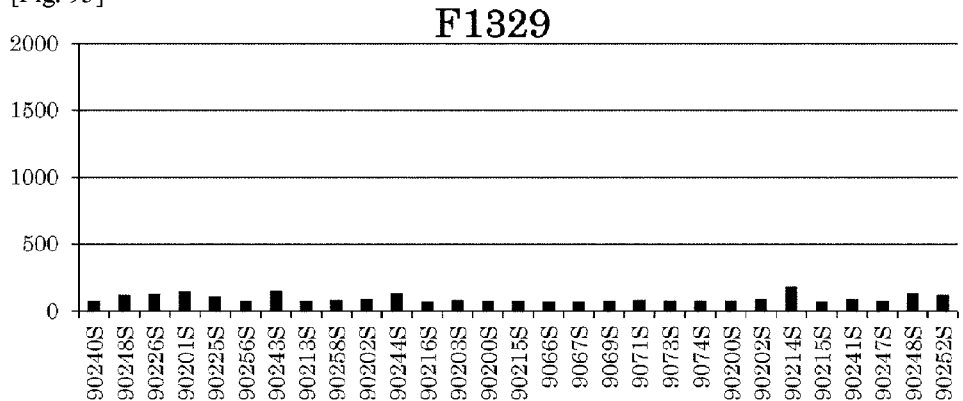

[Fig. 94]
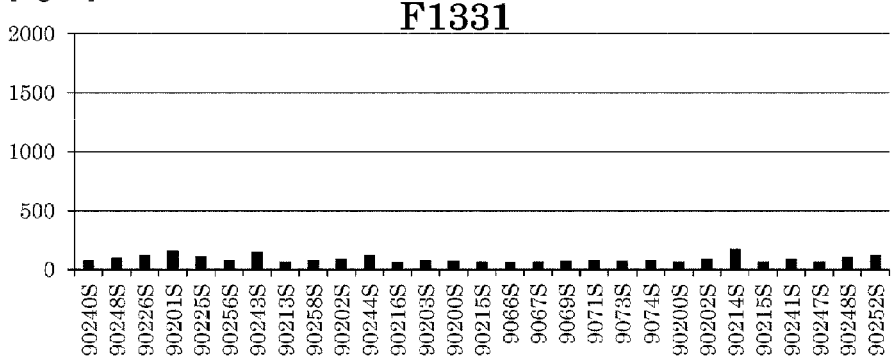
[Fig. 95]
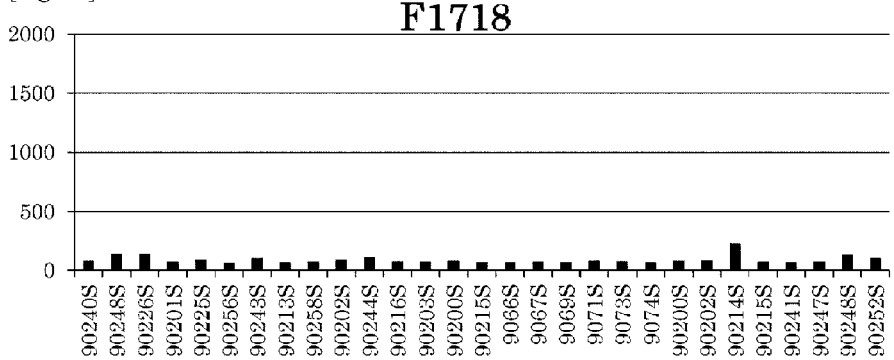
[Fig. 96]
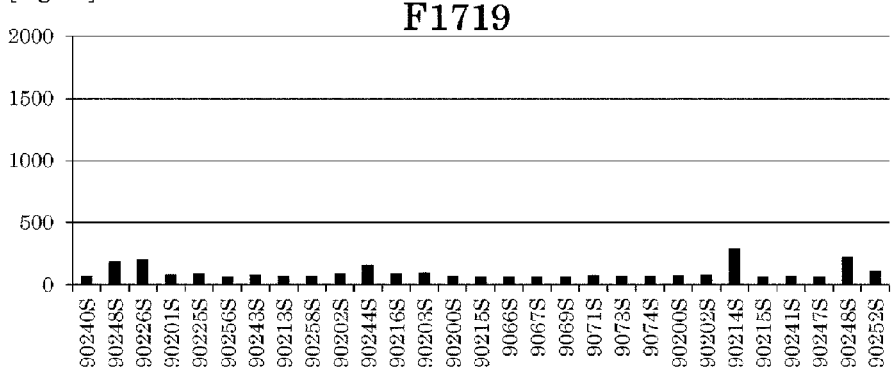

[Fig. 97]
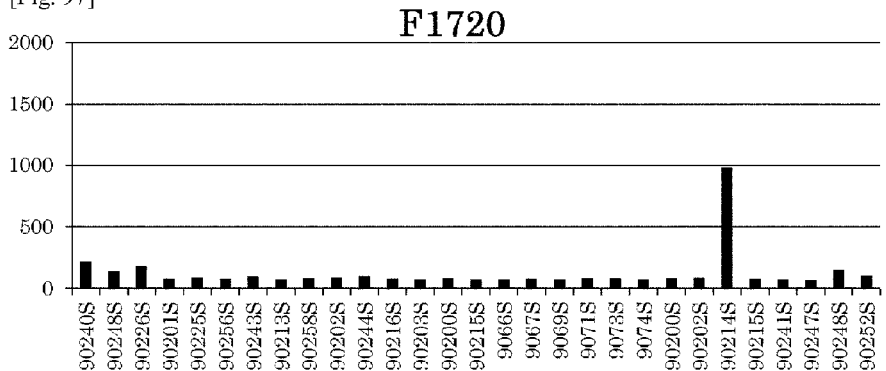
[Fig. 98]
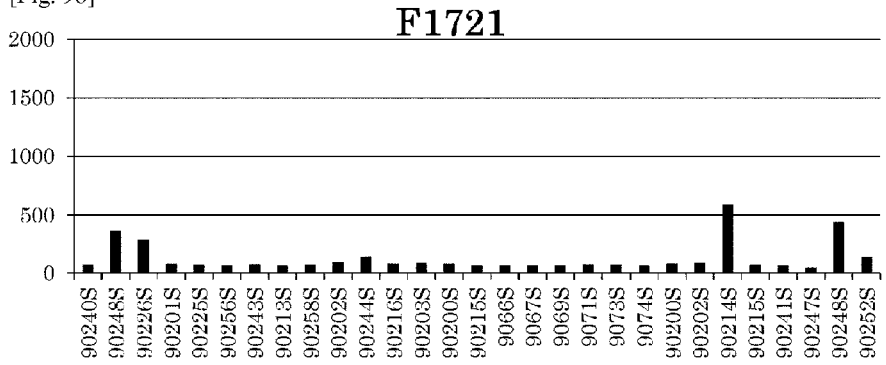
[Fig. 99]
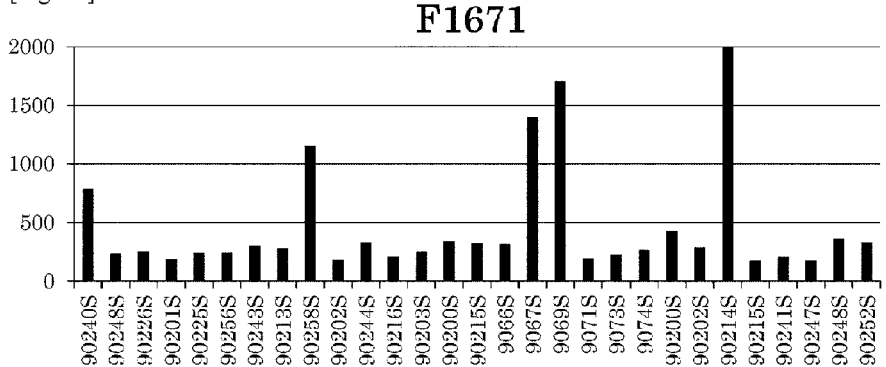

[Fig. 100]
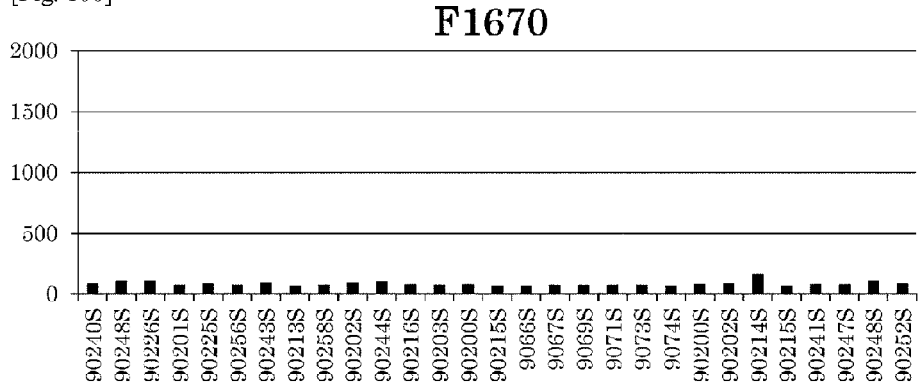
[Fig. 101]
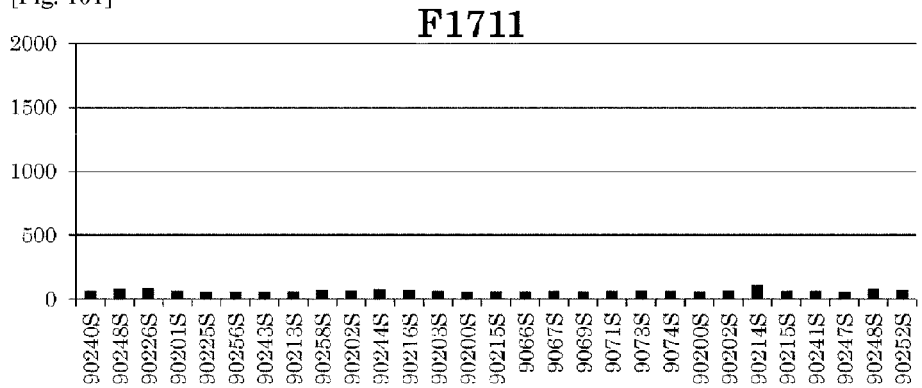
[Fig. 102]
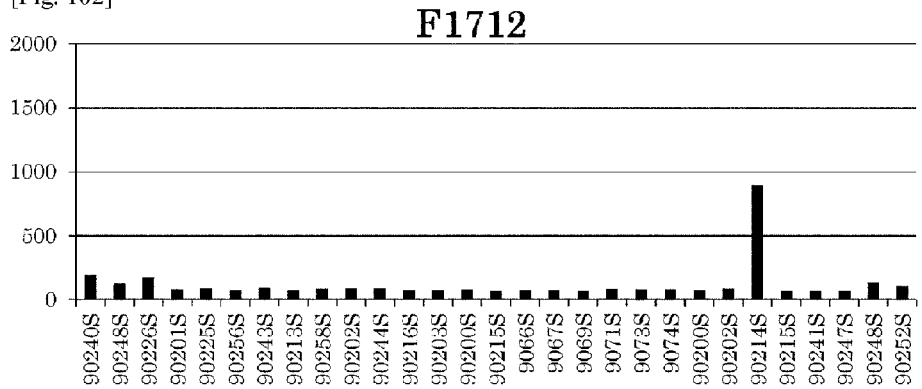

[Fig. 103]
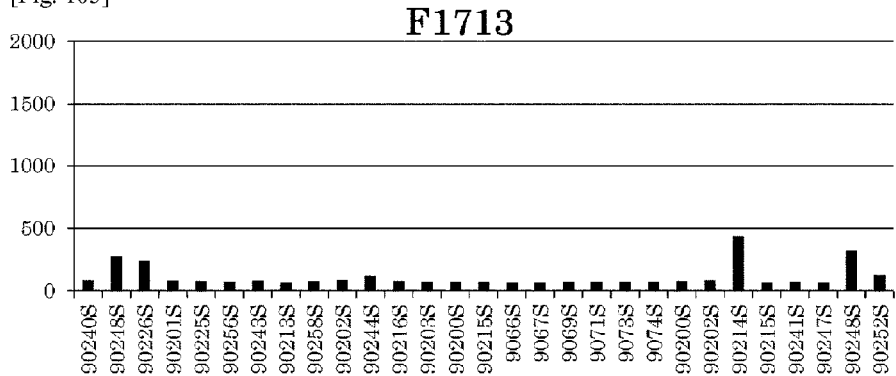
[Fig. 104]
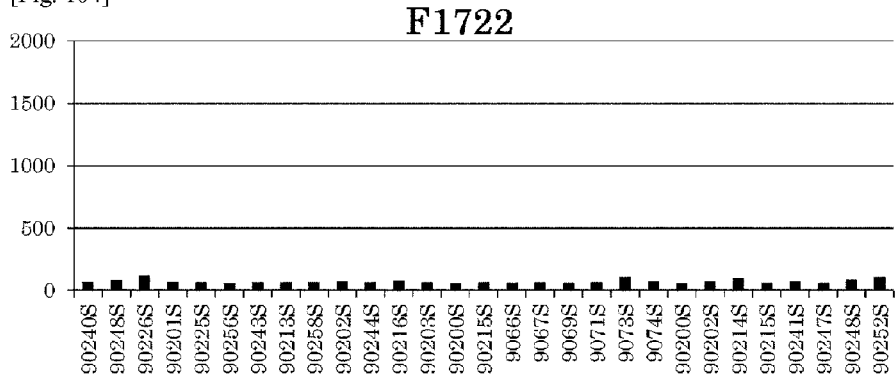
[Fig. 105]
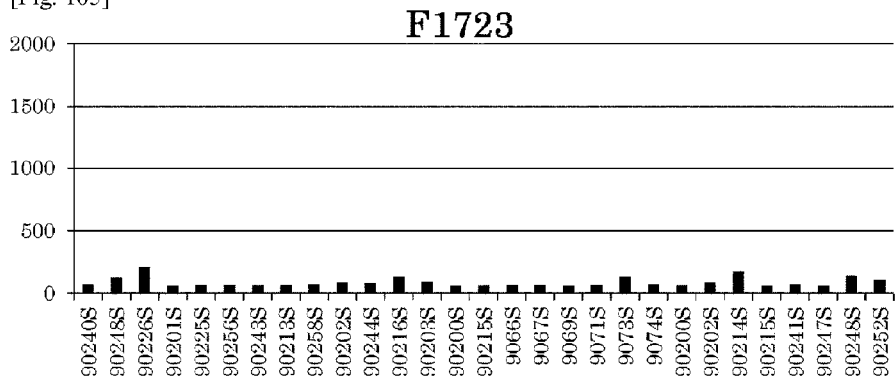

[Fig. 106]
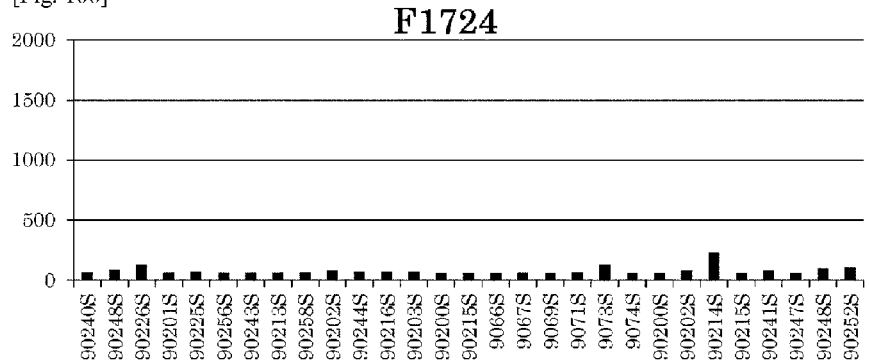
[Fig. 107]
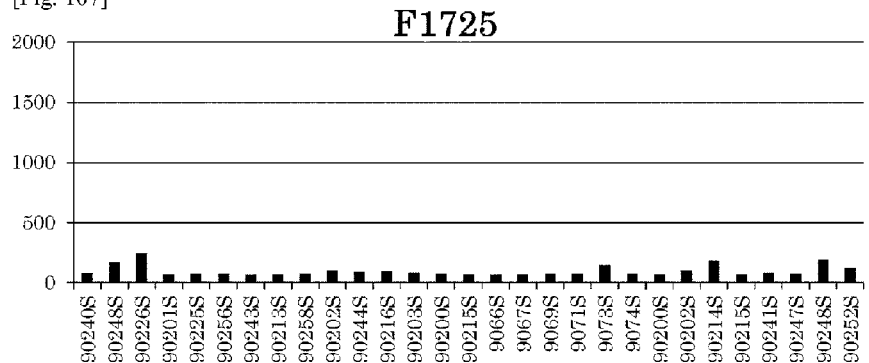
[Fig. 108]
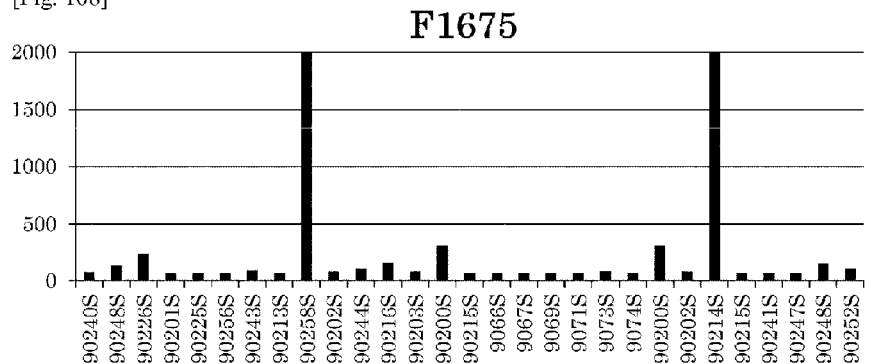

[Fig. 109]
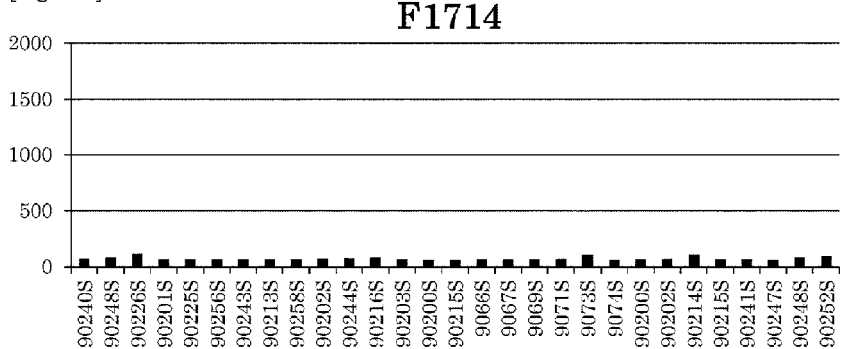
[Fig. 110]
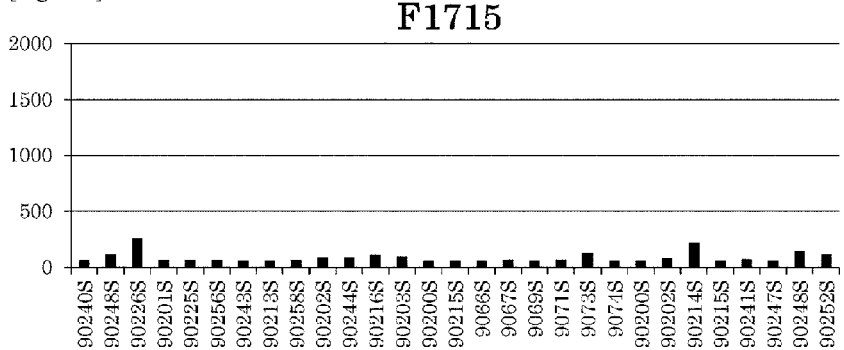
[Fig. 111]
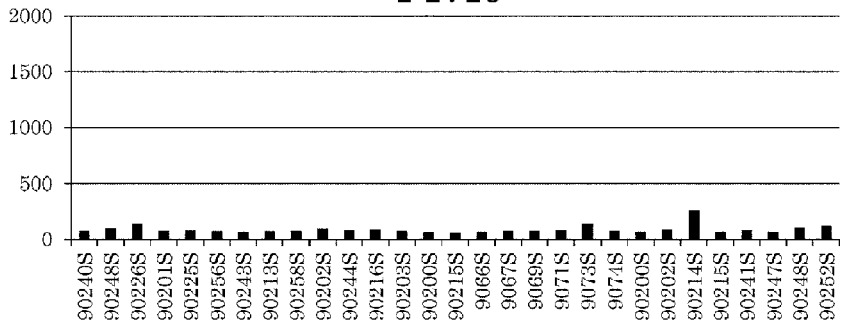

[Fig. 112]
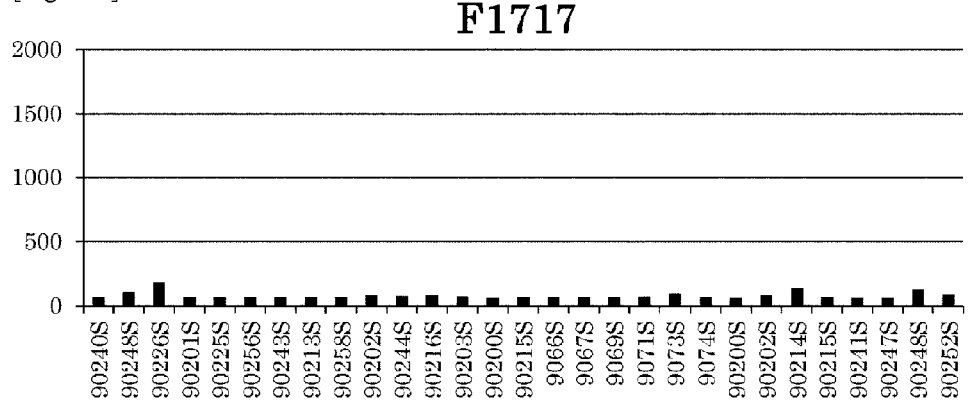
[Fig. 113]
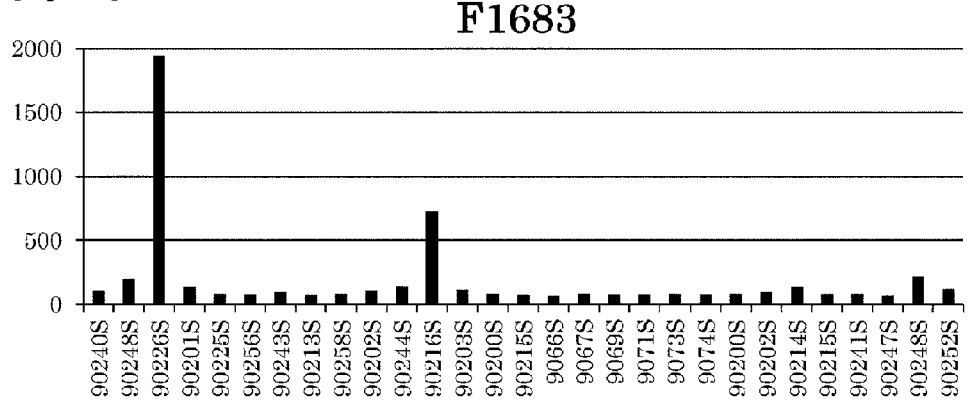
[Fig. 114]
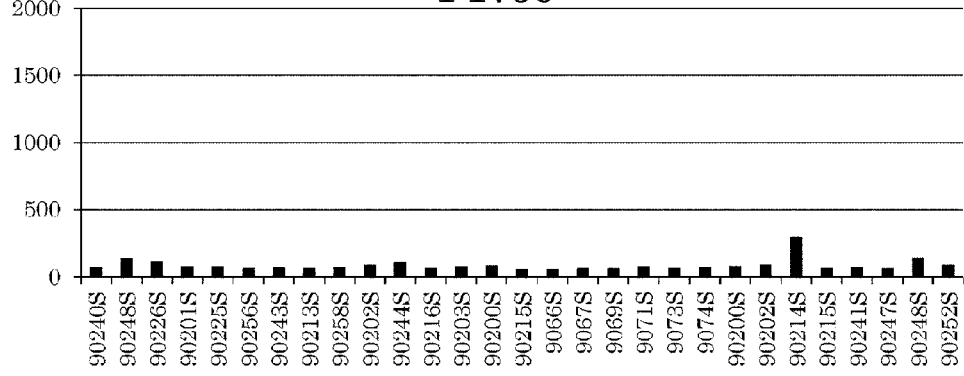

[Fig. 115]
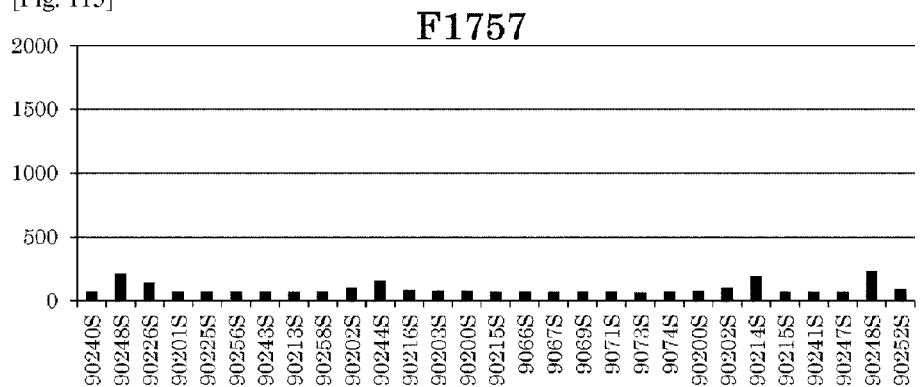
[Fig. 116]
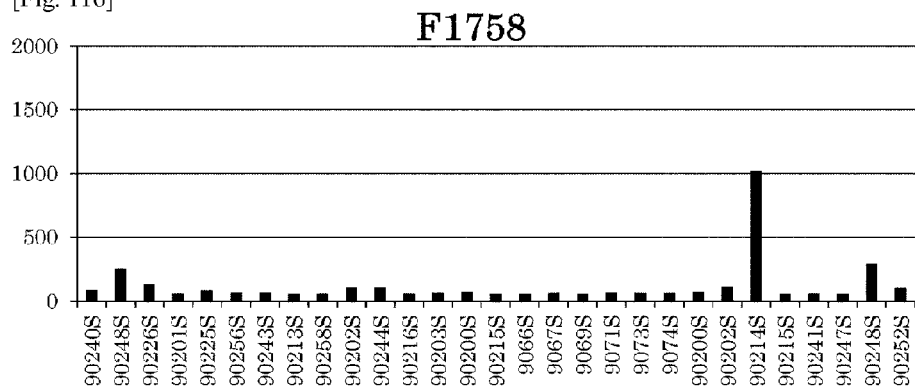
[Fig. 117]
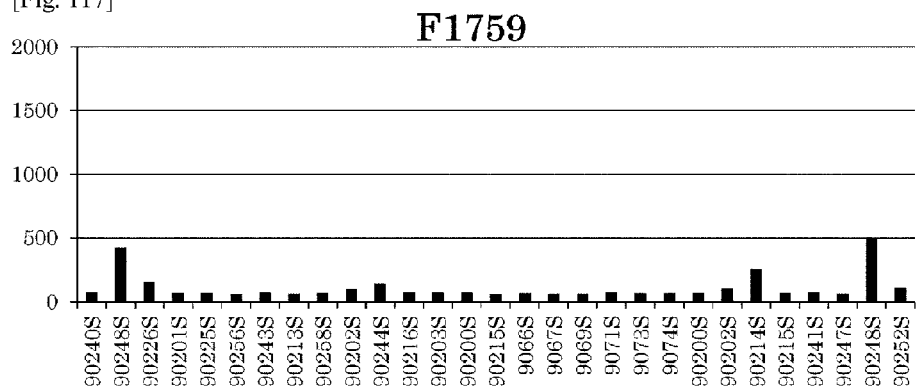

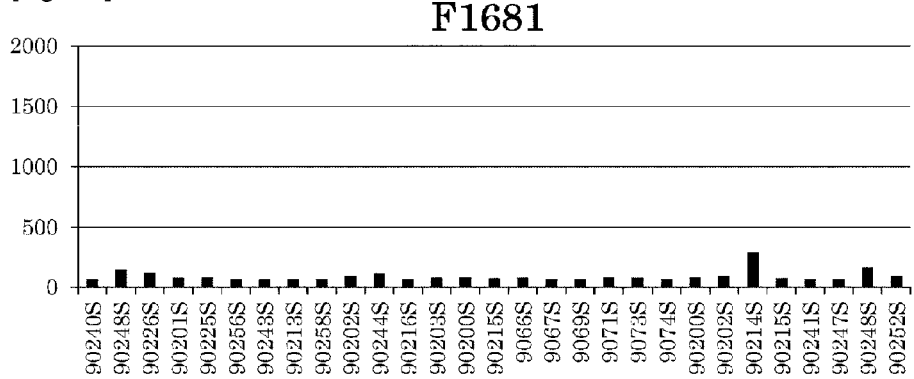
[Fig. 118] F1681
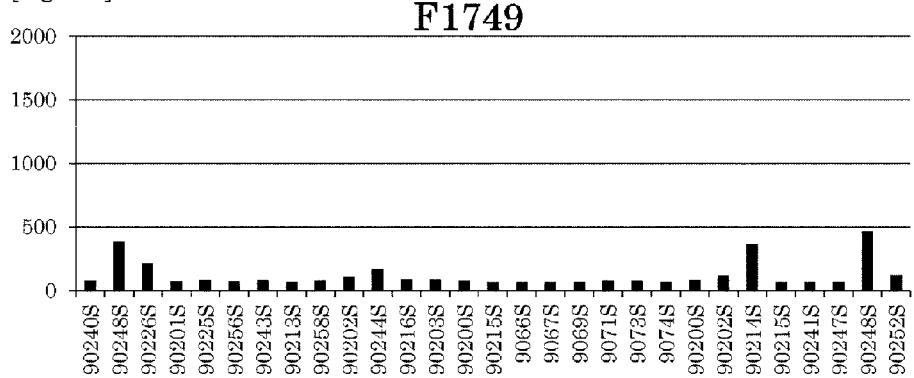
[Fig. 119] F1749
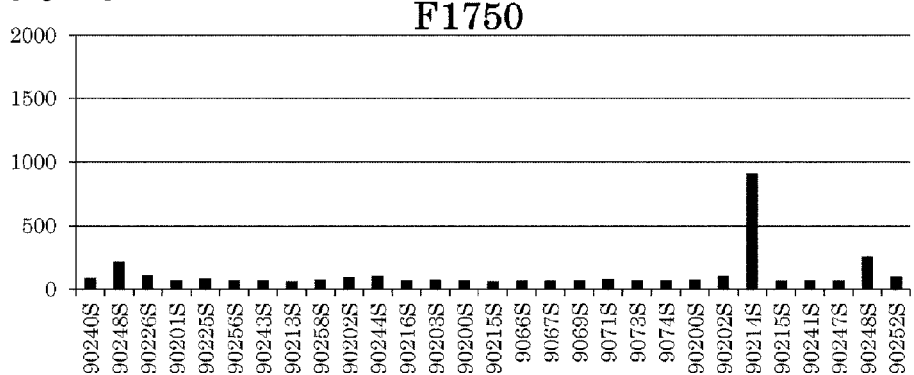
[Fig. 120] F1750

[Fig. 121]
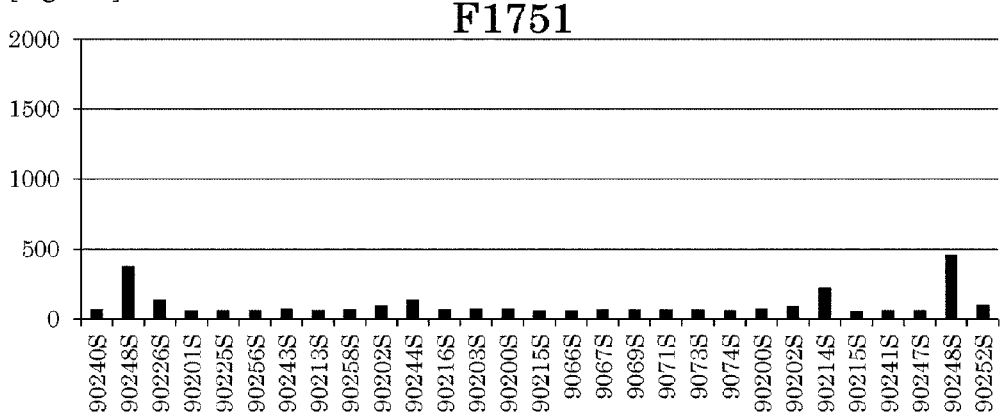
[Fig. 122]
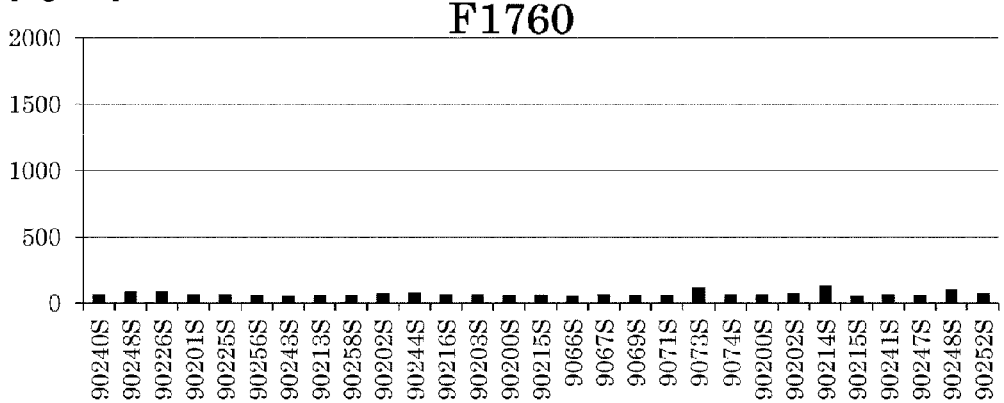
[Fig. 123]
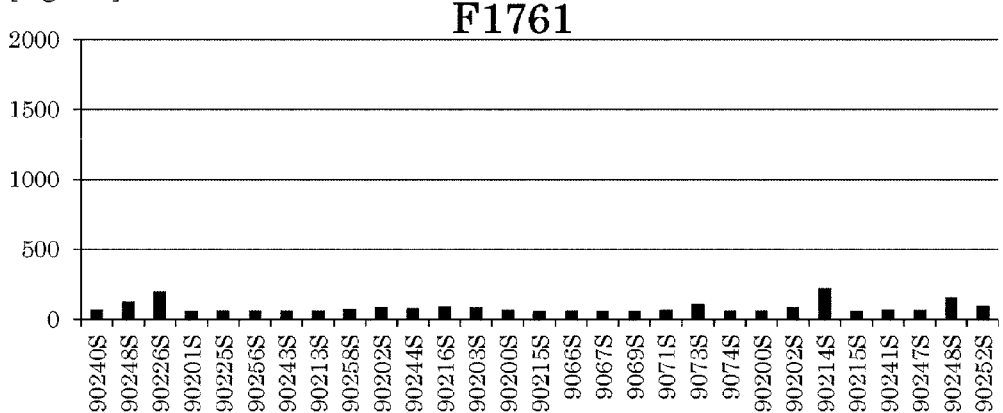

[Fig. 124]
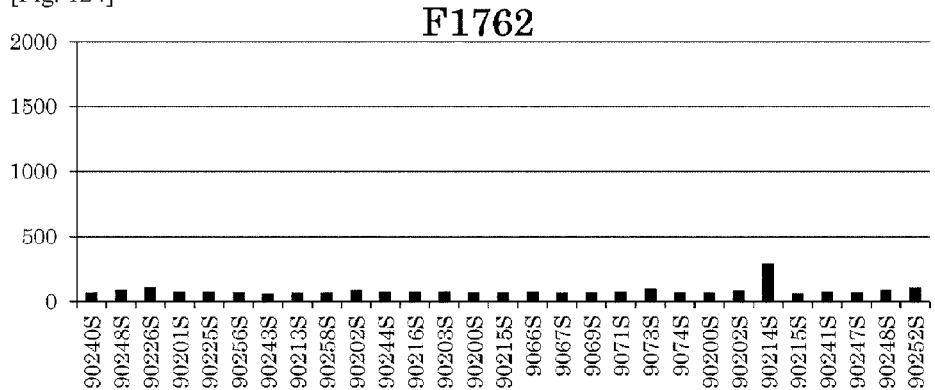
[Fig. 125]
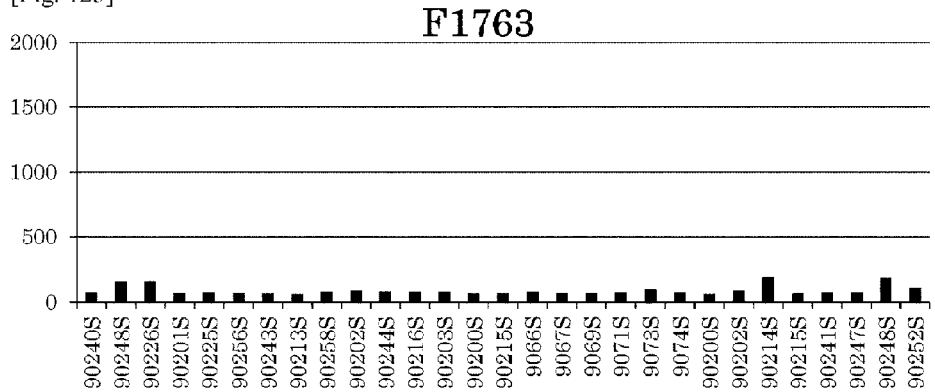
[Fig. 126]
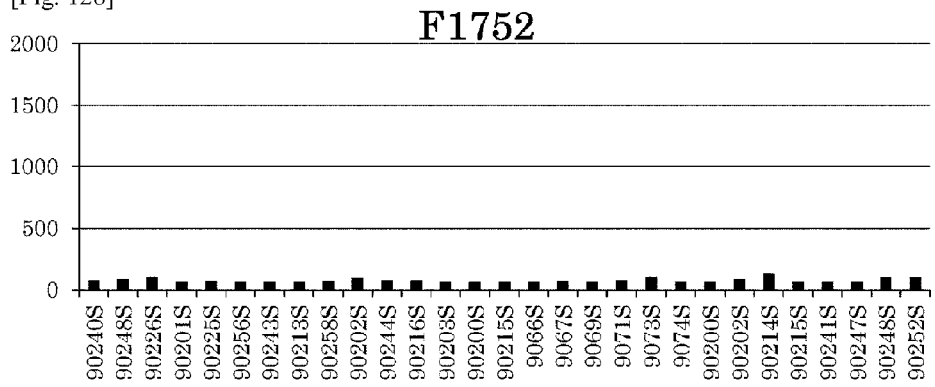

[Fig. 127]
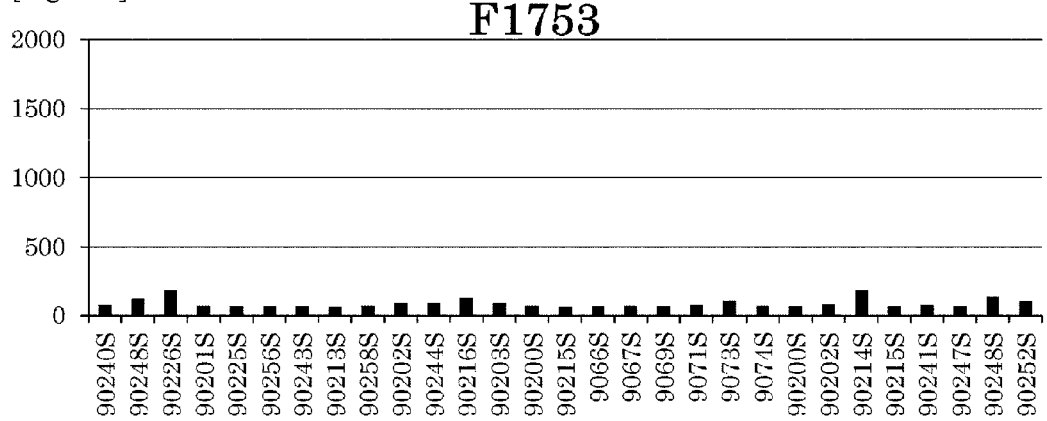
[Fig. 128]
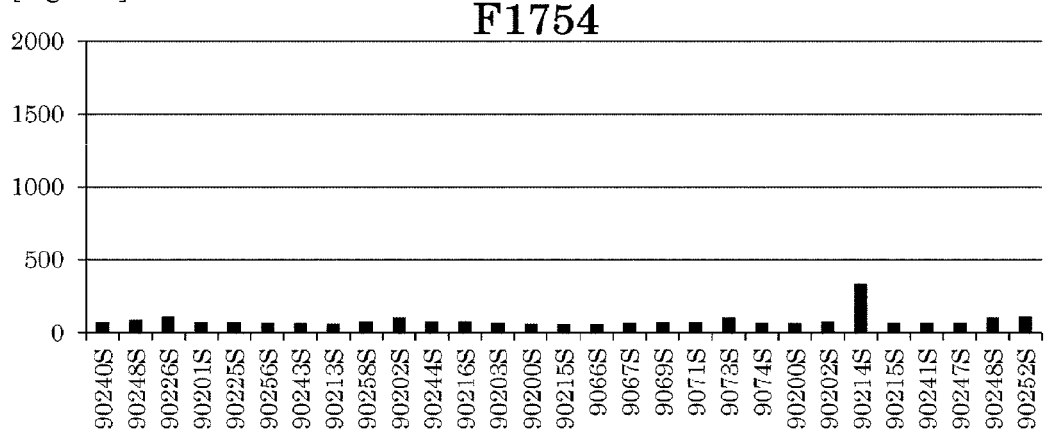
[Fig. 129]
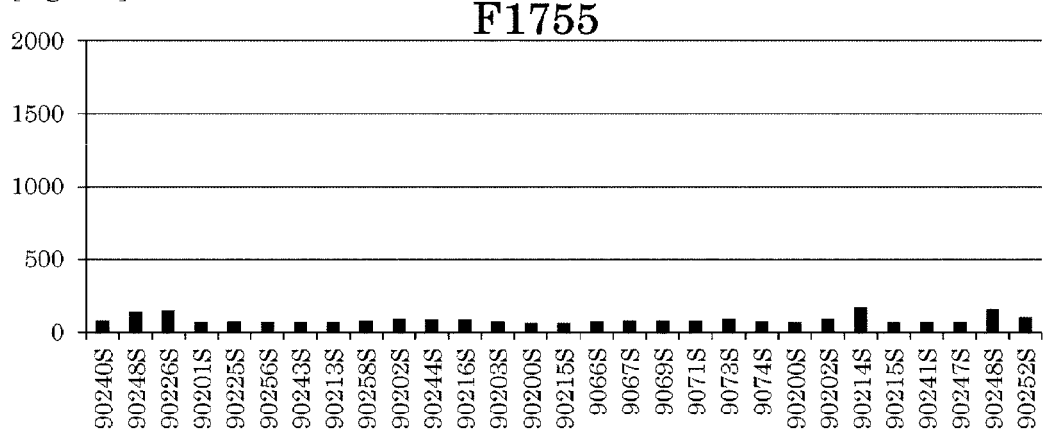

[Fig. 130]
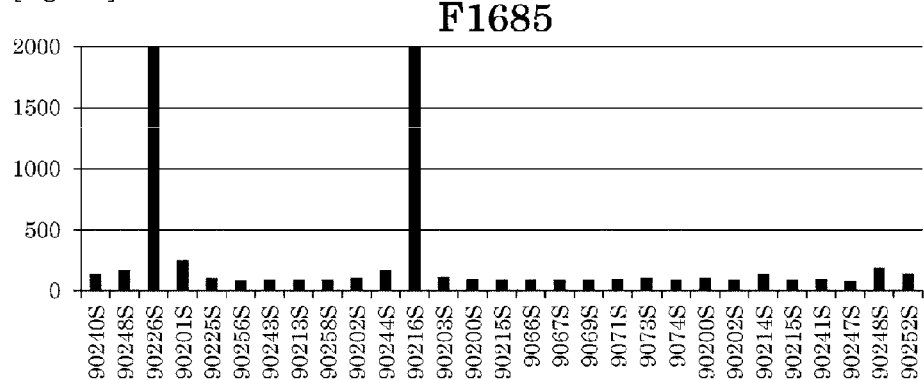
[Fig. 131]
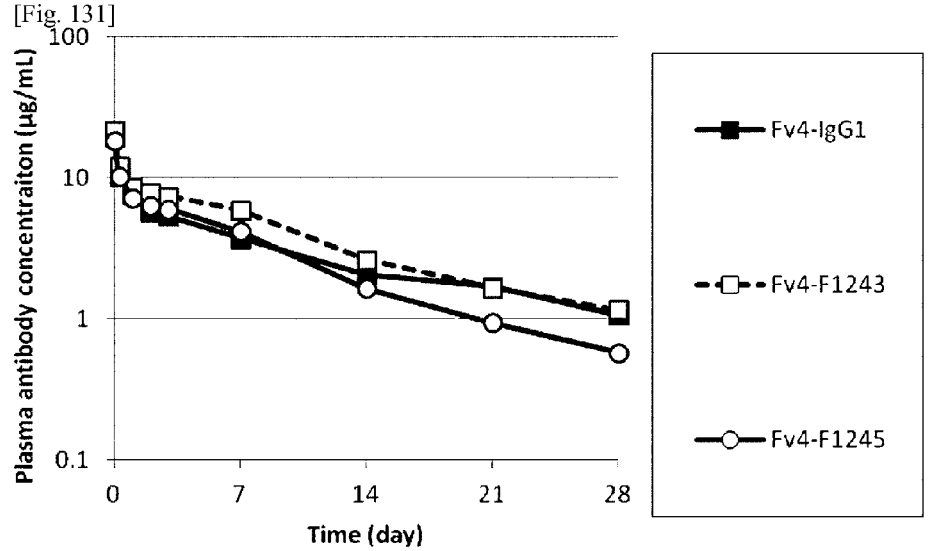

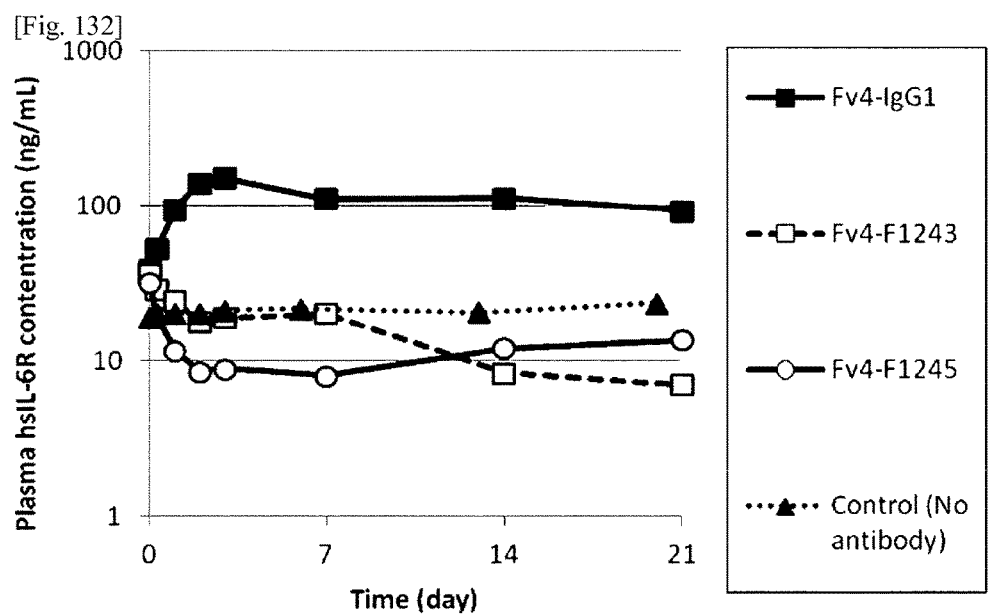
[Fig. 132]
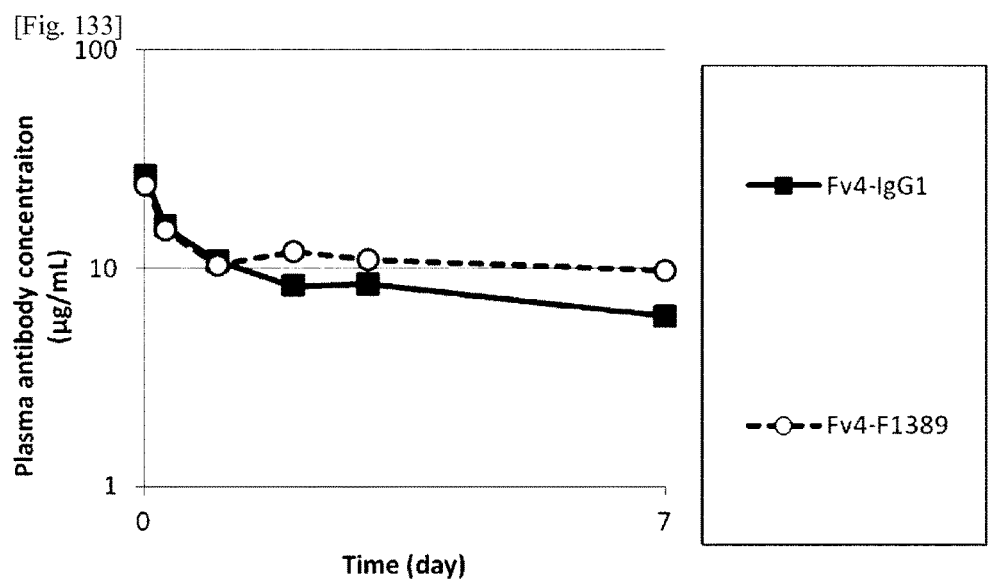
[Fig. 133]

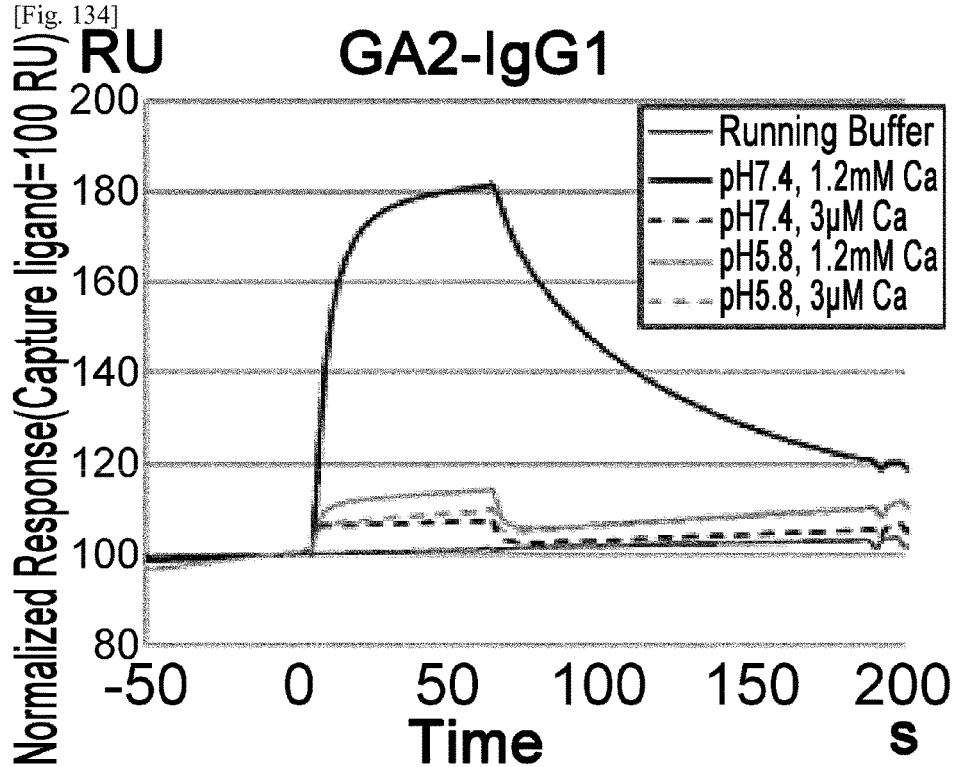
[Fig. 134]
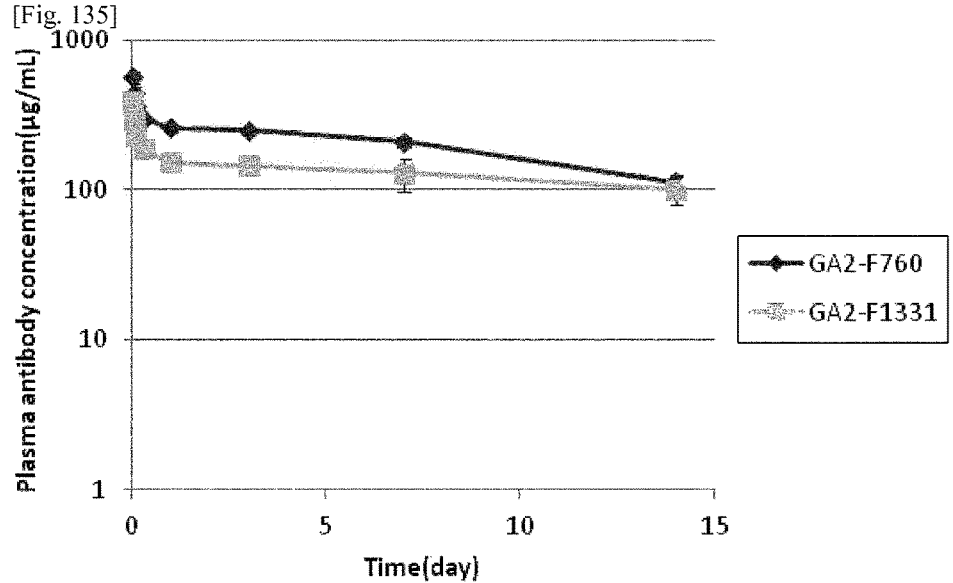
[Fig. 135]

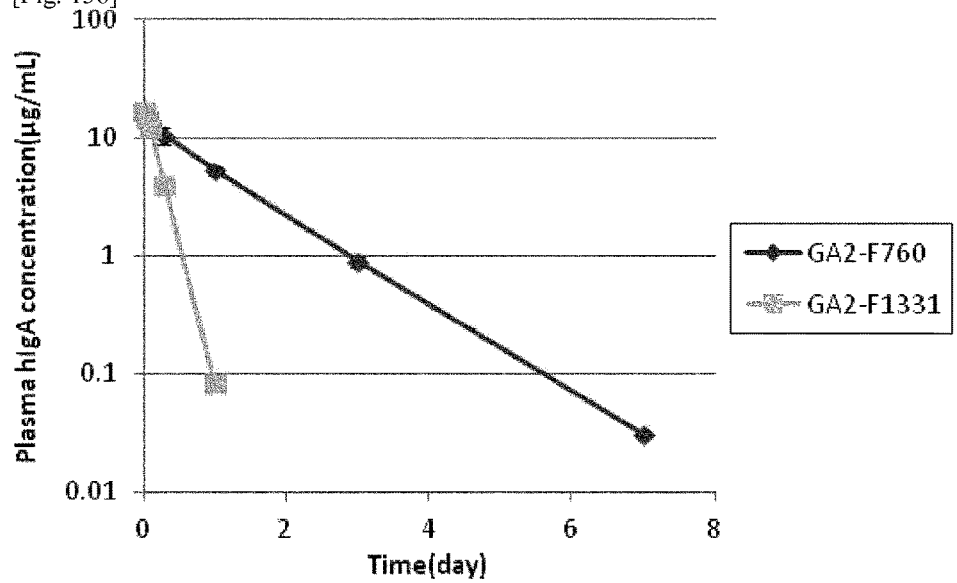
[Fig. 136]
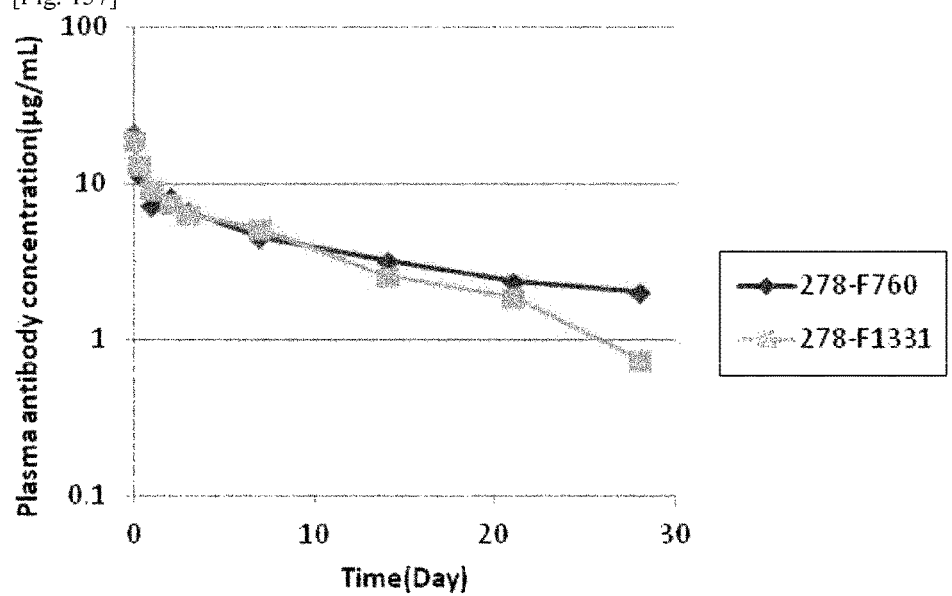
[Fig. 137]

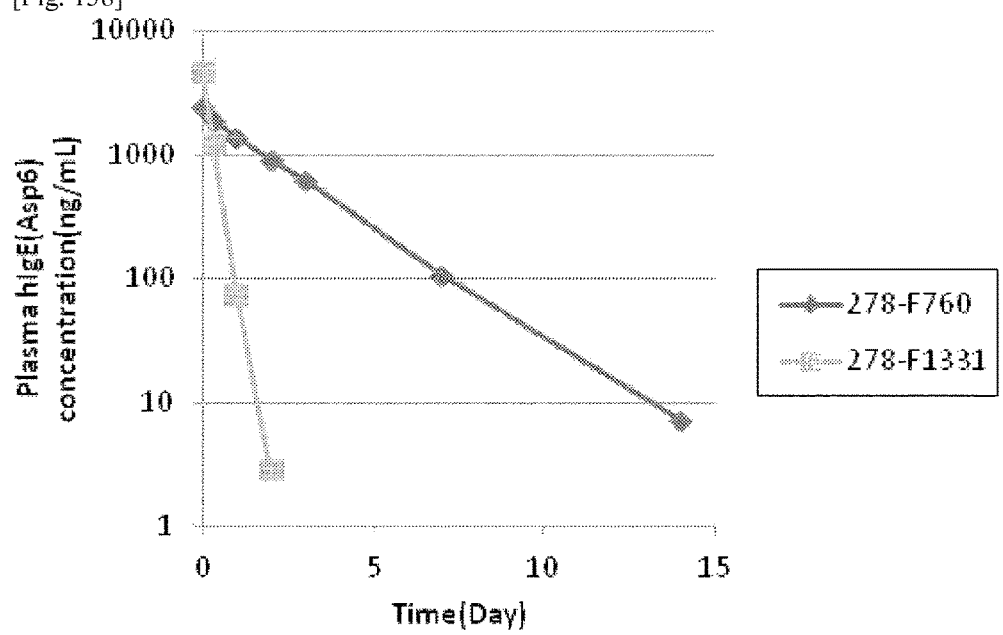
[Fig. 138]

SEQUENCE LISTING

```
<160> NUMBER OF SEQ ID NOS: 29

<210> SEQ ID NO 1
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro
    435                 440                 445

<210> SEQ ID NO 2
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
            85                  90                  95

Thr Phe Gly Gln Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 3

Asp Ile Gln Met Thr Gln Ser Pro Ser Ser Leu Ser Ala Ser Val Gly
1               5                   10                  15

Asp Ser Val Thr Ile Thr Cys Gln Ala Ser Thr Asp Ile Ser Ser His
            20                  25                  30

Leu Asn Trp Tyr Gln Gln Lys Pro Gly Lys Ala Pro Glu Leu Leu Ile
        35                  40                  45

Tyr Tyr Gly Ser His Leu Leu Ser Gly Val Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gly Gln Gly Asn Arg Leu Pro Tyr
                85                  90                  95

Thr Phe Gly Gln Gly Thr Lys Val Glu Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 4
<211> LENGTH: 447
<212> TYPE: PRT
<213> ORGANISM: Artificial Sequence
```

<220> FEATURE:
<223> OTHER INFORMATION: An artificially synthesized peptide sequence

<400> SEQUENCE: 4

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Tyr Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400
```

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
            435                 440                 445

<210> SEQ ID NO 5
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 5

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Asp
225                 230                 235                 240

Ser Val Phe Leu Phe Pro Pro Lys Pro Lys Asp Thr Leu Tyr Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

```
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Tyr Thr Gln Lys Ser Leu Ser Leu Ser Pro
        435                 440                 445

<210> SEQ ID NO 6
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240
```

```
Ser Val Phe Leu Phe Pro Pro Lys Pro Lys Asp Thr Leu Tyr Ile Ser
                245             250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 7
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 7

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Val Leu Tyr Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Gln Val Leu His Ala Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Gln Lys Ser Leu Ser Leu Ser Pro
        435                 440                 445

<210> SEQ ID NO 8
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 8

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Thr Leu Tyr Ile Thr
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Tyr His Val Thr Arg Lys Glu Leu Ser Leu Ser Pro
        435                 440                 445

<210> SEQ ID NO 9
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 9
```

```
Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Arg Gly Gly Pro
225                 230                 235                 240

Lys Val Phe Leu Phe Pro Pro Lys Pro Lys Asp Thr Leu Tyr Ile Thr
                245                 250                 255

Arg Glu Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Tyr His Val Thr Arg Lys Glu Leu Ser Leu Ser Pro
            435                 440                 445

<210> SEQ ID NO 10
<211> LENGTH: 447
<212> TYPE: PRT
<213> ORGANISM: Artificial Sequence
<220> FEATURE:
<223> OTHER INFORMATION: An artificially synthesized peptide sequence

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Ala Val Ser Gly His Ser Ile Ser His Asp
            20                  25                  30

His Ala Trp Ser Trp Val Arg Gln Pro Pro Gly Glu Gly Leu Glu Trp
        35                  40                  45

Ile Gly Phe Ile Ser Tyr Ser Gly Ile Thr Asn Tyr Asn Pro Ser Leu
    50                  55                  60

Gln Gly Arg Val Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Leu Ala Arg Thr Thr Ala Met Asp Tyr Trp Gly Glu Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

-continued

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Leu His Glu
            420                 425                 430

Ala Leu His Ser His Thr Thr Gln Lys Ser Leu Ser Leu Ser Pro
        435                 440                 445

<210> SEQ ID NO 11
<211> LENGTH: 5
<212> TYPE: PRT
<213> ORGANISM: Artificial Sequence
<220> FEATURE:
<223> OTHER INFORMATION: An artificially synthesized peptide sequence

<400> SEQUENCE: 11

Gly Gly Gly Gly Ser
1               5

<210> SEQ ID NO 12
<211> LENGTH: 464
<212> TYPE: PRT
<213> ORGANISM: Artificial Sequence
<220> FEATURE:
<223> OTHER INFORMATION: An artificially synthesized peptide sequence

<400> SEQUENCE: 12

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Pro Thr Ser Pro Lys Val Phe
        115                 120                 125

Pro Leu Ser Leu Cys Ser Thr Gln Pro Asp Gly Asn Val Val Ile Ala
    130                 135                 140

Cys Leu Val Gln Gly Phe Phe Pro Gln Glu Pro Leu Ser Val Thr Trp
145                 150                 155                 160

Ser Glu Ser Gly Gln Gly Val Thr Ala Arg Asn Phe Pro Pro Ser Gln
                165                 170                 175

Asp Ala Ser Gly Asp Leu Tyr Thr Thr Ser Ser Gln Leu Thr Leu Pro
            180                 185                 190

Ala Thr Gln Cys Leu Ala Gly Lys Ser Val Thr Cys His Val Lys His
            195                 200                 205

Tyr Thr Asn Pro Ser Gln Asp Val Thr Val Pro Cys Pro Val Pro Ser
    210                 215                 220

Thr Pro Pro Thr Pro Ser Pro Ser Thr Pro Pro Thr Pro Ser Pro Ser
225                 230                 235                 240

Cys Cys His Pro Arg Leu Ser Leu His Arg Pro Ala Leu Glu Asp Leu
                245                 250                 255

Leu Leu Gly Ser Glu Ala Asn Leu Thr Cys Thr Leu Thr Gly Leu Arg
            260                 265                 270

Asp Ala Ser Gly Val Thr Phe Thr Trp Thr Pro Ser Ser Gly Lys Ser
        275                 280                 285

Ala Val Gln Gly Pro Pro Glu Arg Asp Leu Cys Gly Cys Tyr Ser Val
    290                 295                 300

Ser Ser Val Leu Pro Gly Cys Ala Glu Pro Trp Asn His Gly Lys Thr
305                 310                 315                 320

Phe Thr Cys Thr Ala Ala Tyr Pro Glu Ser Lys Thr Pro Leu Thr Ala
                325                 330                 335

Thr Leu Ser Lys Ser Gly Asn Thr Phe Arg Pro Glu Val His Leu Leu
            340                 345                 350

Pro Pro Pro Ser Glu Glu Leu Ala Leu Asn Glu Leu Val Thr Leu Thr
        355                 360                 365

Cys Leu Ala Arg Gly Phe Ser Pro Lys Asp Val Leu Val Arg Trp Leu
370                 375                 380

Gln Gly Ser Gln Glu Leu Pro Arg Glu Lys Tyr Leu Thr Trp Ala Ser
385                 390                 395                 400

Arg Gln Glu Pro Ser Gln Gly Thr Thr Thr Phe Ala Val Thr Ser Ile
                405                 410                 415

Leu Arg Val Ala Ala Glu Asp Trp Lys Lys Gly Asp Thr Phe Ser Cys
            420                 425                 430

Met Val Gly His Glu Ala Leu Pro Leu Ala Phe Thr Gln Lys Thr Ile
        435                 440                 445

Asp Arg Leu Ala Gly Lys Glu Gln Lys Leu Ile Ser Glu Glu Asp Leu
    450                 455                 460

<210> SEQ ID NO 13
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 451
<212> TYPE: PRT
<213> ORGANISM: Artificial Sequence
<220> FEATURE:
<223> OTHER INFORMATION: An artificially synthesized peptide sequence

<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro
    450

<210> SEQ ID NO 15
<211> LENGTH: 214
<212> TYPE: PRT
<213> ORGANISM: Artificial Sequence
<220> FEATURE:
<223> OTHER INFORMATION: An artificially synthesized peptide sequence

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Asp
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Ser Ser Ser Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 451
<212> TYPE: PRT
<213> ORGANISM: Artificial Sequence
<220> FEATURE:
<223> OTHER INFORMATION: An artificially synthesized peptide sequence

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Trp Glu Thr Ala Ile Ser Ser Asp Ala Phe Asp Ile
            100                 105                 110

Trp Gly Gln Gly Thr Met Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Arg Gly Gly Pro Lys Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
                340                 345                 350

Gln Val Tyr Thr Leu Pro Pro Ser Arg Asp Glu Leu Thr Lys Asn Gln
                355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
    435                 440                 445

Leu Ser Pro
    450

<210> SEQ ID NO 17
<211> LENGTH: 451
<212> TYPE: PRT
<213> ORGANISM: Artificial Sequence
<220> FEATURE:
<223> OTHER INFORMATION: An artificially synthesized peptide sequence

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Pro Arg Trp Glu Thr Ala Ile Ser Ser Asp Ala Phe Asp Ile
                100                 105                 110

Trp Gly Gln Gly Thr Met Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190
```

Thr Val Pro Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Arg Arg Gly Pro Lys Val Phe Leu Phe Pro Pro Lys Pro Lys Asp Thr
            245                 250                 255

Leu Tyr Ile Thr Arg Glu Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Tyr His Val Thr Arg Lys Glu Leu Ser
            435                 440                 445

Leu Ser Pro
    450

<210> SEQ ID NO 18
<211> LENGTH: 543
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr

```
            100                 105                 110
Val Ser Ser Ala Ser Thr Gln Ser Pro Ser Val Phe Pro Leu Thr Arg
            115                 120                 125
Cys Cys Lys Asn Ile Pro Ser Asn Ala Thr Ser Val Thr Leu Gly Cys
            130                 135                 140
Leu Ala Thr Gly Tyr Phe Pro Glu Pro Val Met Val Thr Trp Asp Thr
145                 150                 155                 160
Gly Ser Leu Asn Gly Thr Thr Met Thr Leu Pro Ala Thr Thr Leu Thr
                165                 170                 175
Leu Ser Gly His Tyr Ala Thr Ile Ser Leu Leu Thr Val Ser Gly Ala
                180                 185                 190
Trp Ala Lys Gln Met Phe Thr Cys Arg Val Ala His Thr Pro Ser Ser
            195                 200                 205
Thr Asp Trp Val Asp Asn Lys Thr Phe Ser Val Cys Ser Arg Asp Phe
            210                 215                 220
Thr Pro Pro Thr Val Lys Ile Leu Gln Ser Ser Cys Asp Gly Gly Gly
225                 230                 235                 240
His Phe Pro Pro Thr Ile Gln Leu Leu Cys Leu Val Ser Gly Tyr Thr
                245                 250                 255
Pro Gly Thr Ile Asn Ile Thr Trp Leu Glu Asp Gly Gln Val Met Asp
                260                 265                 270
Val Asp Leu Ser Thr Ala Ser Thr Thr Gln Glu Gly Glu Leu Ala Ser
            275                 280                 285
Thr Gln Ser Glu Leu Thr Leu Ser Gln Lys His Trp Leu Ser Asp Arg
            290                 295                 300
Thr Tyr Thr Cys Gln Val Thr Tyr Gln Gly His Thr Phe Glu Asp Ser
305                 310                 315                 320
Thr Lys Lys Cys Ala Asp Ser Asn Pro Arg Gly Val Ser Ala Tyr Leu
                325                 330                 335
Ser Arg Pro Ser Pro Phe Asp Leu Phe Ile Arg Lys Ser Pro Thr Ile
                340                 345                 350
Thr Cys Leu Val Val Asp Leu Ala Pro Ser Lys Gly Thr Val Asn Leu
            355                 360                 365
Thr Trp Ser Arg Ala Ser Gly Lys Pro Val Asn His Ser Thr Arg Lys
            370                 375                 380
Glu Glu Lys Gln Arg Asn Gly Thr Leu Thr Val Thr Ser Thr Leu Pro
385                 390                 395                 400
Val Gly Thr Arg Asp Trp Ile Glu Gly Glu Thr Tyr Gln Cys Arg Val
                405                 410                 415
Thr His Pro His Leu Pro Arg Ala Leu Met Arg Ser Thr Thr Lys Thr
                420                 425                 430
Ser Gly Pro Arg Ala Ala Pro Glu Val Tyr Ala Phe Ala Thr Pro Glu
            435                 440                 445
Trp Pro Gly Ser Arg Asp Lys Arg Thr Leu Ala Cys Leu Ile Gln Asn
            450                 455                 460
Phe Met Pro Glu Asp Ile Ser Val Gln Trp Leu His Asn Glu Val Gln
465                 470                 475                 480
Leu Pro Asp Ala Arg His Ser Thr Thr Gln Pro Arg Lys Thr Lys Gly
                485                 490                 495
Ser Gly Phe Phe Val Phe Ser Arg Leu Glu Val Thr Arg Ala Glu Trp
                500                 505                 510
Glu Gln Lys Asp Glu Phe Ile Cys Arg Ala Val His Glu Ala Ala Ser
            515                 520                 525
```

```
Pro Ser Gln Thr Val Gln Arg Ala Val Ser Val Asn Pro Gly Lys
        530                 535                 540

<210> SEQ ID NO 19
<211> LENGTH: 219
<212> TYPE: PRT
<213> ORGANISM: Homo sapiens

<400> SEQUENCE: 19

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Arg Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Asn
                85                  90                  95

Thr His Val Pro Pro Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 20
<211> LENGTH: 443
<212> TYPE: PRT
<213> ORGANISM: Artificial Sequence
<220> FEATURE:
<223> OTHER INFORMATION: An artificially synthesized peptide sequence

<400> SEQUENCE: 20

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
    50                  55                  60

Arg Phe Thr Val Ser Lys Thr Ser Thr Thr Val Asp Leu Asn Leu Thr
65                  70                  75                  80
```

Ser Leu Thr Thr Glu Asp Thr Ala Thr Tyr Phe Cys Ala Arg Tyr Val
            85                  90                  95

Phe Ser Ser Gly Ser His Asp Ile Trp Gly Pro Gly Thr Leu Val Thr
        100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
130             135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
            165                 170                 175

Leu Tyr Ser Leu Ser Ser Val Val Thr Val Pro Ser Ser Ser Leu Gly
        180                 185                 190

Thr Gln Thr Tyr Ile Cys Asn Val Asn His Lys Pro Ser Asn Thr Lys
    195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
    275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
            435                 440

<210> SEQ ID NO 21
<211> LENGTH: 217
<212> TYPE: PRT
<213> ORGANISM: Artificial Sequence
<220> FEATURE:
<223> OTHER INFORMATION: An artificially synthesized peptide sequence

<400> SEQUENCE: 21

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Gly Ser Trp
            20                  25                  30

Leu Ala Trp Tyr Gln Gln Lys Pro Gly Gln Pro Pro Lys Glu Leu Ile
        35                  40                  45

Tyr Gly Thr Ser Thr Leu Glu Ser Gly Val Pro Ser Arg Phe Ile Gly
    50                  55                  60

Ser Gly Ser Gly Thr Glu Phe Thr Leu Thr Ile Ser Gly Val Glu Cys
65                  70                  75                  80

Ala Asp Ala Ala Thr Tyr Tyr Cys Gln Gln Gly Tyr Ser Glu Asp Asn
                85                  90                  95

Ile Asp Asn Ala Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 22
<211> LENGTH: 32
<212> TYPE: PRT
<213> ORGANISM: Artificial Sequence
<220> FEATURE:
<223> OTHER INFORMATION: An artificially synthesized peptide sequence

<400> SEQUENCE: 22

Val Asp Asp Ala Pro Gly Asn Ser Gln Gln Ala Thr Pro Lys Asp Asn
1               5                   10                  15

Glu Ile Ser Thr Phe His Asn Leu Gly Asn Val His Ser Pro Leu Lys
            20                  25                  30

<210> SEQ ID NO 23
<211> LENGTH: 443
<212> TYPE: PRT
<213> ORGANISM: Artificial Sequence
<220> FEATURE:
<223> OTHER INFORMATION: An artificially synthesized peptide sequence

<400> SEQUENCE: 23

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr His
            20                  25                  30

Met Ser Trp Val Arg Gln Ala Pro Gly Lys Gly Leu Glu Trp Ile Gly
        35                  40                  45

Val Ile Asn Ser Ala Gly Asn Thr Tyr Tyr Ala Ser Trp Ala Lys Gly
    50                  55                  60

```
Arg Phe Thr Val Ser Lys Ser Thr Thr Val Asp Leu Asn Leu Thr
 65                  70                  75                  80

Ser Leu Thr Thr Glu Asp Thr Ala Thr Tyr Phe Cys Ala Arg Tyr Val
                 85                  90                  95

Phe Ser Ser Gly Ser His Asp Ile Trp Gly Pro Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Arg Gly Gly Pro Lys Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440

<210> SEQ ID NO 24
<211> LENGTH: 443
<212> TYPE: PRT
<213> ORGANISM: Artificial Sequence
<220> FEATURE:
```

<223> OTHER INFORMATION: An artificially synthesized peptide sequence

<400> SEQUENCE: 24

```
Gln Ser Leu Glu Glu Ser Gly Gly Arg Leu Val Thr Pro Gly Thr Pro
1               5                   10                  15
Leu Thr Leu Thr Cys Thr Ala Ser Gly Phe Ser Leu Ser Ser Tyr His
            20                  25                  30
Met Ser Trp Val Arg Gln Ala Pro Gly Lys Gly Leu Glu Trp Ile Gly
        35                  40                  45
Val Ile Asn Ser Ala Gly Asn Thr Tyr Tyr Ala Ser Trp Ala Lys Gly
    50                  55                  60
Arg Phe Thr Val Ser Lys Thr Ser Thr Val Asp Leu Asn Leu Thr
65                  70                  75                  80
Ser Leu Thr Thr Glu Asp Thr Ala Thr Tyr Phe Cys Ala Arg Tyr Val
                85                  90                  95
Phe Ser Ser Gly Ser His Asp Ile Trp Gly Pro Gly Thr Leu Val Thr
            100                 105                 110
Val Ser Ser Ala Ser Thr Lys Gly Pro Ser Val Phe Pro Leu Ala Pro
        115                 120                 125
Ser Ser Lys Ser Thr Ser Gly Gly Thr Ala Ala Leu Gly Cys Leu Val
    130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Arg Arg Gly Pro Lys Val Phe Leu
225                 230                 235                 240
Phe Pro Pro Lys Pro Lys Asp Thr Leu Tyr Ile Thr Arg Glu Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
```

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Tyr
            420                 425                 430

His Val Thr Arg Lys Glu Leu Ser Leu Ser Pro
            435                 440

<210> SEQ ID NO 25
<211> LENGTH: 543
<212> TYPE: PRT
<213> ORGANISM: Artificial Sequence
<220> FEATURE:
<223> OTHER INFORMATION: An artificially synthesized peptide sequence

<400> SEQUENCE: 25

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Glu Met His Trp Val Arg Gln Ala Pro Gly Gln Gly Leu Glu Trp Met
            35                  40                  45

Gly Ala Leu Asp Pro Lys Thr Gly Asp Thr Ala Tyr Ser Gln Lys Phe
        50                  55                  60

Lys Gly Arg Val Thr Leu Thr Ala Asp Lys Ser Thr Ser Thr Ala Tyr
65                  70                  75                  80

Met Glu Leu Ser Ser Leu Thr Ser Glu Asp Thr Ala Val Tyr Tyr Cys
                85                  90                  95

Thr Arg Phe Tyr Ser Tyr Thr Tyr Trp Gly Gln Gly Thr Leu Val Thr
            100                 105                 110

Val Ser Ser Ala Ser Thr Gln Ser Pro Ser Val Phe Pro Leu Thr Arg
        115                 120                 125

Cys Cys Lys Asn Ile Pro Ser Asp Ala Thr Ser Val Thr Leu Gly Cys
130                 135                 140

Leu Ala Thr Gly Tyr Phe Pro Glu Pro Val Met Val Thr Trp Asp Thr
145                 150                 155                 160

Gly Ser Leu Asp Gly Thr Thr Met Thr Leu Pro Ala Thr Thr Leu Thr
                165                 170                 175

Leu Ser Gly His Tyr Ala Thr Ile Ser Leu Leu Thr Val Ser Gly Ala
            180                 185                 190

Trp Ala Lys Gln Met Phe Thr Cys Arg Val Ala His Thr Pro Ser Ser
        195                 200                 205

Thr Asp Trp Val Asp Lys Thr Phe Ser Val Cys Ser Arg Asp Phe
210                 215                 220

Thr Pro Pro Thr Val Lys Ile Leu Gln Ser Ser Cys Asp Gly Gly
225                 230                 235                 240

His Phe Pro Pro Thr Ile Gln Leu Leu Cys Leu Val Ser Gly Tyr Thr
                245                 250                 255

Pro Gly Thr Ile Asp Ile Thr Trp Leu Glu Asp Gly Gln Val Met Asp
            260                 265                 270

Val Asp Leu Ser Thr Ala Ser Thr Thr Gln Glu Gly Glu Leu Ala Ser
        275                 280                 285

Thr Gln Ser Glu Leu Thr Leu Ser Gln Lys His Trp Leu Ser Asp Arg
    290                 295                 300

Thr Tyr Thr Cys Gln Val Thr Tyr Gln Gly His Thr Phe Glu Asp Ser
305                 310                 315                 320
```

Thr Lys Lys Cys Ala Asp Ser Asn Pro Arg Gly Val Ser Ala Tyr Leu
                325                 330                 335

Ser Arg Pro Ser Pro Phe Asp Leu Phe Ile Arg Lys Ser Pro Thr Ile
            340                 345                 350

Thr Cys Leu Val Val Asp Leu Ala Pro Ser Lys Gly Thr Val Asp Leu
            355                 360                 365

Thr Trp Ser Arg Ala Ser Gly Lys Pro Val Asp His Ser Thr Arg Lys
    370                 375                 380

Glu Lys Gln Arg Asn Gly Thr Leu Thr Val Thr Ser Thr Leu Pro
385                 390                 395                 400

Val Gly Thr Arg Asp Trp Ile Glu Gly Glu Thr Tyr Gln Cys Arg Val
            405                 410                 415

Thr His Pro His Leu Pro Arg Ala Leu Met Arg Ser Thr Thr Lys Thr
            420                 425                 430

Ser Gly Pro Arg Ala Ala Pro Glu Val Tyr Ala Phe Ala Thr Pro Glu
            435                 440                 445

Trp Pro Gly Ser Arg Asp Lys Arg Thr Leu Ala Cys Leu Ile Gln Asn
    450                 455                 460

Phe Met Pro Glu Asp Ile Ser Val Gln Trp Leu His Asn Glu Val Gln
465                 470                 475                 480

Leu Pro Asp Ala Arg His Ser Thr Thr Gln Pro Arg Lys Thr Lys Gly
            485                 490                 495

Ser Gly Phe Phe Val Phe Ser Arg Leu Glu Val Thr Arg Ala Glu Trp
            500                 505                 510

Glu Gln Lys Asp Glu Phe Ile Cys Arg Ala Val His Glu Ala Ala Ser
    515                 520                 525

Pro Ser Gln Thr Val Gln Arg Ala Val Ser Val Asn Pro Gly Lys
    530                 535                 540

<210> SEQ ID NO 26
<211> LENGTH: 545
<212> TYPE: PRT
<213> ORGANISM: Homo sapiens

<400> SEQUENCE: 26

Gln Pro Pro Pro Pro Pro Asp Ala Thr Cys His Gln Val Arg Ser
1               5                   10                  15

Phe Phe Gln Arg Leu Gln Pro Gly Leu Lys Trp Val Pro Glu Thr Pro
            20                  25                  30

Val Pro Gly Ser Asp Leu Gln Val Cys Leu Pro Lys Gly Pro Thr Cys
            35                  40                  45

Cys Ser Arg Lys Met Glu Glu Lys Tyr Gln Leu Thr Ala Arg Leu Asn
    50                  55                  60

Met Glu Gln Leu Leu Gln Ser Ala Ser Met Glu Leu Lys Phe Leu Ile
65                  70                  75                  80

Ile Gln Asn Ala Ala Val Phe Gln Glu Ala Phe Glu Ile Val Val Arg
                85                  90                  95

His Ala Lys Asn Tyr Thr Asn Ala Met Phe Lys Asn Asn Tyr Pro Ser
                100                 105                 110

Leu Thr Pro Gln Ala Phe Glu Phe Val Gly Glu Phe Phe Thr Asp Val
            115                 120                 125

Ser Leu Tyr Ile Leu Gly Ser Asp Ile Asn Val Asp Asp Met Val Asn
    130                 135                 140

Glu Leu Phe Asp Ser Leu Phe Pro Val Ile Tyr Thr Gln Leu Met Asn
145                 150                 155                 160

```
Pro Gly Leu Pro Asp Ser Ala Leu Asp Ile Asn Glu Cys Leu Arg Gly
            165                 170                 175

Ala Arg Arg Asp Leu Lys Val Phe Gly Asn Phe Pro Lys Leu Ile Met
        180                 185                 190

Thr Gln Val Ser Lys Ser Leu Gln Val Thr Arg Ile Phe Leu Gln Ala
        195                 200                 205

Leu Asn Leu Gly Ile Glu Val Ile Asn Thr Thr Asp His Leu Lys Phe
    210                 215                 220

Ser Lys Asp Cys Gly Arg Met Leu Thr Arg Met Trp Tyr Cys Ser Tyr
225                 230                 235                 240

Cys Gln Gly Leu Met Met Val Lys Pro Cys Gly Gly Tyr Cys Asn Val
            245                 250                 255

Val Met Gln Gly Cys Met Ala Gly Val Val Glu Ile Asp Lys Tyr Trp
            260                 265                 270

Arg Glu Tyr Ile Leu Ser Leu Glu Glu Leu Val Asn Gly Met Tyr Arg
        275                 280                 285

Ile Tyr Asp Met Glu Asn Val Leu Leu Gly Leu Phe Ser Thr Ile His
    290                 295                 300

Asp Ser Ile Gln Tyr Val Gln Lys Asn Ala Gly Lys Leu Thr Thr Thr
305                 310                 315                 320

Ile Gly Lys Leu Cys Ala His Ser Gln Gln Arg Gln Tyr Arg Ser Ala
            325                 330                 335

Tyr Tyr Pro Glu Asp Leu Phe Ile Asp Lys Lys Val Leu Lys Val Ala
            340                 345                 350

His Val Glu His Glu Thr Leu Ser Ser Arg Arg Glu Leu Ile
        355                 360                 365

Gln Lys Leu Lys Ser Phe Ile Ser Phe Tyr Ser Ala Leu Pro Gly Tyr
    370                 375                 380

Ile Cys Ser His Ser Pro Val Ala Glu Asn Asp Thr Leu Cys Trp Asn
385                 390                 395                 400

Gly Gln Glu Leu Val Glu Arg Tyr Ser Gln Lys Ala Ala Arg Asn Gly
            405                 410                 415

Met Lys Asn Gln Phe Asn Leu His Glu Leu Lys Met Lys Gly Pro Glu
            420                 425                 430

Pro Val Val Ser Gln Ile Ile Asp Lys Leu Lys His Ile Asn Gln Leu
            435                 440                 445

Leu Arg Thr Met Ser Met Pro Lys Gly Arg Val Leu Asp Lys Asn Leu
    450                 455                 460

Asp Glu Glu Gly Phe Glu Ala Gly Asp Cys Gly Asp Asp Glu Asp Glu
465                 470                 475                 480

Cys Ile Gly Gly Ala Gly Asp Gly Met Ile Lys Val Lys Asn Gln Leu
            485                 490                 495

Arg Phe Leu Ala Glu Leu Ala Tyr Asp Leu Asp Val Asp Asp Ala Pro
        500                 505                 510

Gly Asn Ser Gln Gln Ala Thr Pro Lys Asp Asn Glu Ile Ser Thr Phe
    515                 520                 525

His Asn Leu Gly Asn Val His Ser Pro Leu Lys His His His His
    530                 535                 540

His
545

<210> SEQ ID NO 27
<211> LENGTH: 365
```

<212> TYPE: PRT
<213> ORGANISM: Homo sapiens

<400> SEQUENCE: 27

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
    130                 135                 140

Leu Lys Gln Gly Thr Trp Gly Gly Asp Trp Pro Glu Ala Leu Ala Ile
145                 150                 155                 160

Ser Gln Arg Trp Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
    210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
    290                 295                 300

Ile Gly Val Leu Leu Leu Thr Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 28
<211> LENGTH: 119
<212> TYPE: PRT
<213> ORGANISM: Homo sapiens

```
<400> SEQUENCE: 28

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
                100                 105                 110

Val Lys Trp Asp Arg Asp Met
            115

<210> SEQ ID NO 29
<211> LENGTH: 8
<212> TYPE: PRT
<213> ORGANISM: Artificial Sequence
<220> FEATURE:
<223> OTHER INFORMATION: An artificially synthesized peptide sequence

<400> SEQUENCE: 29

Asp Tyr Lys Asp Asp Asp Asp Lys
1               5
```

THERAPEUTIC ANTIGEN-BINDING MOLECULE WITH A FCRN-BINDING DOMAIN THAT PROMOTES ANTIGEN CLEARANCE

CROSS-REFERENCE TO RELATED APPLICATIONS

This application is the National Stage of International Application Serial No. PCT/JP2012/006218, filed on Sep. 28, 2012, which claims the benefit of Japanese Application Serial No. 2011-218736, filed on Sep. 30, 2011, PCT App. Ser. No. PCT/JP2012/058603, filed on Mar. 30, 2012, Japanese Application Serial No. 2012-123781, filed on May 30, 2012, Japanese Application Serial No. 2012-123773, filed on May 30, 2012, Japanese Application Serial No. 2012-123782, filed on May 30, 2012, Japanese Application Serial No. 2012-139211, filed on Jun. 20, 2012, and Japanese Application Serial No. 2012-177311, filed on Aug. 9, 2012.

TECHNICAL FIELD

The present invention relates to: a modified FcRn-binding domain having an enhanced affinity for the Fc Receptor neonatal (FcRn) at neutral pH; an antigen-binding molecule comprising said FcRn-binding domain, which has low immunogenicity, high stability and form only a few aggregates; a modified antigen-binding molecule having an increased FcRn-binding activity at neutral or acidic pH without an increased binding activity at neutral pH for a pre-existing anti-drug antibody; use of the antigen-binding molecules for improving antigen-binding molecule-mediated antigen uptake into cells; use of the antigen-binding molecules for reducing the plasma concentration of a specific antigen; use of the modified FcRn-binding domain for increasing the total number of antigens to which a single antigen-binding molecule can bind before its degradation; use of the modified FcRn-binding domain for improving pharmacokinetics of an antigen-binding molecule; methods for decreasing the binding activity for a pre-existing anti-drug antibody; and methods for producing said antigen-binding molecules.

BACKGROUND ART

Due to their high stability in plasma and few side effects, an increasing number of antibodies are being used as pharmaceuticals. A conventional antibody targeting a soluble antigen binds the antigen in the plasma of the patient after injection and then stably persists in the form of an antibody-antigen complex until degradation. While a typical antibody has generally a long half-life (1-3 weeks), an antigen has a relatively short half-life of less than one day. An antigen in complex with an antibody therefore has a significantly longer half-life than the antigen alone. Consequently, the antigen concentration tends to increase after the injection of a conventional antibody. Such cases have been reported for antibodies targeting various soluble antigens, such as IL-6 (J Immunotoxicol. 2005, 3, 131-9. (NPL 1)), beta amyloid (MAbs. 2010 September-October; 2(5):576-88 (NPL 2)), MCP-1 (ARTHRITIS & RHEUMATISM 2006, 54, 2387-92 (NPL 3)), hepcidin (AAPS J. 2010, 12(4):646-57. (NPL 4)) and sIL-6 receptor (Blood. 2008 Nov. 15; 112(10):3959-64. (NPL 5)). Reports have described an approximately 10 to 1000-fold increase (depending of the antigen) of total plasma antigen concentration from the baseline upon antibody administration.

As such an increase of the total plasma antigen concentration is not desired, strategies for removing the antigen by a therapeutic antibody have been developed. One of these strategies is to dispose the antigen rapidly using a pH-dependent antigen binding antibody that has increased binding affinity to the neonatal Fc receptor for IgG (FcRn) (see e.g. PCT application no. PCT/JP2011/001888 (PTL 1)). The FcRn is a protein found in the membrane of many cells. An antibody with increased binding activity to FcRn at neutral pH will bind FcRn on the cell surface, whereby the receptor with the antibody is internalized into the cells in a vesicle. As the pH in the interior of the vesicle is gradually decreased, the antigen will dissociate from the pH-dependent antigen binding antibody, owing to its low affinity in acidic pH. The dissociated antigen is then degraded while the FcRn and bound antibody are recycled back to the surface of the cells before degradation. Accordingly, a pH-dependent antigen binding antibody having increased binding activity to FcRn at neutral pH can be used to remove an antigen from plasma and decrease its concentration in plasma.

Previous studies have also demonstrated that Fc-engineering to increase the binding affinity to FcRn at acidic pH can also improve the endosomal recycling efficiency and the pharmacokinetics of the antibody. For example, M252Y/S254T/T256E (YTE) variant (J Biol Chem, 2006, 281: 23514-23524. (NPL 6)), M428L/N434S (LS) variant (Nat Biotechnol, 2010 28:157-159. (NPL 7)), T250Q/M428L (J Immunol. 2006, 176(1):346-56. (NPL 8)) and N434H variant (Clinical Pharmacology & Therapeutics (2011) 89(2): 283-290. (NPL 9)) showed improvement in half-life relative to native IgG1.

However, such substitutions have also the risk of altering properties of the antibody that are important for the development of a therapeutic antibody such as the antibody's stability, immunogenicity, aggregation behavior and binding affinity for pre-existing antibodies (e.g. rheumatoid factor). It is therefore the main objective of the present invention to provide a modified FcRn-binding domain which not only enhances the clearance of an antibody but also meets the criteria for developing a therapeutic antigen-binding molecule. These developability criteria are in particular high stability, low immunogenicity, low percentage of aggregates, and low binding affinity for pre-existing anti-drug antibodies (ADA).

Prior art documents related to the present invention are shown below. All documents cited in this specification are incorporated herein by reference.

CITATION LIST

Patent Literature

[PTL 1] PCT/JP2011/00188 (WO/2011/122011), ANTIGEN-BINDING MOLECULES THAT PROMOTE ANTIGEN CLEARANCE

Non Patent Literature

[NPL 1] Martin P L, Cornacoff J, Prabhakar U, Lohr T, Treacy G, Sutherland J E, Hersey S, Martin E; Reviews Preclinical Safety and Immune-Modulating Effects of Therapeutic Monoclonal Antibodies to Interleukin-6 and Tumor Necrosis Factor-alpha in Cynomolgus Macaques; J Immunotoxicol. 2005, 3, 131-9

[NPL 2] Davda J P, Hansen R J.; Properties of a general PK/PD model of antibody-ligand interactions for therapeutic antibodies that bind to soluble endogenous targets; MAbs. 2010 September-October; 2(5):576-88.

[NPL 3] Haringman J J, Gerlag D M, Smeets T J, Baeten D, van den Bosch F, Bresnihan B, Breedveld F C, Dinant H J, Legay F, Gram H, Loetscher P, Schmouder R, Woodworth T, Tak P P.; A randomized controlled trial with an anti-CCL2 (anti-monocyte chemotactic protein 1) monoclonal antibody in patients with rheumatoid arthritis; ARTHRITIS and RHEUMATISM 2006, 54, 2387-92.

[NPL 4] Xiao J J, Krzyzanski W, Wang Y M, Li H, Rose M J, Ma M, Wu Y, Hinkle B, Perez-Ruixo J J.; Pharmacokinetics of anti-hepcidin monoclonal antibody Ab 12B9m and hepcidin in cynomolgus monkeys; AAPS J. 2010, 12(4), 646-57.)

[NPL 5] Nishimoto N, Terao K, Mima T, Nakahara H, Takagi N, Kakehi T.; Mechanisms and pathologic significances in increase in serum interleukin-6 (IL-6) and soluble IL-6 receptor after administration of an anti-IL-6 receptor antibody, tocilizumab, in patients with rheumatoid arthritis and Castleman disease; Blood. 2008 Nov. 15; 112(10):3959-64.

[NPL 6] J Biol Chem, 2006, 281:23514-23524
[NPL 7] Nat Biotechnol, 2010 28:157-159
[NPL 8] J Immunol. 2006, 176(1):346-56
[NPL 9] Clinical Pharmacology & Therapeutics (2011) 89(2):283-290

SUMMARY OF INVENTION

Technical Problem

The present invention was conceived in view of the circumstances described above. An objective of the present invention is to provide a modified FcRn-binding domain which has an enhanced affinity for the FcRn at neutral pH; an antigen-binding molecule comprising said FcRn-binding domain, wherein said antigen-binding molecule has low immunogenicity, high stability and forms only few aggregates; a modified antigen-binding molecule having an increased FcRn-binding activity at neutral or acidic pH without an increased binding activity at neutral pH for a pre-existing anti-drug antibody; use of the antigen-binding molecules for improving antigen-binding molecule-mediated antigen uptake into cells; use of the antigen-binding molecule for reducing the plasma concentration of a specific antigen; use of the modified FcRn-binding domain for increasing the total number of antigens to which a single antigen-binding molecule can bind before its degradation; use of the modified FcRn-binding domain for improving pharmacokinetics of an antigen-binding molecule; and methods for producing said antigen-binding molecules.

Solution to Problem

The present inventors conducted dedicated studies on modified FcRn-binding domains which have an enhanced affinity for FcRn at neutral pH and on antigen-binding molecules comprising said FcRn-binding domain which have low immunogenicity, high stability and form only few aggregates. As a result, the present inventors discovered that substitutions at specific positions of the FcRn-binding domain increases the affinity for the FcRn at neutral pH without substantially increasing the immunogenicity, without substantially decreasing the stability and/or without substantially increasing the ratio of high molecular weight species.

Furthermore, the present inventors conducted dedicated studies on modified FcRn-binding domains with an enhanced affinity for FcRn at neutral pH or acidic pH but without a significantly increased binding activity for a pre-existing anti-drug antibody and on antigen-binding molecules comprising such an FcRn-binding domain. As a result, the present inventors discovered that substitutions at specific positions of the FcRn-binding domain decrease the affinity for a pre-existing anti-drug antibody at neutral pH without substantially decreasing the FcRn-binding activity.

Specifically, the present invention relates to:

[1] An antigen-binding molecule comprising a modified FcRn-binding domain, wherein the modified FcRn-binding domain comprises an amino acid substitution at one or more positions selected from the group consisting of EU238, EU250, EU252, EU254, EU255, EU258, EU286, EU307, EU308, EU309, EU311, EU315, EU428, EU433, EU434, and EU436, wherein the numbers indicate the position of the substitution according to the EU numbering.

[2] The antigen-binding molecule according to [1], wherein the FcRn-binding domain has
a) an amino acid substitution of the amino acid at position EU252 and EU434; and
b) an amino acid substitution at one or more positions selected from the group consisting of EU238, EU250, EU252, EU254, EU255, EU256, EU258, EU286, EU387, EU307, EU308, EU309, EU311, EU315, EU428, EU433, EU434, and EU436.

[3] The antigen-binding molecule according to [1] or [2], wherein the modified FcRn-binding domain comprises
at position EU238 an aspartic acid,
at position EU250 a valine,
at position EU252 a tyrosine,
at position EU254 a threonine,
at position EU255 a leucine,
at position EU256 a glutamic acid,
at position EU258 an aspartic acid or an isoleucine,
at position EU286 a glutamic acid,
at position EU307 a glutamine,
at position EU308 a proline,
at position EU309 a glutamic acid,
at position EU311 an alanine or a histidine,
at position EU315 an aspartic acid,
at position EU428 an isoleucine,
at position EU433 an alanine, a lysine, a proline, an arginine, or a serine,
at position EU434 a tyrosine, or a tryptophan, and/or
at position EU436 an isoleucine, a leucine, a valine, a threonine, or a phenylalanine.

[4] The antigen-binding molecule according to [2], wherein the FcRn-binding domain comprises an amino acid substitution of an amino acid at one or more position combinations selected from the group consisting of
a) EU252, EU434, and EU436;
b) EU252, EU307, EU311 and EU434;
c) EU252, EU315, and EU434;
d) EU252, EU308, and EU434;
e) EU238, EU252, and EU434;
f) EU252, EU434, EU307, EU311, and EU436; and
g) EU252, EU387, and EU434.

[5] The antigen-binding molecule according to [4], wherein the FcRn-binding domain comprises:
a) at position EU252 a tyrosine, at position EU315 an aspartic acid, and at position EU434 a tyrosine; or
b) at position EU252 a tyrosine, at position EU434 a tyrosine, and at position EU436 an isoleucine; or c) at position EU252 a tyrosine, at position EU434 a tyrosine, and at position EU436 a leucine; or
d) at position EU252 a tyrosine, at position EU434 a tyrosine, and at position EU436 a valine; or
e) at position EU252 a tyrosine, at position EU254 a threonine, at position EU434 a tyrosine, and at position EU436 an isoleucine.

[6] The antigen-binding molecule according to [2], wherein the FcRn-binding domain comprises an amino acid substitution at three or more positions, wherein the three or more positions are one of the combinations of the group consisting of
a) EU252/EU434/EU307/EU311/EU286;
b) EU252/EU434/EU307/EU311/EU286/EU254;
c) EU252/EU434/EU307/EU311/EU436;
d) EU252/EU434/EU307/EU311/EU436/EU254;
e) EU252/EU434/EU307/EU311/EU436/EU250;
f) EU252/EU434/EU308/EU250;
g) EU252/EU434/EU308/EU250/EU436; and
h) EU252/EU434/EU308/EU250/EU307/EU311.

[7] The antigen-binding molecule according to [6], wherein the FcRn-binding domain comprises:
a) at position EU252 a tyrosine, at position EU286 a glutamic acid, at position EU307 a glutamine, at position EU311 an alanine and at position EU434 a tyrosine; or
b) at position EU252 a tyrosine, at position EU254 a threonine, at position EU286 a glutamic acid, at position EU307 a glutamine, at position EU311 an alanine and at position EU434 a tyrosine; or
c) at position EU252 a tyrosine, at position EU307 a glutamine, at position EU311 an alanine, at position EU434 a tyrosine and at position 436 an isoleucine; or
d) at position EU252 a tyrosine, at position EU254 a threonine, at position EU286 a glutamic acid, at position EU307 a glutamine, at position EU311 an alanine, at position EU434 a tyrosine and at position EU436 an isoleucine; or
e) at position EU250 a valine, at position EU252 a tyrosine, at position EU254 a threonine, at position EU308 a proline, at position EU434 a tyrosine and at position EU436 a valine; or
f) at position EU250 a valine, at position EU252 a tyrosine, at position EU307 a glutamine, at position EU311 an alanine, at position EU434 a tyrosine and at position EU436 a valine; or
g) at position EU252 a tyrosine, at position EU307 a glutamine, at position EU311 an alanine, at position EU434 a tyrosine and at position EU436 a valine; or
h) at position EU250 a valine, at position EU252 a tyrosine, at position EU308 a proline, and at position EU434 a tyrosine; or
i) at position EU250 a valine, at position EU252 a tyrosine, at position EU307 a glutamine, at position EU308 a proline, at position EU311 an alanine, and at position EU434 a tyrosine.

[8] The antigen-binding molecule according to [2], wherein the FcRn-binding domain comprises an amino acid substitution at three or more positions wherein the three or more positions are one of the combinations of the group consisting of
a) EU252 and EU434 and EU307 and EU311 and EU436 and EU286;
b) EU252 and EU434 and EU307 and EU311 and EU436 and EU250 and EU308;
c) EU252 and EU434 and EU307 and EU311 and EU436 and EU250 and EU286 and EU308;
d) EU252 and EU434 and EU307 and EU311 and EU436 and EU250 and EU286 and EU308 and EU428.

[9] The antigen-binding molecule according to [8], wherein the FcRn-binding domain comprises:
a) at position EU252 a tyrosine, at position EU286 a glutamic acid, at position EU307 a glutamine, at position EU311 an alanine, at position EU434 a tyrosine, and at position EU436 a valine; or
b) at position EU250 a valine, at position EU252 a tyrosine, at position EU307 a glutamine, at position EU308 proline, at position EU311 an alanine, at position EU434 a tyrosine, and at position EU436 a valine; or
c) at position EU250 a valine, at position EU252 a tyrosine, at position EU286 a glutamic acid, at position EU307 a glutamine, at position EU308 proline, at position EU311 an alanine, at position EU434 a tyrosine, and at position EU436 a valine; or
d) at position EU250 a valine, at position EU252 a tyrosine, at position EU286 a glutamic acid, at position EU307 a glutamine, at position EU308 proline, at position EU311 an alanine, at position EU434 a tyrosine, and at position EU436 a valine.

[10] The antigen-binding molecule according to [2], wherein the FcRn-binding domain comprises an amino acid substitution at three or more positions wherein the three or more positions are one of the combinations of the group consisting of:
a) EU434 and EU307 and EU311;
b) EU434 and EU307 and EU309 and EU311; or
c) EU434 and EU250 and EU252 and EU436.

[11] The antigen-binding molecule according to [10], wherein the FcRn-binding domain comprises:
a) at position EU307 a glutamine, at position EU311 a histidine and at position EU434 a tyrosine; or
b) at position EU307 a glutamine, at position EU309 a glutamic acid, at position EU311 an alanine and at position EU434 a tyrosine; or
c) at position EU307 a glutamine, at position EU309 a glutamic acid, at position EU311 an histidine and at position EU434 a tyrosine; or
d) at position EU250 a valine; at position EU252 a tyrosine, at position EU434 a tyrosine and at position EU436 a valine.

[12] The antigen-binding molecule according to any one of [1] to [11], wherein the ratio of high molecular weight species is less than 2%.

[13] The antigen-binding molecule according to any one of [1] to [12], wherein antigen-binding molecule comprises an antigen-binding domain having
a) a lower binding activity for the antigen at pH 5.5-6.5 than at pH 7-8 or
b) a "calcium concentration-dependent binding" activity for the antigen.

[14] The antigen-binding molecule according to any one of [1] to [5], wherein the binding activity of said binding molecule for the FcRn at pH 7 is 50-150 nM, Tm is higher than 63.0 degrees C., and Epibase score is less than 250.

[15]. The antigen-binding molecule according to any one of [1] to [3] and [6] to [7], and wherein the binding activity of said binding molecule for FcRn at pH 7 is 15-50 nM, Tm is higher than 60 degrees C., and Epibase score is less than 500.

[16] The antigen-binding molecule according to any one of [1] to [3] and [8] to [9], and wherein the binding activity of said the binding molecule for FcRn at pH 7 is stronger than 15 nM, Tm is higher than 57.5 degrees C., and Epibase score is less than 500.

[17] The antigen-binding molecule according to any one of [1] to [3], wherein the FcRn-binding domain comprises an amino acid substitution
a) at the positions EU238, EU255 and/or EU258, and
b) at three or more positions, wherein the three or more positions are one of the combinations set forth in Tables 4 to 7.

[18] The antigen-binding molecule according to any one of [1] to [17], wherein
a) at the position EU257 of the FcRn-binding domain the amino acid is not an amino acid selected from the group consisting of alanine, valine, isoleucine, leucine, and threonine, and/or
b) at the position EU252 of the FcRn-binding domain the amino acid is not tryptophan.

[19] The antigen-binding molecule according to any one of [1] to [18], wherein the antigen-binding molecule has a binding activity for a pre-existing anti-drug antibody that is not significantly increased as compared to the binding affinity of a control antibody comprising an intact FcRn-binding domain.

[20] The antigen-binding molecule according to [19], wherein the FcRn binding domain further comprises an amino acid substitution at one or more positions selected from the group consisting of EU387, EU422, EU424, EU426, EU433, EU436, EU438 and EU440.

[21] The antigen-binding molecule according to [20], wherein the FcRn binding domain comprises one or more amino acid substitutions selected from the group consisting of
at position EU387 an arginine,
at position EU422 a glutamic acid, an arginine, or a serine, an aspartic acid, a lysine, a threonine or a glutamine;
at position EU424 a glutamic acid or an arginine, a lysine, or an asparagine;
at position EU426 an aspartic acid, a glutamine, an alanine, or a tyrosine;
at position EU433 an aspartic acid;
at position EU436 a threonine;
at position EU438 a glutamic acid, an arginine, a serine, or a lysine; and
at position EU440 a glutamic acid, aspartic acid or a glutamine.

[22] The antigen-binding molecule according to any one of [1] to [21], wherein the modified FcRn binding domain comprises three or more substitutions, wherein the three or more substitutions are one of the combinations set forth in Tables 12 to 13.

[23] The antigen-binding molecule according to any one of [1] to [22], wherein the modified FcRn-binding domain comprises three or more substitutions, wherein the three or more substitutions are one of the combinations set forth in Tables 14 to 15.

[24] The antigen-binding molecule according to any one of [20] to [23], wherein the FcRn-binding domain comprises:
a) at position EU252 a tyrosine, at position EU387 an arginine, at position EU434 a tyrosine, and at position EU436 a valine; or
b) at position EU252 a tyrosine, at position EU422 a glutamic acid, at position EU434 a tyrosine, and at position EU436 a valine; or
c) at position EU252 a tyrosine, at position EU422 an arginine, at position EU434 a tyrosine, and at position EU436 a valine; or
d) at position EU252 a tyrosine, at position EU422 a serine, at position EU434 a tyrosine, and at position EU436 a valine; or
e) at position EU252 a tyrosine, at position EU424 a glutamic acid, at position EU434 a tyrosine, and at position EU436 a valine; or
f) at position EU252 a tyrosine, at position EU424 an arginine, at position EU434 a tyrosine, and at position EU436 a valine; or
g) at position EU252 a tyrosine, at position EU434 a tyrosine, at position EU436 a valine, and at position EU438 a glutamic acid; or
h) at position EU252 a tyrosine, at position EU434 a tyrosine, at position EU436 a valine, and at position EU438 an arginine; or
i) at position EU252 a tyrosine, at position EU434 a tyrosine, at position EU436 a valine, and at position EU438 a serine; or
j) at position EU252 a tyrosine, at position EU434 a tyrosine, at position EU436 a valine, and at position EU440 a glutamic acid.

[25] The antigen-binding molecule according to any one of [1] to [24], wherein the antigen-binding molecule is an antibody.

[26] Use of the antigen-binding molecule according to any one of [1] to [25] for improving antigen-binding molecule-mediated antigen uptake into cells.

[27] Use of the antigen-binding molecule according to any one of [1] to [25] for reducing the plasma concentration of a specific antigen, wherein the antigen-binding molecule comprises an antigen-binding domain which can bind said antigen.

[28] A method for improving the pharmacokinetics of an antigen-binding molecule, comprising the step of introducing an amino acid substitution into an FcRn-binding domain of said antigen-binding molecules at one or more of the positions selected from the group consisting of EU238, EU250, EU252, EU254, EU255, EU258, EU286, EU307, EU308, EU309, EU311, EU315, EU428, EU433, EU434, and EU436.

[29] A method for delaying the elimination of an antigen-binding molecule in a subject, comprising the step of introducing an amino acid substitution into an FcRn-binding domain of said antigen-binding molecule at one or more of the positions selected from the group consisting of EU238, EU250, EU252, EU254, EU255, EU258 EU286, EU307, EU308, EU309, EU311, EU315, EU428, EU433, EU434, and EU436.

[30] A method of prolonging the plasma retention time of an antigen-binding molecule, comprising the step of introducing an amino acid substitution into an FcRn-binding domain of said antigen-binding molecule at one or more of the positions selected from the group consisting of EU238, EU250, EU252, EU254, EU255, EU258 EU286, EU307, EU308, EU309, EU311, EU315, EU428, EU433, EU434, and EU436.

[31] A method for increasing the plasma antigen-elimination rate of an antigen-binding molecule, comprising the step of introducing an amino acid substitution into an FcRn-binding domain of said antigen-binding molecule at one or more of the positions selected from the group consisting of EU238, EU250, EU252, EU254, EU255, EU258 EU286, EU307, EU308, EU309, EU311, EU315, EU428, EU433, EU434, and EU436.

[32] A method for increasing the ability of an antigen-binding molecule to eliminate plasma antigen, comprising the step of introducing an amino acid substitution into an FcRn-binding domain of said antigen-binding molecule at one or more of the positions selected from the group consisting of EU238, EU250, EU252, EU254, EU255, EU258 EU286, EU307, EU308, EU309, EU311, EU315, EU428, EU433, EU434, and EU436.

[33] The method according to any one of [28] to [32], wherein further an amino acid substitution at position EU256 into the FcRn binding domain is introduced.

[34] The method according to any one of [28] to [33], wherein the method further comprises a step of introducing into the FcRn-binding domain an amino acid substitution at one or more positions selected from the group consisting of EU387, EU422, EU424, EU426, EU433, EU436, EU438 and EU440.

[35] A method for producing antigen-binding molecules according to any one of [1] to [25], which comprises the steps of (a) selecting a parent FcRn-binding domain and altering the parent FcRn by introducing an amino acid substitution at one or more positions selected from the group consisting of EU238, EU250, EU252, EU254, EU255, EU258 EU286, EU307, EU308, EU309, EU311, EU315, EU428, EU433, EU434, and EU436;

(b) selecting an antigen-binding domain of an antigen-binding molecule and altering at least one amino acid in the antigen-binding domain in order to get a pH-dependent antigen-binding domain or a calcium-ion dependent antigen-binding domain;

(c) obtaining a gene encoding an antigen-binding molecule in which the human FcRn-binding domain and the antigen-binding domain prepared in (a) and (b) are linked and (d) producing an antigen-binding molecule using the gene prepared in (c).

[36] The method according to [35], wherein in step a) further an amino acid substitution at position EU256 into the FcRn binding domain is introduced.

[37] The method according to any one of [35] to [36], wherein the method further comprises a step of introducing into the FcRn-binding domain an amino acid substitution at one or more positions selected from the group consisting of EU387, EU422, EU424, EU426, EU433, EU436, EU438 and EU440.

[38] An antigen-binding molecule comprising a modified FcRn binding domain, wherein the modified FcRn binding domain comprises an amino acid substitution at one or more of the positions selected from the group consisting of EU387, EU422, EU424, EU426, EU433, EU436, EU438 and EU440, wherein the binding affinity of said antigen-binding molecule for a pre-existing anti-drug antibody (ADA) at a neutral pH is not significantly increased as compared to the binding affinity of antigen-binding molecule comprising an intact FcRn binding domain.

[39]. The antigen-binding molecule according to [38] wherein the antigen-binding molecule further has an increased binding affinity for an FcRn in the neutral or acidic pH ranges.

[40] The antigen-binding molecule according to [38] or [39], wherein the amino acid substituting one or more of the positions selected from the group consisting of EU387, EU422, EU424, EU426, EU433, EU436, EU438 and EU440 is selected from the group consisting of a) at position EU387 an arginine;
b) at position EU422 a glutamic acid, an arginine, a serine, aspartic acid, lysine, threonine, or glutamine;
c) at position EU424 a glutamic acid, an arginine, a lysine, or asparagines;
d) at position EU426 an aspartic acid, a glutamine, an alanine, or a tyrosine;
e) at position EU433 an aspartic acid
f) at position EU436 a threonine g) at position EU438 a glutamic acid, an arginine, a serine, or a lysine; and
h) at position EU440 a glutamic acid, an aspartic acid, or a glutamine.

[41] The antigen-binding molecule according to any one of [38] to [40], wherein the modified FcRn binding domain comprises an amino acid substitution at one or more positions or one of the combinations set forth in Table 10.

[42] The antigen-binding molecule according to any one of [38] to [40], wherein the modified FcRn binding domain comprises any one of the amino acid substitution or substitution combinations set forth in Table 11.

[43] The antigen-binding molecule according to any one of [39] to [42], wherein the modified FcRn binding domain further comprises an amino acid substitution at one or more positions of the FcRn binding domain selected from the group consisting of EU238, EU250, EU252, EU254, EU255, EU256, EU258, EU286, EU307, EU308, EU309, EU311, EU315, EU428, EU434, and EU436, wherein said substitutions confer an increase in FcRn binding activity in the neutral pH or acidic pH range.

[44] The antigen-binding molecule according to any one of [39] to [43], wherein the modified FcRn binding domain comprises amino acid substitutions at the FcRn binding domain positions
i) a) EU438/EU440 or b) EU424; and
ii) a) EU434, b) EU252/EU254/EU256; c) EU428/EU434; or d) EU250/EU428.

[45] The antigen-binding molecule according to [44], wherein the modified FcRn binding domain comprises amino acid substitutions
i) a) EU438R/EU440E or b) EU424N; and
ii) a) M434H; b) M252Y/S254T/T256E; c) M428L/N434S; or d) T250Q and M428L (EU numbering).

[46] The antigen-binding molecule according to [45], wherein the modified FcRn binding domain comprises three or more amino acid substitutions wherein the three or more substitutions are one of the combinations set forth in Tables 13 and 15.

[47] The antigen-binding molecule according to any one of [39] to [42] wherein the modified FcRn binding domain comprises substitutions
a) at one or more of the positions selected from the group consisting of EU387, EU422, EU424, EU438, EU440, EU433, or at two or more positions wherein the two positions are one of the combinations of the group consisting of EU422/EU424, and EU438/EU440; and
b) two or more positions wherein the two positions are one of the combinations set forth in Table 9.

[48] The antigen-binding molecule according to [47], wherein the modified FcRn binding domain comprises three or more the amino acid substitutions wherein the three or more the amino acid substitutions are one of the combinations set forth in Tables 12 or 14.

[49] The antigen-binding molecule of any one of [39] to [48] wherein said antigen-binding molecule comprises a pH-dependent antigen-binding domain or a calcium ion-dependent antigen-binding domain.

[50] A method for decreasing the binding activity for a pre-existing ADA of an antigen-binding molecule comprising an FcRn binding domain having an increased binding activity for an FcRn at neutral or acidic pH and an increased binding activity for a pre-existing ADA at a neutral pH, said method comprising the steps of a) providing an antigen-binding molecule with an FcRn binding domain having an increased binding activity for FcRn at neutral or acidic pH and an increased binding activity for a pre-existing ADA at a neutral pH; and b) substituting an amino acid in the FcRn binding domain at one or more of the positions selected from the group consisting of EU387, EU422, EU424, EU426, EU433, EU436, EU438 and EU440 to yield an antigen-binding molecule with a modified FcRn binding domain.

[51] The method according to [50], wherein step b) comprises substituting an amino acid at three or more positions wherein the three or more positions are one of the combinations set forth in Table 10.

[52] The method according to [50], wherein step b) comprises introducing three or more the amino acid substitutions into the FcRn-binding domain wherein the three or more the amino acid substitutions are one of the combinations set forth in Table 11.

[53] A method for increasing the total number of antigens to which a single antigen-binding molecule can bind without significantly increasing the binding activity for a pre-existing ADA at neutral pH as compared to a parent antibody, said method comprising the steps of a) providing an antigen-binding molecule comprising a parent FcRn binding domain, b) altering the parent FcRn binding domain of step a) by substituting an amino acid in the amino acid sequence of the parent FcRn binding domain at one or more of the positions selected from the group consisting of EU238, EU250, EU252, EU254, EU255, EU256, EU258, EU286, EU307, EU308, EU309, EU311, EU315, EU428, EU433, EU434, and EU436; and c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

[54] A method for facilitating the extracellular release of an antigen-free antigen-binding molecule taken up into cells in an antigen-bound form without significantly increasing the binding activity of said antigen-binding molecule for a pre-existing ADA at neutral pH as compared to a parent antibody, comprising the steps of a) providing an antigen-binding molecule comprising a parent FcRn-binding domain, b) altering the parent FcRn binding domain by substituting an amino acid in the amino acid sequence of the parent FcRn-binding domain at one or more positions selected from the group consisting of EU238, EU250, EU252, EU254, EU255, EU256, EU258, EU286, EU307, EU308, EU309, EU311, EU315, EU428, EU433, EU434, and EU436, and EU428; and c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

[55] A method for increasing the ability of an antigen-binding molecule to eliminate plasma antigen without significantly increasing the binding activity for pre-existing ADA at neutral pH compared to parent antibody, said method comprising the steps of a) providing an antigen-binding molecule comprising a parent FcRn-binding domain, b) altering the parent FcRn binding domain by substituting an amino acid in the amino acid sequence of the parent FcRn-binding domain at one or more positions selected from the group consisting of EU238, EU250, EU252, EU254, EU255, EU256, EU258, EU286, EU307, EU308, EU309, EU311, EU315, EU428, EU433, EU434, and EU436, and EU428; and c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

[56] A method for improving the pharmacokinetics of an antigen-binding molecule without significantly increasing the binding activity for a pre-existing ADA at neutral pH as compared to a parent antibody, said method comprising the steps of a) providing an antigen-binding molecule comprising a parent FcRn-binding domain, b) altering the parent FcRn-binding domain by substituting an amino acid in the amino acid sequence of the parent FcRn-binding domain at one or more positions selected from the group consisting of EU238, EU250, EU252, EU254, EU255, EU256, EU258, EU286, EU307, EU308, EU309, EU311, EU315, EU428, EU433, EU434, and EU436; and c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

[57] A method for reducing total or free antigen plasma concentration without significantly increasing the binding activity for a pre-existing ADA at neutral pH as compared to a parent antibody, said method comprising the steps of a) providing an antigen-binding molecule comprising a parent FcRn-binding domain, wherein the antigen-binding molecule comprises an antigen-binding domain which can bind said antigen, b) altering the parent FcRn-binding domain by substituting an amino acid in the amino acid sequence of the parent FcRn-binding domain at one or more positions selected from the group consisting of EU238, EU250, EU252, EU254, EU255, EU256, EU258 EU286, EU307, EU308, EU309, EU311, EU315, EU428, EU433, EU434, and EU436; and c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

[58] A method for producing an antigen-binding molecule comprising an FcRn binding domain having an increased binding activity for an FcRn at neutral or acidic pH and a decreased binding activity for an pre-existing ADA at neutral pH, said method comprising the steps of (a) providing an FcRn binding domain having an increased binding activity for an FcRn at neutral or acidic pH ranges and pre-existing ADA at neutral pH ranges, (b) substituting an amino acid at one or more of the positions selected from the group consisting of EU387, EU422, EU424, EU426, EU433, EU436, EU438 and EU440, (c) selecting an antigen-binding domain of an antigen-binding molecule and altering at least one amino acid in the antigen-binding domain in order to get a pH-dependent antigen-binding domain, or selecting an calcium-ion dependent antigen-binding domain;

(d) obtaining a gene encoding an antigen-binding molecule in which the human FcRn-binding domain and the antigen-binding domain prepared in (a) and (b) are linked and (e) producing an antigen-binding molecule using the gene prepared in (c), wherein said antigen-binding molecule produced has an increased binding activity for an FcRn at neutral or acidic pH and a decreased binding activity for an endogenous ADA at neutral pH as compared to a parent antigen-binding domain having an intact FcRn binding domain.

[59] The method according to [58], wherein the FcRn binding domain having an increased binding activity for FcRn and pre-existing ADA at neutral or acidic pH ranges and for pre-existing ADA in the neutral pH ranges comprises an amino acid substitution at one or more positions selected from the group consisting of EU238, EU250, EU252, EU254, EU255, EU256, EU258, EU286, EU307, EU308, EU309, EU311, EU315, EU428, EU433, EU434, and EU436.

[60] The method according to any one of [53] to [57], wherein the amino acid substitution introduced in step a) are at three or more positions wherein said three or more positions are one of the combinations set forth in Tables 4 to 7.

[61] The method according to any one of [53] to [60], wherein the amino acid substitutions introduced in step b) are at three or more positions wherein said three or more positions are one of the combinations set forth in Table 10.

BRIEF DESCRIPTION OF DRAWINGS

FIG. 1A shows a schematic depiction of antigen elimination from plasma of an antibody of the prior art ("conventional antibody") compared with pH-dependent antigen binding antibody with enhanced FcRn, both binding a soluble antigen at neutral pH. The conventional antibody binds to the antigen in the plasma and is non-specifically taken up by cells into acidic endosomes. Under acidic conditions of the endosomes, the conventional antibody binds the FcRn inside a vesicle and is transported back to the surface of the cell where it is again released. The antigen is bound to the antigen-binding domain during the whole internalization and recycling process.

A pH-dependent antigen binding antibody with enhanced FcRn binding at neutral pH binds to the FcRn on the surface of the cell and is internalized rapidly into the cell and therefore in a higher frequency than a conventional antibody. Under the acidic condition in the endosomes, the antigen dissociates from the modified antibody and is transferred to the lysosome where it is proteolytically degraded. The antibody, still bound to the FcRn, is recycled back to cell surface. There, the recycled free antibody can bind to another antigen once again. By repeating this cycle of FcRn-mediated uptake, antigen dissociation and degradation, and antibody recycling, such pH-dependent antigen-binding antibody with improved binding affinity to FcRn at neutral pH can deliver significantly higher amount of antigen to the lysosome than a conventional antibody and therefore can reduce the total antigen concentration in plasma significantly more than a conventional antibody.

FIG. 1B shows a schematic representation of the dissociation of a soluble antigen from an IgG antibody with a pH-dependent antigen-binding domain in the endosome. This results in increased antigen elimination, and allows the antibody to bind to another antigen in the plasma.

FIG. 2 shows the plot of hFcRn binding affinity (x axis) and Tm of antibodies comprising Fc variants on the y axis (Fc variants F1-F599: open square; Fc variants F600-F1052: closed square).

FIG. 3 shows the plot of hFcRn binding affinity (x-axis) and High Molecular Weight (HMW) portion (in %) (y axis) of antibodies comprising Fc variants (Fc variants F1-F599: open square, Fc variants F600-F1050: closed square)

FIG. 4 shows the plot of hFcRn binding affinity (x-axis) and immunogenicity score (Epibase score) of antibodies comprising Fc variants (Fc variants F1-F599: open square, Fc variants F600-F1052: closed square).

FIG. 5 shows the plot of hFcRn binding affinity (x-axis) and melting Temperature Tm (y axis) of antibodies comprising Fc variants whose hFcRn binding affinity is stronger than 15 nM (Fc variants of F1-F599 with Kd less than or equal to 15 nM: open square, Fc variants of F600-F1052 with Kd less than or equal to 15 nM (Group 1): closed square).

FIG. 6 shows the plot of hFcRn binding affinity (x axis) and HMW (in %) (y-axis) of antibodies comprising Fc variants whose hFcRn binding affinity is stronger than 15 nM (Fc variants of F1-F599 with Kd less than or equal to 15 nM: open square; Fc variants of F600-F1052 with Kd less than or equal to 15 nM (Group 1): closed square).

FIG. 7 shows the plot of hFcRn binding affinity and immunogenicity score of antibodies comprising Fc variants whose hFcRn binding affinity is stronger than 15 nM (Fc variants of F1-F599 with Kd less than or equal to 15 nM: open square; Fc variants of F600-F1052 with Kd less than or equal to 15 nM (Group 1): closed square).

FIG. 8 shows the plot of hFcRn binding affinity and Tm of antibodies comprising Fc variants whose hFcRn binding affinity is between 15 nM and 50 nM (Fc variants of F1-F599 with Kd=15-50 nM, open square; Fc variants of F600-F1052 with Kd=15-50 nM (Group 2): closed square)

FIG. 9 shows the plot of hFcRn binding affinity and HMW (%) of antibodies comprising Fc variants whose hFcRn binding affinity is between 15 nM and 50 nM (Fc variants of F1-F599 with Kd=15-50 nM, open square; Fc variants of F600-F1052 with Kd=15-50 nM (Group 2): closed square).

FIG. 10 shows the plot of hFcRn binding affinity and immunogenicity score of antibodies comprising Fc variants whose hFcRn binding affinity is between 15 nM and 50 nM (Fc variants of F1-F599 with Kd=15-50 nM, open square; Fc variants of F600-F1052 with Kd=15-50 nM (Group 2): closed square)

FIG. 11 shows the plot of hFcRn binding affinity and Tm of antibodies comprising Fc variants whose hFcRn binding affinity is between 50 nM and 150 nM (Fc variants of F1-F599 with Kd=50-150 nM, open square; Fc variants of F600-F1052 with Kd=50-150 nM (Group 3): closed square).

FIG. 12 shows the plot of hFcRn binding affinity and HMW (%) of antibodies comprising Fc variants whose hFcRn binding affinity is between 50 nM and 150 nM (Fc variants of F1-F599 with Kd=50-150 nM, open square; Fc variants of F600-F1052 with Kd=50-150 nM (Group 3): closed square).

FIG. 13 shows a plot of hFcRn binding affinity and immunogenicity score of antibodies comprising Fc variants whose hFcRn binding affinity is between 50 nM and 150 nM (Fc variants of F1-F599 with Kd=50-150 nM: open square; Fc variants of F600-F1052 with Kd=50-150 nM (Group 3): closed square.

FIG. 14 shows the plot of hFcRn binding affinity and Tm of antibodies comprising Fc variants whose hFcRn binding affinity is between 150 nM and 700 nM (Fc variants of F1-F599 with Kd=150-700 nM, open square; Fc variants F600-F1052 with Kd=150-700 nM (Group 4): closed square).

FIG. 15 shows the plot of hFcRn binding affinity and HMW (%) of antibodies comprising Fc variants whose hFcRn binding affinity is between 150 nM and 700 nM (Fc variants of F1-F599 with Kd=150-700 nM: open square; Fc variants of F600-F1052 with Kd=150-700 nM (Group 4): closed square).

FIG. 16 shows the plot of hFcRn binding affinity and immunogenicity score of antibodies comprising Fc variants whose hFcRn binding affinity is between 150 nM and 700 nM (Fc variants of F1-F599 with Kd=150-700 nM: open square; Fc variants of F600-F1052 with Kd=150-700 nM (Group 4): closed square).

FIG. 17 shows a graphical depiction of the plasma antigen (hsIL-6R) concentration over time in a human FcRn transgenic mouse after injection of Fv-4-IgG1, Fv-4-F652, Fv-4-F890 and Fv-4-F946 and in a control mouse (no antibody injection).

FIG. 18 shows a graphical depiction of the plasma antibody concentration over time in human FcRn transgenic mouse after injection of Fv-4-IgG1, Fv-4-F652, Fv-4-F890 and Fv-4-F946.

FIG. 19 shows a graphical depiction of the plasma antigen (hsIL-6R) concentration over time in human FcRn transgenic mouse of control (no antibody injection) and after injection of Fv-4-IgG1, Fv-4-F11 and Fv-4-F652.

FIG. 20 shows a graphical depiction of the plasma antibody concentration over time in human FcRn transgenic mouse after injection of Fv-4-IgG1, Fv-4-F11 and Fv-4-F652.

FIG. 21 shows the graphical depiction of the electrochemiluminescence (ECL) response of the serum from 30 individual RA patients against the humanized anti-IL-6 receptor antibody Fv-4-IgG1 (FIG. 21-1), an YTE variant (FIG. 21-2) and a LS variant (FIG. 21-3) thereof.

FIG. 22 shows the graphical depiction of the electrochemiluminescence (ECL) response of the serum from 15 individual RA patients against the humanized anti-IL-6 receptor antibody Fv-4-IgG1 (FIG. 22-1), a Fv-4-N434H (FIG. 22-2), Fv-4-F11 (FIG. 22-3), Fv-4-F68 (FIG. 22-4), Fv-4-890 (FIG. 22-5) and Fv-4-F947 (FIG. 22-6).

FIG. 23 shows the mean (FIG. 23-1), geomean (FIG. 23-2) and median (FIG. 23-3) of the ECL response of the serum from fifteen individual RA patients against Fv-4-IgG1, Fv-4-F11, Fv-4-F68, Fv-4-F890 and Fv-4-F947 shown in FIG. 22.

FIG. 24 shows the graphical depiction of the electrochemiluminescence (ECL) response of the serum from 15 individual RA patients against the humanized anti-IL-6 receptor antibody Fv-4-IgG1 (FIG. 24-1) and of the variants Fv-4-F890, Fv-4-F1058, Fv-4-F1059, Fv-4-F1060, Fv-4-F1061, Fv-4-F1062, Fv-4-F1063, Fv-4-F1064, Fv-4-F1065, Fv-4-F1066, Fv-4-F1067, Fv-4-F1068, Fv-4-F1069, Fv-4-F1070, Fv-4-F1071, Fv-4-F1072, and Fv-4-F1073 (FIG. 24-2 to FIG. 24-18).

FIG. 25 shows the mean (FIG. 25-1), geomean (FIG. 25-2) and median (FIG. 25-3) of the ECL response of the serum from fifteen individual RA patients against Fv-4-IgG1, variants Fv-4-F890, Fv-4-F1058, Fv-4-F1059, Fv-4-F1060, Fv-4-F1061, Fv-4-F1062, Fv-4-F1063, Fv-4-F1064, Fv-4-F1065, Fv-4-F1066, Fv-4-F1067, Fv-4-F1068, Fv-4-F1069, Fv-4-F1070, Fv-4-F1071, Fv-4-F1072, and Fv-4-F1073 shown in FIG. 24.

FIG. 26 shows the graphical depiction of the electrochemiluminescence (ECL) response of the serum from 15 individual RA patients against the variants Fv-4-F1104 (FIG. 26-1), Fv-4-F1105 (FIG. 26-2), and Fv-4-F1106 (FIG. 26-3).

FIG. 27 shows the graphical depiction of the electrochemiluminescence (ECL) response of the serum from 15 individual RA patients against the variants Fv-4-F1107, Fv-4-F1108, Fv-4-F1109, Fv-4-F1110, Fv-4-F1111, Fv-4-F1112, Fv-4-F1113, and Fv-4-F1114 (FIG. 27-1 to FIG. 27-8)

FIG. 28 shows the graphical depiction of the electrochemiluminescence (ECL) response of the serum from 15 individual RA patients against the variants Fv-4-F1230 (FIG. 28-1), Fv-4-F1231 (FIG. 28-2), Fv-4-F1232 (FIG. 28-3).

FIG. 29 shows the graphical depiction of the electrochemiluminescence (ECL) response of the serum from 15 individual RA patients against the variants Fv-4-F947 (FIG. 29-1), Fv-4-F1119 (FIG. 29-2), Fv-4-F1120 (FIG. 29-3), Fv-4-F1121 (FIG. 29-4), Fv-4-F1122 (FIG. 29-5), Fv-4-F1123 (FIG. 29-6), and Fv-4-F1124 (FIG. 29-7).

FIG. 30-1 to FIG. 30-4 show the graphical depiction of the electrochemiluminescence (ECL) response of the serum from 15 individual RA patients against the variants Fv-4-F939, Fv-4-F1291, Fv-4-F1268, and Fv-4-F1269. FIG. 30-5 to FIG. 30-9 show the graphical depiction of the electrochemiluminescence (ECL) response of the serum from 30 individual RA patients against the variants Fv-4-F1243, Fv-4-F1245, Fv-4-F1321, Fv-4-F1340, and Fv-4-F1323.

FIG. 31 shows the graphical depiction of the electrochemiluminescence (ECL) response of the serum from 15 individual RA patients against the variants Fv-4-F890 (FIG. 31-1) and Fv-4-F1115 (=F890+S424N, FIG. 31-2).

FIG. 32 shows the graphical depiction of the electrochemiluminescence (ECL) response of the serum from 15 or 30 individual RA patients against the variants Fv-4-YTE (FIG. 32-1), Fv-4-F1166 (=YTE+Q438R/S440E, FIG. 32-2), Fv-4-F1167 (=YTE+S424N, FIG. 32-3), Fv-4-LS (FIG. 32-4), Fv-4-F1170 (=LS+Q438R/S440E, FIG. 32-5), Fv-4-F1171 (LS+S424N, FIG. 32-6), Fv-4-N434H (FIG. 32-7), Fv-4-F1172 (=N434H+ Q438R/S440E, FIG. 32-8), Fv-4-F1173 (=N434H+ S424N, FIG. 32-9))

FIG. 33 shows the graphical depiction of the electrochemiluminescence (ECL) response of the serum from 30 individual RA patients against the variants Fv-4-LS (FIG. 33-1), Fv-4-F1380 (FIG. 33-2), Fv-4-F1384 (FIG. 33-3), Fv-4-F1385 (FIG. 33-4), Fv-4-F1386 (LS+S426Y, FIG. 33-5), Fv-4-F1388 (FIG. 33-6), and Fv-4-F1389 (LS+Y436T, FIG. 33-7).

FIG. 34 shows the graphical depiction of the electrochemiluminescence (ECL) response of the serum from 30 individual RA patients against the variant F939.

FIG. 35 shows the graphical depiction of the electrochemiluminescence (ECL) response of the serum from 30 individual RA patients against the variant F1378

FIG. 36 shows the graphical depiction of the electrochemiluminescence (ECL) response of the serum from 30 individual RA patients against the variant F1379

FIG. 37 shows the graphical depiction of the electrochemiluminescence (ECL) response of the serum from 30 individual RA patients against the variant F1262

FIG. 38 shows the graphical depiction of the electrochemiluminescence (ECL) response of the serum from 30 individual RA patients against the variant F1138

FIG. 39 shows the graphical depiction of the electrochemiluminescence (ECL) response of the serum from 30 individual RA patients against the variant F1344

FIG. 40 shows the graphical depiction of the electrochemiluminescence (ECL) response of the serum from 30 individual RA patients against the variant F1349

FIG. 41 shows the graphical depiction of the electrochemiluminescence (ECL) response of the serum from 30 individual RA patients against the variant F1350

FIG. 42 shows the graphical depiction of the electrochemiluminescence (ECL) response of the serum from 30 individual RA patients against the variant F1351

FIG. 43 shows the graphical depiction of the electrochemiluminescence (ECL) response of the serum from 30 individual RA patients against the variant F1261

FIG. 44 shows the graphical depiction of the electrochemiluminescence (ECL) response of the serum from 30 individual RA patients against the variant F1263

FIG. 45 shows the graphical depiction of the electrochemiluminescence (ECL) response of the serum from 30 individual RA patients against the variant F1305

FIG. 46 shows the graphical depiction of the electrochemiluminescence (ECL) response of the serum from 30 individual RA patients against the variant F1306

FIG. 47 shows the graphical depiction of the electrochemiluminescence (ECL) response of the serum from 30 individual RA patients against the variant F1268

FIG. 48 shows the graphical depiction of the electrochemiluminescence (ECL) response of the serum from 30 individual RA patients against the variant F1269

FIG. 49 shows the graphical depiction of the electrochemiluminescence (ECL) response of the serum from 30 individual RA patients against the variant F1413

FIG. 50 shows the graphical depiction of the electrochemiluminescence (ECL) response of the serum from 30 individual RA patients against the variant F1416

FIG. 51 shows the graphical depiction of the electrochemiluminescence (ECL) response of the serum from 30 individual RA patients against the variant F1419

FIG. 52 shows the graphical depiction of the electrochemiluminescence (ECL) response of the serum from 30 individual RA patients against the variant F1420

FIG. 53 shows the graphical depiction of the electrochemiluminescence (ECL) response of the serum from 30 individual RA patients against the variant F1370

FIG. 54 shows the graphical depiction of the electrochemiluminescence (ECL) response of the serum from 30 individual RA patients against the variant F1371

FIG. 55 shows the graphical depiction of the electrochemiluminescence (ECL) response of the serum from 30 individual RA patients against the variant F1599

FIG. 56 shows the graphical depiction of the electrochemiluminescence (ECL) response of the serum from 30 individual RA patients against the variant F1600

FIG. 57 shows the graphical depiction of the electrochemiluminescence (ECL) response of the serum from 30 individual RA patients against the variant F1566

FIG. 58 shows the graphical depiction of the electrochemiluminescence (ECL) response of the serum from 30 individual RA patients against the variant F1448

FIG. 59 shows the graphical depiction of the electrochemiluminescence (ECL) response of the serum from 30 individual RA patients against the variant F1601

FIG. 60 shows the graphical depiction of the electrochemiluminescence (ECL) response of the serum from 30 individual RA patients against the variant F1602

FIG. 61 shows the graphical depiction of the electrochemiluminescence (ECL) response of the serum from 30 individual RA patients against the variant F1603

FIG. 62 shows the graphical depiction of the electrochemiluminescence (ECL) response of the serum from 30 individual RA patients against the variant F1531

FIG. 63 shows the graphical depiction of the electrochemiluminescence (ECL) response of the serum from 30 individual RA patients against the variant F1604

FIG. 64 shows the graphical depiction of the electrochemiluminescence (ECL) response of the serum from 30 individual RA patients against the variant F1605

FIG. 65 shows the graphical depiction of the electrochemiluminescence (ECL) response of the serum from 30 individual RA patients against the variant F1586

FIG. 66 shows the graphical depiction of the electrochemiluminescence (ECL) response of the serum from 30 individual RA patients against the variant F1592

FIG. 67 shows the graphical depiction of the electrochemiluminescence (ECL) response of the serum from 30 individual RA patients against the variant F1610

FIG. 68 shows the graphical depiction of the electrochemiluminescence (ECL) response of the serum from 30 individual RA patients against the variant F1611

FIG. 69 shows the graphical depiction of the electrochemiluminescence (ECL) response of the serum from 30 individual RA patients against the variant F1612

FIG. 70 shows the graphical depiction of the electrochemiluminescence (ECL) response of the serum from 30 individual RA patients against the variant F1613

FIG. 71 shows the graphical depiction of the electrochemiluminescence (ECL) response of the serum from 30 individual RA patients against the variant F1614

FIG. 72 shows the graphical depiction of the electrochemiluminescence (ECL) response of the serum from 30 individual RA patients against the variant F1615

FIG. 73 shows the graphical depiction of the electrochemiluminescence (ECL) response of the serum from 30 individual RA patients against the variant F1567

FIG. 74 shows the graphical depiction of the electrochemiluminescence (ECL) response of the serum from 30 individual RA patients against the variant F1572

FIG. 75 shows the graphical depiction of the electrochemiluminescence (ECL) response of the serum from 30 individual RA patients against the variant F1576

FIG. 76 shows the graphical depiction of the electrochemiluminescence (ECL) response of the serum from 30 individual RA patients against the variant F1578

FIG. 77 shows the graphical depiction of the electrochemiluminescence (ECL) response of the serum from 30 individual RA patients against the variant F1579

FIG. 78 shows the graphical depiction of the electrochemiluminescence (ECL) response of the serum from 30 individual RA patients against the variant F1641

FIG. 79 shows the graphical depiction of the electrochemiluminescence (ECL) response of the serum from 30 individual RA patients against the variant F1642

FIG. 80 shows the graphical depiction of the electrochemiluminescence (ECL) response of the serum from 30 individual RA patients against the variant F1643

FIG. 81 shows the graphical depiction of the electrochemiluminescence (ECL) response of the serum from 30 individual RA patients against the variant F1644

FIG. 82 shows the graphical depiction of the electrochemiluminescence (ECL) response of the serum from 30 individual RA patients against the variant F1645

FIG. 83 shows the graphical depiction of the electrochemiluminescence (ECL) response of the serum from 30 individual RA patients against the variant F1646

FIG. 84 shows the graphical depiction of the electrochemiluminescence (ECL) response of the serum from 30 individual RA patients against the variant F1647

FIG. 85 shows the graphical depiction of the electrochemiluminescence (ECL) response of the serum from 30 individual RA patients against the variant F1648

FIG. 86 shows the graphical depiction of the electrochemiluminescence (ECL) response of the serum from 30 individual RA patients against the variant F1649

FIG. 87 shows the graphical depiction of the electrochemiluminescence (ECL) response of the serum from 30 individual RA patients against the variant F1650

FIG. 88 shows the graphical depiction of the electrochemiluminescence (ECL) response of the serum from 30 individual RA patients against the variant F1651

FIG. 89 shows the graphical depiction of the electrochemiluminescence (ECL) response of the serum from 30 individual RA patients against the variant F1652

FIG. 90 shows the graphical depiction of the electrochemiluminescence (ECL) response of the serum from 30 individual RA patients against the variant F1653

FIG. 91 shows the graphical depiction of the electrochemiluminescence (ECL) response of the serum from 30 individual RA patients against the variant F1654

FIG. 92 shows the graphical depiction of the electrochemiluminescence (ECL) response of the serum from 30 individual RA patients against the variant F1655

FIG. 93 shows the graphical depiction of the electrochemiluminescence (ECL) response of the serum from 30 individual RA patients against the variant F1329

FIG. 94 shows the graphical depiction of the electrochemiluminescence (ECL) response of the serum from 30 individual RA patients against the variant F1331

FIG. 95 shows the graphical depiction of the electrochemiluminescence (ECL) response of the serum from 30 individual RA patients against the variant F1718

FIG. 96 shows the graphical depiction of the electrochemiluminescence (ECL) response of the serum from 30 individual RA patients against the variant F1719

FIG. 97 shows the graphical depiction of the electrochemiluminescence (ECL) response of the serum from 30 individual RA patients against the variant F1720

FIG. 98 shows the graphical depiction of the electrochemiluminescence (ECL) response of the serum from 30 individual RA patients against the variant F1721

FIG. 99 shows the graphical depiction of the electrochemiluminescence (ECL) response of the serum from 30 individual RA patients against the variant F1671

FIG. 100 shows the graphical depiction of the electrochemiluminescence (ECL) response of the serum from 30 individual RA patients against the variant F1670

FIG. 101 shows the graphical depiction of the electrochemiluminescence (ECL) response of the serum from 30 individual RA patients against the variant F1711

FIG. 102 shows the graphical depiction of the electrochemiluminescence (ECL) response of the serum from 30 individual RA patients against the variant F1712

FIG. 103 shows the graphical depiction of the electrochemiluminescence (ECL) response of the serum from 30 individual RA patients against the variant F1713

FIG. 104 shows the graphical depiction of the electrochemiluminescence (ECL) response of the serum from 30 individual RA patients against the variant F1722

FIG. 105 shows the graphical depiction of the electrochemiluminescence (ECL) response of the serum from 30 individual RA patients against the variant F1723

FIG. 106 shows the graphical depiction of the electrochemiluminescence (ECL) response of the serum from 30 individual RA patients against the variant F1724

FIG. 107 shows the graphical depiction of the electrochemiluminescence (ECL) response of the serum from 30 individual RA patients against the variant F1725

FIG. 108 shows the graphical depiction of the electrochemiluminescence (ECL) response of the serum from 30 individual RA patients against the variant F1675

FIG. 109 shows the graphical depiction of the electrochemiluminescence (ECL) response of the serum from 30 individual RA patients against the variant F1714

FIG. 110 shows the graphical depiction of the electrochemiluminescence (ECL) response of the serum from 30 individual RA patients against the variant F1715

FIG. 111 shows the graphical depiction of the electrochemiluminescence (ECL) response of the serum from 30 individual RA patients against the variant F1716

FIG. 112 shows the graphical depiction of the electrochemiluminescence (ECL) response of the serum from 30 individual RA patients against the variant F1717

FIG. 113 shows the graphical depiction of the electrochemiluminescence (ECL) response of the serum from 30 individual RA patients against the variant F1683

FIG. 114 shows the graphical depiction of the electrochemiluminescence (ECL) response of the serum from 30 individual RA patients against the variant F1756

FIG. 115 shows the graphical depiction of the electrochemiluminescence (ECL) response of the serum from 30 individual RA patients against the variant F1757

FIG. 116 shows the graphical depiction of the electrochemiluminescence (ECL) response of the serum from 30 individual RA patients against the variant F1758

FIG. 117 shows the graphical depiction of the electrochemiluminescence (ECL) response of the serum from 30 individual RA patients against the variant F1759

FIG. 118 shows the graphical depiction of the electrochemiluminescence (ECL) response of the serum from 30 individual RA patients against the variant F1681

FIG. 119 shows the graphical depiction of the electrochemiluminescence (ECL) response of the serum from 30 individual RA patients against the variant F1749

FIG. 120 shows the graphical depiction of the electrochemiluminescence (ECL) response of the serum from 30 individual RA patients against the variant F1750

FIG. 121 shows the graphical depiction of the electrochemiluminescence (ECL) response of the serum from 30 individual RA patients against the variant F1751

FIG. 122 shows the graphical depiction of the electrochemiluminescence (ECL) response of the serum from 30 individual RA patients against the variant F1760

FIG. 123 shows the graphical depiction of the electrochemiluminescence (ECL) response of the serum from 30 individual RA patients against the variant F1761

FIG. 124 shows the graphical depiction of the electrochemiluminescence (ECL) response of the serum from 30 individual RA patients against the variant F1762

FIG. 125 shows the graphical depiction of the electrochemiluminescence (ECL) response of the serum from 30 individual RA patients against the variant F1763

FIG. 126 shows the graphical depiction of the electrochemiluminescence (ECL) response of the serum from 30 individual RA patients against the variant F1752

FIG. 127 shows the graphical depiction of the electrochemiluminescence (ECL) response of the serum from 30 individual RA patients against the variant F1753

FIG. 128 shows the graphical depiction of the electrochemiluminescence (ECL) response of the serum from 30 individual RA patients against the variant F1754

FIG. 129 shows the graphical depiction of the electrochemiluminescence (ECL) response of the serum from 30 individual RA patients against the variant F1755

FIG. 130 shows the graphical depiction of the electrochemiluminescence (ECL) response of the serum from 30 individual RA patients against the variant F1685

FIG. 131 shows a graphical depiction of the plasma antibody concentration over time in human FcRn transgenic mouse after injection of Fv-4-IgG1, Fv-4-F1243, and Fv-4-F1245.

FIG. 132 shows a graphical depiction of the plasma antigen (hsIL-6R) concentration over time in a human FcRn transgenic mouse after injection of Fv-4-IgG1, Fv-4-F1243, and Fv-4-F1245 and in a control mouse (no antibody injection).

FIG. 133 shows a graphical depiction of the plasma antibody concentration over time in human FcRn transgenic mouse after injection of Fv-4-IgG1, Fv-4-F1389.

FIG. 134 shows a sensorgram of SPR analysis. hIgA binding of anti-hIgA antibody was analyzed under different condition (pH, Ca-concentration).

FIG. 135 shows a graphical depiction of the plasma antibody concentration over time in human FcRn transgenic mouse after injection of GA2-F760 and GA2-F1331.

FIG. 136 shows a graphical depiction of the plasma hIgA concentration over time in human FcRn transgenic mouse after injection of GA2-F760 and GA2-F1331.

FIG. 137. shows a graphical depiction of the plasma antibody concentration over time in human FcRn transgenic mouse after injection of 278-F760 and 278-F1331.

FIG. 138 shows a graphical depiction of the plasma hIgE(Asp6) concentration over time in human FcRn transgenic mouse after injection of 278-F760 and 278-F1331.

DESCRIPTION OF EMBODIMENTS

Detailed Description of the Invention

Before the present materials and methods are described, it should be understood that these descriptions are merely illustrative only and not intended to be limiting. It should also be understood that the present invention is not limited to the particular sizes, shapes, dimensions, materials, methodologies, protocols, etc. described herein, as these may vary in accordance with routine experimentation and/or optimization. The terminology used in the description is for the purpose of describing the particular versions or embodiments only, and is not intended to limit the scope of the present invention that will be limited only by the appended claims. Unless otherwise defined, all technical and scientific terms used herein have the same meaning as commonly understood by one of ordinary skill in the art to which the present invention belongs. In case of conflict, the present specification, including definitions, will control.

The disclosure of each publication, patent or patent application mentioned in this specification is specifically incorporated by reference herein in its entirety. However, nothing herein is to be construed as an admission that the invention is not entitled to antedate such disclosure by virtue or prior invention.

The words "a", "an", and "the" as used herein mean "at least one" unless otherwise specifically indicated.

Studies described in the WO/2011/122011 have demonstrated that antigen-binding molecules (e.g. anti-IL6 receptor antibody) with increased binding to FcRn at pH7.4 are capable of eliminating antigen from plasma and decreasing the total antigen concentration in plasma, and that therefore, the efficiency of antigen elimination can be improved by pH-dependent antigen binding (bind to antigen within plasma at pH7.4 and dissociate the antigen within acidic endosome at pH6.0) or by ionized calcium concentration-dependent antigen binding (bind to antigen within plasma at high ionized calcium concentration and dissociate the antigen within the endosome at low ionized calcium concentration) (see FIG. 1B). The mechanism of antigen elimination from plasma by pH-dependent antigen binding antibody with improved binding affinity to FcRn at neutral pH in comparison to the conventional antibody is shown in FIG. 1A.

The present invention provides novel amino acid substitutions in the FcRn-binding domain that increase FcRn binding activity of an antigen-binding molecule in the acidic and neutral pH ranges, wherein the FcRn-binding activity in the neutral pH range is stronger than the one of an intact IgG or an antigen-binding molecule comprising an intact FcRn-binding domain (e.g. stronger than 3200 nM). The modified antigen-binding molecules can reduce the total antigen concentration in plasma after its administration more than a control antigen-binding molecule comprising the same antigen-binding domain but an intact human IgG FcRn-binding domain.

Fc receptors are proteins on the surface of immune cells such as natural killer cells, macrophages, neutrophils and mast cells. They bind to the Fc (Fragment, crystallizable) region of antibodies that are attached to infected cells or invading pathogens and stimulate phagocytic or cytotoxic cells to destroy microbes, or infected cells by antibody-mediated phagocytosis or antibody-dependent cell-mediated cytotoxicity.

There are several different types of Fc receptors, which are classified based on the type of antibody that they recognize. Herein, the term "FcRn" refers to the neonatal Fc receptor that binds IgG, is similar in structure to MHC class I protein and that, in humans, is encoded by the FCGRT gene.

The term "FcRn binding domain" as used herein refers to a protein domain that directly or indirectly binds to the FcRn. Preferably the FcRn is a mammalian FcRn, more preferably, a human FcRn. An FcRn binding domain binding directly to an FcRn is an antibody Fc region. Meanwhile, regions capable of binding to a polypeptide such as albumin or IgG, which has human FcRn-binding activity, can indirectly bind to human FcRn via albumin, IgG, or such. Thus, such a human FcRn-binding region may be a region that binds to a polypeptide having human FcRn-binding activity.

The term "Fc region" or "Fc region of an antigen-binding molecule" as used herein refers to an FcRn-binding domain that directly binds to FcRn, preferably to a mammalian FcRn, more preferably to a human FcRn. In particular, an Fc region is an Fc region of an antibody. Preferably, the Fc region is a mammalian Fc region, more preferably a human Fc region. In particular, the Fc region of the invention is an Fc region comprising the second and third constant domain of a human immunoglobulin (CH2 and CH3), more preferably the hinge, CH2 and CH3. Preferably, the immunoglobulin is an IgG. Preferably, the Fc region is an Fc region of human IgG1.

The present invention provides an antigen-binding molecule having a modified FcRn-binding domain wherein said antigen-binding molecule has an increased FcRn-binding activity in a neutral pH range as compared to an antigen-binding molecule having an intact FcRn-binding domain.

In particular, the present invention provides an antigen-binding molecule having a modified FcRn-binding domain with an amino acid substitution in an FcRn-binding domain at one or more positions selected from the group consisting of EU238, EU250, EU252, EU254, EU255, EU258 EU286, EU307, EU308, EU309, EU311, EU315, EU428, EU433, EU434, and EU436. The antigen-binding molecule of the present invention may also comprise substitutions at additional positions. For example, the antigen-binding molecule may comprise a substitution at position EU256 in addition to a substitution at the one or more positions mentioned above. Preferably, the amino acid at position EU256 is substituted with a glutamic acid.

The term "binding affinity" or "binding activity" refers to the strength of non-covalent interaction between two substances as measured by the dissociation constant (KD) of the complex formed by the two substances, unless expressly defined otherwise. A binding protein (or "ligand") may, for example, have a KD of less than $10^{-5}$, $10^{-6}$, $10^{-7}$ or $10^{-8}$ M for a particular target molecule, e.g. the FcRn. Higher affinity binding of a binding ligand to a target a first pH range relative to a target at a second pH range can be indicated by a smaller numerical value KD for binding the target at the first pH range than the numerical value KD for binding the target at the second pH range. Differences in binding affinity can be at least 1.5, 2, 3, 4, 5, 10, 15, 20, 50, 70, 80, 100, 500, or 1000 fold. Binding affinity can be determined by a variety of methods including surface plasmon resonance, equilibrium dialysis, equilibrium binding, gel filtration, ELISA, or spectroscopy (e.g., using a fluorescence assay).

An increased binding affinity of an FcRn-binding domain for FcRn at a pH range corresponds to a measured increase of the FcRn-binding affinity as compared to the FcRn-binding affinity measured for an intact FcRn-binding domain. Differences in binding affinity of KD (intact)/KD (variant) is at least 1.5, 2, 3, 4, 5, 10, 15, 20, 50, 70, 80, 100, 500, or 1000 fold. An increased binding affinity of an FcRn-binding domain for FcRn can be in the acidic or neutral pH ranges.

The term "antigen-binding molecule comprising an intact FcRn binding domain" refers to an antigen-binding molecule comprising an unmodified FcRn-binding domain. The term "intact IgG FcRn-binding domain" as used herein refers to an unmodified FcRn-binding domain of a human IgG. In particular, the FcRn-binding domain is the FcRn-binding domain of an intact human IgG. Preferably, an intact FcRn-binding domain is an intact Fc region. The term "antibody comprising an intact Fc region" refers to an antibody comprising an unmodified Fc region. The antibody from which the unmodified Fc region originates is preferably an IgG. More preferably, it is a human IgG1, IgG2, IgG3 or IgG4, still more preferably, a human IgG1. In a particularly preferred embodiment of the present invention an antibody comprising an intact Fc region is an antibody comprising an unmodified Fc region. An antibody comprising an intact Fc region can be an intact human IgG.

The term "intact IgG" as used herein refers to an unmodified IgG and is not limited to a specific class of IgG. This means that human IgG1, IgG2, IgG3, IgG4 or their allotypic variants can be used as "intact human IgG" as long as it can bind to the human FcRn in the acidic pH range. Preferably, "intact IgG" is a human IgG1. Preferably, an intact IgG is an IgG which comprises a wild type Fc region.

In the context of the present invention, an increased FcRn-binding activity of antigen-binding molecule in the neutral pH ranges is preferably stronger than KD 3.2 micromolar. Preferably, the increased FcRn-binding activity in the neutral pH range is stronger than 700 nanomolar, more preferably stronger than 500 nanomolar and most preferably, stronger than 150 nanomolar.

An increased FcRn-binding activity of antigen-binding molecule of the present invention in the acidic pH ranges is generally an FcRn-binding activity in the range of about 2-fold to about 100-fold stronger than the FcRn-binding activity of an intact IgG. Preferably, the increased FcRn-binding activity of antigen-binding molecule in the acidic pH ranges is at least 10-fold stronger than the FcRn-binding activity of an intact IgG. More preferably, the increased FcRn-binding activity of an antigen-binding molecule of the present invention in the acidic pH range is at least 20-fold stronger than the FcRn-binding activity of an intact IgG.

The terms "neutral pH range" and "neutral pH" as used herein, typically refer to pH 6.7 to pH 10.0, preferably any pH value within pH 7.0 to pH 8.0, examples of which include pH 7.0, 7.1, 7.2, 7.3, 7.4, 7.5, 7.6, 7.7, 7.8, 7.9, and 8.0. A particularly preferred acidic pH value is pH 7.4, which approximates plasma (blood) pH in vivo.

The terms "acidic pH range" and "acidic pH" as used herein, typically refer to pH 4.0 to pH 6.5, preferably to any pH value within pH 5.5 to pH 6.5, examples of which include pH 5.5, 5.6, 5.7, 5.8, 5.9, 6.0, 6.1, 6.2, 6.3, 6.4, and 6.5. A particularly preferred acidic pH value ranges from pH 5.8 to pH 6.0, which approximates the pH in early endosome in vivo.

The amino acid positions referred to in this application, such as e.g. "EU387" or "position 387", are, unless otherwise indicated, numbered according to a scheme called the EU numbering system (Kabat, E. A., T. T. Wu, H. M. Perry, K. S. Gottesman, C. Foeler. 1991. Sequences of Proteins of Immunological Interest. No. 91-3242 U.S. Public Health Services, National Institutes of Health, Bethesda) and refer to positions in an FcRn-binding domain, in particular in an Fc region. In a similar fashion, substitutions are indicated as for example "EU387R" or "EU440E", wherein the number given after "EU" indicates the position of the substitution according the EU numbering, and the letter after the number is the substituted amino acid given in the one letter code. Substitutions may also be written as (amino acid 1)-position-(amino acid 2) whereby the first amino acid is the substituted amino acid and the second amino acid is the substituting amino acid at the specified position.

The terms "substitution" and "substitution of an amino acid" as used herein refer to a replacement of an amino acid in an amino acid sequence with another one, wherein the latter is different from the replaced amino acid. Methods for replacing an amino acid are well known to the skilled in the art and include, but are not limited to, mutations of the nucleotide sequence encoding the amino acid sequence.

More particularly, a substitution of an amino acid in an FcRn-binding domain refers to a replacement of an amino acid in reference to the amino acid sequence of a parent FcRn-binding domain. A modified FcRn-binding domain already having the desired substitutions is also included in the FcRn-binding domain of the present invention.

A parent FcRn-binding domain is an FcRn-binding domain having at the position EU238 an proline, at position EU250 a threonine, at position EU252 a methionine, at position EU254 a serine, at position EU255 an arginine, at position EU256 a threonine, at position EU258 a glutamic acid, at position EU286 an asparagine, at position EU307 a threonine, at position EU308 a valine, at position EU309 a leucine, at position EU311 a glutamine, at position EU315 an asparagine, at position EU387 a proline, at position EU422 a valine, at position EU424 a serine, at position EU426 a serine, at position EU428 a methionine, at position EU433 a histidine, at position EU434 an asparagine, at position EU436 a tyrosine, at position EU438 a glutamine, and at position EU440 a serine and no or low affinity for FcRn at neutral pH (weaker than 3200 nM). The parent FcRn-binding domain may comprise substitutions at other positions but preferably, the parent FcRn-binding domain is unmodified. Preferably, the parent FcRn binding domain is an Fc region (parent Fc region). Preferably, the parent Fc region is derived from a mammalian antibody; more preferably, the parent Fc region is the Fc region of a human antibody. An Fc region of a human antibody is herein referred to as a human Fc region.

A parent Fc region is, preferably an intact Fc region, more preferably a human intact Fc region. Preferably, the parent Fc region is the Fc region of an IgG, more preferably of a human IgG. Even more preferably, a parent Fc region is a human Fc region comprising the wild type hinge, wildtype CH2 and wildtype CH3 domain. In the context of the present invention, the term parent antibody refers to an antibody comprising a parent Fc region.

Parent antigen-binding molecules include, but are not limited to, receptor proteins (membrane-bound receptors and soluble receptors), antibodies that recognize a membrane antigen such as cell surface markers, and antibodies that recognize a soluble antigen such as cytokines The term "parent antigen-binding molecule" as used herein refers to an antigen-binding molecule having a parent FcRn-binding domain. The origin of "parent antigen-binding molecule" is not limited and it may be obtained from any organism: of non-human animals or human. Preferably, the organism is selected from the group consisting of mouse, rat, guinea pig, hamster, gerbil, cat, rabbit, dog, goat, sheep, cow, horse, camel, and non-human primate. In another embodiment, "parent antigen-binding molecule" can also be obtained from cynomolgus monkey, marmoset, rhesus monkey, chimpanzee or human. The parent IgG may be a naturally occurring IgG, or a variant or engineered version of a naturally occurring IgG. Parent IgG may refer to the polypeptide itself, compositions that comprise the parent IgG, or the amino acid sequence that encodes it. It should be noted that "parent IgG" includes known commercial, recombinantly produced IgG as outlined below. Preferably, "parent IgG" is obtained from human IgG1 but not limited to a specific subclass of IgG. This means that human IgG1, IgG2, IgG3, or IgG4 can be appropriately used as "parent IgG". In the a similar manner, any subclass of IgGs from any organisms described hereinbefore can be preferably used as "parent IgG". Example of variant or engineered version of a naturally occurring IgG is described in Curr Opin Biotechnol. 2009 December; 20(6): 685-91, Curr Opin Immunol. 2008 August; 20(4): 460-70, Protein Eng Des Sel. 2010 April; 23(4): 195-202, WO 2009/086320, WO 2008/092117, WO 2007/041635 and WO 2006/105338, but not limited thereto.

An FcRn-binding domain or Fc region of the present invention may comprise a substitution at two or more positions which is herein referred to as a "combination" of substitutions. For example an Fc region defined by the combination "EU424/EU434/EU436" is an Fc region that comprises a substitution at the positions EU424, EU434 and EU436.

The substituting amino acid (the amino acid with which the amino acid in the parent FcRn-binding domain is substituted) may be any amino acid unless specifically mentioned herein, including but not limited to the group consisting of: alanine (Ala, A), arginine (arg, R), asparagines (asn, N), aspartic acid (asp, D), cysteine (cys, C), glutamic acid (glu, E), glutamine (gln, Q), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V). Preferably, the substituting amino acid at any one of the positions EU387, EU422, EU424, EU426, EU433, EU436, EU438 and EU440 is selected from the group consisting of: alanine (Ala, A), arginine (arg, R), glutamic acid (glu, E), glutamine (gln, Q), aspartic acid (asp, D), serine (ser, S), threonine (thr, T), tyrosine (tyr, Y), and lysine (lys, K).

In a preferred embodiment of the present invention, the antigen-binding molecule of the present invention has a modified FcRn-binding domain comprising an amino acid substitution with an amino acid different from the substituted one a) at position EU252 and EU434, and b) at one or more positions selected from the group consisting of EU238, EU250, EU252, EU254, EU255, EU256, EU258, EU286, EU307, EU308, EU309, EU311, EU315, EU428, EU433, EU434, and EU436.

The substituting amino acid may be any amino acid unless specifically mentioned herein. Preferred substituting amino acids for the positions EU238, EU250, EU252, EU254, EU255, EU258, EU286, EU307, EU308, EU309, EU311, EU315, EU428, EU433, EU434, and EU436 are shown in Table 1.

TABLE 1

Preferred substituting amino acids

| Position (according to EU numbering scheme) | Substituting amino acid |
|---|---|
| EU238 | an aspartic acid |
| EU250 | a valine |
| EU252 | a tyrosine |
| EU254 | a threonine |
| EU255 | a leucine |
| EU256 | a glutamic acid |
| EU258 | an aspartic acid or an isoleucine |
| EU286 | a glutamic acid |
| EU307 | a glutamine |
| EU308 | a proline |
| EU309 | a glutamic acid |
| EU311 | an alanine or a histidine |
| EU315 | an aspartic acid |
| EU428 | an isoleucine |
| EU433 | an alanine, a lysine, a proline, an arginine or a serine |
| EU434 | a tyrosine, or a tryptophan |
| EU436 | an isoleucine, a leucine, a valine, a threonine, or a phenylalanine. |

Preferably, the modified FcRn-binding domain of the present invention comprises at least one of amino acids substitutions set forth in Table 1. It is possible to use the FcRn-binding domains without any alteration as long as they already have at least one of the above given amino acids at the specified position and said FcRn-binding domain has human FcRn-binding activity in the acidic and neutral pH ranges, whereby the FcRn-binding activity in the neutral pH ranges is increased.

In a preferred embodiment, the modified antigen-binding molecule of the present invention comprises a modification at three or more positions in the FcRn-binding domain, wherein the three or more positions are one of the combinations set forth in Tables 2, 4 to 7.

TABLE 2

| Preferred combinations of positions for substitutions in FcRn-binding domain | |
|---|---|
| a) | EU252/EU434/EU436, |
| b) | EU252/EU434/EU307/EU311, |
| c) | EU252/EU434/EU315, |
| d) | EU252/EU434/EU308, |
| e) | EU252/EU434/EU238, |
| f) | EU252/EU434/EU436/EU307/EU311, |
| g) | EU252/EU434/EU255 |
| h) | EU252/EU434/EU258 |
| i) | EU252/EU434/EU433 |
| j) | EU252/EU434/EU255/EU258 |

In a more preferred embodiment, the antigen-binding molecule of the present invention comprises three or more amino acid substitutions in a FcRn-binding domain, wherein the three or more substitutions are one of the combinations set forth in Tables 3, 12, 14, and 17 to 20.

TABLE 3

| Preferred substitution combinations in FcRn-binding domain | |
|---|---|
| 1 | M252Y/N434Y/Y436V |
| 2 | M252Y/N434Y/Y436T |
| 3 | M252Y/N434Y/Y436F |
| 4 | M252Y/N434Y/Y436V |
| 5 | M252Y/N434Y/Y436V |
| 6 | M252Y/N434Y/Y436T |
| 7 | M252Y/N434Y/Y436T |
| 8 | M252Y/N434Y/Y436F |
| 9 | M252Y/N434Y/Y436F |
| 10 | M252Y/N434Y/Y436V |
| 11 | M252Y/N434Y/Y436V |
| 12 | M252Y/H433D/N434Y/Y436V |
| 13 | M252Y/H433D/N434Y/Y436V |
| 14 | M252Y/H433D/N434Y/Y436V |
| 15 | M252Y/H433D/N434Y/Y436V |
| 16 | M252Y/S254T/T256E/T307Q/Q311A/H433D/N434Y/Y436V |
| 17 | M252Y/S254T/T256E/V308P/H433D/N434Y/Y436V |
| 18 | M252Y/H433D/N434W/Y436V |
| 19 | M252Y/H433D/N434W/Y436V |
| 20 | M252Y/S254T/T256E/H433D/N434Y/Y436V |
| 21 | M252Y/S254T/T256E/H433D/N434Y/Y436V |
| 22 | M252Y/S254T/T256E/H433D/N434Y/Y436V |
| 23 | M252Y/S254T/T256E/H433D/N434Y/Y436V |
| 24 | M252Y/S254T/T256E/N286E/H433D/N434Y/Y436V |
| 25 | M252Y/S254T/T256E/N286E/H433DN434Y/Y436V |
| 26 | M252Y/S254T/T256E/N286E/H433D/N434Y/Y436V |
| 27 | M252Y/S254T/T256E/N286E/H433D/N434Y/Y436V |
| 28 | M252Y/S254T/R255L/T256E/H433D/N434Y/Y436V |
| 29 | M252Y/S254T/R255L/T256E/H433DN434Y/Y436V |
| 30 | M252Y/S254T/R255L/T256E/H433D/N434Y/Y436V |
| 31 | M252Y/S254T/R255L/T256E/H433D/N434Y/Y436V |
| 32 | M252Y/S254T/R255L/T256E/E258D/H433D/N434Y/Y436V |
| 33 | M252Y/S254T/R255L/T256E/E2581/H433D/N434Y/Y436V |
| 34 | M252Y/S254T/R255L/T256E/E258D/H433D/N434Y/Y436V |
| 35 | M252Y/S254T/R255L/T256E/E2581/H433DN434Y/Y436V |
| 36 | M252Y/S254T/R255L/T256E/E258D/H433D/N434Y/Y436V |
| 37 | M252Y/S254T/R255L/T256E/E258I/H433D/N434Y/Y436V |
| 38 | M252Y/S254T/R255L/T256E/E258D/H433D/N434Y/Y436V |
| 39 | M252Y/S254T/R255L/T256E/E2581/H433DN434Y/Y436V |
| 40 | M252Y/S254T/T256E/H433A/N434Y/Y436V |
| 41 | M252Y/S254T/T256E/H433K/N434Y/Y436V |
| 42 | M252Y/S254T/T256E/H433P/N434Y/Y436V |
| 43 | M252Y/S254T/T256E/H433R/N434Y/Y436V |
| 44 | M252Y/S254T/T256E/H433S/N434Y/Y436V |
| 45 | M252Y/S254T/T256E/H433A/N434Y/Y436V |
| 46 | M252Y/S254T/T256E/H433A/N434Y/Y436V |
| 47 | M252Y/S254T/T256E/H433A/N434Y/Y436V |
| 48 | M252Y/S254T/T256E/H433K/N434Y/Y436V |
| 49 | M252Y/S254T/T256E/H433K/N434Y/Y436V |
| 50 | M252Y/S254T/T256E/H433K/N434Y/Y436V |
| 51 | M252Y/S254T/T256E/H433P/N434Y/Y436V |
| 52 | M252Y/S254T/T256E/H433P/N434Y/Y436V |
| 53 | M252Y/S254T/T256E/H433P/N434Y/Y436V |
| 54 | M252Y/S254T/T256E/H433R/N434Y/Y436V |
| 55 | M252Y/S254T/T256E/H433R/N434Y/Y436V |
| 56 | M252Y/S254T/T256E/H433R/N434Y/Y436V |
| 57 | M252Y/S254T/T256E/H433S/N434Y/Y436V |
| 58 | M252Y/S254T/T256E/H433S/N434Y/Y436V |
| 59 | M252Y/S254T/T256E/H433S/N434Y/Y436V |
| 60 | L235R/G236R/S239K/M252Y/S254T/N434Y/Y436V |
| 61 | L235R/G236R/S239K/M252Y/S254T/T256E/N434Y/Y436V |
| 62 | P238D/M252Y/V308P/N434Y |
| 63 | P238D/M252W/N434Y |
| 64 | P238D/M252Y/M428F/N434Y |

Stability, Immunogenicity and Aggregate Formation

Engineering an FcRn-binding domain by introducing substitutions may reduce the stability of the antigen-binding molecule (WO/2007/092772). Stability of a drug protein is critical for manufacturing pharmaceuticals, because proteins with poor stability tend to easily aggregate during storage. Therefore reduced stability caused by substitutions in the Fc region would make the development of a stable formulation difficult (WO2007/092772).

In addition, purity of a drug protein with regard to monomer species and high molecular weight species is also important for pharmaceutical development. Wild type IgG1 after protein A purification does not contain a significant amount of high molecular weight species, but engineering an FcRn-binding domain by introducing substitutions may result in a larger amount of high molecular weight species. In such a case, high molecular weight species need to be removed from bulk drug substances by a purification process which may be difficult in the development of the purification process.

Moreover, immunogenicity of a protein pharmaceutical in human is important, since the presence of anti-drug antibodies would result in clearance of the drug from the body and thus loss of therapeutic efficacy (IDrugs 2009; 12:233-7.). When substitutions are introduced into a wild type Fc domain (such as IgG1 Fc domain), the modified sequence becomes a non-human sequence. Such a modified sequence could be presented by MHC class II and therefore could be immunogenic in human patients.

Proteins will not be developed as a drug if they comprise Fc variants that exhibit poor stability and purity, and poor immunogenicity would hinder clinical development. It is therefore an objective of the present invention to improve the FcRn binding affinity at pH7.4 without losing significant stability;

increasing the amount of high molecular weight species ratio, and increasing the risk of immunogenicity (risk of anti-drug antibody formation)

(Group 1)

Therefore, the present invention also provides an antigen-binding molecule comprising an amino acid substitution in the FcRn-binding domain at the positions EU252, EU434, EU307 and EU311, having a binding activity for the FcRn at pH 7 of more than 15 nM, a melting temperature Tm of 57.5 degrees C. or higher, an HMW of less than 2% and a low immunogenicity wherein a low immunogenicity is equivalent to a score of less than 500 determined with Epibase (Lonza).

Preferably, an antigen-binding molecule comprising an amino acid substitution in the FcRn-binding domain at four or more positions, wherein the four or more positions are one of the combinations of the group consisting of a) EU252/EU434/EU307/EU311/EU436, and b) EU252/EU434/EU307/EU311/EU436 in combination with one or more positions selected from the group consisting of EU286, EU308, and EU428.

The preferred combinations are set forth in Table 4.

TABLE 4

| | |
|---|---|
| a) | EU252 and EU434 and EU307 and EU311 and EU436 and EU286; |
| b) | EU252 and EU434 and EU307 and EU311 and EU436 and EU308 |
| c) | EU252 and EU434 and EU307 and EU311 and EU436 and EU286 and EU308 |
| d) | EU252 and EU434 and EU307 and EU311 and EU436 and EU428 |
| e) | EU252 and EU434 and EU307 and EU311 and EU436 and EU308 and EU428 |
| f) | EU252 and EU434 and EU307 and EU311 and EU436 and EU250 and EU428 |
| g) | EU252 and EU434 and EU307 and EU311 and EU436 and EU250 and EU308 |
| h) | EU252 and EU434 and EU307 and EU311 and EU436 and EU250 and EU286 and EU308 |
| i) | EU252 and EU434 and EU307 and EU311 and EU436 and EU250 and EU286 and EU308 and EU428 |

Particular preferred are combinations a), g), h) and i) of Table 4.

In an even more preferred embodiment, the modified FcRn-binding domain comprises:

a) at position EU252 a tyrosine, at position EU286 a glutamic acid, at position EU307 a glutamine, at position EU311 an alanine, at position EU434 a tyrosine, and at position EU436 a valine; or b) at position EU250 a valine, at position EU252 a tyrosine, at position EU307 a glutamine, at position EU308 a proline, at position EU311 an alanine, at position EU434 a tyrosine, and at position EU436 a valine; or c) at position EU250 a valine, at position EU252 a tyrosine, at position EU286 a glutamic acid, at position EU307 a glutamine, at position EU308 proline, at position EU311 an alanine, at position EU434 a tyrosine, and at position EU436 a valine; or d) at position EU250 a valine, at position EU252 a tyrosine, at position EU286 a glutamic acid, at position EU307 a glutamine, at position EU308 proline, at position EU311 an alanine, at position EU434 a tyrosine, and at position EU436 a valine.

(Group 2)

The present invention also provides an antigen-binding molecule comprising an amino acid substitution in the FcRn-binding domain at three or more positions, wherein said three or more positions are one of the combinations of the group consisting of a) EU252/EU434/EU307/EU311; and b) EU252/EU434/EU308; wherein the FcRn-binding activity of said antigen-binding molecule at neutral pH is 15 to 50 nM, the Tm is higher than 60 degrees C., an HMW of less than 2% and wherein the antigen-binding molecule has a low immunogenicity whereby a low immunogenicity is equivalent to a score of less than 500 determined with Epibase (Lonza).

In a preferred embodiment, the amino acid substitutions are at four or more positions wherein the four or more positions are one of the combinations set forth in Table 5.

TABLE 5

| | preferred combinations |
|---|---|
| a) | EU252/EU434/EU307/EU311/EU286 |
| b) | EU252/EU434/EU307/EU311/EU286/EU254 |
| c) | EU252/EU434/EU307/EU311/EU436 |
| d) | EU252/EU434/EU307/EU311/EU436/EU254 |
| e) | EU252/EU434/EU307/EU311/EU436/EU250 |
| f) | EU252/EU434/EU308/EU250 |
| g) | EU252/EU434/EU308/EU250/EU436/ |
| h) | EU252/EU434/EU308/EU250/EU307/EU311 |

More preferred is an antigen-binding molecule comprising four or more amino acid substitutions wherein the four or more substitutions are one of the combinations of the group consisting of:

a) at position EU252 a tyrosine, at position EU286 a glutamic acid, at position EU307 a glutamine, at position EU311 an alanine and at position EU434 a tyrosine;

b) at position EU252 a tyrosine, at position EU254 a threonine, at position EU286 a glutamic acid, at position EU307 a glutamine, at position EU311 an alanine and at position EU434 a tyrosine;

c) at position EU252 a tyrosine, at position EU307 a glutamine, at position EU311 an alanine, at position EU434 a tyrosine and at position 436 an isoleucine;

d) at position EU252 a tyrosine, at position EU254 a threonine, at position EU286 a glutamic acid, at position EU307 a glutamine, at position EU311 an alanine, at position EU434 a tyrosine and at position EU436 an isoleucine;

e) at position EU250 a valine, at position EU252 a tyrosine, at position EU254 a threonine, at position EU308 a proline, at position EU434 a tyrosine and at position EU436 a valine;

f) at position EU250 a valine, at position EU252 a tyrosine, at position EU307 a glutamine, at position EU311 an alanine, at position EU434 a tyrosine and at position EU436 a valine;

g) at position EU252 a tyrosine, at position EU307 a glutamine, at position EU311 an alanine, at position EU434 a tyrosine and at position EU436 a valine;

h) at position EU250 a valine, at position EU252 a tyrosine, at position EU308 a proline, and at position EU434 a tyrosine; and i) at position EU250 a valine, at position EU252 a tyrosine, at position 307 a glutamine, at position EU308 a proline, at position EU311 an alanine, and at position EU434 a tyrosine.

(Group 3)

The present invention also provides an antigen-binding molecule comprising an amino acid substitution in the FcRn-binding domain a) at the positions EU252/EU434; and b) at position EU436 and/or at position EU254 and/or at position EU315; and having an FcRn-binding activity at pH 7 of 50 to 150 nM, a Tm higher than 63 degrees C., an HMW of less than 2% and a very low immunogenicity, wherein a very low immunogenicity is defined as a score of less than 250 determined with Epibase (Lonza).

Preferably, the amino acid substitutions are at three or more positions, wherein the three or more positions are one of the combinations set forth in Table 6.

TABLE 6

| | preferred combinations |
|---|---|
| a) | EU252/EU315/EU434; |
| b) | EU252/EU434/EU436 |
| c) | EU252/EU254/EU434/EU436 |

In a more preferred embodiment, the modified antigen-binding molecule comprises three or more amino acid substitutions wherein the three or more substitutions are one of the combinations of the group consisting of:
a) at position EU252 a tyrosine, at position EU315 an aspartic acid, and at position EU434 a tyrosine;
b) at position EU252 a tyrosine, at position EU434 a tyrosine, and at position EU436 an isoleucine;
c) at position EU252 a tyrosine, at position EU434 a tyrosine, and at position EU436 a leucine;
d) at position EU252 a tyrosine, at position EU434 a tyrosine, and at position EU436 a valine; and
e) at position EU252 a tyrosine, at position EU254 a threonine, at position EU434 a tyrosine, and at position EU436 an isoleucine.
(Group 4)

The present invention further provides an antigen-binding molecule that comprises an amino acid substitution in the FcRn-binding domain at three or more positions, wherein the three or more positions are one of the combinations set forth in Table 7. Said modified antigen-binding molecules have a binding activity for the FcRn at pH 7 of 150 to 700 nM, a Tm of higher than 66.5 degrees C., an HMW of less than 2% and a very low immunogenicity, wherein a very low immunogenicity is defined as a score of less than 250 determined with Epibase (Lonza).

TABLE 7

| a) | EU307/EU311/EU434 |
|---|---|
| b) | EU307/EU309/EU311/EU434 |
| c) | EU307/EU309/EU311/EU434 |
| d) | EU250/EU252/EU434/EU436 |

Preferably, the modified antigen-binding molecules comprise three or more substitutions wherein the three or more substations are one of the combinations of the group consisting of
a) at position EU307 a glutamine, at position EU311 a histidine, and at position EU434 a tyrosine;
b) at position EU307 a glutamine, at position EU309 a glutamic acid, at position EU311 an alanine, at position EU434 a tyrosine;
c) at position EU307 a glutamine, at position EU309 a glutamic acid, at position EU311 a histidine, at position EU434 a tyrosine; or
d) at position EU250 a valine, at position EU252 a tyrosine, at position EU434 a tyrosine, at position EU436 a valine.
Pre-Existing Anti-Drug Antibody Substitutions of amino acids in an antibody can yield negative consequences, for example an increase in the immunogenicity of the therapeutic antibody which, in turn, can result in a cytokine storm and/or production of anti-drug antibodies (ADAs). Since ADAs can influence the efficacy and pharmacokinetics of therapeutic antibodies and sometimes lead to serious side effects, the clinical utility and efficacy of the therapeutic antibodies can be limited. Many factors influence the immunogenicity of therapeutic antibodies, and the presence of effector T-cell epitopes is one of the factors. Likewise, the presence of pre-existing antibodies against a therapeutic antibody can also be problematic. An example of such pre-existing antibody is the rheumatoid factor (RF), an auto-antibody (an antibody directed against a self protein) against the Fc portion of an antibody (i.e. IgG). The rheumatoid factor is found in particular in patients suffering of systemic lupus erythematosus (SLE) or rheumatoid arthritis. In arthritis patients, RF and IgG join to form immune complexes that contribute to the disease process. Recently, it was reported that a humanized anti-CD4 IgG1 antibody having an Asn434H is mutation elicited significant rheumatoid factor binding (Clin Pharmacol Ther. 2011 February; 89(2):283-90 (NPL 9)). Detailed studies have confirmed that the Asn434His mutation in the human IgG1 increased the binding of rheumatoid factor to the Fc region of the antibody compared to the parent human IgG1.

RF is a polyclonal auto-antibody against human IgG, and the epitope of the RF in the sequence of the human IgG varies among the clones, but the RF epitope seems to be located in the CH2/CH3 interface region as well as CH3 domain which could overlap with the FcRn binding epitope. Therefore, mutations to increase the binding affinity to FcRn at neutral pH might also increase the binding affinity to specific clone of RF.

Accordingly, it is preferable to increase the FcRn binding affinity at neutral and/or acidic pH without also increasing the binding affinity of the therapeutic antibody for a pre-existing antibody in the plasma at neutral pH.

Therefore, present invention also provides antigen-binding molecules comprising a modified FcRn-binding domain (preferably a modified Fc region), whereby the binding activity for a pre-existing ADA at a neutral pH is not significantly increased as compared to the binding affinity of an antigen-binding molecule comprising a wild type Fc region. The modified FcRn-binding domain (modified Fc region) preferably comprises an amino acid substitution at one or more of the positions selected from the group consisting of EU387, EU422, EU424, EU426, EU433, EU436, EU438 and EU440.

The above described substitutions are preferably introduced in an FcRn-binding domain or Fc region of an antigen-binding molecule that has increased affinity for the FcRn at neutral or acidic pH whereby said modified FcRn-binding domain or Fc region has an increased binding activity for a pre-existing ADA at neutral pH. The effect of the substitutions is a decrease of the binding activity for the pre-existing ADA. Therefore, in a preferred embodiment, a modified FcRn-binding domain or a modified Fc region of the present invention has a decreased binding activity to a pre-existing ADA as compared to an FcRn binding domain or an Fc region that has an increased binding activity to the FcRn at neutral or acidic pH, and an increased binding activity to the pre-existing anti-drug antibody in the neutral pH ranges. Preferably, an antigen-binding molecule having an increased binding activity at neutral pH for the FcRn and a pre-existing ADA are the antigen-binding molecules comprising an amino acid substitution at one or more positions selected from the group consisting of EU238, EU250, EU252, EU254, EU255, EU258, EU286, EU307, EU308, EU309, EU311, EU315, EU428, EU433, EU434, and EU436 as described above. It may also comprise a substitution at position EU256 in addition to a substitution at the one or more positions mentioned above. Preferably, the amino acid at position EU256 is substituted with a glutamic acid.

Therefore, the present invention also provides antigen-binding molecules comprising a modified Fc region which has an increased affinity for FcRn at neutral or acidic pH whereby the affinity for a pre-existing anti-drug antibody (ADA) at a neutral pH is not significantly increased compared to the binding affinity of antigen-binding molecule comprising a wild type Fc region. In a preferred embodiment, the present invention provides an antigen-binding molecule comprising a modified Fc region with an increased affinity for FcRn at neutral or acidic pH which comprises an amino acid substitution at one or more of the positions selected from the group consisting of EU387, EU422, EU424, EU426, EU433, EU436, EU438 and EU440.

Preferably, the antigen-binding molecule comprising a modified Fc region with an increased affinity for FcRn at neutral or acidic pH, whereby the binding activity at neutral pH for a pre-existing ADA is not significantly increased as compared to a control antigen-binding molecule, wherein the modified Fc region comprises an amino acid substitution at one or more of the positions selected from the substitutions as shown in Table 8.

TABLE 8

Substituting amino acids:

| position | Substitutions with | | | | | | |
|---|---|---|---|---|---|---|---|
| EU387 | R | | | | | | |
| EU422 | E | R | S | D | K | T | Q |
| EU424 | E | R | K | N | | | |
| EU426 | D | Q | A | Y | | | |
| EU433 | D | | | | | | |
| EU436 | T | | | | | | |
| EU438 | E | R | S | K | | | |
| EU440 | E | D | Q | | | | |

The term "anti-drug antibody" and "ADA" as used herein refers to an endogenous antibody that has binding affinity for an epitope located on a therapeutic antibody and is thus capable of binding said therapeutic antibody. The term "pre-existing anti-drug antibody" and "pre-existing ADA" as used herein refers to an anti-drug antibody that is present and detectable in the blood of a patient prior to the administration of the therapeutic antibody to the patient. Preferably, the pre-existing ADA is a human antibody. In a particularly preferred embodiment, the pre-existing ADA is the rheumatoid factor, a polyclonal or monoclonal autoantibody against the Fc region of human IgG antibody. The epitopes of rheumatoid factor are located in the CH2/CH3 interface region as well as the CH3 domain but can vary among clones.

An antigen-binding molecule comprising an FcRn-binding domain region (or an Fc region) that has an increased affinity for FcRn at neutral or acidic pH and for a pre-existing anti-drug antibody at neutral pH is an antigen-binding molecule comprising an FcRn-binding domain (or an Fc region) that was modified to increase the binding affinity of the FcRn-binding domain (or Fc region) of an antigen-binding molecule for FcRn as compared to an antibody comprising an intact FcRn-binding domain (or intact Fc region). Modifications contemplated include, but are not limited to, substitutions of the amino acids in the amino acid sequence of the Fc portion of an antigen-binding domain. The antigen-binding molecule comprising an FcRn-binding domain or an Fc region, which has an increased binding activity for a) a pre-existing ADA in a neutral pH range and for FcRn at neutral (in case of an antigen-binding molecule of interest having an increased FcRn-binding activity at a neutral pH) or acidic pH (in case of an antigen-binding molecule of interest having an increased FcRn-binding activity at an acidic pH) is referred herein as "Reference Antibody". A "Reference Antibody" is preferably the modified antigen-binding molecule before substituting an amino acid at one or more positions selected from the group consisting of EU387, EU422, EU424, EU426, EU433, EU436, EU438 and EU440, more preferably before introducing any one of the substitutions set for in Table 8. A "Reference Antibody" may be an antigen-binding molecule comprising an amino acid substitution in an FcRn-binding domain at one or more positions selected from the group consisting of EU238, EU250, EU252, EU254, EU255, EU256, EU258 EU286, EU307, EU308, EU309, EU311, EU315, EU428, EU433, EU434, and EU436.

An example for a "Reference Antibody" having an increased FcRn-binding activity in the neutral pH ranges is an antigen-binding molecule comprising an Fc region with increased affinity for FcRn in the neutral pH ranges and having increased affinity for a pre-existing ADA at neutral pH comprising an amino acid substitution in the Fc region at
a) positions EU252 and EU434; and
b) one or more positions selected from the group consisting of EU238, EU250, EU254, EU255, EU256, EU258, EU286, EU307, EU308, EU309, EU311, EU315, EU428, EU433, and EU436.

More preferably, the antigen-binding molecule comprising an Fc region with increased affinity for FcRn in the neutral pH ranges and having increased affinity for a pre-existing ADA at neutral pH ranges comprises one of the combinations set forth in Table 9.

TABLE 9

Preferred combinations of substitutions of a Reference Antibody having an increased FcRn-binding activity in the neutral pH ranges.

1  M252Y/N434Y/
2  M252Y/N434Y/Y436V
3  M252Y/N434Y/Y436F
4  M252Y/N434Y/Y436V
5  M252Y/S254T/T256E/T307Q/Q311A/N434Y/Y436V
6  M252Y/S254T/T256E/V308P/N434Y/Y436V
7  M252Y/N434W/Y436V
8  M252Y/S254T/T256E/N434Y/Y436V
9  M252Y/S254T/T256E/N286E/N434Y/Y436V
10 M252Y/S254T/R255L/T256E/N434Y/Y436V
11 M252Y/S254T/R255L/T256E/N434Y/Y436V
12 M252Y/S254T/R255L/T256E/E258D/N434Y/Y436V
13 M252Y/S254T/R255L/T256E/E258I/N434Y/Y436V
14 M252Y/S254T/T256E/H433A/N434Y/Y436V
15 M252Y/S254T/T256E/H433K/N434Y/Y436V
16 M252Y/S254T/T256E/H433P/N434Y/Y436V
17 M252Y/S254T/T256E/H433R/N434Y/Y436V
18 M252Y/S254T/T256E/H433S/N434Y/Y436V
19 M252Y/S254T/T256E/H433A/N434Y/Y436V
20 L235R/G236R/S239K/M252Y/S254T/N434Y/Y436V
21 L235R/G236R/S239K/M252Y/S254T/T256E/N434Y/Y436V
22 EU238D/EU252Y/EU434Y/EU436V
23 EU252Y/EU434Y/EU436V
24 EU250V/EU252Y/EU434Y/EU436V/EU307Q/EU308P/EU311A
25 EU252Y/EU434Y/EU436V/EU235R/EU239K
26 EU252Y/EU434Y
27 EU252Y/EU434Y/EU436V

An example for a "Reference Antibody" having an increased FcRn-binding activity in the acidic pH ranges is an antigen-binding molecule comprising an Fc region with increased affinity for FcRn in the acidic pH ranges and having increased affinity for a pre-existing ADA at neutral pH ranges preferably comprise a substitution
i) at position EU434, or
ii) at two or more positions, wherein the two or more positions are one of the combinations of the group consisting of a) EU252/EU254/EU256; b) EU428/EU434; and c) EU250/EU428.

Preferably, the antigen-binding molecule comprising an Fc region with increased affinity at acidic pH ranges and having increased affinity for a pre-existing ADA at neutral pH comprises
i) the substitutions M434H; or
ii) one of the combinations of the group consisting of a) M252Y/S254T/T256E; b) M428L/N434S; and c) T250Q and M428L (EU numbering).

Preferably, the antigen-binding molecule comprising an Fc region which comprises one of the following substitutions or combinations a) M252Y/S254T/T256E, b) M428L/N434S or c) T250Q and M428L or d) M434H (EU numbering) has an increased binding activity to the FcRn at acidic pH without increasing the binding activity in the neutral pH ranges.

The binding activity of an Fc region of antigen-binding molecule for a pre-existing anti-drug antibody is expressed in the present application as an electrochemiluminescence (ECL) response at neutral pH; however, there are other suitable methods for determining the binding activity for a pre-existing ADA known to the skilled in the art. An ECL assay is for example described in Moxness et al (Clin Chem, 2005, 51:1983-85) and in the EXAMPLES of the present invention. Conditions used in the assay for determining the binding activity for a pre-existing ADA can be appropriately selected by those skilled in the art, and thus are not particularly limited.

An increased or higher binding affinity for a pre-existing ADA is increased as compared to the binding affinity for the pre-existing ADA of a Control Antigen-binding Molecule.

The term "Control Antigen-binding Molecule" as used herein refers to an antigen-binding molecule comprising an intact human Fc region, preferably an antibody or antibody derivative comprising an intact human Fc region.

The binding affinity for a pre-existing ADA may be assessed at any temperature from 10 degrees Celsius to 50 degrees Celsius. Preferably, a temperature at from 15 degrees Celsius to 40 degrees Celsius is employed in order to determine the binding affinity between human Fc region and human pre-existing ADA. More preferably, any temperature at from 20 degrees Celsius to 35 degrees Celsius, like any one of 20, 21, 22, 23, 24, 25, 26, 27, 28, 29, 30, 31, 32, 33, 34, and 35 degrees C. is employed in order to determine the binding affinity between human Fc region and human pre-existing ADA. Preferably, the temperature is between 20 and 25 degrees C., more preferably at 25 degrees C. In a preferred embodiment, the interaction between human pre-existing ADA and human Fc region is measured at pH 7.4 (or pH7.0) and at 25 degrees C.

In the context of the present invention, the term "an increased binding affinity for a pre-existing ADA" refers to a measured increase in binding affinity (i.e., KD) of an antigen-binding molecule of the present invention for a pre-existing ADA as compared to the binding affinity measured of a Control Antigen-binding Molecule for the pre-existing ADA. Such an increase in binding affinity for a pre-existing ADA can be observed in an individual patient or in a patient group.

The terms "patients" and "patient" as used herein, are not particularly limited and include all human beings who suffer from a disease and to whom in the course of a treatment a therapeutic antigen-binding molecule is administered. Preferably, a patient is a person suffering from an autoimmune disease. More preferably, a patient is a person suffering from an arthritic disease or systemic lupus erythematosus (SLE). Arthritic diseases include in particular rheumatoid arthritis.

In the context of the present invention, a significant increase of the binding activity for a pre-existing ADA in an individual patient corresponds to a measured increase of at least 10%, at least 20%, at least 30%, at least 40%, at least 50%, at least 60% of the binding activity for a pre-existing ADA of a therapeutic antigen-binding molecule (i.e. a therapeutic antibody) comprising a modified Fc region in a patient as compared to the binding affinity for the pre-existing ADA of a Control Antigen-binding Molecule. Preferably the increase is at least 20%, more preferably the increase is at least 30%, even more preferably, it is at least 40% and most preferably the increase is at least 50% of the binding activity of a antigen-binding molecule comprising a modified Fc region as compared to the binding affinity for the pre-existing ADA of a control antigen-binding molecule. Alternatively, a significant increase in the binding activity of an antigen-binding molecule for a pre-existing ADA in a patient is preferably an ECL response to the antigen-binding molecule of more than 250, preferably to an ECL of at least 500, more preferably to an ECL of at least 1000, most preferably to an ECL of at least 2000. More preferably, the increase is an increase as compared with the ECL response of a Control Antigen-binding Molecule of less than 500 (preferably of less than 250). Preferred ranges between an the binding activity for a pre-existing ADA of the Control Antigen-binding Molecule and that of an antigen-binding molecule with a modified Fc region are in particular ECL responses from less than 250 to at least 250, from less than 250 to at least 500, from less than 500 to 500 or more, from less than 500 to 1000 or more, and from less than 500 to at least 2000.

The increase in the binding activity for a pre-existing ADA may also correspond to a measured increase in the portion of patients in a patient population having an ECL response of at least 500 (preferably at least 250) to an the antigen-binding molecule with an increased binding activity to a) the FcRn at neutral or acidic pH and b) an pre-existing ADA at neutral pH as compared to the portion of patients having an ECL response of at least 500 (preferably at least 250) at neutral pH to a control antigen-binding molecule. A "significant" increase in the portion of patients in a patient population is preferably an increase of at least 10%, at least 20%, at least 30%, at least 40%, at least 50% patients having a ECL response of the therapeutic antigen-binding molecule comprising a modified Fc region to the rheumatoid factor at neutral pH of 500 or less (preferably of 250 or more) compared to the portion of patients having an ECL response to a Control Antigen-binding Molecule. Preferably the increase is at least 20%, more preferably at least 30%, even more preferably, it is at least 40% and most preferably it is 50% or more.

In the context of the present invention, a decrease in the binding affinity for a pre-existing ADA refers to a measured decrease in binding activity (i.e., KD or ECL response) as compared to the binding activity measured for a Reference Antibody, Such a decrease of binding affinity for a pre-existing ADA can be observed in an individual patient or in a patient group. The decrease of the affinity of a therapeutic antigen-binding molecule for a pre-existing ADA at neutral pH in an individual patient refers to a measured decrease at neutral pH in the binding activity as compared to the binding activity measured for a Reference Antibody for the pre-existing ADA at neutral pH in said patient. Preferably, a significant decrease in an individual patient is a measured decrease at neutral pH of at least 10%, at least 20%, at least 30%, at least 40%, at least 50% in the binding activity of the modified antigen-binding molecule for a pre-existing ADA as compared to the binding activity of a Reference Antibody for a pre-existing ADA at neutral pH. More preferably, the decrease is at least 30%, even more preferably, it is 40% and most preferably it is 50% or more as compared to a Reference antibody.

Alternatively, the significant decrease in an individual patient of a modified antigen-binding molecule's binding activity for a pre-existing ADA may be measured as a decrease of the ECL response of said antigen-binding molecule as compared with the ECL response of a Reference Antibody from an ECL response of 500 or more, (preferably, from an ECL of 1000 or more, most preferably from an ECL of 2000 or more), to less than 500, preferably of less than 250. Preferred decreases are from an ECL response of 500 or more to an ECL response of less than 500, more preferably from at least 250 to less than 250, even more preferably from at least 500 to less than 250. Preferred ranges are, in particular, from at least 250 to less than 250, from at least 500 to less than 250, from at least 1000 to less than 250, from at least 2000 to less than 250, from at least 500 to less than 500, from at least 1000 to less than 500, and from at least 2000 to less than 500.

The decrease may also be a decrease in the percentage of patients in a patient population that has an increased binding of their pre-existing ADA to the modified antigen-binding molecule in neutral pH ranges. In other words, the decrease may be measured as a decrease of the percentage of people having an ECL response of their pre-existing ADA to a modified antigen-binding molecule as compared to the ECL response to a Reference Antibody. Preferably, a decrease may be a decrease of at least 10%, at least 20%, at least 30%, at least 40%, at least 50% in the portion of patients in a patient population in which the therapeutic antigen-binding molecule has an increased binding activity to a pre-existing ADA as compared to the portion of patients having an increased binding activity of the Reference antibody to the pre-existing ADA, wherein the increased binding is expressed as an ECL response of 500 or more, preferably 250 or more. Preferably the decrease is at least 20%, more preferably the decrease is at least 30%, even more preferably, it is 40% and most preferably it is 50% or more.

In a preferred embodiment, a therapeutic antigen-binding molecule of the present invention has low binding activity for a pre-existing ADA at a neutral pH. In particular, the binding activity of a modified antigen-binding molecule of the present invention for a pre-existing ADA at a neutral pH is preferably significantly decreased compared to the binding activity of a Reference Antibody for a pre-existing ADA at neutral pH. More preferably, the binding activity of a modified antigen-binding molecule of the present invention for a pre-existing ADA at a neutral pH is not significantly increased as compared to the binding affinity of a Control Antigen-binding Molecule (has about the same binding activity for a pre-existing ADA as Control Antigen-binding Molecule). A low binding activity or baseline affinity for a pre-existing ADA is preferably an ECL response of less than 500 in a individual patient. Preferably, a ECL response is less than 250. In a patient population, a low binding activity for a pre-existing ADA is an ECL response of less than 500 in 90% of the patients in the patient population, more preferably in 95% of the patients, most preferably in 98% of the patients.

In a more preferred embodiment, the antigen-binding molecule comprising a modified FcRn-binding domain with an increased affinity for FcRn at neutral or acidic pH, wherein the binding activity at neutral pH for a pre-existing ADA is not significantly increased as compared to a control antigen-binding molecule, whereby the modified FcRn-binding domain of the present invention comprises a substitution at one or more of the positions or combinations set forth in Table 10.

TABLE 10

Positions and combinations of positions for substitutions in FcRn-binding domain:

| | |
|---|---|
| 1) | EU387 |
| 2) | EU422 |
| 3) | EU424 |
| 4) | EU426 |
| 5) | EU436 |
| 6) | EU438 |
| 7) | EU440 |
| 8) | EU438 and EU440 |
| 9) | EU422 and EU424 |
| 10) | EU433 |

In a more preferred embodiment, the antigen-binding molecule of the present invention comprises a modified FcRn-binding domain having one or more of the substitutions or combinations set forth in Table 11.

TABLE 11

Substitutions and combinations of substitutions in FcRn-binding domain:

| | |
|---|---|
| 1 | EU387R |
| 2 | EU422E |
| 3 | EU422R |
| 4 | EU422S |
| 5 | EU424E |
| 6 | EU424R |
| 7 | EU438E |
| 8 | EU438R |
| 9 | EU438S |
| 10 | EU440E |
| 11 | EU422E/EU424R |
| 12 | EU422S/EU424R |
| 13 | EU438R/EU440E |
| 14 | EU422D |
| 15 | EU422K |
| 16 | EU422T |
| 17 | EU422Q |
| 18 | EU438K |
| 19 | EU440D |
| 20 | EU440Q |
| 21 | EU438R/EU440D |
| 22 | EU438K/EU440E |
| 23 | EU438K/EU440D |
| 24 | EU424N |
| 25 | EU426D |
| 26 | EU426A |
| 27 | EU426Q |
| 28 | EU426Y |
| 29 | EU436F |
| 30 | EU436T |
| 31 | EU433D |

In a preferred embodiment, the antigen-binding molecule comprising a modified FcRn-binding domain with a) an increased affinity for FcRn at neutral or acidic pH b) a binding affinity for a pre-existing ADA at neutral pH which is not significantly increased compared to a Control Antigen-binding Molecule, said antigen-binding molecule comprises any one of the combinations of substitutions set forth in Table 12.

Also preferably, an antigen-binding molecule having an increased FcRn binding activity at neutral pH ranges and a binding affinity for a pre-existing ADA at neutral pH that is not significantly increased as compared to an antigen-binding molecule comprising a wild type Fc region comprises an amino acid substitution in an FcRn-binding domain at a) one or more of the positions selected from the group consisting: EU387, EU422, EU424, EU438, EU440, EU433, or b) at two or more positions, wherein the two or more positions are the combination EU422/EU424; or EU438/EU440. More preferably, the substitutions are selected from among the substitutions set forth in Table 11.

Even more preferably, an FcRn-binding domain of an antigen-binding molecule having an increased binding activity for the FcRn at neutral pH ranges and a binding affinity for a pre-existing ADA at neutral pH that is not significantly increased as compared to an antigen-binding molecule comprising a wild type Fc region comprising any one of the substitution combinations set forth in Table 12. In particular, preferred modified antigen-binding molecules having an increased FcRn-binding activity in neutral pH ranges whereby the binding affinity at neutral pH for a pre-existing ADA is not significantly increased comprises three or more substitutions in the FcRn-binding domain, wherein the three or more substitutions are any one of the combinations no. (2) to (26) and (28) to (59) set forth in Table 12.

TABLE 12

Combinations of substitutions in Fc region that increase the FcRn-binding activity in the neutral pH ranges without significantly increasing the binding activity for a pre-existing ADA (positions given according to the EU numbering scheme).

| | |
|---|---|
| 1 | M252Y/N434Y/Y436T |
| 2 | M252Y/N434Y/Y436V/Q438K/S440E |
| 3 | M252Y/N434Y/Y436V/Q438R/S440E |
| 4 | M252Y/N434Y/Y436T/Q438K/S440E |
| 5 | M252Y/N434Y/Y436T/Q438R/S440E |
| 6 | M252Y/N434Y/Y436F/Q438K/S440E |
| 7 | M252Y/N434Y/Y436F/Q438R/S440E |
| 8 | M252Y/N434Y/Y436V/Q438R/S440D |
| 9 | M252Y/N434Y/Y436V/Q438K/S440D |
| 10 | M252Y/H433D/N434Y/Y436V/Q438R/S440D |
| 11 | M252Y/H433D/N434Y/Y436V/Q438K/S440E |
| 12 | M252Y/H433D/N434Y/Y436V/Q438R/S440E |
| 13 | M252Y/H433D/N434Y/Y436V/Q438K/S440D |
| 14 | M252Y/S254T/T256E/T307Q/Q311A/H433D/N434Y/Y436V/Q438K/S440E |
| 15 | M252Y/S254T/T256E/V308P/H433D/N434Y/Y436V/Q438K/S440E |
| 16 | M252Y/H433D/N434W/Y436V/Q438R/S440E |
| 17 | M252Y/H433D/N434W/Y436V/Q438K/S440E |
| 18 | M252Y/S254T/T256E/H433D/N434Y/Y436V/Q438K/S440E |
| 19 | M252Y/S254T/T256E/H433D/N434Y/Y436V/Q438R/S440E |
| 20 | M252Y/S254T/T256E/H433D/N434Y/Y436V/Q438K/S440D |
| 21 | M252Y/S254T/T256E/H433D/N434Y/Y436V/Q438R/S440D |
| 22 | M252Y/S254T/T256E/N286E/H433D/N434Y/Y436V/Q438K/S440E |
| 23 | M252Y/S254T/T256E/N286E/H433D/N434Y/Y436V/Q438R/S440E |
| 24 | M252Y/S254T/T256E/N286E/H433D/N434Y/Y436V/Q438K/S440D |
| 25 | M252Y/S254T/T256E/N286E/H433D/N434Y/Y436V/Q438R/S440D |
| 26 | M252Y/S254T/R255L/T256E/H433D/N434Y/Y436V/Q438K/S440E |
| 27 | M252Y/S254T/R255L/T256E/H433D/N434Y/Y436V/Q438R/S440E |
| 28 | M252Y/S254T/R255L/T256E/H433D/N434Y/Y436V/Q438K/S440D |
| 29 | M252Y/S254T/R255L/T256E/H433D/N434Y/Y436V/Q438R/S440D |
| 30 | M252Y/S254T/R255L/T256E/E258D/H433D/N434Y/Y436V/Q438R/S440E |
| 31 | M252Y/S254T/R255L/T256E/E258I/H433D/N434Y/Y436V/Q438R/S440E |
| 32 | M252Y/S254T/R255L/T256E/E258D/H433D/N434Y/Y436V/Q438K/S440E |
| 33 | M252Y/S254T/R255L/T256E/E258I/H433D/N434Y/Y436V/Q438K/S440E |
| 34 | M252Y/S254T/R255L/T256E/E258D/H433D/N434Y/Y436V/Q438K/S440D |
| 35 | M252Y/S254T/R255L/T256E/E258I/H433D/N434Y/Y436V/Q438K/S440D |
| 36 | M252Y/S254T/R255L/T256E/E258D/H433D/N434Y/Y436V/Q438R/S440D |
| 37 | M252Y/S254T/R255L/T256E/E258I/H433D/N434Y/Y436V/Q438R/S440D |
| 38 | M252Y/S254T/T256E/H433A/N434Y/Y436V/Q438R/S440E |
| 39 | M252Y/S254T/T256E/H433K/N434Y/Y436V/Q438R/S440E |
| 40 | M252Y/S254T/T256E/H433P/N434Y/Y436V/Q438R/S440E |
| 41 | M252Y/S254T/T256E/H433R/N434Y/Y436V/Q438R/S440E |
| 42 | M252Y/S254T/T256E/H433S/N434Y/Y436V/Q438R/S440E |
| 43 | M252Y/S254T/T256E/H433A/N434Y/Y436V/Q438K/S440E |
| 44 | M252Y/S254T/T256E/H433A/N434Y/Y436V/Q438R/S440D |
| 45 | M252Y/S254T/T256E/H433A/N434Y/Y436V/Q438K/S440D |
| 46 | M252Y/S254T/T256E/H433K/N434Y/Y436V/Q438K/S440E |
| 47 | M252Y/S254T/T256E/H433K/N434Y/Y436V/Q438R/S440D |
| 48 | M252Y/S254T/T256E/H433K/N434Y/Y436V/Q438K/S440D |
| 49 | M252Y/S254T/T256E/H433P/N434Y/Y436V/Q438K/S440E |
| 50 | M252Y/S254T/T256E/H433P/N434Y/Y436V/Q438R/S440D |
| 51 | M252Y/S254T/T256E/H433P/N434Y/Y436V/Q438K/S440D |
| 52 | M252Y/S254T/T256E/H433R/N434Y/Y436V/Q438K/S440E |
| 53 | M252Y/S254T/T256E/H433R/N434Y/Y436V/Q438R/S440D |
| 54 | M252Y/S254T/T256E/H433R/N434Y/Y436V/Q438K/S440D |
| 55 | M252Y/S254T/T256E/H433S/N434Y/Y436V/Q438K/S440E |
| 56 | M252Y/S254T/T256E/H433S/N434Y/Y436V/Q438R/S440D |
| 57 | M252Y/S254T/T256E/H433S/N434Y/Y436V/Q438K/S440D |
| 58 | L235R/G236R/S239K/M252Y/S254T/N434Y/Y436V/Q438R/S440E |
| 59 | L235R/G236R/S239K/M252Y/S254T/T256E/N434Y/Y436V/Q438R/S440E |
| 60 | EU238D/EU252Y/EU434Y/EU436V/EU387R |
| 61 | EU238D/EU252Y/EU434Y/EU436V/EU422E |
| 62 | EU238D/EU252Y/EU434Y/EU436V/EU422R |
| 63 | EU238D/EU252Y/EU434Y/EU436V/EU422S |

TABLE 12-continued

Combinations of substitutions in Fc region that increase the FcRn-binding activity in the neutral pH ranges without significantly increasing the binding activity for a pre-existing ADA (positions given according to the EU numbering scheme).

| | |
|---|---|
| 64 | EU238D/EU252Y/EU434Y/EU436V/EU424E, |
| 65 | EU238D/EU252Y/EU434Y/EU436V/EU424R |
| 66 | EU238D/EU252Y/EU434Y/EU436V/EU438E |
| 67 | EU238D/EU252Y/EU434Y/EU436V/EU438R |
| 68 | EU238D/EU252Y/EU434Y/EU436V/EU438S, |
| 69 | EU238D/EU252Y/EU434Y/EU436V/EU440E |
| 70 | EU252Y/EU387R/EU434Y/EU436V |
| 71 | EU252Y/EU422E/EU434Y/EU436V |
| 72 | EU252Y/EU422R/EU434Y/EU436V |
| 73 | EU252Y/EU422S/EU434Y/EU436V |
| 74 | EU252Y/EU424E/EU434Y/EU436V |
| 75 | EU252Y/EU424R/EU434Y/EU436V |
| 76 | EU252Y/EU434Y/EU436V/EU438E |
| 77 | EU252Y/EU434Y/EU436V/EU438R |
| 78 | EU252Y/EU434Y/EU436V/EU438S |
| 79 | EU252Y/EU434Y/EU436V/EU440E |
| 80 | EU252Y/EU422E/EU424R/EU434Y/EU436V |
| 81 | EU252Y/EU422S/EU424R/EU434Y/EU436V |
| 82 | EU252Y/EU434Y/EU436V/EU438R/EU440E |
| 83 | EU252Y/EU422D/EU434Y/EU436V |
| 84 | EU252Y/EU422K/EU434Y/EU436V |
| 85 | EU252Y/EU422T/EU434Y/EU436V |

TABLE 13-continued

Combinations of substitutions in Fc region that increase the FcRn-binding activity in the acidic pH ranges without significantly increasing the binding activity for a pre-existing ADA (positions given according to the EU numbering scheme).

| | |
|---|---|
| 24 | N434Y/Y436T/Q438K/S440D |
| 25 | H433D/N434Y/Y436T/Q438R/S440E |
| 26 | H433D/N434Y/Y436T/Q438R/S440D |
| 27 | H433D/N434Y/Y436T/Q438K/S440E |
| 28 | H433D/N434Y/Y436T/Q438K/S440D |

In addition to a substitution at any one of the positions EU387, EU422, EU424, EU426, EU433, EU436, EU438 and EU440, the Fc region of the present invention may also comprise further substitution of an amino acid at one or more of the following positions: EU248, EU249, EU250, EU251, EU252, EU253, EU254, EU255, EU256, EU257, EU305, EU306, EU307, EU308, EU309, EU310, EU311, EU312, EU313, EU314, EU342, EU343, EU344, EU345, EU346, EU347, EU348, EU349, EU350, EU351, EU352, EU380, EU381, EU382, EU383, EU384, EU385, EU386, EU388, EU414, EU415, EU416, EU417, EU418, EU419, EU420, EU421, EU423, EU425, EU427, EU428, EU429, EU430, EU431, EU432, EU433, EU434, EU435, EU436, EU437, EU441, EU442, EU443, and EU444.

Substituting an Fc region at any one of these positions may reduce the binding affinity for a pre-existing ADA, in particular for the rheumatoid factor, without negatively affecting the binding affinity for FcRn.

Furthermore, the methods of the present invention may further comprise the step of substituting the Fc region of the antigen-binding molecule as described above at one or more of the following positions:
EU248, EU249, EU250, EU251, EU252, EU253, EU254, EU255, EU256, EU257, EU305, EU306, EU307, EU308, EU309, EU310, EU311, EU312, EU313, EU314, EU342, EU343, EU344, EU345, EU346, EU347, EU348, EU349, EU350, EU351, EU352, EU380, EU381, EU382, EU383, EU384, EU385, EU386, EU388, EU414, EU415, EU416, EU417, EU418, EU419, EU420, EU421, EU423, EU425, EU427, EU428, EU429, EU430, EU431, EU432, EU433, EU434, EU435, EU436, EU437, EU441, EU442, EU443, and EU444.

Weak or No Binding Activity for an Effector Receptor or a Complement Protein

Binding to Fc gamma receptors or complement proteins may also cause undesired effects (e.g. inappropriate platelet activation). A modified antigen-binding molecule that does not bind effector receptors such as Fc gamma RIIa receptor is safer and/or more effective. Therefore, in a preferred embodiment, the modified antigen-binding molecules of the present invention additionally have a weak binding activity for an effector receptor or do not bind to an effector receptor. Examples of an effector receptor include but are not limited to activating Fc gamma receptors, in particular Fc gamma receptor I, Fc gamma receptor II and Fc gamma receptor III. Fc gamma receptor I includes Fc gamma receptor Ia, Fc gamma receptor Ib, and Fc gamma receptor Ic, and subtypes thereof. Fc gamma receptor II includes Fc gamma receptor IIa (which has two allotypes R131 and H131) and Fc gamma receptor IIb. Fc gamma receptor III includes Fc gamma receptor IIIa (which has two allotypes: V158 and F158) and Fc gamma receptor IIIb (which has two allotypes: Fc gamma IIIb-NA1 and Fc gamma IIIb-NA2). Antibodies that have a weak binding activity for effector receptors or do not bind to them are for examples antibodies comprising a silent Fc region or antibodies without an Fc region (e.g. Fab, F(ab)'2, scFv, sc(Fv)2, diabodies).

Examples for Fc regions having a weak or no binding activity for effector receptors are e.g. described in Strohl et al. (Current Opinion in Biotechnology (2009) 20(6), 685-691). In particular it describes for example deglycosylated Fc regions (N297A, N297Q), and examples of a silent Fc region, which are Fc regions engineered for silenced (or immunosuppressive) effector functionality (IgG1-L234A/L235A, IgG1-H268Q/A330S/P331S, IgG1-C226S/C229S, IgG1-C226S/C229S/E233P/L234V/L235A, IgG1-L234F/L235E/P331S, IgG2-V234A/G237A, IgG2-H268Q/V309L/A330S/A331S, IgG4-L235A/G237A/E318A, IgG4-L236E). WO2008/092117 discloses antibodies comprising silent Fc regions that comprise the substitutions G236R/L328R, L235G/G236R, N325A/L328R, or N325L/L328R (positions according to the EU numbering system). Furthermore, WO 2000/042072 discloses antibodies comprising silent Fc regions which comprise substitutions at one or more of the positions EU233, EU234, EU235, and EU237. WO 2009/011941 discloses antibodies comprising silent Fc regions which comprise deletion of residues from EU231 to EU238. Davis et al (Journal of Rheumatology (2007) 34(11): 2204-2210) discloses antibodies comprising silent Fc regions which comprise the substitutions C220S/C226S/C229S/P238S. Shields et al (Journal of Biological Chemistry (2001) 276 (9), 6591-6604) discloses antibodies comprising silent Fc regions which comprise the substitution D265A.

The term "weak binding for effector receptors" refers to a binding activity that is 95% or less, preferably 90% or less, 85% or less, 80% or less, 75% or less, more preferably 70% or less, 65% or less, 60% or less, 55% or less, 50% or less, 45% or less, 40% or less, 35% or less, 30% or less, 25% or less, 20% or less, 15% or less, 10% or less, 9% or less, 8% or less, 7% or less, 6% or less, 5% or less, 4% or less, 3% or less, 2% or less, 1% or less of the binding activity of an intact IgG (or an antibody comprising an intact Fc region) for the effector receptor. The binding activity to an Fc gamma R preferably reduced by a factor of at least about 10 fold or more, about 50-fold or more, about 100-fold or more as compared with the binding activity of an intact IgG (or an antibody comprising an intact Fc region) for the effector receptor.

A silent Fc region is a modified Fc region comprising one or more amino acid substitutions, insertions, additions and/or deletions which reduce the binding for an effector receptor as compared to an intact Fc region. The binding activity for an effector receptor may be so much reduced that the Fc region does not bind an effector receptor anymore. Examples of a silent Fc region include but are not limited to Fc regions which comprise an amino acid substitution at one or more of the positions selected from the group consisting of: EU234, EU235, EU236, EU237, EU238, EU239, EU265, EU266, EU267, EU269, EU270, EU271, EU295, EU296, EU297, EU298, EU300, EU324, EU325, EU327, EU328, EU329, EU331, and EU332.

In particular, a silent Fc region has a substitution at one or more the positions selected from the group consisting of EU234, EU235, EU236, EU237, EU238, EU239, EU265, EU266, EU267, EU269, EU270, EU271, EU295, EU296, EU297, EU298, EU300, EU324, EU325, EU327, EU328, EU329, EU331, and EU332 with an amino acid selected from the list below. Preferably, a silent Fc region has a substitution at one or more positions selected from the group consisting of EU235, EU237, EU238, EU239, EU270, EU298, EU325, and EU329 with an amino acid selected from the list below. The amino acid at position EU234 is preferably replaced with one of an amino acid selected from the group consisting of: Ala, Arg, Asn, Asp, Gln, Glu, Gly, His, Lys, Met, Phe, Pro, Ser, and Thr.

The amino acid at position EU235 is preferably replaced with one of an amino acid selected from the group consisting of: Ala, Asn, Asp, Gln, Glu, Gly, His, Ile, Lys, Met, Pro, Ser, Thr, Val and Arg.

The amino acid at position EU236 is preferably replaced with one of an amino acid selected from the group consisting of: Arg, Asn, Gln, His, Leu, Lys, Met, Phe, Pro and Tyr.

The amino acid at position EU237 is preferably replaced with one of an amino acid selected from the group consisting of: Ala, Asn, Asp, Gln, Glu, His, Ile, Leu, Lys, Met, Pro, Ser, Thr, Val, Tyr and Arg.

The amino acid at position EU238 is preferably replaced with one of an amino acid selected from the group consisting of: Ala, Asn, Gln, Glu, Gly, His, Ile, Lys, Thr, Trp and Arg.

The amino acid at position EU239 is preferably replaced with one of an amino acid selected from the group consisting of: Gln, His, Lys, Phe, Pro, Trp, Tyr and Arg.

The amino acid at position EU265 is preferably replaced with one of an amino acid selected from the group consisting of: Ala, Arg, Asn, Gln, Gly, His, Ile, Leu, Lys, Met, Phe, Ser, Thr, Trp, Tyr and Val.

The amino acid at position EU266 is preferably replaced with one of an amino acid selected from the group consisting of: Ala, Arg, Asn, Asp, Gln, Glu, Gly, His, Lys, Phe, Pro, Ser, Thr, Trp and Tyr.

The amino acid at position EU267 is preferably replaced with one of an amino acid selected from the group consisting of: Arg, His, Lys, Phe, Pro, Trp and Tyr.

The amino acid at position EU269 is preferably replaced with one of an amino acid selected from the group consisting of: Ala, Arg, Asn, Gln, Gly, His, Ile, Leu, Lys, Met, Phe, Pro, Ser, Thr, Trp, Tyr and Val.

The amino acid at position EU270 is preferably replaced with one of an amino acid selected from the group consisting of: Ala, Arg, Asn, Gln, Gly, His, Ile, Leu, Lys, Met, Phe, Pro, Ser, Thr, Trp, Tyr and Val.

The amino acid at position EU271 is preferably replaced with one of an amino acid selected from the group consisting of: Arg, His, Phe, Ser, Thr, Trp and Tyr.

The amino acid at position EU295 is preferably replaced with one of an amino acid selected from the group consisting of: Arg, Asn, Asp, Gly, His, Phe, Ser, Trp and Tyr.

The amino acid at position EU296 is preferably replaced with one of an amino acid selected from the group consisting of: Arg, Gly, Lys and Pro.

The amino acid at position EU297 is preferably replaced with Ala,

The amino acid at position EU298 is preferably replaced with one of an amino acid selected from the group consisting of: Arg, Gly, Lys, Pro, Trp and Tyr.

The amino acid at position EU300 is preferably replaced with one of an amino acid selected from the group consisting of: Arg, Lys and Pro.

The amino acid at position EU324 is preferably replaced with Lys or Pro.

The amino acid at position EU325 is preferably replaced with one of an amino acid selected from the group consisting of: Ala, Arg, Gly, His, Ile, Lys, Phe, Pro, Thr, Trp, Tyr, and Val.

The amino acid at position EU327 is preferably replaced with one of an amino acid selected from the group consisting of: Arg, Gln, His, Ile, Leu, Lys, Met, Phe, Pro, Ser, Thr, Trp, Tyr and Val.

The amino acid at position EU328 is preferably replaced with one of an amino acid selected from the group consisting of: Arg, Asn, Gly, His, Lys and Pro.

The amino acid at position EU329 is preferably replaced with one of an amino acid selected from the group consisting of: Asn, Asp, Gln, Glu, Gly, His, Ile, Leu, Lys, Met, Phe, Ser, Thr, Trp, Tyr, Val and Arg.

The amino acid at position EU330 is preferably replaced with Pro or Ser.

The amino acid at position EU331 is preferably replaced with one of an amino acid selected from the group consisting of: Arg, Gly and Lys.

The amino acid at position EU332 is preferably replaced with one of an amino acid selected from the group consisting of: Arg, Lys and Pro.

Preferably, a silent Fc region comprises a substitution at position EU235 with Lys or Arg, EU237 with Lys or Arg, EU238 with Lys or Arg, EU239 with Lys or Arg, EU270 with Phe, EU298 with Gly, EU325 with Gly or EU329 with Lys or Arg. More preferably, a silent Fc region comprises a substitution at position EU235 with arginine and at position EU239 with lysine. More preferably, it comprises the substitutions L235R/S239K.

Furthermore, the modified antigen-binding molecules of the present invention are preferably deglycosylated. More preferably, the modified antigen-binding molecule of the present invention comprises a mutation at a heavy chain glycosylation site to prevent glycosylation at the site such as e.g. described in WO2005/03175. Thus, in a preferred embodiment of the present invention, the modified aglycosyl antigen-binding molecules are prepared by modifying the heavy chain glycosylation site, i.e., introducing the substitution N297Q or N297A (position according to EU numbering system), and expressing the protein in an appropriate host cell. For introducing a substitution a method as described in the EXAMPLES can be used.

In a specific embodiment of the present invention, the modified antigen-binding molecules of the present invention thereof have a weak binding activity for a complement protein or do not bind to a complement protein. Preferably, the complement protein is C1q. A weak binding activity for a complement protein is preferably a binding activity for a complement protein which is reduced by a factor of about 10 fold or more, about 50-fold or more, about 100-fold or more as compared to the binding activity for a complement protein of an intact IgG or an antibody comprising an intact Fc region. The binding activity of an Fc region for a complement protein can be reduced by modification of the amino acid sequence such as amino acid substitutions, insertions, additions and/or deletions In a preferred embodiment of the present invention, the antigen-binding molecule has an increased FcRn-binding affinity in the acidic or neutral pH and has a weak or no binding activity for an effector receptor and/or a complement protein. Preferably, such an antigen-binding molecule comprises a substitution in the FcRn-binding domain at a) one or more positions selected from the group consisting of EU238, EU250, EU252, EU254, EU255, EU256, EU258, EU286, EU307, EU308, EU309, EU311, EU315, EU428, EU433, EU434, and EU436, and b) at one or more positions selected from the group consisting of: EU234, EU235, EU236, EU237, EU238, EU239, EU265, EU266, EU267, EU269, EU270, EU271, EU295, EU296, EU297 EU298, EU300, EU324, EU325, EU327, EU328, EU329, EU331, and EU332 (according to the EU numbering system). More preferably, the modified antigen-binding molecule of the present invention having a reduced or no binding activity for effector receptors and/or complement proteins comprises one or more substitutions in the Fc regions selected from the group consisting of a substitution at position EU235 with Lys or Arg, at position EU237 with Lys or Arg, at position EU238 with Lys or Arg, at position EU239 with Lys or Arg, at position EU270 with Phe, EU298 with Gly, at position EU325 with Gly and at position EU329 with Lys or Arg. Even more preferably, it comprises a substitution in the Fc region at position EU235 with Arg and at position EU239 with Lys. And even more preferably, it comprises the substitution combination L235R/S239K in the Fc region.

Preferably, such antigen-binding molecules have also no significantly increased binding activity for a pre-existing ADA. Therefore, the antigen-binding molecule of the present invention having a reduced or no binding activity for effector receptor(s) and/or complement proteins further comprises an amino acid substitutions at c) one or more positions selected from the group consisting of EU387, EU422, EU424, EU426, EU433, EU436, EU438 and EU440. In a more preferred embodiment of the present invention, the modified antigen-binding molecules comprise three or more amino acid substitutions in the FcRn-binding domain, wherein the three or more substitutions are one of the combinations set forth in Tables 14 and 15.

TABLE 14

Substitution combinations that increase FcRn-binding activity at neutral pH without significantly increasing the binding activity for a pre-existing ADA, and reducing the binding activity for effector receptor(s) and/or complement proteins 1  L235R/S239K/M252Y/N434Y/Y436T
2  L235R/S239K/M252Y/N434Y/Y436V/Q438K/S440E
3  L235R/S239K/M252Y/N434Y/Y436V/Q438R/S440E
4  L235R/S239K/M252Y/N434Y/Y436T/Q438K/S440E
5  L235R/S239K/M252Y/N434Y/Y436T/Q438R/S440E
6  L235R/S239K/M252Y/N434Y/Y436F/Q438K/S440E
7  L235R/S239K/M252Y/N434Y/Y436F/Q438R/S440E
8  L235R/S239K/M252Y/N434Y/Y436V/Q438R/S440D
9  L235R/S239K/M252Y/N434Y/Y436V/Q438K/S440D
10 L235R/S239K/M252Y/H433D/N434Y/Y436V/Q438R/S440D
11 L235R/S239K/M252Y/H433D/N434Y/Y436V/Q438K/S440E
12 L235R/S239K/M252Y/H433D/N434Y/Y436V/Q438R/S440E
13 L235R/S239K/M252Y/H433D/N434Y/Y436V/Q438K/S440D
14 L235R/S239K/M252Y/S254T/T256E/T307Q/Q311A/H433D/N434Y/Y436V/Q438K/S440E
15 L235R/S239K/M252Y/S254T7T256E/V308P/H433D/N434Y/Y436V/Q438K/S440E
16 L235R/S239K/M252Y/H433D/N434W/Y436V/Q438R/S440E
17 L235R/S239K/M252Y/H433D/N434W/Y436V/Q438K/S440E
18 L235R/S239K/M252Y/S254T/T256E/H433D/N434Y/Y436V/Q438K/S440E
19 L235R/S239K/M252Y/S254T/T256E/H433D/N434Y/Y436V/Q438R/S440E
20 L235R/S239K/M252Y/S254T/T256E/H433D/N434Y/Y436V/Q438K/S440D
21 L235R/S239K/M252Y/S254T/T256E/H433D/N434Y/Y436V/Q438R/S440D
22 L235R/S239K/M252Y/S254T/T256E/N286E/H433D/N434Y/Y436V/Q438K/S440E
23 L235R/S239K/M252Y/S254T/T256E/N286E/H433D/N434Y/Y436V/Q438R/S440E
24 L235R/S239K/M252Y/S254T/T256E/N286E/H433D/N434Y/Y436V/Q438K/S440D
25 L235R/S239K/M252Y/S254T/T256E/N286E/H433D/N434Y/Y436V/Q438R/S440D
26 L235R/S239K/M252Y/S254T/R255L/T256E/H433D/N434Y/Y436V/Q438K/S440E
27 L235R/S239K/M252Y/S254T/R255L/T256E/H433D/N434Y/Y436V/Q438R/S440E
28 L235R/S239K/M252Y/S254T/R255L/T256E/H433D/N434Y/Y436V/Q438K/S440D
29 L235R/S239K/M252Y/S254T/R255L/T256E/H433D/N434Y/Y436V/Q438R/S440D
30 L235R/S239K/M252Y/S254T/R255L/T256E/E258D/H433D/N434Y/Y436V/Q438R/S440E
31 L235R/S239K/M252Y/S254T/R255L/T256E/E258I/H433D/N434Y/Y436V/Q438R/S440E
32 L235R/S239K/M252Y/S254T/R255L/T256E/E258D/H433D/N434Y/Y436V/Q438K/S440E
33 L235R/S239K/M252Y/S254T/R255L/T256E/E258I/H433D/N434Y/Y436V/Q438K/S440E
34 L235R/S239K/M252Y/S254T/R255L/T256E/E258D/H433D/N434Y/Y436V/Q438K/S440D
35 L235R/S239K/M252Y/S254T/R255L/T256E/E258T/H433D/N434Y/Y436V/Q438K/S440D
36 L235R/S239K/M252Y/S254T/R255L/T256E/E258D/H433D/N434Y/Y436V/Q438R/S440D
37 L235R/S239K/M252Y/S254T/R255L/T256E/E258I/H433D/N434Y/Y436V/Q438R/S440D
38 L235R/S239K/M252Y/S254T7T256E/H433A/N434Y/Y436V/Q438R/S440E
39 L235R/S239K/M252Y/S254T/T256E/H433K/N434Y/Y436V/Q438R/S440E
40 L235R/S239K/M252Y/S254T/T256E/H433P/N434Y/Y436V/Q438R/S440E
41 L235R/S239K/M252Y/S254T/T256E/H433R/N434Y/Y436V/Q438R/S440E
42 L235R/S239K/M252Y/S254T/T256E/H433S/N434Y/Y436V/Q438R/S440E
43 L235R/S239K/M252Y/S254T/T256E/H433A/N434Y/Y436V/Q438K/S440E
44 L235R/S239K/M252Y/S254T/T256E/H433A/N434Y/Y436V/Q438R/S440D
45 L235R/S239K/M252Y/S254T/T256E/H433A/N434Y/Y436V/Q438K/S440D
46 L235R/S239K/M252Y/S254T/T256E/H433K/N434Y/Y436V/Q438K/S440E
47 L235R/S239K/M252Y/S254T/T256E/H433K/N434Y/Y436V/Q438R/S440D
48 L235R/S239K/M252Y/S254T/T256E/H433K/N434Y/Y436V/Q438K/S440D
49 L235R/S239K/M252Y/S254T/T256E/H433P/N434Y/Y436V/Q438K/S440E
50 L235R/S239K/M252Y/S254T/T256E/H433P/N434Y/Y436V/Q438K/S440D
51 L235R/S239K/M252Y/S254T/T256E/H433P/N434Y/Y436V/Q438K/S440D
52 L235R/S239K/M252Y/S254T/T256E/H433R/N434Y/Y436V/Q438K/S440E
53 L235R/S239K/M252Y/S254T/T256E/H433R/N434Y/Y436V/Q438R/S440D
54 L235R/S239K/M252Y/S254T/T256E/H433R/N434Y/Y436V/Q438K/S440D
55 L235R/S239K/M252Y/S254T/T256E/H433S/N434Y/Y436V/Q438K/S440E
56 L235R/S239K/M252Y/S254T/T256E/H433S/N434Y/Y436V/Q438R/S440D
57 L235R/S239K/M252Y/S254T/T256E/H433S/N434Y/Y436V/Q438K/S440D

TABLE 14-continued

Substitution combinations that increase FcRn-binding activity at neutral pH without significantly increasing the binding activity for a pre-existing ADA, and reducing the binding activity for effector receptor(s) and/or complement proteins

| | |
|---|---|
| 58 | L235R/G236R/S239K/M252Y/S254T/N434Y/Y436V/Q438R/S440E |
| 59 | L235R/G236R/S239K/M252Y/S254T/T256E/N434Y/Y436V/Q438R/S440E |

TABLE 15

Substitution combinations that increase FcRn-binding activity at acidic pH without significantly increasing the binding activity for a pre-existing ADA, and reducing the binding activity for effector receptor(s) and/or complement proteins

| | |
|---|---|
| 1 | L235R/S239K/N434Y/Y436V/Q438R/S440E |
| 2 | L235R/S239K/N434Y/Y436V/Q438R/S440D |
| 3 | L235R/S239K/N434Y/Y436V/Q438K/S440E |
| 4 | L235R/S239K/N434Y/Y436V/Q438K/S440D |
| 5 | L235R/S239K/H433D/N434Y/Y436V/Q438R/S440E |
| 6 | L235R/S239K/H433D/N434Y/Y436V/Q438R/S440D |
| 7 | L235R/S239K/H433D/N434Y/Y436V/Q438K/S440E |
| 8 | L235R/S239K/H433D/N434Y/Y436V/Q438K/S440D |
| 9 | L235R/S239K/N434Y/Y436T/Q438R/S440E |
| 10 | L235R/S239K/N434Y/Y436T/Q438R/S440D |
| 11 | L235R/S239K/N434Y/Y436T/Q438K/S440E |
| 12 | L235R/S239K/N434Y/Y436T/Q438K/S440D |
| 13 | L235R/S239K/H433D/N434Y/Y436T/Q438R/S440E |
| 14 | L235R/S239K/H433D/N434Y/Y436T/Q438R/S440D |
| 15 | L235R/S239K/H433D/N434Y/Y436T/Q438K/S440E |
| 16 | L235R/S239K/H433D/N434Y/Y436T/Q438K/S440D |

Further Modifications

Furthermore, the antigen-binding molecule of the present invention comprises in addition to the modifications described above, at the position EU257 of the FcRn-binding domain not an amino acid selected from the group consisting of: alanine, valine, isoleucine, leucine, and threonine, and/or at the position EU252 of the FcRn-binding domain not a tryptophan. In other words, the preferred antigen-binding molecule of the present invention comprises in addition to any of the modifications described above at positions EU257 an alanine, a valine, an isoleucine, aleucine, a threonine, an arginine, an asparagine, an aspartic acid, a cysteine, a glutamic acid, a glutamine, a glycine, a histidine, a lysine, a methione, a phenylalanine, a proline, a serine, a tryptophan, or a tyrosine, and at position EU252 an arginine, an asparagine, an aspartic acid, a cysteine, a glutamic acid, a glutamine, a glycine, a histidine, a lysine, a methione, a phenylalanine, a proline, a serine, or a tyrosine Also preferred is a modified FcRn-binding domain which comprises in addition to the substitutions at any one of the herein mentioned positions or combinations of positions, at position EU239 a lysine and/or at position EU270 a phenylalanine.

Antigen-Binding Molecule

The antigen-binding molecules of the present invention are not particularly limited, as long as they include an antigen-binding domain having a binding activity specific to a target antigen and an FcRn-binding domain of the present invention. Preferred antigen-binding domains comprise, for example, domains having an antigen-binding region of an antibody. The antigen-binding region of an antibody comprises, for example, CDRs. The antigen-binding region of an antibody may contain all six CDRs from the whole antibody, or one, two, or more CDRs. The antigen-binding region of antibody comprise amino acid deletions, substitutions, additions, and/or insertions, or it may comprise a portion of CDR.

On the other hand, antigen-binding molecules of the present invention include antigen-binding molecules that have an antagonistic activity (antagonistic antigen-binding molecules), antigen-binding molecules that have an agonistic activity (agonistic antigen-binding molecule), and molecules having cytotoxicity. In a preferred embodiment, the antigen-binding molecules are antagonistic antigen-binding molecules, in particular, antagonistic antigen-binding molecules that recognize an antigen such as a receptor or cytokine.

The antigen-binding molecule of the present invention is preferably an antibody. The antibodies preferred in the context of the present invention include, for example, IgG antibodies. When the antibody to be used is an IgG antibody, the type of IgG is not particularly limited; thus, the IgG may belong to any isotype (subclass) such as IgG1, IgG2, IgG3, or IgG4. For a human IgG1, IgG2, IgG3, or IgG4 constant region, gene polymorphisms (allotypes) are described in "Sequences of proteins of immunological interest, NIH Publication No. 91-3242". These allotypes can also be used for constant region in this application. Especially, for human IgG1, both of the amino acids Asp-Glu-Leu (DEL) and Glu-Glu-Met (EEM) can be used for residues in 356-358 in EU numbering. Similarly, for human immunoglobulin kappa constant region, gene polymorphisms (allotypes) are described in "Sequences of proteins of immunological interest, NIH Publication No. 91-3242". These allotypes can also be used for constant region in this application. Furthermore, the antigen-binding molecules of the present invention may include antibody constant region, and amino acid mutations may be introduced into the constant region. Amino acid mutations to be introduced include, for example, those potentiate or impair the binding to Fcgamma receptor (Proc Natl Acad Sci USA. 2006 Mar. 14; 103(11): 4005-10), but are not limited to these examples. Alternatively, it is also possible to alter the pH-dependent binding by selecting an appropriate constant region such as of IgG2 (WO09125825).

When an antigen-binding molecule of the present invention is an antibody, the antibody may be derived from any animal, such as a mouse, human, rat, rabbit, goat, or camel. Preferably, the antibody is a human antibody. Furthermore, the antibody may be an altered antibody, for example, a chimeric antibody, and in particular, an altered antibody that comprises an amino acid substitution in the sequence of a humanized antibody, etc. The category of antibodies contemplated by the present invention also include bispecific antibodies, antibody modification products linked with various molecules, and polypeptides that comprise antibody fragments (particularly immunogenic and/or immunoreactive antibody fragments). In a preferred embodiment, the antigen-binding molecule is a monoclonal antibody.

"Chimeric antibodies" are antibodies prepared by combining sequences derived from different animals. Specifically, a chimeric antibody includes, for example, antibodies having heavy and light chain variable (V) regions from a mouse antibody and heavy and light chain constant (C) regions from a human antibody. Methods for generating chimeric antibodies are known. In the case of a human-mouse chimeric antibody, for example, a DNA encoding an antibody V region may be linked to a DNA encoding a human antibody C region; this can be inserted into an expression vector and introduced into a host to produce the chimeric antibody.

"Humanized antibodies", also referred to as reshaped human antibodies, are known in the art as antibodies in which complementarity determining regions (CDRs) of an antibody derived from a nonhuman mammal, for example, a mouse, are transplanted into the CDRs of a human antibody. Methods for identifying CDRs are known (Kabat et al., Sequence of Proteins of Immunological Interest (1987), National Institute of Health, Bethesda, Md.; Chothia et al., Nature (1989) 342: 877). General genetic recombination technologies suitable for this purpose are also known (see European Patent Application EP 125023; and WO 96/02576). Humanized antibodies can be produced by known methods, for example, the CDR of a mouse antibody can be determined, and a DNA encoding an antibody in which the CDR is linked to the framework region (FR) of a human antibody is obtained. Humanized antibodies can then be produced using a system that uses conventional expression vectors. Such DNAs can be synthesized by PCR, using as primers several oligonucleotides prepared to have portions that overlap with the end regions of both the CDR and FR (see the method described in WO 98/13388). Human antibody FRs linked via CDRs are selected such that the CDRs form a suitable antigen binding site. If required, amino acids in the FRs of an antibody variable region may be altered so that the CDRs of the reshaped human antibody can form a suitable antigen binding site (Sato et al., Cancer Res. (1993) 53: 10.01-6). Amino acid residues in the FRs that can be altered include portions that directly bind to an antigen via non-covalent bonds (Amit et al., Science (1986) 233: 747-53), portions that influence or have an effect on the CDR structure (Chothia et al., J. Mol. Biol. (1987) 196: 901-17), and portions involved in VH-VL interactions (EP 239400).

When the antigen-binding molecules of the present invention are chimeric antibodies or humanized antibodies, the constant regions of these antibodies are preferably derived from human antibodies. For example, C-gamma1, C-gamma2, C-gamma3, and C-gamma4 can be used for the H chain, while C-kappa and C-lambda can be used for the L chain. Moreover, if required, amino acid mutations may be introduced into the human antibody C region to enhance or lower the binding to Fc-gamma receptor or to improve antibody stability or productivity. A chimeric antibody of the present invention preferably includes a variable region of an antibody derived from a nonhuman mammal and a constant region derived from a human antibody. Meanwhile, a humanized antibody preferably includes CDRs of an antibody derived from a nonhuman mammal and FRs and C regions derived from a human antibody. The constant regions derived from human antibodies preferably include a human FcRn-binding region. Such antibodies include, for example, IgGs (IgG1, IgG2, IgG3, and IgG4). The constant regions used for the humanized antibodies of the present invention may be constant regions of antibodies of any isotype. A constant region derived from human IgG1 is preferably used, though it is not limited thereto. The FRs derived from a human antibody, which are used for the humanized antibodies, are not particularly limited either, and may be derived from an antibody of any isotype.

The term "bispecific antibody" as used herein refers to an antibody that has, in the same antibody molecule, variable regions that recognize different epitopes. A bispecific antibody may be an antibody that recognizes two or more different antigens, or an antibody that recognizes two or more different epitopes on a same antigen.

Furthermore, polypeptides including antibody fragments may be, for example, scFv-Fc (WO 2005/037989), dAb-Fc, and Fc fusion proteins. Antibody fragments in such polypeptides can be for example Fab fragments, F(ab')2 fragments, scFvs (Nat. Biotechnol. 2005 September; 23(9): 1126-36), domain antibodies (dAbs) (WO 2004/058821, WO 2003/002609), Fc region can be used as a human FcRn-binding domain when a molecule includes an Fc region. Alternatively, an FcRn-binding domain may be fused to these molecules.

Further, antigen-binding molecules that are applicable to the present invention can be or can comprise antibody-like molecules (e.g. a fusion protein of an Fc region of the present invention with an antibody-like molecule). An antibody-like molecule (scaffold molecule, peptide molecule) is a molecule that can exhibit functions by binding to a target molecule (Current Opinion in Biotechnology (2006) 17: 653-658; Current Opinion in Biotechnology (2007) 18: 1-10; Current Opinion in Structural Biology (1997) 7: 463-469; Protein Science (2006) 15: 14-27), and includes, for example, DARPins (WO 2002/020565), Affibody (WO 1995/001937), Avimer (WO 2004/044011; WO 2005/040229), and Adnectin (WO 2002/032925). If these antibody-like molecules can bind to target molecules in a pH-dependent or calcium-dependent manner and/or have human FcRn-binding activity in the neutral pH range, it is possible to facilitate antigen uptake into cells by antigen-binding molecules, facilitate the reduction of plasma antigen concentration by administering antigen-binding molecules, and improve pharmacokinetics of the antigen-binding molecules, and increase the number of antigens to which a single antigen-binding molecule can bind.

Furthermore, the antigen-binding molecule can be a protein resulting from fusion between an FcRn-binding domain of the present invention and a receptor protein that binds to a target including a ligand, and includes, for example, TNFR-Fc fusion proteins, IL1R-Fc fusion proteins, VEGFR-Fc fusion proteins, and CTLA4-Fc fusion proteins (Nat Med. 2003, January; 9(1): 47-52; BioDrugs. (2006) 20(3): 151-60). If these receptor-FcRn-binding domain fusion proteins bind to a target molecule including a ligand in a pH-dependent or calcium-dependent manner in addition to having FcRn-binding activity in the neutral pH range, it is possible to facilitate antigen uptake into cells by antigen-binding molecules, facilitate the reduction of plasma antigen concentration by administering antigen-binding molecules, and improve pharmacokinetics of the antigen-binding molecules, and increase the number of antigens to which a single antigen-binding molecule can bind. A receptor protein is appropriately designed and modified so as to include a binding domain of the receptor protein to a target including a ligand. As referred to the examples hereinbefore (i.e. TNFR-Fc fusion proteins, IL1R-Fc fusion proteins, VEGFR-Fc fusion proteins and CTLA4-Fc fusion proteins) a soluble receptor molecule comprising an extracellular domain of those receptor proteins that is required for binding to those targets including ligands is particularly preferred. Such designed and modified receptor molecules are referred to as artificial receptors in the present invention. Methods for designing and modifying a receptor molecule to construct an artificial receptor molecule are known and indeed conventional in the art.

Furthermore, the antibodies of the present invention can have modified sugar chains. Antibodies with modified sugar chains include, for example, antibodies with modified glycosylation (WO 99/54342), antibodies that are deficient in fucose that is added to the sugar chain (WO 00/61739; WO 02/31140; WO 2006/067847; WO2006/067913), and antibodies having sugar chains with bisecting GlcNAc (WO 02/79255).

According to the Journal of Immunology (2009) 182: 7663-7671, the human FcRn-binding activity of intact human IgG1 in the acidic pH range (pH 6.0) is KD 1.7 micromolar (microM), while in the neutral pH range the activity is almost undetectable. Thus, in a preferred embodiment, the antigen-binding molecule of the present invention includes antigen-binding molecules whose human FcRn-binding activity in the acidic pH range is stronger than KD 1.7 micromolar and is identical or stronger in the neutral pH range than that of intact human IgG. In a more preferred embodiment its binding activity for a pre-existing ADA in the neutral pH ranges is not significantly increased compared to intact IgG1. The above KD values are determined by the method described in the Journal of Immunology (2009) 182: 7663-7671 (by immobilizing the antigen-binding molecule onto a chip and loading human FcRn as an analyte).

Dissociation constant (KD) can be used as a value of human FcRn-binding activity. However, the human FcRn-binding activity of intact human IgG has little human FcRn-binding activity in the neutral pH range (pH 7.4). Accordingly, it is often difficult to calculate the activity as KD. Methods for assessing whether the human FcRn-binding activity is higher than that of intact human IgG at pH 7.4 include assessment methods by comparing the intensities of Biacore response after loading analytes at the same concentration. Specifically, when the response after loading a human FcRn chip immobilized with an antigen-binding molecule at pH 7.4 is stronger than the response after loading human FcRn onto a chip immobilized with intact human IgG at pH 7.4, the human FcRn-binding activity of the antigen-binding molecule is judged to be higher than that of intact human IgG at pH 7.4.

In the context of the present invention, pH 7.0 can be used as the neutral pH range. Using pH 7.0 as a neutral pH can facilitate weak interaction between human FcRn and FcRn-binding domain. As a temperature employed in the assay condition, a binding affinity may be assessed at any temperature from 10 degrees Celsius to 50 degrees Celsius. Preferably, a temperature ranging from 15 degrees Celsius to 40 degrees Celsius is employed in order to determine the binding affinity between human FcRn-binding domain and human FcRn. More preferably, any temperature ranging from 20 degrees Celsius to 35 degrees Celsius, like any one of 20, 21, 22, 23, 24, 25, 26, 27, 28, 29, 30, 31, 32, 33, 34, and 35 degrees C. is also employed in order to determine the binding affinity between human FcRn-binding domain and human FcRn. A temperature at 25 degrees C. described in EXAMPLE 5 of WO2011/122011 is one example for the embodiment of this invention. In a preferred embodiment, an interaction between human FcRn and FcRn-binding domain can be measured at pH 7.0 and at 25 degrees C. as described in EXAMPLE 5 of WO2011/122011. Binding affinity of antigen-binding molecule to human FcRn can be measured by Biacore as described in EXAMPLE 5 of WO2011/122011.

Preferably the binding affinity at neutral pH ranges is measured at pH 7.4, which is close to in vivo plasma (blood) pH. pH 7.0 can be used as an alternative to pH 7.4 when it is difficult to assess the binding affinity between human FcRn-binding domain and human FcRn due its low affinity at pH 7.4. Preferably the binding affinity at acidic pH ranges is measured at pH 6.0, which is close to the pH in early endosome in vivo. As a temperature employed in the assay condition, a binding affinity between human FcRn-binding domain and human FcRn may be assessed at any temperature from 10 degrees C. to 50 degrees C. Preferably, a temperature from 15 degrees C. to 40 degrees C. is employed in order to determine the binding affinity between human FcRn-binding domain and human FcRn. More preferably, any temperature at from 20 degrees C. to 35 degrees C., like any one of 20, 21, 22, 23, 24, 25, 26, 27, 28, 29, 30, 31, 32, 33, 34, and 35 degrees C. is also employed in order to determine the binding affinity between human FcRn-binding domain and human FcRn. A temperature at 25 degrees C. is described for example in Example 5 of WO2011/122011 and in the EXAMPLES of this invention.

An intact human IgG1, IgG2, IgG3 or IgG4 is preferably used as the reference intact human IgG to be compared with the antigen-binding molecules for their human FcRn binding activity or in vivo activity. Preferably, an antigen-binding molecule that comprises the same antigen-binding domain as the antigen-binding molecule of the interest and an intact human IgG Fc region as a human FcRn-binding domain is used as reference. More preferably, an intact human IgG1 is used as reference intact human IgG for comparing its human FcRn binding activity or in vivo activity with the human FcRn binding activity or in vivo activity of an antigen-binding molecule of the present invention.

Conditions used in the assay for the antigen-binding or human FcRn-binding activity other than pH can be appropriately selected by those skilled in the art, and the conditions are not particularly limited. For example, the conditions of using MES buffer at 37 degrees C. as described in WO 2009/125825 may be used to determine the activity. In another embodiment, Na-phosphate buffer at 25 degrees C. as described in Example 4 or 5 of WO2011/122011 may be used to determine the activity. Meanwhile, the antigen-binding activity and human FcRn-binding activity of antigen-binding molecule can be determined by methods known to those skilled in the art, for example, using Biacore (GE Healthcare) or such. When the antigen is a soluble antigen, the activity of an antigen-binding molecule to bind to the soluble antigen can be determined by loading the antigen as an analyte onto a chip immobilized with the antigen-binding molecule. Alternatively, when the antigen is a membrane-type antigen, the activity of the antigen-binding molecule to bind to the membrane-type antigen can be determined by loading the antigen-binding molecule as an analyte onto an antigen-immobilized chip. The human FcRn-binding activity of an antigen-binding molecule can be determined by loading human FcRn or the antigen-binding molecule as an analyte onto a chip immobilized with the antigen-binding molecule or human FcRn, respectively.

The present invention provides an antigen-binding molecule of the present invention that comprises an antigen-binding domain and a human Fc region having an increased FcRn-binding activity in the neutral pH ranges. Preferably, its binding activity for a pre-existing ADA in the neutral pH ranges is not significantly increased. The FcRn-binding activity of such antigen-binding molecule in the neutral pH ranges is preferably stronger than KD 3.2 micromolar. More preferably, the FcRn-binding activity in the neutral pH range is stronger than 700 nanomolar, even more preferably stronger than 500 nanomolar and most preferably, stronger than 150 nanomolar. Preferably, the antigen-binding molecule has an increased human FcRn-binding activity in the neutral pH ranges and an antigen-binding activity that is lower in the acidic pH range than in the neutral pH range or that is lower at a low calcium concentration than at a high calcium concentration condition. Preferably, binding activity of such an antigen-binding molecule for a pre-existing ADA in the neutral pH ranges is not significantly increased. The present invention also provides an antigen-binding molecule of the present invention that comprises an antigen-binding domain and a human FcRn-binding domain, wherein its human FcRn-binding activity is increased in the neutral pH ranges, further wherein the human FcRn-binding activity in the neutral pH ranges is 28-fold stronger than that of an intact human IgG, more preferably, the human FcRn-binding activity in the neutral pH ranges is 38-fold stronger than that of an intact human IgG. Preferably, binding activity of such an antigen-binding molecule for a pre-existing ADA in the neutral pH ranges is not significantly increased. The antigen-binding molecule of the present invention with an increased FcRn-binding activity in the neutral pH ranges. Preferably a binding activity for a pre-existing ADA in the neutral pH ranges that is not significantly increased preferably, has human FcRn-binding activity at pH 7.0 and at 25 degrees C. which is 28-fold stronger, preferably 38-fold stronger, than intact human IgG than intact human IgG. Alternatively, the human FcRn-binding activity of the antigen-binding molecule with an increased FcRn binding activity at pH 7.0 and at 25 degrees C. is preferably stronger than KD 3.2 micromolar. More preferably, the FcRn-binding activity in at pH 7.0 and at 25 degrees Celsius is stronger than 700 nanomolar, more preferably stronger than 500 nanomolar and most preferably, stronger than 150 nanomolar.

The present invention provides an antigen-binding molecule of the present invention, comprising an antigen-binding domain and a human Fc region of the present invention, with an increased FcRn-binding activity in the acidic pH ranges and a binding activity for a pre-existing ADA in the neutral pH ranges that is not significantly increased. The present invention also provides an antigen-binding molecule of the present invention comprising an antigen-binding domain and a human FcRn-binding domain having an increased human FcRn-binding activity in the acidic pH range and a binding activity for a pre-existing ADA in the neutral pH ranges that is not significantly increased as compared to the binding activity for a pre-existing ADA of an intact IgG, wherein the human FcRn-binding activity in the acidic pH ranges is in the range of about 2-fold to about 100-fold stronger than the human FcRn-binding activity of an intact human IgG. Preferably, the human FcRn-binding activity of antigen-binding molecule of the present invention in the acidic pH ranges is at least 10-fold stronger than the FcRn-binding activity of an intact human IgG, more preferably, the human FcRn-binding activity in the acidic pH ranges is at least 20-fold stronger than that of an intact human IgG. The antigen-binding molecule of the present invention with an increased FcRn-binding activity in the acidic pH ranges whereby its binding activity for a pre-existing ADA in the neutral pH ranges is not significantly increased has human FcRn-binding activity at pH 6.0 and at 25 degrees C. which is 10-fold stronger, preferably 20-fold stronger, than intact human IgG.

The antigen-binding molecules of the present invention may have an increased FcRn-binding activity in the neutral pH ranges as well as an antigen-binding activity in the acidic pH range that is lower than the antigen-binding activity in the neutral pH range or an antigen-binding activity at a low calcium concentration that is lower than the antigen-binding activity at a high calcium concentration condition. Specific examples of such antigen-binding molecules include those that have a higher binding activity for human FcRn at pH 7.4 than an intact Ig, and whose antigen-binding activity is lower at pH 5.8 than at pH 7.4 which are presumed to be the in vivo pH of the early endosome and plasma, respectively. An antigen-binding molecule whose antigen-binding activity is lower at pH 5.8 than at pH 7.4 can also be referred to as an antigen-binding molecule whose antigen-binding activity is stronger at pH 7.4 than at pH 5.8. The value of KD (pH 5.8)/KD (pH 7.4), which is a ratio of dissociation constant (KD) against an antigen at pH 5.8 and pH 7.4, is 1.5, 2, 3, 4, 5, 10, 15, 20, 50, 70, 80, 100, 500, 1000 or 10,000 preferably 2 or greater, more preferably 10 or greater, and still more preferably 40 or greater. The upper limit of the KD (pH 5.8)/KD (pH 7.4) value is not particularly limited, and may be any value, for example, 400, 1,000, or 10,000, as long as production is possible using the technologies of those skilled in the art.

Also preferred are antigen-binding molecules of the present invention that have an increased FcRn-binding activity in the acidic pH ranges, as well as a lower antigen-binding activity in the acidic pH range than that in the neutral pH range or a lower antigen-binding activity at a low calcium concentration than that at a high calcium concentration. Preferably, binding activity of such an antigen-binding molecule for a pre-existing ADA in the neutral pH ranges is not significantly increased. Specific examples of such antigen-binding molecules include those that have a higher binding activity for human FcRn at pH 5.8 to pH 6.0 than an IgG, which is presumed to be the in vivo pH of the early endosome and whose antigen-binding activity is lower at pH 5.8 than at pH 7.4. An antigen-binding molecule whose antigen-binding activity is lower at pH 5.8 than at pH 7.4 can also be referred to as an antigen-binding molecule whose antigen-binding activity is weaker at pH 5.8 than at pH 7.4. Preferably, an antigen-binding molecule having an increased binding activity for FcRn in the acidic pH ranges has stronger FcRn-binding activity than intact human IgG in the neutral pH range.

The modified FcRn-binding domains of the present invention are applicable to any antigen-binding molecules, regardless of the type of target antigen.

An antigen-binding molecule of the present invention may have other properties. For example, it may be an agonistic or antagonistic antigen-binding molecule, provided that it has a) the requisite increased human FcRn-binding activity neutral pH ranges, or b) an increased human FcRn-binding activity for in the acidic ranges and its binding activity for a pre-existing ADA is not significantly increased. Preferably, the antigen-binding activity of such an antigen-binding molecule is lower in the acidic pH range than in the neutral pH range. Preferred antigen-binding molecules of the present invention include, for example, antagonistic antigen-binding molecules. Such an antagonistic antigen-binding molecule is typically an antigen-binding molecule that inhibits receptor-mediated intracellular signaling by blocking the binding between ligand (agonist) and receptor.

Meanwhile, an antigen-binding molecule of the present invention may recognize any antigen. Specific antigens recognized by an antigen-binding molecule of the present invention include, for example, the above-described receptor proteins (membrane-bound receptors and soluble receptors), membrane antigens such as cell-surface markers, and soluble antigens such as cytokines Such antigens include, for example, the antigens described below.

Antigen-binding molecules of the present invention comprising an antigen-binding domain can utilize a difference of pH as an environmental difference between plasma and endosome for differential binding affinity of an antigen binding molecule to an antigen at plasma and endosome (strong binding at plasma and weak binding at endosome). Since environmental difference between plasma and endosome is not limited to a difference of pH, pH dependent binding property on binding of an antigen-binding molecule to an antigen can be substituted by utilizing other factors whose concentration is different within the plasma and the endosome, such as for example the ionized calcium concentration. Such factor may also be used to generate an antibody that binds to the antigen within plasma but dissociates the antigen within endosome. Therefore, the present invention also includes an antigen-binding molecule comprising a human FcRn-binding domain, whose human FcRn-binding activity is increased in the neutral pH ranges and whose antigen-binding activity in the endosome is lower as compared to the plasma. Preferably, the binding activity of these antigen-binding molecules in the neutral pH ranges for a pre-existing ADA is not significantly increased. The human FcRn-binding activity of such an antigen-binding molecule is in the plasma stronger than that of intact human IgG, and further the antigen-binding domain of such an antigen-binding molecule has a lower affinity for the antigen inside the endosome than in the plasma. Preferably, the antigen-binding domain is an antigen-binding domain whose antigen-binding activity in the acidic pH range is lower than that in the neutral pH range (pH-dependent antigen-binding domain) or an antigen-binding domain whose antigen-binding activity is lower with a low calcium concentration than under a high calcium concentration condition (calcium-concentration-dependent antigen-binding domain). The present invention also includes an antigen-binding molecule with a human FcRn-binding domain, which has an increased human FcRn-binding activity in the acidic pH ranges, and said antigen-binding molecule further comprises an antigen-binding domain which has a lower affinity for the antigen inside the endosome than in the plasma, such that the human FcRn-binding activity of the antigen-binding molecule in the endosome is stronger than that of intact human IgG, and the antigen-binding activity of the antigen-binding molecule in the endosome is stronger than in the plasma. Preferably, the binding activity of these antigen-binding molecules in the neutral pH ranges for a pre-existing ADA is not significantly increased. Preferably, the antigen-binding domain is an antigen-binding domain whose antigen-binding activity in the acidic pH range is lower than that in the neutral pH range (pH-dependent antigen-binding domain) or an antigen-binding domain whose antigen-binding activity is lower with a low calcium concentration than under a high calcium concentration condition (calcium-concentration-dependent antigen-binding domain).

The antigen-binding molecules of the present invention facilitate antigen uptake into cells, in particular when the antigen-binding molecules of the present invention comprising an antigen-binding domain that is a pH-dependent antigen-binding domain or a calcium-concentration-dependent antigen-binding domain. The antigen-binding molecules are easily dissociated from the antigen in the endosome, and then released to the outside of the cell by binding to human FcRn. The antigen-binding molecules of the present invention are presumed to bind easily to an antigen in the plasma again. Thus, for example, when the antigen-binding molecule of the present invention is a neutralizing antigen-binding molecule, reduction of the plasma antigen concentration can be facilitated by administering the molecule.

Antigen-Binding Domain

Preferably, the antigen-binding domain of the antigen-binding molecule has a decreased affinity for the antigen at an acidic pH or at low calcium ion concentration. More preferably, the antigen-binding domain is a pH-dependent antigen-binding domain or a ionized calcium concentration dependent antigen-binding domain described herein.

A) pH-Dependent Antigen-Binding Domain,

Furthermore, the antigen-binding molecule of the present invention comprises preferably a pH-dependent antigen-binding domain whose antigen-binding activity in the acidic pH range is lower than that in the neutral pH range. Said antigen-binding molecule has preferably a lower antigen-binding activity in the acidic pH range than in the neutral pH range. The binding activity ratio is not limited, provided that the antigen-binding activity is lower in the acidic pH range than in the neutral pH range. In a preferred embodiment, the antigen-binding molecules of the present invention include antigen-binding molecules whose antigen-binding activity at pH 7.4 is twice or higher than that at pH 5.8, preferably the antigen-binding activity at pH 7.4 is ten times or higher than that at pH 5.8. In a still more preferred embodiment, the antigen-binding molecules of the present invention include antigen-binding molecules whose antigen-binding activity at pH 7.4 is 40 times or higher than that at pH 5.8.

Specific examples of antigen-binding molecules of the present invention include the embodiments described in WO 2009/125825. In a preferred embodiment, the antigen-binding molecule of the present invention comprising a pH-dependent antigen-binding domain has an antigen-binding activity at pH 5.8 that is lower than that at pH 7.4, wherein the value of KD (pH5.8)/KD (pH7.4), which is a ratio of KD for the antigen at pH 5.8 and that at pH 7.4, is preferably 2 or greater, more preferably 10 or greater, and still more preferably 40 or greater. The upper limit of the KD (pH5.8)/KD (pH7.4) value is not particularly limited, and may be any value, for example, 400, 1,000, or 10,000, as long as production is possible using the technologies of those skilled in the art.

In another preferred embodiment, the antigen-binding molecule of the present invention whose antigen-binding activity at pH 5.8 is lower than that at pH 7.4, has a value of KD (pH5.8)/KD (pH7.4), which is a ratio of the KD for the antigen at pH 5.8 and the KD for the antigen at pH 7.4, that is 2 or greater, more preferably 5 or greater, even more preferably 10 or greater, and still more preferably 30 or greater. The upper limit of the KD (pH5.8)/KD (pH7.4) value is not particularly limited, and may be any value, for example, 50, 100, or 200, provided that the production is possible using the technologies of those skilled in the art.

Conditions other than the pH at which the antigen-binding activity, binding activity for a pre-existing ADA and human FcRn-binding activity are measured can be appropriately selected by those skilled in the art, and such conditions are not particularly limited; however, the measurements can be carried out, for example, under conditions of MES buffer and at 37 degrees C., as described in the Examples. Furthermore, the antigen-binding activity of an antigen-binding molecule can be determined by methods known to those skilled in the art, for example, using Biacore T100 (GE Healthcare) or the like, as described in the Examples.

Methods for reducing (impairing) the antigen-binding activity of an antigen-binding molecule in the acidic pH range to less than that the antigen-binding activity in the neutral pH range (methods for conferring the pH-dependent binding ability) are not particularly limited and suitable methods are known to the skilled in the art. WO 2009/

125825, for example, describes methods for reducing (impairing) the antigen-binding activity in the acidic pH range to less than that in the neutral pH range by substituting histidine for an amino acid in the antigen-binding domain or inserting histidine into the antigen-binding domain. It is further known that an antibody can be conferred with a pH-dependent antigen-binding activity by substituting histidine for an amino acid in the antibody (FEBS Letter (1992) 309(1): 85-88). Other suitable methods include methods for substituting non-natural amino acids for amino acids in the antigen-binding domain or inserting non-natural amino acids into the antigen-binding domain. It is known that pKa can be artificially adjusted by using non-natural amino acids (Angew. Chem. Int. Ed. 2005, 44, 34; Chem Soc Rev. 2004 Sep. 10, 33 (7): 422-30; Amino Acids. (1999) 16(3-4): 345-79). Any non-natural amino acid may be used in context of the present invention. In fact, it is possible to use non-natural amino acids known to those skilled in the art.

In a preferred embodiment, the antigen-binding molecule of the present invention comprising an antigen-binding domain with an antigen-binding activity that is lower in the acidic pH range than that in the neutral pH range, includes antigen-binding molecules in which at least one amino acid in the antigen-binding molecule is replaced with histidine or a non-natural amino acid, and/or in which at least one histidine or a non-natural amino acid has been inserted. The site into which the histidine or non-natural amino acid mutation is introduced is not particularly limited and may be any site deemed suitable by those of skilled in the art, provided that the resultant antigen-binding activity in the acidic pH range is weaker than that in the neutral pH range (the KD (in the acidic pH range)/KD (in the neutral pH range) value is greater or the kd (in the acidic pH range)/kd (in the neutral pH range) value is greater) as compared to before substitution. Examples include variable regions and CDRs of an antibody in the case the antigen-binding molecule is an antibody. The number of amino acids to be replaced with histidine or non-natural amino acid and the number of amino acids to be inserted can be appropriately determined by those skilled in the art. One amino acid may be replaced with histidine or non-natural amino acid, or one amino acid may be inserted, or two or more amino acids may be replaced with histidine or non-natural amino acids, or two or more amino acids may be inserted. Moreover, apart from the substitutions of histidine or non-natural amino acid or insertion of histidine or of non-natural amino acid, deletion, addition, insertion, and/or substitution and such of other amino acids may also be simultaneously carried out. Substitutions of histidine or non-natural amino acid or insertion of histidine or of non-natural amino acid may be carried out at random using a method such as histidine scanning, which uses histidine instead of alanine in alanine scanning which is known to those skilled in the art. Antigen-binding molecules whose KD (pH5.8)/KD (pH7.4) or kd (pH5.8)/kd (pH7.4) is increased as compared to before mutation can be selected from antigen-binding molecules into which histidine or non-natural amino acid mutation has been introduced at random.

Preferably, the binding activity of the antigen-binding domain at neutral pH (i.e. pH7.4) is maintained. When the antigen-binding activity of an antigen-binding molecule before histidine or non-natural amino acid mutation is set as 100%, the antigen-binding activity of the antigen-binding molecule at pH7.4 after histidine or non-natural amino acid mutation is at least 10% or more, preferably 50% or more, more preferably 80% or more, and still more preferably 90% or more. The antigen-binding activity at pH 7.4 after histidine or non-natural amino acid mutation may be stronger than the antigen-binding activity at pH 7.4 before histidine or non-natural amino acid mutation. When the antigen-binding activity of the antigen-binding molecule is decreased due to substitution or insertion of histidine or non-natural amino acid, the antigen-binding activity may be adjusted by introducing substitution, deletion, addition, and/or insertion and such of one or more amino acids into the antigen-binding molecule so that the antigen-binding activity becomes equivalent to that before histidine substitution or insertion.

In the context of present invention, when the antigen-binding molecule is an antibody, possible sites of histidine or non-natural amino acid substitution include, for example, CDR sequences and sequences responsible for the CDR structure of an antibody, including, for example, the sites described in WO 2009/125825.

Furthermore, the present invention provides antigen-binding molecules having substitution of histidine or a non-natural amino acid for at least one amino acid at one of the following sites
Heavy chain: H27, H31, H32, H33, H35, H50, H58, H59, H61, H62, H63, H64, H65, H99, H100b, and H102
Light chain: L24, L27, L28, L32, L53, L54, L56, L90, L92, and L94

H32, H61, L53, L90, and L94 of these alteration sites, are presumed to be highly general alteration sites. The amino acid positions are shown according to Kabat numbering (Kabat et al., Sequences of Immunological Interest. 5th Ed. Public Health Service, National Institutes of Health, Bethesda, Md. (1991)). The Kabat numbering system is generally used when referring to a residue in the variable domain (approximately residues 1-107 of the light chain and residues 1-113 of the heavy chain). Specifically preferred combinations of sites for histidine or non-natural amino acid substitutions include, for example, the combination of H27, H31, and H35; the combination of H27, H31, H32, H35, H58, H62, and H102; the combination of L32 and L53; and the combination of L28, L32, and L53. Furthermore, preferred combinations of substitutions sites in the heavy and light chains include, for example, the combination of H27, H31, L32, and L53.

When the antigen is an IL-6 receptor (for example, human IL-6 receptor), preferred alteration sites include but are not particularly limited to the following:
Heavy chain: H27, H31, H32, H35, H50, H58, H61, H62, H63, H64, H65, H100b, and H102
Light chain: L24, L27, L28, L32, L53, L56, L90, L92, and L94

Specifically preferred combinations of sites for histidine or non-natural amino acid substitution include, for example, the combination of H27, H31, and H35; the combination of H27, H31, H32, H35, H58, H62, and H102; the combination of L32 and L53; and the combination of L28, L32, and L53. Furthermore, preferred combinations of substitution sites in the heavy and light chains include, for example, the combination of H27, H31, L32, and L53.

Histidine or non-natural amino acids can be substituted at one or more of the positions mentioned above.

Alternatively, the antigen-binding molecule of the present invention may comprise an antibody constant region that was altered so that the antigen-binding activity at pH 5.8 is lower than that at pH 7.4. Methods for altering antibody constant regions contained in the antigen-binding molecules are known and indeed conventional to the skilled in the art. Specific examples of antibody constant regions after alteration include the constant regions described in the Examples in WO 2009/125825 (SEQ ID NOs: 11, 12, 13, and 14).

Meanwhile, methods for altering an antibody constant region include, for example, methods for assessing various constant region isotypes (IgG1, IgG2, IgG3, and IgG4) and selecting isotypes that reduce the antigen-binding activity in the acidic pH range (increase the dissociation rate in the acidic pH range) are known. Such methods also include methods for reducing the antigen-binding activity in the acidic pH range (increasing the dissociation rate in the acidic pH range) by introducing amino acid substitutions into the amino acid sequences of wild-type isotypes (amino acid sequences of wild type IgG1, IgG2, IgG3, or IgG4). The sequence of hinge region in the antibody constant region is considerably different among isotypes (IgG1, IgG2, IgG3, and IgG4), and the difference in the hinge region amino acid sequence has a great impact on the antigen-binding activity. Thus, it is possible to select an appropriate isotype to reduce the antigen-binding activity in the acidic pH range (increase the dissociation rate in the acidic pH range) depending on the type of antigen or epitope. Furthermore, since the difference in the hinge region amino acid sequence has a great impact on the antigen-binding activity, preferred amino acid substitution sites in the amino acid sequences of wild type isotypes are presumed to be within the hinge region.

The above-described methods can be used to produce antigen-binding molecules whose antigen-binding activity in the acidic pH range is reduced (weakened) to less than that in the neutral pH range (antigen-binding molecules that bind in a pH-dependent manner) by amino acid substitution or insertion from antigen-binding molecules that do not have such property. Other methods include methods for directly obtaining antigen-binding molecules having the above-described property. For example, antibodies having a desired property of interest may be directly selected by screening using the pH-dependent antigen binding as an indicator from antibodies obtained by immunizing animals (mice, rats, hamsters, rabbits, human immunoglobulin-transgenic mice, human immunoglobulin-transgenic rats, human immunoglobulin-transgenic rabbits, llamas, camels, etc.) with an antigen. Antibodies can be generated by hybridoma technology or B-cell cloning technology (Bernasconi et al, Science (2002) 298, 2199-2202; WO2008/081008) which are methods known to those skilled in the art, but not limited thereto. Alternatively, antibodies that have the property of interest may be directly selected by screening using the pH-dependent antigen binding as an indicator from a library of presenting antigen-binding domain in vitro. Such library includes human naive library, immunized library from non-human animal and human, semi-synthetic library and synthetic library which are libraries known to those skilled in the art (Methods Mol Biol. 2002; 178: 87-100; J Immunol Methods. 2004 June; 289(1-2): 65-80; and Expert Opin Biol Ther. 2007 May; 7(5): 763-79), but not limited thereto. However, the methods are not particularly limited to these examples.

B) Ionized Calcium-Dependent Antigen-Binding Domain

In another preferred embodiment, the antigen-binding molecule of the present invention comprises a calcium-ion dependent antigen-binding domain. The antigen-binding activity of such an antigen-binding molecule depends of the calcium concentration, whereby the antigen-binding activity at a low calcium concentration is lower than that at a high calcium concentration.

Preferably, the antigen-binding activity includes the antigen-binding activity at an ionized calcium concentration of 0.5 to 10 micromolar. More preferable ionized calcium concentrations include the ionized calcium concentration in the early endosome in vivo. Specifically, the antigen-binding activity includes the activity at 1 to 5 micromolar. Meanwhile, the antigen-binding activity of an antigen-binding molecule at a high calcium concentration is not particularly limited, provided that it is the antigen-binding activity at an ionized calcium concentration of 100 micromolar to 10 mM. Preferably, the antigen-binding activity includes the antigen-binding activity at an ionized calcium concentration of 200 micromolar to 5 mM. Preferably, a low calcium concentration is an ionized calcium concentration of 0.1 to 30 micromolar, and a high calcium concentration is an ionized calcium concentration of 100 micromolar to 10 mM.

Preferably, the low calcium concentration is an intraendosomal concentration of ionized calcium, and the high calcium concentration is a plasma concentration of ionized calcium. More specifically, the antigen-binding molecules comprising said calcium-dependent antigen-binding domain include antigen-binding molecules whose antigen-binding activity at the ionized calcium concentration in the early endosome in vivo (a low calcium concentration of such as 1 to 5 micromolar) is lower than that at the ionized calcium concentration in plasma in vivo (a high calcium concentration of such as 0.5 to 2.5 mM).

With respect to the antigen-binding activity of an antigen-binding molecule whose antigen-binding activity at a low calcium concentration is lower than that at a high calcium concentration, there is no limitation on this difference in the antigen-binding activity, provided that the antigen-binding activity at a low calcium concentration is lower than that at a high calcium concentration. It is even acceptable that the antigen-binding activity of an antigen-binding molecule is only slightly lower under a low calcium concentration condition.

In a preferred embodiment, for an antigen-binding molecule of the present invention whose antigen-binding activity at a low calcium concentration (low Ca) is lower than that at a high calcium concentration (high Cal), the value of KD (low Ca)/KD (high Ca), which is the KD ratio between low and high calcium concentration, is 2 or more, preferably the value of KD (low Ca)/KD (high Ca) is 10 or more, and more preferably the value of KD (low Ca)/KD (high Ca) is 40 or more. The upper limit of the KD (low Ca)/KD (high Ca) value is not particularly limited, and may be any value such as 400, 1,000, and 10,000 provided that it can be produced by techniques known to those skilled in the art.

In another preferred embodiment, for an antigen-binding molecule comprising a calcium-dependent antigen-binding domain whose antigen-binding activity at a low calcium concentration is lower than that at a high calcium concentration, the value of kd (low Ca)/kd (high Ca), which is the ratio of kd for an antigen between a low calcium concentration condition and pH 7.4, is 2 or more, preferably the value of kd (low Ca)/kd (high Ca) is 5 or more, more preferably the value of kd (low Ca)/kd (high Ca) is 10 or more, and still more preferably the value of kd (low Ca)/kd (high Ca) is 30 or more. The upper limit of kd (low Ca)/kd (high Ca) value is not particularly limited, and may be any value such as 50, 100, and 200 as long as it can be produced by techniques known to those skilled in the art.

The antigen-binding activity of an antigen-binding molecule can be determined by methods known to those skilled in the art. Appropriate conditions besides ionized calcium concentration can be selected by those skilled in the art. The antigen-binding activity of an antigen-binding molecule can be assessed by using KD (dissociation constant), apparent KD (apparent dissociation constant), dissociation rate kd (dissociation rate), apparent kd (apparent dissociation: apparent dissociation rate), or the like. They can be determined by methods known to those skilled in the art, for example, using Biacore (GE Healthcare), Scatchard plot, FACS, or such.

Antigen-binding molecules to be screened by the screening method of the present invention may be any antigen-binding molecules. It is possible to screen, for example, antigen-binding molecules having a natural sequence or antigen-binding molecules having an amino acid sequence with a substitution. Antigen-binding molecules comprising a calcium-ion dependent antigen-binding domain to be screened by the screening method of the present invention may be prepared by any methods. It is possible to use, for example, preexisting antibodies, preexisting libraries (phage libraries, etc.), and antibodies and libraries prepared from B cells of immunized animals or hybridomas prepared by immunizing animals, antibodies or libraries obtained by introducing amino acids capable of chelating calcium (for example, aspartic acid or glutamic acid) or non-natural amino acid mutations into such antibodies or libraries (libraries with high content of non-natural amino acids or amino acids capable of chelating calcium (for example, aspartic acid or glutamic acid), libraries introduced with non-natural amino acid mutations or mutations with amino acids capable of chelating calcium (for example, aspartic acid or glutamic acid) at specific sites, or such), or the like.

An antigen-binding molecule whose antigen-binding activity under a low calcium concentration condition is lower than that under a high calcium concentration condition can be readily screened, identified and isolated using methods conventional in the art (see e.g. PCT application no. PCT/JP2011/077619. Examples of such screening methods include the step of assaying for an antigen-binding molecule having at least one function selected from:
(i) the function to promote uptake of an antigen into cells;
(ii) the function to bind to an antigen two or more times;
(iii) the function to promote reduction of the plasma antigen concentration; and
(iv) the function of superior plasma retention.

Specifically, the present invention provides methods of screening for an antigen-binding molecule comprising a calcium-ion dependent antigen-binding domain, which comprises the steps of:
(a) determining the antigen-binding activity of an antigen-binding molecule under a low calcium concentration condition;
(b) determining the antigen-binding activity of the antigen-binding molecule under a high calcium concentration condition; and
(c) selecting an antigen-binding molecule whose antigen-binding activity under the low calcium concentration condition is lower than that under the high calcium concentration condition.

A method for producing an antigen-binding molecule with a calcium-ion dependent antigen-binding domain is for example a method comprising the steps of:
(a) determining the antigen-binding activity of an antigen-binding molecule under a low calcium concentration condition;
(b) determining the antigen-binding activity of the antigen-binding molecule under a high calcium concentration condition; and
(c) selecting an antigen-binding molecule whose antigen-binding activity under the low calcium concentration condition is lower than that under the high calcium concentration condition.

Another method of producing an antigen-binding molecule with a calcium-ion dependent antigen-binding domain is the method comprising the steps of:
(a) contacting an antigen with an antigen-binding molecule or a library of antigen-binding molecules under a high calcium concentration condition;
(b) obtaining an antigen-binding molecule that bound to the antigen in step (a);
(c) allowing the antigen-binding molecule obtained in step (b) to stand under a low calcium concentration condition;
(d) obtaining an antigen-binding molecule whose antigen-binding activity in step (c) is lower than the activity for the selection in step (b);
(e) obtaining a gene encoding the antigen-binding molecule obtained in step (d); and
(f) producing the antigen-binding molecule using the gene obtained in step (e).

Steps (a) to (e) may be repeated two or more times. Thus, the present invention provides the methods further comprising the step of repeating steps (a) to (e) two or more times in the above-described methods. The number of repetitions of steps (a) to (e) is not particularly limited; however, the number is generally ten or less.

Antigen-binding molecules that are used in the production methods of the present invention may be prepared by any conventional method. For example, it is possible to use pre-existing antibodies, pre-existing libraries (phage libraries and the like), antibodies and libraries that are prepared from hybridomas obtained by immunizing animals or from B cells of immunized animals, antibodies and libraries prepared by introducing histidine or non-natural amino acid mutations into the above-described antibodies and libraries (libraries with high content of histidine or non-natural amino acid, libraries introduced with histidine or non-natural amino acid at specific sites, and the like), and such.

Further methods to screen such calcium-ion dependent antigen-binding molecules or calcium-ion dependent antigen-binding domains are described in the PCT application no. PCT/JP2011/077619.

Antigens

Antigens that are recognized by antigen-binding molecules of the present invention, such as the antibodies of the present invention, are not particularly limited. Such antigen-binding molecules of the present invention may recognize any antigen. Specific examples of an antigen that is recognized by the antigen-binding molecule of the present invention include but are not limited to: 17-IA, 4-1 BB, 4Dc, 6-keto-PGF1a, 8-iso-PGF2a, 8-oxo-dG, A1 Adenosine Receptor, A33, ACE, ACE-2, Activin, Activin A, Activin AB, Activin B, Activin C, Activin RIA, Activin RIA ALK-2, Activin RIB ALK-4, Activin RIIA, Activin RIIB, ADAM, ADAM10, ADAM12, ADAM15, ADAM17/TACE, ADAMS, ADAM9, ADAMTS, ADAMTS4, ADAMTS5, Addressins, adiponectin, ADP ribosyl cyclase-1, aFGF, AGE, ALCAM, ALK, ALK-1, ALK-7, allergen, alpha1-antichemotrypsin, alpha1-antitrypsin, alpha-synuclein, alpha-V/beta-1 antagonist, aminin, amylin, amyloid beta, amyloid immunoglobulin heavy chain variable region. amyloid immunoglobulin light chain variable region, Androgen, ANG, angiotensinogen, Angiopoietin ligand-2, anti-Id, anti-thrombin III, Anthrax, APAF-1, APE, APJ, apo A1, apo serum amyloid A, Apo-SAA, APP, APRIL, AR, ARC, ART, Artemin, ASPARTIC, Atrial natriuretic factor, Atrial natriuretic peptide, atrial natriuretic peptides A, atrial natriuretic peptides B, atrial natriuretic peptides C, av/b3 integrin, Axl, B7-1, B7-2, B7-H, BACE, BACE-1, *Bacillus anthracis* protective antigen, Bad, BAFF, BAFF-R, Bag-1, BAK, Bax, BCA-1, BCAM, Bcl, BCMA, BDNF, b-ECGF, beta-2-microglobulin, betalactamase, bFGF, BID, Bik, BIM, BLC, BL-CAM, BLK, B-lymphocyte Stimulator (BIyS), BMP, BMP-2 (BMP-2a), BMP-3 (Osteogenin), BMP-4 (BMP-2b), BMP-5, BMP-6 (Vgr-1), BMP-7 (OP-1), BMP-8 (BMP-8a), BMPR, BMPR-IA (ALK-3), BMPR-IB (ALK-6), BMPR-II (BRK-3), BMPs, BOK, Bombesin, Bone-derived neurotrophic factor, bovine growth hormone, BPDE, BPDE-DNA, BRK-2, BTC, B-lymphocyte cell adhesion molecule, C10, C1-inhibitor, C1q, C3, C3a, C4, C5, C5a (complement 5a), CA125, CAD-8, Cadherin-3, Calcitonin, cAMP, Carbonic anhydrase-IX, carcinoembryonic antigen (CEA), carcinoma-associated antigen, Cardiotrophin-1, Cathepsin A, Cathepsin B, Cathepsin C/DPPI, Cathepsin D, Cathepsin E, Cathepsin H, Cathepsin L, Cathepsin O, Cathepsin S, Cathepsin V, Cathepsin X/Z/P, CBL, CCI, CCK2, CCL, CCL1/I-309, CCL11/Eotaxin, CCL12/MCP-5, CCL13/MCP-4, CCL14/HCC-1, CCL15/HCC-2, CCL16/HCC-4, CCL17/TARC, CCL18/PARC, CCL19/ELC, CCL2/MCP-1, CCL20/MIP-3-alpha, CCL21/SLC, CCL22/MDC, CCL23/MPIF-1, CCL24/Eotaxin-2, CCL25/TECK, CCL26/Eotaxin-3, CCL27/CTACK, CCL28/MEC, CCL3/M1P-1-alpha, CCL3L1/LD-78-beta, CCL4/MIP-1-beta, CCL5/RANTES, CCL6/C10, CCL7/MCP-3, CCL8/MCP-2, CCL9/10/MTP-1-gamma, CCR, CCR1, CCR10, CCR2, CCR3, CCR4, CCR5, CCR6, CCR7, CCR8, CCR9, CD1, CD10, CD105, CD11a, CD11b, CD11c, CD123, CD13, CD137, CD138, CD14, CD140a, CD146, CD147, CD148, CD15, CD152, CD16, CD164, CD18, CD19, CD2, CD20, CD21, CD22, CD23, CD25, CD26, CD27L, CD28, CD29, CD3, CD30, CD30L, CD32, CD33 (p67 proteins), CD34, CD37, CD38, CD3E, CD4, CD40, CD40L, CD44, CD45, CD46, CD49a, CD49b, CD5, CD51, CD52, CD54, CD55, CD56, CD6, CD61, CD64, CD66e, CD7, CD70, CD74, CD8, CD80 (B7-1), CD89, CD95, CD105, CD158a, CEA, CEACAM5, CFTR, cGMP, CGRP receptor, CINC, CKb8-1, Claudin 18, CLC, *Clostridium botulinum* toxin, *Clostridium difficile* toxin, *Clostridium perfringens* toxin, c-Met, CMV, CMV UL, CNTF, CNTN-1, complement factor 3 (C3), complement factor D, corticosteroid-binding globulin, Colony stimulating factor-1 receptor, COX, C-Ret, CRG-2, CRTH2, CT-1, CTACK, CTGF, CTLA-4, CX3CL1/Fractalkine, CX3CR1, CXCL, CXCL1/Gro-alpha, CXCL10, CXCL11/1-TAC, CXCL12/SDF-1-alpha/beta, CXCL13/BCA-1, CXCL14/BRAK, CXCL15/Lungkine CXCL16, CXCL16, CXCL2/Gro-beta CXCL3/Gro-gamma, CXCL3, CXCL4/PF4, CXCL5/ENA-78, CXCL6/GCP-2, CXCL7/NAP-2, CXCL8/IL-8, CXCL9/Mig, CXCL10/IP-10, CXCR, CXCR1, CXCR2, CXCR3, CXCR4, CXCR5, CXCR6, cystatin C, cytokeratin tumor-associated antigen, DAN, DCC, DcR3, DC-SIGN, Decay accelerating factor, Delta-like protein ligand 4, des(1-3)-IGF-1 (brain IGF-1), Dhh, DHICA oxidase, Dickkopf-1, digoxin, Dipeptidyl peptidase IV, DK1, DNAM-1, Dnase, Dpp, DPPIV/CD26, Dtk, ECAD, EDA, EDA-A1, EDA-A2, EDAR, EGF, EGFR (ErbB-1), EGF like domain containing protein 7, Elastase, elastin, EMA, EMMPRIN, ENA, ENA-78, Endosialin, endothelin receptor, endotoxin, Enkephalinase, eNOS, Eot, Eotaxin, Eotaxin-2, eotaxini, EpCAM, Ephrin B2/EphB4, Epha2 tyrosine kinase receptor, epidermal growth factor receptor (EGFR), ErbB2 receptor, ErbB3 tyrosine kinase receptor, ERCC, erythropoietin (EPO), Erythropoietin receptor, E-selectin, ET-1, Exodus-2, F protein of RSV, F10, F11, F12, F13, F5, F9, Factor Ia, Factor IX, Factor Xa, Factor VII, factor VIII, Factor VIIIc, Fas, FcalphaR, FcepsilonRI, FcgammaIIb, FcgammaRI, FcgammaRIIa, FcgammaRIIIa, FcgammaRIIIb, FcRn, FEN-1, Ferritin, FGF, FGF-19, FGF-2, FGF-2 receptor, FGF-3, FGF-8, FGF-acidic, FGF-basic, FGFR, FGFR-3, Fibrin, fibroblast activation protein (FAP), fibroblast growth factor, fibroblast growth factor-10, fibronectin, FL, FLIP, Flt-3, FLT3 ligand, Folate receptor, follicle stimulating hormone (FSH), Fractalkine (CX3C), free heavy chain, free light chain, FZD1, FZD10, FZD2, FZD3, FZD4, FZD5, FZD6, FZD7, FZD8, FZD9, G250, Gas 6, GCP-2, GCSF, G-CSF, G-CSF receptor, GD2, GD3, GDF, GDF-1, GDF-15 (MIC-1), GDF-3 (Vgr-2), GDF-5 (BMP-14/CDMP-1), GDF-6 (BMP-13/CDMP-2), GDF-7 (BMP-12/CDMP-3), GDF-8 (Myostatin), GDF-9, GDNF, Gelsolin, GFAP, GF-CSF, GFR-alpha1, GFR-alpha2, GFR-alpha3, GF-beta1, gH envelope glycoprotein, GITR, Glucagon, Glucagon receptor, Glucagon-like peptide 1 receptor, Glut 4, Glutamate carboxypeptidase II, glycoprotein hormone receptors, glycoprotein IIb/IIIa (GP IIb/IIIa), Glypican-3, GM-CSF, GM-CSF receptor, gp130, gp140, gp72, granulocyte-CSF (G-CSF), GRO/MGSA, Growth hormone releasing factor, GRO-beta, GRO-gamma, *H. pylori*, Hapten (NP-cap or NIP-cap), HB-EGF, HCC, HCC 1, HCMV gB envelope glycoprotein, HCMV UL, Hemopoietic growth factor (HGF), Hep B gp120, heparanase, heparin cofactor II, hepatic growth factor, *Bacillus anthracis* protective antigen, Hepatitis C virus E2 glycoprotein, Hepatitis E, Hepcidin, Her1, Her2/neu (ErbB-2), Her3 (ErbB-3), Her4 (ErbB-4), herpes simplex virus (HSV) gB glycoprotein, HGF, HGFA, High molecular weight melanoma-associated antigen (HMW-MAA), HIV envelope proteins such as GP120, HIV MIB gp120 V3 loop, HLA, HLA-DR, HM1.24, HMFG PEM, HMGB-1, HRG, Hrk, HSP47, Hsp90, HSV gD glycoprotein, human cardiac myosin, human cytomegalovirus (HCMV), human growth hormone (hGH), human serum albumin, human tissue-type plasminogen activator (t-PA), Huntingtin, HVEM, IAP, ICAM, ICAM-1, ICAM-3, ICE, ICOS, IFN-alpha, IFN-beta, IFN-gamma, IgA, IgA receptor, IgE, IGF, IGF binding proteins, IGF-1, IGF-1R, IGF-2, IGFBP, IGFR, IL, IL-1, IL-10, IL-10 receptors, IL-11, IL-11 receptors, IL-12, IL-12 receptors, IL-13, IL-13 receptors, IL-15, IL-15 receptors, IL-16, IL-16 receptors, IL-17, IL-17 receptors, IL-18 (IGIF), IL-18 receptors, IL-1alpha, IL-1beta, IL-1 receptors, IL-2, IL-2 receptors, IL-20, IL-20 receptors, IL-21, IL-21 receptors, IL-23, IL-23 receptors, IL-2 receptors, IL-3, IL-3 receptors, IL-31, IL-31 receptors, IL-3 receptors, IL-4, IL-4 receptors IL-5, IL-5 receptors, IL-6, IL-6 receptors, IL-7, IL-7 receptors, IL-8, IL-8 receptors, IL-9, IL-9 receptors, immunoglobulin immune complex, immunoglobulins, INF-alpha, INF-alpha receptors, INF-beta, INF-beta receptors, INF-gamma, INF-gamma receptors, IFN type-I, IFN type-I receptor, influenza, inhibin, Inhibin alpha, Inhibin beta, iNOS, insulin, Insulin A-chain, Insulin B-chain, Insulin-like growth factor 1, insulin-like growth factor 2, insulin-like growth factor binding proteins, integrin, integrin alpha2, integrin alpha3, integrin alpha4, integrin alpha4/beta1, integrin alpha-V/beta-3, integrin alpha-V/beta-6, integrin alpha4/beta7, integrin alpha5/beta1, integrin alpha5/beta3, integrin alpha5/beta6, integrin alpha-delta (alphaV), integrin alpha-theta, integrin beta1, integrin beta2, integrin beta3 (GPIIb-IIIa), IP-10, I-TAC, JE, kalliklein, Kallikrein 11, Kallikrein 12, Kallikrein 14, Kallikrein 15, Kallikrein 2, Kallikrein 5, Kallikrein 6, Kallikrein L1, Kallikrein L2, Kallikrein L3, Kallikrein L4, kallistatin, KC, KDR, Keratinocyte Growth Factor (KGF), Keratinocyte Growth Factor-2 (KGF-2), KGF, killer immunoglobulin-like receptor, kit ligand (KL), Kit tyrosine kinase, laminin 5, LAMP, LAPP (Amylin, islet-amyloid polypeptide), LAP (TGF-1), latency associated peptide, Latent TGF-1, Latent TGF-1 bp1, LBP, LDGF, LDL, LDL receptor, LECT2, Lefty, Leptin, leutinizing hormone (LH), Lewis-Y antigen, Lewis-Y related antigen, LFA-1, LFA-3, LFA-3 receptors, Lfo, LIF, LIGHT, lipoproteins, LIX, LKN, Lptn, L-Selectin, LT-a, LT-b, LTB4, LTBP-1, Lung surfactant, Luteinizing hormone, Lymphotactin, Lymphotoxin Beta Receptor, Lysosphingolipid receptor, Mac-1, macrophage-CSF (M-CSF), MAdCAM, MAG, MAP2, MARC, maspin, MCAM, MCK-2, MCP, MCP-1, MCP-2, MCP-3, MCP-4, MCP-I (MCAF), M-CSF, MDC, MDC (67 a.a.), MDC (69 a.a.), megsin, Mer, MET tyrosine kinase receptor family, METALLOPROTEASES, Membrane glycoprotein OX2, Mesothelin, MGDF receptor, MGMT, MHC(HLA-DR), microbial protein, MIF, MIG, MIP, MIP-1 alpha, MIP-1 beta, MIP-3 alpha, MIP-3 beta, MIP-4, MK, MMAC1, MMP, MMP-1, MMP-10, MMP-11, MMP-12, MMP-13, MMP-14, MMP-15, MMP-2, MMP-24, MMP-3, MMP-7, MMP-8, MMP-9, monocyte attractant protein, monocyte colony inhibitory factor, mouse gonadotropin-associated peptide, MPIF, Mpo, MSK, MSP, MUC-16, MUC18, mucin (Mud), Muellerian-inhibiting substance, Mug, MuSK, Myelin associated glycoprotein, myeloid progenitor inhibitor factor-1 (MPIF-I), NAIP, Nanobody, NAP, NAP-2, NCA 90, NCAD, N-Cadherin, NCAM, Neprilysin, Neural cell adhesion molecule, neroserpin, Neuronal growth factor (NGF), Neurotrophin-3, Neurotrophin-4, Neurotrophin-6, Neuropilin 1, Neurturin, NGF-beta, NGFR, NKG20, N-methionyl human growth hormone, nNOS, NO, Nogo-A, Nogo receptor, non-structural protein type 3 (NS3) from the hepatitis C virus, NOS, Npn, NRG-3, NT, NT-3, NT-4, NTN, OB, OGG1, Oncostatin M, OP-2, OPG, OPN, OSM, OSM receptors, osteoinductive factors, osteopontin, OX40L, OX40R, oxidized LDL, p150, p95, PADPr, parathyroid hormone, PARC, PARP, PBR, PBSF, PCAD, P-Cadherin, PCNA, PCSK9, PDGF, PDGF receptor, PDGF-AA, PDGF-AB, PDGF-BB, PDGF-D, PDK-1, PECAM, PEDF, PEM, PF-4, PGE, PGF, PGI2, PGD2, PIGF, PIN, PLA2, Placenta growth factor, placental alkaline phosphatase (PLAP), placental lactogen, plasminogen activator inhibitor-1, platelet-growth factor, plgR, PLP, poly glycol chains of different size (e.g. PEG-20, PEG-30, PEG40), PP14, prekallikrein, prion protein, pro-calcitonin, Programmed cell death protein 1, proinsulin, prolactin, Proprotein convertase PC9, prorelaxin, prostate specific membrane antigen (PSMA), Protein A, Protein C, Protein D, Protein S, Protein Z, PS, PSA, PSCA, PsmAr, PTEN, PTHrp, Ptk, PTN, P-selectin glycoprotein ligand-1, R51, RAGE, RANK, RANKL, RANTES, relaxin, Relaxin A-chain, Relaxin B-chain, renin, respiratory syncytial virus (RSV) F, Ret, reticulon 4, Rheumatoid factors, RLI P76, RPA2, RPK-1, RSK, RSV Fgp, S100, RON-8, SCF/KL, SCGF, Sclerostin, SDF-1, SDF1 alpha, SDF1 beta, SERINE, Serum Amyloid P, Serum albumin, sFRP-3, Shh, Shiga like toxin II, SIGIRR, SK-1, SLAM, SLPI, SMAC, SMDF, SMOH, SOD, SPARC, sphingosine 1-phosphate receptor 1, Staphylococcal lipoteichoic acid, Stat, STEAP, STEAP-II, stem cell factor (SCF), streptokinase, superoxide dismutase, syndecan-1, TACE, TACI, TAG-72 (tumor-associated glycoprotein-72), TARC, TB, TCA-3, T-cell receptor alpha/beta, TdT, TECK, TEM1, TEM5, TEM7, TEM8, Tenascin, TERT, testicular PLAP-like alkaline phosphatase, TfR, TGF, TGF-alpha, TGF-beta, TGF-beta Pan Specific, TGF-beta RII, TGF-beta RIIb, TGF-beta RIII, TGF-beta R1 (ALK-5), TGF-beta1, TGF-beta2, TGF-beta3, TGF-beta4, TGF-beta5, TGF-I, Thrombin, thrombopoietin (TPO), Thymic stromal lymphoprotein receptor, Thymus Ck-1, thyroid stimulating hormone (TSH), thyroxine, thyroxine-binding globulin, Tie, TIMP, TIQ, Tissue Factor, tissue factor protease inhibitor, tissue factor protein, TMEFF2, Tmpo, TMPRSS2, TNF receptor I, TNF receptor II, TNF-alpha, TNF-beta, TNF-beta2, TNFc, TNF-RI, TNF-RII, TNFRSF10A (TRAIL R1Apo-2/DR4), TNFRSF10B (TRAIL R2 DR5/KILLER/TRICK-2A/TRICK-B), TNFRSF10C (TRAIL R3DcR1/LIT/TRID), TNFRSF10D (TRAIL R4DcR2/TRUNDD), TNFRSF11A (RANK ODF R/TRANCE R), TNFRSF11B (OPG OCIF/TR1), TNFRSF12 (TWEAK R FN14), TNFRSF12A, TNFRSF13B (TAL1), TNFRSF13C (BAFF R), TNFRSF14 (HVEM ATAR/HveA/LIGHT R/TR2), TNFRSF16 (NGFR p75NTR), TNFRSF17 (BCMA), TNFRSF18 (GITR AITR), TNFRSF19 (TROY TAJ/TRADE), TNFRSF19L (RELT), TNFRSF1A (TNF R1CD120a/p55-60), TNFRSF1B (TNF RIICD120b/p75-80), TNFRSF21 (DR6), TNFRSF22 (DcTRAIL R2TNFRH2), TNFRSF25 (DR3Apo-3/LARD/TR-3/TRAMP/WSL-1), TNFRSF26 (TNFRH3), TNFRSF3 (LTbR TNF RIII/TNFC R), TNFRSF4 (OX40 ACT35/TXGP1R), TNFRSF5 (CD40 p50), TNFRSF6 (Fas Apo-1/APT1/CD95), TNFRSF6B (DcR3M68/TR6), TNFRSF7 (CD27), TNFRSF8 (CD30), TNFRSF9 (4-1 BB CD137/ILA), TNFRST23 (DcTRAIL R1 TNFRH1), TNFSF10 (TRAIL Apo-2 Ligand/TL2), TNFSF11 (TRANCE/RANK Ligand ODF/OPG Ligand), TNFSF12 (TWEAK Apo-3 Ligand/DR3Ligand), TNFSF13 (APRIL TALL2), TNFSF13B (BAFF BLYS/TALL1/THANK/TNFSF20), TNFSF14 (LIGHT HVEM Ligand/LTg), TNFSF15 (TL1A/VEGI), TNFSF18 (GITR Ligand AITR Ligand/TL6), TNFSF1A (TNF-a Conectin/DIF/TNFSF2), TNFSF1B (TNF-b LTa/TNFSF1), TNFSF3 (LTb TNFC/p33), TNFSF4 (OX40 Ligand gp34/TXGP1), TNFSF5 (CD40 Ligand CD154/gp39/HIGM1/IMD3/TRAP), TNFSF6 (Fas Ligand Apo-1 Ligand/APT1 Ligand), TNFSF7 (CD27 Ligand CD70), TNFSF8 (CD30 Ligand CD153), TNFSF9 (4-1 BB Ligand CD137 Ligand), TNF-alpha, TNF-beta, TNIL-1, toxic metabolite, TP-1, t-PA, Tpo, TRAIL, TRAIL R, TRAIL-R1, TRAIL-R2, TRANCE, transferrin receptor, transforming growth factors (TGF) such as TGF-alpha and TGF-beta, Transmembrane glycoprotein NMB, Transthyretin, TRF, Trk, TROP-2, Trophoblast glycoprotein, TSG, TSLP, Tumor Necrosis Factor (TNF), tumor-associated antigen CA 125, tumor-associated antigen expressing Lewis Y related carbohydrate, TWEAK, TXB2, Ung, uPAR, uPAR-1, Urokinase, VAP-1, vascular endothelial growth factor (VEGF), vaspin, VCAM, VCAM-1, VECAD, VE-Cadherin, VE-Cadherin-2, VEFGR-1 (flt-1), VEFGR-2, VEGF receptor (VEGFR), VEGFR-3 (flt-4), VEGI, VIM, Viral antigens, VitB12 receptor, Vitronectin receptor, VLA, VLA-1, VLA-4, VNR integrin, von Willebrand Factor (vWF), WIF-1, WNT1, WNT10A, WNT10B, WNT11, WNT16, WNT2, WNT2B/13, WNT3, WNT3A, WNT4, WNT5A, WNT5B, WNT6, WNT7A, WNT7B, WNT8A, WNT8B, WNT9A, WNT9B, XCL1, XCL2/SCM-1-beta, XCL1/Lymphotactin, XCR1, XEDAR, XIAP, XPD, HMGB1, IgA, Aa, CD81, CD97, CD98, DDR1, DKK1, EREG, Hsp90, IL-17/IL-17R, IL-20/IL-20R, oxidized LDL, PCSK9, prekallikrein, RON, TMEM16F, SOD1, Chromogranin A, Chromogranin B, tau, VAP1, High molecular weight kininogen, IL-31, IL-31R, Nav1.1, Nav1.2, Nav1.3, Nav1.4, Nav1.5, Nav1.6, Nav1.7, Nav1.8, Nav1.9, EPCR, C1, C1q, C1r, C1s, C2, C2a, C2b, C3, C3a, C3b, C4, C4a, C4b, C5, C5a, C5b, C6, C7, C8, C9, factor B, factor D, factor H, properdin, sclerostin, fibrinogen, fibrin, prothrombin, thrombin, tissue factor, factor V, factor Va, factor VII, factor VIIa, factor VIII, factor VIIIa, factor IX, factor IXa, factor X, factor Xa, factor XI, factor XIa, factor XII, factor XIIa, factor XIII, factor XIIIa, TFPI, antithrombin III, EPCR, thrombomodulin, TAPI, tPA, plasminogen, plasmin, PAI-1, PAI-2, GPC3, Syndecan-1, Syndecan-2, Syndecan-3, Syndecan-4, LPA, SIP.

Antigen binding molecules described in present invention are capable of reducing total antigen concentration of the above-described antigens in plasma. Antigen binding molecules described in present invention are also capable of eliminating virus, bacteria, and fungus from plasma by binding to structural components of virus, bacteria and fungus. Particularly, F protein of RSV, Staphylococcal lipoteichoic acid, *Clostridium difficile* toxin, Shiga like toxin II, *Bacillus anthracis* protective antigen and Hepatitis C virus E2 glycoprotein can be used as a structural components of virus, bacteria and fungus.

Use

The present invention also provides many uses of the antigen-binding molecules of the present invention as described above.

Thus, the present invention provides the use of the modified antigen-binding molecules of the present invention for improving the antigen-binding molecule-mediated antigen uptake into cells. Furthermore, the present invention also provides methods for improving antigen-binding molecule-mediated antigen uptake into cells comprising altering an antigen-binding molecule comprising a parent FcRn-binding domain, by substituting an amino acid in the parent FcRn-binding domain at one or more positions selected from the group consisting of EU238, EU250, EU252, EU254, EU255, EU258, EU286, EU307, EU308, EU309, EU311, EU315, EU428, EU433, EU434, and EU436 and thereby increasing the FcRn-binding activity at neutral pH as compared to an antigen-binding molecule having an intact FcRn-binding domain.

Herein, the term "antigen uptake into cells" mediated by an antigen-binding molecule means that antigens are taken up into cells by endocytosis. Meanwhile, herein, the term "facilitate the uptake into cells" means that the rate of intracellular uptake of antigen-binding molecule bound to an antigen in plasma is enhanced, and/or the quantity of recycling of uptaken antigen to the plasma is reduced. This means that the rate of uptake into cells is facilitated as compared to the antigen-binding molecule before the modification of the FcRn-binding domain and thus before increasing the human FcRn-binding activity of the antigen-binding molecule in the neutral pH range, or before increasing the human FcRn-binding activity and reducing the antigen-binding activity (binding ability) of the antigen-binding molecule in the acidic pH range to less than its antigen-binding activity in the neutral pH range. The rate is improved preferably as compared to intact IgG, and more preferably as compared to intact human IgG. Thus, in the present invention, whether antigen uptake into cells is facilitated by an antigen-binding molecule can be assessed based on an increase in the rate of antigen uptake into cells. The rate of antigen uptake into cells can be calculated, for example, by monitoring over time reduction in the antigen concentration in the culture medium containing human FcRn-expressing cells after adding the antigen and antigen-binding molecule to the medium, or monitoring over time the amount of antigen uptake into human FcRn-expressing cells. Using methods of the present invention for facilitating the rate of antigen-binding molecule-mediated antigen uptake into cells, for example, the rate of antigen elimination from the plasma can be enhanced by administering antigen-binding molecules of the present invention. Thus, whether antigen-binding molecule-mediated antigen uptake into cells is facilitated can also be assessed, for example, by testing whether the rate of antigen elimination from the plasma is accelerated or whether the total antigen concentration in plasma is reduced by administering an antigen-binding molecule of the present invention.

Herein, the term "total antigen concentration in plasma" means the sum of antigen-binding molecule bound antigen and non-bound antigen concentration, or "free antigen concentration in plasma" which is antigen-binding molecule non-bound antigen concentration. Various methods to measure "total antigen concentration in plasma" and "free antigen concentration in plasma" are well known in the art as described hereinafter.

The present invention also provides use of the antigen-binding molecule of the present invention for increasing the total number of antigens to which a single antigen-binding molecule can bind before its degradation. The present invention also provides methods for increasing the number of antigens to which a single antigen-binding molecule can bind, by using an antigen-binding molecule of the present invention. Specifically, the present invention provides methods for increasing the total number of antigens to which a single antigen-binding molecule can bind, by substituting an amino acid in the parent FcRn-binding domain of said antigen-binding molecule at one or more positions selected from the group consisting of EU238, EU250, EU252, EU254, EU255, EU258, EU286, EU307, EU308, EU309, EU311, EU315, EU428, EU433, EU434, and EU436 and thereby increasing the FcRn-binding activity at neutral pH as compared to an antigen-binding molecule having an intact FcRn-binding domain.

A "conventional antibody" can usually bind only one or two antigens before it is degraded in the endosome. An antigen-binding molecule of the present invention can increase the number of cycles achieved until the antigen-binding molecule is degraded, whereby each cycle consists of: binding of an antigen to the antigen-binding molecule in plasma, intracellular uptake of the antigen-binding molecule bound to the antigen, and dissociation from the antigen in the endosome, followed by return of the antigen-binding molecule to the plasma. This means that the number of cycles is increased as compared to the antigen-binding molecule before the modification of the FcRn-binding domain and thus before increasing the human FcRn-binding activity of the antigen-binding molecule in the neutral pH or acidic range, or before increasing the human FcRn-binding activity and reducing the antigen-binding activity (binding ability) of the antigen-binding molecule in the acidic pH range to less than its antigen-binding activity in the neutral pH range. Thus, whether the number of cycles is increased can be assessed by testing whether the above-described "intracellular uptake is facilitated" or whether the "pharmacokinetics is improved" as described below.

The present invention also provides for the use of the antigen-binding molecules of the present invention for improving the antigen-removal from the blood in mammals, i.e. in humans. In particular, the present invention provides the use of the antigen-binding molecule of the present invention for reducing the plasma concentration of a specific antigen, wherein the antigen-binding molecule comprises an antigen-binding domain which can bind said antigen. The present invention also provides a method for reducing the plasma concentration of a specific antigen, wherein the antigen-binding molecule comprises an antigen-binding domain which can bind said antigen, by substituting an amino acid in a parent FcRn-binding domain at one or more positions selected from the group consisting of EU238, EU250, EU252, EU254, EU255, EU258, EU286, EU307, EU308, EU309, EU311, EU315, EU428, EU433, EU434, and EU436 and thereby increasing the FcRn-binding activity at neutral pH as compared to an antigen-binding molecule having an intact FcRn-binding domain.

The present invention also provides the use of the antigen-binding molecules of the present invention for facilitating the extracellular release of antigen-free antigen-binding molecule taken up into cells in an antigen-bound form. More specifically, the present invention provides methods for facilitating the extracellular release of antigen-free antigen-binding molecule taken up into cells in an antigen-bound form without significantly increasing the binding activity for a pre-existing ADA at neutral pH compared to parent antibody, by substituting an amino acid in the parent FcRn-binding domain at one or more positions selected from the group consisting of EU238, EU250, EU252, EU254, EU255, EU258, EU286, EU307, EU308, EU309, EU311, EU315, EU428, EU433, EU434, and EU436 and thereby increasing the FcRn-binding activity at neutral pH as compared to an antigen-binding molecule having an intact FcRn-binding domain Herein, the "extracellular release of antigen-free antigen-binding molecule taken up into cells in an antigen-bound form" does not necessarily mean that all of the antigen-binding molecules bound to antigen taken up into cells are released in an antigen-free form outside of the cell. It is acceptable that the proportion of antigen-binding molecules released in an antigen-free form to the outside of the cell is increased as compared to before the modification of the FcRn-binding domain and thus before reducing the antigen-binding activity of the antigen-binding molecule in the acidic pH range to less than that in the neutral pH range and increasing the human FcRn-binding activity in the neutral pH range. The antigen-binding molecule released to the outside of the cell preferably retains the antigen-binding activity.

The present invention also provides the use of an FcRn-binding domain of the present invention for increasing the ability of the antigen-binding molecule to eliminate plasma antigen. In the present invention, "methods for increasing the ability to eliminate plasma antigen" is synonymous to "methods for augmenting the ability of an antigen-binding molecule to eliminate antigen from plasma". More specifically, the present invention provides methods for increasing the ability of an antigen-binding molecule to eliminate plasma antigen by substituting an amino acid in the parent FcRn-binding domain at one or more positions selected from the group consisting of EU238, EU250, EU252, EU254, EU255, EU258, EU286, EU307, EU308, EU309, EU311, EU315, EU428, EU433, EU434, and EU436 and thereby increasing the FcRn-binding activity at neutral and/or acidic pH as compared to an antigen-binding molecule having an intact FcRn-binding domain.

Herein, the term "ability to eliminate plasma antigen" means the ability to remove antigen from the plasma when antigen-binding molecules are administered or secreted in vivo. Thus, "increase in the ability of antigen-binding molecule to eliminate plasma antigen" herein means that the rate of antigen elimination from the plasma is accelerated upon administration of the antigen-binding molecule as compared to before the modification of the FcRn-binding domain and thus before increasing the human FcRn-binding activity of the antigen-binding molecule in the neutral pH range or before increasing the human FcRn-binding activity and simultaneously reducing its antigen-binding activity in the acidic pH range to less than that in the neutral pH range. The increase in the activity of an antigen-binding molecule to eliminate antigen from the plasma can be assessed, for example, by administering a soluble antigen and an antigen-binding molecule in vivo, and measuring the concentration of the soluble antigen in plasma after administration. When the concentration of soluble antigen in plasma after administration of the soluble antigen and modified antigen-binding molecule is reduced, the ability of antigen-binding molecule to eliminate plasma antigen can be judged to be increased. A form of soluble antigen can be antigen-binding molecule bound antigen or antigen-binding molecule non-bound antigen whose concentration can be determined as "antigen-binding molecule bound antigen concentration in plasma" and "antigen-binding molecule non-bound antigen concentration in plasma" respectively. The latter is synonymous to "free antigen concentration in plasma". Since "total antigen concentration in plasma" means the sum of antigen-binding molecule bound antigen and non-bound antigen concentration, or "free antigen concentration in plasma" which is antigen-binding molecule non-bound antigen concentration, the concentration of soluble antigen can be determined as "total antigen concentration in plasma". Various methods for measuring "total antigen concentration in plasma" or "free antigen concentration in plasma" are well known in the art as described hereinafter.

The present invention also provides the use of the FcRn-binding domain of the present invention for improving the pharmacokinetics of antigen-binding molecules. More specifically, the present invention provides methods for improving the pharmacokinetics of the antigen-binding molecule by substituting an amino acid in the parent FcRn-binding domain at one or more positions selected from the group consisting of EU238, EU250, EU252, EU254, EU255, EU258, EU286, EU307, EU308, EU309, EU311, EU315, EU428, EU433, EU434, and EU436 and thereby increasing the FcRn-binding activity at neutral and/or acidic pH as compared to an antigen-binding molecule having an intact FcRn-binding domain.

Herein, the terms "enhancement of pharmacokinetics", "improvement of pharmacokinetics", and "superior pharmacokinetics" can be restated as "enhancement of plasma (blood) retention", "improvement of plasma (blood) retention", "superior plasma (blood) retention", and "prolonged plasma (blood) retention". These terms are used herein as synonyms.

Improving the pharmacokinetics particularly encompasses:
(1) a delayed elimination: prolonging the time between administration and elimination of the antigen-binding molecules from plasma as compared to a Control Antigen-binding Molecule (e.g. antigen-binding molecules having an intact FcRn-binding domain); and/or
(2) prolonging the plasma retention time of the antigen-binding molecules, preferably in a form in which the antibody or antibody derivative can bind to its antigen after administration of the Antigen-binding molecules as compared to the plasma retention time of a Control Antigen-binding Molecule (e.g. antigen-binding molecules having an intact FcRn-binding domain); and/or
(3) shortening the period during which the antigen is free (not bound to an antigen-binding molecule in the body) between administration and elimination of the antigen-binding molecules as compared to a Control Antigen-binding Molecule (prolonging of the period between administration and elimination during which the antigen-binding molecules is bound to its antigen in the body of a subject as compared to a control antigen-binding molecules (e.g. antigen-binding molecules having an intact FcRn-binding domain); and/or (4) increasing the ratio of antigen bound to an antigen-binding molecules vs. total antigen in the body as compared to the ratio of antigen bound to a Control Antigen-binding Molecule (e.g. antigen-binding molecules having an intact FcRn-binding domain) before degradation of the antibody (increasing the number of binding events of the antigen-binding molecules with its antigen between administration and degradation of the antibody or antibody derivative as compared to the number of binding events of a control antigen-binding molecules between administration and degradation).

(5) reducing plasma total or free antigen concentration after the administration of the antigen-binding molecules compared to the plasma total or free antigen concentration after the administration of a Control Antigen-binding Molecule (e.g. antigen-binding molecules having an intact FcRn-binding domain).

The present invention also provides a method for delaying the elimination of an antigen-binding molecule in a subject, comprising the step of introducing a modification into a FcRn-binding domain of said antigen-binding molecule at one or more of the positions selected from the group consisting of EU238, EU250, EU252, EU254, EU255, EU258, EU286, EU307, EU308, EU309, EU311, EU315, EU428, EU433, EU434, and EU436.

The term "improvement of pharmacokinetics" as used herein refers not only to prolongation of the period between administration of the antigen-binding molecule to a subject (humans, or non-human animals such as mice, rats, monkeys, rabbits, and dogs) and elimination from the plasma (for example, until the antigen-binding molecule is degraded intracellularly or the like and cannot return to the plasma) to, but also to the prolongation of the plasma retention of the antigen-binding molecule in a form that allows antigen binding (for example, in an antigen-free form of the antigen-binding molecule) during the period from administration until degradation of the antigen-binding molecule.

Therefore, the present invention also provides a method of prolonging the plasma retention time of an antigen-binding molecule, comprising the step of introducing a modification into a FcRn-binding domain of said antigen-binding molecule at one or more of the positions selected from the group consisting of EU238, EU250, EU252, EU254, EU255, EU258, EU286, EU307, EU308, EU309, EU311, EU315, EU428, EU433, EU434, and EU436. Intact human IgG can bind to FcRn from non-human animals. For example, administration to mice is preferably used to confirm the property of the antigen-binding molecule of the invention since intact human IgG can bind to mouse FcRn stronger than to human FcRn (Int Immunol. 2001 December; 13(12): 1551-9). As another example, mouse in which its native FcRn genes are disrupted and a transgene for human FcRn gene is harbored to be expressed (Methods Mol Biol. 2010; 602: 93-104) can also be preferably used to be administered in order to confirm the property of the antigen-binding molecule of the invention described hereinafter.

Specifically, "improvement of pharmacokinetics" also includes prolongation of the period between administration and degradation of the antigen-binding molecule during which it is not bound to an antigen (the antigen-free form of antigen-binding molecule). The antigen-binding molecule in plasma cannot bind to a new antigen when the antigen-binding molecule has already bound to an antigen. Thus, the longer the period during which the antigen-binding molecule is not bound to an antigen, the longer is the period during which it has the potential to bind to a new antigen (the higher the chance of binding to another antigen). In other words, more antigens are bound during a shorter period of time. Therefore, the plasma concentration of the antigen-free form of antigen-binding molecule can be increased and the total period during which antigen is bound to the antigen-binding molecule can be prolonged by accelerating the antigen elimination from the plasma by administration of the modified antigen-binding molecule.

Specifically, herein "improvement of the pharmacokinetics of antigen-binding molecule" includes the improvement of a pharmacokinetic parameter of the antigen-free form of the antigen-binding molecule (any of prolongation of the half-life in plasma, prolongation of mean retention time in plasma, and impairment of plasma clearance), prolongation of the period during which the antigen is bound to the antigen-binding molecule after administration of the modified antigen-binding molecule, and acceleration of antigen-binding molecule-mediated antigen elimination from the plasma.

The improvement of pharmacokinetics of antigen-binding molecule can be assessed by determining any one of the parameters, half-life in plasma, mean plasma retention time, and plasma clearance for the antigen-binding molecule or the antigen-free form thereof ("Pharmacokinetics: Enshu ni yoru Rikai (Understanding through practice)" Nanzando). For example, the plasma concentration of the antigen-binding molecule or antigen-free form thereof is determined after administration of the antigen-binding molecule to mice, rats, monkeys, rabbits, dogs, or humans. Then, each parameter is determined. When the plasma half-life or mean plasma retention time is prolonged, the pharmacokinetics of the antigen-binding molecule can be judged to be improved. The parameters can be determined by methods known to those skilled in the art. The parameters can be appropriately assessed, for example, by non-compartmental analysis using the pharmacokinetics analysis software WinNonlin (Pharsight) according to the appended instruction manual. The plasma concentration of antigen-free antigen-binding molecule can be determined by methods known to those skilled in the art, for example, using the assay method described in Clin Pharmacol. 2008 April; 48(4): 406-17.

Herein, the term "improvement of pharmacokinetics" also includes prolongation of the period that an antigen is bound to an antigen-binding molecule after administration of the antigen-binding molecule. Whether the period that antigen is bound to the antigen-binding molecule after administration of the antigen-binding molecule is prolonged can be assessed by determining the plasma concentration of free antigen. The prolongation can be judged based on the determined plasma concentration of free antigen or the time period required for an increase in the ratio of free antigen concentration to the total antigen concentration.

The present invention also provides the use of the antigen-binding molecules of the present invention for reducing total or free antigen plasma concentration of a specific antigen, wherein the antigen-binding molecule comprises an antigen-binding domain which can bind said antigen. More specifically, the present invention provides methods for reducing total or free antigen plasma concentration, said method comprising the steps of:

a) providing an antigen-binding molecule comprising a parent FcRn-binding domain, wherein the antigen-binding molecule comprises an antigen-binding domain which can bind said antigen, b) substituting an amino acid in the parent FcRn-binding domain at one or more positions selected from the group consisting of EU238, EU250, EU252, EU254, EU255, EU258, EU286, EU307, EU308, EU309, EU311, EU315, EU428, EU433, EU434, and EU436 and thereby increasing the FcRn-binding activity at neutral pH as compared to an antigen-binding molecule having an intact FcRn-binding domain.

Moreover, the present invention provides, comprising the step of introducing a modification into an FcRn-binding domain of said antigen-binding molecule at one or more of the positions selected from the group consisting of EU238, EU250, EU252, EU254, EU255, EU258, EU286, EU307, EU308, EU309, EU311, EU315, EU428, EU433, EU434, and EU436. The term "antigen-elimination rate" as used herein refers to the number of antigens that an antigen-binding molecule can remove from the plasma in the time between administration and elimination (i.e. degradation) of the antibody or antibody derivative.

The plasma concentration of free antigen not bound to the antigen-binding molecule or the ratio of free antigen concentration to the total concentration can be determined by methods known to those skilled in the art, for example, by the method described in Pharm Res. 2006 January; 23 (1): 95-103. Alternatively, when an antigen exhibits a particular function in vivo, whether the antigen is bound to an antigen-binding molecule that neutralizes the antigen function (antagonistic molecule) can be assessed by testing whether the antigen function is neutralized. Whether the antigen function is neutralized can be assessed by assaying an in vivo marker that reflects the antigen function. Whether the antigen is bound to an antigen-binding molecule that activates the antigen function (agonistic molecule) can be assessed by assaying an in vivo marker that reflects the antigen function.

Determination of the plasma concentration of free antigen and ratio of the amount of free antigen in plasma to the amount of total antigen in plasma, in vivo marker assay, and such measurements are not particularly limited; however, the assays are preferably carried out after a certain period of time has passed after administration of the antigen-binding molecule. In the present invention, the period after administration of the antigen-binding molecule is not particularly limited; those skilled in the art can determine the appropriate period depending on the properties and the like of the administered antigen-binding molecule. Such periods include, for example, one day after administration of the antigen-binding molecule, three days after administration of the antigen-binding molecule, seven days after administration of the antigen-binding molecule, 14 days after administration of the antigen-binding molecule, and 28 days after administration of the antigen-binding molecule. Herein, the term "plasma antigen concentration" means either "total antigen concentration in plasma" which is the sum of antigen-binding molecule bound antigen and non-bound antigen concentration or "free antigen concentration in plasma" which is antigen-binding molecule non-bound antigen concentration.

Total antigen concentration in plasma can be lowered by administration of antigen-binding molecule of the present invention by 2-fold, 5-fold, 10-fold, 20-fold, 50-fold, 100-fold, 200-fold, 500-fold, 1,000-fold, or even higher compared to the administration of a reference antigen-binding molecule comprising the intact human IgG Fc region as a human FcRn-binding domain or compared to when antigen-binding domain molecule of the present invention is not administered.

Molar antigen/antigen-binding molecule ratio can be calculated as shown below;
value A: Molar antigen concentration at each time point
value B: Molar antigen-binding molecule concentration at each time point
value C: Molar antigen concentration per molar antigen-binding molecule concentration (molar antigen/antigen-binding molecule ratio) at each time point $C=A/B.$ Smaller value C indicates higher efficiency of antigen elimination per antigen-binding molecule whereas higher value C indicates lower efficiency of antigen elimination per antigen-binding molecule.

Molar antigen/antigen-binding molecule ratio can be lowered by administration of antigen-binding molecule of present invention by 2-fold, 5-fold, 10-fold, 20-fold, 50-fold, 100-fold, 200-fold, 500-fold, 1,000-fold, or even higher as compared to the administration of a reference antigen-binding molecule comprising the intact human IgG Fc region as a human FcRn-binding domain.

Herein, an intact human IgG1, IgG2, IgG3 or IgG4 is preferably used as the intact human IgG for a purpose of a reference intact human IgG to be compared with the antigen-binding molecules for their human FcRn binding activity or in vivo activity. Preferably, a reference antigen-binding molecule comprising the same antigen-binding domain as an antigen-binding molecule of the interest and intact human IgG Fc region as a human FcRn-binding domain can be appropriately used. More preferably, an intact human IgG1 is used for a purpose of a reference intact human IgG to be compared with the antigen-binding molecules for their human FcRn binding activity or in vivo activity.

Reduction of total antigen concentration in plasma or molar antigen/antibody ratio can be assessed as described in Examples 6, 8, and 13 of WO2011/122011. More specifically, using human FcRn transgenic mouse line 32 or line 276 (Jackson Laboratories, Methods Mol Biol. (2010) 602: 93-104.), they can be assessed by either antigen-antibody co-injection model or steady-state antigen infusion model when the antigen-binding molecule of interest does not cross-react with the mouse counterpart antigen. When antigen-binding molecule cross-react with mouse counterpart, they can be assessed by simply injecting antigen-binding molecule to human FcRn transgenic mouse line 32 or line 276 (Jackson Laboratories). In the co-injection model, a mixture of antigen-binding molecule and antigen is administered to the mouse. In the steady-state antigen infusion model, an infusion pump containing an antigen solution is implanted to the mouse to achieve a constant plasma antigen concentration, and then the antigen-binding molecule is injected to the mouse. The same dosage is used for all administered test antigen-binding molecules. Total antigen concentration in plasma, free antigen concentration in plasma and plasma antigen-binding molecule concentration is measured at an appropriate time point using methods known to those skilled in the art.

Total or free antigen concentration in plasma and molar antigen/antigen-binding molecule ratio can be measured at 2, 4, 7, 14, 28, 56, or 84 days after administration to evaluate the long-term effect of the present invention. In other words, a long term plasma antigen concentration is determined by measuring total or free antigen concentration in plasma and molar antigen/antigen-binding molecule ratio at 2, 4, 7, 14, 28, 56, or 84 days after administration of an antigen-binding molecule in order to evaluate the property of the antigen-binding molecule of the present invention. Whether the reduction of plasma antigen concentration or molar antigen/antigen-binding molecule ratio is achieved by antigen-binding molecule described in the present invention can be determined by the evaluation of the reduction at any one or more of the time points described above.

Total or free antigen concentration in plasma and molar antigen/antigen-binding molecule ratio can be measured at 15 min, 1, 2, 4, 8, 12, or 24 hours after administration to evaluate the short-term effect of the present invention. In other words, a short term plasma antigen concentration is determined by measuring total or free antigen concentration in plasma and molar antigen/antigen-binding molecule ratio at 15 min, 1, 2, 4, 8, 12, or 24 hours after administration of an antigen-binding molecule in order to evaluate the property of the antigen-binding molecule of the present invention.

More specifically, those antigen-binding molecules having a long term effect on activity for eliminating antigen in plasma as described in the present invention have human FcRn-binding activity at pH 7.0 and 25 degrees C. within a range of 28-fold to 440-fold stronger than intact human IgG1 or KD within a range of 3.0 micromolar to 0.2 micromolar. Preferably, the KD is within a range of 700 nanomolar to 0.2 nanomolar, more preferably, the KD is within a range of 500 nanomolar to 3.5 nanomolar, more preferably, within a range of 150 nanomolar to 3.5 nanomolar. A long term plasma antigen concentration is determined by measuring total or free antigen concentration in plasma and molar antigen/antigen-binding molecule ratio at 2, 4, 7, 14, 28, 56, or 84 days after administration of an antigen-binding molecule in order to evaluate the long term effect of the antigen-binding molecule of the present invention on activity for eliminating antigen in plasma. Whether the reduction of plasma antigen concentration or molar antigen/antigen-binding molecule ratio is achieved by antigen-binding molecule described in the present invention can be determined by the evaluation of the reduction at any one or more of the time points described above.

Still more specifically, those antigen-binding molecules having a short term effect on for eliminating antigen in plasma as described in the present invention have human FcRn-binding activity at pH 7.0 and at 25 degrees Celsius 440-fold stronger than intact human IgG or KD stronger than 0.2 micromolar, preferably stronger than 700 nanomolar, more preferably stronger than 500 nanomolar, most preferably, stronger than 150 nanomolar. A short term plasma antigen concentration is determined by measuring total or free antigen concentration in plasma and molar antigen/antigen-binding molecule ratio at 15 min, 1, 2, 4, 8, 12, or 24 hours after administration of an antigen-binding molecule in order to evaluate the short term effect of the antigen-binding molecule of the present invention on activity for eliminating antigen in plasma.

Route of administration of an antigen-binding molecule of the present invention can be selected from intradermal, intravenous, intravitreal, subcutaneous, intraperitoneal, parenteral and intramuscular injection.

In the context of the present invention, improvement of pharmacokinetics in human is preferred. When the plasma retention in human is difficult to determine, it may be predicted based on the plasma retention in mice (for example, normal mice, human antigen-expressing transgenic mice, human FcRn-expressing transgenic mice) or monkeys (for example, cynomolgus monkeys).

Herein the term "reducing the antigen-binding activity of an antigen-binding molecule in the acidic pH range to less than that in the neutral pH range" means that the antigen-binding activity of the antigen-binding molecule at pH 4.0 to pH 6.5 is impaired as compared to its antigen-binding activity at pH 6.7 to pH 10.0. Preferably, the above phrase means that the antigen-binding activity of an antigen-binding molecule at pH 5.5 to pH 6.5 is impaired as compared to that at pH 7.0 to pH 8.0, more preferably means that its antigen-binding activity at the early endosomal pH is impaired as compared to its antigen-binding activity at the plasma pH in vivo. Specifically, the antigen-binding activity of an antigen-binding molecule at pH 5.8 to pH 6.0 is impaired as compared to the antigen-binding activity of the antigen-binding molecule at pH 7.4. Herein the term "reducing the antigen-binding activity of an antigen-binding molecule in the neutral pH range to less than that in the acidic pH range" means that the antigen-binding activity of the antigen-binding molecule at pH 6.7 to pH 10.0 is impaired as compared to its antigen-binding activity at pH 4.0 to pH 6.5. Preferably, the above phrase means that the antigen-binding activity of an antigen-binding molecule at pH 7.0 to pH 8.0 is impaired as compared to that at pH 5.5 to pH 6.5, more preferably means that its antigen-binding activity at the plasma pH in vivo is impaired as compared to its antigen-binding activity at the early endosomal pH. Specifically, the antigen-binding activity of an antigen-binding molecule at pH 7.4 is impaired as compared to the antigen-binding activity of the antigen-binding molecule at pH 5.8 to pH 6.0.

Meanwhile, herein the expression "reducing the antigen-binding activity of an antigen-binding molecule in the acidic pH range to less than that in the neutral pH range" is also expressed as "increasing the antigen-binding activity of an antigen-binding molecule in the neutral pH range to more than that in the acidic pH range". Specifically, in the present invention, it is possible to increase the ratio of antigen binding activity of an antigen-binding molecule between acidic and neutral pH ranges. For example, the value of KD (pH 5.8)/KD (pH 7.4) is increased in an embodiment described below. The ratio of antigen-binding activity of an antigen-binding molecule between acidic and neutral pH ranges can be increased, for example, by reducing its antigen-binding activity in the acidic pH range, increasing its antigen-binding activity in the neutral pH range, or both. The expression "reducing the antigen-binding activity of an antigen-binding molecule in the neutral pH range to less than that in the acidic pH range" is also expressed as "increasing the antigen-binding activity of an antigen-binding molecule in the acidic pH range to more than that in the neutral pH range". Specifically, in the present invention, it is possible to increase the ratio of antigen binding activity of an antigen-binding molecule between acidic and neutral pH ranges. For example, the value of KD (pH7.4)/KD (pH 5.8) is increased in an embodiment described below. The ratio of antigen-binding activity of an antigen-binding molecule between acidic and neutral pH ranges can be increased, for example, by reducing its antigen-binding activity in the neutral pH range, increasing its antigen-binding activity in the acidic pH range, or both.

The term "reducing the antigen-binding activity (binding ability) at low calcium-ion concentrations to less than its antigen-binding activity at high calcium-ion concentration" as used herein refers to decreasing the binding affinity of the antigen-binding domain for the antigen at a low calcium-ion concentration compared with the binding affinity for the antigen of said antigen-binding domain at a high calcium-ion concentration. The low calcium concentration is preferably 0.5 to 10 micromolar, more preferably 0.1 to 30 micromolar of ionized calcium, and the high calcium concentration is 100 micromolar to 10 mM, more preferably 200 micromolar to 5 mM of ionized calcium.

Herein, the expression "impairing the antigen-binding activity in the acidic pH range as compared to that in the neutral pH range" is sometimes used instead of "reducing the antigen-binding activity in the acidic pH range to less than that in the neutral pH range".

Herein, the human FcRn-binding activity in the acidic pH range means the human FcRn-binding activity at pH 4.0 to pH 6.5, preferably the human FcRn-binding activity at pH 5.5 to pH 6.5, and particularly preferably the human FcRn-binding activity at pH 5.8 to pH 6.0, which is comparable to the in vivo early endosomal pH. Meanwhile, herein the human FcRn-binding activity in the neutral pH range means the human FcRn-binding activity at pH 6.7 to pH 10.0, preferably the human FcRn-binding activity at pH 7.0 to pH 8.0, and particularly preferably the human FcRn-binding activity at pH 7.4, which is comparable to the in vivo plasma pH.

Although the antigen-binding molecule and uses of the present invention are not limited to any particular theory, the relationship between the reduction (impairment) of the antigen-binding ability of antigen-binding molecule in the acidic pH range to less than that in the neutral pH range and/or the increase (enhancement) of the human FcRn-binding activity in the neutral pH range and the increase in the number of antigens to which a single antigen-binding molecule can bind, due to facilitation of uptake of antigen-binding molecules into cells, and the enhancement of antigen elimination from the plasma can be explained as follows.

For example, when the antigen-binding molecule is an antibody that binds to a membrane antigen, the antibody administered into the body binds to the antigen and then is taken up via internalization into endosomes in the cells together with the antigen while the antibody is kept bound to the antigen. Then, the antibody translocates to lysosomes while the antibody is kept bound to the antigen, and the antibody is degraded by the lysosome together with the antigen. The internalization-mediated elimination from the plasma is called antigen-dependent elimination, and such elimination has been reported with numerous antibody molecules (Drug Discov Today. 2006 January; 11(1-2): 81-8). When a single molecule of IgG antibody binds to antigens in a divalent manner, the single antibody molecule is internalized while the antibody is kept bound to the two antigen molecules, and degraded in the lysosome. Accordingly, in the case of typical antibodies, one molecule of IgG antibody cannot bind to three or more molecules of antigen. For example, a single IgG antibody molecule having a neutralizing activity cannot neutralize three or more antigen molecules.

The relatively prolonged retention (slow elimination) of IgG molecules in the plasma is due to the function of human FcRn which is known as a salvage receptor of IgG molecules. When taken up into endosomes via pinocytosis, IgG molecules bind to human FcRn expressed in the endosomes under the acidic condition in the endosomes. While IgG molecules that did not bind to human FcRn transfer to lysosomes where they are degraded, IgG molecules that are bound to human FcRn translocate to the cell surface and return again in the plasma by dissociating from human FcRn under the neutral condition in the plasma.

Alternatively, when the antigen-binding molecule is an antibody that binds to a soluble antigen, the antibody administered into the body binds to the antigen and then is taken up into cells while the antibody is kept bound to the antigen. Many antibodies taken up into cells are released to the outside of the cell via FcRn. However, since the antibodies are released to the outside of the cell, with the antibodies kept bound to antigens, the antibodies cannot bind to antigens again. Thus, similar to antibodies that bind to membrane antigens, in the case of typical antibodies, one molecule of IgG antibody cannot bind to three or more antigen molecules.

pH-dependent antigen-binding antibodies that strongly bind to an antigen under the neutral conditions in plasma but dissociate from the antigen under acidic conditions in the endosome (i.e., antibodies that bind under neutral conditions but dissociate under acidic conditions) can dissociate from the antigen in the endosome. Such pH-dependent antigen-binding antibodies can bind to antigens again when they are recycled to the plasma by FcRn after antigen dissociation; thus, each antibody can repeatedly bind to a number of antigens. Furthermore, the antigen bound to the antigen-binding molecule is dissociated in the endosome and not recycled to the plasma. This facilitates the antigen-binding molecule-mediated antigen uptake into cells. Thus, the administration of an antigen-binding molecule can enhance the antigen elimination and thereby reduces the plasma antigen concentration.

A calcium concentration-dependent antigen-binding antibody, which strongly binds to an antigen under a high calcium concentration condition in plasma, and dissociates from the antigen under a low calcium concentration condition in the endosome, can dissociate from the antigen within the endosome. The calcium concentration-dependent antigen-binding antibody can bind to an antigen again when recycled to plasma via FcRn after antigen dissociation. Thus, such a single antibody can repeatedly bind to multiple antigens. Meanwhile, an antigen bound to the antigen-binding molecule is not recycled to plasma because the antigen dissociates in the endosome, and thus, the antigen-binding molecule promotes uptake of the antigen into cells. The administration of the antigen-binding molecule promotes the elimination of an antigen, and this allows a decrease in the antigen concentration in plasma.

The antigen-binding molecule-mediated antigen uptake into cells can be further facilitated by conferring the human FcRn-binding activity under neutral conditions (pH 7.4) to an antibody that binds to an antigen in a pH-dependent manner (binds under neutral conditions but dissociates under acidic conditions). Thus, the administration of an antigen-binding molecule can enhance the antigen elimination and thereby reduces the plasma antigen concentration. Normally, both antibody and antigen-antibody complex are taken up into cells by non-specific endocytosis, and then transported to the cell surface by binding to FcRn under acidic conditions in the endosome. The antibody and antigen-antibody complex are recycled to the plasma via dissociation from FcRn under the neutral condition on cell surface. Thus, when an antibody that exhibits sufficient pH dependency in antigen binding (binds under neutral conditions but dissociates under acidic conditions) binds to the antigen in the plasma and then is dissociated from the bound antigen in the endosome, the antigen elimination rate is presumed to be equal to the rate of antigen uptake into cells via non-specific endocytosis. On the other hand, when the pH dependency is insufficient, the antigen that did not dissociate in the endosome is also recycled to the plasma. Meanwhile, when the pH dependency is sufficient, the rate-determining step in the antigen elimination is the uptake into cells by non-specific endocytosis. Some of FcRn is presumed to be localized on the cell surface because FcRn transports antibodies from the endosome to the cell surface.

The present inventors presumed that IgG-type immunoglobulins, which are one of antigen-binding molecules, typically have little FcRn-binding ability in the neutral pH range, but those that exhibit FcRn-binding ability in the neutral pH range could bind to FcRn on the cell surface and thus are taken up into cells in an FcRn-dependent manner by binding to cell-surface FcRn. The rate of FcRn-mediated uptake into cells is more rapid than the rate of uptake into cells by non-specific endocytosis. Thus, the rate of antigen elimination can be further accelerated by conferring FcRn-binding ability in the neutral pH range. Specifically, an antigen-binding molecule having FcRn-binding ability in the neutral pH range transports an antigen into cells more rapidly than the typical (intact human) IgG-type immunoglobulin, and then the antigen-binding molecule is dissociated from the antigen in the endosome. The antigen-binding molecule is recycled to the cell surface or plasma, and again binds to another antigen and is taken up into cells via FcRn. The rate of this cycle can be accelerated by improving FcRn-binding ability in the neutral pH range, thereby accelerating the rate of antigen elimination from the plasma. Furthermore, the efficiency can be further improved by reducing the antigen-binding activity of an antigen-binding molecule in the acidic pH range to less than that in the neutral pH range. In addition, the number of antigens to which a single antigen-binding molecule can bind is presumed to increase with an increasing number of cycles achieved by a single antigen-binding molecule. The antigen-binding molecule of the present invention comprises an antigen-binding domain and an FcRn-binding domain. Since the FcRn-binding domain does not affect antigen binding, or in view of the mechanism described above, facilitation of the antigen-binding molecule-mediated antigen uptake into cells can be expected regardless of the type of antigen, and as a result increases the antigen elimination rate by reducing the antigen-binding activity of an antigen-binding molecule in the acidic pH range (binding ability) to less than that in the neutral pH range and/or increasing its FcRn-binding activity at the plasma pH.

In all forgoing uses the antigen-binding molecules of the present invention may also comprise a substitution at position EU256 in addition to a substitution at the mentioned one or more positions. Preferably, the amino acid at position EU256 is substituted with a glutamic acid. Furthermore, all foregoing methods of use may also comprise a substitution at position EU256 in addition to a substitution at the one or more positions selected from the group consisting of EU238, EU250, EU252, EU254, EU255, EU258, EU286, EU307, EU308, EU309, EU311, EU315, EU428, EU433, EU434, and EU436, whereby the amino acid at position EU256 is preferably substituted with a glutamic acid.

In a preferred embodiment of all foregoing uses and methods, the FcRn-binding region is an Fc region in more preferably, it is a human Fc region.

Moreover, the substitution in the amino acid sequence of the parent FcRn-binding domain for increasing the FcRn-binding activity at neutral or acidic pH are preferably at position EU252 and EU434 and one at one or more positions selected from the group consisting of EU238, EU250, EU254, EU255, EU256, EU258, EU286, EU307, EU308, EU309, EU311, EU315, EU428, EU433, and EU436. More preferably, the substitutions are at three or more positions wherein said three or more positions are one of the combinations set forth in Tables 2, and 4 to 7. Even more preferably, the substitutions are one of the combinations set forth in Table 3

Furthermore, the foregoing methods of use may additionally comprise a step introducing an amino acid substitution at one or more positions selected from the group consisting of EU387, EU422, EU424, EU426, EU433, EU436, EU438 and EU440, and thereby decreasing an increased binding activity for a pre-existing ADA. Preferably, the substitutions are combinations selected from Table 11.

In addition, the forgoing methods of use may also comprise an additional step of introducing in an amino acid substitution in an FcRn-binding domain at one or more positions selected from the group consisting of EU234, EU235, EU236, EU237, EU238, EU239, EU265, EU266, EU267, EU269, EU270, EU271, EU295, EU296, EU297 EU298, EU300, EU324, EU325, EU327, EU328, EU329, EU331, and EU332 (according to the EU numbering system). Preferably, the substitutions L235R/S239K are introduced. Preferably, the substitutions are combinations selected from Table 14.

The antigen-binding molecule of all foregoing uses and method of uses may comprise a pH-dependent antigen-binding domain or a calcium ion-dependent antigen-binding domain. The antigen uptake into cells mediated by the antigen-binding molecules of the present invention is further improved by reducing the antigen-binding activity (binding ability) in the acidic pH range of the above-described antigen-binding molecule to less than its antigen-binding activity in the neutral pH range. Also preferred is the further improvement of the antigen uptake into cells by reducing the antigen-binding activity (binding ability) of the antigen-binding molecule of the present invention at low calcium-ion concentration (i.e. at 0.5 to 10 micromolar.) to less than its antigen-binding activity at high calcium-ion concentration (i.e. 100 micromolar to 10 mM), for example by replacing the antigen-binding domain of the antigen-binding molecule with an ionized calcium-concentration dependent antigen-binding domain. Alternatively, the parent antigen-binding molecule already comprises an ionized calcium-concentration dependent antigen-binding domain. Methods for reducing the antigen-binding activity (binding ability) in the acidic pH range by altering at least one amino acid in the antigen-binding domain of the above-described antigen-binding molecule are described above. Preferably, the antigen-binding domain is altered by substituting histidine for at least one amino acid or inserting at least one histidine into the antigen-binding domain of the above-described antigen-binding molecule which facilitates antigen uptake into cells.

Clearance of modified antigen-binding molecule that has an increased FcRn-binding activity at neutral or acidic pH can be decreased when these modifications increase the antigen-binding molecule's affinity for a pre-existing ADA, e.g. the rheumatoid factor. This means by further modifying such an antibody and thereby decreasing the affinity for a pre-existing ADA, the number of cycles can be increased compared to the antigen-binding molecule before the second modification, and thus before the affinity for a pre-existing ADA was decreased.

Those antigen-binding molecules of the present invention whose affinity for a pre-existing anti-drug antibody is not significantly increased at a neutral pH as compared to a wild type Fc region, in particular those that comprise in the FcRn binding domain an amino acid substitution at one or more positions selected from the group consisting of EU387, EU422, EU424, EU426, EU433, EU436, EU438 and EU440, are particularly useful as therapeutic antibodies for treating human patients suffering from an autoimmune disease, transplant rejections (graft-vs.-host disease), other inflammatory diseases and allergic diseases.

An autoimmune disease is an illness that occurs when body tissue is attacked by its own immune system. Examples of autoimmune diseases contemplated herein include systemic lupus erythematosus, lupus nephritis, pemphigoid, pemphigus, dermatomyositis, autoimmune hepatitis, Sjogren syndrome, Hashimoto thyroiditis, rheumatoid arthritis, juvenile (type 1) diabetes, polymyositis, scleroderma, Addison disease, Coeliac disease, Guillain-Barre syndrome, dilated cardiomyopathy, mixed connective tissue disease, Wegener's granulomatosis, anti-phospholipid antibody syndrome, vitiligo, pernicious anemia, glomerulonephritis, and pulmonary fibrosis. Myasthenia gravis, Graves' disease, idiopathic thrombocytopenia purpura, hemolytic anemia, diabetes mellitus, inflammatory bowel disease, Crohn's disease, ulcerative colitis, multiple sclerosis, psoriasis, and drug-induced autoimmune diseases, e.g., drug-induced lupus. Preferably, the autoimmune disease is systemic lupus erythematosus or Lupus nephritis. Transplant rejection include graft-versus-host disease is a process in which a transplant recipient's immune system attacks the transplanted organ or tissue. Other inflammatory and allergic diseases include atherosclerosis and hay fever.

An increased binding affinity for a pre-existing ADA can reduce the clinical utility and efficacy of a therapeutic antibody. As such the utility of a therapeutic antibody can be limited by the pre-existing ADAs, since these ADA can influence their efficacy and pharmacokinetics (e.g. degradation rate). Sometimes this binding can lead to serious side effects. Furthermore, the present invention provides a method for decreasing the binding activity at neutral pH for a pre-existing ADA of antigen-binding domain comprising an Fc region with an increased binding activity for FcRn at neutral or acidic pH and an increased binding activity for a pre-existing ADA at neutral pH.

The present invention also provides the use of the antigen-binding molecules of the present invention comprising a modified FcRn-binding domain for decreasing the binding activity for a pre-existing ADA at neutral pH of an antigen-binding molecule that has an increased affinity for FcRn at neutral or acidic pH and an increased binding activity for a pre-existing ADA.

In particular, the present invention provides a method for decreasing the binding activity at neutral pH for a pre-existing ADA of an Fc region of an antigen-binding molecule that has an increased binding activity for FcRn at neutral or acidic pH, said method comprising a) providing a Fc region having an increased binding activity for FcRn at neutral or acidic pH and for a pre-existing ADA at neutral pH and b) substituting an amino acid at one or more of the positions selected from the group consisting of: EU387, EU422, EU424, EU426, EU433, EU436, EU438 and EU440. The preferred Fc region in step a) is a human Fc region. Preferably, the Fc region having an increased binding activity for FcRn at neutral or acidic pH ranges and for pre-existing ADA in the neutral pH ranges comprises a substitution of an amino acid at one or more positions selected from the group consisting of: EU238, EU250, EU252, EU254, EU255, EU256, EU258 EU286, EU307, EU308, EU309, EU311, EU315, EU428, EU433, EU434, and EU436. More preferably, it comprises a substitution at the positions at any one of the combinations of positions selected from Table 2 and 4 to 7. Even more preferably, it comprises any one of the substitutions or combinations of substitutions set forth in any one of Tables 3 and 17 to 20.

Preferably, step b) comprises substituting an amino acid at any one of the positions in Table 8. More preferably, step b) comprises introducing one of the substitutions or combinations selected from Table 11.

Also preferably, the antigen-binding molecule comprises additionally a pH-dependent antigen-binding domain or a calcium ion-dependent antigen-binding domain.

Moreover, the present invention provides a method for decreasing the binding activity for a pre-existing ADA of an antigen-binding molecule that comprises an Fc region having an increased binding activity for FcRn at neutral pH, said method comprising the steps of:

a) providing an antigen-binding molecule comprising a Fc region with an increased binding activity for FcRn at acidic pH and for a pre-existing ADA at a neutral pH and b) substituting an amino acid in the Fc region at one or more of the positions selected from the group consisting of: EU387, EU422, EU424, EU426, EU433, EU436, EU438 and EU440.

The preferred Fc region in step a) is a human Fc region. Preferably, the Fc region having an increased binding activity for FcRn at neutral pH ranges and for pre-existing ADA in the neutral pH ranges comprises a substitution of an amino acid at one or more positions selected from the group consisting of: EU238, EU250, EU252, EU254, EU255, EU258, EU286, EU307, EU308, EU309, EU311, EU315, EU428, EU433, EU434, and EU436. It may also comprise a substitution at position EU256 in addition to a substitution at the one or more positions mentioned above, whereby the amino acid at position EU256 is preferably substituted with a glutamic acid. More preferably, it comprises a substitution at the positions of any one of the position combinations selected from Tables 2 and 4 to 7. Even more preferably, it comprises any one of the substitutions or substitution combinations selected from any one of Table 3 and 17 to 20.

Preferably, step b) comprises substituting an amino acid at any one of the positions in Table 10. More preferably, the positions are selected from the group consisting of a) EU387, b) EU422, c) EU424, d) EU438, e) EU440, f) EU422/EU424, and g) EU438/EU440. Even more preferably, step b) comprises introducing one of the substitutions or combinations selected from Table 11.

Moreover, the present invention provides a method for decreasing the binding activity for a pre-existing ADA of an antigen-binding molecule that comprises an Fc region having an increased binding activity for FcRn at acidic pH, said method comprising the steps of:

a) providing an antigen-binding molecule comprising a Fc region with an increased binding activity for FcRn at acidic pH and for a pre-existing ADA at a neutral pH and b) substituting an amino acid in the Fc region at one or more of the positions selected from the group consisting of: EU387, EU422, EU424, EU426, EU433, EU436, EU438 and EU440.

The preferred Fc region in step a) is a human Fc region. Preferably, the Fc region having an increased binding activity for FcRn at acidic pH and for pre-existing ADA in the neutral pH ranges comprises an amino acid substitution comprise a substitution i) at position EU434, or ii) at two or more positions, wherein the two or more positions are one of the combinations of the group consisting of a) EU252/EU254/EU256; b) EU428/EU434; and c) EU250/EU428. Preferably, the Fc region comprises i) the substitution M434H; or ii) one of the combinations of the group consisting of a) M252Y/S254T/T256E; b) M428L/N434S; and c) T250Q and M428L (EU numbering).

In a preferred embodiment, in step b) an amino acid is substituted at a) position EU424 or b) the positions EU438/EU440. More preferably, the substitutions are a) EU424N or b) the combination EU438R/EU440E.

In a further preferred embodiment, the methods for decreasing the binding activity for a pre-existing ADA further comprises the step c) confirming that said antigen-binding molecule with a modified Fc domain has a decreased binding activity for an endogenous ADA as compared the binding activity for the original antigen-binding molecule as set forth in step a) comprised of an intact Fc domain.

Also preferably, the antigen-binding molecule comprises additionally a pH-dependent antigen-binding domain or a Calcium ion-dependent antigen-binding domain.

The present invention provides the use of an antigen-binding molecule of the present invention for increasing antigen removal from blood of a mammal, preferably a human patient suffering from an autoimmune disease.

The present invention further provides a method for increasing the total number of antigens to which a single antigen-binding molecule can bind without significantly increasing the binding activity for a pre-existing ADA at neutral pH as compared to a parent antibody, said method comprising the steps of
a) providing an antigen-binding molecule comprising a parent FcRn binding domain,
b) altering the parent FcRn binding domain of step a) by substituting an amino acid in the amino acid sequence of the parent FcRn binding domain at one or more of the positions selected from the group consisting of EU238, EU250, EU252, EU254, EU255, EU256, EU258 EU286, EU307, EU308, EU309, EU311, EU315, EU428, EU433, EU434, and EU436; and
c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

The present invention further provides a method for facilitating the extracellular release of an antigen-free antigen-binding molecule taken up into cells in an antigen-bound form without significantly increasing the binding activity of said antigen-binding molecule for a pre-existing ADA at neutral pH as compared to a parent antibody, comprising the steps of
a) providing an antigen-binding molecule comprising a parent FcRn-binding domain,
b) altering the parent FcRn binding domain by substituting an amino acid in the amino acid sequence of the parent FcRn-binding domain at one or more positions selected from the group consisting of EU238, EU250, EU252, EU254, EU255, EU256, EU258 EU286, EU307, EU308, EU309, EU311, EU315, EU428, EU433, EU434, and EU436, and EU428; and
c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

The present invention further provides a method for increasing the ability of an antigen-binding molecule to eliminate plasma antigen without significantly increasing the binding activity for pre-existing ADA at neutral pH compared to parent antibody, said method comprising the steps of
a) providing an antigen-binding molecule comprising a parent FcRn-binding domain,
b) altering the parent FcRn binding domain by substituting an amino acid in the amino acid sequence of the parent FcRn-binding domain at one or more positions selected from the group consisting of EU238, EU250, EU252, EU254, EU255, EU256, EU258 EU286, EU307, EU308, EU309, EU311, EU315, EU428, EU433, EU434, and EU436, and EU428; and
c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

The present invention further provides a method for improving the pharmacokinetics of an antigen-binding molecule without significantly increasing the binding activity for a pre-existing ADA at neutral pH as compared to a parent antibody, said method comprising the steps of
a) providing an antigen-binding molecule comprising a parent FcRn-binding domain,
b) altering the parent FcRn binding domain by substituting an amino acid in the amino acid sequence of the parent FcRn-binding domain at one or more positions selected from the group consisting of EU238, EU250, EU252, EU254, EU255, EU256, EU258 EU286, EU307, EU308, EU309, EU311, EU315, EU428, EU433, EU434, and EU436; and
c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

The present invention further provides a method for reducing total or free antigen plasma concentration without significantly increasing the binding activity for a pre-existing ADA at neutral pH as compared to a parent antibody, said method comprising the steps of
a) providing an antigen-binding molecule comprising a parent FcRn-binding domain, wherein the antigen-binding molecule comprises an antigen-binding domain which can bind said antigen,
b) altering the parent FcRn binding domain by substituting an amino acid in the amino acid sequence of the parent FcRn-binding domain at one or more positions selected from the group consisting of EU238, EU250, EU252, EU254, EU255, EU256, EU258 EU286, EU307, EU308, EU309, EU311, EU315, EU428, EU433, EU434, and EU436; and
c) altering the modified FcRn-binding domain of step b) by substituting an amino acid in the amino acid sequence of the parent FcRn-binding domain at one or more positions selected from the group consisting of EU387, EU422, EU424, EU426, EU433, EU436, EU438 and EU440.

The preferred Fc region in step a) in the foregoing methods of use is a human Fc region. In a preferred embodiment, the amino acid substitution at one or more positions in step b) is a substitution at one or more positions selected from the group consisting of: EU238, EU250, EU252, EU254, EU255, EU258, EU286, EU307, EU308, EU309, EU311, EU315, EU428, EU433, EU434, and EU436, whereby the Fc region of step b) has an increased binding activity for FcRn and a pre-existing ADA in the neutral pH ranges. It may also comprise a substitution at position EU256 in addition to a substitution at the one or more positions mentioned above, whereby the amino acid at position EU256 is preferably substituted with a glutamic acid. More preferably, it comprises a substitution at the positions of any one of the position combinations selected from Tables 2 and 4 to 7. Even more preferably, it comprises any one of the substitutions or substitution combinations selected from any one of Table 3 and 17 to 20.

Preferably, step c) comprises substituting an amino acid at any one of the positions in Table 10. More preferably, the positions are selected from the group consisting of a) EU387, b) EU422, c) EU424, d) EU438, e) EU440, f) EU422/EU424, and g) EU438/EU440. Even more preferably, step c) comprises introducing one of the substitutions or combinations selected from Table 11.

In another preferred embodiment, the amino acid substitution at one or more positions in step b) is a substitution
i) at position EU434, or
ii) at two or more positions, wherein the two or more positions are one of the combinations of the group consisting of a) EU252/EU254/EU256; b) EU428/EU434; and c) EU250/EU428, whereby the Fc region of step b) has an increased FcRn-binding activity in the acidic ranges and an increased binding activity for a pre-existing ADA in the neutral pH ranges. Preferably, the Fc region comprises i) the substitution M434H; or
ii) one of the combinations of the group consisting of a) M252Y/S254T/T256E; b) M428L/N434S; and c) T250Q and M428L (EU numbering). In a preferred embodiment, in step c) an amino acid is substituted at a) position EU424 or b) the positions EU438/EU440. More preferably, the substitutions are a) EU424N or b) the combination EU438R/EU440E.

Pharmaceutical Composition

The present invention also relates to pharmaceutical compositions that include antigen-binding molecules of the present invention, or antigen-binding molecules produced by the production methods of the present invention. The antigen-binding molecules of the present invention and antigen-binding molecules produced by the production methods of the present invention have greater activity to reduce plasma antigen concentration by administration as compared to typical antigen-binding molecules, and are therefore useful as pharmaceutical compositions. The pharmaceutical composition of the present invention may include pharmaceutically acceptable carriers. In the present invention, pharmaceutical compositions ordinarily refer to agents for treating or preventing, or testing and diagnosing diseases.

The pharmaceutical compositions of the present invention can be formulated by methods known to those skilled in the art. For example, they can be used parenterally, in the form of injections of sterile solutions or suspensions including water or other pharmaceutically acceptable liquid. For example, such compositions may be formulated by mixing in the form of unit dose required in the generally approved medicine manufacturing practice by appropriately combining with pharmaceutically acceptable carriers or media, specifically with sterile water, physiological saline, vegetable oil, emulsifier, suspension, surfactant, stabilizer, flavoring agent, excipient, vehicle, preservative, binder, or such. In such formulations, the amount of active ingredient may be readily and routinely adjusted to obtain an appropriate amount in a pre-determined range.

Sterile compositions for injection can be formulated using vehicles such as distilled water for injection, according to standard formulation practice. Aqueous solutions for injection include, for example, physiological saline and isotonic solutions containing dextrose or other adjuvants (for example, D-sorbitol, D-mannose, D-mannitol, and sodium chloride). It is also possible to use in combination appropriate solubilizers, for example, alcohols (ethanol and such), polyalcohols (propylene glycol, polyethylene glycol, and such), non-ionic surfactants (polysorbate 80™, HCO-50, and such).

Oils include sesame oil and soybean oils. Benzyl benzoate and/or benzyl alcohol can be used in combination as solubilizers. It is also possible to combine buffers (for example, phosphate buffer and sodium acetate buffer), soothing agents (for example, procaine hydrochloride), stabilizers (for example, benzyl alcohol and phenol), and/or antioxidants. Appropriate ampules are filled with the prepared injections.

The pharmaceutical compositions of the present invention are preferably administered parenterally. For example, the compositions may be in the dosage form for injections, transnasal administration, transpulmonary administration, or transdermal administration. Such compositions may be administered systemically or locally by intravenous injection, intramuscular injection, intraperitoneal injection, subcutaneous injection, or such.

Administration methods can be appropriately selected in consideration of the patient's age and symptoms. The dose of a pharmaceutical composition containing an antigen-binding molecule may be, for example, from 0.0001 to 1,000 mg/kg for each administration. Alternatively, the dose may be, for example, from 0.001 to 100,000 mg per patient. However, the present invention is not limited by the numeric values described above. The doses and administration methods vary depending on the patient's weight, age, symptoms, and such. Those skilled in the art can set appropriate doses and administration methods in consideration of the factors described above.

Amino acids contained in the amino acid sequences of the present invention may be post-translationally modified. For example, the modification of an N-terminal glutamine into a pyroglutamic acid by pyroglutamylation is well-known to those skilled in the art. Naturally, such post-translationally modified amino acids are included in the amino acid sequences in the present invention.

Production Methods

The present invention provides methods for producing antigen-binding molecules of the present invention. In particular, the present invention provides a method for producing antigen-binding molecules having an FcRn-binding domain with an increased binding activity for FcRn at neutral pH as compared to an antigen-binding molecule comprising a wild type Fc region.

The present invention provides a method for producing an antigen-binding molecule, which comprises the steps of:
(a) selecting a parent FcRn-binding domain and altering the parent FcRn with a substitution of an amino acid in the amino acid sequence with another amino acid at one or more positions selected from the group consisting of EU252, EU434, EU436, EU315, EU311, EU308, EU307, EU286, EU254, EU250, EU238, EU387, EU422, EU424, EU428, EU438 and EU440;
(b) selecting an antigen-binding domain of an antigen-binding molecule and altering at least one amino acid in the antigen-binding domain in order to get a pH-dependent antigen-binding domain or a calcium-ion dependent antigen-binding domain;
(c) obtaining a gene encoding an antigen-binding molecule in which the human FcRn-binding domain and the antigen-binding domain prepared in (a) and (b) are linked; and
(d) producing an antigen-binding molecule using the gene prepared in (c).

Preferably, the selected antigen-binding molecule comprises an antigen-binding domain that has a lower binding activity for the antigen at a pH 5.5-6.5 than at pH 7-8 or has a calcium dependent antigen binding activity. Preferably, the FcRn-binding domain of step a) is a FcRn-binding domain of the present invention. More preferably, the FcRn-binding domain comprises an amino acid substations at three or more positions, wherein said three or more positions are one of the combinations set forth in Tables 2, and 4 to 7. Even more preferably, the FcRn-binding domain comprises three or more substitutions wherein said three or more substitutions are one of the combinations set forth in Tables 3, 17 to 20.

Steps (a) may comprise substituting an amino acid substitution at one or more positions selected from the group consisting of EU238, EU250, EU252, EU254, EU255, EU258, EU286, EU307, EU308, EU309, EU311, EU315, EU428, EU433, EU434, and EU436 and selecting a FcRn-binding domain that has stronger human FcRn-binding activity in the neutral pH range than KD 3.2 micromolar.

Step (b) may comprise selecting an antigen-binding domain and altering at least one amino acid in the antigen-binding domain as described above in order to get a pH-dependent antigen-binding domain, or selecting a calcium-ion dependent antigen-binding domain. Altering an amino acid is preferably substituting histidine for at least one amino acid or inserting at least one histidine. Meanwhile, the site where the at least one histidine mutation is introduced is not particularly limited, and thus it may be introduced at any position as long as the histidine mutation reduces the antigen-binding activity in the acidic pH range to less than that in the neutral pH range. Such histidine mutations may be introduced at a single site or two or more sites. Steps a) and b) may be repeated twice or more times. The number of times of repeating steps (a) and (b) is not particularly limited; however, the number is typically ten times or less.

A linker operably linking the FcRn-binding domain and the antigen-binding domain prepared in (a) and (b) is not limited to any form. The human FcRn-binding domain and the antigen-binding domain can be linked by either covalent or non-covalent forces. In particular, the linker can be a peptide linker or a chemical linker or a binding pair like a combination of biotin and streptavidin. Modification of a polypeptide including the human FcRn-binding domain and the antigen-binding domain is known in the art. In another embodiment, the human FcRn-binding domain and the antigen-binding domain of the present invention can be linked by forming a fusion protein between the human FcRn-binding domain and the antigen-binding domain. In order to construct fusion protein between the human FcRn-binding domain and the antigen-binding domain, genes encoding the human FcRn-binding domain and the antigen-binding domain can be operationally linked so as to form in frame fusion polypeptide. Appropriately, a linker comprising peptide consisting of several amino acids can be inserted between the human FcRn-binding domain and the antigen-binding domain. Various flexible linkers like the linker whose sequence consists of (GGGGS)n (SEQ ID NO: 11) is known in the art.

The present invention further provides a method for producing an antigen-binding molecule comprising an FcRn-binding domain with an increased binding activity for FcRn at neutral or acidic pH without a significantly increased binding activity for a pre-existing ADA at neutral pH compared to an antigen-binding molecule comprising a wild type Fc region.

Preferably, the methods for producing an antigen-binding molecule comprising a Fc region with an increased binding activity for FcRn at neutral or acidic pH and a decreased binding activity for an pre-existing ADA at neutral pH, comprises the steps of:

(a) providing a Fc region having an increased binding activity for FcRn in the neutral or acidic pH ranges and an increased binding activity for a pre-existing ADA in the neutral pH ranges, b) substituting an amino acid in the amino acid sequence of the Fc region at one or more of the positions selected from the group consisting of EU387, EU422, EU424, EU426, EU433, EU436, EU438 and EU440.

(c) altering at least one amino acid in the antigen-binding domain of an antigen-binding molecule and selecting an antigen-binding molecule that has stronger antigen-binding activity in the neutral pH range than in the acidic pH range;

(d) obtaining a gene encoding an antigen-binding molecule in which the human FcRn-binding domain prepared in (b) and the antigen-binding domain prepared in (c) are linked and (e) producing an antigen-binding molecule using the gene prepared in (d).

The preferred Fc region in step a) is a human Fc region. Preferably, the Fc region having an increased binding activity for FcRn and pre-existing ADA at neutral or acidic pH ranges and for pre-existing ADA in the neutral pH ranges comprises a substitution of an amino acid at one or more positions selected from the group consisting of: EU238, EU250, EU252, EU254, EU255, EU258, EU286, EU307, EU308, EU309, EU311, EU315, EU428, EU433, EU434, and EU436. More preferably, it comprises substitutions at the positions of any one of the position combinations selected from Tables 2 and 4 to 7. Even more preferably, it comprises any one of the substitutions or combinations of substitutions set forth in any one of Tables 3 and 17 to 20. Preferably, step a) includes providing a nucleotide sequence encoding an Fc region having an increased binding activity for FcRn and pre-existing ADA at neutral or acidic pH ranges. Preferably, the substitutions in step b) amino acid substitutions at one or more positions or a position combination as set forth in Table 10. More preferably, the substitutions of step b) are one of the substitution combinations set forth in Table 11. The amino acid at one or more of the positions selected from the group consisting of EU387, EU422, EU424, EU426, EU433, EU436, EU438 and EU440 in step b) is preferably substituted by replacing one or more nucleotides in the nucleotide sequence.

Steps (b) and (c) may be carried out in either order. Furthermore, step c) may comprise altering at least one amino acid in the antigen-binding domain as described above in order to get a pH-dependent antigen-binding domain, or selecting a calcium-ion dependent antigen-binding domain. In step (c), altering an amino acid is preferably substituting histidine for at least one amino acid or inserting at least one histidine. Meanwhile, the site where the at least one histidine mutation is introduced is not particularly limited, and thus it may be introduced at any position as long as the histidine mutation reduces the antigen-binding activity in the acidic pH range to less than that in the neutral pH range. Such histidine mutations may be introduced at a single site or two or more sites. Steps b) and c) may be repeated twice or more times. The number of times of repeating steps (b) and (c) is not particularly limited; however, the number is typically ten times or less.

A linker operably linking the FcRn-binding domain and the antigen-binding domain prepared in (b) and (c) is not limited to any form. The human FcRn-binding domain and the antigen-binding domain can be linked by either covalent or non-covalent forces. In particular, the linker can be a peptide linker or a chemical linker or a binding pair like a combination of biotin and streptavidin. Modification of a polypeptide including the human FcRn-binding domain and the antigen-binding domain is known in the art. In another embodiment, the human FcRn-binding domain and the antigen-binding domain of the present invention can be linked by forming a fusion protein between the human FcRn-binding domain and the antigen-binding domain. In order to construct the fusion protein between the human FcRn-binding domain and the antigen-binding domain, genes encoding the human FcRn-binding domain and the antigen-binding domain can be operationally linked so as to form in frame fusion polypeptide. Appropriately, a linker comprising peptide consisting of several amino acids can be inserted between the human FcRn-binding domain and the antigen-binding domain. Various flexible linkers like the linker whose sequence consists of (GGGGS)n (SEQ ID NO: 11) is known in the art.

Thus, the production methods of the present invention may further comprise the steps of altering the above-described amino acids and substituting or inserting histidine. In the production methods of the present invention, non-natural amino acids may be used instead of histidine. Therefore, the present invention can also be understood by replacing the above-mentioned histidine with non-natural amino acids.

Step a) of the production methods of the present invention may also comprise a substitution at position EU256 in addition to a substitution at the one or more positions mentioned above, whereby the amino acid at position EU256 is preferably substituted with a glutamic acid.

Furthermore, the production methods of the present invention may further comprise a step comprising substituting an amino acid in the amino acid sequence of the Fc region at one or more of the positions selected from the group consisting of EU234, EU235, EU236, EU237, EU238, EU239, EU265, EU266, EU267, EU269, EU270, EU271, EU295, EU296, EU297 EU298, EU300, EU324, EU325, EU327, EU328, EU329, EU331, and EU332 (according to the EU numbering system). Preferably, the substitutions L235R/S239K are introduced.

Parent FcRn-binding domains and antigen-binding molecules comprising them that are used in the production methods of the present invention may be prepared by any method. For example, it is possible to use pre-existing antibodies, pre-existing libraries (phage libraries and the like), antibodies and libraries that are prepared from hybridomas obtained by immunizing animals or from B cells of immunized animals, antibodies and libraries prepared by introducing random amino acid alterations into the above-described antibodies and libraries, antibodies and libraries prepared by introducing histidine or non-natural amino acid mutations into the above-described antibodies and libraries (libraries with high content of histidine or non-natural amino acid, libraries introduced with histidine or non-natural amino acid at specific sites, and the like), and such.

The antigen-binding activity and human FcRn binding activity of an antigen-binding molecule can be determined by methods known to those skilled in the art. Conditions except for pH can be appropriately determined by those skilled in the art.

In the above-described production methods, the antigen and antigen-binding molecule may bind to each other in any state, and the human FcRn and antigen-binding molecule may bind to each other in any state. The state is not particularly limited; for example, the antigen or human FcRn may be contacted with an immobilized antigen-binding molecule to bind the antigen-binding molecule. Alternatively, the antigen-binding molecule may be contacted with an immobilized antigen or human FcRn to bind the antigen-binding molecule. Alternatively, the antigen-binding molecule may be contacted with the antigen or human FcRn in a solution to bind the antigen-binding molecule.

The antigen-binding molecules produced by the above-described methods may be any antigen-binding molecule of the present invention; and preferred antigen-binding molecules include, for example, those having an antigen-binding domain which is an ionized calcium-concentration dependent antigen-binding domain or an antigen-binding domain with histidine substitution for amino acid(s) or insertion of at least one histidine, and said antigen-binding molecule further comprising a human FcRn-binding domain, which comprise an amino acid substitution at one or more positions selected from the group consisting of EU238, EU250, EU252, EU254, EU255, EU258, EU286, EU307, EU308, EU309, EU311, EU315, EU428, EU433, EU434, and EU436 (EU numbering). The antigen-binding molecule of the present invention may also comprise a substitution at position EU256 in addition to a substitution at the one or more positions mentioned above. Preferably, the amino acid at position EU256 is substituted with a glutamic acid. More preferably, the FcRn-binding domain comprises an amino acid substations at three or more positions, wherein said three or more positions are one of the combinations set forth in Tables 2, and 4 to 7. Even more preferably, the FcRn-binding domain comprises three or more substitutions wherein said three or more substitutions are one of the combinations set forth in Tables 3, 17 to 20.

Further preferred antigen-binding molecules include for example, those having an antigen-binding domain which is an ionized calcium-concentration dependent antigen-binding domain or an antigen-binding domain with histidine substitution for amino acid(s) or insertion of at least one histidine, and said antigen-binding molecule further comprising a human Fc region with substitutions of the amino acid at one or more of the positions selected from the group consisting of: EU387, EU422, EU424, EU426, EU433, EU436, EU438 and EU440. More preferably, the FcRn-binding domain contains substitutions of an amino acid in the human FcRn-binding domain at three or more positions wherein said three or more positions are one of the combinations set forth in Tables 9 and 10.

A more preferred antigen-binding molecule includes those having those having an antigen-binding domain which is an ionized calcium-concentration dependent antigen-binding domain or an antigen-binding domain with histidine substitution for amino acid(s) or insertion of at least one histidine, and said antigen-binding molecule further comprising a human Fc region with substitutions of the amino acid
a) at one or more of the positions selected from the group consisting of EU238, EU250, EU252, EU254, EU255, EU256, EU258, EU286, EU307, EU308, EU309, EU311, EU315, EU428, EU433, EU434, and EU436, and
b) at one or more of the positions selected from the group consisting of: EU387, EU422, EU424, EU426, EU433, EU436, EU438 and EU440 (EU numbering).

Preferably, the amino acid at position EU256 is substituted with a glutamic acid. More preferably, the antigen-binding molecules comprise a substitution combination set forth in Tables 11 to 13.

An antibody having a desired activity may be selected by screening from a number of antibodies obtained from the antibody libraries or hybridomas described below.

When altering amino acids in an antigen-binding molecule, it is possible to use a known sequence for the amino acid sequence of an antigen-binding molecule before alteration or the amino acid sequence of an antigen-binding molecule newly identified by methods known to those skilled in the art. For example, when the antigen-binding molecule is an antibody, it can be obtained from antibody libraries or by cloning an antibody-encoding gene from monoclonal antibody-producing hybridomas.

Regarding antibody libraries, many antibody libraries are already known, and methods for producing antibody libraries are also known; therefore, those skilled in the art can appropriately obtain antibody libraries. For example, regarding phage libraries, one can refer to the literature such as Clackson et al., Nature (1991) 352: 624-8; Marks et al., J. Mol. Biol. (1991) 222: 581-97; Waterhouses et al., Nucleic Acids Res. (1993) 21: 2265-6; Griffiths et al., EMBO J. (1994) 13: 324.0-60; Vaughan et al., Nature Biotechnology (1996) 14: 309-14; and Japanese Patent Kohyo Publication No. (JP-A) H20-504970 (unexamined Japanese national phase publication corresponding to a non-Japanese international publication). In addition, it is possible to use known methods, such as methods using eukaryotic cells as libraries (WO 95/15393) and ribosome display methods. Furthermore, technologies to obtain human antibodies by panning using human antibody libraries are also known. For example, variable regions of human antibodies can be expressed on the surface of phages as single chain antibodies (scFvs) using phage display methods, and phages that bind to antigens can be selected. Genetic analysis of the selected phages can determine the DNA sequences encoding the variable regions of human antibodies that bind to the antigens. Once the DNA sequences of scFvs that bind to the antigens is revealed, suitable expression vectors can be produced based on these sequences to obtain human antibodies. These methods are already well known, and one can refer to WO 92/01047, WO 92/20791, WO 93/06213, WO 93/11236, WO 93/19172, WO 95/01438, and WO 95/15388.

As for methods for obtaining genes encoding antibodies from hybridomas, known technologies may be basically used, which involve the use of desired antigens or cells expressing the desired antigens as sensitizing antigens, using these to perform immunizations according to conventional immunization methods, fusing the resulting immune cells with known parent cells by conventional cell fusion methods, screening monoclonal antibody producing cells (hybridomas) by conventional screening methods, synthesizing cDNAs of antibody variable regions (V regions) from mRNAs of the obtained hybridomas using reverse transcriptase, and linking them with DNAs encoding the desired antibody constant regions (C regions).

More specifically, sensitizing antigens to obtain the above-described antigen-binding molecule genes encoding the H chains and L chains may include, for example, both complete antigens with immunogenicity and incomplete antigens including haptens and the like with no immunogenicity; however they are not limited to these examples. For example, it is possible to use whole proteins and partial peptides of proteins of interest. In addition, it is known that substances comprising polysaccharides, nucleic acids, lipids, and such can be antigens. Thus, the antigens of the antigen-binding molecules of the present invention are not particularly limited. The antigens can be prepared by methods known to those skilled in the art, for example, by baculovirus-based methods (for example, WO 98/46777) and such. Hybridomas can be produced, for example, by the method of Milstein et al. (G. Kohler and C. Milstein, Methods Enzymol. (1981) 73: 3-46) and such. When the immunogenicity of an antigen is low, immunization may be performed after linking the antigen with a macromolecule having immunogenicity, such as albumin. Alternatively, if necessary, antigens may be converted into soluble antigens by linking them with other molecules. When transmembrane molecules such as membrane antigens (for example, receptors) are used as antigens, portions of the extracellular regions of the membrane antigens can be used as a fragment, or cells expressing transmembrane molecules on their cell surface may be used as immunogens.

Antigen-binding molecule-producing cells can be obtained by immunizing animals using appropriate sensitizing antigens described above. Alternatively, antigen-binding molecule-producing cells can be prepared by in vitro immunization of lymphocytes that can produce antigen-binding molecules. Various mammals can be used for immunization; such commonly used animals include rodents, lagomorphas, and primates. Such animals include, for example, rodents such as mice, rats, and hamsters; lagomorphas such as rabbits; and primates including monkeys such as cynomolgus monkeys, rhesus monkeys, baboons, and chimpanzees. In addition, transgenic animals carrying human antibody gene repertoires are also known, and human antibodies can be obtained by using these animals (see WO 96/34096; Mendez et al., Nat. Genet. (1997) 15: 146-56). Instead of using such transgenic animals, for example, desired human antibodies having binding activity against antigens can be obtained by in vitro sensitization of human lymphocytes with desired antigens or cells expressing the desired antigens, and then fusing the sensitized lymphocytes with human myeloma cells such as U266 (see Japanese Patent Application Kokoku Publication No. (JP-B) H01-59878 (examined, approved Japanese patent application published for opposition)). Furthermore, desired human antibodies can be obtained by immunizing transgenic animals carrying a complete repertoire of human antibody genes, with desired antigens (see WO 93/12227, WO 92/03918, WO 94/02602, WO 96/34096, and WO 96/33735).

Animal immunization can be carried out by appropriately diluting and suspending a sensitizing antigen in phosphate buffered saline (PBS), physiological saline, or such, and mixing it with an adjuvant to emulsify, if necessary. This is then intraperitoneally or subcutaneously injected into animals. Then, the sensitizing antigen mixed with Freund's incomplete adjuvant is preferably administered several times every four to 21 days. Antibody production can be confirmed by measuring the titer of the antibody of interest in animal sera using conventional methods.

Antigen-binding molecule-producing cells obtained from lymphocytes or animals immunized with a desired antigen can be fused with myeloma cells to generate hybridomas using conventional fusing agents (for example, polyethylene glycol) (Goding, Monoclonal Antibodies: Principles and Practice, Academic Press, (1986) 59-103). When required, hybridoma cells can be cultured and grown, and the binding specificity of the antigen-binding molecule produced from these hybridomas can be measured using known analysis methods, such as immunoprecipitation, radioimmunoassay (RIA), and enzyme-linked immunosorbent assay (ELISA). Thereafter, if necessary, hybridomas producing antigen-binding molecules of interest whose specificity, affinity, or activity has been determined can be subcloned by methods such as limiting dilution.

Next, genes encoding the selected antigen-binding molecules can be cloned from hybridomas or antigen-binding molecule-producing cells (sensitized lymphocytes, and such) using probes that can specifically bind to the antigen-binding molecules (for example, oligonucleotides complementary to sequences encoding the antibody constant regions). It is also possible to clone the genes from mRNA using RT-PCR. Immunoglobulins are classified into five different classes, IgA, IgD, IgE, IgG, and IgM. These classes are further divided into several subclasses (isotypes) (for example, IgG-1, IgG-2, IgG-3, and IgG-4; IgA-1 and IgA-2; and such). H chains and L chains used in the present invention to produce antigen-binding molecules are not particularly limited and may originate from antibodies belonging to any of these classes or subclasses; however, IgG is particularly preferred.

Herein, it is possible to alter H-chain-encoding genes and L-chain-encoding genes using genetic engineering technologies. Genetically altered antibodies, such as chimeric antibodies and humanized antibodies, which have been artificially altered for the purpose of decreasing heterologous immunogenicity and such against humans, can be appropriately produced for antibodies such as mouse antibodies, rat antibodies, rabbit antibodies, hamster antibodies, sheep antibodies, and camel antibodies. Chimeric antibodies are antibodies including H-chain and L-chain variable regions of nonhuman mammal antibody, such as mouse antibody, and the H-chain and L-chain constant regions of human antibody. Chimeric antibodies can be obtained by ligating a DNA encoding a variable region of a mouse antibody to a DNA encoding a constant region of a human antibody, inserting this into an expression vector, and introducing the vector into a host to produce the antibody. A humanized antibody, which is also called a reshaped human antibody, can be synthesized by PCR using several oligonucleotides produced so that they have overlapping portions at the ends of DNA sequences designed to link the complementarity determining regions (CDRs) of an antibody of a nonhuman mammal such as a mouse. The resulting DNA can be ligated to a DNA encoding a human antibody constant region. The ligated DNA can be inserted into an expression vector, and the vector can be introduced into a host to produce the antibody (see EP 239400 and WO 96/02576). Human antibody FRs that are ligated via the CDR are selected when the CDR forms a favorable antigen-binding site. If necessary, amino acids in the framework region of an antibody variable region may be replaced such that the CDR of the reshaped human antibody forms an appropriate antigen-binding site (K. Sato et al., Cancer Res. (1993) 53: 10.01-10.06).

In addition to the humanization described above, antibodies may be altered to improve their biological properties, for example, the binding to the antigen. In the present invention, such alterations can be achieved by methods such as site-directed mutagenesis (see for example, Kunkel (1910.0) Proc. Natl. Acad. Sci. USA 82: 488), PCR mutagenesis, and cassette mutagenesis. In general, mutant antibodies whose biological properties have been improved show amino acid sequence homology and/or similarity of 70% or higher, more preferably 80% or higher, and even more preferably 90% or higher (for example, 95% or higher, 97%, 98%, or 99%), when compared to the amino acid sequence of the original antibody variable region. Herein, sequence homology and/or similarity is defined as the ratio of amino acid residues that are homologous (same residue) or similar (amino acid residues classified into the same group based on the general properties of amino acid side chains) to the original antibody residues, after the sequence homology value has been maximized by sequence alignment and gap introduction, if necessary. In general, natural amino acid residues are classified into groups based on the characteristics of their side chains as follows:

(1) hydrophobic: alanine, isoleucine, valine, methionine, and leucine;
(2) neutral hydrophilic: asparagine, glutamine, cysteine, threonine, and serine;
(3) acidic: aspartic acid and glutamic acid;
(4) basic: arginine, histidine, and lysine;
(5) residues that affect the orientation of the chain: glycine, and proline; and
(6) aromatic: tyrosine, tryptophan, and phenylalanine Furthermore, the present invention provides genes encoding the FcRn-binding domain of the present invention and the antigen-binding molecules of the present invention. The genes encoding the antigen-binding molecules of the present invention may be any genes, and may be DNAs, RNAs, nucleic acid analogs, or the like.

Furthermore, the present invention also provides host cells carrying the genes described above. The host cells are not particularly limited and include, for example, *E. coli* and various animal cells. The host cells may be used, for example, as a production system to produce and express the antibodies of the present invention. In vitro and in vivo production systems are available for polypeptide production systems. Such in vitro production systems include, for example, production systems using eukaryotic cells or prokaryotic cells.

Eukaryotic cells that can be used as host cells include, for example, animal cells, plant cells, and fungal cells. Animal cells include: mammalian cells, for example, CHO(Chinese hamster ovary cell line), COS (Monkey kidney cell line), myeloma (Sp2/O, NS0 etc), BHK (baby hamster kidney cell line) Hela, Vero, HEK293 (human embryonic kidney cell line with sheared adenovirus (Ad)5 DNA), PER.C6 cell (human embryonic retinal cell line transformed with the Adenovirus Type 5 (Ad5) E1A and E1B genes) 293, etc (see Current Protocols in Protein Science (May, 2001, Unit 5.9, Table 5.9.1)), amphibian cells such as *Xenopus laevis* oocytes (Valle et al., Nature (1981) 291: 338-340); and insect cells such as Sf9, Sf21, and Tn5.CHO-DG44, CHO-DX11B, COS7 cells, HEK293 cells, and BHK cells are preferably used to express the antibodies of the present invention. Among animal cells, CHO cells are particularly preferable for large-scale expression. Vectors can be introduced into host cells, for example, by calcium phosphate methods, DEAE-dextran methods, methods using cationic liposome DOTAP (Boehringer-Mannheim), electroporation methods, and lipofection methods.

Regarding plant cells, for example, *Nicotiana tabacum*-derived cells and duckweed (*Lemna minor*) are known as a protein production system. Calluses can be cultured from these cells to produce the antigen-binding molecules of the present invention. Regarding fungal cells, known protein expression systems are those using yeast cells, for example, cells of genus *Saccharomyces* (such as *Saccharomyces cerevisiae* and *Saccharomyces pombe*); and cells of filamentous fungi, for example, genus *Aspergillus* (such as *Aspergillus niger*). These cells can be used as a host to produce the antigen-binding molecules of the present invention.

Bacterial cells can be used in the prokaryotic production systems. Regarding bacterial cells, production systems using *Bacillus subtilis* are known in addition to the production systems using *E. coli* described above. Such systems can be used in producing the antigen-binding molecules of the present invention.

Genes obtained by the production methods of the present invention are typically carried by (inserted into) appropriate vectors, and then introduced into host cells. The vectors are not particularly limited as long as they stably retain the inserted nucleic acids. For example, when *E. coli* is used as the host, preferred cloning vectors include pBluescript vector (Stratagene); however, various commercially available vectors may be used. When using vectors to produce the antigen-binding molecules of the present invention, expression vectors are particularly useful. The expression vectors are not particularly limited as long as the vectors express the antigen-binding molecules in vitro, in *E. coli*, in culture cells, or in a body of an organism. For example, pBEST vector (Promega) is preferred for in vitro expression; pET vector (Invitrogen) is preferred for *E. coli*; pME18S-FL3 vector (GenBank Accession No. AB009864) is preferred for culture cells; and pME18S vector (Mol Cell Biol. (1988) 8: 466-472) is preferred for bodies of organisms. In addition, EBNA1 protein may be co-expressed to increase the number of copies of the gene of interest. In this case, a vector that includes OriP as a initiation site of replication is used (Biotechnol Bioeng. 2001 Oct. 20; 75(2):197-203, Biotechnol Bioeng. 2005 Sep. 20; 91(6):670-7.) DNAs of the present invention can be inserted into the vectors by conventional methods, for example, by ligation using restriction enzyme sites (Current protocols in Molecular Biology, edit. Ausubel et al., (1987) Publish. John Wiley & Sons, Section 11.4-11.11).

The above host cells are not particularly limited, and various host cells may be used depending on the purpose. Examples of cells for expressing the antigen-binding molecules include bacterial cells (such as those of *Streptococcus, Staphylococcus, E. coli, Streptomyces,* and *Bacillus subtilis*), eukaryotic cells (such as those of yeast and *Aspergillus*), insect cells (such as *Drosophila* S2 and *Spodoptera* SF9), animal cells (such as CHO, COS, HeLa, C127, 3T3, BHK, HEK293, and Bowes melanoma cells), and plant cells. Vectors can be introduced into a host cell by known methods, for example, calcium phosphate precipitation methods, electroporation methods (Current protocols in Molecular Biology edit. Ausubel et al. (1987) Publish. John Wiley & Sons, Section 9.1-9.9), lipofection methods, and microinjection methods.

The host cells can be cultured by known methods. For example, when using animal cells as a host, DMEM, MEM, RPMI1640, or IMDM may be used as the culture medium. They may be used with serum supplements such as FBS or fetal calf serum (FCS). The cells may be cultured in serum-free cultures. The preferred pH is about 6 to 8 during the course of culturing. Incubation is carried out typically at 30 to 40 degrees C. for about 15 to 200 hours. Medium is exchanged, aerated, or agitated, as necessary.

Appropriate secretion signals may be incorporated to polypeptides of interest so that the antigen-binding molecules expressed in the host cell are secreted into the lumen of the endoplasmic reticulum, into the periplasmic space, or into the extracellular environment. These signals may be endogenous to the antigen-binding molecules of interest or may be heterologous signals.

On the other hand, for example, production systems using animals or plants may be used as systems for producing polypeptides in vivo. A polynucleotide of interest is introduced into an animal or plant and the polypeptide is produced in the body of the animal or plant, and then collected. The "hosts" of the present invention include such animals and plants.

The production system using animals include those using mammals or insects. It is possible to use mammals such as goats, pigs, sheep, mice, and bovines (Vicki Glaser SPECTRUM Biotechnology Applications (1993)). The mammals may be transgenic animals.

For example, a polynucleotide encoding an antigen-binding molecule of the present invention is prepared as a fusion gene with a gene encoding a polypeptide specifically produced in milk, such as the goat beta-casein. Next, goat embryos are injected with polynucleotide fragments containing the fusion gene, and then transplanted to female goats. Desired antigen-binding molecules can be obtained from milk produced by the transgenic goats, which are born from the goats that received the embryos, or from their offspring. Hormones may be administered as appropriate to increase the volume of milk containing the antigen-binding molecule produced by the transgenic goats (Ebert et al., Bio/Technology (1994) 12: 699-702).

Insects such as silkworms may be used to produce the antigen-binding molecules of the present invention. When silkworms are used, baculoviruses carrying a polynucleotide encoding an antigen-binding molecule of interest can be used to infect silkworms, and the antigen-binding molecule of interest can be obtained from their body fluids.

Furthermore, when plants are used to produce the antigen-binding molecules of the present invention, for example, tobacco may be used. When tobacco is used, a polynucleotide encoding an antigen-binding molecule of interest is inserted into a plant expression vector, for example, pMON 530, and then the vector is introduced into bacteria, such as *Agrobacterium tumefaciens*. The bacteria are then allowed to infect tobacco such as *Nicotiana tabacum*, and the desired antigen-binding molecules can be collected from their leaves (Ma et al., Eur. J. Immunol. (1994) 24: 131-138). Alternatively, it is possible to infect duckweed (*Lemna minor*) with similar bacteria. After cloning, the desired antigen-binding molecules can be obtained from the duckweed cells (Cox K M et al., Nat. Biotechnol. 2006 December; 24(12): 1591-1597).

The thus obtained antigen-binding molecules may be isolated from the inside or outside (such as the medium and milk) of host cells, and purified as substantially pure and homogenous antigen-binding molecules. The methods for isolating and purifying antigen-binding molecules are not particularly limited, and isolation and purification methods usually used for polypeptide purification can be used. Antigen-binding molecules may be isolated and purified, by appropriately selecting and combining, for example, chromatographic columns, filtration, ultrafiltration, salting out, solvent precipitation, solvent extraction, distillation, immunoprecipitation, SDS-polyacrylamide gel electrophoresis, isoelectric focusing, dialysis, and recrystallization.

Examples of chromatography techniques include, but are not limited to, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., (1996) Cold Spring Harbor Laboratory Press). Such chromatographic methods can be conducted using liquid phase chromatography such as HPLC and FPLC. Columns used for affinity chromatography include, protein A columns and protein G columns. Columns using protein A include, for example, Hyper D, POROS, and Sepharose F. F. (Pharmacia).

If necessary, an antigen-binding molecule can be modified arbitrarily, and peptides can be partially deleted by allowing an appropriate protein modification enzyme to act before or after purification of the antigen-binding molecule. Such protein modification enzymes include, for example, trypsin, chymotrypsin, lysyl endopeptidases, protein kinases, and glucosidases.

EXAMPLES

While the present invention is herein described in detail and with reference to specific embodiments thereof, it is to be understood that the foregoing description is exemplary and explanatory in nature and is intended to illustrate the present invention and its preferred embodiments. Through routine experimentation, one skilled in the art will readily recognize that various changes and modifications can be made therein without departing from the spirit and scope of the present invention, the metes and bounds of which are defined by the appended claims.

[Example 1] Construction of New Neutral pH FcRn Binding Affinity Improved Fc Variants Fc regions of the antigen-binding molecule (antibody) which interacts with FcRn (Nat Rev Immunol. 2007 September; 7(9):715-25) were engineered to have an improved binding affinity to FcRn at neutral pH in order to enhance the antigen elimination from plasma. The mechanism of antigen elimination from plasma by pH-dependent antigen binding antibody with improved binding affinity to FcRn at neutral pH in comparison to the conventional antibody is shown in FIG. 1A.

The Examples 1-17 of WO2011/122011 disclose mutations (amino acid substitutions) that improve the binding affinity to FcRn at neutral pH and describes Fc variants F1 to F599 (Table 16) that were generated with the focus on improving the binding affinity to FcRn at neutral pH of antibodies. However, for the pharmaceutical development of antibodies comprising such Fc variants, not only their pharmacological property (i.e improved FcRn binding) but also stability, purity and immunogenicity should be considered. Antibodies which exhibit poor stability and purity are not suitable as a drug, and poor immunogenicity would hinder their clinical development.

1-1. Design and Generation of Fc Variants with Improved Binding Affinity to hFcRn at Neutral pH Various Fc variants with improved binding affinity to hFcRn at neutral pH while maintaining high stability, high purity and low immunogenicity risk were designed. Mutations (amino acid substitutions) introduced into Fc region of wild type IgG1 are shown for each Fc variants in Table 16 (IgG1-F1 to F1434). The amino acid substitutions were introduced into VH3-IgG1 (SEQ ID NO: 1) to generate Fc variants by the method known to those skilled in the art described in Reference Example 1 of WO2011/122011.

TABLE 16

| Fc variants | | | | | |
|---|---|---|---|---|---|
| Variant name | hFcRn KD (M) | Tm (° C.) | HMW (%) | Immuno-genicity score | Mutation |
| IgG | 8.8E−5 | nd | nd | nd | none |
| M73 | 1.4E−05 | nd | nd | nd | (see WO209/125825) |
| F1 | 8.1E−07 | 67.6 | 12.64 | 91 | N434W |
| F2 | 3.2E−06 | 64.7 | 2.96 | 39 | M252Y/S254T/T256E |
| F3 | 2.5E−06 | 68.5 | 1.43 | 112 | N434Y |
| F4 | 5.8E−06 | 68.5 | 0.58 | 38 | N434S |
| F5 | 6.8E−06 | 69.2 | 0.29 | 16 | N434A |
| F7 | 5.6E−06 | 65.5 | 0.60 | 131 | M252Y |
| F8 | 4.2E−06 | 64.3 | 0.97 | 84 | M252W |
| F9 | 1.4E−07 | 62.6 | 0.72 | 152 | M252Y/S254T/T256E/N434Y |
| F10 | 6.9E−08 | 61.7 | 0.94 | 130 | M252Y/S254T/T256E/N434W |
| F11 | 3.1E−07 | 64.6 | 0.73 | 243 | M252Y/N434Y |
| F12 | 1.7E−07 | 63.8 | 10.11 | 222 | M252Y/N434W |
| F13 | 3.2E−07 | 63.7 | 1.21 | 196 | M252W/N434Y |
| F14 | 1.8E−07 | 62.9 | 17.73 | 175 | M252W/N434W |
| F19 | 4.6E−07 | 63.8 | 2.88 | 228 | P257L/N434Y |
| F20 | 4.6E−07 | 54.8 | 1.96 | 327 | V308F/N434Y |
| F21 | 3.0E−08 | 56.6 | 0.81 | 424 | M252Y/V308P/N434Y |
| F22 | 2.0E−06 | 69.8 | 1.26 | 116 | M428L/N434S |
| F25 | 9.2E−09 | 54.9 | 9.95 | 311 | M252Y/S254T/T256E/V308P/N434W |
| F26 | 1.0E−06 | 68.4 | 0.31 | 2 | I332V |
| F27 | 7.4E−06 | 69.6 | 0.85 | 113 | G237M |
| F29 | 1.4E−06 | 67.1 | 0.79 | 114 | I332V/N434Y |
| F31 | 2.8E−06 | 56.3 | 0.97 | 328 | G237M/V308F |
| F32 | 8.0E−07 | 67.7 | 11.90 | 122 | S254T/N434W |
| F33 | 2.3E−06 | 68.4 | 0.49 | 144 | S254T/N434Y |
| F34 | 2.8E−07 | 64.6 | 10.22 | 93 | T256E/N434W |
| F35 | 8.4E−07 | 66.1 | 1.15 | 115 | T256E/N434Y |
| F36 | 3.6E−07 | 64.9 | 14.88 | 118 | S254T/T256E/N434W |
| F37 | 1.1E−06 | 65.6 | 0.68 | 140 | S254T/T256E/N434Y |
| F38 | 1.0E−07 | 64.1 | 11.74 | 193 | M252Y/S254T/N434W |
| F39 | 3.0E−07 | 64.8 | 0.84 | 214 | M252Y/S254T/N434Y |
| F40 | 8.2E−08 | 61.4 | 11.54 | 130 | M252Y/T256E/N434W |
| F41 | 1.5E−07 | 61.7 | 0.77 | 152 | M252Y/T256E/N434Y |
| F42 | 1.0E−06 | 63.2 | 0.81 | 56 | M252Y/S254T/T256E/N434A |
| F43 | 1.7E−06 | 64.3 | 0.63 | 147 | M252Y/N434A |
| F44 | 1.1E−06 | 64.5 | 1.81 | 100 | M252W/N434A |
| F47 | 2.4E−07 | 62.4 | 7.75 | 153 | M252Y/T256Q/N434W |
| F48 | 3.2E−07 | 64.2 | 0.82 | 175 | M252Y/T256Q/N434Y |

TABLE 16-continued Fc variants

| Variant name | hFcRn KD (M) | Tm (° C.) | HMW (%) | Immunogenicity score | Mutation |
|---|---|---|---|---|---|
| F49 | 5.1E-07 | 61.2 | 16.63 | 173 | M252F/T256D/N434W |
| F50 | 1.2E-06 | 63.7 | 1.20 | 195 | M252F/T256D/N434Y |
| F51 | 8.1E-06 | 69.1 | 2.64 | 68 | N434F/Y436H |
| F52 | 3.1E-06 | 69.7 | 1.07 | 68 | H433K/N434F/Y436H |
| F53 | 1.0E-06 | 66.5 | 8.01 | 92 | I332V/N434W |
| F54 | 8.4E-08 | 64.2 | 8.27 | 271 | V308P/N434W |
| F56 | 9.4E-07 | 66.7 | 1.22 | 169 | I332V/M428L/N434Y |
| F57 | 1.1E-05 | 70.4 | 1.76 | 0 | G385D/Q386P/N389S |
| F58 | 7.7E-07 | 67.9 | 6.43 | 91 | G385D/Q386P/N389S/N434W |
| F59 | 2.4E-06 | 68.7 | 2.12 | 112 | G385D/Q386P/N389S/N434Y |
| F60 | 1.1E-05 | 69 | 2.17 | 14 | G385H |
| F61 | 9.7E-07 | 67.6 | 10.94 | 104 | G385H/N434W |
| F62 | 1.9E-06 | 68.5 | 0.98 | 126 | G385H/N434Y |
| F63 | 2.5E-06 | 68.5 | 1.18 | 95 | N434F |
| F64 | 5.3E-06 | 69 | 0.78 | 24 | N434H |
| F65 | 2.9E-07 | 62.9 | 4.38 | 135 | M252Y/S254T/T256E/N434F |
| F66 | 4.3E-07 | 63.3 | 2.96 | 63 | M252Y/S254T/T256E/N434H |
| F67 | 6.3E-07 | 63.1 | 1.08 | 227 | M252Y/N434F |
| F68 | 9.3E-07 | 63.6 | 0.89 | 155 | M252Y/N434H |
| F69 | 5.1E-07 | 67.9 | 7.45 | 167 | M428L/N434W |
| F70 | 1.5E-06 | 69 | 1.82 | 167 | M428L/N434Y |
| F71 | 8.3E-08 | 59.7 | 1.49 | 207 | M252Y/S254T/T256E/M428L/N434W |
| F72 | 2.0E-07 | 62.6 | 2.46 | 207 | M252Y/S254T/T256E/M428L/N434Y |
| F73 | 1.7E-07 | 63.4 | 1.86 | 298 | M252Y/M428L/N434W |
| F74 | 4.6E-07 | 64.6 | 1.52 | 298 | M252Y/M428L/N434Y |
| F75 | 1.4E-06 | 62.6 | 0.98 | 226 | M252Y/M428L/N434A |
| F76 | 1.0E-06 | 62.4 | 1.08 | 134 | M252Y/S254T/T256E/M428L/N434A |
| F77 | 9.9E-07 | 66.7 | 1.62 | 170 | T256E/M428L/N434Y |
| F78 | 7.8E-07 | 67.9 | 10.76 | 199 | S254T/M428L/N434W |
| F79 | 5.9E-06 | 67.7 | 0.96 | 44 | S254T/T256E/N434A |
| F80 | 2.7E-06 | 63.8 | 0.86 | 79 | M252Y/T256Q/N434A |
| F81 | 1.6E-06 | 63.3 | 1.85 | 56 | M252Y/T256E/N434A |
| F82 | 1.1E-06 | 67.4 | 10.30 | 120 | T256Q/N434W |
| F83 | 2.6E-06 | 65.4 | 1.37 | 142 | T256Q/N434Y |
| F84 | 2.8E-07 | 62.5 | 13.96 | 139 | M252W/T256Q/N434W |
| F85 | 5.5E-07 | 59.9 | 1.61 | 161 | M252W/T256Q/N434Y |
| F86 | 1.5E-06 | 67.6 | 10.35 | 118 | S254T/T256Q/N434W |
| F87 | 4.3E-06 | 68.6 | 1.36 | 139 | S254T/T256Q/N434Y |
| F88 | 1.9E-07 | 63.5 | 10.67 | 128 | M252Y/S254T/T256Q/N434W |
| F89 | 3.6E-07 | 64 | 1.38 | 149 | M252Y/S254T/T256Q/N434Y |
| F90 | 1.9E-08 | 64 | 10.23 | 311 | M252Y/T256E/V308P/N434W |
| F91 | 4.8E-08 | 53.7 | 1.63 | 479 | M252Y/V308P/M428L/N434Y |
| F92 | 1.1E-08 | 56.2 | 11.80 | 388 | M252Y/S254T/T256E/V308P/M428L/N434W |
| F93 | 7.4E-07 | 62.2 | 12.74 | 252 | M252W/M428L/N434W |
| F94 | 3.7E-07 | 63.4 | 11.86 | 283 | P257L/M428L/N434Y |
| F95 | 2.6E-07 | 53.2 | 1.36 | 212 | M252Y/S254T/T256E/M428L/N434F |
| F99 | 6.2E-07 | 62.9 | 1.27 | 63 | M252Y/T256E/N434H |
| F101 | 1.1E-06 | 60.7 | 4.54 | 179 | M252W/T256Q/P257L/N434Y |
| F103 | 4.4E-08 | 48.3 | 1.21 | 541 | P238A/M252Y/V308P/N434Y |
| F104 | 3.7E-08 | 48.6 | 1.03 | 424 | M252Y/D265A/V308P/N434Y |
| F105 | 7.5E-08 | 55.1 | 1.06 | 441 | M252Y/T307A/V308P/N434Y |
| F106 | 3.7E-08 | 53.9 | 1.31 | 415 | M252Y/V303A/V308P/N434Y |
| F107 | 3.4E-08 | 53.2 | 1.85 | 562 | M252Y/V308P/D376A/N434Y |
| F108 | 4.1E-08 | 53 | 0.98 | 414 | M252Y/V305A/V308P/N434Y |
| F109 | 3.2E-08 | 56.8 | 1.13 | 454 | M252Y/V308P/Q311A/N434Y |
| F111 | 3.2E-08 | 56.3 | 1.36 | 446 | M252Y/V308P/K317A/N434Y |
| F112 | 6.4E-08 | 48.4 | 2.11 | 510 | M252Y/V308P/E380A/N434Y |
| F113 | 3.2E-08 | 54.6 | 0.71 | 466 | M252Y/V308P/E382A/N434Y |
| F114 | 3.8E-08 | 57.1 | 0.97 | 467 | M252Y/V308P/S424A/N434Y |
| F115 | 6.6E-06 | 70 | 0.53 | 228 | T307A/N434A |
| F116 | 8.7E-06 | 64.2 | 0.91 | 102 | E380A/N434A |
| F118 | 1.4E-05 | 71.2 | 0.96 | 77 | M428L |
| F119 | 5.4E-06 | 65.3 | 1.23 | 112 | T250Q/M428L |
| F120 | 6.3E-08 | 54.2 | 3.54 | 464 | P257L/V308P/M428L/N434Y |
| F121 | 1.5E-06 | 49.2 | 2.37 | 388 | M252Y/T256E/V308P/M428L/N434W |
| F122 | 1.2E-07 | 61.4 | 1.71 | 207 | M252Y/T256E/M428L/N434W |
| F123 | 3.0E-08 | 49.3 | 1.79 | 332 | M252Y/T256E/V308P/N434Y |
| F124 | 2.9E-07 | 62.7 | 1.49 | 207 | M252Y/T256E/M428L/N434Y |
| F125 | 2.4E-08 | 49.1 | 1.35 | 388 | M252Y/S254T/T256E/V308P/M428L/N434Y |
| F128 | 1.7E-07 | 63.8 | 7.11 | 283 | P257L/M428L/N434W |
| F129 | 2.2E-07 | 64.8 | 3.28 | 244 | P257A/M428L/N434Y |
| F131 | 3.0E-06 | 61.6 | 7.07 | 229 | P257G/M428L/N434Y |
| F132 | 2.1E-07 | 61.3 | 8.23 | 288 | P257I/M428L/N434Y |
| F133 | 4.1E-07 | 62.7 | 6.78 | 254 | P257M/M428L/N434Y |

TABLE 16-continued

Fc variants

| Variant name | hFcRn KD (M) | Tm (° C.) | HMW (%) | Immunogenicity score | Mutation |
|---|---|---|---|---|---|
| F134 | 2.7E-07 | 57.6 | 8.30 | 268 | P257N/M428L/N434Y |
| F135 | 7.5E-07 | 63.3 | 8.81 | 251 | P257S/M428L/N434Y |
| F136 | 3.8E-07 | 62 | 10.86 | 251 | P257T/M428L/N434Y |
| F137 | 4.6E-07 | 65 | 13.28 | 283 | P257V/M428L/N434Y |
| F139 | 1.5E-08 | 55 | 5.08 | 356 | M252W/V308P/N434W |
| F140 | 3.6E-08 | 62.4 | 3.51 | 483 | S239K/M252Y/V308P/N434Y |
| F141 | 3.5E-08 | 60.2 | 8.80 | 438 | M252Y/S298G/V308P/N434Y |
| F142 | 3.7E-08 | 60.8 | 1.35 | 454 | M252Y/D270F/V308P/N434Y |
| F143 | 2.0E-07 | 61.1 | 6.55 | 444 | M252Y/V308A/N434Y |
| F145 | 5.3E-08 | 48 | 17.47 | 458 | M252Y/V308F/N434Y |
| F147 | 2.4E-07 | 65.4 | 7.78 | 419 | M252Y/V308I/N434Y |
| F149 | 1.9E-07 | 58.9 | 1.49 | 430 | M252Y/V308L/N434Y |
| F150 | 2.0E-07 | 56.3 | 1.64 | 447 | M252Y/V308M/N434Y |
| F154 | 1.8E-07 | 59.3 | 1.05 | 436 | M252Y/V308T/N434Y |
| F157 | 1.5E-07 | 53.3 | 1.24 | 425 | P257A/V308P/M428L/N434Y |
| F158 | 5.9E-08 | 45.7 | 6.38 | 431 | P257T/V308P/M428L/N434Y |
| F159 | 4.4E-08 | 53.3 | 9.24 | 464 | P257V/V308P/M428L/N434Y |
| F160 | 8.5E-07 | 63 | 1.96 | 240 | M252W/M428I/N434Y |
| F162 | 1.6E-07 | 66.9 | 1.11 | 216 | M252W/M428Y/N434Y |
| F163 | 4.2E-07 | 66.8 | 1.22 | 208 | M252W/M428F/N434Y |
| F164 | 3.7E-07 | 57.6 | 1.50 | 313 | P238A/M252W/N434Y |
| F165 | 2.9E-07 | 58.1 | 1.53 | 196 | M252W/D265A/N434Y |
| F166 | 1.5E-07 | 64.6 | 1.37 | 342 | M252W/T307Q/N434Y |
| F167 | 2.9E-07 | 60.7 | 2.02 | 429 | M252W/V303A/N434Y |
| F168 | 3.2E-07 | 59.8 | 2.33 | 335 | M252W/D376A/N434Y |
| F169 | 2.9E-07 | 61.5 | 1.18 | 377 | M252W/V305A/N434Y |
| F170 | 1.7E-07 | 63.3 | 1.46 | 335 | M252W/Q311A/N434Y |
| F171 | 1.9E-07 | 55.3 | 1.58 | 249 | M252W/D312A/N434Y |
| F172 | 2.2E-07 | 62.7 | 1.18 | 218 | M252W/K317A/N434Y |
| F173 | 7.7E-07 | 58.1 | 1.40 | 283 | M252W/E380A/N434Y |
| F174 | 3.4E-07 | 61.9 | 5.58 | 238 | M252W/E382A/N434Y |
| F175 | 2.7E-07 | 63.6 | 0.88 | 239 | M252W/S424A/N434Y |
| F176 | 2.9E-07 | 68.8 | 0.98 | 255 | S239K/M252W/N434Y |
| F177 | 2.8E-07 | 66.7 | 5.20 | 210 | M252W/S298G/N434Y |
| F178 | 2.7E-07 | 67.1 | 2.39 | 226 | M252W/D270F/N434Y |
| F179 | 3.1E-07 | 66.8 | 1.32 | 286 | M252W/N325G/N434Y |
| F182 | 6.6E-08 | 62.8 | 4.26 | 244 | P257A/M428L/N434W |
| F183 | 2.2E-07 | 59.6 | 10.28 | 251 | P257T/M428L/N434W |
| F184 | 2.7E-07 | 63.3 | 11.21 | 283 | P257V/M428L/N434W |
| F185 | 2.6E-07 | 62.1 | 0.98 | 198 | M252W/I332V/N434Y |
| F188 | 3.0E-06 | 59.2 | 3.09 | 282 | P257I/Q311I |
| F189 | 1.9E-07 | 65.3 | 1.35 | 456 | M252Y/T307A/N434Y |
| F190 | 1.1E-07 | 65.5 | 0.98 | 389 | M252Y/T307Q/N434Y |
| F191 | 1.6E-07 | 62.4 | 0.91 | 495 | P257L/T307A/M428L/N434Y |
| F192 | 1.1E-07 | 63.2 | 0.82 | 456 | P257A/T307A/M428L/N434Y |
| F193 | 8.5E-08 | 58.6 | 7.10 | 463 | P257T/T307A/M428L/N434Y |
| F194 | 1.2E-07 | 62.2 | 0.61 | 495 | P257V/T307A/M428L/N434Y |
| F195 | 5.6E-08 | 63.2 | 1.22 | 429 | P257L/T307Q/M428L/N434Y |
| F196 | 3.5E-08 | 64.3 | 0.73 | 390 | P257A/T307Q/M428L/N434Y |
| F197 | 3.3E-08 | 60.9 | 8.30 | 396 | P257T/T307Q/M428L/N434Y |
| F198 | 4.8E-08 | 63.3 | 3.41 | 429 | P257V/T307Q/M428L/N434Y |
| F201 | 2.1E-07 | 61.9 | 0.74 | 331 | M252Y/T307D/N434Y |
| F203 | 2.4E-07 | 60.3 | 6.07 | 415 | M252Y/T307F/N434Y |
| F204 | 2.1E-07 | 63.3 | 0.70 | 397 | M252Y/T307G/N434Y |
| F205 | 2.0E-07 | 62.6 | 0.70 | 369 | M252Y/T307H/N434Y |
| F206 | 2.3E-07 | 61.7 | 3.45 | 392 | M252Y/T307I/N434Y |
| F207 | 9.4E-07 | 64.6 | 0.62 | 379 | M252Y/T307K/N434Y |
| F208 | 3.9E-07 | 60.8 | 6.14 | 416 | M252Y/T307L/N434Y |
| F209 | 1.3E-07 | 62.1 | 1.19 | 416 | M252Y/T307M/N434Y |
| F210 | 2.9E-07 | 63.4 | 0.72 | 398 | M252Y/T307N/N434Y |
| F211 | 2.4E-07 | 69 | 0.60 | 390 | M252Y/T307P/N434Y |
| F212 | 6.8E-07 | 65.6 | 0.99 | 414 | M252Y/T307R/N434Y |
| F213 | 2.3E-07 | 64.5 | 0.94 | 423 | M252Y/T307S/N434Y |
| F214 | 1.7E-07 | 63.4 | 1.28 | 415 | M252Y/T307V/N434Y |
| F215 | 9.6E-08 | 59.4 | 3.41 | 392 | M252Y/T307W/N434Y |
| F216 | 2.3E-07 | 61.3 | 1.03 | 430 | M252Y/T307Y/N434Y |
| F217 | 2.3E-07 | 62.3 | 1.08 | 268 | M252Y/K334L/N434Y |
| F218 | 2.6E-07 | 64.2 | 0.91 | 257 | M252Y/G385H/N434Y |
| F219 | 2.5E-07 | 62.6 | 0.87 | 266 | M252Y/T289H/N434Y |
| F220 | 2.5E-07 | 63.3 | 0.92 | 318 | M252Y/Q311H/N434Y |
| F221 | 3.1E-07 | 58.6 | 1.13 | 282 | M252Y/D312H/N434Y |
| F222 | 3.4E-07 | 62.2 | 0.98 | 243 | M252Y/N315H/N434Y |
| F223 | 2.7E-07 | 64.4 | 1.44 | 243 | M252Y/K360H/N434Y |
| F225 | 1.5E-06 | 61.5 | 0.92 | 265 | M252Y/L314R/N434Y |

TABLE 16-continued

Fc variants

| Variant name | hFcRn KD (M) | Tm (° C.) | HMW (%) | Immunogenicity score | Mutation |
|---|---|---|---|---|---|
| F226 | 5.4E-07 | 61 | 0.94 | 265 | M252Y/L314K/N434Y |
| F227 | 1.2E-07 | 62.5 | 0.94 | 306 | M252Y/N286E/N434Y |
| F228 | 2.3E-07 | 65.3 | 0.69 | 330 | M252Y/L309E/N434Y |
| F229 | 5.1E-07 | 61.2 | 0.83 | 241 | M252Y/R255E/N434Y |
| F230 | 2.5E-07 | 66.2 | 0.66 | 243 | M252Y/P387E/N434Y |
| F236 | 8.9E-07 | 67.7 | 2.23 | 229 | K248I/M428L/N434Y |
| F237 | 2.3E-07 | 64.3 | 1.02 | 270 | M252Y/M428A/N434Y |
| F238 | 7.4E-07 | 63.9 | 0.97 | 255 | M252Y/M428D/N434Y |
| F240 | 7.2E-07 | 66.9 | 0.69 | 255 | M252Y/M428F/N434Y |
| F241 | 1.5E-06 | 62.5 | 1.41 | 278 | M252Y/M428G/N434Y |
| F242 | 8.5E-07 | 68.7 | 0.73 | 220 | M252Y/M428H/N434Y |
| F243 | 1.8E-07 | 63.8 | 0.81 | 286 | M252Y/M428I/N434Y |
| F244 | 1.3E-06 | 58.1 | 1.87 | 253 | M252Y/M428K/N434Y |
| F245 | 4.7E-07 | 63.1 | 0.82 | 279 | M252Y/M428N/N434Y |
| F246 | 1.1E-06 | 54.8 | 8.29 | 286 | M252Y/M428P/N434Y |
| F247 | 4.4E-07 | 59.9 | 1.00 | 275 | M252Y/M428Q/N434Y |
| F249 | 6.4E-07 | 64.2 | 0.72 | 273 | M252Y/M428S/N434Y |
| F250 | 2.9E-07 | 62.5 | 0.74 | 271 | M252Y/M428T/N434Y |
| F251 | 1.9E-07 | 63.4 | 1.20 | 289 | M252Y/M428V/N434Y |
| F252 | 1.0E-06 | 68.4 | 0.83 | 255 | M252Y/M428W/N434Y |
| F253 | 7.1E-07 | 67.2 | 0.79 | 263 | M252Y/M428Y/N434Y |
| F254 | 7.5E-08 | 69 | 1.30 | 362 | M252W/T307Q/M428Y/N434Y |
| F255 | 1.1E-07 | 66.5 | 1.23 | 355 | M252W/Q311A/M428Y/N434Y |
| F256 | 5.4E-08 | 67.7 | 1.27 | 403 | M252W/T307Q/Q311A/M428Y/N434Y |
| F257 | 5.0E-07 | 67.9 | 0.60 | 475 | M252Y/T307A/M428Y/N434Y |
| F258 | 3.2E-07 | 68.2 | 0.63 | 409 | M252Y/T307Q/M428Y/N434Y |
| F259 | 2.8E-07 | 68.1 | 1.15 | 273 | M252Y/D270F/N434Y |
| F260 | 1.3E-07 | 64.4 | 0.78 | 496 | M252Y/T307A/Q311A/N434Y |
| F261 | 8.4E-08 | 64.9 | 0.82 | 430 | M252Y/T307Q/Q311A/N434Y |
| F262 | 1.9E-07 | 64.1 | 0.82 | 448 | M252Y/T307A/Q311H/N434Y |
| F263 | 1.1E-07 | 64.6 | 0.80 | 358 | M252Y/T307Q/Q311H/N434Y |
| F264 | 2.8E-07 | 62.9 | 1.15 | 285 | M252Y/E382A/N434Y |
| F265 | 6.8E-07 | 65.1 | 0.57 | 305 | M252Y/E382A/M428Y/N434Y |
| F266 | 4.7E-07 | 65.9 | 0.77 | 517 | M252Y/T307A/E382A/M428Y/N434Y |
| F267 | 3.2E-07 | 66.4 | 0.81 | 450 | M252Y/T307Q/E382A/M428Y/N434Y |
| F268 | 6.3E-07 | 61.4 | 0.81 | 371 | P238A/M252Y/M428F/N434Y |
| F269 | 5.2E-07 | 65.2 | 0.65 | 435 | M252Y/V305A/M428F/N434Y |
| F270 | 6.6E-07 | 70.3 | 0.41 | 344 | M252Y/N325G/M428F/N434Y |
| F271 | 6.9E-07 | 63.3 | 0.87 | 393 | M252Y/D376A/M428F/N434Y |
| F272 | 6.8E-07 | 60 | 1.15 | 341 | M252Y/E380A/M428F/N434Y |
| F273 | 6.5E-07 | 65.3 | 0.69 | 297 | M252Y/E382A/M428F/N434Y |
| F274 | 7.6E-07 | 58.4 | 2.46 | 392 | M252Y/E380A/E382A/M428F/N434Y |
| F275 | 4.2E-08 | 61.3 | 0.69 | 525 | S239K/M252Y/V308P/E382A/N434Y |
| F276 | 4.1E-08 | 59.2 | 0.74 | 496 | M252Y/D270F/V308P/E382A/N434Y |
| F277 | 1.3E-07 | 65.5 | 0.57 | 503 | S239K/M252Y/V308P/M428Y/N434Y |
| F278 | 3.0E-08 | 55 | 0.62 | 411 | M252Y/T307Q/V308P/E382A/N434Y |
| F279 | 6.1E-08 | 53.5 | 0.67 | 462 | M252Y/V308P/Q311H/E382A/N434Y |
| F280 | 4.1E-08 | 65.5 | 0.58 | 513 | S239K/M252Y/D270F/V308P/N434Y |
| F281 | 9.2E-08 | 57.2 | 0.71 | 477 | M252Y/V308P/E382A/M428F/N434Y |
| F282 | 2.9E-08 | 49.2 | 0.82 | 521 | M252Y/V308P/E382A/M428L/N434Y |
| F283 | 1.0E-07 | 57 | 0.49 | 485 | M252Y/V308P/E382A/M428Y/N434Y |
| F284 | 1.0E-07 | 59.3 | 0.79 | 444 | M252Y/V308P/M428Y/N434Y |
| F285 | 9.9E-08 | 59.4 | 0.60 | 436 | M252Y/V308P/M428F/N434Y |
| F286 | 1.2E-07 | 63.6 | 0.64 | 544 | S239K/M252Y/V308P/E382A/M428Y/N434Y |
| F287 | 1.0E-07 | 47 | 2.92 | 573 | M252Y/V308P/E380A/E382A/M428F/N434Y |
| F288 | 1.9E-07 | 60.9 | 1.04 | 193 | M252Y/T256E/E382A/N434Y |
| F289 | 4.8E-07 | 65.2 | 1.13 | 171 | M252Y/T256E/M428F/N434Y |
| F290 | 4.6E-07 | 63.2 | 0.98 | 213 | M252Y/T256E/E382A/M428Y/N434Y |
| F292 | 2.3E-08 | 60.8 | 1.16 | 568 | S239K/M252Y/V308P/E382A/M428I/N434Y |
| F293 | 5.3E-08 | 46.3 | 3.40 | 604 | M252Y/V308P/E380A/E382A/M428I/N434Y |
| F294 | 1.1E-07 | 65 | 0.64 | 495 | S239K/M252Y/V308P/M428F/N434Y |
| F295 | 6.8E-07 | 65.5 | 1.58 | 451 | S239K/M252Y/E380A/E382A/M428F/N434Y |
| F296 | 4.9E-07 | 66.6 | 0.76 | 401 | M252Y/Q311A/M428Y/N434Y |
| F297 | 5.1E-07 | 59.1 | 0.81 | 315 | M252Y/D312A/M428Y/N434Y |
| F298 | 4.8E-07 | 58.5 | 1.09 | 464 | M252Y/Q311A/D312A/M428Y/N434Y |
| F299 | 9.4E-08 | 64.8 | 0.71 | 532 | S239K/M252Y/V308P/Q311A/M428Y/N434Y |
| F300 | 8.3E-08 | 56.6 | 1.39 | 555 | S239K/M252Y/V308P/D312A/M428Y/N434Y |
| F301 | 7.2E-08 | 56 | 1.08 | 627 | S239K/M252Y/V308P/Q311A/D312A/M428Y/N434Y |
| F302 | 1.9E-07 | 67.2 | 0.77 | 298 | M252Y/T256E/T307P/N434Y |
| F303 | 6.7E-07 | 71.8 | 0.59 | 409 | M252Y/T307P/M428Y/N434Y |
| F304 | 1.6E-08 | 58.9 | 1.10 | 397 | M252W/V308P/M428Y/N434Y |
| F305 | 2.7E-08 | 48.9 | 0.76 | 374 | M252Y/T256E/V308P/E382A/N434Y |
| F306 | 3.6E-08 | 53.5 | 0.93 | 419 | M252W/V308P/E382A/N434Y |
| F307 | 3.6E-08 | 60 | 1.76 | 478 | S239K/M252W/V308P/E382A/N434Y |

TABLE 16-continued

Fc variants

| Variant name | hFcRn KD (M) | Tm (° C.) | HMW (%) | Immuno-genicity score | Mutation |
|---|---|---|---|---|---|
| F308 | 1.9E-08 | 63.2 | 1.19 | 497 | S239K/M252W/V308P/E382A/M428Y/N434Y |
| F310 | 9.4E-08 | 59.8 | 2.44 | 521 | S239K/M252W/V308P/E382A/M428I/N434Y |
| F311 | 2.8E-08 | 64.1 | 0.98 | 448 | S239K/M252W/V308P/M428F/N434Y |
| F312 | 4.5E-07 | 64.3 | 1.33 | 404 | S239K/M252W/E380A/E382A/M428F/N434Y |
| F313 | 6.5E-07 | 77.9 | 0.77 | 468 | S239K/M252Y/T307P/M428Y/N434Y |
| F314 | 3.2E-07 | 56.1 | 1.27 | 372 | M252Y/T256E/Q311A/D312A/M428Y/N434Y |
| F315 | 6.8E-07 | 72.8 | 0.80 | 322 | S239K/M252Y/M428Y/N434Y |
| F316 | 7.0E-07 | 75.3 | 1.07 | 351 | S239K/M252Y/D270F/M428Y/N434Y |
| F317 | 1.1E-07 | 68.5 | 0.84 | 532 | S239K/M252Y/D270F/V308P/M428Y/N434Y |
| F318 | 1.8E-08 | 62 | 0.96 | 526 | S239K/M252Y/V308P/M428I/N434Y |
| F320 | 2.0E-08 | 63.9 | 1.00 | 657 | S239K/M252Y/V308P/N325G/E382A/M428I/N434Y |
| F321 | 3.2E-08 | 65.6 | 0.80 | 602 | S239K/M252Y/D270F/V308P/N325G/N434Y |
| F322 | 9.2E-08 | 61.8 | 0.87 | 448 | S239K/M252Y/D270F/T307P/V308P/N434Y |
| F323 | 2.7E-08 | 63.1 | 1.10 | 421 | S239K/M252Y/T256E/D270F/V308P/N434Y |
| F324 | 2.8E-08 | 63 | 1.07 | 458 | S239K/M252Y/D270F/T307Q/V308P/N434Y |
| F325 | 2.1E-08 | 62.4 | 0.84 | 473 | S239K/M252Y/D270F/T307Q/V308P/Q311A/N434Y |
| F326 | 7.5E-08 | 73.2 | 0.90 | 518 | S239K/M252Y/D270F/T307Q/Q311A/N434Y |
| F327 | 6.5E-08 | 70.4 | 1.19 | 427 | S239K/M252Y/T256E/D270F/T307Q/Q311A/N434Y |
| F328 | 1.9E-08 | 62.3 | 0.76 | 556 | S239K/M252Y/D270F/V308P/M428I/N434Y |
| F329 | 1.2E-08 | 64.2 | 0.97 | 575 | S239K/M252Y/D270F/N286E/V308P/N434Y |
| F330 | 3.6E-08 | 65.5 | 0.75 | 414 | S239K/M252Y/D270F/V308P/L309E/N434Y |
| F331 | 3.0E-08 | 63.8 | 0.77 | 513 | S239K/M252Y/D270F/V308P/P387E/N434Y |
| F333 | 7.4E-08 | 75.3 | 1.00 | 418 | S239K/M252Y/D270F/T307Q/L309E/Q311A/N434Y |
| F334 | 1.9E-08 | 65.2 | 1.25 | 645 | S239K/M252Y/D270F/V308P/N325G/M428I/N434Y |
| F335 | 1.5E-08 | 63.2 | 1.15 | 464 | S239K/M252Y/T256E/D270F/V308P/M428I/N434Y |
| F336 | 1.4E-08 | 64.7 | 0.95 | 516 | S239K/M252Y/D270F/T307Q/V308P/Q311A/M428I/N434Y |
| F337 | 5.6E-08 | 72.9 | 1.20 | 562 | S239K/M252Y/D270F/T307Q/Q311A/M428I/N434Y |
| F338 | 7.7E-09 | 63.4 | 1.03 | 618 | S239K/M252Y/D270F/N286E/V308P/M428I/N434Y |
| F339 | 1.9E-08 | 65.2 | 1.09 | 457 | S239K/M252Y/D270F/V308P/L309E/M428I/N434Y |
| F343 | 3.2E-08 | 60.2 | 1.28 | 568 | S239K/M252Y/D270F/V308P/M428L/N434Y |
| F344 | 3.0E-08 | 56.3 | 0.92 | 538 | S239K/M252Y/V308P/M428L/N434Y |
| F349 | 1.5E-07 | 57.8 | 0.97 | 530 | S239K/M252Y/V308P/L309P/M428L/N434Y |
| F350 | 1.7E-07 | 58.2 | 1.01 | 538 | S239K/M252Y/V308P/L309R/M428L/N434Y |
| F352 | 6.0E-07 | 67.7 | 1.12 | 496 | S239K/M252Y/L309P/M428L/N434Y |
| F353 | 1.1E-06 | 73.1 | 1.01 | 504 | S239K/M252Y/L309R/M428L/N434Y |
| F354 | 2.8E-08 | 57.5 | 0.86 | 483 | S239K/M252Y/T307Q/V308P/M428L/N434Y |
| F356 | 3.4E-08 | 67.2 | 0.85 | 414 | S239K/M252Y/D270F/V308P/L309E/P387E/N434Y |
| F357 | 1.6E-08 | 62.7 | 1.16 | 554 | S239K/M252Y/T256E/D270F/V308P/N325G/M428I/N434Y |
| F358 | 1.0E-07 | 70.8 | 0.79 | 448 | S239K/M252Y/T307Q/N434Y |
| F359 | 4.2E-07 | 63.5 | 7.84 | 417 | P257V/T307Q/M428I/N434Y |
| F360 | 1.3E-06 | 63.9 | 4.93 | 419 | P257V/T307Q/M428V/N434Y |
| F362 | 5.4E-08 | 70.1 | 13.44 | 518 | P257V/T307Q/N325G/M428L/N434Y |
| F363 | 4.1E-08 | 63.3 | 15.02 | 470 | P257V/T307Q/Q311A/M428L/N434Y |
| F364 | 3.5E-08 | 68.9 | 3.25 | 559 | P257V/T307Q/Q311A/N325G/M428L/N434Y |
| F365 | 5.1E-08 | 60.2 | 3.22 | 458 | P257V/V305A/T307Q/M428L/N434Y |
| F367 | 1.5E-08 | 59.4 | 1.25 | 500 | S239K/M252Y/E258H/D270F/T307Q/V308P/Q311A/N434Y |
| F368 | 2.0E-08 | 64 | 0.97 | 687 | S239K/M252Y/D270F/V308P/N325G/E382A/M428I/N434Y |
| F369 | 7.5E-08 | 62.8 | 4.07 | 408 | M252Y/P257V/T307Q/M428I/N434Y |
| F372 | 1.3E-08 | 65.4 | 1.09 | 456 | S239K/M252W/V308P/M428Y/N434Y |
| F373 | 1.1E-08 | 64.5 | 1.89 | 485 | S239K/M252W/V308P/Q311A/M428Y/N434Y |
| F374 | 1.2E-08 | 63 | 1.30 | 399 | S239K/M252W/T256E/V308P/M428Y/N434Y |
| F375 | 5.5E-08 | 63.5 | 1.18 | 518 | S239K/M252W/N286E/V308P/M428Y/N434Y |
| F376 | 9.6E-09 | 61.9 | 14.59 | 483 | S239K/M252W/T256E/D270F/N286E/V308P/N434Y |
| F377 | 1.3E-07 | 77.7 | 0.95 | 421 | S239K/M252W/T307P/M428Y/N434Y |
| F379 | 9.0E-09 | 62.2 | 54.64 | 428 | S239K/M252W/T256E/V308P/Q311A/M428Y/N434Y |
| F380 | 5.6E-09 | 60.8 | 0.97 | 461 | S239K/M252W/T256E/N286E/V308P/M428Y/N434Y |
| F381 | 1.1E-07 | 61.7 | 7.47 | 536 | P257V/T307A/Q311A/M428L/N434Y |
| F382 | 8.7E-08 | 58.6 | 3.55 | 489 | P257V/V305A/T307A/M428L/N434Y |
| F386 | 3.2E-08 | 56.7 | 2.02 | 325 | M252Y/V308P/L309E/N434Y |
| F387 | 1.5E-07 | 57.9 | 1.64 | 330 | M252Y/V308P/L309D/N434Y |
| F388 | 7.0E-08 | 57.4 | 1.12 | 401 | M252Y/V308P/L309A/N434Y |
| F389 | 1.7E-08 | 59.2 | 1.19 | 298 | M252W/V308P/L309E/M428Y/N434Y |
| F390 | 6.8E-08 | 60.2 | 1.29 | 302 | M252W/V308P/L309D/M428Y/N434Y |
| F391 | 3.6E-08 | 59.4 | 0.91 | 374 | M252W/V308P/L309A/M428Y/N434Y |
| F392 | 6.9E-08 | 60.3 | 0.92 | 588 | S239K/M252Y/N286E/V308P/M428I/N434Y |
| F393 | 1.2E-08 | 61.1 | 0.83 | 545 | S239K/M252Y/N286E/V308P/N434Y |
| F394 | 5.3E-08 | 70.3 | 0.99 | 532 | S239K/M252Y/T307Q/Q311A/M428I/N434Y |
| F395 | 2.4E-08 | 60.1 | 1.46 | 391 | S239K/M252Y/T256E/V308P/N434Y |
| F396 | 2.0E-08 | 71.7 | 1.53 | 624 | S239K/M252Y/D270F/N286E/T307Q/Q311A/M428I/N434Y |
| F397 | 4.5E-08 | 75.1 | 1.23 | 562 | S239K/M252Y/D270F/T307Q/Q311A/P387E/M428I/N434Y |
| F398 | 4.4E-09 | 63.3 | 1.14 | 578 | S239K/M252Y/D270F/N286E/T307Q/V308P/Q311A/M428I/N434Y |
| F399 | 6.5E-09 | 63.2 | 1.02 | 563 | S239K/M252Y/D270F/N286E/T307Q/V308P/M428I/N434Y |
| F400 | 6.1E-09 | 63.4 | 1.22 | 647 | S239K/M252Y/D270F/N286E/V308P/Q311A/M428I/N434Y |
| F401 | 6.9E-09 | 65.3 | 1.11 | 618 | S239K/M252Y/D270F/N286E/V308P/P387E/M428I/N434Y |

TABLE 16-continued

Fc variants

| Variant name | hFcRn KD (M) | Tm (° C.) | HMW (%) | Immuno- genicity score | Mutation |
|---|---|---|---|---|---|
| F402 | 2.3E-08 | 63.7 | 11.07 | 429 | P257V/T307Q/M428L/N434W |
| F403 | 5.1E-08 | 61.9 | 11.06 | 495 | P257V/T307A/M428L/N434W |
| F404 | 9.4E-08 | 66.3 | 2.14 | 342 | P257A/T307Q/L309P/M428L/N434Y |
| F405 | 1.7E-07 | 68.1 | 6.73 | 381 | P257V/T307Q/L309P/M428L/N434Y |
| F406 | 1.5E-07 | 66.7 | 1.14 | 342 | P257A/T307Q/L309R/M428L/N434Y |
| F407 | 1.6E-07 | 64.3 | 7.87 | 381 | P257V/T307Q/L309R/M428L/N434Y |
| F408 | 2.5E-07 | 63.2 | 8.96 | 345 | P257V/N286E/M428L/N434Y |
| F409 | 2.0E-07 | 64.4 | 10.17 | 283 | P257V/P387E/M428L/N434Y |
| F410 | 2.2E-07 | 62.1 | 10.56 | 408 | P257V/T307H/M428L/N434Y |
| F411 | 1.3E-07 | 62.4 | 10.50 | 438 | P257V/T307N/M428L/N434Y |
| F412 | 8.8E-08 | 60.4 | 8.29 | 437 | P257V/T307G/M428L/N434Y |
| F413 | 1.2E-07 | 66.9 | 7.29 | 430 | P257V/T307P/M428L/N434Y |
| F414 | 1.1E-07 | 63.6 | 9.61 | 463 | P257V/T307S/M428L/N434Y |
| F415 | 5.6E-08 | 61.1 | 8.69 | 558 | P257V/N286E/T307A/M428L/N434Y |
| F416 | 9.4E-08 | 62.5 | 6.73 | 495 | P257V/T307A/P387E/M428L/N434Y |
| F418 | 6.2E-07 | 81.7 | 0.58 | 558 | S239K/M252Y/T307P/N325G/M428Y/N434Y |
| F419 | 1.6E-07 | 64.2 | 5.96 | 448 | M252Y/T307A/Q311H/K360H/N434Y |
| F420 | 1.5E-07 | 65.9 | 1.10 | 448 | M252Y/T307A/Q311H/P387E/N434Y |
| F421 | 1.3E-07 | 63.4 | 0.56 | 474 | M252Y/T307A/Q311H/M428A/N434Y |
| F422 | 1.8E-07 | 62.4 | 0.46 | 489 | M252Y/T307A/Q311H/E382A/N434Y |
| F423 | 8.4E-08 | 58.2 | 1.22 | 405 | M252Y/T307W/Q311H/N434Y |
| F424 | 9.4E-08 | 57.9 | 1.25 | 484 | S239K/P257A/V308P/M428L/N434Y |
| F425 | 8.0E-08 | 54.7 | 1.36 | 326 | P257A/V308P/L309E/M428L/N434Y |
| F426 | 8.4E-08 | 65.3 | 3.50 | 374 | P257V/T307Q/N434Y |
| F427 | 1.1E-07 | 63.1 | 3.79 | 411 | M252Y/P257V/T307Q/M428V/N434Y |
| F428 | 8.0E-08 | 63.9 | 10.27 | 420 | M252Y/P257V/T307Q/M428L/N434Y |
| F429 | 3.7E-08 | 63.5 | 10.07 | 365 | M252Y/P257V/T307Q/N434Y |
| F430 | 8.1E-08 | 64.7 | 2.99 | 385 | M252Y/P257V/T307Q/M428Y/N434Y |
| F431 | 6.5E-08 | 64.9 | 4.77 | 377 | M252Y/P257V/T307Q/M428F/N434Y |
| F432 | 9.2E-07 | 67.1 | 6.21 | 550 | P257V/T307Q/Q311A/N325G/M428V/N434Y |
| F433 | 6.0E-08 | 68.4 | 2.56 | 504 | P257V/T307Q/Q311A/N325G/N434Y |
| F434 | 2.0E-07 | 69.3 | 1.66 | 524 | P257V/T307Q/Q311A/N325G/M428Y/N434Y |
| F435 | 2.5E-08 | 69.2 | 1.85 | 516 | P257V/T307Q/Q311A/N325G/M428F/N434Y |
| F436 | 2.5E-07 | 63.4 | 4.67 | 380 | P257A/T307Q/M428V/N434Y |
| F437 | 5.7E-08 | 65.3 | 0.75 | 335 | P257A/T307Q/N434Y |
| F438 | 3.6E-08 | 68.6 | 0.74 | 354 | P257A/T307Q/M428Y/N434Y |
| F439 | 4.0E-08 | 67.9 | 3.44 | 346 | P257A/T307Q/M428F/N434Y |
| F440 | 1.5E-08 | 68.7 | 9.15 | 622 | P257V/N286E/T307Q/Q311A/N325G/M428L/N434Y |
| F441 | 1.8E-07 | 64 | 2.87 | 383 | P257A/Q311A/M428L/N434Y |
| F442 | 2.0E-07 | 63.5 | 1.91 | 318 | P257A/Q311H/M428L/N434Y |
| F443 | 5.5E-08 | 64.5 | 8.58 | 431 | P257A/T307Q/Q311A/M428L/N434Y |
| F444 | 1.4E-07 | 62.8 | 1.96 | 497 | P257A/T307A/Q311A/M428L/N434Y |
| F445 | 6.2E-08 | 64.4 | 1.22 | 359 | P257A/T307Q/Q311H/M428L/N434Y |
| F446 | 1.1E-07 | 62.6 | 1.00 | 448 | P257A/T307A/Q311H/M428L/N434Y |
| F447 | 1.4E-08 | 63.9 | 1.20 | 452 | P257A/N286E/T307Q/M428L/N434Y |
| F448 | 5.3E-08 | 61.9 | 1.05 | 519 | P257A/N286E/T307A/M428L/N434Y |
| F449 | 5.7E-07 | 81.9 | 0.64 | 587 | S239K/M252Y/D270F/T307P/N325G/M428Y/N434Y |
| F450 | 5.2E-07 | 82.5 | 0.67 | 501 | S239K/M252Y/T307P/L309E/N325G/M428Y/N434Y |
| F451 | 1.0E-07 | 60.4 | 4.14 | 463 | P257S/T307A/M428L/N434Y |
| F452 | 1.4E-07 | 60.8 | 4.31 | 466 | P257M/T307A/M428L/N434Y |
| F453 | 7.8E-08 | 55.5 | 7.22 | 480 | P257N/T307A/M428L/N434Y |
| F454 | 9.6E-08 | 60.4 | 5.16 | 500 | P257I/T307A/M428L/N434Y |
| F455 | 2.7E-08 | 66.3 | 2.85 | 393 | P257V/T307Q/M428Y/N434Y |
| F456 | 3.4E-08 | 66.2 | 2.45 | 385 | P257V/T307Q/M428F/N434Y |
| F457 | 4.0E-08 | 61.2 | 5.82 | 523 | S239K/P257V/V308P/M428L/N434Y |
| F458 | 1.5E-08 | 57.1 | 7.48 | 499 | P257V/T307Q/V308P/M428L/N434Y |
| F459 | 1.3E-08 | 56.5 | 5.57 | 514 | P257V/T307Q/V308P/Q311A/N325G/M428L/N434Y |
| F460 | 4.7E-08 | 55.5 | 8.56 | 570 | P257V/T307A/V308P/N325G/M428L/N434Y |
| F462 | 8.5E-08 | 57.2 | 1.10 | 514 | P257A/V308P/N325G/M428L/N434Y |
| F463 | 1.3E-07 | 53 | 0.92 | 442 | P257A/T307A/V308P/M428L/N434Y |
| F464 | 5.5E-08 | 54.3 | 1.14 | 370 | P257A/T307Q/V308P/M428L/N434Y |
| F465 | 2.1E-08 | 69.2 | 9.95 | 581 | P257V/N286E/T307Q/N325G/M428L/N434Y |
| F466 | 3.5E-07 | 63.6 | 0.35 | 167 | T256E/P257V/N434Y |
| F467 | 5.7E-07 | 60.5 | 0.52 | 142 | T256E/P257T/N434Y |
| F468 | 5.7E-08 | 55.8 | 0.71 | 490 | S239K/P257T/V308P/M428L/N434Y |
| F469 | 5.6E-08 | 48.6 | 1.49 | 521 | P257T/V308P/N325G/M428L/N434Y |
| F470 | 5.4E-08 | 48.2 | 1.81 | 467 | T256E/P257T/V308P/N325G/M428L/N434Y |
| F471 | 6.6E-08 | 48.4 | 1.43 | 563 | P257T/V308P/N325G/E382A/M428L/N434Y |
| F472 | 5.4E-08 | 48.8 | 5.04 | 521 | P257T/V308P/N325G/P387E/M428L/N434Y |
| F473 | 4.5E-07 | 48.7 | 2.13 | 513 | P257T/V308P/L309P/N325G/M428L/N434Y |
| F474 | 3.5E-07 | 48.4 | 1.04 | 521 | P257T/V308P/L309R/N325G/M428L/N434Y |
| F475 | 4.3E-08 | 61.9 | 3.67 | 368 | T256E/P257V/T307Q/M428L/N434Y |
| F476 | 5.5E-08 | 61.8 | 4.57 | 471 | P257V/T307Q/E382A/M428L/N434Y |
| F477 | 4.3E-08 | 62.8 | 2.35 | 429 | P257V/T307Q/P387E/M428L/N434Y |

TABLE 16-continued

Fc variants

| Variant name | hFcRn KD (M) | Tm (° C.) | HMW (%) | Immunogenicity score | Mutation |
|---|---|---|---|---|---|
| F480 | 3.9E-08 | 53.8 | 2.30 | 409 | P257L/V308P/N434Y |
| F481 | 5.6E-08 | 59.2 | 1.26 | 341 | P257T/T307Q/N434Y |
| F482 | 7.0E-08 | 66.4 | 1.32 | 463 | P257V/T307Q/N325G/N434Y |
| F483 | 5.7E-08 | 62.1 | 1.42 | 415 | P257V/T307Q/Q311A/N434Y |
| F484 | 6.2E-08 | 58.6 | 1.84 | 403 | P257V/V305A/T307Q/N434Y |
| F485 | 9.7E-08 | 60.4 | 2.64 | 503 | P257V/N286E/T307A/N434Y |
| F486 | 3.4E-07 | 60.4 | 0.76 | 381 | P257V/T307Q/L309R/Q311H/M428L/N434Y |
| F488 | 3.5E-08 | 56.4 | 3.69 | 553 | P257V/V308P/N325G/M428L/N434Y |
| F490 | 7.5E-08 | 59.4 | 2.29 | 519 | S239K/P257V/V308P/Q311H/M428L/N434Y |
| F492 | 9.8E-08 | 61.7 | 3.29 | 579 | P257V/V305A/T307A/N325G/M428L/N434Y |
| F493 | 4.9E-07 | 84 | 0.52 | 456 | S239K/D270F/T307P/N325G/M428Y/N434Y |
| F497 | 3.1E-06 | 58.2 | 4.34 | 453 | P257T/T307A/M428V/N434Y |
| F498 | 1.3E-06 | 62.2 | 6.16 | 234 | P257A/M428V/N434Y |
| F499 | 5.2E-07 | 61.3 | 2.03 | 447 | P257A/T307A/M428V/N434Y |
| F500 | 4.3E-08 | 61 | 2.81 | 396 | P257S/T307Q/M428L/N434Y |
| F506 | 1.9E-07 | 57.1 | 8.70 | 454 | P257V/N297A/T307Q/M428L/N434Y |
| F507 | 5.1E-08 | 59.9 | 4.51 | 499 | P257V/N286A/T307Q/M428L/N434Y |
| F508 | 1.1E-07 | 65.1 | 3.93 | 429 | P257V/T307Q/N315A/M428L/N434Y |
| F509 | 5.8E-08 | 62.8 | 3.94 | 447 | P257V/T307Q/N384A/M428L/N434Y |
| F510 | 5.3E-08 | 62.7 | 4.35 | 429 | P257V/T307Q/N389A/M428L/N434Y |
| F511 | 4.2E-07 | 63 | 2.28 | 228 | P257V/N434Y |
| F512 | 5.8E-07 | 60 | 3.41 | 195 | P257T/N434Y |
| F517 | 3.1E-07 | 61.4 | 2.82 | 290 | P257V/N286E/N434Y |
| F518 | 4.2E-07 | 58.5 | 4.05 | 258 | P257T/N286E/N434Y |
| F519 | 2.6E-08 | 61.3 | 2.45 | 436 | P257V/N286E/T307Q/N434Y |
| F521 | 1.1E-08 | 63.5 | 1.51 | 456 | P257V/N286E/T307Q/M428Y/N434Y |
| F523 | 2.6E-08 | 62.6 | 1.39 | 422 | P257V/V305A/T307Q/M428Y/N434Y |
| F526 | 1.9E-08 | 62.2 | 1.60 | 361 | P257T/T307Q/M428Y/N434Y |
| F527 | 9.4E-09 | 60.6 | 0.94 | 463 | P257V/T307Q/V308P/N325G/M428Y/N434Y |
| F529 | 2.5E-08 | 61.7 | 1.82 | 353 | P257T/T307Q/M428F/N434Y |
| F533 | 1.2E-08 | 64.8 | 1.01 | 409 | P257A/N286E/T307Q/M428F/N434Y |
| F534 | 1.2E-08 | 65.6 | 0.84 | 417 | P257A/N286E/T307Q/M428Y/N434Y |
| F535 | 3.9E-08 | 63.3 | 4.36 | 449 | T250A/P257V/T307Q/M428L/N434Y |
| F538 | 9.9E-08 | 66.7 | 2.57 | 484 | T250F/P257V/T307Q/M428L/N434Y |
| F541 | 6.0E-08 | 65.9 | 3.53 | 484 | T250I/P257V/T307Q/M428L/N434Y |
| F544 | 3.1E-08 | 64.5 | 4.00 | 484 | T250M/P257V/T307Q/M428L/N434Y |
| F549 | 5.4E-08 | 61.8 | 5.82 | 415 | T250S/P257V/T307Q/M428L/N434Y |
| F550 | 5.9E-08 | 66.6 | 3.19 | 484 | T250V/P257V/T307Q/M428L/N434Y |
| F551 | 1.2E-07 | 65.1 | 3.72 | 484 | T250W/P257V/T307Q/M428L/N434Y |
| F552 | 1.1E-07 | 65.4 | 2.98 | 484 | T250Y/P257V/T307Q/M428L/N434Y |
| F553 | 1.7E-07 | 64.1 | 1.52 | 382 | M252Y/Q311A/N434Y |
| F554 | 2.8E-08 | 62.8 | 1.39 | 454 | S239K/M252Y/S254T/V308P/N434Y |
| F556 | 1.5E-06 | 66.5 | 0.96 | 318 | M252Y/T307Q/Q311A |
| F559 | 8.0E-08 | 62.8 | 1.20 | 277 | M252Y/S254T/N286E/N434Y |
| F560 | 2.8E-08 | 56.9 | 1.15 | 395 | M252Y/S254T/V308P/N434Y |
| F561 | 1.4E-07 | 65.5 | 1.23 | 427 | M252Y/S254T/T307A/N434Y |
| F562 | 8.3E-08 | 65.7 | 1.21 | 360 | M252Y/S254T/T307Q/N434Y |
| F563 | 1.3E-07 | 64.2 | 1.02 | 353 | M252Y/S254T/Q311A/N434Y |
| F564 | 1.9E-07 | 63.7 | 1.02 | 289 | M252Y/S254T/Q311H/N434Y |
| F565 | 9.2E-08 | 65 | 1.00 | 467 | M252Y/S254T/T307A/Q311A/N434Y |
| F566 | 6.1E-08 | 64.9 | 1.24 | 401 | M252Y/S254T/T307Q/Q311A/N434Y |
| F567 | 2.2E-07 | 64.2 | 1.52 | 257 | M252Y/S254T/M428I/N434Y |
| F568 | 1.1E-07 | 61.6 | 0.99 | 356 | M252Y/T256E/T307A/Q311H/N434Y |
| F569 | 2.0E-07 | 64.4 | 0.96 | 379 | M252Y/T256Q/T307A/Q311H/N434Y |
| F570 | 1.3E-07 | 64.5 | 1.04 | 419 | M252Y/S254T/T307A/Q311H/N434Y |
| F571 | 8.1E-08 | 62.4 | 1.03 | 510 | M252Y/N286E/T307A/Q311H/N434Y |
| F572 | 1.0E-07 | 63.6 | 1.33 | 491 | M252Y/T307A/Q311H/M428I/N434Y |
| F576 | 1.6E-06 | 62.7 | 0.99 | 154 | M252Y/T256E/T307Q/Q311H |
| F577 | 1.3E-06 | 64.4 | 1.44 | 447 | M252Y/N286E/T307A/Q311A |
| F578 | 5.7E-07 | 64.3 | 1.33 | 380 | M252Y/N286E/T307A/Q311A |
| F580 | 8.6E-07 | 63.9 | 1.06 | 308 | M252Y/N286E/T307Q/Q311H |
| F581 | 7.2E-08 | 59.8 | 1.22 | 214 | M252Y/T256E/N286E/N434Y |
| F582 | 7.5E-07 | 64.5 | 1.10 | 371 | S239K/M252Y/V308P |
| F583 | 7.8E-07 | 63 | 1.01 | 412 | S239K/M252Y/V308P/E382A |
| F584 | 6.3E-07 | 61.8 | 1.45 | 279 | S239K/M252Y/T256E/V308P |
| F585 | 2.9E-07 | 62.7 | 1.15 | 433 | S239K/M252Y/N286E/V308P |
| F586 | 1.4E-07 | 62 | 1.21 | 498 | S239K/M252Y/N286E/V308P/M428I |
| F587 | 1.9E-07 | 61.9 | 1.47 | 361 | M252Y/N286E/M428L/N434Y |
| F592 | 2.0E-07 | 62.9 | 0.99 | 256 | M252Y/S254T/E382A/N434Y |
| F593 | 3.1E-08 | 60.8 | 1.27 | 497 | S239K/M252Y/S254T/V308P/M428I/N434Y |
| F594 | 1.6E-08 | 59.3 | 1.32 | 434 | S239K/M252Y/T256E/V308P/M428I/N434Y |
| F595 | 1.8E-07 | 69.4 | 0.91 | 345 | S239K/M252Y/M428I/N434Y |
| F596 | 4.0E-07 | 56.6 | 1.05 | 357 | M252Y/D312A/E382A/M428Y/N434Y |
| F597 | 2.2E-07 | 64.6 | 0.78 | 283 | M252Y/E382A/P387E/N434Y |

TABLE 16-continued

Fc variants

| Variant name | hFcRn KD (M) | Tm (° C.) | HMW (%) | Immuno-genicity score | Mutation |
|---|---|---|---|---|---|
| F598 | 1.4E-07 | 58.1 | 1.06 | 296 | M252Y/D312A/P387E/N434Y |
| F599 | 5.2E-07 | 68.9 | 0.76 | 263 | M252Y/P387E/M428Y/N434Y |
| F600 | 2.8E-07 | 62.5 | 0.89 | 217 | M252Y/T256Q/E382A/N434Y |
| F601 | 9.6E-09 | 54.7 | 0.96 | 486 | M252Y/N286E/V308P/N434Y |
| F611 | 2.8E-07 | 69.5 | 0.96 | 358 | M252Y/V305T/T307P/V308I/L309A/N434Y |
| F612 | 3.6E-07 | 70.8 | 0.92 | 360 | M252Y/T307P/V308I/L309A/N434Y |
| F617 | 7.4E-07 | 71.6 | 1.41 | 149 | S239K/N434W |
| F618 | 6.4E-07 | 60.7 | 2.70 | 386 | S239K/V308F/N434Y |
| F619 | 3.1E-07 | 70 | 0.67 | 302 | S239K/M252Y/N434Y |
| F620 | 2.1E-07 | 69.6 | 1.18 | 273 | S239K/M252Y/S254T/N434Y |
| F621 | 1.5E-07 | 70 | 0.76 | 506 | S239K/M252Y/T307A/Q311H/N434Y |
| F622 | 3.5E-07 | 69.9 | 0.74 | 234 | S239K/M252Y/T256Q/N434Y |
| F623 | 1.8E-07 | 68 | 2.39 | 234 | S239K/M252W/N434W |
| F624 | 1.4E-08 | 69.1 | 1.99 | 511 | S239K/P257A/N286E/T307Q/M428L/N434Y |
| F625 | 7.6E-08 | 69.7 | 1.85 | 449 | S239K/P257A/T307Q/M428L/N434Y |
| F626 | 1.3E-06 | 62.7 | 0.81 | 181 | V308P |
| F629 | 3.9E-08 | 52 | 0.56 | 481 | M252Y/V279L/V308P/N434Y |
| F630 | 3.7E-08 | 58.5 | 0.87 | 540 | S239K/M252Y/V279L/V308P/N434Y |
| F633 | 2.4E-08 | 53.7 | 0.65 | 446 | M252Y/V282D/V308P/N434Y |
| F634 | 3.2E-08 | 59.5 | 0.88 | 505 | S239K/M252Y/V282D/V308P/N434Y |
| F636 | 4.8E-08 | 57.1 | 0.91 | 520 | S239K/M252Y/V284K/V308P/N434Y |
| F637 | 1.5E-07 | 54.9 | 1.05 | 455 | M252Y/K288S/V308P/N434Y |
| F638 | 1.4E-07 | 60.9 | 0.90 | 514 | S239K/M252Y/K288S/V308P/N434Y |
| F639 | 2.7E-08 | 56.2 | 0.92 | 424 | M252Y/V308P/G385R/N434Y |
| F640 | 3.6E-08 | 62.1 | 0.83 | 483 | S239K/M252Y/V308P/G385R/N434Y |
| F641 | 3.0E-08 | 56.3 | 0.83 | 438 | M252Y/V308P/Q386K/N434Y |
| F642 | 3.0E-08 | 62.2 | 0.87 | 497 | S239K/M252Y/V308P/Q386K/N434Y |
| F643 | 3.2E-08 | 62.4 | 0.73 | 479 | L235G/G236R/S239K/M252Y/V308P/N434Y |
| F644 | 3.0E-08 | 62.1 | 0.80 | 518 | G236R/S239K/M252Y/V308P/N434Y |
| F645 | 3.3E-08 | 54.6 | 1.25 | 551 | S239K/M252Y/V308P/L328R/N434Y |
| F646 | 3.8E-08 | 48.5 | 3.58 | 509 | S239K/M252Y/N297A/V308P/N434Y |
| F647 | 2.9E-08 | 43 | 8.59 | 502 | P238D/M252Y/V308P/N434Y |
| F649 | 1.2E-07 | 68.3 | 0.90 | 364 | S239K/M252Y/N286E/N434Y |
| F650 | 1.7E-07 | 68.1 | 1.19 | 210 | S239K/M252Y/T256E/N434Y |
| F651 | 1.8E-07 | 69.4 | 0.69 | 441 | S239K/M252Y/Q311A/N434Y |
| F652 | 2.4E-07 | 54.8 | 0.95 | 322 | P238D/M252Y/N434Y |
| F654 | 3.2E-08 | 62.2 | 0.80 | 493 | L235K/S239K/M252Y/V308P/N434Y |
| F655 | 3.4E-08 | 62.5 | 0.50 | 489 | L235R/S239K/M252Y/V308P/N434Y |
| F656 | 3.3E-08 | 60 | 0.74 | 482 | G237K/S239K/M252Y/V308P/N434Y |
| F657 | 3.2E-08 | 61.3 | 0.54 | 485 | G237R/S239K/M252Y/V308P/N434Y |
| F658 | 3.2E-08 | 48.4 | 6.06 | 531 | P238K/S239K/M252Y/V308P/N434Y |
| F659 | 3.0E-08 | 47.2 | 9.54 | 547 | P238R/S239K/M252Y/V308P/N434Y |
| F660 | 3.1E-08 | 60.3 | 0.82 | 564 | S239K/M252Y/V308P/P329K/N434Y |
| F661 | 3.4E-08 | 61 | 0.66 | 541 | S239K/M252Y/V308P/P329R/N434Y |
| F663 | 6.4E-09 | 60.7 | 0.81 | 506 | S239K/M252Y/N286E/T307Q/V308P/Q311A/N434Y |
| F664 | 3.9E-08 | 54.4 | 0.90 | 494 | M252Y/N286A/V308P/N434Y |
| F665 | 2.0E-08 | 56.9 | 1.09 | 438 | M252Y/N286D/V308P/N434Y |
| F666 | 2.1E-08 | 52.7 | 1.06 | 494 | M252Y/N286F/V308P/N434Y |
| F667 | 3.0E-08 | 56.1 | 0.59 | 486 | M252Y/N286G/V308P/N434Y |
| F668 | 4.0E-08 | 56.2 | 0.55 | 486 | M252Y/N286H/V308P/N434Y |
| F670 | 2.1E-07 | 52.1 | 0.13 | 486 | M252Y/N286K/V308P/N434Y |
| F671 | 2.2E-08 | 49.5 | 0.67 | 494 | M252Y/N286L/V308P/N434Y |
| F672 | 2.4E-08 | 53.4 | 0.87 | 494 | M252Y/N286M/V308P/N434Y |
| F673 | 2.3E-08 | 48.2 | 5.02 | 486 | M252Y/N286P/V308P/N434Y |
| F674 | 3.2E-08 | 53.3 | 0.39 | 486 | M252Y/N286Q/V308P/N434Y |
| F675 | 5.1E-08 | 49.3 | 0.67 | 494 | M252Y/N286R/V308P/N434Y |
| F676 | 3.2E-08 | 55.6 | 0.64 | 494 | M252Y/N286S/V308P/N434Y |
| F677 | 4.7E-08 | 57.1 | 0.92 | 486 | M252Y/N286T/V308P/N434Y |
| F679 | 1.7E-08 | 48.7 | 4.00 | 486 | M252Y/N286W/V308P/N434Y |
| F680 | 1.5E-08 | 56 | 0.80 | 494 | M252Y/N286Y/V308P/N434Y |
| F681 | 4.9E-08 | 54.4 | 0.95 | 455 | M252Y/K288A/V308P/N434Y |
| F682 | 8.2E-08 | 54.5 | 0.98 | 424 | M252Y/K288D/V308P/N434Y |
| F683 | 5.0E-08 | 56.2 | 1.17 | 432 | M252Y/K288E/V308P/N434Y |
| F684 | 5.1E-08 | 56.6 | 1.27 | 458 | M252Y/K288F/V308P/N434Y |
| F685 | 5.3E-08 | 48.5 | 1.14 | 432 | M252Y/K288G/V308P/N434Y |
| F686 | 4.6E-08 | 56.3 | 1.00 | 455 | M252Y/K288H/V308P/N434Y |
| F687 | 4.9E-08 | 59.1 | 1.13 | 463 | M252Y/K288I/V308P/N434Y |
| F688 | 2.8E-08 | 56.5 | 1.07 | 466 | M252Y/K288L/V308P/N434Y |
| F689 | 4.1E-08 | 56.4 | 0.95 | 455 | M252Y/K288M/V308P/N434Y |
| F690 | 1.0E-07 | 54.9 | 0.98 | 455 | M252Y/K288N/V308P/N434Y |
| F692 | 3.9E-08 | 56 | 1.18 | 440 | M252Y/K288Q/V308P/N434Y |
| F693 | 3.6E-08 | 56.2 | 0.82 | 478 | M252Y/K288R/V308P/N434Y |
| F694 | 4.7E-08 | 57.5 | 0.88 | 466 | M252Y/K288V/V308P/N434Y |
| F695 | 4.0E-08 | 55 | 1.09 | 481 | M252Y/K288W/V308P/N434Y |

TABLE 16-continued

Fc variants

| Variant name | hFcRn KD (M) | Tm (° C.) | HMW (%) | Immunogenicity score | Mutation |
|---|---|---|---|---|---|
| F696 | 4.4E-08 | 56.4 | 0.93 | 486 | M252Y/K288Y/V308P/N434Y |
| F697 | 3.1E-08 | 65.1 | 0.56 | 572 | S239K/M252Y/V308P/N325G/N434Y |
| F698 | 2.2E-08 | 62.8 | 0.69 | 492 | M252Y/N286E/T307Q/Q311A/N434Y |
| F699 | 2.3E-08 | 68.3 | 0.74 | 551 | S239K/M252Y/N286E/T307Q/Q311A/N434Y |
| F705 | 7.1E-09 | 53.7 | 0.71 | 530 | M252Y/N286E/V308P/M428I/N434Y |
| F706 | 1.8E-08 | 62 | 0.86 | 535 | M252Y/N286E/T307Q/Q311A/M428I/N434Y |
| F707 | 5.9E-09 | 54.5 | 0.73 | 447 | M252Y/N286E/T307Q/V308P/Q311A/N434Y |
| F708 | 4.1E-09 | 53.6 | 0.43 | 490 | M252Y/N286E/T307Q/V308P/Q311A/M428I/N434Y |
| F709 | 2.0E-08 | 68.3 | 0.77 | 594 | S239K/M252Y/N286E/T307Q/Q311A/M428I/N434Y |
| F710 | 1.5E-08 | 48.6 | 1.68 | 614 | P238D/M252Y/N286E/T307Q/Q311A/M428I/N434Y |
| F711 | 6.5E-08 | 70.7 | 0.79 | 489 | S239K/M252Y/T307Q/Q311A/N434Y |
| F712 | 6.0E-08 | 55.2 | 0.89 | 508 | P238D/M252Y/T307Q/Q311A/N434Y |
| F713 | 2.0E-08 | 52.7 | 0.88 | 571 | P238D/M252Y/N286E/T307Q/Q311A/N434Y |
| F714 | 2.3E-07 | 57.9 | 0.70 | 437 | P238D/M252Y/N325S/N434Y |
| F715 | 2.3E-07 | 57.6 | 2.42 | 451 | P238D/M252Y/N325M/N434Y |
| F718 | 2.8E-07 | 56.3 | 0.52 | 348 | P238D/M252Y/Q295M/N434Y |
| F719 | 7.4E-08 | 57.3 | 0.76 | 411 | P238D/M252Y/N325G/N434Y |
| F720 | 2.4E-08 | 56.4 | 0.66 | 385 | M252Y/T307Q/V308P/Q311A/N434Y |
| F721 | 1.5E-08 | 55.3 | 0.77 | 428 | M252Y/T307Q/V308P/Q311A/M428I/N434Y |
| F722 | 2.7E-07 | 53.7 | 0.43 | 322 | P238D/M252Y/A327G/N434Y |
| F723 | 2.8E-07 | 45.3 | 7.75 | 347 | P238D/M252Y/L328D/N434Y |
| F724 | 2.5E-07 | 43 | 24.31 | 355 | P238D/M252Y/L328E/N434Y |
| F725 | 4.2E-08 | 61.5 | 0.56 | 485 | L235K/G237R/S239K/M252Y/V308P/N434Y |
| F729 | 9.2E-07 | 68.3 | 0.61 | 365 | T307A/Q311A/N434Y |
| F730 | 6.0E-07 | 69.1 | 0.52 | 299 | T307Q/Q311A/N434Y |
| F731 | 8.5E-07 | 67.9 | 0.63 | 316 | T307A/Q311H/N434Y |
| F732 | 6.8E-07 | 69 | 0.66 | 227 | T307Q/Q311H/N434Y |
| F733 | 3.2E-07 | 48.8 | 2.59 | 276 | M252Y/L328E/N434Y |
| F734 | 3.1E-07 | 46.8 | 9.34 | 340 | G236D/M252Y/L328E/N434Y |
| F736 | 3.1E-07 | 52.2 | 2.27 | 298 | M252Y/S267M/L328E/N434Y |
| F737 | 3.1E-07 | 48.6 | 2.82 | 298 | M252Y/S267L/L328E/N434Y |
| F738 | 3.5E-07 | 59.8 | 0.91 | 468 | P238D/M252Y/T307P/N434Y |
| F739 | 2.2E-07 | 68.1 | 0.77 | 430 | M252Y/T307P/Q311A/N434Y |
| F740 | 2.9E-07 | 67.7 | 0.76 | 360 | M252Y/T307P/Q311H/N434Y |
| F741 | 3.1E-07 | 52.9 | 1.14 | 322 | P238D/T250A/M252Y/N434Y |
| F744 | 9.9E-07 | 58.6 | 1.09 | 357 | P238D/T250F/M252Y/N434Y |
| F747 | 2.8E-07 | 59.4 | 0.93 | 357 | P238D/T250I/M252Y/N434Y |
| F749 | 5.1E-07 | 58.6 | 1.13 | 357 | P238D/T250L/M252Y/N434Y |
| F750 | 3.0E-07 | 53 | 1.34 | 357 | P238D/T250M/M252Y/N434Y |
| F753 | 1.8E-07 | 45 | 6.13 | 345 | P238D/T250Q/M252Y/N434Y |
| F755 | 3.5E-07 | 47.8 | 1.24 | 322 | P238D/T250S/M252Y/N434Y |
| F756 | 3.7E-07 | 59.9 | 0.81 | 357 | P238D/T250V/M252Y/N434Y |
| F757 | 1.2E-06 | 55.3 | 1.29 | 357 | P238D/T250W/M252Y/N434Y |
| F758 | 1.4E-06 | 60 | 0.77 | 357 | P238D/T250Y/M252Y/N434Y |
| F761 | 1.1E-06 | 59.7 | 0.56 | 191 | P238D/N434Y |
| F762 | 3.6E-08 | 68.8 | 0.79 | 561 | L235K/S239K/M252Y/N286E/T307Q/Q311A/N434Y |
| F763 | 3.5E-08 | 69.2 | 0.76 | 557 | L235R/S239K/M252Y/N286E/T307Q/Q311A/N434Y |
| F764 | 6.3E-07 | 60 | 0.48 | 377 | P238D/T307Q/Q311A/N434Y |
| F765 | 8.5E-08 | 56.8 | 1.06 | 407 | P238D/M252Y/T307Q/L309E/Q311A/N434Y |
| F766 | 6.0E-07 | 69.2 | 0.61 | 286 | T307A/L309E/Q311A/N434Y |
| F767 | 4.3E-07 | 69.9 | 0.63 | 198 | T307Q/L309E/Q311A/N434Y |
| F768 | 6.4E-07 | 68.8 | 0.65 | 286 | T307A/L309E/Q311H/N434Y |
| F769 | 4.6E-07 | 69.5 | 0.77 | 190 | T307Q/L309E/Q311H/N434Y |
| F770 | 3.0E-07 | 61.8 | 0.84 | 226 | M252Y/T256A/N434Y |
| F771 | 4.0E-07 | 60 | 0.57 | 275 | M252Y/E272A/N434Y |
| F772 | 3.8E-07 | 62.7 | 0.57 | 293 | M252Y/K274A/N434Y |
| F773 | 3.9E-07 | 62 | 0.50 | 285 | M252Y/V282A/N434Y |
| F774 | 4.0E-07 | 61.5 | 0.64 | 314 | M252Y/N286A/N434Y |
| F775 | 6.2E-07 | 56.1 | 9.28 | 243 | M252Y/K338A/N434Y |
| F776 | 3.9E-07 | 61.9 | 0.64 | 273 | M252Y/K340A/N434Y |
| F777 | 3.9E-07 | 64.2 | 0.59 | 278 | M252Y/E345A/N434Y |
| F779 | 3.9E-07 | 64.2 | 0.56 | 273 | M252Y/N361A/N434Y |
| F780 | 3.9E-07 | 64.3 | 0.65 | 256 | M252Y/Q362A/N434Y |
| F781 | 3.7E-07 | 64.2 | 0.58 | 307 | M252Y/S375A/N434Y |
| F782 | 3.5E-07 | 63.9 | 0.93 | 243 | M252Y/Y391A/N434Y |
| F783 | 4.0E-07 | 64.2 | 0.50 | 514 | M252Y/D413A/N434Y |
| F784 | 5.0E-07 | 65.6 | 0.70 | 367 | M252Y/L309A/N434Y |
| F785 | 7.4E-07 | 64.7 | 0.70 | 359 | M252Y/L309H/N434Y |
| F786 | 2.8E-08 | 62.6 | 0.61 | 463 | M252Y/S254T/N286E/T307Q/Q311A/N434Y |
| F787 | 8.8E-08 | 66.1 | 0.72 | 300 | M252Y/S254T/T307Q/L309E/Q311A/N434Y |
| F788 | 4.1E-07 | 65.5 | 0.53 | 251 | M252Y/N315A/N434Y |
| F789 | 1.5E-07 | 64.3 | 0.67 | 243 | M252Y/N315D/N434Y |
| F790 | 2.7E-07 | 63.9 | 0.97 | 265 | M252Y/N315E/N434Y |
| F791 | 4.4E-07 | 60.6 | 1.27 | 243 | M252Y/N315F/N434Y |

TABLE 16-continued

Fc variants

| Variant name | hFcRn KD (M) | Tm (° C.) | HMW (%) | Immuno- genicity score | Mutation |
|---|---|---|---|---|---|
| F792 | 4.4E-07 | 65 | 0.59 | 243 | M252Y/N315G/N434Y |
| F793 | 3.3E-07 | 61.4 | 0.75 | 251 | M252Y/N315I/N434Y |
| F794 | 4.1E-07 | 62.8 | 0.64 | 243 | M252Y/N315K/N434Y |
| F795 | 3.1E-07 | 62.8 | 0.85 | 265 | M252Y/N315L/N434Y |
| F796 | 3.4E-07 | 64.4 | 0.85 | 251 | M252Y/N315M/N434Y |
| F798 | 3.5E-07 | 64.3 | 0.72 | 273 | M252Y/N315Q/N434Y |
| F799 | 4.1E-07 | 62.7 | 1.36 | 243 | M252Y/N315R/N434Y |
| F800 | 3.8E-07 | 65.8 | 0.61 | 243 | M252Y/N315S/N434Y |
| F802 | 3.3E-07 | 61.5 | 0.67 | 273 | M252Y/N315V/N434Y |
| F803 | 3.6E-07 | 59.6 | 0.86 | 251 | M252Y/N315W/N434Y |
| F804 | 4.0E-07 | 60.5 | 1.55 | 251 | M252Y/N315Y/N434Y |
| F805 | 3.0E-07 | 65 | 0.70 | 397 | M252Y/N325A/N434Y |
| F806 | 3.1E-07 | 64.3 | 0.70 | 262 | M252Y/N384A/N434Y |
| F807 | 3.2E-07 | 64.2 | 0.71 | 243 | M252Y/N389A/N434Y |
| F808 | 3.2E-07 | 64.1 | 0.69 | 274 | M252Y/N389A/N390A/N434Y |
| F809 | 2.2E-07 | 63.3 | 0.56 | 202 | M252Y/S254T/T256S/N434Y |
| F810 | 2.2E-07 | 65.2 | 0.68 | 360 | M252Y/A378V/N434Y |
| F811 | 4.9E-07 | 59.4 | 1.03 | 301 | M252Y/E380S/N434Y |
| F812 | 2.7E-07 | 62.8 | 0.69 | 267 | M252Y/E382V/N434Y |
| F813 | 2.8E-07 | 64.3 | 0.77 | 284 | M252Y/S424E/N434Y |
| F814 | 1.2E-07 | 63.3 | 0.90 | 188 | M252Y/N434Y/Y436I |
| F815 | 5.5E-07 | 62.4 | 0.65 | 218 | M252Y/N434Y/T437R |
| F816 | 3.6E-07 | 63.1 | 0.73 | 503 | P238D/T250V/M252Y/T307P/N434Y |
| F817 | 9.8E-08 | 60.6 | 0.78 | 543 | P238D/T250V/M252Y/T307Q/Q311A/N434Y |
| F819 | 1.4E-07 | 49.1 | 0.74 | 384 | P238D/M252Y/N286E/N434Y |
| F820 | 3.4E-07 | 70.4 | 0.56 | 312 | L235K/S239K/M252Y/N434Y |
| F821 | 3.1E-07 | 71 | 0.67 | 309 | L235R/S239K/M252Y/N434Y |
| F823 | 1.1E-06 | 44.2 | 10.39 | 367 | P238D/T250Y/M252Y/W313F/N434Y |
| F828 | 2.5E-06 | 60.8 | 0.80 | 361 | P238D/T250V/M252Y/I253V/N434Y |
| F831 | 1.6E-06 | 59.1 | 0.70 | 333 | P238D/T250V/M252Y/R255A/N434Y |
| F832 | 2.6E-06 | 52.6 | 1.46 | 290 | P238D/T250V/M252Y/R255D/N434Y |
| F833 | 8.0E-07 | 56.6 | 0.82 | 343 | P238D/T250V/M252Y/R255E/N434Y |
| F834 | 8.1E-07 | 55 | 0.96 | 386 | P238D/T250V/M252Y/R255F/N434Y |
| F836 | 5.0E-07 | 58.9 | 0.66 | 317 | P238D/T250V/M252Y/R255H/N434Y |
| F837 | 5.6E-07 | 49.1 | 2.06 | 365 | P238D/T250V/M252Y/R255I/N434Y |
| F838 | 4.3E-07 | 56.2 | 1.02 | 351 | P238D/T250V/M252Y/R255K/N434Y |
| F839 | 3.4E-07 | 58.1 | 0.76 | 376 | P238D/T250V/M252Y/R255L/N434Y |
| F840 | 4.2E-07 | 56.6 | 0.77 | 379 | P238D/T250V/M252Y/R255M/N434Y |
| F841 | 1.1E-06 | 59.6 | 0.70 | 330 | P238D/T250V/M252Y/R255N/N434Y |
| F843 | 6.6E-07 | 57.2 | 0.72 | 343 | P238D/T250V/M252Y/R255Q/N434Y |
| F844 | 1.3E-06 | 58.3 | 0.69 | 347 | P238D/T250V/M252Y/R255S/N434Y |
| F847 | 3.4E-07 | 47.1 | 3.82 | 355 | P238D/T250V/M252Y/R255W/N434Y |
| F848 | 8.3E-07 | 55.7 | 0.87 | 368 | P238D/T250V/M252Y/R255Y/N434Y |
| F849 | 3.3E-07 | 61.1 | 0.84 | 331 | M252Y/D280A/N434Y |
| F850 | 2.9E-07 | 62.2 | 0.64 | 310 | M252Y/D280E/N434Y |
| F852 | 3.3E-07 | 61.8 | 0.61 | 285 | M252Y/D280G/N434Y |
| F853 | 3.2E-07 | 58.4 | 2.55 | 302 | M252Y/D280H/N434Y |
| F855 | 3.2E-07 | 52.9 | 6.55 | 366 | M252Y/D280K/N434Y |
| F858 | 3.2E-07 | 62.6 | 0.60 | 357 | M252Y/D280N/N434Y |
| F860 | 3.3E-07 | 61.1 | 0.82 | 365 | M252Y/D280Q/N434Y |
| F861 | 3.2E-07 | 49.2 | 9.26 | 363 | M252Y/D280R/N434Y |
| F862 | 3.0E-07 | 61 | 0.72 | 310 | M252Y/D280S/N434Y |
| F863 | 2.7E-07 | 55.3 | 16.98 | 326 | M252Y/D280T/N434Y |
| F867 | 2.8E-07 | 64.4 | 0.75 | 262 | M252Y/N384A/N389A/N434Y |
| F870 | 7.3E-08 | 69.9 | 0.93 | 499 | L235K/S239K/M252Y/T307Q/Q311A/N434Y |
| F871 | 7.1E-08 | 70.7 | 0.92 | 495 | L235R/S239K/M252Y/T307Q/Q311A/N434Y |
| F872 | 1.3E-07 | 68.8 | 0.85 | 374 | L235K/S239K/M252Y/N286E/N434Y |
| F873 | 1.2E-07 | 69 | 0.92 | 371 | L235R/S239K/M252Y/N286E/N434Y |
| F875 | 4.8E-07 | 63.7 | 0.88 | 165 | M252Y/N434Y/Y436A |
| F877 | 8.3E-07 | 65.2 | 0.99 | 147 | M252Y/N434Y/Y436E |
| F878 | 1.9E-07 | 65 | 0.68 | 210 | M252Y/N434Y/Y436F |
| F879 | 9.2E-07 | 64.2 | 0.89 | 172 | M252Y/N434Y/Y436G |
| F880 | 3.9E-07 | 65 | 0.81 | 170 | M252Y/N434Y/Y436H |
| F881 | 3.1E-07 | 62.7 | 0.93 | 183 | M252Y/N434Y/Y436K |
| F882 | 1.3E-07 | 64 | 1.04 | 188 | M252Y/N434Y/Y436L |
| F883 | 2.1E-07 | 64.5 | 0.83 | 222 | M252Y/N434Y/Y436M |
| F884 | 4.0E-07 | 64.1 | 0.84 | 177 | M252Y/N434Y/Y436N |
| F888 | 4.8E-07 | 63.9 | 0.83 | 163 | M252Y/N434Y/Y436S |
| F889 | 2.2E-07 | 63.4 | 0.84 | 171 | M252Y/N434Y/Y436T |
| F890 | 1.1E-07 | 63.4 | 0.73 | 200 | M252Y/N434Y/Y436V |
| F891 | 1.7E-07 | 62.9 | 2.54 | 208 | M252Y/N434Y/Y436W |
| F892 | 7.1E-08 | 63.9 | 1.83 | 159 | M252Y/S254T/N434Y/Y436I |
| F893 | 9.8E-08 | 70.2 | 0.73 | 257 | L235K/S239K/M252Y/N434Y/Y436I |
| F894 | 9.2E-08 | 70.6 | 0.87 | 253 | L235R/S239K/M252Y/N434Y/Y436I |

TABLE 16-continued

Fc variants

| Variant name | hFcRn KD (M) | Tm (° C.) | HMW (%) | Immunogenicity score | Mutation |
|---|---|---|---|---|---|
| F895 | 2.1E−08 | 68.7 | 0.76 | 573 | L235K/S239K/M252Y/N286E/T307Q/Q311A/N315E/N434Y |
| F896 | 2.0E−08 | 68.7 | 0.65 | 569 | L235R/S239K/M252Y/N286E/T307Q/Q311A/N315E/N434Y |
| F897 | 9.7E−08 | 64.6 | 0.87 | 262 | M252Y/N315D/N384A/N389A/N434Y |
| F898 | 1.7E−07 | 64.1 | 0.92 | 283 | M252Y/N315E/N384A/N389A/N434Y |
| F899 | 1.1E−07 | 58.4 | 0.72 | 243 | M252Y/N315D/G316A/N434Y |
| F900 | 1.7E−07 | 52.3 | 2.50 | 243 | M252Y/N315D/G316D/N434Y |
| F901 | 1.3E−07 | 55.6 | 0.67 | 243 | M252Y/N315D/G316E/N434Y |
| F902 | 2.2E−07 | 57.2 | 0.90 | 266 | M252Y/N315D/G316F/N434Y |
| F903 | 2.3E−07 | 58.6 | 0.84 | 243 | M252Y/N315D/G316H/N434Y |
| F904 | 1.0E−07 | 48.6 | 3.34 | 266 | M252Y/N315D/G316I/N434Y |
| F905 | 1.3E−07 | 54.7 | 0.70 | 243 | M252Y/N315D/G316K/N434Y |
| F906 | 1.5E−07 | 54 | 0.59 | 266 | M252Y/N315D/G316L/N434Y |
| F907 | 1.3E−07 | 55.8 | 0.62 | 266 | M252Y/N315D/G316M/N434Y |
| F908 | 1.5E−07 | 58.1 | 0.87 | 243 | M252Y/N315D/G316N/N434Y |
| F910 | 1.4E−07 | 55.8 | 0.68 | 243 | M252Y/N315D/G316Q/N434Y |
| F911 | 1.3E−07 | 56.3 | 0.71 | 243 | M252Y/N315D/G316R/N434Y |
| F912 | 1.2E−07 | 59.1 | 0.57 | 243 | M252Y/N315D/G316S/N434Y |
| F913 | 1.1E−07 | 53.6 | 0.58 | 243 | M252Y/N315D/G316T/N434Y |
| F914 | 1.5E−07 | 48.9 | 2.04 | 266 | M252Y/N315D/G316V/N434Y |
| F915 | 2.3E−07 | 54.8 | 0.61 | 243 | M252Y/N315D/G316W/N434Y |
| F917 | 2.5E−07 | 63.4 | 0.64 | 314 | M252Y/N286S/N434Y |
| F918 | 2.8E−07 | 61.8 | 0.72 | 329 | M252Y/D280E/N384A/N389A/N434Y |
| F919 | 3.3E−07 | 61.7 | 0.67 | 303 | M252Y/D280G/N384A/N389A/N434Y |
| F920 | 2.5E−07 | 63.3 | 0.72 | 332 | M252Y/N286S/N384A/N389A/N434Y |
| F921 | 1.2E−07 | 62.3 | 0.74 | 324 | M252Y/N286E/N384A/N389A/N434Y |
| F922 | 5.9E−08 | 69 | 0.88 | 319 | L235K/S239K/M252Y/N286E/N434Y/Y436I |
| F923 | 6.0E−08 | 68.9 | 0.87 | 316 | L235R/S239K/M252Y/N286E/N434Y/Y436I |
| F924 | 3.4E−08 | 70.5 | 0.78 | 444 | L235K/S239K/M252Y/T307Q/Q311A/N434Y/Y436I |
| F925 | 3.2E−08 | 70.8 | 0.75 | 440 | L235R/S239K/M252Y/T307Q/Q311A/N434Y/Y436I |
| F926 | 1.1E−07 | 70.6 | 0.87 | 228 | L235K/S239K/M252Y/S254T/N434Y/Y436I |
| F927 | 1.0E−07 | 70.8 | 0.80 | 224 | L235R/S239K/M252Y/S254T/N434Y/Y436I |
| F928 | 2.9E−08 | 63.9 | 0.76 | 375 | M252Y/T307Q/Q311A/N434Y/Y436I |
| F929 | 2.9E−08 | 64.2 | 0.87 | 346 | M252Y/S254T/T307Q/Q311A/N434Y/Y436I |
| F930 | 1.4E−07 | 58.6 | 0.78 | 419 | P238D/T250V/M252Y/N286E/N434Y |
| F931 | 1.2E−07 | 60.1 | 1.00 | 301 | P238D/T250V/M252Y/N434Y/Y436I |
| F932 | 3.2E−07 | 69.7 | 0.60 | 278 | T250V/M252Y/N434Y |
| F933 | 3.0E−07 | 63.2 | 0.67 | 323 | L234R/P238D/T250V/M252Y/N434Y |
| F934 | 3.1E−07 | 63.2 | 0.70 | 361 | G236K/P238D/T250V/M252Y/N434Y |
| F935 | 3.2E−07 | 64.2 | 0.61 | 354 | G237K/P238D/T250V/M252Y/N434Y |
| F936 | 3.2E−07 | 64.2 | 0.73 | 382 | G237R/P238D/T250V/M252Y/N434Y |
| F937 | 3.1E−07 | 66.2 | 0.65 | 320 | P238D/S239K/T250V/M252Y/N434Y |
| F938 | 1.6E−07 | 69.9 | 0.85 | 269 | L235K/S239K/M252Y/N434Y/Y436V |
| F939 | 1.5E−07 | 70 | 0.83 | 265 | L235R/S239K/M252Y/N434Y/Y436V |
| F940 | 1.5E−07 | 59.9 | 1.04 | 313 | P238D/T250V/M252Y/N434Y/Y436V |
| F941 | 1.2E−08 | 61.4 | 1.17 | 449 | M252Y/N286E/T307Q/Q311A/N434Y/Y436V |
| F942 | 4.2E−08 | 70.3 | 0.98 | 455 | L235K/S239K/M252Y/T307Q/Q311A/N434Y/Y436V |
| F943 | 4.0E−08 | 70.4 | 0.77 | 452 | L235R/S239K/M252Y/T307Q/Q311A/N434Y/Y436V |
| F944 | 1.7E−07 | 69.2 | 1.06 | 235 | T250V/M252Y/N434Y/Y436V |
| F945 | 1.7E−08 | 61 | 0.95 | 416 | T250V/M252Y/V308P/N434Y/Y436V |
| F946 | 4.3E−08 | 69 | 1.25 | 421 | T250V/M252Y/T307Q/Q311A/N434Y/Y436V |
| F947 | 1.1E−08 | 60.5 | 1.18 | 376 | T250V/M252Y/T307Q/V308P/Q311A/N434Y/Y436V |
| F954 | 5.3E−07 | 62.5 | 3.12 | 217 | M252Y/N434Y/H435K/Y436V |
| F957 | 7.7E−07 | 62.4 | 3.82 | 186 | M252Y/N434Y/H435N/Y436V |
| F960 | 8.0E−07 | 62.3 | 1.36 | 191 | M252Y/N434Y/H435R/Y436V |
| F966 | 3.1E−07 | 63.1 | 1.06 | 246 | M252Y/S254A/N434Y |
| F970 | 2.5E−06 | 64.8 | 0.90 | 214 | M252Y/S254G/N434Y |
| F971 | 2.6E−06 | 64.7 | 0.75 | 230 | M252Y/S254H/N434Y |
| F972 | 2.6E−07 | 58.7 | 2.25 | 239 | M252Y/S254I/N434Y |
| F978 | 1.3E−06 | 63.4 | 0.82 | 235 | M252Y/S254Q/N434Y |
| F980 | 1.8E−07 | 59.7 | 0.81 | 261 | M252Y/S254V/N434Y |
| F987 | 4.0E−08 | 59.5 | 0.87 | 500 | P238D/T250V/M252Y/T307Q/Q311A/N434Y/Y436V |
| F988 | 6.9E−08 | 56.8 | 1.08 | 375 | P238D/T250V/M252Y/N286E/N434Y/Y436V |
| F989 | 1.4E−08 | 61.6 | 0.82 | 446 | L235R/S239K/M252Y/V308P/N434Y/Y436V |
| F990 | 9.4E−09 | 61 | 0.88 | 406 | L235R/S239K/M252Y/T307Q/V308P/Q311A/N434Y/Y436V |
| F991 | 1.3E−08 | 68.4 | 1.24 | 514 | L235R/S239K/M252Y/N286E/T307Q/Q311A/N434Y/Y436V |
| F992 | 5.1E−08 | 66.7 | 1.34 | 495 | L235R/S239K/M252Y/T307Q/Q311A/M428I/N434Y/Y436V |
| F993 | 3.8E−08 | 63.4 | 0.93 | 387 | M252Y/T307Q/Q311A/N434Y/Y436V |
| F994 | 2.8E−07 | 67 | 0.67 | 333 | M252Y/N325G/N434Y |
| F995 | 2.9E−07 | 59.9 | 0.71 | 279 | L235R/P238D/S239K/M252Y/N434Y |
| F996 | 1.3E−07 | 58.6 | 1.04 | 235 | L235R/P238D/S239K/M252Y/N434Y/Y436V |
| F997 | 3.8E−07 | 69.1 | 2.40 | 300 | K248I/T250V/M252Y/N434Y/Y436V |
| F998 | 8.5E−07 | 66.2 | 2.51 | 262 | K248Y/T250V/M252Y/N434Y/Y436V |
| F999 | 2.1E−07 | 67.4 | 1.13 | 273 | T250V/M252Y/E258H/N434Y/Y436V |
| F1008 | 1.7E−07 | 74.5 | 1.18 | 300 | L235R/S239K/T250V/M252Y/N434Y/Y436V |

TABLE 16-continued

Fc variants

| Variant name | hFcRn KD (M) | Tm (° C.) | HMW (%) | Immunogenicity score | Mutation |
|---|---|---|---|---|---|
| F1009 | 1.2E−08 | 66.6 | 0.37 | 441 | L235R/S239K/T250V/M252Y/T307Q/V308P/Q311A/N434Y/Y436V |
| F1010 | 1.9E−07 | 70.6 | 0.29 | 513 | L235R/S239K/M252Y/T307A/Q311H/N434Y |
| F1011 | 4.5E−08 | 62.2 | 0.43 | 459 | T250V/M252Y/V308P/N434Y |
| F1012 | 4.7E−08 | 67.9 | 0.31 | 524 | L235R/S239K/T250V/M252Y/V308P/N434Y |
| F1013 | 3.0E−08 | 61.8 | 0.44 | 419 | T250V/M252Y/T307Q/V308P/Q311A/N434Y |
| F1014 | 3.2E−08 | 67.2 | 0.40 | 485 | L235R/S239K/T250V/M252Y/T307Q/V308P/Q311A/N434Y |
| F1015 | 2.2E−08 | 63 | 0.34 | 450 | L235R/S239K/M252Y/T307Q/V308P/Q311A/N434Y |
| F1016 | 3.8E−09 | 58.5 | 0.61 | 438 | T250V/M252Y/N286E/T307Q/V308P/Q311A/N434Y/Y436V |
| F1017 | 4.2E−09 | 65.1 | 0.56 | 504 | L235R/S239K/T250V/M252Y/N286E/T307Q/V308P/Q311A/N434Y/Y436V |
| F1018 | 3.2E−09 | 60 | 0.52 | 469 | L235R/S239K/M252Y/N286E/T307Q/V308P/Q311A/N434Y/Y436V |
| F1019 | 3.4E−07 | 62.4 | 0.45 | 446 | P238D/T250V/M252Y/N325G/N434Y |
| F1020 | 8.5E−08 | 63 | 0.54 | 633 | P238D/T250V/M252Y/T307Q/Q311A/N325G/N434Y |
| F1021 | 3.3E−07 | 61.9 | 0.47 | 510 | P238D/T250V/M252Y/N325A/N434Y |
| F1026 | 8.4E−08 | 63.3 | 0.47 | 404 | M252Y/T307A/Q311H/N434Y/Y436V |
| F1027 | 8.6E−08 | 70.1 | 0.39 | 469 | L235R/S239K/M252Y/T307A/Q311H/N434Y/Y436V |
| F1032 | 4.3E−08 | 61.7 | 0.67 | 589 | P238D/T250V/M252Y/T307Q/Q311A/N325G/N434Y/Y436V |
| F1033 | 1.0E−06 | 58.1 | 1.89 | 169 | P238D/N434W |
| F1034 | 1.5E−08 | 61.1 | 0.83 | 450 | L235K/S239K/M252Y/V308P/N434Y/Y436V |
| F1035 | 1.0E−08 | 60.1 | 1.69 | 410 | L235K/S239K/M252Y/T307Q/V308P/Q311A/N434Y/Y436V |
| F1036 | 1.4E−08 | 68.9 | 0.87 | 518 | L235K/S239K/M252Y/N286E/T307Q/V308P/Q311A/N434Y/Y436V |
| F1037 | 6.1E−08 | 67.7 | 1.44 | 498 | L235K/S239K/M252Y/T307Q/V308P/Q311A/M428I/N434Y/Y436V |
| F1038 | 2.8E−07 | 60.3 | 0.78 | 264 | L235K/P238D/S239K/M252Y/N434Y |
| F1039 | 1.3E−07 | 58.9 | 0.81 | 220 | L235K/P238D/S239K/M252Y/N434Y/Y436V |
| F1040 | 2.0E−07 | 74.4 | 1.08 | 304 | L235K/S239K/T250V/M252Y/N434Y/Y436V |
| F1041 | 1.4E−08 | 63.5 | 0.84 | 445 | L235K/S239K/T250V/M252Y/T307Q/V308P/Q311A/N434Y/Y436V |
| F1042 | 2.0E−07 | 70.3 | 0.82 | 516 | L235K/S239K/M252Y/T307A/Q311H/N434Y |
| F1043 | 5.2E−08 | 64.8 | 0.64 | 528 | L235K/S239K/T250V/M252Y/V308P/N434Y |
| F1044 | 3.5E−08 | 64 | 0.53 | 488 | L235K/S239K/T250V/M252Y/T307Q/V308P/Q311A/N434Y |
| F1045 | 2.5E−08 | 62.8 | 0.59 | 453 | L235K/S239K/M252Y/T307Q/V308P/Q311A/N434Y |
| F1046 | 4.5E−09 | 64.5 | 0.96 | 507 | L235K/S239K/T250V/M252Y/N286E/T307Q/V308P/Q311A/N434Y/Y436V |
| F1047 | 3.4E−09 | 60 | 0.96 | 472 | L235K/S239K/M252Y/N286E/T307Q/V308P/Q311A/N434Y/Y436V |
| F1048 | 9.9E−08 | 69.9 | 1.16 | 473 | L235K/S239K/M252Y/T307A/Q311H/N434Y/Y436V |
| F1050 | 3.5E−09 | 58.2 | 0.90 | 481 | T250V/M252Y/N286E/T307Q/V308P/Q311A/M428I/N434Y/Y436V |
| F1051 | 3.9E−09 | 65 | 0.72 | 547 | L235R/S239K/T250V/M252Y/N286E/T307Q/V308P/Q311A/M428I/N434Y/Y436V |
| F1052 | 3.2E−09 | 59.6 | 1.08 | 512 | L235R/S239K/M252Y/N286E/T307Q/V308P/Q311A/M428I/N434Y/Y436V |
| F1058 | 1.3E−07 | 63.7 | 0.74 | 214 | M252Y/Q386E/N434Y/Y436V |
| F1059 | 1.4E−07 | 63.1 | 0.63 | 214 | M252Y/Q386R/N434Y/Y436V |
| F1060 | 1.4E−07 | 63.3 | 0.62 | 214 | M252Y/Q386S/N434Y/Y436V |
| F1061 | 1.2E−07 | 64.7 | 0.60 | 200 | M252Y/P387E/N434Y/Y436V |
| F1062 | 1.2E−07 | 61 | 0.58 | 208 | M252Y/P387R/N434Y/Y436V |
| F1063 | 1.4E−07 | 63 | 0.58 | 214 | M252Y/P387S/N434Y/Y436V |
| F1064 | 1.3E−07 | 63 | 0.73 | 200 | M252Y/V422E/N434Y/Y436V |
| F1065 | 1.4E−07 | 62.9 | 0.54 | 242 | M252Y/V422R/N434Y/Y436V |
| F1066 | 1.4E−07 | 62.9 | 0.75 | 223 | M252Y/V422S/N434Y/Y436V |
| F1067 | 1.3E−07 | 63.5 | 0.73 | 241 | M252Y/S424E/N434Y/Y436V |
| F1068 | 1.7E−07 | 62.7 | 0.47 | 250 | M252Y/S424R/N434Y/Y436V |
| F1069 | 1.4E−07 | 62.9 | 0.87 | 186 | M252Y/N434Y/Y436V/Q438E |
| F1070 | 1.7E−07 | 62.9 | 0.62 | 209 | M252Y/N434Y/Y436V/Q438R |
| F1071 | 1.2E−07 | 63.1 | 0.57 | 235 | M252Y/N434Y/Y436V/Q438S |
| F1072 | 1.3E−07 | 63.3 | 0.75 | 133 | M252Y/N434Y/Y436V/S440E |
| F1073 | 1.3E−07 | 63 | 0.56 | 166 | M252Y/N434Y/Y436V/S440R |
| F1074 | 1.3E−07 | 57.7 | 0.67 | 200 | S239D/M252Y/N434Y/Y436V |
| F1075 | 1.4E−07 | 58.8 | 0.74 | 237 | M252Y/K326D/L328Y/N434Y/Y436V |
| F1076 | 1.3E−07 | 52.8 | 0.55 | 237 | S239D/M252Y/K326D/L328Y/N434Y/Y436V |
| F1077 | 2.0E−06 | 58 | 2.77 | 271 | K248N/M252Y/N434Y |
| F1078 | 4.7E−07 | 57.3 | 1.26 | 324 | M252Y/E380N/E382S/N434Y |
| F1079 | 3.4E−07 | 62.2 | 0.75 | 270 | M252Y/E382N/N384S/N434Y |
| F1080 | 3.2E−07 | 64 | 0.66 | 286 | M252Y/S424N/N434Y |
| F1081 | 6.2E−07 | 63.6 | 0.93 | 169 | M252Y/N434Y/Y436N/Q438T |
| F1082 | 2.8E−07 | 64.5 | 8.15 | 261 | M252Y/N434Y/Q438N |
| F1083 | 3.5E−07 | 64 | 0.81 | 188 | M252Y/N434Y/S440N |
| F1094 | 2.6E−07 | 63.8 | 0.61 | 230 | M252Y/N434Y/S442N |
| F1095 | 2.9E−07 | 64.3 | 0.64 | 265 | M252Y/S383N/G385S/N434Y |
| F1096 | 2.7E−07 | 64.3 | 0.66 | 257 | M252Y/Q386T/N434Y |
| F1097 | 2.8E−07 | 64.2 | 0.69 | 279 | M252Y/G385N/P387S/N434Y |
| F1098 | 2.6E−07 | 58.9 | 0.63 | 243 | S239D/M252Y/N434Y |
| F1099 | 2.6E−07 | 60 | 0.48 | 280 | M252Y/K326D/L328Y/N434Y |
| F1100 | 2.4E−07 | 54.5 | 0.61 | 280 | S239D/M252Y/K326D/L328Y/N434Y |
| F1101 | 6.6E−08 | 59.4 | 0.47 | 430 | S239D/M252Y/T307Q/Q311A/N434Y |
| F1102 | 6.5E−08 | 60.2 | 0.58 | 467 | M252Y/T307Q/Q311A/K326D/L328Y/N434Y |
| F1103 | 6.1E−08 | 54.8 | 0.83 | 467 | S239D/M252Y/T307Q/Q311A/K326D/L328Y/N434Y |
| F1104 | 1.8E−07 | 62.9 | 0.61 | 242 | M252Y/V422E/S424R/N434Y/Y436V |
| F1105 | 1.5E−07 | 62.6 | 0.59 | 258 | M252Y/V422S/S424R/N434Y/Y436V |
| F1106 | 1.4E−07 | 63.1 | 0.60 | 158 | M252Y/N434Y/Y436V/Q438R/S440E |

TABLE 16-continued

Fc variants

| Variant name | hFcRn KD (M) | Tm (° C.) | HMW (%) | Immuno-genicity score | Mutation |
|---|---|---|---|---|---|
| F1107 | 1.2E-07 | 63.2 | 0.75 | 208 | M252Y/V422D/N434Y/Y436V |
| F1108 | 1.3E-07 | 63.2 | 0.59 | 234 | M252Y/V422K/N434Y/Y436V |
| F1109 | 1.3E-07 | 63.4 | 0.58 | 200 | M252Y/V422T/N434Y/Y436V |
| F1110 | 1.3E-07 | 63.4 | 0.61 | 208 | M252Y/V422Q/N434Y/Y436V |
| F1111 | 1.6E-07 | 63.1 | 0.65 | 242 | M252Y/S424K/N434Y/Y436V |
| F1112 | 1.2E-07 | 63.1 | 0.57 | 209 | M252Y/N434Y/Y436V/Q438K |
| F1113 | 1.2E-07 | 63.6 | 0.68 | 133 | M252Y/N434Y/Y436V/S440D |
| F1114 | 1.3E-07 | 63.5 | 0.57 | 145 | M252Y/N434Y/Y436V/S440Q |
| F1115 | 1.3E-07 | 64 | 0.75 | 243 | M252Y/S424N/N434Y/Y436V |
| F1116 | 7.4E-08 | 64.4 | 0.58 | 473 | M252Y/T307Q/Q311A/S424N/N434Y |
| F1117 | 4.9E-08 | 69.3 | 0.71 | 465 | T250V/M252Y/T307Q/Q311A/S424N/N434Y/Y436V |
| F1118 | 1.3E-08 | 61 | 0.72 | 419 | T250V/M252Y/T307Q/V308P/Q311A/S424N/N434Y/Y436V |
| F1119 | 1.0E-08 | 60.5 | 0.72 | 376 | T250V/M252Y/T307Q/V308P/Q311A/V422E/N434Y/Y436V |
| F1120 | 1.0E-08 | 59.7 | 0.61 | 426 | T250V/M252Y/T307Q/V308P/Q311A/S424R/N434Y/Y436V |
| F1121 | 1.0E-08 | 59.9 | 0.54 | 418 | T250V/M252Y/T307Q/V308P/Q311A/V422E/S424R/N434Y/Y436V |
| F1122 | 1.4E-08 | 59.6 | 0.41 | 385 | T250V/M252Y/T307Q/V308P/Q311A/N434Y/Y436V/Q438R |
| F1123 | 9.5E-09 | 60.8 | 0.61 | 309 | T250V/M252Y/T307Q/V308P/Q311A/N434Y/Y436V/S440E |
| F1124 | 1.2E-08 | 59.9 | 0.61 | 334 | T250V/M252Y/T307Q/V308P/Q311A/N434Y/Y436V/Q438R/S440E |
| F1125 | 5.2E-08 | 64.3 | 0.59 | 346 | M252Y/T307Q/N434Y/Y436V |
| F1126 | 9.0E-08 | 64.3 | 0.58 | 412 | M252Y/T307A/N434Y/Y436V |
| F1127 | 7.9E-08 | 62.8 | 0.53 | 338 | M252Y/Q311A/N434Y/Y436V |
| F1128 | 1.2E-07 | 62.3 | 0.41 | 274 | M252Y/Q311H/N434Y/Y436V |
| F1129 | 4.5E-08 | 63.2 | 0.51 | 315 | M252Y/T307Q/Q311H/N434Y/Y436V |
| F1130 | 5.5E-08 | 63.7 | 0.54 | 453 | M252Y/T307A/Q311A/N434Y/Y436V |
| F1131 | 1.3E-07 | 69.5 | 0.81 | 265 | L235R/S239K/M252Y/V422E/N434Y/Y436V |
| F1132 | 1.4E-07 | 69.1 | 0.87 | 288 | L235R/S239K/M252Y/V422S/N434Y/Y436V |
| F1133 | 1.6E-07 | 69.5 | 0.71 | 316 | L235R/S239K/M252Y/S424R/N434Y/Y436V |
| F1134 | 1.7E-07 | 70.4 | 0.58 | 274 | L235R/S239K/M252Y/N434Y/Y436V/Q438R |
| F1135 | 1.3E-07 | 69.8 | 0.72 | 198 | L235R/S239K/M252Y/N434Y/Y436V/S440E |
| F1136 | 1.6E-07 | 68.5 | 0.74 | 308 | L235R/S239K/M252Y/V422E/S424R/N434Y/Y436V |
| F1137 | 1.6E-07 | 69.4 | 0.82 | 323 | L235R/S239K/M252Y/V422S/S424R/N434Y/Y436V |
| F1138 | 1.7E-07 | 70.5 | 0.67 | 223 | L235R/S239K/M252Y/N434Y/Y436V/Q438R/S440E |
| F1139 | 1.5E-07 | 71.2 | 0.58 | 308 | L235R/S239K/M252Y/S424N/N434Y/Y436V |
| F1140 | 1.6E-07 | 62.6 | 0.89 | 201 | M252Y/V422E/S424R/N434Y/Y436V/Q438R/S440E |
| F1141 | 1.8E-07 | 62.7 | 0.94 | 216 | M252Y/V422S/S424R/N434Y/Y436V/Q438R/S440E |
| F1142 | 1.9E-07 | 70 | 0.80 | 266 | L235R/S239K/M252Y/V422E/S424R/N434Y/Y436V/Q438R/S440E |
| F1143 | 2.0E-07 | 70.2 | 0.90 | 281 | L235R/S239K/M252Y/V422S/S424R/N434Y/Y436V/Q438R/S440E |
| F1144 | 1.4E-08 | 66.7 | 0.81 | 400 | L235R/S239K/T250V/M252Y/T307Q/V308P/Q311A/N434Y/Y436V/Q438R/S440E |
| F1145 | 5.2E-08 | 68.9 | 0.89 | 380 | T250V/M252Y/T307Q/Q311A/N434Y/Y436V/Q438R/S440E |
| F1146 | 6.2E-08 | 75.6 | 0.85 | 445 | L235R/S239K/T250V/M252Y/T307Q/Q311A/N434Y/Y436V/S440E |
| F1147 | 7.2E-08 | 64.1 | 0.68 | 367 | M252Y/T307Q/Q311A/N434Y/Y436V/S440E |
| F1148 | 7.6E-08 | 70.9 | 0.69 | 432 | L235R/S239K/M252Y/T307Q/Q311A/N434Y/Y436V/S440E |
| F1151 | 2.5E-07 | 71.3 | 0.52 | 352 | L235R/S239K/M252Y/S424N/N434Y |
| F1152 | 7.4E-07 | 71.3 | 0.56 | 538 | L235R/S239K/M252Y/T307Q/Q311A/S424N/N434Y |
| F1153 | 4.8E-08 | 76.7 | 0.90 | 530 | L235R/S239K/T250V/M252Y/T307Q/Q311A/S424N/N434Y/Y436V |
| F1154 | 1.3E-08 | 67.6 | 0.68 | 484 | L235R/S239K/T250V/M252Y/T307Q/V308P/Q311A/S424N/N434Y/Y436V |
| F1157 | 2.1E-07 | 64.2 | 0.13 | 180 | M252Y/N434Y/Q438R/S440E |
| F1158 | 2.4E-07 | 70.9 | 0.67 | 245 | L235R/S239K/M252Y/N434Y/Q438R/S440E |
| F1159 | 4.8E-07 | 67.9 | 0.54 | 134 | S424N/N434W |
| F1160 | 2.9E-07 | 54 | 2.75 | 370 | V308F/S424N/N434Y |
| F1161 | 1.1E-06 | 67.3 | 0.77 | 157 | I332V/S424N/N434Y |
| F1162 | 3.4E-07 | 58.1 | 0.93 | 313 | P238D/T250V/M252Y/N434Y/Y436V |
| F1163 | 1.5E-07 | 60.2 | 0.84 | 543 | P238D/T250V/M252Y/T307Q/Q311A/N434Y |
| F1164 | 7.0E-08 | 58.2 | 0.91 | 500 | P238D/T250V/M252Y/T307Q/Q311A/N434Y/Y436V |
| F1165 | 1.6E-08 | 46.6 | 1.26 | 454 | P238D/T250V/M252Y/T307Q/V308P/Q311A/N434Y/Y436V |
| F1174 | 4.9E-07 | 60.3 | 1.38 | 145 | P257I/N434H |
| F1176 | 2.0E-06 | 57 | 1.10 | 215 | V308F |
| F1178 | 8.7E-07 | 60.1 | 1.09 | 353 | V259I/V308F/M428L |
| F1183 | 1.3E-06 | 63.9 | 0.61 | 203 | E380A/M428L/N434S |
| F1184 | 1.0E-06 | 70.1 | 0.40 | 329 | T307A/M428L/N434S |
| F1185 | 9.2E-07 | 64.6 | 0.55 | 415 | T307A/E380A/M428L/N434S |
| F1188 | 1.7E-06 | 64.3 | 0.56 | 322 | T307A/E380A/N434H |
| F1189 | 1.6E-07 | 63 | 0.52 | 161 | M252Y/H433D/N434Y/Y436V/Q438R/S440E |
| F1190 | 2.4E-07 | 63.7 | 0.58 | 161 | M252Y/H433E/N434Y/Y436V/Q438R/S440E |
| F1191 | 2.1E-07 | 63 | 0.70 | 147 | M252Y/N434Y/Y436V/T437A/Q438R/S440E |
| F1192 | 1.3E-07 | 62.3 | 0.82 | 133 | M252Y/N434Y/Y436V/T437G/Q438R/S440E |
| F1194 | 1.6E-07 | 60.3 | 0.84 | 168 | M252Y/N434Y/Y436V/Q438R/K439D/S440E |
| F1195 | 1.8E-07 | 60.5 | 2.91 | 156 | M252Y/N434Y/Y436V/Q438R/S440E/L441A |
| F1196 | 1.5E-07 | 60.4 | 0.90 | 161 | M252Y/N434Y/Y436V/Q438R/S440E/L441E |
| F1197 | 9.5E-08 | 63.2 | 0.48 | 129 | M252Y/S254T/N434Y/Y436V/Q438R/S440E |
| F1198 | 7.8E-08 | 60.8 | 0.68 | 67 | M252Y/T256E/N434Y/Y436V/Q438R/S440E |
| F1199 | 6.2E-08 | 61.2 | 0.74 | 67 | M252Y/S254T/T256E/N434Y/Y436V/Q438R/S440E |
| F1200 | 1.3E-07 | 68.8 | 0.68 | 164 | T250V/M252Y/S254T/N434Y/Y436V/Q438R/S440E |
| F1201 | 1.1E-07 | 66.3 | 0.97 | 101 | T250V/M252Y/T256E/N434Y/Y436V/Q438R/S440E |

TABLE 16-continued

Fc variants

| Variant name | hFcRn KD (M) | Tm (° C.) | HMW (%) | Immunogenicity score | Mutation |
|---|---|---|---|---|---|
| F1202 | 8.8E-08 | 66 | 0.77 | 101 | T250V/M252Y/S254T/T256E/N434Y/Y436V/Q438R/S440E |
| F1203 | 1.5E-07 | 62.4 | 0.60 | 90 | M252Y/T256Q/N434Y/Y436V/Q438R/S440E |
| F1204 | 1.2E-07 | 62.6 | 0.35 | 64 | M252Y/S254T/T256Q/N434Y/Y436V/Q438R/S440E |
| F1205 | 2.0E-07 | 68.4 | 0.87 | 125 | T250V/M252Y/T256Q/N434Y/Y436V/Q438R/S440E |
| F1206 | 1.7E-07 | 68.5 | 0.71 | 99 | T250V/M252Y/S254T/T256Q/N434Y/Y436V/Q438R/S440E |
| F1207 | 1.1E-06 | 59.6 | 0.70 | 116 | I332E/M428L/N434S |
| F1208 | 5.7E-07 | 57.5 | 2.22 | 114 | L251A/M252Y/N434Y/Y436V |
| F1211 | 1.2E-06 | 55.8 | 3.02 | 89 | L251H/M252Y/N434Y/Y436V |
| F1216 | 1.2E-06 | 55.8 | 3.33 | 91 | L251S/M252Y/N434Y/Y436V |
| F1217 | 1.1E-06 | 55.5 | 2.65 | 116 | L251T/M252Y/N434Y/Y436V |
| F1218 | 2.5E-07 | 57.3 | 1.11 | 200 | L251V/M252Y/N434Y/Y436V |
| F1229 | 2.8E-06 | 62.9 | 0.76 | 204 | M252Y/I253V/N434Y/Y436V |
| F1230 | 1.1E-07 | 63.1 | 0.68 | 145 | M252Y/N434Y/Y436V/Q438R/S440D |
| F1231 | 9.7E-08 | 63 | 0.87 | 145 | M252Y/N434Y/Y436V/Q438K/S440E |
| F1232 | 9.8E-08 | 63.2 | 0.86 | 145 | M252Y/N434Y/Y436V/Q438K/S440D |
| F1243 | 1.3E-07 | 70.6 | 0.73 | 194 | L235R/S239K/M252Y/S254T/N434Y/Y436V/Q438R/S440E |
| F1244 | 1.0E-07 | 69.2 | 0.85 | 132 | L235R/S239K/M252Y/T256E/N434Y/Y436V/Q438R/S440E |
| F1245 | 8.2E-08 | 69.3 | 0.97 | 132 | L235R/S239K/M252Y/S254T/T256E/N434Y/Y436V/Q438R/S440E |
| F1246 | 1.7E-07 | 75.1 | 0.74 | 229 | L235R/S239K/T250V/M252Y/S254T/N434Y/Y436V/Q438R/S440E |
| F1247 | 1.5E-07 | 72.9 | 1.20 | 167 | L235R/S239K/T250V/M252Y/T256E/N434Y/Y436V/Q438R/S440E |
| F1248 | 1.2E-07 | 73 | 0.94 | 167 | L235R/S239K/T250V/M252Y/S254T/T256E/N434Y/Y436V/Q438R/S440E |
| F1249 | 2.1E-07 | 70.5 | 0.78 | 155 | L235R/S239K/M252Y/T256Q/N434Y/Y436V/Q438R/S440E |
| F1250 | 1.7E-07 | 70.7 | 0.72 | 129 | L235R/S239K/M252Y/S254T/T256Q/N434Y/Y436V/Q438R/S440E |
| F1251 | 2.8E-07 | 74.6 | 1.13 | 190 | L235R/S239K/T250V/M252Y/T256Q/N434Y/Y436V/Q438R/S440E |
| F1252 | 2.3E-07 | 75 | 0.90 | 164 | L235R/S239K/T250V/M252Y/S254T/T256Q/N434Y/Y436V/Q438R/S440E |
| F1253 | 1.1E-07 | 70.9 | 0.87 | 436 | L235R/S239K/M252Y/T307A/N434Y/Y436V/Q438R/S440E |
| F1254 | 6.4E-08 | 71.6 | 0.67 | 369 | L235R/S239K/M252Y/T307Q/N434Y/Y436V/Q438R/S440E |
| F1255 | 1.1E-07 | 69.9 | 0.74 | 362 | L235R/S239K/M252Y/Q311A/N434Y/Y436V/Q438R/S440E |
| F1256 | 1.6E-07 | 69.6 | 0.74 | 298 | L235R/S239K/M252Y/Q311H/N434Y/Y436V/Q438R/S440E |
| F1257 | 7.8E-08 | 70.5 | 0.83 | 477 | L235R/S239K/M252Y/T307A/Q311A/N434Y/Y436V/Q438R/S440E |
| F1258 | 1.1E-07 | 70.1 | 0.60 | 428 | L235R/S239K/M252Y/T307A/Q311H/N434Y/Y436V/Q438R/S440E |
| F1259 | 4.5E-08 | 71 | 0.79 | 410 | L235R/S239K/M252Y/T307Q/Q311A/N434Y/Y436V/Q438R/S440E |
| F1260 | 6.5E-08 | 70.7 | 0.49 | 338 | L235R/S239K/M252Y/T307Q/Q311H/N434Y/Y436V/Q438R/S440E |
| F1261 | 1.4E-07 | 70.3 | 0.69 | 210 | L235R/S239K/M252Y/N434Y/Y436V/Q438R/S440D |
| F1262 | 1.3E-07 | 70.1 | 0.70 | 210 | L235R/S239K/M252Y/N434Y/Y436V/Q438K/S440E |
| F1263 | 1.2E-07 | 70.3 | 0.67 | 210 | L235R/S239K/M252Y/N434Y/Y436V/Q438K/S440D |
| F1264 | 1.3E-07 | 68.6 | 0.67 | 206 | L235R/S239K/M252Y/T256A/N434Y/Y436V/Q438R/S440E |
| F1265 | 1.6E-07 | 65.8 | 0.72 | 182 | L235R/S239K/M252Y/T256G/N434Y/Y436V/Q438R/S440E |
| F1266 | 1.0E-07 | 69.7 | 0.70 | 210 | L235R/S239K/M252Y/T256N/N434Y/Y436V/Q438R/S440E |
| F1267 | 1.5E-07 | 69 | 0.73 | 226 | L235R/S239K/M252Y/S254A/N434Y/Y436V/Q438R/S440E |
| F1268 | 2.0E-07 | 70.3 | 0.70 | 226 | L235R/S239K/M252Y/H433D/N434Y/Y436V/Q438R/S440E |
| F1269 | 1.7E-07 | 70.5 | 0.80 | 212 | L235R/S239K/M252Y/H433D/N434Y/Y436V/Q438K/S440D |
| F1270 | 1.2E-07 | 69 | 0.66 | 212 | L235R/S239K/M252Y/S254A/N434Y/Y436V/Q438K/S440D |
| F1271 | 2.0E-07 | 69 | 0.69 | 228 | L235R/S239K/M252Y/S254A/H433D/N434Y/Y436V/Q438R/S440E |
| F1272 | 1.7E-07 | 69.2 | 0.86 | 215 | L235R/S239K/M252Y/S254A/H433D/N434Y/Y436V/Q438K/S440D |
| F1273 | 1.5E-07 | 70.4 | 0.79 | 142 | L235R/S239K/M252Y/T256Q/N434Y/Y436V/Q438K/S440D |
| F1274 | 2.5E-07 | 70.4 | 0.70 | 158 | L235R/S239K/M252Y/T256Q/H433D/N434Y/Y436V/Q438R/S440E |
| F1275 | 2.1E-07 | 70.7 | 0.78 | 144 | L235R/S239K/M252Y/T256Q/H433D/N434Y/Y436V/Q438K/S440D |
| F1276 | 1.0E-07 | 68.7 | 0.77 | 192 | L235R/S239K/M252Y/T256A/N434Y/Y436V/Q438K/S440D |
| F1277 | 1.7E-07 | 68.8 | 0.69 | 208 | L235R/S239K/M252Y/T256A/H433D/N434Y/Y436V/Q438R/S440E |
| F1278 | 1.4E-07 | 68.9 | 0.97 | 195 | L235R/S239K/M252Y/T256A/H433D/N434Y/Y436V/Q438K/S440D |
| F1279 | 1.2E-07 | 66.2 | 0.79 | 169 | L235R/S239K/M252Y/T256G/N434Y/Y436V/Q438K/S440D |
| F1280 | 2.1E-07 | 66.1 | 1.03 | 185 | L235R/S239K/M252Y/T256G/H433D/N434Y/Y436V/Q438R/S440E |
| F1281 | 1.7E-07 | 66.4 | 0.99 | 171 | L235R/S239K/M252Y/T256G/H433D/N434Y/Y436V/Q438K/S440D |
| F1282 | 7.7E-08 | 69.8 | 0.77 | 196 | L235R/S239K/M252Y/T256N/N434Y/Y436V/Q438K/S440D |
| F1283 | 1.3E-07 | 69.8 | 0.81 | 212 | L235R/S239K/M252Y/T256N/H433D/N434Y/Y436V/Q438R/S440E |
| F1284 | 1.1E-07 | 70 | 1.02 | 198 | L235R/S239K/M252Y/T256N/H433D/N434Y/Y436V/Q438K/S440D |
| F1285 | 9.4E-08 | 70.4 | 0.72 | 181 | L235R/S239K/M252Y/S254T/N434Y/Y436V/Q438K/S440D |
| F1286 | 1.6E-07 | 70.4 | 0.86 | 197 | L235R/S239K/M252Y/S254T/H433D/N434Y/Y436V/Q438R/S440E |
| F1287 | 1.5E-07 | 71.2 | 0.63 | 183 | L235R/S239K/M252Y/S254T/H433D/N434Y/Y436V/Q438K/S440D |
| F1288 | 7.9E-08 | 68.8 | 0.92 | 118 | L235R/S239K/M252Y/T256E/N434Y/Y436V/Q438K/S440D |
| F1289 | 1.3E-07 | 68.8 | 0.76 | 134 | L235R/S239K/M252Y/T256E/H433D/N434Y/Y436V/Q438R/S440E |
| F1290 | 1.1E-07 | 69.2 | 0.91 | 121 | L235R/S239K/M252Y/T256E/H433D/N434Y/Y436V/Q438K/S440D |
| F1291 | 1.5E-07 | 70.4 | 0.62 | 275 | L235R/S239K/M252Y/H433D/N434Y/Y436V |
| F1292 | 4.2E-08 | 71.1 | 0.66 | 95 | L235R/S239K/H433D/N434Y/Y436V/Q438R/S440E |
| F1293 | 1.6E-07 | 68.6 | 0.73 | 153 | L235R/S239K/M252Y/T256E/N434Y/Q438R/S440E |
| F1294 | 2.0E-07 | 68.9 | 0.90 | 106 | L235R/S239K/M252Y/T256E/N434Y/Y436T/Q438R/S440E |
| F1295 | 9.8E-08 | 68.7 | 0.81 | 128 | L235R/S239K/M252Y/T256E/N434Y/Y436F/Q438R/S440E |
| F1296 | 2.3E-07 | 68.8 | 0.76 | 152 | L235R/S239K/M252Y/T256E/H433D/N434Y/Q438R/S440E |
| F1297 | 2.5E-07 | 69.1 | 0.81 | 107 | L235R/S239K/M252Y/T256E/H433D/N434Y/Y436T/Q438R/S440E |
| F1298 | 1.5E-07 | 69.1 | 0.82 | 106 | L235R/S239K/M252Y/T256E/H433D/N434Y/Y436F/Q438R/S440E |
| F1299 | 1.5E-07 | 68.7 | 0.72 | 140 | L235R/S239K/M252Y/T256E/N434Y/Q438K/S440D |
| F1300 | 1.6E-07 | 69 | 0.86 | 118 | L235R/S239K/M252Y/T256E/N434Y/Y436T/Q438K/S440D |
| F1301 | 8.3E-08 | 69 | 0.85 | 140 | L235R/S239K/M252Y/T256E/N434Y/Y436F/Q438K/S440D |

TABLE 16-continued

Fc variants

| Variant name | hFcRn KD (M) | Tm (° C.) | HMW (%) | Immunogenicity score | Mutation |
|---|---|---|---|---|---|
| F1302 | 2.2E−07 | 69.2 | 0.75 | 138 | L235R/S239K/M252Y/T256E/H433D/N434Y/Q438K/S440D |
| F1303 | 2.1E−07 | 69.1 | 0.81 | 119 | L235R/S239K/M252Y/T256E/H433D/N434Y/Y436T/Q438K/S440D |
| F1304 | 1.2E−07 | 69.4 | 0.75 | 118 | L235R/S239K/M252Y/T256E/H433D/N434Y/Y436F/Q438K/S440D |
| F1305 | 2.0E−07 | 70.8 | 0.77 | 212 | L235R/S239K/M252Y/H433D/N434Y/Y436V/Q438K/S440D |
| F1306 | 1.9E−07 | 70.5 | 0.70 | 238 | L235R/S239K/M252Y/H433D/N434Y/Y436V/Q438K/S440E |
| F1307 | 1.4E−07 | 69.5 | 0.68 | 337 | L235R/S239K/M252Y/V422A/S424A/N434Y/Y436V |
| F1308 | 2.1E−07 | 68.5 | 0.56 | 345 | L235R/S239K/M252Y/V422L/S424L/N434Y/Y436V |
| F1309 | 1.3E−07 | 70.2 | 0.83 | 284 | L235R/S239K/M252Y/N434Y/Y436V/Q438A/S440A |
| F1310 | 2.3E−07 | 68.2 | 1.27 | 325 | L235R/S239K/M252Y/N434Y/Y436V/Q438L/S440L |
| F1311 | 1.7E−07 | 70.6 | 0.59 | 347 | L235R/S239K/M252Y/V422A/S424A/H433D/N434Y/Y436V |
| F1312 | 1.8E−07 | 70.4 | 0.55 | 355 | L235R/S239K/M252Y/V422L/S424L/H433D/N434Y/Y436V |
| F1313 | 1.8E−07 | 70.5 | 0.75 | 300 | L235R/S239K/M252Y/H433D/N434Y/Y436V/Q438A/S440A |
| F1314 | 2.3E−07 | 69.4 | 1.15 | 302 | L235R/S239K/M252Y/H433D/N434Y/Y436V/Q438L/S440L |
| F1315 | 1.5E−07 | 67.5 | 0.67 | 258 | G237K/S239K/M252Y/N434Y/Y436V |
| F1316 | 1.5E−07 | 67.7 | 0.70 | 260 | G237R/S239K/M252Y/N434Y/Y436V |
| F1317 | 1.4E−07 | 65.8 | 0.59 | 340 | S239K/M252Y/P329K/N434Y/Y436V |
| F1318 | 1.4E−07 | 66.2 | 0.57 | 317 | S239K/M252Y/P329R/N434Y/Y436V |
| F1319 | 2.7E−07 | 60.2 | 0.54 | 310 | M252Y/L328Y/N434Y |
| F1320 | 1.2E−07 | 70.5 | 0.71 | 181 | L235R/S239K/M252Y/S254T/N434Y/Y436V/Q438K/S440D |
| F1321 | 1.0E−07 | 70.4 | 0.73 | 181 | L235R/S239K/M252Y/S254T/N434Y/Y436V/Q438K/S440E |
| F1322 | 1.6E−07 | 70.7 | 0.77 | 183 | L235R/S239K/M252Y/S254T/H433D/N434Y/Y436V/Q438R/S440D |
| F1323 | 1.5E−07 | 70.8 | 0.88 | 209 | L235R/S239K/M252Y/S254T/H433D/N434Y/Y436V/Q438K/S440E |
| F1324 | 1.3E−07 | 63.8 | 0.52 | 223 | L234A/L235A/M252Y/N434Y/Y436V |
| F1325 | 2.1E−07 | 55.1 | 1.87 | 249 | L234A/L235A/M252Y/N297A/N434Y/Y436V |
| F1326 | 1.1E−08 | 60.4 | 0.62 | 399 | L234A/L235A/T250V/M252Y/T307Q/V308P/Q311A/N434Y/Y436V |
| F1327 | 1.4E−08 | 48.2 | 0.91 | 425 | L234A/L235A/T250V/M252Y/N297A/T307Q/V308P/Q311A/N434Y/Y436V |
| F1328 | 1.5E−07 | 71.2 | 0.68 | 258 | L235R/G236R/S239K/M252Y/N434Y/Y436V/Q438R/S440E |
| F1329 | 1.3E−07 | 71.2 | 0.74 | 229 | L235R/G236R/S239K/M252Y/S254T/N434Y/Y436V/Q438R/S440E |
| F1330 | 1.0E−07 | 69.8 | 0.80 | 167 | L235R/G236R/S239K/M252Y/T256E/N434Y/Y436V/Q438R/S440E |
| F1331 | 7.7E−08 | 70 | 0.90 | 167 | L235R/G236R/S239K/M252Y/S254T/T256E/N434Y/Y436V/Q438R/S440E |
| F1333 | 1.2E−07 | 70.4 | 0.60 | 300 | L235R/G236R/S239K/M252Y/N434Y/Y436V |
| F1334 | 1.0E−07 | 71.1 | 0.59 | 245 | L235R/G236R/S239K/M252Y/N434Y/Y436V/Q438K/S440D |
| F1335 | 8.8E−08 | 71.3 | 0.54 | 216 | L235R/G236R/S239K/M252Y/S254T/N434Y/Y436V/Q438K/S440D |
| F1336 | 7.2E−08 | 69.8 | 0.84 | 153 | L235R/G236R/S239K/M252Y/T256E/N434Y/Y436V/Q438K/S440D |
| F1337 | 7.4E−08 | 68.9 | 0.69 | 118 | L235R/S239K/M252Y/T256E/N434Y/Y436V/Q438K/S440E |
| F1338 | 1.0E−07 | 69.2 | 0.84 | 146 | L235R/S239K/M252Y/T256E/H433D/N434Y/Y436V/Q438K/S440E |
| F1339 | 2.5E−07 | 69.5 | 0.59 | 144 | L235R/S239K/M252Y/S254T/T256E/H433D/N434Y/Y436T/Q438K/S440E |
| F1340 | 5.6E−08 | 69.1 | 0.76 | 118 | L235R/S239K/M252Y/S254T/T256E/N434Y/Y436V/Q438K/S440E |
| F1341 | 3.2E−07 | 70.7 | 0.44 | 181 | L235R/S239K/M252Y/S254T/N434Y/Y436T/Q438K/S440E |
| F1342 | 2.5E−07 | 69.2 | 0.68 | 118 | L235R/S239K/M252Y/N434Y/Y436T/Q438K/S440E |
| F1343 | 2.0E−07 | 69.1 | 0.56 | 118 | L235R/S239K/M252Y/S254T/T256E/N434Y/Y436T/Q438K/S440E |
| F1344 | 4.0E−07 | 70.5 | 0.53 | 210 | L235R/S239K/M252Y/N434Y/Y436T/Q438K/S440E |
| F1345 | 1.0E−07 | 71.2 | 0.77 | 245 | L235R/G236R/S239K/M252Y/N434Y/Y436V/Q438K/S440E |
| F1346 | 8.6E−08 | 71.3 | 0.70 | 216 | L235R/G236R/S239K/M252Y/S254T/N434Y/Y436V/Q438K/S440E |
| F1347 | 7.1E−08 | 69.9 | 0.95 | 153 | L235R/G236R/S239K/M252Y/T256E/N434Y/Y436V/Q438K/S440E |
| F1348 | 5.5E−08 | 70.1 | 0.72 | 153 | L235R/G236R/S239K/M252Y/S254T/T256E/N434Y/Y436V/Q438K/S440E |
| F1349 | 3.4E−07 | 70.2 | 0.67 | 198 | L235R/S239K/M252Y/N434Y/Y436T/Q438R/S440E |
| F1350 | 1.2E−07 | 70.6 | 0.70 | 232 | L235R/S239K/M252Y/N434Y/Q438K/S440E |
| F1351 | 1.6E−07 | 70.4 | 0.68 | 220 | L235R/S239K/M252Y/N434Y/Y436F/Q438R/S440E |
| F1352 | 3.9E−07 | 70.5 | 0.75 | 236 | L235R/S239K/M252Y/H433D/N434Y/Y436T/Q438K/S440E |
| F1353 | 4.3E−07 | 70.4 | 0.73 | 199 | L235R/S239K/M252Y/H433D/N434Y/Y436T/Q438R/S440E |
| F1354 | 2.3E−07 | 70.7 | 0.66 | 210 | L235R/S239K/M252Y/H433D/N434Y/Y436F/Q438K/S440E |
| F1355 | 2.5E−07 | 70.8 | 0.64 | 198 | L235R/S239K/M252Y/H433D/N434Y/Y436F/Q438R/S440E |
| F1356 | 1.6E−07 | 58.9 | 0.62 | 412 | G236R/M252Y/L328R/N434Y/Y436V |
| F1357 | 2.8E−07 | 70.5 | 0.61 | 169 | L235R/S239K/M252Y/S254T/N434Y/Y436T/Q438R/S440E |
| F1358 | 9.1E−08 | 71 | 0.64 | 203 | L235R/S239K/M252Y/S254T/N434Y/Y436F/Q438K/S440E |
| F1359 | 1.3E−07 | 71.1 | 0.67 | 191 | L235R/S239K/M252Y/S254T/N434Y/Y436F/Q438R/S440E |
| F1360 | 3.1E−07 | 70.6 | 0.57 | 207 | L235R/S239K/M252Y/S254T/H433D/N434Y/Y436T/Q438K/S440E |
| F1361 | 3.5E−07 | 70.5 | 0.63 | 170 | L235R/S239K/M252Y/S254T/H433D/N434Y/Y436T/Q438R/S440E |
| F1362 | 1.4E−07 | 71 | 0.67 | 181 | L235R/S239K/M252Y/S254T/H433D/N434Y/Y436F/Q438K/S440E |
| F1363 | 1.9E−07 | 71 | 0.48 | 169 | L235R/S239K/M252Y/S254T/H433D/N434Y/Y436F/Q438R/S440E |
| F1364 | 7.5E−08 | 69 | 0.84 | 140 | L235R/S239K/M252Y/T256E/N434Y/Y436F/Q438K/S440E |
| F1365 | 3.1E−07 | 69.1 | 0.78 | 144 | L235R/S239K/M252Y/T256E/H433D/N434Y/Y436T/Q438K/S440E |
| F1366 | 1.2E−07 | 69.3 | 0.71 | 118 | L235R/S239K/M252Y/T256E/H433D/N434Y/Y436F/Q438K/S440E |
| F1367 | 1.8E−07 | 69.2 | 0.68 | 106 | L235R/S239K/M252Y/S254T/T256E/N434Y/Y436T/Q438R/S440E |
| F1368 | 5.5E−08 | 69 | 0.89 | 140 | L235R/S239K/M252Y/S254T/T256E/N434Y/Y436F/Q438K/S440E |
| F1369 | 7.6E−08 | 69.2 | 0.84 | 128 | L235R/S239K/M252Y/S254T/T256E/N434Y/Y436F/Q438R/S440E |
| F1370 | 9.1E−08 | 69.5 | 0.77 | 146 | L235R/S239K/M252Y/S254T/T256E/H433D/N434Y/Y436V/Q438K/S440E |
| F1371 | 1.1E−07 | 69.1 | 0.51 | 134 | L235R/S239K/M252Y/S254T/T256E/H433D/N434Y/Y436V/Q438R/S440E |
| F1372 | 2.3E−07 | 69.4 | 0.70 | 107 | L235R/S239K/M252Y/S254T/T256E/H433D/N434Y/Y436T/Q438R/S440E |
| F1373 | 8.7E−08 | 69.5 | 0.77 | 118 | L235R/S239K/M252Y/S254T/T256E/H433D/N434Y/Y436F/Q438K/S440E |
| F1374 | 1.2E−07 | 69.3 | 0.54 | 106 | L235R/S239K/M252Y/S254T/T256E/H433D/N434Y/Y436F/Q438R/S440E |
| F1375 | 1.0E−07 | 69.9 | 0.47 | 236 | L235R/S239K/M252Y/S254T/N434Y/Y436V |
| F1376 | 9.1E−08 | 68.7 | 0.70 | 173 | L235R/S239K/M252Y/S254T/T256E/N434Y/Y436V |

TABLE 16-continued

Fc variants

| Variant name | hFcRn KD (M) | Tm (° C.) | HMW (%) | Immuno-genicity score | Mutation |
|---|---|---|---|---|---|
| F1377 | 8.3E-08 | 68.4 | 0.73 | 173 | L235R/S239K/M252Y/T256E/N434Y/Y436V |
| F1378 | 3.6E-07 | 70.6 | 0.65 | 236 | L235R/S239K/M252Y/N434Y/Y436T |
| F1379 | 2.8E-07 | 71.1 | 0.68 | 275 | L235R/S239K/M252Y/N434Y/Y436F |
| F1410 | 1.9E-06 | 61.1 | 0.59 | 183 | V308P/I332V |
| F1411 | 1.7E-07 | 60.2 | 0.55 | 299 | V308P/I332V/M428L/N434S |
| F1413 | 3.7E-08 | 68.3 | 2.19 | 332 | L235R/S239K/M252Y/S254T/T256E/T307Q/Q311A/H433D/N434Y/Y436V/Q438K/S440E |
| F1414 | 5.6E-08 | 69.7 | 0.76 | 292 | L235R/S239K/M252Y/S254T/T256E/T307Q/H433D/N434Y/Y436V/Q438K/S440E |
| F1415 | 5.9E-08 | 68.4 | 2.01 | 284 | L235R/S239K/M252Y/S254T/T256E/Q311A/H433D/N434Y/Y436V/Q438K/S440E |
| F1416 | 1.3E-08 | 60.1 | 1.20 | 327 | L235R/S239K/M252Y/S254T/T256E/V308P/H433D/N434Y/Y436V/Q438K/S440E |
| F1417 | 5.9E-08 | 68.6 | 1.72 | 121 | L235R/S239K/M252Y/S254T/T256E/H433D/N434W/Y436V/Q438K/S440E |
| F1418 | 7.5E-08 | 68.4 | 1.25 | 134 | L235R/S239K/M252Y/S254T/T256E/H433D/N434W/Y436V/Q438R/S440E |
| F1419 | 1.5E-07 | 69.5 | 0.71 | 226 | L235R/S239K/M252Y/H433D/N434W/Y436V/Q438R/S440E |
| F1420 | 1.3E-07 | 69.5 | 0.70 | 212 | L235R/S239K/M252Y/H433D/N434W/Y436V/Q438K/S440E |
| F1421 | 3.2E-08 | 58.9 | 2.59 | 348 | V308P/M428L/N434W |
| F1422 | 1.9E-08 | 59.8 | 1.27 | 315 | L235R/S239K/M252Y/T256E/V308P/H433D/N434Y/Y436V/Q438R/S440E |
| F1423 | 1.6E-08 | 45.4 | 4.03 | 157 | L235R/S239K/M252Y/T256E/V302D/V308P/H433D/N434Y/Y436V/Q438R/S440E |
| F1424 | 1.6E-08 | 49 | 0.90 | 159 | L235R/S239K/M252Y/T256E/V302E/V308P/H433D/N434Y/Y436V/Q438R/S440E |
| F1425 | 1.9E-08 | 49.4 | 2.04 | 185 | L235R/S239K/M252Y/T256E/V303D/V308P/H433D/N434Y/Y436V/Q438R/S440E |
| F1426 | 1.8E-08 | 59.7 | 1.53 | 212 | L235R/S239K/M252Y/T256E/V303E/V308P/H433D/N434Y/Y436V/Q438R/S440E |
| F1428 | 1.5E-08 | 45 | 8.91 | 243 | L235R/S239K/M252Y/T256E/S304E/V308P/H433D/N434Y/Y436V/Q438R/S440E |
| F1430 | 3.1E-08 | 48.6 | 1.97 | 156 | L235R/S239K/M252Y/T256E/V305E/V308P/H433D/N434Y/Y436V/Q438R/S440E |
| F1433 | 4.5E-08 | 46.2 | 9.04 | 181 | L235R/S239K/M252Y/T256E/T307D/V308P/H433D/N434Y/Y436V/Q438R/S440E |
| F1434 | 3.6E-08 | 49.5 | 2.54 | 206 | L235R/S239K/M252Y/T256E/T307E/V308P/H433D/N434Y/Y436V/Q438R/S440E |

The variants (IgG1-F600 to IgG-F1434) each comprising a heavy chain prepared as described above and L(WT)-CK (SEQ ID NO: 2) were expressed and purified by the method known to those skilled in the art described in Reference Example 2 of WO2011/122011.

1-2. Evaluation of FcRn Binding Affinity of Fc Variants Using Biacore hFcRn binding affinity of new Fc variants prepared in Example 1 (F600-F1434) and previous Fc variants prepared in Example 1 of WO2011/122011 (F1-F599) was evaluated using Biacore T100 (GE Healthcare). For this purpose, human FcRn was prepared as described in Reference Example A2. An appropriate amount of protein L (ACTI-GEN) was immobilized onto Sensor chip CM4 (GE Healthcare) by the amino coupling method, and the chip was allowed to capture an antibody of interest. Then, diluted FcRn solutions and running buffer (as a reference solution) were injected to allow human FcRn to interact with the antibody captured on the sensor chip. The running buffer used comprised 50 mmol/l sodium phosphate, 150 mmol/l NaCl, and 0.05% (w/v) Tween20 (pH 7.0). FcRn was diluted using each buffer. The chip was regenerated using 10 mmol/l glycine-HCl (pH 1.5). Assays were carried out exclusively at 25 degrees C. The association rate constant ka (1/Ms) and dissociation rate constant $k_d$ (1/s), both of which are kinetic parameters, were calculated based on the sensorgrams obtained in the assays, and KD (M) of each antibody for human FcRn was determined from these values. Each parameter was calculated using Biacore T100 Evaluation Software (GE Healthcare). The binding affinity of all Fc variants is shown in Table 16.

1-3. Evaluation of Stability of Fc Variants Using Differential Scanning Fluorimetry (DSF)

Stability of new Fc variants prepared in Example 1 (F600-F1434) and previous Fc variants prepared in Example 1 of WO2011/122011 (F1-F599) was evaluated using differential scanning fluorimetry (DSF). This method consists of measuring the fluorescence intensity of a polarity sensitive probe at gradually increasing temperatures, and obtaining the transition temperature of exposure of the hydrophobic regions of proteins. It is already reported that the transition temperatures acquired using DSF are in a good correlation with the melting temperatures acquired using differential scanning calorimetry (Journal of Pharmaceutical Science 2010; 4: 1707-1720). The SYPRO orange dye (Molecular Probes) was diluted into PBS (Sigma), and added to the protein solutions. Each sample was used with 20 microliter of the dyed solution. The fluorescence emission was collected at 555 nm with a fixed excitation wavelength at 470 nm. During the DSF experiment, the temperature was increased from 30 to 99 degrees C. and at 0.4 degrees C. increments with an equilibration time of 6 seconds at each temperature prior to measurement. The data were analyzed using Rotor-Gene Q Series Software (QIAGEN). The temperature of the fluorescence transition is defined as the melting temperature (Tm). Tm values of the Fc variants F1-F1434 are shown in Table 16.

1-4. Evaluation of Purity of Fc Variants Using Size Exclusion Chromatography (SEC)

High molecular weight species percentage (HMW (%)) of the new Fc variants prepared in Example 1 (F600-F1434) and previous Fc variants prepared in Example 1 of WO2011/122011 (F1-F599) was evaluated using size exclusion chromatography (SEC). SEC was performed in ACQUITY UPLC H-Class system (waters). The antibodies were injected onto a BEH200 SEC column (1.7 micrometer, 4.6×150 mm, waters). The mobile phase was 0.05 M sodium phosphate, 0.3 M sodium chloride (pH7.0, Isekyu), running isocratically at a flow rate of 0.3 mL/min. Eluted protein was detected by UV absorbance at 215 nm. The data were analyzed using Empower2 (waters). Peaks eluting earlier than the antibody monomer peak were recorded in the HMW components percentile. The HMW (%) of all Fc variants (F1-F1434) are shown in Table 16.

1-5. Evaluation of Immunogenicity Risk of Fc Variants Using in Silico Immunogenicity Prediction Tool Epibase Clinical utility and efficacy of the therapeutic antibodies can be limited by the production of anti-drug antibodies (ADAs), since ADA can influence their efficacy and pharmacokinetics and sometimes lead to serious side effects. Although many factors influence the immunogenicity of therapeutic antibodies, a number of reports describe the importance of effector T-cell epitopes present in the therapeutic protein.

In silico tools to predict T-cell epitopes, such as Epibase (Lonza), iTope/TCED (Antitope) and EpiMatrix (EpiVax) have been developed. By using these in silico tools, the presence of T-cell epitope in each amino acid sequence can be predicted (Expert Opin Biol Ther. 2007 March; 7(3):405-18.), allowing the evaluation of potential immunogenicity of the Fc variants. Epibase Light (Lonza) was used to evaluate the potential immunogenicity of the Fc variants.

Epibase Light (Lonza) is an in silico tool to calculate the binding affinity of 9-mer peptide to major DRB1 alleles using FASTER algorism (Expert Opin Biol Ther. 2007 March; 7(3):405-18.). Epibase Light (Lonza) identifies T-cell epitopes with strong binding and medium binding to MHC class II. In silico immunogenicity score for each Fc variants was calculated using the following formula incorporated in Epibase Light (Lonza) system. Immunogenicity score=Sum ((each DRB1 allotype population frequency)× (number of critical epitopes)).

For DRB1 allotype population frequency used in the formula, following DRB1 allotype population frequency based on Caucasian population was used.
DRB1*0701 (25.3%), DRB1*1501 (23.1%), DRB1*0301 (21.7%), DRB1*0101 (15.3%), DRB1*0401 (13.8%), DRB1*1101 (11.8%), DRB1*1302 (8.0%), DRB1*1401 (4.9%), DRB1*0403 (2.3%), DRB1*0901 (1.8%)

The total number of any strong and medium binding epitopes identified in constant region (CH1-hinge-CH2-CH3) of the variants by FASTER algorism was used as number of critical epitopes in the formula. Filtered epitopes are those with human antibody germline sequence or junction regions between variable region and constant region, and only non-filtered epitopes are considered (counted as critical epitope) in the immunogenicity score calculation.

Immunogenicity score of amino acid sequence of new Fc variants described in Example 1 (F600-F1434) and previous Fc variants described in Example 1 of WO2011/122011 (F1-F599) was calculated using above described Epibase Light (Lonza) system. Immunogenicity score of all Fc variants (F1-F1434) are shown in Table 16.

[Example 2] Identification FcRn Binding Improved Fc Variants with High Stability, Low High Molecular Weight Species and Low Immunogenicity Risk 2-1. Analysis of Previous and New Fc Variants by Plotting Tm, HMW (%) and Immunogenicity Score Against hFcRn Binding Affinity hFcRn binding affinity and Tm of previous Fc variants (F1-F599) described in Example 1 of WO2011/122011 and new Fc variants (F600-F1052) generated and evaluated in Example 1 were plotted and are shown in FIG. 2. hFcRn binding affinity and HMW (%) of previous and new Fc variants were plotted and are shown in FIG. 3. hFcRn binding affinity and immunogenicity score of Fc variants F1-F599 and new Fc variants (F600-F1052) were plotted and are shown in FIG. 4.

The new Fc variants (F600-F1052) and previous Fc variants (F1-F599) variants having Ser239Lys or Asp270Phe mutation were deleted from the plots. Since Ser239Lys and Asp270Phe mutation improved the stability (Tm) while it did not improve FcRn binding affinity and reduced the binding affinity to all human Fc gamma receptors, in the following detailed analysis of Group 1-4, stability of Fc variants should be compared within the variants that do not have Ser239Lys nor Asp270Phe mutation.

In addition, new Fc variants (F600-F1052) and previous Fc variants (F1-F599) variants having Pro257Xxx (Xxx is Ala or Val or Ile or Leu or Thr) or Met252Trp mutation were deleted from the plots although these variants improve FcRn binding affinity. Pro257Xxx and Met252Trp mutation did not exhibit significant reduction in Tm suggesting that variants with Pro257Xxx and Met252Trp mutation have high stability. Nevertheless, these variants having Pro257Xxx or Met252Trp mutations showed significant aggregation and precipitation during an accelerated stability study or when stored refrigerated. Due to their detrimental stability, Fc variants with Pro257Xxx and Met252Trp mutation are not acceptable for pharmaceutical development and therefore, in the following detailed analysis of Group 1-4, such Fc variants should be deleted from the plots.

2-2. Detailed Analysis of Group 1 (Binding Affinity to hFcRn Stronger than 15 nM)

New Fc variants (F600-F1052) generated and evaluated in Example 1, and previous Fc variants (F1-F599) described in Example 1 of WO2011/122011, with binding affinity to hFcRn stronger than 15 nM (described as Group 1 hereafter), were analyzed in detail by plotting hFcRn binding affinity in X-axis and Tm, HMW (%) and immunogenicity score in Y-axis.

Detail analysis of Group 1 by plotting hFcRn binding affinity (KD stronger than 15 nM) in X-axis and Tm, HMW (%) and immunogenicity score in Y-axis are shown respectively in FIGS. 5, 6 and 7.

As for developability criteria of Fc variants in Group 1, Tm criteria was set as higher than 57.5 degrees C., HMW (%) criteria was set as lower than 2%, and immunogenicity score was set as lower than 500.

Fc variants in Group 1 which satisfies all the developability criteria (Tm higher than 57.5 degrees C., HMW (%) lower than 2%, and immunogenicity score lower than 500) are shown in Table 17.

TABLE 17

| Variant name | hFcRn KD (M) | Tm (° C.) | HMW (%) | Immunogenicity score | Mutation |
|---|---|---|---|---|---|
| F941 | 1.2E−08 | 61.4 | 1.2 | 449 | M252Y/N286E/ T307Q/Q311A/ N434Y/Y436V |
| F947 | 1.1E−08 | 60.5 | 1.2 | 376 | T250V/M252Y/ T307Q/V308P/ Q311A/N434Y/Y436V |
| F1016 | 3.8E−09 | 58.5 | 0.6 | 438 | T250V/M252Y/N286E/ T307Q/V308P/Q311A/ N434Y/Y436V |
| F1050 | 3.5E−09 | 58.2 | 0.9 | 481 | T250V/M252Y/N286E/ T307Q/V308P/Q311A/ M428I/N434Y/Y436V |

None of the previous Fc variants (F1-F599) had an affinity stronger than 15 nM, whereas the several new Fc variants generated in EXAMPLE 1 were stronger than 15 nM and met all the developability criteria. Such Group 1 new Fc variants described in Table 17 are extremely valuable for Fc domain to enable very rapid and extensive antigen elimination from plasma especially when used in combination with pH-dependent antigen-binding domain.

2-3. Detailed Analysis of Group 2 (Binding Affinity to hFcRn Between 15 nM and 50 nM)

New Fc variants (F600-F1052) generated and evaluated in Example 1, and previous Fc variants (F1-F599) described in Example 1 of WO2011/122011, with binding affinity to hFcRn between 15 nM and 50 nM (hereafter called "Group 2"), were analyzed in detail by plotting hFcRn binding affinity on the X-axis and Tm, HMW (%) and immunogenicity score on Y-axis.

Detailed analysis of Group 2 by plotting hFcRn binding affinity (KD between 15 nM and 50 nM) on the x-axis, and Tm, HMW (%) or immunogenicity score on the Y-axis are shown in FIGS. 8, 9 and 10, respectively.

As for developability criteria of Fc variants in Group 2, Tm criteria was set as higher than 60 degrees C., HMW (%) criteria was set as lower than 2%, and immunogenicity score was set as lower than 500.

Fc variants in Group 2 which satisfies all the developability criteria (Tm higher than 60 degrees C., HMW (%) lower than 2%, and immunogenicity score lower than 500) are shown in Table 18.

TABLE 18

| Variant name | hFcRn KD (M) | Tm (° C.) | HMW (%) | Immuno-genicity score | Mutation |
|---|---|---|---|---|---|
| F928 | 2.9E−08 | 63.9 | 0.8 | 375 | M252Y/T307Q/Q311A/N434Y/Y436I |
| F929 | 2.9E−08 | 64.2 | 0.9 | 346 | M252Y/S254T/T307Q/Q311A/N434Y/Y436I |
| F945 | 1.7E−08 | 61 | 1 | 416 | T250V/M252Y/V308P/N434Y/Y436V |
| F946 | 4.3E−08 | 69 | 1.3 | 421 | T250V/M252Y/T307Q/Q311A/N434Y/Y436V |
| F993 | 3.8E−08 | 63.4 | 0.9 | 387 | M252Y/T307Q/Q311A/N434Y/Y436V |
| F1011 | 4.5E−08 | 62.2 | 0.4 | 459 | T250V/M252Y/V308P/N434Y |

None of the previous Fc variants (F1-F599) satisfied all the developability criteria, but several of the new Fc variants generated in Example 1 met all. Such Fc variants of Group 2 which meet the developability criteria are extremely valuable to enable rapid and extensive antigen elimination from plasma especially when used in combination with pH-dependent antigen-binding domain.

2-4. Detailed Analysis of Group 3 (Binding Affinity to hFcRn Between 50 nM and 150 nM)

New Fc variants (F600-F1052) generated and evaluated in Example 1, and previous Fc variants (F1-F599) described in Example 1 of WO2011/122011, with binding affinity to hFcRn between 50 nM and 150 nM (called hereinafter "Group 3"), were analyzed in detail by plotting hFcRn binding affinity on the X-axis and Tm, HMW (%) and immunogenicity score on the Y-axis.

Detail analysis of Group 3 by plotting hFcRn binding affinity (KD between 50 nM and 150 nM) in X-axis, and Tm, HMW (%) or immunogenicity score on Y-axis are shown in FIGS. 11, 12 and 13, respectively.

As for developability criteria of Fc variants in Group 3, Tm criteria was set as higher than 63.0 degrees C., HMW (%) criteria was set as lower than 2%, and immunogenicity score was set as lower than 250.

Fc variants in Group 3 which satisfies all the developability criteria (Tm higher than 63.0 degrees C., HMW (%) lower than 2%, and immunogenicity score lower than 250) are shown in Table 19.

TABLE 19

| Variant name | hF cRn KD (M) | Tm (° C.) | HMW (%) | Immuno-genicity score | Mutation |
|---|---|---|---|---|---|
| F789 | 1.5E−07 | 64.3 | 0.7 | 243 | M252Y/N315D/N434Y |
| F814 | 1.2E−07 | 63.3 | 0.9 | 188 | M252Y/N434Y/Y436I |
| F882 | 1.3E−07 | 64 | 1 | 188 | M252Y/N434Y/Y436L |
| F890 | 1.1E−07 | 63.4 | 0.7 | 200 | M252Y/N434Y/Y436V |
| F892 | 7.1E−08 | 63.9 | 1.8 | 159 | M252Y/S254T/N434Y/Y436I |

None of the previous Fc variants (F1-F599) satisfied all the developability criteria, whereas the several new Fc variants generated in Example 1 met all. Such new Fc variants of Group 3 which meet all developability criteria are extremely valuable to enable moderate and sustained antigen elimination from plasma especially used in combination with pH-dependent antigen-binding domain.

2-5. Detailed Analysis of Group 4 (Binding Affinity to hFcRn Between 150 nM and 700 nM)

New Fc variants (F600-F1052) generated and evaluated in Example 1, and previous Fc variants (F1-F599) described in Example 1 of WO2011/122011, with binding affinity to hFcRn between 150 nM and 700 nM (called hereinafter "Group 4"), were analyzed in detail by plotting hFcRn binding affinity on X-axis and Tm, HMW (%) and immunogenicity score on Y-axis.

Detail analysis of Group 4 by plotting hFcRn binding affinity (KD between 150 nM and 700 nM) on X-axis, and Tm, HMW (%) or immunogenicity score on Y-axis are shown in FIGS. 14, 15 and 16, respectively.

As for developability criteria of Fc variants in Group 4, Tm criteria was set as higher than 66.5 degrees C., HMW (%) criteria was set as lower than 2%, and immunogenicity score was set as lower than 250.

Fc variants in Group 4 which satisfies all the developability criteria (Tm higher than 66.5 degrees C., HMW (%) lower than 2%, and immunogenicity score lower than 250) are shown in Table 20.

TABLE 20

| Variant name | hFcRn KD (M) | Tm (° C.) | HMW (%) | Immuno-genicity score | Mutation |
|---|---|---|---|---|---|
| F732 | 6.8E−07 | 69 | 0.7 | 227 | T307Q/Q311H/N434Y |
| F767 | 4.3E−07 | 69.9 | 0.6 | 198 | T307Q/L309E/Q311A/N434Y |
| F769 | 4.6E−07 | 69.5 | 0.8 | 190 | T307Q/L309E/Q311H/N434Y |
| F944 | 1.7E−07 | 69.2 | 1.1 | 235 | T250V/M252Y/N434Y/Y436V |

None of the previous Fc variants (F1-F599) satisfied all the developability criteria, whereas the several new Fc variants generated in Example 1 met them all. Such new Fc variants of Group 4 which meet all developability criteria are extremely valuable to enable moderate and sustained antigen elimination from plasma especially used in combination with pH-dependent antigen-binding domain.

In summary, new Fc variants described in Table 17 to 20 have high Tm, low HMW (%), and low immunogenicity score which are suitable for pharmaceutical development of antigen-binding molecule capable of removing antigen from the plasma.

[Example 3] In Vivo Antigen Elimination Study of New Fc Variants in Human IL-6 Receptor Steady-State Infusion Model Using Human FcRn Transgenic

3-1. Preparation of Antibodies for In Vivo Study pH-dependent anti-human IL6 receptor IgG1 antibody, Fv-4-IgG1 comprising VH3-IgG1 (SEQ ID NO: 1) and VL3-CK (SEQ ID NO: 3), previous Fc variant Fv-4-F11 comprising VH3-F11 (SEQ ID NO: 4) and VL3-CK (SEQ ID NO: 3), new Fc variants, Fv-4-F652 comprising VH3-F652 (SEQ ID NO: 5) and VL3-CK (SEQ ID NO: 3), and Fv-4-F890 comprising VH3-F890 (SEQ ID NO: 6) and VL3-CK (SEQ ID NO: 3), and Fv-4-F946 comprising VH3-F946 (SEQ ID NO: 7) and VL3-CK (SEQ ID NO: 3) were expressed and purified by the method known to those skilled in the art described in Reference Example 2 of WO2011/122011.

In vivo antigen elimination study of Fv-4-IgG1, Fv-4-F11, Fv-4-F652, Fv-4-F890 and Fv-4-F946 were performed in human IL-6 receptor steady-state infusion model using human FcRn transgenic.

3-2. In Vivo Study of Antibodies by Steady-State Infusion Model Using Human FcRn Transgenic Mouse Line 32

An in vivo test was conducted by steady-state infusion model using human FcRn transgenic mouse line 32. An infusion pump (MINI-OSMOTIC PUMP MODEL 2004; alzet) containing soluble human IL-6 receptor was implanted under the skin on the back of human FcRn transgenic mouse line 32 (B6.mFcRn-/-.hFcRn Tg line 32+/+ mouse (B6.mFcRn-/- hFCRN Tg32 B6.Cg-Fcgrt<tm1Dcr> Tg(FCGRT)32Dcr), Jackson Laboratories; Methods Mol Biol. (2010) 602: 93-104) to prepare model animals in which the plasma concentration of soluble human IL-6 receptor was kept constant. Anti-human IL-6 receptor antibodies were administered to the model animals to assess the in vivo dynamics after administration of soluble human IL-6 receptor. Monoclonal anti-mouse CD4 antibody (in house) was administered at 20 mg/kg before implanting infusion pump, and 7 and 17 days after antibody administration into the caudal vein to suppress the production of neutralizing antibody against soluble human IL-6 receptor. Then, an infusion pump containing 92.8 microgram/ml soluble human IL-6 receptor was implanted under the skin on the back of the mice. Three days after implantation of an infusion pump, anti-human IL-6 receptor antibodies were administered once into the caudal vein. In study 1, Fv-4-IgG1, Fv-4-F652, Fv-4-F890 and Fv-4-F946 were administered at as dosage of 1 mg/kg together with approximately 1 g/kg Sanglopor (CSL Behring), and in study 2, Fv-4-IgG1, Fv-4-F11 and Fv-4-F652 were administered at 1 mg/kg. In both studies, no antibody was administered to the control group (no antibody injection). Blood was collected at appropriate time points after the administration of the anti-human IL-6 receptor antibody. The collected blood was immediately centrifuged at 15,000 rpm and 4 degrees C. for 15 minutes to separate plasma. The separated plasma was stored in a refrigerator at −20 degrees C. or below before the assay.

3-3. Measurement of Anti-Human IL-6 Receptor Antibody Plasma Concentration by ELISA The concentration of anti-human IL-6 receptor antibody in mouse plasma was measured by ELISA. Anti-human IgG (gamma-chain specific) F(ab')2 antibody fragment (Sigma) was dispensed onto a Nunc-ImmunoPlate MaxiSorp (Nalge Nunc International) and allowed to stand overnight at 4 degrees C. to prepare anti-human IgG-immobilized plates. Calibration curve samples having plasma concentrations of 0.8, 0.4, 0.2, 0.1, 0.05, 0.025, and 0.0125 microgram/ml, and mouse plasma samples diluted 100-fold or more were prepared. 200 microliter of 20 ng/ml hsIL-6R were added to 100 microliter of the calibration curve samples and plasma samples, and then the samples were allowed to stand for one hour at room temperature. Subsequently, the samples were dispensed onto the anti-human IgG-immobilized plates, and allowed to stand for one hour at room temperature. Then, Biotinylated Anti-Human IL-6R Antibody (R&D) was added to react for one hour at room temperature. Subsequently, Streptavidin-PolyHRP80 (Stereospecific Detection Technologies) was added to react for one hour at room temperature, and chromogenic reaction was carried out using TMP One Component HRP Microwell Substrate (BioFX Laboratories) as a substrate. After stopping the reaction with 1 N sulfuric acid (Showa Chemical), the absorbance at 450 nm was measured by a microplate reader. The concentration in mouse plasma was calculated from the absorbance of the calibration curve using the analytical software SOFTmax PRO (Molecular Devices).

3-4. Measurement of hsIL-6R Plasma Concentration by Electrochemiluminescence Assay The concentration of hsIL-6R in mouse plasma was measured by electrochemiluminescence. hsIL-6R calibration curve samples adjusted to concentrations of 2,000, 1,000, 500, 250, 125, 62.5, and 31.25 pg/ml, and mouse plasma samples diluted 50-fold or more were prepared. The samples were mixed with a solution of Monoclonal Anti-human IL-6R Antibody (R&D) ruthenium-labeled with Sulfo-Tag NHS Ester (Meso Scale Discovery), Biotinylated Anti-human IL-6R Antibody (R&D, Systems Inc., USA), and tocilizumab (Chugai Pharmaceutical Co., Ltd.)), and then allowed to react overnight at 37 degrees C. The final concentration of tocilizumab as an anti-human IL-6 receptor antibody was 333 microgram/ml, which is in excess of the concentration of anti-human IL-6 receptor antibody contained in the samples, for the purpose of binding nearly all of the hsIL-6R molecules in the samples to tocilizumab. Subsequently, the samples were dispensed into an MA400 PR Streptavidin Plate (Meso Scale Discovery), and allowed to react for one hour at room temperature, and washing was performed. Immediately after Read Buffer T (×4) (Meso Scale Discovery) was dispensed, the measurement was performed by the Sector PR 400 Reader (Meso Scale Discovery). The hsIL-6R concentration was calculated based on the response of the calibration curve using the analytical software SOFTmax PRO (Molecular Devices).

3-5. Result of Study 1; In Vivo Antigen Elimination Effect of New Fc Variants FIG. 17 shows plasma hsIL-6R concentration time profile and FIG. 18 shows plasma antibody concentration time profile after injection of Fv-4-IgG1, Fv-4-F652, Fv-4-F890 and Fv-4-F946. Compared to Fv-4-IgG1 and control (no antibody injection), Fv-4-F652, Fv-4-F890 and Fv-4-F946 having new Fc variants with improved binding to FcRn at neutral pH exhibited significant reduction of plasma hsIL-6R concentration demonstrating in vivo antigen elimination effect of pH-dependent antigen binding antibody with improved binding to FcRn at neutral pH. Despite that Fv-4-F652 and Fv-4-F890 demonstrated 30-fold and 10-fold antigen elimination effect at day 7 compared to Fv-4-IgG1, respectively, plasma antibody concentration time profile of Fv-4-F652 and Fv-4-F890 were comparable to Fv-4-IgG1.

Therefore, this study demonstrated that Fv-4-F652 and Fv-4-F890 were able to selectively eliminate soluble antigen from plasma while maintaining antibody pharmacokinetics comparable to that of Fv-4-IgG1. Fv-4-F890 belongs to Group 3, and this study demonstrated that Fc variants in Group 3 can reduce then plasma antigen concentration by approximately 10-fold while maintaining the antibody pharmacokinetic comparable to IgG1. This means that applying Group 3 Fc variant to pH-dependent antigen binding IgG1 antibody can lower the antibody dosage by 10-fold. Such reduction in antibody dosage by Group 3 Fc variant is especially meaningful when antibody dosage needs to be reduced, and simultaneously requires infrequent dosing.

On the other hand, Fv-4-F946 demonstrated 100-fold reduction of plasma hsIL-6R concentration compared to Fv-4-IgG1, and antibody clearance of Fv-4-F946 was larger than Fv-4-IgG1. Fv-4-F946 belongs to Group 2, and this study demonstrated that Fc variants in Group 2 can reduce the plasma antigen concentration by approximately 100-fold although the antibody clearance is larger than IgG1. This means that applying Group 2 Fc variant to pH-dependent antigen binding IgG1 antibody can reduce the total plasma antigen concentration by approximately 100-fold. In case the target plasma antigen concentration is too high to neutralize by realistic antibody dosage (i.e 100 mg/kg), 100-fold reduction of total antigen concentration regardless of the increase of antigen clearance by Group 2 Fc variant means that target antigen can be neutralized by less than 10 mg/kg, which is a realistic antibody dosage.

hFcRn binding affinity of Fv-4-F652 and Fv-4-F890 were measured in multiplicates, and affinity against hFcRn was 2.4E-07 M (n=7) for F652, and 1.1E-07 M (n=12) for F890. Previous studies described in Example 1 of WO2011/122011 revealed that the extent of antigen elimination and antibody clearance correlated with binding affinity to FcRn at neutral pH. As shown in FIG. 17, Fv-4-F652 exhibited larger extent of antigen elimination compared to Fv-4-F890 although antibody pharmacokinetics was comparable to Fv-4-F890. Therefore, it was suggested that specific mutation in F652 contributed to enhanced antigen sweeping effect.

In order to identify which residue contributed to the enhanced antigen sweeping effect of F652, study 2 was performed using F11 (Met252Tyr, Asn434Tyr double mutant) and F652 (Pro238Asp, Met252Tyr, Asn434Tyr triple mutant). Affinity against hFcRn was 3.1E-07 M (n=12) for F11, which was comparable to the affinity measured for F652.

3-6. Result of Study 2; In Vivo Antigen Elimination Effect of Pro238Asp Mutation FIG. 19 shows plasma hsIL-6R concentration time profile and FIG. 20 shows plasma antibody concentration time profile after injection of Fv-4-IgG1, Fv-4-F11 and Fv-4-F652. Although Fv-4-F11 exhibited reduction of plasma hsIL-6R concentration, Fv-4-F652 exhibited larger reduction of plasma hsIL-6R concentration. Fv-4-F11 and Fv-4-F652 exhibited comparable plasma antibody concentration time profile.

Therefore, this study demonstrated that Pro238Asp mutation were able to enhance antigen elimination plasma while maintaining antibody pharmacokinetics comparable to Fv-4-IgG1. Therefore, Pro238Asp mutation is extremely valuable for enhancing antigen elimination by pH-dependent antigen binding antibody.

[Example 4] Elimination of Rheumatoid Factor Binding to FcRn Binding Improved Fc Variants by Site-Directed Mutagenesis Clinical utility and efficacy of the therapeutic antibodies can be limited by the production of anti-drug antibodies (ADAs), since ADA can influence their efficacy and pharmacokinetics and sometimes lead to serious side effects. Many factors influence the immunogenicity of therapeutic antibodies, and the presence of effector T-cell epitopes is one of the factors. In addition, presence of pre-existing antibodies against therapeutic antibody can also be problematic from the point of ADA. Especially in case of therapeutic antibody for patients with autoimmune disease such as rheumatoid arthritis, rheumatoid factor, an autoantibody against human IgG, could be an issue of pre-existing antibody. Recently, it was reported that humanized anti-CD4 IgG1 antibody with Asn434H is mutation elicited significant rheumatoid factor binding (Clin Pharmacol Ther. 2011 February; 89(2):283-90). Detail study have confirmed that Asn434H is mutation in the human IgG1 increased the binding of rheumatoid factor to the Fc region of the antibody compared to the parent human IgG1.

Rheumatoid factor is a polyclonal autoantibody against human IgG, and their epitope in human IgG varies among the clone, but their epitope seems to be located in the CH2/CH3 interface region as well as CH3 domain which could overlap with the FcRn binding epitope. Therefore, mutations to increase the binding affinity to FcRn might also increase the binding affinity to specific clone of rheumatoid factor.

Previous studies have demonstrated that Fc-engineering to increase the binding affinity to FcRn at acidic pH improved the endosomal recycling efficiency and prolonged the pharmacokinetics of the antibody. For example, M252Y/S254T/T256E (YTE) variant (J Biol Chem 2006 281:23514-23524.), M428L/N434S (LS) variant (Nat Biotechnol, 2010 28:157-159.) and N434H variant (Clinical Pharmacology & Therapeutics (2011) 89(2):283-290.) showed improvement in half-life relative to native IgG1.

To achieve antigen elimination from plasma, Fc regions of the antigen-binding molecule (antibody) which interacts with FcRn (Nat Rev Immunol. 2007 September; 7(9):715-25) was engineered to have improved binding affinity to FcRn at neutral pH, such engineered Fc variants include F11 variant, F68 variant, F890 variant and F947 variant. The mechanism of antigen elimination from plasma by pH-dependent antigen binding antibody with improved binding affinity to FcRn at neutral pH in comparison to the conventional antibody is shown in FIG. 1.

Such Fc variant with improved FcRn-binding (either at pH 6.0 and/or neutral pH) could exhibit increased binding to rheumatoid factor as in the case of previously reported Asn434H is mutation. Therefore, we tested whether these FcRn binding improved Fc variants would exhibit increased binding to rheumatoid factor. Variant antibodies used in the following study were Fv-4-hIgG1, Fv-4-YTE, Fv-4-LS, Fv-4-N434H, Fv-4-F11, Fv-4-F68, Fv-4-890 and Fv-4-F947.

4-1. Rheumatoid Factor Binding Study of FcRn Binding Improved Fc Variants

Binding assay against rheumatoid factor was performed by Electrochemiluminescence (ECL) at pH7.4. The assays were performed with the serum of 15 or 30 individual RA patients (Proteogenex). 50-fold diluted serum samples, Biotin labeled test antibody (1 microgram/mL) and SULFO-TAG NHS Ester (Meso Scale Discovery) labeled test antibody (1 microgram/mL) were mixed and incubated for 3 hr at room temperature. Then, the mixtures were added to Streptavidin coated MULTI-ARRAY 96 well plates (Meso Scale Discovery), and the plates were incubated for 2 hr at room temperature and washed. After Read Buffer T (×4) (Meso Scale Discovery) was added to each well, plates were immediately set on the SECTOR imager 2400 Reader (Meso Scale Discovery) and the chemiluminescence was measured.

Results of this study are shown in FIGS. 21 and 22. FIGS. 21 and 22 are the ECL response of the serum from 15 or 30 individual RA patients. Fv-4-hIgG1 with native human IgG1 (FIGS. 21-1 and 22-1) showed only weak rheumatoid factor binding, whereas all the FcRn binding improved Fc variants (Fv-4-YTE (FIG. 21-2), Fv-4-LS (FIG. 21-3), Fv-4-N434H (FIG. 22-2), Fv-4-F11 (FIG. 22-3), Fv-4-F68 (FIG. 22-4), Fv-4-890 (FIG. 22-5) and Fv-4-F947 (FIG. 22-6)) significantly enhanced the rheumatoid factor binding in more than the two donors. This study clearly demonstrates that immunogenicity related to the pre-existing rheumatoid factor can be an issue when considering the clinical development of the therapeutic antibody with improved binding affinity to FcRn for autoimmune disease such as rheumatoid arthritis. FIG. 23 shows the mean, geomean and median of the ECL response of the serum of the above mentioned antibody variants with the blood of fifteen RA patients.

Therefore, in the next study, we have generated panels of variants that could potentially reduce the polyclonal rheumatoid factor binding while maintaining FcRn binding capability.

4-2. Reduction of Rheumatoid Factor Binding of FcRn Binding Improved Fc Variants by Introducing Mutations in the Fc Region In order to generate the variants with reduced polyclonal rheumatoid factor binding while maintaining FcRn binding capability, mutations were rationally introduced to the surface residues near the CH2/CH3 interface which was assumed not to interfere with human FcRn/human IgG interaction.

Fv-4-F890 was selected as parent Fc variant, and single mutation and combined Fc variants of single mutation were introduced into Fv-4-F890. The novel Fc variants F1058 to F1073, F1107 to F1114, F1104 to F1106, and F1230 to F1232 described in Table 21 were generated. In addition, Fv-4-F947 was selected as parent Fc variant and same single and combined mutations were introduced. The novel Fc variants F1119-F1124 described in Table 21 were generated. First the variants were evaluated for their binding affinity to human FcRn at pH7.0. Results are also described in Table 21. Compared to either parent Fv-4-F890 or Fv-4-F947, these variants did not show significant reduction in binding affinity against human FcRn, demonstrating that these mutations did not affect human FcRn binding.

TABLE 21

| Variant name | hFcRn KD (M) at pH 7.0 | Mutations |
| --- | --- | --- |
| F890 | 1.07E−07 | M252Y/N434Y/Y436V |
| F1058 | 1.30E−07 | M252Y/Q386E/N434Y/Y436V |
| F1059 | 1.40E−07 | M252Y/Q386R/N434Y/Y436V |
| F1060 | 1.40E−07 | M252Y/Q386S/N434Y/Y436V |
| F1061 | 1.20E−07 | M252Y/P387E/N434Y/Y436V |
| F1062 | 1.20E−07 | M252Y/P387R/N434Y/Y436V |
| F1063 | 1.40E−07 | M252Y/P387S/N434Y/Y436V |
| F1064 | 1.30E−07 | M252Y/V422E/N434Y/Y436V |
| F1065 | 1.40E−07 | M252Y/V422R/N434Y/Y436V |
| F1066 | 1.40E−07 | M252Y/V422S/N434Y/Y436V |
| F1067 | 1.30E−07 | M252Y/S424E/N434Y/Y436V |
| F1068 | 1.70E−07 | M252Y/S424R/N434Y/Y436V |
| F1069 | 1.40E−07 | M252Y/N434Y/Y436V/Q438E |
| F1070 | 1.70E−07 | M252Y/N434Y/Y436V/Q438R |
| F1071 | 1.20E−07 | M252Y/N434Y/Y436V/Q438S |
| F1072 | 1.30E−07 | M252Y/N434Y/Y436V/S440E |
| F1073 | 1.34E−07 | M252Y/N434Y/Y436V/S440R |
| F1107 | 1.20E−07 | M252Y/V422D/N434Y/Y436V |
| F1108 | 1.30E−07 | M252Y/V422K/N434Y/Y436V |
| F1109 | 1.30E−07 | M252Y/V422T/N434Y/Y436V |
| F1110 | 1.30E−07 | M252Y/V422Q/N434Y/Y436V |
| F1111 | 1.60E−07 | M252Y/S424K/N434Y/Y436V |
| F1112 | 1.20E−07 | M252Y/N434Y/Y436V/Q438K |
| F1113 | 1.20E−07 | M252Y/N434Y/Y436V/S440D |
| F1114 | 1.30E−07 | M252Y/N434Y/Y436V/S440Q |
| F1104 | 1.80E−07 | M252Y/V422E/S424R/N434Y/Y436V |
| F1105 | 1.50E−07 | M252Y/V422S/S424R/N434Y/Y436V |
| F1106 | 1.40E−07 | M252Y/N434Y/Y436V/Q438R/S440E |
| F1230 | 1.12E−07 | M252Y/N434Y/Y436V/Q438R/S440D |
| F1231 | 9.73E−08 | M252Y/N434Y/Y436V/Q438K/S440E |
| F1232 | 9.79E−08 | M252Y/N434Y/Y436V/Q438K/S440D |
| F947 | 1.11E−08 | T250V/M252Y/T307Q/V308P/Q311A/N434Y/Y436V |
| F1119 | 1.00E−08 | T250V/M252Y/T307Q/V308P/Q311A/V422E/N434Y/Y436V |
| F1120 | 1.00E−08 | T250V/M252Y/T307Q/V308P/Q311A/S424R/N434Y/Y436V |
| F1121 | 1.00E−08 | T250V/M252Y/T307Q/V308P/Q311A/V422E/S424R/N434Y/Y436V |
| F1122 | 1.40E−08 | T250V/M252Y/T307Q/V308P/Q311A/N434Y/Y436V/Q438R |
| F1123 | 9.50E−09 | T250V/M252Y/T307Q/V308P/Q311A/N434Y/Y436V/S440E |
| F1124 | 1.20E−08 | T250V/M252Y/T307Q/V308P/Q311A/N434Y/Y436V/Q438R/S440E |

Then we performed rheumatoid factor binding study at pH 7 for the variants in Table 21. Results of this study are shown in FIGS. 24 to 29. These figures show the ECL response of the serum from fifteen individual RA patients for the following variants of the antibody: Fv-4-IgG1, Fv-4-F890, Fv-4-F1058 to Fv-4-1073 (FIG. 24), Fv-4-F1104 to Fv-4-F1106 (FIG. 26), Fv-4-F1107 to Fv-4-F1114 (FIG. 27), Fv-4-F1230 to Fv-4-F1232 (FIG. 28), Fv-4-947 and Fv-4-F1119 to Fv-4-F1124 (FIG. 29). FIGS. 25-1, 25-2 and 25-3 are the mean, geomean and median of the ECL response of the serum from fifteen RA patients for the variants Fv-4-IgG1, Fv-4-F890, and Fv-4-F1058 to Fv-4-1073. Surprisingly, compared to F890 which exhibited strong rheumatoid factor binding, novel Fc variants with single mutation to F890, such as F1062, F1064-F1072 and F1107-F1114 exhibited significant reduction in rheumatoid factor binding. Especially, F1062, F1064, F1068, F1070, F1072, F1107 to F1109 and F1111-F1113 exhibited comparable rheumatoid factor binding as native IgG1 demonstrating that the increased immunogenicity risk of F890 variant was completely eliminated by introducing additional single mutation to reduce rheumatoid factor binding without affecting human FcRn binding. Since rheumatoid factor in patients is a polyclonal antibody binding to multiple epitopes in the Fc region, it was surprising that a single mutation significantly eliminated the binding of rheumatoid factor to the Fc region.

Furthermore, compared to single mutated Fc F1070 (Q438R) or F1072 (S440E), double mutated Fc F1106 (Q438R/S440E) showed significant reduction in rheumatoid factor binding. Likewise, double mutated Fc F1230 (Q438R/S440D), F1231 (Q438K/S440E) and F1232 (Q438K/S440D) also showed additional reduction in rheumatoid factor binding by combination of mutations. Meanwhile, F1104 (V422E/S424R) or F1105 (V422S/S424R) did not show any combination effect.

In addition, with Fv-4-F939 selected as parent Fc variant, other mutations for increasing FcRn binding (S254T or T256E) and for reducing rheumatoid factor binding (H433D) were evaluated. Novel Fc variants (F1291, F1268, F1269, F1243, F1245, F1321, F1340 and F1323) described in Table 22 were generated. First, the variants were evaluated for their binding affinity to human FcRn at pH7.0. Results are also described in Table 22.

TABLE 22

| Variant name | hFcRn KD (M) at pH 7.0 | Mutations |
|---|---|---|
| F939 | 1.5E−07 | L235R/S239K/M252Y/N434Y/Y436V |
| F1291 | 1.5E−07 | L235R/S239K/M252Y/H433D/N434Y/Y436V |
| F1268 | 2.0E−07 | L235R/S239K/M252Y/H433D/N434Y/Y436V/Q438R/S440E |
| F1269 | 1.7E−07 | L235R/S239K/M252Y/H433D/N434Y/Y436V/Q438K/S440D |
| F1243 | 1.3E−07 | L235R/S239K/M252Y/S254T/N434Y/Y436V/Q438R/S440E |
| F1245 | 8.2E−08 | L235R/S239K/M252Y/S254T/T256E/N434Y/Y436V/Q438R/S440E |
| F1321 | 1.0E−07 | L235R/S239K/M252Y/S254T/N434Y/Y436V/Q438K/S440E |
| F1340 | 5.6E−08 | L235R/S239K/M252Y/S254T/T256E/N434Y/Y436V/Q438K/S440E |
| F1323 | 1.5E−07 | L235R/S239K/M252Y/S254T/H433D/N434Y/Y436V/Q438K/S440E |

Then we performed rheumatoid factor binding study for these variants as described above. Results of this study are shown in FIG. 30. Surprisingly, compared to F939, F1291 (single H433D mutation to F939) exhibited significant reduction in rheumatoid factor binding in some donors. Similarly, compared to F1321, F1323 (single H433D mutation to F1321) exhibited significant reduction in rheumatoid factor binding in some donors. Furthermore, Q438R/S440E, Q438K/S440D and Q438K/S440E mutations showed significant reduction in rheumatoid factor binding with variants having other mutations for increasing FcRn binding (S254T or T256E).

4-3. Reduction of Rheumatoid Factor Binding of FcRn Binding Improved Fc Variants by Introducing Additional N-Glycosylation in the Fc Region Introduction of additional N-glycosylation near the rheumatoid factor binding epitope may also abrogate rheumatoid factor binding, due to steric hindrance with bulky N-glycosylation. Mutation can be selected from the point so that the mutation introduces N-glycosylation sequence (Asn-Xxx-Ser/Thr) while maintaining FcRn binding. In order to introduce additional N-glycosylation sequence into Fc region, single or double mutation(s) were introduced into Fv-4-F11. Novel Fc variants (F1077-F1083, F1094-F1097) described in Table 23 were generated. The variants were evaluated for their binding affinity to human FcRn at pH7.0 and the presence of additional glycosylation by SDS-Page. Results are described in Table 23. F1077 (K248N), F1080 (S424N), F1081 (Y436N/Q438T) and F1082 (Q438N) were found to have additional glycosylation, and especially F1080 (S424N) maintained binding affinity against human FcRn.

TABLE 23

| Variant name | hFcRn KD (M) at pH 7.0 | Glycosylation | Mutations |
|---|---|---|---|
| F11 | 3.3E−07 | | M252Y/N434Y |
| F1077 | 2.0E−06 | ++ | K248N/M252Y/N434Y |
| F1078 | 4.7E−07 | − | M252Y/E380N/E382S/N434Y |
| F1079 | 3.4E−07 | − | M252Y/E382N/N384S/N434Y |
| F1080 | 3.2E−07 | ++ | M252Y/S424N/N434Y |
| F1081 | 6.2E−07 | ++ | M252Y/N434Y/Y436N/Q438T |
| F1082 | 2.8E−07 | + | M252Y/N434Y/Q438N |
| F1083 | 3.5E−07 | − | M252Y/N434Y/S440N |
| F1094 | 2.6E−07 | − | M252Y/N434Y/S442N |
| F1095 | 2.9E−07 | − | M252Y/S383N/G385S/N434Y |
| F1096 | 2.7E−07 | − | M252Y/Q386T/N434Y |
| F1097 | 2.8E−07 | − | M252Y/G385N/P387S/N434Y |

Therefore, in the next study, S424N mutation was introduced into Fv-4-F890, Fv-4-F1115 described in Table 24 was generated and evaluated for their binding affinity to human FcRn at pH7.0. Results are also described in Table 24.

TABLE 24

| Variant name | hFcRn KD (M) at pH 7.0 | Mutations |
|---|---|---|
| F890 | 1.1E−07 | M252Y/N434Y/Y436V |
| F1115 | 1.3E−07 | M252Y/S424N/N434Y/Y436V |

Then we performed rheumatoid factor binding study for these variants as described above. Result of this study is shown in FIG. 31. Surprisingly, single S424N mutant, Fv-4-F1115, exhibited significant reduction in rheumatoid factor binding. This result suggests that the introduction of additional N-glycosylation is effective approach for abrogating rheumatoid factor binding.

4-4. Reduction of Rheumatoid Factor Binding of YTE, N434H and LS Variant

In order to reduce rheumatoid factor binding of Fv-4-YTE, Fv-4-N434H and Fv-4-LS variants, which improves FcRn binding at acidic pH and prolongs antibody pharmacokinetics, Q438R/S440E mutations or S424N mutation were introduced into these variants. Novel Fc variants (F1166, F1167, F1172, F1173, F1170 and F1171) described in Table 25 were generated. First the variants were evaluated for their binding affinity to human FcRn at pH6.0. Results are also described in Table 25.

TABLE 25

| Variant name | hFcRn KD (M) at pH 6.0 | Mutations |
| --- | --- | --- |
| IgG1 | 2.4E−06 | none |
| YTE | 2.1E−07 | M252Y/S254T/T256E |
| F1166 | 2.1E−07 | M252Y/S254T/T256E/Q438R/S440E |
| F1167 | 2.5E−07 | M252Y/S254T/T256E/S424N |
| LS | 1.6E−07 | M428L/N434S |
| F1170 | 1.5E−07 | M428L/N434S/Q438R/S440E |
| F1171 | 2.4E−07 | S424N/M428L/N434S |
| N434H | 4.3E−07 | N434H |
| F1172 | 4.0E−07 | N434H/Q438R/S440E |
| F1173 | 5.3E−07 | S424N/N434H |

Then we performed rheumatoid factor binding study for these variants (Fv-4-F1166, F1167, F1172, F1173, F1170 and F1171) as described above. Result of this study is shown in FIG. 32. Compared to YTE which exhibited strong rheumatoid factor binding in two donors (90216S and 90214S), F1166 (Q438R/S440E) and F1167 (S424N) exhibited significant reduction in rheumatoid factor binding. Furthermore, F1173 and F1171 show that S424N mutation could also abrogate rheumatoid factor binding of N434H and LS variant. However, Q438R/S440E mutations could not abrogate rheumatoid factor binding of N434H and LS variant completely, rheumatoid factor binding was observed in one or two donors.

4-5. Alternative Mutations for Reduction of Rheumatoid Factor Binding of LS Variant Novel single mutations were introduced into Fv-4-LS, Fc variants (Fv-4-F1380 to Fv-4-F1392) described in Table 26 were generated.

TABLE 26

| Variant name | hFcRn KD (M) at pH 6.0 | Mutations |
| --- | --- | --- |
| F22 (=LS) | 7.1E−08 | M428L/N434S |
| F1380 | 7.3E−08 | S426D/M428L/N434S |
| F1381 | 8.6E−08 | S426E/M428L/N434S |
| F1382 | 1.3E−07 | S426K/M428L/N434S |
| F1383 | 1.6E−07 | S426R/M428L/N434S |
| F1384 | 8.6E−08 | S426A/M428L/N434S |
| F1385 | 7.7E−08 | S426Q/M428L/N434S |
| F1386 | 1.6E−07 | S426Y/M428L/N434S |
| F1387 | 1.5E−07 | M428L/N434S/Y436M |
| F1388 | 8.0E−08 | M428L/N434S/Y436F |
| F1389 | 6.8E−08 | M428L/N434S/Y436T |
| F1390 | 4.0E−07 | M428L/N434S/Y436H |
| F1391 | 4.2E−07 | M428L/N434S/Y436N |
| F1392 | 2.7E−07 | M428L/N434S/Y436K |

Then we performed rheumatoid factor binding study for the variants which maintains FcRn binding at pH6.0 (Fv-4-F1380, F1384-F1386, F1388 and F1389). Result of this study is shown in FIG. 33. These variants exhibited significant reduction in rheumatoid factor binding in some donors. Especially, Fv-4-F1389 exhibited comparable rheumatoid factor binding as native IgG1.

Therefore, mutation such as Pro387Arg, Val422Glu, Val422Arg, Val422Ser, Val422Asp, Val422Lys, Val422Thr, Val422Gln, Ser424Glu, Ser424Arg, Ser424Lys, Ser424Asn, Ser426Asp, Ser426Ala, Ser426Gln, Ser426Tyr, His433Asp, Tyr436Thr, Gln438Glu, Gln438Arg, Gln438Ser, Gln438Lys, Ser440Glu, Ser440Asp, Ser440Gln (positions are given in EU numbering) are extremely useful for reducing the immunogenicity of antigen-binding molecule containing FcRn binding increased Fc region (for example F1-F1434) such as pH-dependent antigen binding antibody with improved binding affinity to FcRn at neutral pH which is capable of eliminating antigen from plasma and antibody with improved binding affinity to FcRn at acidic pH which is capable of improving antibody pharmacokinetics.

Mutation sites other than EU387, EU422, EU424, EU426, EU433, EU436, EU438 and EU440 for reducing the binding of rheumatoid factor without affecting human FcRn binding could be selected from 248-257, 305-314, 342-352, 380-386, 388, 414-421, 423, 425-437, 439, and 441-444 in EU numbering.

[Example 5] Reduction of Rheumatoid Factor Binding of Novel Fc Variants with Improved Binding to Human FcRn at Neutral pH Novel Fc variants (F939, F1378, F1379, F1262, F1138, F1344, F1349, F1350, F1351, F1261, F1263, F1305, F1306, F1268, F1269, F1413, F1416, F1419, F1420, F1370, F1371, F1599, F1600, F1566, F1448, F1601-F1603, F1531, F1604, F1605, F1586, F1592, F1610-F1615, F1567, F1572, F1576, F1578, F1579, F1641-F1655, F1329, F1331) described in Table 27 were generated. First the variants were evaluated for their binding affinity to human FcRn at pH7.0. Results are also described in Table 27.

TABLE 27

| Variant name | hFcRn KD (M) at pH 7.0 | Mutations |
| --- | --- | --- |
| F939 | 1.5E−07 | L235R/S239K/M252Y/N434Y/Y436V |
| F1378 | 3.6E−07 | L235R/S239K/M252Y/N434Y/Y436T |
| F1379 | 2.8E−07 | L235R/S239K/M252Y/N434Y/Y436F |
| F1262 | 1.3E−07 | L235R/S239K/M252Y/N434Y/Y436V/Q438K/S440E |
| F1138 | 1.7E−07 | L235R/S239K/M252Y/N434Y/Y436V/Q438R/S440E |
| F1344 | 4.0E−07 | L235R/S239K/M252Y/N434Y/Y436T/Q438K/S440E |
| F1349 | 3.4E−07 | L235R/S239K/M252Y/N434Y/Y436T/Q438R/S440E |
| F1350 | 1.2E−07 | L235R/S239K/M252Y/N434Y/Y436F/Q438K/S440E |
| F1351 | 1.6E−07 | L235R/S239K/M252Y/N434Y/Y436F/Q438R/S440E |
| F1261 | 1.4E−07 | L235R/S239K/M252Y/N434Y/Y436V/Q438R/S440D |
| F1263 | 1.2E−07 | L235R/S239K/M252Y/N434Y/Y436V/Q438K/S440D |
| F1305 | 2.0E−07 | L235R/S239K/M252Y/H433D/N434Y/Y436V/Q438R/S440D |
| F1306 | 1.9E−07 | L235R/S239K/M252Y/H433D/N434Y/Y436V/Q438K/S440E |
| F1268 | 2.0E−07 | L235R/S239K/M252Y/H433D/N434Y/Y436V/Q438R/S440E |

TABLE 27-continued

| Variant name | hFcRn KD (M) at pH 7.0 | Mutations |
|---|---|---|
| F1269 | 1.7E−07 | L235R/S239K/M252Y/H433D/N434Y/Y436V/Q438K/S440D |
| F1413 | 3.7E−08 | L235R/S239K/M252Y/S254T/T256E/T307Q/Q311A/H433D/N434Y/Y436V/Q438K/S440E |
| F1416 | 1.3E−08 | L235R/S239K/M252Y/S254T/T256E/V308P/H433D/N434Y/Y436V/Q438K/S440E |
| F1419 | 1.5E−07 | L235R/S239K/M252Y/H433D/N434W/Y436V/Q438R/S440E |
| F1420 | 1.3E−07 | L235R/S239K/M252Y/H433D/N434W/Y436V/Q438K/S440E |
| F1370 | 9.1E−08 | L235R/S239K/M252Y/S254T/T256E/H433D/N434Y/Y436V/Q438K/S440E |
| F1371 | 1.1E−07 | L235R/S239K/M252Y/S254T/T256E/H433D/N434Y/Y436V/Q438R/S440E |
| F1599 | 7.4E−08 | L235R/S239K/M252Y/S254T/T256E/H433D/N434Y/Y436V/Q438K/S440D |
| F1600 | 8.5E−08 | L235R/S239K/M252Y/S254T/T256E/H433D/N434Y/Y436V/Q438R/S440D |
| F1566 | 4.0E−08 | L235R/S239K/M252Y/S254T/T256E/N286E/H433D/N434Y/Y436V/Q438K/S440E |
| F1448 | 4.9E−08 | L235R/S239K/M252Y/S254T/T256E/N286E/H433D/N434Y/Y436V/Q438R/S440E |
| F1601 | 3.5E−08 | L235R/S239K/M252Y/S254T/T256E/N286E/H433D/N434Y/Y436V/Q438K/S440D |
| F1602 | 3.6E−08 | L235R/S239K/M252Y/S254T/T256E/N286E/H433D/N434Y/Y436V/Q438R/S440D |
| F1603 | 5.9E−08 | L235R/S239K/M252Y/S254T/R255L/T256E/H433D/N434Y/Y436V/Q438K/S440E |
| F1531 | 7.6E−08 | L235R/S239K/M252Y/S254T/R255L/T256E/H433D/N434Y/Y436V/Q438R/S440E |
| F1604 | 6.0E−08 | L235R/S239K/M252Y/S254T/R255L/T256E/H433D/N434Y/Y436V/Q438K/S440D |
| F1605 | 6.1E−08 | L235R/S239K/M252Y/S254T/R255L/T256E/H433D/N434Y/Y436V/Q438R/S440D |
| F1586 | 5.5E−08 | L235R/S239K/M252Y/S254T/R255L/T256E/E258D/H433D/N434Y/Y436V/Q438R/S440E |
| F1592 | 5.5E−08 | L235R/S239K/M252Y/S254T/R255L/T256E/E258I/H433D/N434Y/Y436V/Q438R/S440E |
| F1610 | 4.8E−08 | L235R/S239K/M252Y/S254T/R255L/T256E/E258D/H433D/N434Y/Y436V/Q438K/S440E |
| F1611 | 5.2E−08 | L235R/S239K/M252Y/S254T/R255L/T256E/E258I/H433D/N434Y/Y436V/Q438K/S440E |
| F1612 | 4.9E−08 | L235R/S239K/M252Y/S254T/R255L/T256E/E258D/H433D/N434Y/Y436V/Q438K/S440D |
| F1613 | 5.2E−08 | L235R/S239K/M252Y/S254T/R255L/T256E/E258I/H433D/N434Y/Y436V/Q438K/S440D |
| F1614 | 5.1E−08 | L235R/S239K/M252Y/S254T/R255L/T256E/E258D/H433D/N434Y/Y436V/Q438R/S440D |
| F1615 | 6.0E−08 | L235R/S239K/M252Y/S254T/R255L/T256E/E258I/H433D/N434Y/Y436V/Q438R/S440D |
| F1567 | 4.8E−08 | L235R/S239K/M252Y/S254T/T256E/H433A/N434Y/Y436V/Q438R/S440E |
| F1572 | 4.1E−08 | L235R/S239K/M252Y/S254T/T256E/H433K/N434Y/Y436V/Q438R/S440E |
| F1576 | 4.3E−08 | L235R/S239K/M252Y/S254T/T256E/H433P/N434Y/Y436V/Q438R/S440E |
| F1578 | 4.6E−08 | L235R/S239K/M252Y/S254T/T256E/H433R/N434Y/Y436V/Q438R/S440E |
| F1579 | 5.4E−08 | L235R/S239K/M252Y/S254T/T256E/H433S/N434Y/Y436V/Q438R/S440E |
| F1641 | 4.1E−08 | L235R/S239K/M252Y/S254T/T256E/H433A/N434Y/Y436V/Q438K/S440E |
| F1642 | 4.1E−08 | L235R/S239K/M252Y/S254T/T256E/H433A/N434Y/Y436V/Q438R/S440D |
| F1643 | 3.9E−08 | L235R/S239K/M252Y/S254T/T256E/H433A/N434Y/Y436V/Q438K/S440D |
| F1644 | 3.5E−08 | L235R/S239K/M252Y/S254T/T256E/H433K/N434Y/Y436V/Q438K/S440E |
| F1645 | 3.6E−08 | L235R/S239K/M252Y/S254T/T256E/H433K/N434Y/Y436V/Q438R/S440D |
| F1646 | 3.5E−08 | L235R/S239K/M252Y/S254T/T256E/H433K/N434Y/Y436V/Q438K/S440D |
| F1647 | 3.8E−08 | L235R/S239K/M252Y/S254T/T256E/H433P/N434Y/Y436V/Q438K/S440E |
| F1648 | 3.8E−08 | L235R/S239K/M252Y/S254T/T256E/H433P/N434Y/Y436V/Q438R/S440D |
| F1649 | 3.7E−08 | L235R/S239K/M252Y/S254T/T256E/H433P/N434Y/Y436V/Q438K/S440D |
| F1650 | 4.0E−08 | L235R/S239K/M252Y/S254T/T256E/H433R/N434Y/Y436V/Q438K/S440E |
| F1651 | 4.4E−08 | L235R/S239K/M252Y/S254T/T256E/H433R/N434Y/Y436V/Q438R/S440D |
| F1652 | 4.0E−08 | L235R/S239K/M252Y/S254T/T256E/H433R/N434Y/Y436V/Q438K/S440D |
| F1653 | 4.5E−08 | L235R/S239K/M252Y/S254T/T256E/H433S/N434Y/Y436V/Q438K/S440E |
| F1654 | 4.5E−08 | L235R/S239K/M252Y/S254T/T256E/H433S/N434Y/Y436V/Q438R/S440D |
| F1655 | 4.4E−08 | L235R/S239K/M252Y/S254T/T256E/H433S/N434Y/Y436V/Q438K/S440D |
| F1329 | 1.3E−07 | L235R/G236R/S239K/M252Y/S254T/N434Y/Y436V/Q438R/S440E |
| F1331 | 7.7E−08 | L235R/G236R/S239K/M252Y/S254T/T256E/N434Y/Y436V/Q438R/S440E |

Then we performed rheumatoid factor binding study at pH 7.4 for the variants in Table 27. Results of this study are shown in FIGS. 34 to 94.

Double mutations for decreasing rheumatoid factor binding (Q438R/S440E, Q438R/S440D, Q438K/S440E and Q438K/S440D) showed significant reduction in rheumatoid factor binding to other mutations for increasing FcRn binding at neutral pH.

5-1. Reduction of Rheumatoid Factor Binding of Novel Fc Variants with Improved Binding to Human FcRn at Acidic pH Novel Fc variants (F1718-F1721, F1671, F1670, F1711-F1713, F1722-F1725, F1675, F1714-F1717, F1683, F1756-F1759, F1681, F1749-F1751, F1760-F1763, F1752-F1755, F1685) described in Table 28 were generated. First the variants were evaluated for their binding affinity to human FcRn at pH6.0. Results are also described in Table 28.

TABLE 28

| Variant name | hFcRn KD (M) at pH 6.0 | Mutations |
|---|---|---|
| F1718 | 6.1E−08 | N434Y/Y436V/Q438R/S440F |
| F1719 | 5.2E−08 | N434Y/Y436V/Q438R/S440D |
| F1720 | 4.5E−08 | N434Y/Y436V/Q438K/S440E |
| F1721 | 5.5E−08 | N434Y/Y436V/Q438K/S440D |
| F1671 | 9.5E−08 | L235R/S239K/N434Y/Y436V |
| F1670 | 6.4E−08 | L235R/S239K/N434Y/Y436V/Q438R/S440E |
| F1711 | 5.5E−08 | L235R/S239K/N434Y/Y436V/Q438R/S440D |
| F1712 | 5.5E−08 | L235R/S239K/N434Y/Y436V/Q438K/S440E |
| F1713 | 5.1E−08 | L235R/S239K/N434Y/Y436V/Q438K/S440D |
| F1722 | 1.0E−07 | H433D/N434Y/Y436V/Q438R/S440E |
| F1723 | 9.6E−08 | H433D/N434Y/Y436V/Q438R/S440D |
| F1724 | 9.9E−08 | H433D/N434Y/Y436V/Q438K/S440E |
| F1725 | 9.3E−08 | H433D/N434Y/Y436V/Q438K/S440D |
| F1675 | 9.7E−08 | L235R/S239K/H433D/N434Y/Y436V |
| F1714 | 1.1E−07 | L235R/S239K/H433D/N434Y/Y436V/Q438R/S440E |
| F1715 | 1.1E−07 | L235R/S239K/H433D/N434Y/Y436V/Q438R/S440D |
| F1716 | 9.6E−08 | L235R/S239K/H433D/N434Y/Y436V/Q438K/S440E |

TABLE 28-continued

| Variant name | hFcRn KD (M) at pH 6.0 | Mutations |
|---|---|---|
| F1717 | 9.5E−08 | L235R/S239K/H433D/N434Y/Y436V/Q438K/S440D |
| F1683 | 5.7E−08 | L235R/S239K/N434Y/Y436F/Q438R/S440E |
| F1756 | 8.0E−08 | N434Y/Y436T/Q438R/S440E |
| F1757 | 7.2E−08 | N434Y/Y436T/Q438R/S440D |
| F1758 | 7.0E−08 | N434Y/Y436T/Q438K/S440E |
| F1759 | 6.3E−08 | N434Y/Y436T/Q438K/S440D |
| F1681 | 8.4E−08 | L235R/S239K/N434Y/Y436T/Q438R/S440E |
| F1749 | 8.7E−08 | L235R/S239K/N434Y/Y436T/Q438R/S440D |
| F1750 | 7.0E−08 | L235R/S239K/N434Y/Y436T/Q438K/S440E |
| F1751 | 6.9E−08 | L235R/S239K/N434Y/Y436T/Q438K/S440D |
| F1760 | 1.2E−07 | H433D/N434Y/Y436T/Q438R/S440E |
| F1761 | 1.3E−07 | H433D/N434Y/Y436T/Q438R/S440D |
| F1762 | 1.1E−07 | H433D/N434Y/Y436T/Q438K/S440E |
| F1763 | 1.1E−07 | H433D/N434Y/Y436T/Q438K/S440D |
| F1752 | 1.5E−07 | L235R/S239K/H433D/N434Y/Y436T/Q438R/S440E |
| F1753 | 1.3E−07 | L235R/S239K/H433D/N434Y/Y436T/Q438R/S440D |
| F1754 | 1.2E−07 | L235R/S239K/H433D/N434Y/Y436T/Q438K/S440E |
| F1755 | 1.3E−07 | L235R/S239K/H433D/N434Y/Y436T/Q438K/S440D |
| F1685 | 8.7E−08 | L235R/S239K/N434Y/Q438R/S440E |

Then we performed rheumatoid factor binding study at pH 7.4 for the variants in Table 28. Results of this study are shown in FIGS. 95 to 130.

Double mutations for decreasing rheumatoid factor binding (Q438R/S440E, Q438R/S440D, Q438K/S440E and Q438K/S440D) showed significant reduction in rheumatoid factor binding to other mutations for increasing FcRn binding at acidic pH.

[Example 6] In Vivo Antigen Elimination Study of Novel Fc Variants in Human IL-6 Receptor Steady-State Infusion Model Using Human FcRn Transgenic Mice 6-1. Preparation of Antibodies for In Vivo Study pH-dependent anti-human IL6 receptor IgG1 antibody, Fv-4-IgG1 comprising VH3-IgG1 (SEQ ID NO: 1) and VL3-CK (SEQ ID NO: 3), new Fc variants, Fv-4-F1243 comprising VH3-F1243 (SEQ ID NO: 8) and VL3-CK (SEQ ID NO: 3), and Fv-4-F1245 comprising VH3-F1245 (SEQ ID NO: 9) and VL3-CK (SEQ ID NO: 3) were expressed and purified by the method known to those skilled in the art described in Example 2 of WO2011/122011.

As described in Example 4, Fv-4-F1243 and Fv-4-F1245 have novel Fc region with improved binding affinity to human FcRn at neutral pH, but significantly reduced binding to rheumatoid factor. In order to evaluate antigen elimination effect of these variants, an in vivo study of Fv-4-IgG1, Fv-4-F1243 and Fv-4-F1245 was performed in a human IL-6 receptor steady-state infusion model using human FcRn transgenic mice.

6-2. In Vivo Study of Antibodies by Steady-State Infusion Model Using Human FcRn Transgenic Mouse Line 32

An in vivo test was conducted by steady-state infusion model using human FcRn transgenic mouse line 32 by the same methods described in Example 13 of WO2011/122011.

6-3. Result of Study; In Vivo Antigen Elimination Effect of New Fc Variants

FIG. 131 shows plasma hsIL-6R concentration time profile and FIG. 132 shows plasma antibody concentration time profile after injection of Fv-4-IgG1, Fv-4-F1243 and Fv-4-F1245. Compared to Fv-4-IgG1 and control (no antibody injection), Fv-4-F1243 and Fv-4-F1245 having novel Fc variants with improved binding to FcRn at neutral pH exhibited significant reduction of plasma hsIL-6R concentration demonstrating in vivo antigen elimination of pH-dependent antigen binding antibody with improved binding to FcRn at neutral pH. Fv-4-F1243 and Fv-4-F1245 demonstrated 10-fold antigen elimination effect at day 21 or day 7 compared to Fv-4-IgG1, respectively, whereby the plasma antibody concentration time profile of Fv-4-F1243 and Fv-4-F1245 was comparable to Fv-4-IgG1.

[Example 7] In Vivo PK Study of Novel Fc Variants Using Human FcRn Transgenic Mice 7-1. Preparation of Antibodies for In Vivo Study pH-dependent anti-human IL6 receptor IgG1 antibody, Fv-4-IgG1 comprising VH3-IgG1 (SEQ ID NO: 1) and VL3-CK (SEQ ID NO: 3), a new Fc variant, Fv-4-F1389 comprising VH3-F1389 (SEQ ID NO: 10) and VL3-CK (SEQ ID NO: 3), were expressed and purified by the method known to those skilled in the art described in Reference Example 2 of WO2011/122011.

As described in Example 4 and 5, Fv-4-F1389 has a novel Fc region with improved binding affinity to human FcRn at acidic pH, but significantly reduced binding to rheumatoid factor. In order to evaluate the pharmacokinetics of this variant, an in vivo study of Fv-4-IgG1 and Fv-4-F1389 was performed using human FcRn transgenic mice.

7-2. In Vivo Study of Antibodies by Using Human FcRn Transgenic Mouse Line 32

An in vivo test was conducted using human FcRn transgenic mouse line 32 by the same methods described in Example 13 of WO2011/122011.

7-3. Result of In Vivo PK Study of New Fc Variants

FIG. 133 shows plasma antibody concentration time profile after injection of Fv-4-IgG1 and Fv-4-F1389. Compared to Fv-4-IgG1, Fv-4-F1389 having novel Fc variants with improved binding to FcRn at acidic pH and reduced binding to rheumatoid factor exhibited improved pharmacokinetics. Novel Fc variants described in Table 28 have increased binding affinity to FcRn at pH6.0 to a same level as F1389. Therefore, these variants are also expected to exhibit improved pharmacokinetics using human FcRn transgenic mouse line 32 while having reduced binding to rheumatoid factor.

[Example 8] Preparation of Antibodies that Bind to Human IgA in a Calcium-Dependent Manner 8-1. Preparation of Human IgA (hIgA)

Human IgA (hereinafter also abbreviated as "hIgA") was prepared as an antigen by using the following recombinant techniques. hIgA (the variable region is derived from an anti-human IL-6 Receptor antibody) was expressed by culturing host cells carrying recombinant vectors inserted with H (WT)-IgA1 (SEQ ID NO: 12) and L (WT) (SEQ ID NO: 13) and purified by a method known to those skilled in the art using ion-exchange chromatography and gel filtration chromatography.

8-2. Expression and Purification of Antibodies that Bind to hIgA

GA2-IgG1 (heavy chain SEQ ID NO: 14; light chain SEQ ID NO: 15) is an antibody that bind to hIgA. The DNA sequences encoding heavy chain of GA2-IgG1 (SEQ ID NO: 14) and light chain of GA2-IgG1 (SEQ ID NO: 15) were inserted into animal cell expression plasmids by a method known to those skilled in the art. The antibody was expressed by the method described below. Cells of human fetal kidney cell-derived line FreeStyle 293-F (Invitrogen) were suspended in FreeStyle 293 Expression Medium (Invitrogen). The cell suspension was seeded into a 6-well plate (3 mL/well) at a cell density of $1.33 \times 10^6$ cells/ml. Then, the constructed plasmids were introduced into the cells by a lipofection method. The cells were cultured for four days in a $CO_2$ incubator (37 degrees C., 8% $CO_2$, 90 rpm). The antibodies were purified from the isolated culture supernatants by a method known to those skilled in the art using rProtein A Sepharose™ Fast Flow (Amersham Biosciences). The absorbance (wavelength: 280 nm) of the purified antibody solutions was measured using a spectrophotometer. The antibody concentrations were determined from the measured values using the absorption coefficient calculated by the PACE method (Protein Science (1995) 4, 2411-2423).

8-3. Assessment of Obtained Antibodies for Calcium-Dependent hIgA-Binding Activity The antibodies isolated as described in 8-2 were assessed for their hIgA-binding activity (dissociation constant $K_D$ (M)) using Biacore T200 (GE Healthcare). Running buffers used in the measurement were 0.05% tween20/20 mmol/L ACES/150 mmol/L NaCl (pH 7.4 or 5.8) containing 3 microM or 1.2 mM $CaCl_2$.

The antibody was allowed to bind to Sensor chip CM5 (GE Healthcare) immobilized with a suitable amount of recombinant Protein A/G (Thermo Scientific) by the amino coupling method. Then, an appropriate concentration of hIgA (described in 8-1) was injected as an analyte to allow interaction with the antibody on the sensor chip. The measurement was carried out at 37 degrees C. After the measurement, 10 mmol/L glycine-HCl (pH 1.5) was injected to regenerate the sensor chip. The dissociation constant $K_D$ (M) was calculated from the measurement result by curve fitting analysis and equilibrium parameter analysis using Biacore T200 Evaluation Software (GE Healthcare). The result and obtained sensorgrams are shown in Table 29 and FIG. 134, respectively. It was revealed that GA2-IgG1 bound strongly to hIgA at a $Ca^{2+}$ concentration of 1.2 mM whereas the antibody bound weakly to hIgA at a $Ca^{2+}$ concentration of 3 microM. Furthermore, at a $Ca^{2+}$ concentration of 1.2 mM, GA2-IgG1 was shown to bind to human IgA strongly at pH 7.4 but weakly at pH 5.8. More specifically, GA2-IgG1 was revealed to bind to human IgA in a pH- and calcium-dependent manner.

TABLE 29

| Antibody name | Conditions | Fit | ka | kd | KD [M] |
|---|---|---|---|---|---|
| GA2-IgG1 | pH 7.4, 1.2 mM Ca | 1:1 binding model | 4.0E+05 | 1.6E−02 | 3.9E−08 |
| | pH 7.4, 3 microM Ca | Steady State Affinity | — | — | 6.7E−06 |
| | pH 5.8, 1.2 mM Ca | Steady State Affinity | — | — | 4.0E−06 |
| | pH 5.8, 3 microM Ca | Steady State Affinity | — | — | 5.0E−06 |

[Example 9] Preparation of Antibodies with Modified Fc Region that Bind to hIgA in a Calcium-Dependent Manner Next, to evaluate the effect of FcRn binding on antigen (hIgA) elimination from plasma, GA2-F760 (heavy chain SEQ ID NO: 16; light chain SEQ ID NO: 15) was constructed by introducing amino acid substitutions L235R and S239K into GA2-IgG1 to eliminate binding to FcgammaR. Furthermore GA2-F1331 (heavy chain SEQ ID NO: 17; light chain SEQ ID NO: 15) was constructed by introducing amino acid substitution G236R, M252Y, S254T, T256E, N434Y, Y436V, Q438R and S440E into GA2-F760, which binds to FcRn stronger than GA2-F760 at pH 7.4. The modified antibodies were expressed by the method described above using animal expression plasmids inserted with DNA sequences encoding GA2-F1331 (heavy chain SEQ ID NO: 17; light chain SEQ ID NO: 15) and GA2-F760 (heavy chain SEQ ID NO: 16; light chain SEQ ID NO: 15) by a method known to those skilled in the art. The antibody concentrations were determined after purification. GA2-F760 was assessed for its binding to various mouse FcgammaR (mFcgammaRI, mFcgammaRII, mFcgammaRIII, and mFcgammaRIV). The result showed that GA2-F760 did not bind to any of the receptors.

[Example 10] Assessment of the Effect of Ca-Dependent hIgA-Binding Antibodies on Plasma Retention of an Antigen Using Human FcRn Transgenic Mice 10-1. In Vivo Test Using Human FcRn Transgenic Mice Pharmacokinetics of hIgA and anti-hIgA antibody was assessed after administration of hIgA (human IgA; prepared as described in Example 8) alone or in combination with an anti-hIgA antibody to human FcRn transgenic mice (B6.mFcRn−/−.hFcRn Tg line 32+/+ mouse, Jackson Laboratories; Methods Mol. Biol. (2010) 602: 93-104). A mixture of hIgA and anti-hIgA antibody was administered once at a dose of 10 mL/kg via the caudal vein. GA2-F760 and GA2-F1331 described above were the anti-hIgA antibodies that were used.

In every mixture, the hIgA concentration was 80 microg/mL and the anti-hIgA antibody concentration was 2.69 mg/mL. Under the conditions described above, the majority of hIgA is predicted to bind to the antibody since the anti-hIgA antibody is present in sufficient excess over hIgA. Blood was collected from the mice fifteen minutes, one hour, two hours, seven hours, one day, three days, seven days and fourteen days after administration. The collected blood was immediately centrifuged for 15 minutes at 12,000 rpm and 4 degrees C. to obtain the plasma. The separated plasma was stored in a freezer at −20 degrees C. or below until measurement.

10-2. Determination of Plasma Anti-hIgA Antibody Concentration in Human FcRn Transgenic Mice by ELISA The anti-hIgA antibody concentrations in mouse plasma were determined by ELISA. First, Anti-Human IgG-immobilized plates were prepared by aliquoting Anti-Human IgG (gamma-chain specific) F(ab')2 Fragment Antibody (SIGMA) to each well of Nunc-Immuno Plate, MaxiSorp (Nalge nunc International) and allowing the plates to stand at 4 degrees C. overnight. Anti-hIgA antibody standard curve samples prepared as standard solutions at plasma concentrations of 0.5, 0.25, 0.125, 0.0625, 0.03125, 0.01563, and 0.007813 microg/mL and assay samples prepared by diluting mouse plasma samples 100-fold or more were aliquoted into the Anti-Human IgG-immobilized plates, and then the plates were incubated at 25 degrees C. for one hour. Next, Goat Anti-Human IgG (gamma-chain specific) Biotin (BIOT) Conjugate (Southern Biotechnology Associates Inc.) was aliquoted into each well of the plates, and then the plates were incubated at 25 degrees C. for one hour. Then, Streptavidin-PolyHRP80 (Stereospecific Detection Technologies) was added to each well of the plates, after which the plates were incubated at 25 degrees C. for one hour. The chromogenic reaction using TMB One Component HRP Microwell Substrate (BioFX Laboratories) as a substrate was terminated with 1N sulfuric acid (Showa Chemical), and then the reaction mixture in each well was measured using a microplate reader to measure the absorbance at 450 nm. The anti-hIgA antibody concentration in mouse plasma was calculated from the absorbance of the standard curve using analysis software SOFTmax PRO (Molecular Devices). The time course of plasma antibody concentrations of GA2-F1331, and GA2-F760 in human FcRn transgenic mice, which were determined by the method described above, is shown in FIG. 135.

10-3. Determination of hIgA Concentration in Plasma by ELISA hIgA concentrations in mouse plasma were measured by ELISA. First, Anti-Human IgA-immobilized plates were prepared by aliquoting Goat anti-Human IgA Antibody (BETHYL) into each well of Nunc-Immuno Plate, MaxiSorp (Nalge nunc International) and allowing the plates to stand at 4 degrees C. overnight. hIgA standard curve samples were prepared as standard solutions at plasma concentrations of 0.4, 0.2, 0.1, 0.05, 0.025, 0.0125, and 0.00625 microg/mL and assay samples were prepared by diluting mouse plasma samples 100-fold or more. Each sample (100 microL) was mixed with 200 microL of 500 ng/mL hsIL-6R at room temperature for one hour, and then it was aliquoted at 100 microL/well into the Anti-Human IgA-immobilized plates. The resulting plates were allowed to stand at room temperature for one hour. Next, after adding Biotinylated Anti-human IL-6R Antibody (R&D) into each well of the plates, the plates were incubated at room temperature for one hour. Then, after aliquoting Streptavidin-PolyHRP80 (Stereospecific Detection Technologies) into each well of the plates, the plates were incubated at room temperature for one hour. The chromogenic reaction using as a substrate TMB One Component HRP Microwell Substrate (BioFX Laboratories) was terminated with 1N sulfuric acid (Showa Chemical), and then the reaction mixture in each well was measured using a microplate reader to measure the absorbance at 450 nm. The concentration in mouse plasma was calculated from the absorbance of the standard curve using analysis software SOFTmax PRO (Molecular Devices). The time course of plasma hIgA concentrations in human FcRn transgenic mice after intravenous administration, as determined by the method described above, is shown in FIG. 136.

The result showed that the elimination of hIgA was markedly accelerated when hIgA was administered in combination with GA2-F1331, an antibody that exhibits strong human FcRn binding, as compared to when hIgA was administered in combination with GA2-F760, which has very weak affinity to human FcRn.

[Example 11] Preparation of pH-Dependent Anti-IgE Antibody 11-1. Preparation of Anti-Human IgE Antibody To prepare pH-dependent anti-human IgE antibodies, human IgE (heavy chain SEQ ID NO: 18; light chain SEQ ID NO: 19) (the variable region is derived from an anti-human glypican3 antibody) as an antigen was expressed using FreeStyle293 (Life Technologies). Human IgE was prepared by purifying the expressed human IgE using a conventional chromatographic method known to those skilled in the art.

An antibody that binds to human IgE in a pH-dependent manner was selected from a number of obtained antibodies. The selected anti-human IgE antibody was expressed using human IgG1 heavy chain constant region and human light chain constant region, and then purified. The produced antibody was named clone 278 (heavy chain SEQ ID NO: 20; light chain SEQ ID NO: 21).

11-2. Assessment of Anti-Human IgE Antibodies for their Binding Activity and pH-Dependent Binding Activity Antibodies capable of dissociating from antigens within the endosome can be created not only by designing them so as to bind to antigens in a pH-dependent manner, but also by designing them so as to bind to antigens in a Ca-dependent manner. Thus, clone 278 and the control Xolair (omalizumab; Novartis) whose IgE-binding activity does not depend on pH/Ca were assessed for their pH dependency and pH/Ca dependency of the human IgE (hIgE)-binding activity.

More specifically, the hIgE-binding activities (dissociation constant $K_D$ (M)) of clone 278 and Xolair were assessed using Biacore T200 (GE Healthcare). Running buffers used in the assay were:

1.2 mmol/l $CaCl_2$/0.05% tween20, 20 mmol/l ACES, 150 mmol/l NaCl, pH 7.4;

1.2 mmol/l $CaCl_2$/0.05% tween20, 20 mmol/l ACES, 150 mmol/l NaCl, pH 5.8; and 3 micromol/l $CaCl_2$/0.05% tween20, 20 mmol/l ACES, 150 mmol/l NaCl, pH 5.8.

A chemically-synthetized peptide having a human glypican 3 protein-derived sequence (SEQ ID NO: 22) whose C-terminal Lys is biotinylated (hereinafter abbreviated as "biotinylated GPC3 peptide") was added in an appropriate amount and immobilized onto Sensor chip SA (GE Healthcare) based on the affinity between biotin and streptavidin. Human IgE was immobilized onto the chip by injecting it at an appropriate concentration so as to be trapped by the biotinylated GPC3 peptide. As an analyte, clone 278 was injected at an appropriate concentration and allowed to interact with the human IgE on the sensor chip. Then, 10 mmol/L glycine-HCl (pH 1.5) was injected to regenerate the sensor chip. The interaction was always measured at 37 degrees C. The measurement result was analyzed by curve fitting using Biacore T200 Evaluation Software (GE Healthcare) to calculate the association rate constant ka (1/Ms) and dissociation rate constant kd (1/s). The dissociation constant $K_D$ (M) was calculated from the above-described constants. Furthermore, the KD ratios in each antibody under the conditions of [pH 5.8, 1.2 mM Ca] to [pH 7.4, 1.2 mM Ca] were calculated to assess the pH-dependent binding, while the KD ratios in each antibody under the conditions of [pH 5.8, 3 microM Ca] to [pH 7.4, 1.2 mM Ca] were calculated to assess the pH/Ca-dependent binding. The result is shown in Table 30.

TABLE 30

| Antibody name (abbreviation) | Buffer conditions | ka (1/Ms) | kd (1/s) | KD (M) | pH dependency KD (pH 5.8, 1.2 mM Ca)/KD (pH 7.4, 1.2 mM Ca) | pH/Ca dependency KD (pH 5.8, 3 microM Ca)/KD (pH 7.4, 1.2 mM Ca) |
|---|---|---|---|---|---|---|
| Clone 278 | pH 7.4, 1.2 mM | 1.5E+06 | 3.6E−03 | 2.4E−09 | 842.5 | 1636.5 |

TABLE 30-continued

| Antibody name (abbreviation) | Buffer conditions | ka (1/Ms) | kd (1/s) | KD (M) | pH dependency KD (pH 5.8, 1.2 mM Ca)/KD (pH 7.4, 1.2 mM Ca) | pH/Ca dependency KD (pH 5.8, 3 microM Ca)/KD (pH 7.4, 1.2 mM Ca) |
|---|---|---|---|---|---|---|
| | Ca pH 5.8, 1.2 mM Ca | 1.2E+05 | 2.3E−01 | 2.0E−06 | | |
| | pH 5.8, 3 microM Ca | 6.2E+04 | 2.4E−01 | 3.9E−06 | | |
| Xolair | pH 7.4, 1.2 mM Ca | 2.5E+06 | 1.1E−02 | 4.4E−09 | 2.3 | 2.9 |
| | pH 5.8, 1.2 mM Ca | 2.4E+06 | 2.4E−02 | 9.9E−09 | | |
| | pH 5.8, 3 microM Ca | 1.4E+06 | 1.7E−02 | 1.3E−08 | | |

[Example 12] Preparation of Antibodies with Modified Fc Region that Bind to Human IgE for In Vivo Testing Next, to evaluate the effect of FcRn binding on antigen (human IgE) elimination from plasma, 278-F760 (heavy chain SEQ ID NO: 23; light chain SEQ ID NO: 21) was constructed to eliminate binding to FcgammaR. Furthermore 278-F1331 (heavy chain SEQ ID NO: 24; light chain SEQ ID NO: 21) was constructed by introducing amino acid substitution G236R, M252Y, S254T, T256E, N434Y, Y436V, Q438R and S440E into 278-F760, which binds to FcRn stronger than 278-F760 at pH 7.4. The modified antibodies were expressed by the method described above using animal expression plasmids inserted with DNA sequences encoding 278-F1331 (heavy chain SEQ ID NO: 24; light chain SEQ ID NO: 21) and 278-F760 (heavy chain SEQ ID NO: 23; light chain SEQ ID NO: 21) by a method known to those skilled in the art. The antibody concentrations were determined after purification.

[Example 13] In Vivo Assessment of Clone 278

13-1. Preparation of Human IgE (hIgE(Asp6)) for In Vivo Assessment hIgE(Asp6) (the variable region is derived from an anti-human glypican3 antibody), which is a human IgE for in vivo assessment consisting of a heavy chain (SEQ ID NO: 25) and a light chain (SEQ ID NO: 19), was produced by the same method as described in Example 11. hIgE(Asp6) is a modified molecule resulting from asparagine-to-aspartic acid alteration at the six N-linked glycosylation sites in human IgE so that the heterogeneity in the N-linked sugar chain of human IgE is not affected by time-dependent changes in the plasma concentration of human IgE as an antigen.

13-2. Assessment of Clone 278 for the Effect of Accelerating Human IgE Elimination Using Human FcRn Transgenic Mice Pharmacokinetics of hIgE(Asp6) and anti-human IgE antibody was assessed after administration of hIgE(Asp6) in combination with an anti-hIgE antibody (278-F760 and 278-F1331) and Sanglopor (Human normal Immunoglobulin, CSL Behring) to human FcRn transgenic mice (B6.mFcRn−/−.hFcRn Tg line 32+/+ mouse, Jackson Laboratories; Methods Mol Biol. (2010) 602: 93-104). A mixture of hIgE(Asp6), anti-human IgE antibody and Sanglopor (the concentrations are shown in Table 31) was administered once at a dose of 10 mL/kg via the caudal vein. Under the conditions described above, hIgE(Asp6) is predicted to bind almost completely to the antibody since each antibody is present sufficiently in excess over hIgE(Asp6). Blood was collected from the mice five minutes, two hours, seven hours, one day, two days, four or five days, seven days, fourteen days, twenty-one days, and twenty-eight days after administration. The collected blood was immediately centrifuged at 15,000 rpm and 4 degrees C. for 5 minutes to obtain plasma. The separated plasma was stored in a freezer at −20 degrees C. or below until measurement.

TABLE 31

| Anti-hIgE antibody | hIgE(Asp6) concentration in administered solution (microgram/mL) | Anti-hIgE antibody concentration in administered solution (microgram/mL) | Sanglopor concentration in adminstered solution (mg/mL) |
|---|---|---|---|
| 278-F760 | 20 | 100 | 100 |
| 278-F1331 | 20 | 100 | 100 |

13-3. Determination of Plasma Anti-Human IgE Antibody Concentration in Human FcRn Transgenic Mice Anti-hIgE antibody concentrations in mouse plasma were determined by electrochemiluminescence (ECL) assay. Standard curve samples were prepared at plasma concentrations of 32, 16, 8, 4, 2, 1, 0.5, and 0.25 microgram/mL. The standard curve samples and mouse plasma assay samples were aliquoted into ECL plates immobilized with hIgE(Asp6). The plates were allowed to stand at 4 degrees C. overnight. Then, Anti Rabbit Antibody (Goat), SULFO-TAG Labeled (Meso Scale Discovery) was reacted at room temperature for one hour. Immediately after Read Buffer T (×4) (Meso Scale Discovery) was dispensed, the measurement was performed by the Sector Imager 2400 Reader (Meso Scale Discovery). The concentration in mouse plasma was calculated from the response of the standard curve using analysis software SOFTmax PRO (Molecular Devices). A time course of the plasma antibody concentration after intravenous administration, which was determined by the method described above, is shown in FIG. 137.

13-4. Determination of Plasma hIgE(Asp6) Concentration in Human FcRn Transgenic Mice hIgE(Asp6) concentrations in mouse plasma were determined by ELISA. Standard curve samples were prepared at plasma concentrations of 192, 96, 48, 24, 12, 6, and 3 ng/mL. Xolair (Novartis) was added at 10 microgram/mL to the standard curve samples and mouse plasma assay samples to equalize the immune complex of hIgE(Asp6) and anti-hIgE antibody. After 30 minutes of incubation at room temperature, the standard curve samples and mouse plasma assay samples were aliquoted into immunoplates (MABTECH) immobilized with anti-human IgE antibody or immunoplates (Nunc F96 MicroWell Plate (Nalge nunc International)) immobilized with anti-human IgE antibody (clone 107; MABTECH). The plates were allowed to stand at room temperature for two hours or at 4 degrees C. overnight. Then, human GPC3 core protein (SEQ ID NO: 26), anti-GPC3 antibody biotinylated with NHS-PEG4-Biotin (Thermo Fisher Scientific) (prepared in Chugai pharmaceutical Co., Ltd.), and Sterptavidin-PolyHRP80 (Stereospecific Detection Technologies) were reacted sequentially for one hour each. The chromogenic reaction using as a substrate TMB One Component HRP Microwell Substrate (BioFX Laboratories) was terminated with 1N sulfuric acid (Showa Chemical), and then the concentration in mouse plasma was determined by a method in which the color development is assessed by measuring the absorbance at 450 nm using a microplate reader or a method in which a luminescent reaction is carried out using SuperSignal® ELISA Pico Chemiluminescent Substrate (Thermo Fisher Scientific) as a substrate and the luminescence intensity is measured with a microplate reader. The concentration in mouse plasma was calculated from the absorbance or luminescence intensity of the standard curve using analysis software SOFTmax PRO (Molecular Devices). The time course of plasma hIgE(Asp6) concentration after intravenous administration, which was determined by the method described above, is shown in FIG. 138.

The result showed that the elimination of human IgE was significantly accelerated when human IgE was administered in combination with 278-F1331, which binds to human FcRn much stronger than 278-F760. Specifically, it was demonstrated that not only in the case of IL6R and IgA, but also in the case of IgE, a pH-dependent antigen binding antibody having increased binding activity to FcRn can accelerate antigen clearance from plasma and decrease concentration of antigen in plasma.

[Reference Example A1] Preparation of Soluble Human IL-6 Receptor (hsIL-6R)

Recombinant human IL-6 receptor as an antigen was prepared as follows. A cell line constitutively expressing soluble human IL-6 receptor (hereinafter referred to as hsIL-6R) having the amino acid sequence of positions 1 to 357 from the N terminus as reported in J. Immunol. 152: 4958-4968 (1994) was established by a method known to those skilled in the art. The cells were cultured to express hsIL-6R. The hsIL-6R was purified from the culture supernatant by two steps: Blue Sepharose 6 FF column chromatography and gel filtration chromatography. A fraction eluted as the main peak in the final stage was used as the final purification product.

[Reference Example A2] Preparation of Human FcRn

FcRn is a heterodimer of FcRn alpha chain and beta2-microglobulin. Oligo-DNA primers were prepared based on the published human FcRn gene sequence (J Exp Med. 1994 Dec. 1; 180(6): 2377-81). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the extracellular domain containing the signal region (Met1-Leu290) was amplified by PCR, and inserted into a mammalian cell expression vector. Likewise, oligo-DNA primers were prepared based on the published human beta2-microglobulin gene sequence (Proc. Natl. Acad. Sci. U.S.A. 99 (26): 16899-16903 (2002)). A DNA fragment encoding the whole gene was prepared by PCR using human cDNA (Human Placenta Marathon-Ready cDNA, Clontech) as a template and the prepared primers. Using the obtained DNA fragment as a template, a DNA fragment encoding the whole protein containing a signal region (Met1-Met119) was amplified by PCR and inserted into a mammalian cell expression vector.

Soluble human FcRn was expressed by the following procedure. The plasmids constructed for expressing human FcRn alpha chain (SEQ ID NO: 27) and beta2-microglobulin (SEQ ID NO: 28) were introduced into cells of the human embryonic kidney cancer-derived cell line HEK293H (Invitrogen) by the lipofection method using PEI (Polyscience). The resulting culture supernatant was collected, and FcRn was purified using IgG Sepharose 6 Fast Flow (Amersham Biosciences), followed by further purification using HiTrap Q HP (GE Healthcare) (J Immunol. 2002 Nov. 1; 169(9): 5171-80).

[Reference Example A3] Preparation of Human IgA (hIgA)

hIgA comprising H (WT)-IgA1 (SEQ ID NO: 12) and L (WT) (SEQ ID NO: 13) was expressed and purified by the method known to those skilled in the art using rProtein L-agarose (ACTIgen) followed by gel filtration chromatography.

[Reference Example A4] Preparation of Soluble Human Plexin A1 (hsPlexin A1)

Recombinant soluble human plexin A1 as an antigen (hereinafter referred to as hsPlexin A1) was prepared as follows. hsPlexin A1 was constructed by reference to NCBI Reference Sequence (NP_115618). Specially, hsPlexin A1 was comprised of the amino acid sequence of positions 27-1243 from the above-mentioned NCBI Reference FLAG-tag (DYKDDDDK, SEQ ID NO: 29) was connected to its C terminus. hsPlexin A1 was transiently expressed using FreeStyle293 (Invitrogen) and purified from the culture supernatant by two steps: anti-FLAG column chromatography and gel filtration chromatography. A fraction eluted as the main peak in the final stage was used as the final purification product.

INDUSTRIAL APPLICABILITY

When a conventional antibody targeting soluble antigen is administered to a subject, the antigen binds to the antibody and persists stably in plasma. Since an antigen bound to an antibody has a significantly longer half-life than an antigen alone, the antigen concentration increases after the injection of a conventional antibody to approximately 10 to 1000-folds of total plasma antigen concentration from the baseline. Such an increase of the total plasma antigen concentration is not preferable for a therapeutic antibody, because the antibody concentration (dosage) has to be 10 to 1000-fold higher than necessary compared to when no substantial increase in total plasma antigen concentration occurs. Therefore, an antibody which eliminates the antigen from plasma and also reduces the total plasma antigen concentration compared to a conventional antibody is extremely valuable since the required dosage would be 10 to 1000-fold lower than that required for a conventional antibody.

The present inventors conducted dedicated studies on modified FcRn-binding domains which have an enhanced affinity for FcRn at neutral pH and antigen-binding molecules comprising said FcRn-binding domain which have low immunogenicity, high stability and form only a few aggregates. As a result, it was discovered that substitutions at specific positions of the FcRn-binding domain increases the affinity for the FcRn at neutral pH without substantially increasing the immunogenicity and the ratio of high molecular weight species, and without substantially decreasing stability of antigen-binding molecules comprising the FcRn-binding domain. The antigen-binding molecules comprising the FcRn-binding domain of the present invention are superior in pharmacokinetics in facilitating the reduction of the plasma antigen concentration and meet the developability criteria of low immunogenicity, high stability and very few aggregates.

Furthermore, Fc-engineering to increase the binding affinity to FcRn at neutral or acidic pH can improve the endosomal recycling efficiency and the pharmacokinetics of the antibody. However, modifications of the amino acid sequence of an antibody (e.g. amino acid substitutions and insertions) can also increase the immunogenicity of the therapeutic antibody which, in turn, can result in a cytokine storm and/or production of anti-drug antibodies (ADA).

The present inventors conducted dedicated studies on antigen-binding molecules comprising a modified FcRn-binding domain whose binding activity for a pre-existing anti-drug antibody (ADA) was increased at neutral pH due to substitutions in the FcRn-binding domain that increased the affinity for FcRn at neutral pH or acidic pH. As a result, it was discovered that other substitutions at specific positions of the FcRn-binding domain decrease the binding activity for a pre-existing anti-drug antibody (ADA) at neutral pH while maintaining to a high extent the increased FcRn-binding activity in the respective pH ranges. The antigen-binding molecules of the present invention are superior in pharmacokinetics in facilitating the reduction of the plasma antigen concentration without increasing the antibody clearance.

[Sequence Listing]

The invention claimed is:

1. An antibody comprising a modified IgG1 Fc region,
wherein the amino acid at position EU438 of the modified Fc region is glutamic acid, arginine, serine, or lysine; and
wherein the amino acid at position EU440 of the modified Fc region is glutamic acid, aspartic acid, or glutamine.

2. The antibody of claim 1, wherein the modified Fc region comprises one of the following combinations of amino acid substitutions at the indicated positions:
EU438R/EU440E;
EU438R/EU440D;
EU438K/EU440E;
EU438K/EU440D.

3. The antibody of claim 1, wherein the modified Fc region comprises one of the following combinations of amino acid substitutions at the indicated positions:
EU252Y/EU434Y/EU436V/EU438K/EU440E;
EU252Y/EU434Y/EU436V/EU438R/EU440E;
EU252Y/EU434Y/EU436T/EU438K/EU440E;
EU252Y/EU434Y/EU436T/EU438R/EU440E;
EU252Y/EU434Y/EU436F/EU438K/EU440E;
EU252Y/EU434Y/EU436F/EU438R/EU440E;
EU252Y/EU434Y/EU436V/EU438R/EU440D;
EU252Y/EU434Y/EU436V/EU438K/EU440D;
EU252Y/EU433D/EU434Y/EU436V/EU438R/EU440D;
EU252Y/EU433D/EU434Y/EU436V/EU438K/EU440E;
EU252Y/EU433D/EU434Y/EU436V/EU438R/EU440E;
EU252Y/EU433D/EU434Y/EU436V/EU438K/EU440D;
EU252Y/EU254T/EU256E/EU307Q/EU311A/EU433D/EU434Y/EU436V/EU438K/EU440E;
EU252Y/EU254T/EU256E/EU308P/EU433D/EU434Y/EU436V/EU438K/EU440E;
EU252Y/EU433D/EU434W/EU436V/EU438R/EU440E;
EU252Y/EU433D/EU434W/EU436V/EU438K/EU440E;
EU252Y/EU254T/EU256E/EU433D/EU434Y/EU436V/EU438K/EU440E;
EU252Y/EU254T/EU256B/EU433D/EU434Y/EU436V/EU438R/EU440E;
EU252Y/EU254T/EU256E/EU433D/EU434Y/EU436V/EU438K/EU440D;
EU252Y/EU254T/EU256E/EU433D/EU434Y/EU436V/EU438R/EU440D;
EU252Y/EU254T/EU256E/EU286E/EU433D/EU434Y/EU436V/EU438K/EU440E;
EU252Y/EU254T/EU256E/EU286E/EU433D/EU434Y/EU436V/EU438R/EU440E;
EU252Y/EU254T/EU256E/EU286E/EU433D/EU434Y/EU436V/EU438K/EU440D;
EU252Y/EU254T/EU256E/EU286E/EU433D/EU434Y/EU436V/EU438R/EU440D;
EU252Y/EU254T/EU255L/EU256E/EU433D/EU434Y/EU436V/EU438K/EU440E;
EU252Y/EU254T/EU255L/EU256E/EU433D/EU434Y/EU436V/EU438R/EU440E;
EU252Y/EU254T/EU255L/EU256E/EU433D/EU434Y/EU436V/EU438K/EU440D;
EU252Y/EU254T/EU255L/EU256E/EU433D/EU434Y/EU436V/EU438R/EU440D;

EU252Y/EU254T/EU255L/EU256E/EU258D/EU433D/
EU434Y/EU436V/EU438R/EU440E;
EU252Y/EU254T/EU255L/EU256E/EU258I/EU433D/
EU434Y/EU436V/EU438R/EU440E;
EU252Y/EU254T/EU255L/EU256E/EU258D/EU433D/
EU434Y/EU436V/EU438K/EU440E;
EU252Y/EU254T/EU255L/EU256E/EU258I/EU433D/
EU434Y/EU436V/EU438K/EU440E;
EU252Y/EU254T/EU255L/EU256E/EU258D/EU433D/
EU434Y/EU436V/EU438K/EU440D;
EU252Y/EU254T/EU255L/EU256E/EU258I/EU433D/
EU434Y/EU436V/EU438K/EU440D;
EU252Y/EU254T/EU255L/EU256E/EU258D/EU433D/
EU434Y/EU436V/EU438R/EU440D;
EU252Y/EU254T/EU255L/EU256E/EU258I/EU433D/
EU434Y/EU436V/EU438R/EU440D;
EU252Y/EU254T/EU256E/EU433A/EU434Y/EU436V/
EU438R/EU440E;
EU252Y/EU254T/EU256E/EU433K/EU434Y/EU436V/
EU438R/EU440E;
EU252Y/EU254T/EU256E/EU433P/EU434Y/EU436V/
EU438R/EU440E;
EU252Y/EU254T/EU256E/EU433R/EU434Y/EU436V/
EU438R/EU440E;
EU252Y/EU254T/EU256E/EU433S/EU434Y/EU436V/
EU438R/EU440E;
EU252Y/EU254T/EU256E/EU433A/EU434Y/EU436V/
EU438K/EU440E;
EU252Y/EU254T/EU256E/EU433A/EU434Y/EU436V/
EU438R/EU440D;
EU252Y/EU254T/EU256E/EU433A/EU434Y/EU436V/
EU438K/EU440D;
EU252Y/EU254T/EU256E/EU433K/EU434Y/EU436V/
EU438K/EU440E;
EU252Y/EU254T/EU256E/EU433K/EU434Y/EU436V/
EU438R/EU440D;
EU252Y/EU254T/EU256E/EU433K/EU434Y/EU436V/
EU438K/EU440D;
EU252Y/EU254T/EU256E/EU433P/EU434Y/EU436V/
EU438K/EU440E;
EU252Y/EU254T/EU256E/EU433P/EU434Y/EU436V/
EU438R/EU440D;
EU252Y/EU254T/EU256E/EU433P/EU434Y/EU436V/
EU438K/EU440D;
EU252Y/EU254T/EU256E/EU433R/EU434Y/EU436V/
EU438K/EU440E;
EU252Y/EU254T/EU256E/EU433R/EU434Y/EU436V/
EU438R/EU440D;
EU252Y/EU254T/EU256E/EU433R/EU434Y/EU436V/
EU438K/EU440D;
EU252Y/EU254T/EU256E/EU433S/EU434Y/EU436V/
EU438K/EU440E;
EU252Y/EU254T/EU256E/EU433S/EU434Y/EU436V/
EU438R/EU440D;
EU252Y/EU254T/EU256E/EU433S/EU434Y/EU436V/
EU438K/EU440D;
EU235R/EU236R/EU239K/EU252Y/EU254T/EU434Y/
EU436V/EU438R/EU440E;
EU235R/EU236R/EU239K/EU252Y/EU254T/EU256E/
EU434Y/EU436V/EU438R/EU440E;
EU250V/EU252Y/EU307Q/EU308P/EU311A/EU434Y/
EU436V/EU438R/EU440E;
EU252Y/EU254T/EU256E/EU438R/EU440E;
EU428L/EU434S/EU438R/EU440E;
EU434H/EU438R/EU440E;
EU434Y/EU436V/EU438R/EU440E;
EU434Y/EU436V/EU438R/EU440D;
EU434Y/EU436V/EU438K/EU440E;
EU434Y/EU436V/EU438K/EU440D;
EU433D/EU434Y/EU436V/EU438R/EU440E;
EU433D/EU434Y/EU436V/EU438R/EU440D;
EU433D/EU434Y/EU436V/EU438K/EU440E;
EU433D/EU434Y/EU436V/EU438K/EU440D;
EU434Y/EU436T/EU438R/EU440E;
EU434Y/EU436T/EU438R/EU440D;
EU434Y/EU436T/EU438K/EU440E;
EU434Y/EU436T/EU438K/EU440D;
EU433D/EU434Y/EU436T/EU438R/EU440E;
EU433D/EU434Y/EU436T/EU438R/EU440D;
EU433D/EU434Y/EU436T/EU438K/EU440E;
EU433D/EU434Y/EU436T/EU438K/EU440D;
EU235R/EU239K/EU252Y/EU434Y/EU436V/EU438K/
EU440E;
EU235R/EU239K/EU252Y/EU434Y/EU436V/EU438R/
EU440E;
EU235R/EU239K/EU252Y/EU434Y/EU436T/EU438K/
EU440E;
EU235R/EU239K/EU252Y/EU434Y/EU436T/EU438R/
EU440E;
EU235R/EU239K/EU252Y/EU434Y/EU436F/EU438K/
EU440E;
EU235R/EU239K/EU252Y/EU434Y/EU436F/EU438R/
EU440E;
EU235R/EU239K/EU252Y/EU434Y/EU436V/EU438R/
EU440D;
EU235R/EU239K/EU252Y/EU434Y/EU436V/EU438K/
EU440D;
EU235R/EU239K/EU252Y/EU433D/EU434Y/EU436V/
EU438R/EU440D;
EU235R/EU239K/EU252Y/EU433D/EU434Y/EU436V/
EU438K/EU440E;
EU235R/EU239K/EU252Y/EU433D/EU434Y/EU436V/
EU438R/EU440E;
EU235R/EU239K/EU252Y/EU433D/EU434Y/EU436V/
EU438K/EU440D;
EU235R/EU239K/EU252Y/EU254T/EU256E/EU307Q/
EU311A/EU433D/EU434Y/EU436V/EU438K/
EU440E;
EU235R/EU239K/EU252Y/EU254T/EU256E/EU308P/
EU433D/EU434Y/EU436V/EU438K/EU440E;
EU235R/EU239K/EU252Y/EU433D/EU434W/
EU436V/EU438R/EU440E;
EU235R/EU239K/EU252Y/EU433D/EU434W/
EU436V/EU438K/EU440E;
EU235R/EU239K/EU252Y/EU254T/EU256E/EU433D/
EU434Y/EU436V/EU438K/EU440E;
EU235R/EU239K/EU252Y/EU254T/EU256E/EU433D/
EU434Y/EU436V/EU438R/EU440E;
EU235R/EU239K/EU252Y/EU254T/EU256E/EU433D/
EU434Y/EU436V/EU438K/EU440D;
EU235R/EU239K/EU252Y/EU254T/EU256E/EU433D/
EU434Y/EU436V/EU438R/EU440D;
EU235R/EU239K/EU252Y/EU254T/EU256E/EU286E/
EU433D/EU434Y/EU436V/EU438K/EU440E;
EU235R/EU239K/EU252Y/EU254T/EU256E/EU286E/
EU433D/EU434Y/EU436V/EU438R/EU440E;
EU235R/EU239K/EU252Y/EU254T/EU256E/EU286E/
EU433D/EU434Y/EU436V/EU438K/EU440D;
EU235R/EU239K/EU252Y/EU254T/EU256E/EU286E/
EU433D/EU434Y/EU436V/EU438R/EU440D;
EU235R/EU239K/EU252Y/EU254T/EU255L/EU256E/
EU433D/EU434Y/EU436V/EU438K/EU440E;
EU235R/EU239K/EU252Y/EU254T/EU255L/EU256E/
EU433D/EU434Y/EU436V/EU438R/EU440E;

EU235R/EU239K/EU252Y/EU254T/EU255L/EU256E/
EU433D/EU434Y/EU436V/EU438K/EU440D;
EU235R/EU239K/EU252Y/EU254T/EU255L/EU256E/
EU433D/EU434Y/EU436V/EU438R/EU440D;
EU235R/EU239K/EU252Y/EU254T/EU255L/EU256E/
EU258D/EU433D/EU434Y/EU436V/EU438R/
EU440E;
EU235R/EU239K/EU252Y/EU254T/EU255L/EU256E/
EU258I/EU433D/EU434Y/EU436V/EU438R/
EU440E;
EU235R/EU239K/EU252Y/EU254T/EU255L/EU256E/
EU258D/EU433D/EU434Y/EU436V/EU438K/
EU440E;
EU235R/EU239K/EU252Y/EU254T/EU255L/EU256E/
EU258I/EU433D/EU434Y/EU436V/EU438K/
EU440E;
EU235R/EU239K/EU252Y/EU254T/EU255L/EU256E/
EU258D/EU433D/EU434Y/EU436V/EU438K/
EU440D;
EU235R/EU239K/EU252Y/EU254T/EU255L/EU256E/
EU258I/EU433D/EU434Y/EU436V/EU438K/
EU440D;
EU235R/EU239K/EU252Y/EU254T/EU255L/EU256E/
EU258D/EU433D/EU434Y/EU436V/EU438R/
EU440D;
EU235R/EU239K/EU252Y/EU254T/EU255L/EU256E/
EU258I/EU433D/EU434Y/EU436V/EU438R/
EU440D;
EU235R/EU239K/EU252Y/EU254T/EU256E/EU433A/
EU434Y/EU436V/EU438R/EU440E;
EU235R/EU239K/EU252Y/EU254T/EU256E/EU433K/
EU434Y/EU436V/EU438R/EU440E;
EU235R/EU239K/EU252Y/EU254T/EU256E/EU433P/
EU434Y/EU436V/EU438R/EU440E;
EU235R/EU239K/EU252Y/EU254T/EU256E/EU433R/
EU434Y/EU436V/EU438R/EU440E;
EU235R/EU239K/EU252Y/EU254T/EU256E/EU433S/
EU434Y/EU436V/EU438R/EU440E;
EU235R/EU239K/EU252Y/EU254T/EU256E/EU433A/
EU434Y/EU436V/EU438K/EU440E;
EU235R/EU239K/EU252Y/EU254T/EU256E/EU433A/
EU434Y/EU436V/EU438R/EU440D;
EU235R/EU239K/EU252Y/EU254T/EU256E/EU433A/
EU434Y/EU436V/EU438K/EU440D;
EU235R/EU239K/EU252Y/EU254T/EU256E/EU433K/
EU434Y/EU436V/EU438K/EU440E;
EU235R/EU239K/EU252Y/EU254T/EU256E/EU433K/
EU434Y/EU436V/EU438R/EU440D;
EU235R/EU239K/EU252Y/EU254T/EU256E/EU433K/
EU434Y/EU436V/EU438K/EU440D;
EU235R/EU239K/EU252Y/EU254T/EU256E/EU433P/
EU434Y/EU436V/EU438K/EU440E;
EU235R/EU239K/EU252Y/EU254T/EU256E/EU433P/
EU434Y/EU436V/EU438R/EU440D;
EU235R/EU239K/EU252Y/EU254T/EU256E/EU433P/
EU434Y/EU436V/EU438K/EU440D;
EU235R/EU239K/EU252Y/EU254T/EU256E/EU433R/
EU434Y/EU436V/EU438K/EU440E;
EU235R/EU239K/EU252Y/EU254T/EU256E/EU433R/
EU434Y/EU436V/EU438R/EU440D;
EU235R/EU239K/EU252Y/EU254T/EU256E/EU433R/
EU434Y/EU436V/EU438K/EU440D;
EU235R/EU239K/EU252Y/EU254T/EU256E/EU433S/
EU434Y/EU436V/EU438K/EU440E;
EU235R/EU239K/EU252Y/EU254T/EU256E/EU433S/
EU434Y/EU436V/EU438R/EU440D;
EU235R/EU239K/EU252Y/EU254T/EU256E/EU433S/
EU434Y/EU436V/EU438K/EU440D;
EU235R/EU236R/EU239K/EU252Y/EU254T/EU434Y/
EU436V/EU438R/EU440E;
EU235R/EU236R/EU239K/EU252Y/EU254T/EU256E/
EU434Y/EU436V/EU438R/EU440E;
EU235R/EU239K/EU252Y/EU254T/EU434Y/EU436V/
EU438K/EU440E;
EU235R/EU239K/EU252Y/EU254T/EU256E/EU434Y/
EU436V/EU438K/EU440E;
EU235R/EU239K/EU252Y/EU254T/EU434Y/EU436V/
EU438R/EU440E;
EU235R/EU239K/EU252Y/EU254T/EU256E/EU434Y/
EU436V/EU438R/EU440E;
EU235R/EU239K/EU252Y/EU254T/EU433D/EU434Y/
EU436V/EU438R/EU440E;
EU235R/EU239K/EU434Y/EU436V/EU438R/EU440E;
EU235R/EU239K/EU434Y/EU436V/EU438R/EU440D;
EU235R/EU239K/EU434Y/EU436V/EU438K/EU440E;
EU235R/EU239K/EU434Y/EU436V/EU438K/EU440D;
EU235R/EU239K/EU433D/EU434Y/EU436V/EU438R/
EU440E;
EU235R/EU239K/EU433D/EU434Y/EU436V/EU438R/
EU440D;
EU235R/EU239K/EU433D/EU434Y/EU436V/EU438K/
EU440E;
EU235R/EU239K/EU433D/EU434Y/EU436V/EU438K/
EU440D;
EU235R/EU239K/EU434Y/EU436T/EU438R/EU440E;
EU235R/EU239K/EU434Y/EU436T/EU438R/EU440D;
EU235R/EU239K/EU434Y/EU436T/EU438K/EU440E;
EU235R/EU239K/EU434Y/EU436T/EU438K/EU440D;
EU235R/EU239K/EU433D/EU434Y/EU436T/EU438R/
EU440E;
EU235R/EU239K/EU433D/EU434Y/EU436T/EU438R/
EU440D;
EU235R/EU239K/EU433D/EU434Y/EU436T/EU438K/
EU440E;
EU235R/EU239K/EU433D/EU434Y/EU436T/EU438K/
EU440D;
EU235R/EU239K/EU434Y/EU436F/EU438R/EU440E;
EU235R/EU239K/EU434Y/EU438R/EU440E.

4. The antibody of claim 1, wherein the modified Fc region further comprises at least one additional amino acid substitution compared to a native human IgG1 Fc region, wherein the at least one additional amino acid substitution comprises a substitution at one or more of the following positions (EU numbering): 238, 250, 252, 254, 255, 256, 258, 286, 307, 308, 309, 311, 315, 428, 434, and 436.

5. The antibody of claim 1, wherein the modified Fc region further comprises at least one additional amino acid substitution compared to a native human IgG1 Fc region, wherein the at least one additional amino acid substitution comprises substitution(s) at any one of the following sets of positions (EU numbering):
   (a) position 434,
   (b) positions 252, 254, and 256,
   (c) positions 428 and 434,
   (d) positions 250 and 428.

6. The antibody of claim 5, wherein the at least one additional amino acid substitution includes any one of the following sets of substitutions at the indicated position(s) (EU numbering):
   (a) histidine at position 434,
   (b) tyrosine at position 252, threonine at position 254, and glutamic acid at position 256,
   (c) leucine at position 428 and serine at position 434, or
   (d) glutamine at position 250 and leucine at position 428.

7. The antibody of claim 1, wherein the modified Fc region comprises at least one additional amino acid substitution compared to a native human IgG1 Fc region, wherein the at least one additional amino acid substitution comprises any one of the combinations of substitutions listed in Table 9 (all positions by EU numbering).

8. A composition comprising the antibody of claim 1, wherein at least 98% of the antibody molecules in the composition are in the form of antibody monomers containing two heavy chains and two light chains.

9. A pharmaceutical composition comprising the antibody of claim 1 and a pharmaceutically acceptable carrier.

10. An antibody comprising a modified IgG2 Fc region, wherein the amino acid at position EU438 of the modified Fc region is glutamic acid, arginine, serine, or lysine; and
wherein the amino acid at position EU440 of the modified Fc region is glutamic acid, aspartic acid, or glutamine.

11. The antibody of claim 10, wherein the modified Fc region comprises one of the following combinations of amino acid substitutions at the indicated positions:
EU438R/EU440E;
EU438R/EU440D;
EU438K/EU440E;
EU438K/EU440D.

12. A composition comprising the antibody of claim 10, wherein at least 98% of the antibody molecules in the composition are in the form of antibody monomers containing two heavy chains and two light chains.

13. A pharmaceutical composition comprising the antibody of claim 10 and a pharmaceutically acceptable carrier.

14. The antibody of claim 10, wherein the modified Fc region comprises one of the following combinations of amino acid substitutions at the indicated positions:
EU252Y/EU434Y/EU436V/EU438K/EU440E;
EU252Y/EU434Y/EU436V/EU438R/EU440E;
EU252Y/EU434Y/EU436T/EU438K/EU440E;
EU252Y/EU434Y/EU436T/EU438R/EU440E;
EU252Y/EU434Y/EU436F/EU438K/EU440E;
EU252Y/EU434Y/EU436F/EU438R/EU440E;
EU252Y/EU434Y/EU436V/EU438R/EU440D;
EU252Y/EU434Y/EU436V/EU438K/EU440D;
EU252Y/EU433D/EU434Y/EU436V/EU438R/EU440D;
EU252Y/EU433D/EU434Y/EU436V/EU438K/EU440E;
EU252Y/EU433D/EU434Y/EU436V/EU438R/EU440E;
EU252Y/EU433D/EU434Y/EU436V/EU438K/EU440D;
EU252Y/EU254T/EU256E/EU307Q/EU311A/EU433D/EU434Y/EU436V/EU438K/EU440E;
EU252Y/EU254T/EU256E/EU308P/EU433D/EU434Y/EU436V/EU438K/EU440E;
EU252Y/EU433D/EU434W/EU436V/EU438R/EU440E;
EU252Y/EU433D/EU434W/EU436V/EU438K/EU440E;
EU252Y/EU254T/EU256E/EU433D/EU434Y/EU436V/EU438K/EU440E;
EU252Y/EU254T/EU256B/EU433D/EU434Y/EU436V/EU438R/EU440E;
EU252Y/EU254T/EU256E/EU433D/EU434Y/EU436V/EU438K/EU440D;
EU252Y/EU254T/EU256E/EU433D/EU434Y/EU436V/EU438R/EU440D;
EU252Y/EU254T/EU256E/EU286E/EU433D/EU434Y/EU436V/EU438K/EU440E;
EU252Y/EU254T/EU256E/EU286E/EU433D/EU434Y/EU436V/EU438R/EU440E;
EU252Y/EU254T/EU256E/EU286E/EU433D/EU434Y/EU436V/EU438K/EU440D;
EU252Y/EU254T/EU256E/EU286E/EU433D/EU434Y/EU436V/EU438R/EU440D;
EU252Y/EU254T/EU255L/EU256E/EU433D/EU434Y/EU436V/EU438K/EU440E;
EU252Y/EU254T/EU255L/EU256E/EU433D/EU434Y/EU436V/EU438R/EU440E;
EU252Y/EU254T/EU255L/EU256E/EU433D/EU434Y/EU436V/EU438K/EU440D;
EU252Y/EU254T/EU255L/EU256E/EU433D/EU434Y/EU436V/EU438R/EU440D;
EU252Y/EU254T/EU255L/EU256E/EU258D/EU433D/EU434Y/EU436V/EU438R/EU440E;
EU252Y/EU254T/EU255L/EU256E/EU258I/EU433D/EU434Y/EU436V/EU438R/EU440E;
EU252Y/EU254T/EU255L/EU256E/EU258D/EU433D/EU434Y/EU436V/EU438K/EU440E;
EU252Y/EU254T/EU255L/EU256E/EU258I/EU433D/EU434Y/EU436V/EU438K/EU440E;
EU252Y/EU254T/EU255L/EU256E/EU258D/EU433D/EU434Y/EU436V/EU438K/EU440D;
EU252Y/EU254T/EU255L/EU256E/EU258I/EU433D/EU434Y/EU436V/EU438K/EU440D;
EU252Y/EU254T/EU255L/EU256E/EU258D/EU433D/EU434Y/EU436V/EU438R/EU440D;
EU252Y/EU254T/EU255L/EU256E/EU258I/EU433D/EU434Y/EU436V/EU438R/EU440D;
EU252Y/EU254T/EU256E/EU433A/EU434Y/EU436V/EU438R/EU440E;
EU252Y/EU254T/EU256E/EU433K/EU434Y/EU436V/EU438R/EU440E;
EU252Y/EU254T/EU256E/EU433P/EU434Y/EU436V/EU438R/EU440E;
EU252Y/EU254T/EU256E/EU433R/EU434Y/EU436V/EU438R/EU440E;
EU252Y/EU254T/EU256E/EU433S/EU434Y/EU436V/EU438R/EU440E;
EU252Y/EU254T/EU256E/EU433A/EU434Y/EU436V/EU438K/EU440E;
EU252Y/EU254T/EU256E/EU433A/EU434Y/EU436V/EU438R/EU440D;
EU252Y/EU254T/EU256E/EU433A/EU434Y/EU436V/EU438K/EU440D;
EU252Y/EU254T/EU256E/EU433K/EU434Y/EU436V/EU438K/EU440E;
EU252Y/EU254T/EU256E/EU433K/EU434Y/EU436V/EU438R/EU440D;
EU252Y/EU254T/EU256E/EU433K/EU434Y/EU436V/EU438K/EU440D;
EU252Y/EU254T/EU256E/EU433P/EU434Y/EU436V/EU438K/EU440E;
EU252Y/EU254T/EU256E/EU433P/EU434Y/EU436V/EU438R/EU440D;
EU252Y/EU254T/EU256E/EU433P/EU434Y/EU436V/EU438K/EU440D;
EU252Y/EU254T/EU256E/EU433R/EU434Y/EU436V/EU438K/EU440E;
EU252Y/EU254T/EU256E/EU433R/EU434Y/EU436V/EU438R/EU440D;
EU252Y/EU254T/EU256E/EU433R/EU434Y/EU436V/EU438K/EU440D;
EU252Y/EU254T/EU256E/EU433S/EU434Y/EU436V/EU438K/EU440E;
EU252Y/EU254T/EU256E/EU433S/EU434Y/EU436V/EU438R/EU440D;

EU252Y/EU254T/EU256E/EU433S/EU434Y/EU436V/
EU438K/EU440D;
EU235R/EU236R/EU239K/EU252Y/EU254T/EU434Y/
EU436V/EU438R/EU440E;
EU235R/EU236R/EU239K/EU252Y/EU254T/EU256E/
EU434Y/EU436V/EU438R/EU440E;
EU250V/EU252Y/EU307Q/EU308P/EU311A/EU434Y/
EU436V/EU438R/EU440E;
EU252Y/EU254T/EU256E/EU438R/EU440E;
EU428L/EU434S/EU438R/EU440E;
EU434H/EU438R/EU440E;
EU434Y/EU436V/EU438R/EU440E;
EU434Y/EU436V/EU438R/EU440D;
EU434Y/EU436V/EU438K/EU440E;
EU434Y/EU436V/EU438K/EU440D;
EU433D/EU434Y/EU436V/EU438R/EU440E;
EU433D/EU434Y/EU436V/EU438R/EU440D;
EU433D/EU434Y/EU436V/EU438K/EU440E;
EU433D/EU434Y/EU436V/EU438K/EU440D;
EU434Y/EU436T/EU438R/EU440E;
EU434Y/EU436T/EU438R/EU440D;
EU434Y/EU436T/EU438K/EU440E;
EU434Y/EU436T/EU438K/EU440D;
EU433D/EU434Y/EU436T/EU438R/EU440E;
EU433D/EU434Y/EU436T/EU438R/EU440D;
EU433D/EU434Y/EU436T/EU438K/EU440E;
EU433D/EU434Y/EU436T/EU438K/EU440D;
EU235R/EU239K/EU252Y/EU434Y/EU436V/EU438K/
EU440E;
EU235R/EU239K/EU252Y/EU434Y/EU436V/EU438R/
EU440E;
EU235R/EU239K/EU252Y/EU434Y/EU436T/EU438K/
EU440E;
EU235R/EU239K/EU252Y/EU434Y/EU436T/EU438R/
EU440E;
EU235R/EU239K/EU252Y/EU434Y/EU436F/EU438K/
EU440E;
EU235R/EU239K/EU252Y/EU434Y/EU436F/EU438R/
EU440E;
EU235R/EU239K/EU252Y/EU434Y/EU436V/EU438R/
EU440D;
EU235R/EU239K/EU252Y/EU434Y/EU436V/EU438K/
EU440D;
EU235R/EU239K/EU252Y/EU433D/EU434Y/EU436V/
EU438R/EU440D;
EU235R/EU239K/EU252Y/EU433D/EU434Y/EU436V/
EU438K/EU440E;
EU235R/EU239K/EU252Y/EU433D/EU434Y/EU436V/
EU438R/EU440E;
EU235R/EU239K/EU252Y/EU433D/EU434Y/EU436V/
EU438K/EU440D;
EU235R/EU239K/EU252Y/EU254T/EU256E/EU307Q/
EU311A/EU433D/EU434Y/EU436V/EU438K/
EU440E;
EU235R/EU239K/EU252Y/EU254T/EU256E/EU308P/
EU433D/EU434Y/EU436V/EU438K/EU440E;
EU235R/EU239K/EU252Y/EU433D/EU434W/
EU436V/EU438R/EU440E;
EU235R/EU239K/EU252Y/EU433D/EU434W/
EU436V/EU438K/EU440E;
EU235R/EU239K/EU252Y/EU254T/EU256E/EU433D/
EU434Y/EU436V/EU438K/EU440E;
EU235R/EU239K/EU252Y/EU254T/EU256E/EU433D/
EU434Y/EU436V/EU438R/EU440E;
EU235R/EU239K/EU252Y/EU254T/EU256E/EU433D/
EU434Y/EU436V/EU438K/EU440D;
EU235R/EU239K/EU252Y/EU254T/EU256E/EU433D/
EU434Y/EU436V/EU438R/EU440D;
EU235R/EU239K/EU252Y/EU254T/EU256E/EU286E/
EU433D/EU434Y/EU436V/EU438K/EU440E;
EU235R/EU239K/EU252Y/EU254T/EU256E/EU286E/
EU433D/EU434Y/EU436V/EU438R/EU440E;
EU235R/EU239K/EU252Y/EU254T/EU256E/EU286E/
EU433D/EU434Y/EU436V/EU438K/EU440D;
EU235R/EU239K/EU252Y/EU254T/EU256E/EU286E/
EU433D/EU434Y/EU436V/EU438R/EU440D;
EU235R/EU239K/EU252Y/EU254T/EU255L/EU256E/
EU433D/EU434Y/EU436V/EU438K/EU440E;
EU235R/EU239K/EU252Y/EU254T/EU255L/EU256E/
EU433D/EU434Y/EU436V/EU438R/EU440E;
EU235R/EU239K/EU252Y/EU254T/EU255L/EU256E/
EU433D/EU434Y/EU436V/EU438K/EU440D;
EU235R/EU239K/EU252Y/EU254T/EU255L/EU256E/
EU433D/EU434Y/EU436V/EU438R/EU440D;
EU235R/EU239K/EU252Y/EU254T/EU255L/EU256E/
EU258D/EU433D/EU434Y/EU436V/EU438R/
EU440E;
EU235R/EU239K/EU252Y/EU254T/EU255L/EU256E/
EU258I/EU433D/EU434Y/EU436V/EU438R/
EU440E;
EU235R/EU239K/EU252Y/EU254T/EU255L/EU256E/
EU258D/EU433D/EU434Y/EU436V/EU438K/
EU440E;
EU235R/EU239K/EU252Y/EU254T/EU255L/EU256E/
EU258I/EU433D/EU434Y/EU436V/EU438K/
EU440E;
EU235R/EU239K/EU252Y/EU254T/EU255L/EU256E/
EU258D/EU433D/EU434Y/EU436V/EU438K/
EU440D;
EU235R/EU239K/EU252Y/EU254T/EU255L/EU256E/
EU258I/EU433D/EU434Y/EU436V/EU438K/
EU440D;
EU235R/EU239K/EU252Y/EU254T/EU255L/EU256E/
EU258D/EU433D/EU434Y/EU436V/EU438R/
EU440D;
EU235R/EU239K/EU252Y/EU254T/EU255L/EU256E/
EU258I/EU433D/EU434Y/EU436V/EU438R/
EU440D;
EU235R/EU239K/EU252Y/EU254T/EU256E/EU433A/
EU434Y/EU436V/EU438R/EU440E;
EU235R/EU239K/EU252Y/EU254T/EU256E/EU433K/
EU434Y/EU436V/EU438R/EU440E;
EU235R/EU239K/EU252Y/EU254T/EU256E/EU433P/
EU434Y/EU436V/EU438R/EU440E;
EU235R/EU239K/EU252Y/EU254T/EU256E/EU433R/
EU434Y/EU436V/EU438R/EU440E;
EU235R/EU239K/EU252Y/EU254T/EU256E/EU433S/
EU434Y/EU436V/EU438R/EU440E;
EU235R/EU239K/EU252Y/EU254T/EU256E/EU433A/
EU434Y/EU436V/EU438K/EU440E;
EU235R/EU239K/EU252Y/EU254T/EU256E/EU433A/
EU434Y/EU436V/EU438R/EU440D;
EU235R/EU239K/EU252Y/EU254T/EU256E/EU433A/
EU434Y/EU436V/EU438K/EU440D;
EU235R/EU239K/EU252Y/EU254T/EU256E/EU433K/
EU434Y/EU436V/EU438K/EU440E;
EU235R/EU239K/EU252Y/EU254T/EU256E/EU433K/
EU434Y/EU436V/EU438R/EU440D;
EU235R/EU239K/EU252Y/EU254T/EU256E/EU433K/
EU434Y/EU436V/EU438K/EU440D;
EU235R/EU239K/EU252Y/EU254T/EU256E/EU433P/
EU434Y/EU436V/EU438K/EU440E;

EU235R/EU239K/EU252Y/EU254T/EU256E/EU433P/
    EU434Y/EU436V/EU438R/EU440D;
EU235R/EU239K/EU252Y/EU254T/EU256E/EU433P/
    EU434Y/EU436V/EU438K/EU440D;
EU235R/EU239K/EU252Y/EU254T/EU256E/EU433R/
    EU434Y/EU436V/EU438K/EU440E;
EU235R/EU239K/EU252Y/EU254T/EU256E/EU433R/
    EU434Y/EU436V/EU438R/EU440D;
EU235R/EU239K/EU252Y/EU254T/EU256E/EU433R/
    EU434Y/EU436V/EU438K/EU440D;
EU235R/EU239K/EU252Y/EU254T/EU256E/EU433S/
    EU434Y/EU436V/EU438K/EU440E;
EU235R/EU239K/EU252Y/EU254T/EU256E/EU433S/
    EU434Y/EU436V/EU438R/EU440D;
EU235R/EU239K/EU252Y/EU254T/EU256E/EU433S/
    EU434Y/EU436V/EU438K/EU440D;
EU235R/EU236R/EU239K/EU252Y/EU254T/EU434Y/
    EU436V/EU438R/EU440E;
EU235R/EU236R/EU239K/EU252Y/EU254T/EU256E/
    EU434Y/EU436V/EU438R/EU440E;
EU235R/EU239K/EU252Y/EU254T/EU434Y/EU436V/
    EU438K/EU440E;
EU235R/EU239K/EU252Y/EU254T/EU256E/EU434Y/
    EU436V/EU438K/EU440E;
EU235R/EU239K/EU252Y/EU254T/EU434Y/EU436V/
    EU438R/EU440E;
EU235R/EU239K/EU252Y/EU254T/EU256E/EU434Y/
    EU436V/EU438R/EU440E;
EU235R/EU239K/EU252Y/EU254T/EU433D/EU434Y/
    EU436V/EU438R/EU440E;
EU235R/EU239K/EU434Y/EU436V/EU438R/EU440E;
EU235R/EU239K/EU434Y/EU436V/EU438R/EU440D;
EU235R/EU239K/EU434Y/EU436V/EU438K/EU440E;
EU235R/EU239K/EU434Y/EU436V/EU438K/EU440D;
EU235R/EU239K/EU433D/EU434Y/EU436V/EU438R/
    EU440E;
EU235R/EU239K/EU433D/EU434Y/EU436V/EU438R/
    EU440D;
EU235R/EU239K/EU433D/EU434Y/EU436V/EU438K/
    EU440E;
EU235R/EU239K/EU433D/EU434Y/EU436V/EU438K/
    EU440D;
EU235R/EU239K/EU434Y/EU436T/EU438R/EU440E;
EU235R/EU239K/EU434Y/EU436T/EU438R/EU440D;
EU235R/EU239K/EU434Y/EU436T/EU438K/EU440E;
EU235R/EU239K/EU434Y/EU436T/EU438K/EU440D;
EU235R/EU239K/EU433D/EU434Y/EU436T/EU438R/
    EU440E;
EU235R/EU239K/EU433D/EU434Y/EU436T/EU438R/
    EU440D;
EU235R/EU239K/EU433D/EU434Y/EU436T/EU438K/
    EU440E;
EU235R/EU239K/EU433D/EU434Y/EU436T/EU438K/
    EU440D;
EU235R/EU239K/EU434Y/EU436F/EU438R/EU440E;
EU235R/EU239K/EU434Y/EU438R/EU440E.

15. The antibody of claim 10, wherein the modified Fc region further comprises at least one additional amino acid substitution compared to a native human IgG2 Fc region, wherein the at least one additional amino acid substitution comprises a substitution at one or more of the following positions (EU numbering): 238, 250, 252, 254, 255, 256, 258, 286, 307, 308, 309, 311, 315, 428, 434, and 436.

16. The antibody of claim 10, wherein the modified Fc region further comprises at least one additional amino acid substitution compared to a native human IgG2 Fc region, wherein the at least one additional amino acid substitution comprises substitution(s) at any one of the following sets of positions (EU numbering):
    (a) position 434,
    (b) positions 252, 254, and 256,
    (c) positions 428 and 434,
    (d) positions 250 and 428.

17. The antibody of claim 16, wherein the at least one additional amino acid substitution includes any one of the following sets of substitutions at the indicated position(s) (EU numbering):
    (a) histidine at position 434,
    (b) tyrosine at position 252, threonine at position 254, and glutamic acid at position 256,
    (c) leucine at position 428 and serine at position 434, or
    (d) glutamine at position 250 and leucine at position 428.

18. The antibody of claim 10, wherein the modified Fc region comprises at least one additional amino acid substitution compared to a native human IgG2 Fc region, wherein the at least one additional amino acid substitution comprises any one of the combinations of substitutions listed in Table 9 (all positions by EU numbering).

19. An antibody comprising a modified IgG3 Fc region, wherein the amino acid at position EU438 of the modified Fc region is glutamic acid, arginine, serine, or lysine; and
    wherein the amino acid at position EU440 of the modified Fc region is glutamic acid, aspartic acid, or glutamine.

20. The antibody of claim 19, wherein the modified Fc region comprises one of the following combinations of amino acid substitutions at the indicated positions:
    EU438R/EU440E;
    EU438R/EU440D;
    EU438K/EU440E;
    EU438K/EU440D.

21. A composition comprising the antibody of claim 19, wherein at least 98% of the antibody molecules in the composition are in the form of antibody monomers containing two heavy chains and two light chains.

22. A pharmaceutical composition comprising the antibody of claim 19 and a pharmaceutically acceptable carrier.

23. The antibody of claim 19, wherein the modified Fc region comprises one of the following combinations of amino acid substitutions at the indicated positions:
    EU252Y/EU434Y/EU436V/EU438K/EU440E;
    EU252Y/EU434Y/EU436V/EU438R/EU440E;
    EU252Y/EU434Y/EU436T/EU438K/EU440E;
    EU252Y/EU434Y/EU436T/EU438R/EU440E;
    EU252Y/EU434Y/EU436F/EU438K/EU440E;
    EU252Y/EU434Y/EU436F/EU438R/EU440E;
    EU252Y/EU434Y/EU436V/EU438R/EU440D;
    EU252Y/EU434Y/EU436V/EU438K/EU440D;
    EU252Y/EU433D/EU434Y/EU436V/EU438R/EU440D;
    EU252Y/EU433D/EU434Y/EU436V/EU438K/EU440E;
    EU252Y/EU433D/EU434Y/EU436V/EU438R/EU440E;
    EU252Y/EU433D/EU434Y/EU436V/EU438K/EU440D;
    EU252Y/EU254T/EU256E/EU307Q/EU311A/EU433D/
        EU434Y/EU436V/EU438K/EU440E;
    EU252Y/EU254T/EU256E/EU308P/EU433D/EU434Y/
        EU436V/EU438K/EU440E;
    EU252Y/EU433D/EU434W/EU436V/EU438R/
        EU440E;
    EU252Y/EU433D/EU434W/EU436V/EU438K/
        EU440E;
    EU252Y/EU254T/EU256E/EU433D/EU434Y/EU436V/
        EU438K/EU440E;

EU252Y/EU254T/EU256B/EU433D/EU434Y/EU436V/
EU438R/EU440E;
EU252Y/EU254T/EU256E/EU433D/EU434Y/EU436V/
EU438K/EU440D;
EU252Y/EU254T/EU256E/EU433D/EU434Y/EU436V/
EU438R/EU440D;
EU252Y/EU254T/EU256E/EU286E/EU433D/EU434Y/
EU436V/EU438K/EU440E;
EU252Y/EU254T/EU256E/EU286E/EU433D/EU434Y/
EU436V/EU438R/EU440E;
EU252Y/EU254T/EU256E/EU286E/EU433D/EU434Y/
EU436V/EU438K/EU440D;
EU252Y/EU254T/EU256E/EU286E/EU433D/EU434Y/
EU436V/EU438R/EU440D;
EU252Y/EU254T/EU255L/EU256E/EU433D/EU434Y/
EU436V/EU438K/EU440E;
EU252Y/EU254T/EU255L/EU256E/EU433D/EU434Y/
EU436V/EU438R/EU440E;
EU252Y/EU254T/EU255L/EU256E/EU433D/EU434Y/
EU436V/EU438K/EU440D;
EU252Y/EU254T/EU255L/EU256E/EU433D/EU434Y/
EU436V/EU438R/EU440E;
EU252Y/EU254T/EU255L/EU256E/EU258D/EU433D/
EU434Y/EU436V/EU438R/EU440E;
EU252Y/EU254T/EU255L/EU256E/EU258I/EU433D/
EU434Y/EU436V/EU438R/EU440E;
EU252Y/EU254T/EU255L/EU256E/EU258D/EU433D/
EU434Y/EU436V/EU438K/EU440E;
EU252Y/EU254T/EU255L/EU256E/EU258I/EU433D/
EU434Y/EU436V/EU438K/EU440E;
EU252Y/EU254T/EU255L/EU256E/EU258D/EU433D/
EU434Y/EU436V/EU438K/EU440D;
EU252Y/EU254T/EU255L/EU256E/EU258I/EU433D/
EU434Y/EU436V/EU438K/EU440D;
EU252Y/EU254T/EU255L/EU256E/EU258D/EU433D/
EU434Y/EU436V/EU438R/EU440D;
EU252Y/EU254T/EU255L/EU256E/EU258I/EU433D/
EU434Y/EU436V/EU438R/EU440D;
EU252Y/EU254T/EU256E/EU433A/EU434Y/EU436V/
EU438R/EU440E;
EU252Y/EU254T/EU256E/EU433K/EU434Y/EU436V/
EU438R/EU440E;
EU252Y/EU254T/EU256E/EU433P/EU434Y/EU436V/
EU438R/EU440E;
EU252Y/EU254T/EU256E/EU433R/EU434Y/EU436V/
EU438R/EU440E;
EU252Y/EU254T/EU256E/EU433S/EU434Y/EU436V/
EU438R/EU440E;
EU252Y/EU254T/EU256E/EU433A/EU434Y/EU436V/
EU438K/EU440E;
EU252Y/EU254T/EU256E/EU433A/EU434Y/EU436V/
EU438R/EU440D;
EU252Y/EU254T/EU256E/EU433A/EU434Y/EU436V/
EU438K/EU440D;
EU252Y/EU254T/EU256E/EU433K/EU434Y/EU436V/
EU438K/EU440E;
EU252Y/EU254T/EU256E/EU433K/EU434Y/EU436V/
EU438R/EU440D;
EU252Y/EU254T/EU256E/EU433K/EU434Y/EU436V/
EU438K/EU440D;
EU252Y/EU254T/EU256E/EU433P/EU434Y/EU436V/
EU438K/EU440E;
EU252Y/EU254T/EU256E/EU433P/EU434Y/EU436V/
EU438R/EU440D;
EU252Y/EU254T/EU256E/EU433P/EU434Y/EU436V/
EU438K/EU440D;
EU252Y/EU254T/EU256E/EU433R/EU434Y/EU436V/
EU438K/EU440E;
EU252Y/EU254T/EU256E/EU433R/EU434Y/EU436V/
EU438R/EU440D;
EU252Y/EU254T/EU256E/EU433R/EU434Y/EU436V/
EU438K/EU440D;
EU252Y/EU254T/EU256E/EU433S/EU434Y/EU436V/
EU438K/EU440E;
EU252Y/EU254T/EU256E/EU433S/EU434Y/EU436V/
EU438R/EU440D;
EU252Y/EU254T/EU256E/EU433S/EU434Y/EU436V/
EU438K/EU440D;
EU235R/EU236R/EU239K/EU252Y/EU254T/EU434Y/
EU436V/EU438R/EU440E;
EU235R/EU236R/EU239K/EU252Y/EU254T/EU256E/
EU434Y/EU436V/EU438R/EU440E;
EU250V/EU252Y/EU307Q/EU308P/EU311A/EU434Y/
EU436V/EU438R/EU440E;
EU252Y/EU254T/EU256E/EU438R/EU440E;
EU428L/EU434S/EU438R/EU440E;
EU434H/EU438R/EU440E;
EU434Y/EU436V/EU438R/EU440E;
EU434Y/EU436V/EU438R/EU440D;
EU434Y/EU436V/EU438K/EU440E;
EU434Y/EU436V/EU438K/EU440D;
EU433D/EU434Y/EU436V/EU438R/EU440E;
EU433D/EU434Y/EU436V/EU438R/EU440D;
EU433D/EU434Y/EU436V/EU438K/EU440E;
EU433D/EU434Y/EU436V/EU438K/EU440D;
EU434Y/EU436T/EU438R/EU440E;
EU434Y/EU436T/EU438R/EU440D;
EU434Y/EU436T/EU438K/EU440E;
EU434Y/EU436T/EU438K/EU440D;
EU433D/EU434Y/EU436T/EU438R/EU440E;
EU433D/EU434Y/EU436T/EU438R/EU440D;
EU433D/EU434Y/EU436T/EU438K/EU440E;
EU433D/EU434Y/EU436T/EU438K/EU440D;
EU235R/EU239K/EU252Y/EU434Y/EU436V/EU438K/
EU440E;
EU235R/EU239K/EU252Y/EU434Y/EU436V/EU438R/
EU440E;
EU235R/EU239K/EU252Y/EU434Y/EU436T/EU438K/
EU440E;
EU235R/EU239K/EU252Y/EU434Y/EU436T/EU438R/
EU440E;
EU235R/EU239K/EU252Y/EU434Y/EU436F/EU438K/
EU440E;
EU235R/EU239K/EU252Y/EU434Y/EU436F/EU438R/
EU440E;
EU235R/EU239K/EU252Y/EU434Y/EU436V/EU438R/
EU440D;
EU235R/EU239K/EU252Y/EU434Y/EU436V/EU438K/
EU440D;
EU235R/EU239K/EU252Y/EU433D/EU434Y/EU436V/
EU438R/EU440D;
EU235R/EU239K/EU252Y/EU433D/EU434Y/EU436V/
EU438K/EU440E;
EU235R/EU239K/EU252Y/EU433D/EU434Y/EU436V/
EU438R/EU440E;
EU235R/EU239K/EU252Y/EU433D/EU434Y/EU436V/
EU438K/EU440D;
EU235R/EU239K/EU252Y/EU254T/EU256E/EU307Q/
EU311A/EU433D/EU434Y/EU436V/EU438K/
EU440E;
EU235R/EU239K/EU252Y/EU254T/EU256E/EU308P/
EU433D/EU434Y/EU436V/EU438K/EU440E;

EU235R/EU239K/EU252Y/EU433D/EU434W/
EU436V/EU438R/EU440E;
EU235R/EU239K/EU252Y/EU433D/EU434W/
EU436V/EU438K/EU440E;
EU235R/EU239K/EU252Y/EU254T/EU256E/EU433D/
EU434Y/EU436V/EU438K/EU440E;
EU235R/EU239K/EU252Y/EU254T/EU256E/EU433D/
EU434Y/EU436V/EU438R/EU440E;
EU235R/EU239K/EU252Y/EU254T/EU256E/EU433D/
EU434Y/EU436V/EU438K/EU440D;
EU235R/EU239K/EU252Y/EU254T/EU256E/EU433D/
EU434Y/EU436V/EU438R/EU440D;
EU235R/EU239K/EU252Y/EU254T/EU256E/EU286E/
EU433D/EU434Y/EU436V/EU438K/EU440E;
EU235R/EU239K/EU252Y/EU254T/EU256E/EU286E/
EU433D/EU434Y/EU436V/EU438R/EU440E;
EU235R/EU239K/EU252Y/EU254T/EU256E/EU286E/
EU433D/EU434Y/EU436V/EU438K/EU440D;
EU235R/EU239K/EU252Y/EU254T/EU256E/EU286E/
EU433D/EU434Y/EU436V/EU438R/EU440D;
EU235R/EU239K/EU252Y/EU254T/EU255L/EU256E/
EU433D/EU434Y/EU436V/EU438K/EU440E;
EU235R/EU239K/EU252Y/EU254T/EU255L/EU256E/
EU433D/EU434Y/EU436V/EU438R/EU440E;
EU235R/EU239K/EU252Y/EU254T/EU255L/EU256E/
EU433D/EU434Y/EU436V/EU438K/EU440D;
EU235R/EU239K/EU252Y/EU254T/EU255L/EU256E/
EU433D/EU434Y/EU436V/EU438R/EU440D;
EU235R/EU239K/EU252Y/EU254T/EU255L/EU256E/
EU258D/EU433D/EU434Y/EU436V/EU438R/
EU440E;
EU235R/EU239K/EU252Y/EU254T/EU255L/EU256E/
EU258I/EU433D/EU434Y/EU436V/EU438R/
EU440E;
EU235R/EU239K/EU252Y/EU254T/EU255L/EU256E/
EU258D/EU433D/EU434Y/EU436V/EU438K/
EU440E;
EU235R/EU239K/EU252Y/EU254T/EU255L/EU256E/
EU258I/EU433D/EU434Y/EU436V/EU438K/
EU440E;
EU235R/EU239K/EU252Y/EU254T/EU255L/EU256E/
EU258D/EU433D/EU434Y/EU436V/EU438K/
EU440D;
EU235R/EU239K/EU252Y/EU254T/EU255L/EU256E/
EU258I/EU433D/EU434Y/EU436V/EU438K/
EU440D;
EU235R/EU239K/EU252Y/EU254T/EU255L/EU256E/
EU258D/EU433D/EU434Y/EU436V/EU438R/
EU440D;
EU235R/EU239K/EU252Y/EU254T/EU255L/EU256E/
EU258I/EU433D/EU434Y/EU436V/EU438R/
EU440D;
EU235R/EU239K/EU252Y/EU254T/EU256E/EU433A/
EU434Y/EU436V/EU438R/EU440E;
EU235R/EU239K/EU252Y/EU254T/EU256E/EU433K/
EU434Y/EU436V/EU438R/EU440E;
EU235R/EU239K/EU252Y/EU254T/EU256E/EU433P/
EU434Y/EU436V/EU438R/EU440E;
EU235R/EU239K/EU252Y/EU254T/EU256E/EU433R/
EU434Y/EU436V/EU438R/EU440E;
EU235R/EU239K/EU252Y/EU254T/EU256E/EU433S/
EU434Y/EU436V/EU438R/EU440E;
EU235R/EU239K/EU252Y/EU254T/EU256E/EU433A/
EU434Y/EU436V/EU438K/EU440E;
EU235R/EU239K/EU252Y/EU254T/EU256E/EU433A/
EU434Y/EU436V/EU438R/EU440D;
EU235R/EU239K/EU252Y/EU254T/EU256E/EU433A/
EU434Y/EU436V/EU438K/EU440D;
EU235R/EU239K/EU252Y/EU254T/EU256E/EU433K/
EU434Y/EU436V/EU438K/EU440E;
EU235R/EU239K/EU252Y/EU254T/EU256E/EU433K/
EU434Y/EU436V/EU438R/EU440D;
EU235R/EU239K/EU252Y/EU254T/EU256E/EU433K/
EU434Y/EU436V/EU438K/EU440D;
EU235R/EU239K/EU252Y/EU254T/EU256E/EU433P/
EU434Y/EU436V/EU438K/EU440E;
EU235R/EU239K/EU252Y/EU254T/EU256E/EU433P/
EU434Y/EU436V/EU438R/EU440D;
EU235R/EU239K/EU252Y/EU254T/EU256E/EU433P/
EU434Y/EU436V/EU438K/EU440D;
EU235R/EU239K/EU252Y/EU254T/EU256E/EU433R/
EU434Y/EU436V/EU438K/EU440E;
EU235R/EU239K/EU252Y/EU254T/EU256E/EU433R/
EU434Y/EU436V/EU438R/EU440D;
EU235R/EU239K/EU252Y/EU254T/EU256E/EU433R/
EU434Y/EU436V/EU438K/EU440D;
EU235R/EU239K/EU252Y/EU254T/EU256E/EU433S/
EU434Y/EU436V/EU438K/EU440E;
EU235R/EU239K/EU252Y/EU254T/EU256E/EU433S/
EU434Y/EU436V/EU438R/EU440D;
EU235R/EU239K/EU252Y/EU254T/EU256E/EU433S/
EU434Y/EU436V/EU438K/EU440D;
EU235R/EU236R/EU239K/EU252Y/EU254T/EU434Y/
EU436V/EU438R/EU440E;
EU235R/EU236R/EU239K/EU252Y/EU254T/EU256E/
EU434Y/EU436V/EU438R/EU440E;
EU235R/EU239K/EU252Y/EU254T/EU434Y/EU436V/
EU438K/EU440E;
EU235R/EU239K/EU252Y/EU254T/EU256E/EU434Y/
EU436V/EU438K/EU440E;
EU235R/EU239K/EU252Y/EU254T/EU434Y/EU436V/
EU438R/EU440E;
EU235R/EU239K/EU252Y/EU254T/EU256E/EU434Y/
EU436V/EU438R/EU440E;
EU235R/EU239K/EU252Y/EU254T/EU433D/EU434Y/
EU436V/EU438R/EU440E;
EU235R/EU239K/EU434Y/EU436V/EU438R/EU440E;
EU235R/EU239K/EU434Y/EU436V/EU438R/EU440D;
EU235R/EU239K/EU434Y/EU436V/EU438K/EU440E;
EU235R/EU239K/EU434Y/EU436V/EU438K/EU440D;
EU235R/EU239K/EU433D/EU434Y/EU436V/EU438R/
EU440E;
EU235R/EU239K/EU433D/EU434Y/EU436V/EU438R/
EU440D;
EU235R/EU239K/EU433D/EU434Y/EU436V/EU438K/
EU440E;
EU235R/EU239K/EU433D/EU434Y/EU436V/EU438K/
EU440D;
EU235R/EU239K/EU434Y/EU436T/EU438R/EU440E;
EU235R/EU239K/EU434Y/EU436T/EU438R/EU440D;
EU235R/EU239K/EU434Y/EU436T/EU438K/EU440E;
EU235R/EU239K/EU434Y/EU436T/EU438K/EU440D;
EU235R/EU239K/EU433D/EU434Y/EU436T/EU438R/
EU440E;
EU235R/EU239K/EU433D/EU434Y/EU436T/EU438R/
EU440D;
EU235R/EU239K/EU433D/EU434Y/EU436T/EU438K/
EU440E;
EU235R/EU239K/EU433D/EU434Y/EU436T/EU438K/
EU440D;
EU235R/EU239K/EU434Y/EU436F/EU438R/EU440E;
EU235R/EU239K/EU434Y/EU438R/EU440E.

24. The antibody of claim 19, wherein the modified Fc region further comprises at least one additional amino acid substitution compared to a native human IgG3 Fc region, wherein the at least one additional amino acid substitution comprises a substitution at one or more of the following positions (EU numbering): 238, 250, 252, 254, 255, 256, 258, 286, 307, 308, 309, 311, 315, 428, 434, and 436.

25. The antibody of claim 19, wherein the modified Fc region further comprises at least one additional amino acid substitution compared to a native human IgG3 Fc region, wherein the at least one additional amino acid substitution comprises substitution(s) at any one of the following sets of positions (EU numbering):
    (a) position 434,
    (b) positions 252, 254, and 256,
    (c) positions 428 and 434,
    (d) positions 250 and 428.

26. The antibody of claim 25, wherein the at least one additional amino acid substitution includes any one of the following sets of substitutions at the indicated position(s) (EU numbering):
    (a) histidine at position 434,
    (b) tyrosine at position 252, threonine at position 254, and glutamic acid at position 256,
    (c) leucine at position 428 and serine at position 434, or
    (d) glutamine at position 250 and leucine at position 428.

27. The antibody of claim 19, wherein the modified Fc region comprises at least one additional amino acid substitution compared to a native human IgG3 Fc region, wherein the at least one additional amino acid substitution comprises any one of the combinations of substitutions listed in Table 9 (all positions by EU numbering).

28. An antibody comprising a modified IgG4 Fc region, wherein the amino acid at position EU438 of the modified Fc region is glutamic acid, arginine, serine, or lysine; and
wherein the amino acid at position EU440 of the modified Fc region is glutamic acid, aspartic acid, or glutamine.

29. The antibody of claim 28, wherein the modified Fc region comprises one of the following combinations of amino acid substitutions at the indicated positions:
    EU438R/EU440E;
    EU438R/EU440D;
    EU438K/EU440E;
    EU438K/EU440D.

30. A composition comprising the antibody of claim 28, wherein at least 98% of the antibody molecules in the composition are in the form of antibody monomers containing two heavy chains and two light chains.

31. A pharmaceutical composition comprising the antibody of claim 28 and a pharmaceutically acceptable carrier.

32. The antibody of claim 28, wherein the modified Fc region comprises one of the following combinations of amino acid substitutions at the indicated positions:
    EU252Y/EU434Y/EU436V/EU438K/EU440E;
    EU252Y/EU434Y/EU436V/EU438R/EU440E;
    EU252Y/EU434Y/EU436T/EU438K/EU440E;
    EU252Y/EU434Y/EU436T/EU438R/EU440E;
    EU252Y/EU434Y/EU436F/EU438K/EU440E;
    EU252Y/EU434Y/EU436F/EU438R/EU440E;
    EU252Y/EU434Y/EU436V/EU438R/EU440D;
    EU252Y/EU434Y/EU436V/EU438K/EU440D;
    EU252Y/EU433D/EU434Y/EU436V/EU438R/EU440D;
    EU252Y/EU433D/EU434Y/EU436V/EU438K/EU440E;
    EU252Y/EU433D/EU434Y/EU436V/EU438R/EU440E;
    EU252Y/EU433D/EU434Y/EU436V/EU438K/EU440D;
    EU252Y/EU254T/EU256E/EU307Q/EU311A/EU433D/EU434Y/EU436V/EU438K/EU440E;
    EU252Y/EU254T/EU256E/EU308P/EU433D/EU434Y/EU436V/EU438K/EU440E;
    EU252Y/EU433D/EU434W/EU436V/EU438R/EU440E;
    EU252Y/EU433D/EU434W/EU436V/EU438K/EU440E;
    EU252Y/EU254T/EU256E/EU433D/EU434Y/EU436V/EU438K/EU440E;
    EU252Y/EU254T/EU256B/EU433D/EU434Y/EU436V/EU438R/EU440E;
    EU252Y/EU254T/EU256E/EU433D/EU434Y/EU436V/EU438K/EU440D;
    EU252Y/EU254T/EU256E/EU433D/EU434Y/EU436V/EU438R/EU440D;
    EU252Y/EU254T/EU256E/EU286E/EU433D/EU434Y/EU436V/EU438K/EU440E;
    EU252Y/EU254T/EU256E/EU286E/EU433D/EU434Y/EU436V/EU438R/EU440E;
    EU252Y/EU254T/EU256E/EU286E/EU433D/EU434Y/EU436V/EU438K/EU440D;
    EU252Y/EU254T/EU256E/EU286E/EU433D/EU434Y/EU436V/EU438R/EU440D;
    EU252Y/EU254T/EU255L/EU256E/EU433D/EU434Y/EU436V/EU438K/EU440E;
    EU252Y/EU254T/EU255L/EU256E/EU433D/EU434Y/EU436V/EU438R/EU440E;
    EU252Y/EU254T/EU255L/EU256E/EU433D/EU434Y/EU436V/EU438K/EU440D;
    EU252Y/EU254T/EU255L/EU256E/EU433D/EU434Y/EU436V/EU438R/EU440D;
    EU252Y/EU254T/EU255L/EU256E/EU258D/EU433D/EU434Y/EU436V/EU438R/EU440E;
    EU252Y/EU254T/EU255L/EU256E/EU258I/EU433D/EU434Y/EU436V/EU438R/EU440E;
    EU252Y/EU254T/EU255L/EU256E/EU258D/EU433D/EU434Y/EU436V/EU438K/EU440E;
    EU252Y/EU254T/EU255L/EU256E/EU258I/EU433D/EU434Y/EU436V/EU438K/EU440E;
    EU252Y/EU254T/EU255L/EU256E/EU258D/EU433D/EU434Y/EU436V/EU438K/EU440D;
    EU252Y/EU254T/EU255L/EU256E/EU258I/EU433D/EU434Y/EU436V/EU438K/EU440D;
    EU252Y/EU254T/EU255L/EU256E/EU258D/EU433D/EU434Y/EU436V/EU438R/EU440D;
    EU252Y/EU254T/EU255L/EU256E/EU258I/EU433D/EU434Y/EU436V/EU438R/EU440D;
    EU252Y/EU254T/EU256E/EU433A/EU434Y/EU436V/EU438R/EU440E;
    EU252Y/EU254T/EU256E/EU433K/EU434Y/EU436V/EU438R/EU440E;
    EU252Y/EU254T/EU256E/EU433P/EU434Y/EU436V/EU438R/EU440E;
    EU252Y/EU254T/EU256E/EU433R/EU434Y/EU436V/EU438R/EU440E;
    EU252Y/EU254T/EU256E/EU433S/EU434Y/EU436V/EU438R/EU440E;
    EU252Y/EU254T/EU256E/EU433A/EU434Y/EU436V/EU438K/EU440E;
    EU252Y/EU254T/EU256E/EU433A/EU434Y/EU436V/EU438R/EU440D;
    EU252Y/EU254T/EU256E/EU433A/EU434Y/EU436V/EU438K/EU440D;
    EU252Y/EU254T/EU256E/EU433K/EU434Y/EU436V/EU438K/EU440E;

EU252Y/EU254T/EU256E/EU433K/EU434Y/EU436V/
  EU438R/EU440D;
EU252Y/EU254T/EU256E/EU433K/EU434Y/EU436V/
  EU438K/EU440D;
EU252Y/EU254T/EU256E/EU433P/EU434Y/EU436V/
  EU438K/EU440E;
EU252Y/EU254T/EU256E/EU433P/EU434Y/EU436V/
  EU438R/EU440D;
EU252Y/EU254T/EU256E/EU433P/EU434Y/EU436V/
  EU438K/EU440D;
EU252Y/EU254T/EU256E/EU433R/EU434Y/EU436V/
  EU438K/EU440E;
EU252Y/EU254T/EU256E/EU433R/EU434Y/EU436V/
  EU438R/EU440D;
EU252Y/EU254T/EU256E/EU433R/EU434Y/EU436V/
  EU438K/EU440D;
EU252Y/EU254T/EU256E/EU433S/EU434Y/EU436V/
  EU438K/EU440E;
EU252Y/EU254T/EU256E/EU433S/EU434Y/EU436V/
  EU438R/EU440D;
EU252Y/EU254T/EU256E/EU433S/EU434Y/EU436V/
  EU438K/EU440E;
EU235R/EU236R/EU239K/EU252Y/EU254T/EU434Y/
  EU436V/EU438R/EU440E;
EU235R/EU236R/EU239K/EU252Y/EU254T/EU256E/
  EU434Y/EU436V/EU438R/EU440E;
EU250V/EU252Y/EU307Q/EU308P/EU311A/EU434Y/
  EU436V/EU438R/EU440E;
EU252Y/EU254T/EU256E/EU438R/EU440E;
EU428L/EU434S/EU438R/EU440E;
EU434H/EU438R/EU440E;
EU434Y/EU436V/EU438R/EU440E;
EU434Y/EU436V/EU438R/EU440D;
EU434Y/EU436V/EU438K/EU440E;
EU434Y/EU436V/EU438K/EU440D;
EU433D/EU434Y/EU436V/EU438R/EU440E;
EU433D/EU434Y/EU436V/EU438R/EU440D;
EU433D/EU434Y/EU436V/EU438K/EU440E;
EU433D/EU434Y/EU436V/EU438K/EU440D;
EU434Y/EU436T/EU438R/EU440E;
EU434Y/EU436T/EU438R/EU440D;
EU434Y/EU436T/EU438K/EU440E;
EU434Y/EU436T/EU438K/EU440D;
EU433D/EU434Y/EU436T/EU438R/EU440E;
EU433D/EU434Y/EU436T/EU438R/EU440D;
EU433D/EU434Y/EU436T/EU438K/EU440E;
EU433D/EU434Y/EU436T/EU438K/EU440D;
EU235R/EU239K/EU252Y/EU434Y/EU436V/EU438K/
  EU440E;
EU235R/EU239K/EU252Y/EU434Y/EU436V/EU438R/
  EU440E;
EU235R/EU239K/EU252Y/EU434Y/EU436T/EU438K/
  EU440E;
EU235R/EU239K/EU252Y/EU434Y/EU436T/EU438R/
  EU440E;
EU235R/EU239K/EU252Y/EU434Y/EU436F/EU438K/
  EU440E;
EU235R/EU239K/EU252Y/EU434Y/EU436F/EU438R/
  EU440E;
EU235R/EU239K/EU252Y/EU434Y/EU436V/EU438R/
  EU440D;
EU235R/EU239K/EU252Y/EU434Y/EU436V/EU438K/
  EU440D;
EU235R/EU239K/EU252Y/EU433D/EU434Y/EU436V/
  EU438R/EU440D;
EU235R/EU239K/EU252Y/EU433D/EU434Y/EU436V/
  EU438K/EU440E;
EU235R/EU239K/EU252Y/EU433D/EU434Y/EU436V/
  EU438R/EU440E;
EU235R/EU239K/EU252Y/EU433D/EU434Y/EU436V/
  EU438K/EU440D;
EU235R/EU239K/EU252Y/EU254T/EU256E/EU307Q/
  EU311A/EU433D/EU434Y/EU436V/EU438K/
  EU440E;
EU235R/EU239K/EU252Y/EU254T/EU256E/EU308P/
  EU433D/EU434Y/EU436V/EU438K/EU440E;
EU235R/EU239K/EU252Y/EU433D/EU434W/
  EU436V/EU438R/EU440E;
EU235R/EU239K/EU252Y/EU433D/EU434W/
  EU436V/EU438K/EU440E;
EU235R/EU239K/EU252Y/EU254T/EU256E/EU433D/
  EU434Y/EU436V/EU438K/EU440E;
EU235R/EU239K/EU252Y/EU254T/EU256E/EU433D/
  EU434Y/EU436V/EU438R/EU440E;
EU235R/EU239K/EU252Y/EU254T/EU256E/EU433D/
  EU434Y/EU436V/EU438K/EU440D;
EU235R/EU239K/EU252Y/EU254T/EU256E/EU433D/
  EU434Y/EU436V/EU438R/EU440D;
EU235R/EU239K/EU252Y/EU254T/EU256E/EU286E/
  EU433D/EU434Y/EU436V/EU438K/EU440E;
EU235R/EU239K/EU252Y/EU254T/EU256E/EU286E/
  EU433D/EU434Y/EU436V/EU438R/EU440E;
EU235R/EU239K/EU252Y/EU254T/EU256E/EU286E/
  EU433D/EU434Y/EU436V/EU438K/EU440D;
EU235R/EU239K/EU252Y/EU254T/EU256E/EU286E/
  EU433D/EU434Y/EU436V/EU438R/EU440D;
EU235R/EU239K/EU252Y/EU254T/EU255L/EU256E/
  EU433D/EU434Y/EU436V/EU438K/EU440E;
EU235R/EU239K/EU252Y/EU254T/EU255L/EU256E/
  EU433D/EU434Y/EU436V/EU438R/EU440E;
EU235R/EU239K/EU252Y/EU254T/EU255L/EU256E/
  EU433D/EU434Y/EU436V/EU438K/EU440D;
EU235R/EU239K/EU252Y/EU254T/EU255L/EU256E/
  EU433D/EU434Y/EU436V/EU438R/EU440D;
EU235R/EU239K/EU252Y/EU254T/EU255L/EU256E/
  EU258D/EU433D/EU434Y/EU436V/EU438R/
  EU440E;
EU235R/EU239K/EU252Y/EU254T/EU255L/EU256E/
  EU258I/EU433D/EU434Y/EU436V/EU438R/
  EU440E;
EU235R/EU239K/EU252Y/EU254T/EU255L/EU256E/
  EU258D/EU433D/EU434Y/EU436V/EU438K/
  EU440E;
EU235R/EU239K/EU252Y/EU254T/EU255L/EU256E/
  EU258I/EU433D/EU434Y/EU436V/EU438K/
  EU440E;
EU235R/EU239K/EU252Y/EU254T/EU255L/EU256E/
  EU258D/EU433D/EU434Y/EU436V/EU438K/
  EU440D;
EU235R/EU239K/EU252Y/EU254T/EU255L/EU256E/
  EU258I/EU433D/EU434Y/EU436V/EU438K/
  EU440D;
EU235R/EU239K/EU252Y/EU254T/EU255L/EU256E/
  EU258D/EU433D/EU434Y/EU436V/EU438R/
  EU440D;
EU235R/EU239K/EU252Y/EU254T/EU255L/EU256E/
  EU258I/EU433D/EU434Y/EU436V/EU438R/
  EU440D;
EU235R/EU239K/EU252Y/EU254T/EU256E/EU433A/
  EU434Y/EU436V/EU438R/EU440E;
EU235R/EU239K/EU252Y/EU254T/EU256E/EU433K/
  EU434Y/EU436V/EU438R/EU440E;
EU235R/EU239K/EU252Y/EU254T/EU256E/EU433P/
  EU434Y/EU436V/EU438R/EU440E;

EU235R/EU239K/EU252Y/EU254T/EU256E/EU433R/
EU434Y/EU436V/EU438R/EU440E;
EU235R/EU239K/EU252Y/EU254T/EU256E/EU433S/
EU434Y/EU436V/EU438R/EU440E;
EU235R/EU239K/EU252Y/EU254T/EU256E/EU433A/
EU434Y/EU436V/EU438K/EU440E;
EU235R/EU239K/EU252Y/EU254T/EU256E/EU433A/
EU434Y/EU436V/EU438R/EU440D;
EU235R/EU239K/EU252Y/EU254T/EU256E/EU433A/
EU434Y/EU436V/EU438K/EU440D;
EU235R/EU239K/EU252Y/EU254T/EU256E/EU433K/
EU434Y/EU436V/EU438K/EU440E;
EU235R/EU239K/EU252Y/EU254T/EU256E/EU433K/
EU434Y/EU436V/EU438R/EU440D;
EU235R/EU239K/EU252Y/EU254T/EU256E/EU433K/
EU434Y/EU436V/EU438K/EU440D;
EU235R/EU239K/EU252Y/EU254T/EU256E/EU433P/
EU434Y/EU436V/EU438K/EU440E;
EU235R/EU239K/EU252Y/EU254T/EU256E/EU433P/
EU434Y/EU436V/EU438R/EU440D;
EU235R/EU239K/EU252Y/EU254T/EU256E/EU433P/
EU434Y/EU436V/EU438K/EU440D;
EU235R/EU239K/EU252Y/EU254T/EU256E/EU433R/
EU434Y/EU436V/EU438K/EU440E;
EU235R/EU239K/EU252Y/EU254T/EU256E/EU433R/
EU434Y/EU436V/EU438R/EU440D;
EU235R/EU239K/EU252Y/EU254T/EU256E/EU433R/
EU434Y/EU436V/EU438K/EU440D;
EU235R/EU239K/EU252Y/EU254T/EU256E/EU433S/
EU434Y/EU436V/EU438K/EU440E;
EU235R/EU239K/EU252Y/EU254T/EU256E/EU433S/
EU434Y/EU436V/EU438R/EU440D;
EU235R/EU239K/EU252Y/EU254T/EU256E/EU433S/
EU434Y/EU436V/EU438K/EU440D;
EU235R/EU236R/EU239K/EU252Y/EU254T/EU434Y/
EU436V/EU438R/EU440E;
EU235R/EU236R/EU239K/EU252Y/EU254T/EU256E/
EU434Y/EU436V/EU438R/EU440E;
EU235R/EU239K/EU252Y/EU254T/EU434Y/EU436V/
EU438K/EU440E;
EU235R/EU239K/EU252Y/EU254T/EU256E/EU434Y/
EU436V/EU438K/EU440E;
EU235R/EU239K/EU252Y/EU254T/EU434Y/EU436V/
EU438R/EU440E;
EU235R/EU239K/EU252Y/EU254T/EU256E/EU434Y/
EU436V/EU438R/EU440E;
EU235R/EU239K/EU252Y/EU254T/EU433D/EU434Y/
EU436V/EU438R/EU440E;
EU235R/EU239K/EU434Y/EU436V/EU438R/EU440E;
EU235R/EU239K/EU434Y/EU436V/EU438R/EU440D;
EU235R/EU239K/EU434Y/EU436V/EU438K/EU440E;
EU235R/EU239K/EU434Y/EU436V/EU438K/EU440D;
EU235R/EU239K/EU433D/EU434Y/EU436V/EU438R/
EU440E;
EU235R/EU239K/EU433D/EU434Y/EU436V/EU438R/
EU440D;
EU235R/EU239K/EU433D/EU434Y/EU436V/EU438K/
EU440E;
EU235R/EU239K/EU433D/EU434Y/EU436V/EU438K/
EU440D;
EU235R/EU239K/EU434Y/EU436T/EU438R/EU440E;
EU235R/EU239K/EU434Y/EU436T/EU438R/EU440D;
EU235R/EU239K/EU434Y/EU436T/EU438K/EU440E;
EU235R/EU239K/EU434Y/EU436T/EU438K/EU440D;
EU235R/EU239K/EU433D/EU434Y/EU436T/EU438R/
EU440E;
EU235R/EU239K/EU433D/EU434Y/EU436T/EU438R/
EU440D;
EU235R/EU239K/EU433D/EU434Y/EU436T/EU438K/
EU440E;
EU235R/EU239K/EU433D/EU434Y/EU436T/EU438K/
EU440D;
EU235R/EU239K/EU434Y/EU436F/EU438R/EU440E;
EU235R/EU239K/EU434Y/EU438R/EU440E.

33. The antibody of claim 28, wherein the modified Fc region further comprises at least one additional amino acid substitution compared to a native human IgG4 Fc region, wherein the at least one additional amino acid substitution comprises a substitution at one or more of the following positions (EU numbering): 238, 250, 252, 254, 255, 256, 258, 286, 307, 308, 309, 311, 315, 428, 434, and 436.

34. The antibody of claim 28, wherein the modified Fc region further comprises at least one additional amino acid substitution compared to a native human IgG4 Fc region, wherein the at least one additional amino acid substitution comprises substitution(s) at any one of the following sets of positions (EU numbering):
  (a) position 434,
  (b) positions 252, 254, and 256,
  (c) positions 428 and 434,
  (d) positions 250 and 428.

35. The antibody of claim 34, wherein the at least one additional amino acid substitution includes any one of the following sets of substitutions at the indicated position(s) (EU numbering):
  (a) histidine at position 434,
  (b) tyrosine at position 252, threonine at position 254, and glutamic acid at position 256,
  (c) leucine at position 428 and serine at position 434, or
  (d) glutamine at position 250 and leucine at position 428.

36. The antibody of claim 28, wherein the modified Fc region comprises at least one additional amino acid substitution compared to a native human IgG4 Fc region, wherein the at least one additional amino acid substitution comprises any one of the combinations of substitutions listed in Table 9 (all positions by EU numbering).

* * * * *